(12) United States Patent
Aissaoui et al.

(10) Patent No.: US 9,255,090 B2
(45) Date of Patent: Feb. 9, 2016

(54) HETEROCYCLYL DERIVATIVES AND THEIR USE AS PROSTAGLANDIN D2 RECEPTOR MODULATORS

(71) Applicant: Actelion Pharmaceuticals Ltd., Allschwil (CH)

(72) Inventors: Hamed Aissaoui, Allschwil (CH); Christoph Boss, Allschwil (CH); Sylvia Richard-Bildstein, Allschwil (CH); Romain Siegrist, Allschwil (CH)

(73) Assignee: ACTELION PHARMACEUTICALS LTD., Allschwil (CH)

( * ) Notice: Subject to any disclaimer, the term of this patent is extended or adjusted under 35 U.S.C. 154(b) by 0 days.

(21) Appl. No.: 14/367,823

(22) PCT Filed: Dec. 20, 2012

(86) PCT No.: PCT/IB2012/057541
§ 371 (c)(1),
(2) Date: Jun. 20, 2014

(87) PCT Pub. No.: WO2013/093842
PCT Pub. Date: Jun. 27, 2013

(65) Prior Publication Data
US 2015/0252036 A1    Sep. 10, 2015

(30) Foreign Application Priority Data

Dec. 20, 2012  (WO) .................. PCT/IB2012/057541

(51) Int. Cl.
| | | |
|---|---|---|
| C07D 209/44 | (2006.01) | |
| C07D 217/06 | (2006.01) | |
| C07D 223/06 | (2006.01) | |
| C07D 223/16 | (2006.01) | |
| C07D 401/06 | (2006.01) | |
| C07D 405/06 | (2006.01) | |
| C07D 413/06 | (2006.01) | |
| C07D 417/06 | (2006.01) | |
| A61K 31/47 | (2006.01) | |
| C07D 401/12 | (2006.01) | |

(52) U.S. Cl.
CPC ............ *C07D 417/06* (2013.01); *C07D 209/44* (2013.01); *C07D 217/06* (2013.01); *C07D 223/06* (2013.01); *C07D 223/16* (2013.01); *C07D 401/06* (2013.01); *C07D 401/12* (2013.01); *C07D 405/06* (2013.01); *C07D 413/06* (2013.01)

(58) Field of Classification Search
None
See application file for complete search history.

(56) References Cited

U.S. PATENT DOCUMENTS

| 8,575,158 B2 | 11/2013 | Aissaoui et al. |
|---|---|---|
| 2007/0010526 A1 | 1/2007 | Haeberlein et al. |
| 2008/0004272 A1 | 1/2008 | Vohra et al. |

FOREIGN PATENT DOCUMENTS

| EP | 1 413 306 | 4/2004 |
|---|---|---|
| EP | 1 435 356 | 7/2004 |
| GB | 238854 | 2/1926 |
| WO | WO 02/094830 | 11/2002 |
| WO | WO 03/097042 | 11/2003 |
| WO | WO 03/097598 | 11/2003 |
| WO | WO 2004/032848 | 4/2004 |
| WO | WO 2004/035543 | 4/2004 |
| WO | WO 2004/058164 | 7/2004 |
| WO | WO 2004/089884 | 10/2004 |
| WO | WO 2004/089885 | 10/2004 |
| WO | WO 2004/096777 | 11/2004 |
| WO | WO 2005/018529 | 3/2005 |
| WO | WO 2005/073234 | 8/2005 |
| WO | WO 2005/087743 | 9/2005 |
| WO | WO 2005/100321 | 10/2005 |
| WO | WO 2005/102338 | 11/2005 |

(Continued)

OTHER PUBLICATIONS

Arimura, A. et al., "Prevention of Allergic Inflammation by a Novel Prostaglandin Receptor Antagonist, S-5751," J. Pharmacol. Exp. Ther. (2001), vol. 298, No. 2, pp. 411-419.

(Continued)

*Primary Examiner* — Zinna Northington Davis
(74) *Attorney, Agent, or Firm* — Arent Fox LLP

(57) ABSTRACT

The present invention relates to phenyl-substituted heterocyclyl derivatives of the formula (I),

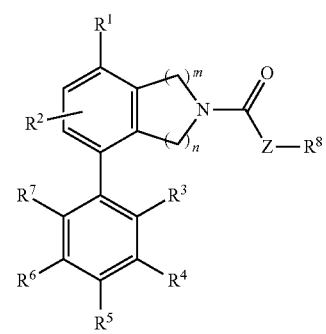

wherein Z, n, m, $R^1$, $R^2$, $R^3$, $R^4$, $R^5$, $R^6$, $R^7$ and $R^8$ are as described in the description and their use as prostaglandin receptor modulators, most particularly as prostaglandin $D_2$ receptor modulators, in the treatment of various prostaglandin-mediated diseases and disorders, to pharmaceutical compositions containing these compounds and to processes for their preparation.

20 Claims, No Drawings

(56) References Cited

FOREIGN PATENT DOCUMENTS

| WO | WO 2005/105727 | 11/2005 |
|---|---|---|
| WO | WO 2005/115382 | 12/2005 |
| WO | WO 2006/005909 | 1/2006 |
| WO | WO 2006/021759 | 3/2006 |
| WO | WO 2006/037982 | 4/2006 |
| WO | WO 2006/044732 | 4/2006 |
| WO | WO 2006/056752 | 6/2006 |
| WO | WO 2006/063763 | 6/2006 |
| WO | WO 2006/081343 | 8/2006 |
| WO | WO 2006/091674 | 8/2006 |
| WO | WO 2006/125593 | 11/2006 |
| WO | WO 2006/125596 | 11/2006 |
| WO | WO 2007/010964 | 1/2007 |
| WO | WO 2007/010965 | 1/2007 |
| WO | WO 2007/029629 | 3/2007 |
| WO | WO 2007/036743 | 4/2007 |
| WO | WO 2007/037187 | 4/2007 |
| WO | WO 2007/039736 | 4/2007 |
| WO | WO 2007/039741 | 4/2007 |
| WO | WO 2007/052023 | 5/2007 |
| WO | WO 2007/062678 | 6/2007 |
| WO | WO 2007/062773 | 6/2007 |
| WO | WO 2007/121280 | 10/2007 |
| WO | WO 2007/143745 | 12/2007 |
| WO | WO 2007/144625 | 12/2007 |
| WO | WO 2007/146838 | 12/2007 |
| WO | WO 2008/072784 | 6/2008 |
| WO | WO 2008/119917 | 10/2008 |
| WO | WO 2008/122784 | 10/2008 |
| WO | WO 2009/004379 | 1/2009 |
| WO | WO 2009/060209 | 5/2009 |
| WO | WO 2009/061730 | 5/2009 |
| WO | WO 2009/089192 | 7/2009 |
| WO | WO 2009/099901 | 8/2009 |
| WO | WO 2009/099902 | 8/2009 |
| WO | WO 2009/102893 | 8/2009 |
| WO | WO 2009/108720 | 9/2009 |
| WO | WO 2009/145989 | 12/2009 |
| WO | WO 2010/003120 | 1/2010 |
| WO | WO 2010/003127 | 1/2010 |
| WO | WO 2010/018109 | 2/2010 |
| WO | WO 2010/018112 | 2/2010 |
| WO | WO 2010/018113 | 2/2010 |
| WO | WO 2010/042652 | 4/2010 |
| WO | WO 2010/055004 | 5/2010 |
| WO | WO 2010/089391 | 8/2010 |
| WO | WO 2010/092043 | 8/2010 |
| WO | WO 2010/102154 | 9/2010 |
| WO | WO 2011/002814 | 1/2011 |
| WO | WO 2011/014587 | 2/2011 |
| WO | WO 2011/014588 | 2/2011 |
| WO | WO 2011/017201 | 2/2011 |
| WO | WO 2011/055270 | 5/2011 |
| WO | WO 2012/004722 | 1/2012 |
| WO | WO 2012/087861 | 6/2012 |
| WO | WO 2013/061977 | 5/2013 |
| WO | WO 2013/087544 | 6/2013 |
| WO | WO 2013/127841 | 9/2013 |
| WO | 2014006585 A1 | 1/2014 |

OTHER PUBLICATIONS

Barnes, N. et al., "A randomized, double-blind, placebo-controlled study of the CRTH2 antagonist OC000459 in moderate persistent asthma," Clin. Exp. Allergy, (2012), vol. 42, No. 1, pp. 38-48.

Crosignani, S. et al., "Discovery of Potent, Selective and Orally Bioavailable Alkynyl-Phenoxyacetic Acid CRTH2 (DP2) Receptor Antagonists for the Treatement of Allergic Inflammatory Diseases," J. Med. Chem. (2011), vol. 54, No. 20, pp. 7299-7317.

Gould, Philip, "Salt selection for basic drugs," International Journal of Pharmaceuticals (1986), vol. 33, pp. 201-217.

Greene, T. W. et al., "Protection for the Amino Group," in Protecting Groups in Organic Synthesis (3rd Edition, 1999), pp. 749-779.

Horak, F. et al., "The CRTH2 antagonist OC000459 reduces nasal and ocular symptoms in allergic subjects exposed to grass pollen, a randomised, placebo-controlled, double-blind trial," Eur. J. of Allergy & Clin. Immun. (2012), vol. 67, No. 12, pp. 1572-1579.

Ishizuka, T. et al., "Ramatroban (BAY u3405): A Novel Dual Antagonist of $TXA_2$ Receptor and CRTh2, A Newly Identified Prostaglandin $D_2$ Receptor," Cardiovascular Drug Rev. (2004), vol. 22, No. 2, pp. 71-90.

Jain, A. et al., "QSAR study of 2,4-disubstituted phenoxyacetic acid derivatives as a $CRTh_2$ receptor antagonists," Chemical Papers (2009), vol. 63, No. 4, pp. 464-470.

Kolb, H. et al., "A Simplified Procedure for the Stereospecific Transformation of 1,2-Diols into Epoxides," Tetrahedron (1992), vol. 48, No. 48, pp. 10515-10530.

Liu, J. et al., "Benzodiazepinone Derivatives as CRTH2 Antagonist," ACS Medicinal Chemistry Letters (2011), vol. 2., No. 7, pp. 515-518.

Luker, T. et al., "Switching between agonists and antagonists at CRTh2 in a series of highly potent and selective biaryl phenoxyacetic acids," Bioorg. Med. Chem. Lett. (2011), vol. 21, pp. 3616-3621.

Gennaro, Remington: The Science and Practice of Pharmacy (21st Edition, 2005) (5 pages, TOC).

Sandham, D. A. et al., "2-Cycloaklyl phenoxyacetic acid CRTh2 receptor antagonists," Bioorg. Med. Chem. Lett. (2007), vol. 17, No. 15, pp. 4347-4350.

Sandham, D. A. et al., "7-Azaindole-3-acetic derivatives: Potent and selective CRTh2 receptor antagonists," Bioorg. Med. Chem. Lett. (2009), vol. 19, pp. 4794-4798.

Sawyer, N. et al., "Molecular Pharmacology of the Human Prostaglandin $D_2$ Receptor, CRTH2," Br. J. Pharmacology (2002), vol. 137, pp. 1163-1172.

Scott J. M. et al., "Discovery and optimization of a biphenylacetic acid series of prostaglandin $D_2$ receptor DP2 antagonists with efficacy in a murine model of allergic rhinitis," Bioorg. Med. Chem. Lett. (2011), vol. 21, pp. 6608-6612.

Sharpless, K et al., "The Osmium-Catalyzed Asymmetric Dihydroxylation: A New Ligand Class and a Process Improvement," J. Org. Chem. (1992), vol. 57, No. 10, pp. 2768-2771.

Stebbins, K. et al., "Therapeutic efficacy of AM156, a novel prostanoid $DP_2$ receptor antagonist, in murine models of allergic rhinitis and house dust mite-induced pulmonary inflammation," European Journal of Pharmacology (2010), vol. 638 , pp. 142-149.

Stebbins, K. et al., "DP2 (CRTh2) Antagonism Reduces Ocular Inflammation Induced by Allergen Challenge and Respiratory Syncytial Virus," International Archives of Allergy and Immunology (2012), vol. 157, No. 3, pp. 259-268.

Stock, N. et al., "Sodium [2'-[(cyclopropanecarbonyl-ethyl-amino)-methyl]-4'-(6-ethoxy-pyridin-3-yl)-6-methoxy-biphenyl-3-yl]-acetate (AM432): A potent, selective prostaglandin D2 receptor antagonist," Bioorg. Med. Chem. Lett. (2011), vol. 21, pp. 1036-1040.

Sugimoto, H. et al., "An Orally Bioavalable Small Molecule Antagonist of CRTH2, Ramatroban (BAY u3405), Inhibits Prostaglandin D2-Induced Eosinophil Migration in Vitro," J. Pharmacol. Exp. Ther. (2003), vol. 305, No. 1, pp. 347-352.

Ulven, T. et al., "Novel Selective Orally Active CRTH2 Antagonists for Allergic Inflammation Developed from in Silico Derived Hits," J. Med. Chem. (2006), vol. 49, No. 23, pp. 6638-6641.

Co-pending U.S. Appl. No. 14/412,877, filed Jan. 5, 2015.

HETEROCYCLYL DERIVATIVES AND THEIR USE AS PROSTAGLANDIN D2 RECEPTOR MODULATORS

CROSS-REFERENCE TO RELATED APPLICATIONS

This application is the U.S. National Phase of International Patent Application No. PCT/IB2012/057541, filed Dec. 20, 2012, which claims priority to International Patent Application No. PCT/IB2011/055866, filed Dec. 21, 2011, the contents of each are hereby incorporated by reference in their entireties.

FIELD OF THE INVENTION

The present invention relates to heterocyclyl derivatives of formula (I) and their use as prostaglandin receptor modulators, most particularly as prostaglandin $D_2$ receptor ("DP receptor") modulators, in the treatment of various prostaglandin-mediated diseases and disorders, to pharmaceutical compositions containing these compounds and to processes for their preparation. In particular, such derivatives may be used alone or in pharmaceutical compositions for the treatment of both, chronic and acute allergic/immune diseases/disorders such as asthma, allergic asthma, eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, systemic mast cell disorders, anaphylactic shock, urticaria, eczema, ulcerative colitis, chronic obstructive pulmonary disease (COPD), inflammatory bowel disease and rheumatoid arthritis; eosinophil-related diseases comprising small vessel vasculitides like Churg-Strauss syndrome, Wegener's granulomatosis, microscopic polyangiitis (and organ-specific subsets of the latter), hypereosinophilic syndromes like eosinophilic pneumonia, eosinophilic esophagitis, reflux esophagitis, eosinophilic endocarditis (Loeffler's endocarditis), eosinophilia-myalgia syndrome, eosinophilic fasciitis, eosinophilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia and DRESS syndrome (Drug Rash with Eosinophilia and Systemic Symptoms); and basophil-related diseases, comprising basophilic leukemia and basophilic leukocytosis.

BACKGROUND OF THE INVENTION

As a response to allergen exposure in allergic conditions, mast cells are activated and release mediators like histamine, thromboxane A2 (TxA2), cysteinyl leukotrienes (CysLTs) and prostaglandin $D_2$ ($PGD_2$). These mediators interact with their respective receptors and cause physiological effects such as increased vascular permeability, edema, pruritus, nasal and pulmonary congestion, bronchoconstriction, and mucus secretion. An increased vascular permeability for example, allows excessive infiltration of eosinophilic and basophilic leukocytes into the tissue and thus amplifies the allergic response. Current treatments of allergic diseases comprise agents that can block or otherwise interrupt such interactions, e.g. anti-histamines (histamine H1 receptor antagonists), leukotriene receptor antagonists, beta-adrenergic receptor agonists, and corticosteroids. Generally, treatments with anti-histamines and leukotriene antagonists are limited in efficacy, and long-term usage of corticosteroids is often associated with unwanted side effects.

$PGD_2$ is an agonist known to act on two G-protein-coupled receptors, the $PGD_2$ receptor DP1 and the recently identified CRTH2 (chemoattractant receptor-homologous molecule expressed on Th2 cells) receptor (also referred to as "DP2 receptor").

Elevated $PGD_2$ levels are considered to cause inflammation as observed in allergic diseases such as allergic rhinitis, allergic asthma, allergic conjunctivitis, atopic dermatitis and the like. Therefore, blocking the interaction of $PGD_2$ with its receptors is considered a useful therapeutic strategy for the treatment of such diseases.

GB 2388540 discloses the use of ramatroban ((3R)-3-(4-fluorobenzene-sulfonamido)-1,2,3,4-tetrahydrocarbazole-9-propionic acid), a TxA2 receptor (also referred to as "TP receptor") antagonist with additional antagonistic activity on CRTH2, for the prophylaxis and treatment of allergic diseases, such as asthma, allergic rhinitis or allergic conjunctivitis. In T. Ishizuka et al., *Cardiovascular Drug Rev.* 2004, 22(2), 71-90 effects of ramatroban on late-phase inflammation are described. Furthermore, oral bioavailability of ramatroban and its ability to inhibit prostaglandin $D_2$-induced eosinophil migration in vitro has been reported (*Journal of Pharmacology and Experimental Therapeutics*, 305(1), p. 347-352 (2003)). A different CRTH2 receptor antagonist has been recently described to have positive clinical effects in the treatment of allergic rhinoconjunctivitis (F. Horak et al., *Allergy*, 2012, 67(12), 1572-9) and asthma (N. Barnes et al., *Clin. Exp. Allergy*, 2012, 42(1), 38-48).

CRTH2 receptor antagonists containing a biphenyl-acetic acid moiety have been for instance described in WO 2009/099901, WO 2009/099902, WO 2009/108720, WO 2010/042652 and WO 2011/017201. Biphenyloxy-acetic acid derivatives as CRTH2 receptor antagonists have been disclosed in WO 2009/089192. Phenyl-substituted heterocyclyl derivatives have been described in WO 2012/004722.

DESCRIPTION OF THE INVENTION

1) The present invention relates to phenyl-substituted heterocyclyl derivatives of the formula (I),

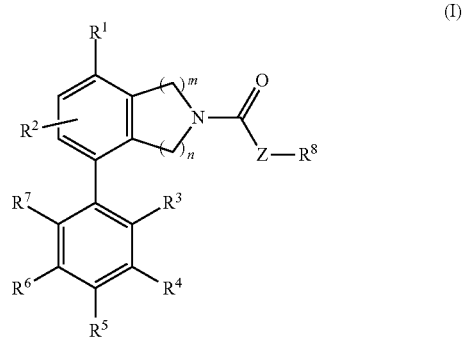

(I)

wherein $R^1$ represents hydrogen, $(C_1-C_4)$alkyl, $(C_1-C_4)$alkoxy, $(C_1-C_4)$fluoroalkyl, $(C_1-C_4)$alkylsulfonyl, halogen or cyano;

$R^2$ represents hydrogen or halogen;

one of $R^3$, $R^4$ and $R^5$ represents carboxy-$(C_1-C_3)$alkyl, carboxy-cyclopropyl or carboxy-$(C_1-C_3)$alkoxy and the other two represent independently of each other hydrogen, $(C_1-C_4)$alkoxy or halogen;

$R^6$ represents hydrogen, $(C_1-C_4)$alkoxy or halogen;

$R^7$ represents hydrogen, $(C_1-C_4)$alkyl, $(C_1-C_4)$alkoxy, $(C_3-C_6)$cycloalkyl-methoxy, $(C_3-C_6)$cycloalkyloxy, methoxy-ethoxy, di-[$(C_1-C_2)$alkyl]-amino, $(C_1-C_4)$fluoroalkyl, $(C_1-C_4)$fluoroalkoxy, halogen or $(C_1-C_4)$alkylsulfonyl;

or $R^6$ and $R^7$ together represent methylendioxy or ethylendioxy;

$R^8$ represents $(C_2-C_5)$alkyl;

$(C_1-C_5)$alkyl which is mono- or di-substituted wherein the substituents are independently selected from the group consisting of hydroxy, $(C_1-C_4)$alkoxy, oxo, —$NR^9R^{10}$, optionally substituted $(C_3-C_6)$cycloalkyl, optionally substituted aryl, optionally substituted heteroaryl, optionally substituted heterocyclyl, optionally substituted aryloxy, optionally substituted heteroaryloxy or optionally substituted aryl-$(C_1-C_2)$alkoxy;

$(C_3-C_5)$alkenyl;

$(C_2-C_3)$alkenyl which is mono-substituted with optionally substituted aryl or optionally substituted heteroaryl;

$(C_3-C_5)$alkynyl;

$(C_3-C_6)$cycloalkyl which is unsubstituted, mono-, di-, tri- or tetra-substituted with methyl; mono-substituted with oxo; mono-substituted with optionally substituted aryl; or mono-substituted with optionally substituted heteroaryl; or heterocyclyl which is optionally mono-substituted with oxo;

$R^9$ represents $(C_1-C_4)$alkyl;

$R^{10}$ represents optionally substituted diphenylmethyl;

n represents 1 or 2;

m represents 1 or 2; and

Z represents —NH—, —O— or a bond;

and to the salts (in particular pharmaceutically acceptable salts) of such compounds.

The compounds of formula (I) according to embodiment 1) may contain one or more stereogenic or asymmetric centers, such as one or more asymmetric carbon atoms. Substituents at a double bond may be present in the (Z)- or (E)-configuration unless indicated otherwise. The compounds of formula (I) may thus be present as mixtures of stereoisomers or preferably as pure stereoisomers. Mixtures of stereoisomers may be separated in a manner known to a person skilled in the art.

Notably, the compounds of formula (I) may be present as atropisomers, i.e. they may have the conformation as depicted in formula ($I_{St1}$) or as depicted in formula ($I_{St2}$). Atropisomers may have a sufficiently high rotational barrier to be conformationally stable at a temperature around rt. In that case mixtures of atropisomers may be separated into single isomers. It is to be understood that formula (I) comprises mixtures of atropisomers (notably racemates) as well as separated atropisomers of formula ($I_{St1}$) and of formula ($I_{St2}$). In one embodiment compounds of formula (I) are either achiral or present as mixtures of atropisomers. In another embodiment compounds of formula (I) are either achiral or atropisomers of formula ($I_{St1}$). In still another embodiment compounds of formula (I) are either achiral or atropisomers of formula ($I_{St2}$).

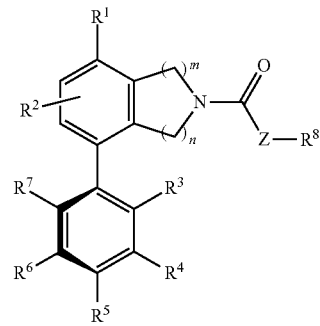

$I_{St1}$

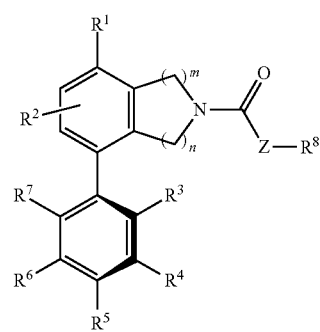

$I_{St2}$

In this patent application, variably attached bonds may be used for substituents or groups. In such case it is meant that the substituent or group is attached to either atom linked by the bond into which the variably attached bond is drawn into. For example, formula (I) encompasses the following two formulas:

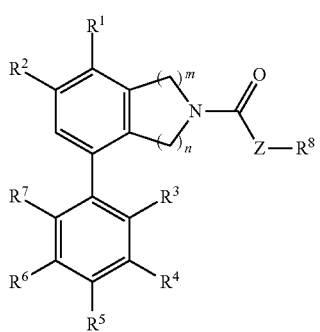

(I-1)

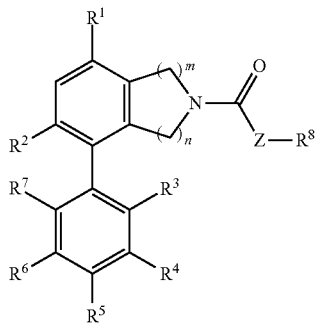

(I-2)

The following paragraphs provide definitions of the various chemical moieties for the compounds according to the invention (except for the compounds of formula $I_P$ which have their own definitions) and are intended to apply uniformly throughout the specification and claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The term "alkyl", used alone or in combination, refers to a straight or branched chain alkyl group containing one to five carbon atoms. The term "$(C_x-C_y)$alkyl" (x and y each being an integer), refers to an alkyl group as defined before containing x to y carbon atoms. For example a $(C_1-C_5)$alkyl group contains from one to five carbon atoms. Representative examples of $(C_1-C_5)$alkyl groups include methyl, ethyl, n-propyl, iso-propyl, n-butyl, iso-butyl, sec-butyl, tert-butyl, pent-1-yl, pent-2-yl, pent-3-yl, 2-methyl-but-1-yl, 3-methyl-but-1-yl, 2-methyl-but-2-yl, 3-methyl-but-2-yl and 2,2-dimethyl-prop-1-yl. The alkyl group may be unsubstituted or substituted as explicitly defined.

In case "$R^1$" represents "$(C_1-C_4)$alkyl" the term means $(C_1-C_4)$alkyl groups as defined above. Examples of said groups are methyl, ethyl, n-propyl, iso-propyl, n-butyl, iso-butyl, sec-butyl and tert-butyl. Preferred is methyl.

In case "$R^7$" represents "$(C_1-C_4)$alkyl" the term means $(C_1-C_4)$alkyl groups as defined above. Examples of said groups are methyl, ethyl, n-propyl, iso-propyl, n-butyl, iso-butyl, sec-butyl and tert-butyl. Preferred are methyl, n-propyl and iso-propyl.

In case "$R^8$" represents "$(C_2-C_5)$alkyl" the term means $(C_2-C_5)$alkyl groups as defined above. Examples of said groups are ethyl, n-propyl, iso-propyl, n-butyl, iso-butyl, sec-butyl, tert-butyl, pent-1-yl, pent-2-yl, pent-3-yl, 2-methyl-but-1-yl, 3-methyl-but-1-yl, 2-methyl-but-2-yl, 3-methyl-but-2-yl and 2,2-dimethyl-prop-1-yl. Preferred are ethyl, n-propyl, iso-propyl, n-butyl, iso-butyl, 2-methyl-but-1-yl, 3-methyl-but-1-yl and 2,2-dimethyl-prop-1-yl.

In case "$R^8$" represents mono- or di-substituted $(C_1-C_5)$ alkyl the term "$(C_1-C_5)$alkyl" means $(C_1-C_5)$alkyl groups as defined above. Examples of said groups are methyl, ethyl, n-propyl, iso-propyl, n-butyl, iso-butyl, sec-butyl, tert-butyl, pent-1-yl, pent-2-yl, pent-3-yl, 2-methyl-but-1-yl, 3-methyl-but-1-yl, 2-methyl-but-2-yl, 3-methyl-but-2-yl and 2,2-dimethyl-prop-1-yl. Preferred are methyl, ethyl, n-propyl, iso-propyl and iso-butyl.

In case "$R^9$" represents "$(C_1-C_4)$alkyl" the term means $(C_1-C_4)$alkyl groups as defined above. Examples of said groups are methyl, ethyl, n-propyl, iso-propyl, n-butyl, iso-butyl, sec-butyl and tert-butyl. Preferred is methyl.

In case "$(C_1-C_4)$alkyl" is a substituent to a $(C_3-C_6)$cycloalkyl, an aryl, a heteroaryl, a heterocyclyl, an aryloxy, a heteroaryloxy or an aryl-$(C_1-C_2)$alkoxy group, the term "$(C_1-C_4)$alkyl" means $(C_1-C_4)$alkyl groups as defined above. Examples of said groups are methyl, ethyl, n-propyl, iso-propyl, n-butyl, iso-butyl, sec-butyl and tert-butyl. Preferred is methyl.

The term "carboxy-$(C_x-C_y)$alkyl" (x and y each being an integer) refers to an alkyl group as defined before containing x to y carbon atoms in which one hydrogen atom has been replaced with —COOH. For example a carboxy-$(C_1-C_3)$alkyl group contains in the alkyl group from one to three carbon atoms in which one hydrogen atom has been replaced with —COOH. Representative examples of carboxy-$(C_1-C_3)$alkyl groups include carboxy-methyl, 1-carboxy-ethyl, 2-carboxy-ethyl, 1-carboxy-propyl, 2-carboxy-propyl and 3-carboxy-propyl. Preferred are carboxy-methyl and 1-carboxy-ethyl.

The term "$(C_x-C_y)$fluoroalkyl" (x and y each being an integer) refers to an alkyl group as defined before containing x to y carbon atoms in which one or more (and possibly all) hydrogen atoms have been replaced with fluoro. For example a $(C_1-C_4)$fluoroalkyl group contains from one to four carbon atoms in which one to nine hydrogen atoms have been replaced with fluoro.

In case "$R^1$" represents "$(C_1-C_4)$fluoroalkyl" the term means a $(C_1-C_4)$fluoroalkyl group as defined above. Representative examples of said groups are difluoromethyl, trifluoromethyl, 2,2-difluoroethyl and 2,2,2-trifluoroethyl. Preferred is trifluoromethyl.

In case "$R^7$" represents "$(C_1-C_4)$fluoroalkyl" the term means a $(C_1-C_4)$fluoroalkyl group as defined above. Representative examples of said groups are difluoromethyl, trifluoromethyl, 2,2-difluoroethyl and 2,2,2-trifluoroethyl. Preferred is trifluoromethyl.

In case "$(C_1-C_4)$fluoroalkyl" is a substituent to a $(C_3-C_6)$ cycloalkyl, an aryl, a heteroaryl, a heterocyclyl, an aryloxy, a heteroaryloxy or an aryl-$(C_1-C_2)$alkoxy group, the term "$(C_1-C_4)$fluoroalkyl" means $(C_1-C_4)$fluoroalkyl groups as defined above. Examples of said groups are difluoromethyl, trifluoromethyl, 2,2-difluoroethyl and 2,2,2-trifluoroethyl. Preferred is trifluoromethyl.

The term "$(C_x-C_y)$alkenyl" (x and y each being an integer) refers to a straight or branched chain alkenyl group containing x to y carbon atoms. For example a $(C_2-C_3)$alkenyl group contains from two to three carbon atoms. Examples of $(C_2-C_3)$alkenyl groups include ethenyl and propenyl. Preferred is ethenyl. The $(C_2-C_3)$alkenyl group is substituted as explicitly defined. A $(C_3-C_5)$alkenyl group contains from three to five carbon atoms. Representative examples of $(C_3-C_5)$alkenyl groups include propenyl, butenyl and pentenyl. Preferred are 3-methyl-2-butenyl and 3-methyl-3-butenyl.

The term "$(C_x-C_y)$alkynyl" (x and y each being an integer) refers to a straight or branched chain alkynyl group containing x to y carbon atoms. For example a $(C_3-C_5)$alkynyl group contains from three to five carbon atoms. Representative examples of $(C_3-C_5)$alkynyl groups include propynyl, butynyl and pentynyl. Preferred is 3-butynyl.

The term "alkoxy", used alone or in combination, refers to an alkyl-O— group wherein the alkyl group is as defined before. The term "$(C_x-C_y)$alkoxy" (x and y each being an integer) refers to an alkoxy group as defined before containing x to y carbon atoms. For example a $(C_1-C_4)$alkoxy group contains from one to four carbon atoms. Representative examples of alkoxy groups include methoxy, ethoxy, n-propoxy, iso-propoxy, n-butoxy, iso-butoxy, sec-butoxy and tert-butoxy.

In case "$R^1$" represents "$(C_1-C_4)$alkoxy" the term means $(C_1-C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

In case "$R^3$" represents "$(C_1-C_4)$alkoxy" the term means $(C_1-C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

In case "$R^4$" represents "$(C_1-C_4)$alkoxy" the term means $(C_1-C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

In case "$R^5$" represents "$(C_1-C_4)$alkoxy" the term means $(C_1-C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

In case "$R^6$" represents "$(C_1-C_4)$alkoxy" the term means $(C_1-C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

In case "$R^7$" represents "$(C_1-C_4)$alkoxy" the term means $(C_1-C_4)$alkoxy groups as defined above. Examples of said groups are methoxy, ethoxy, n-propoxy, iso-propoxy, n-butoxy, iso-butoxy, sec-butoxy and tert-butoxy. Preferred are methoxy, ethoxy, n-propoxy, iso-propoxy, iso-butoxy and tert-butoxy.

In case "$R^8$" represents "$(C_1-C_5)$alkyl which is substituted with $(C_1-C_4)$alkoxy" the term "$(C_1-C_4)$alkoxy" means $(C_1-C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

In case "$(C_1-C_4)$alkoxy" is a substituent to a $(C_3-C_6)$cycloalkyl, an aryl, a heteroaryl, a heterocyclyl, an aryloxy, a heteroaryloxy or an aryl-$(C_1-C_2)$alkoxy group, the term "$(C_1-C_4)$alkoxy" means $(C_1-C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

The term "aryl-$(C_1-C_2)$alkoxy" refers to an $(C_1-C_2)$alkoxy group as defined above in which one hydrogen atom has been replaced with an aryl group as defined below. Examples of aryl-$(C_1-C_2)$alkoxy groups are aryl-methoxy, 1-aryl-ethoxy and 2-aryl-ethoxy. Preferred is aryl-methoxy.

The term "carboxy-$(C_x-C_y)$alkoxy" (x and y each being an integer) refers to an alkoxy group as defined before containing x to y carbon atoms in which one hydrogen atom has been replaced with —COOH. For example a carboxy-$(C_1-C_3)$ alkoxy group contains in the alkoxy group from one to three carbon atoms in which one hydrogen atom has been replaced with —COOH. Representative examples of carboxy-$(C_1-C_3)$ alkoxy groups include carboxy-methoxy, 1-carboxy-ethoxy, 2-carboxy-ethoxy, 1-carboxy-propoxy, 2-carboxy-propoxy and 3-carboxy-propoxy. Preferred is carboxy-methoxy.

The term "$(C_x-C_y)$fluoroalkoxy" (x and y each being an integer) refers to an alkoxy group as defined before containing x to y carbon atoms in which one or more (and possibly all) hydrogen atoms have been replaced with fluoro. For example a $(C_1-C_4)$fluoroalkoxy group contains from one to four carbon atoms in which one to nine hydrogen atoms have been replaced with fluoro.

In case "$R^7$" represents "$(C_1-C_4)$fluoroalkoxy" the term means a $(C_1-C_4)$fluoroalkoxy group as defined above. Representative examples of said groups are difluoromethoxy, trifluoromethoxy, 2-fluoroethoxy, 2,2-difluoroethoxy and 2,2,2-trifluoroethoxy. Preferred are trifluoromethoxy, 2,2-difluoroethoxy and 2,2,2-trifluoroethoxy.

In case "$(C_1-C_4)$fluoroalkoxy" is a substituent to a $(C_3-C_6)$ cycloalkyl, an aryl, a heteroaryl, a heterocyclyl, an aryloxy, a heteroaryloxy or an aryl-$(C_1-C_2)$alkoxy group, the term "$(C_1-C_4)$fluoroalkoxy" means $(C_1-C_4)$fluoroalkoxy groups as defined above. Representative examples of said groups are difluoromethoxy, trifluoromethoxy, 2,2-difluoroethoxy and 2,2,2-trifluoroethoxy. Preferred is trifluoromethoxy.

The term "alkylsulfonyl", used alone or in combination, refers to an alkyl-$S(O)_2$— group wherein the alkyl group is as defined before, which is attached to the rest of the molecule via the sulfur-atom. The term "$(C_x-C_y)$alkylsulfonyl" (x and y each being an integer) refers to an alkylsulfonyl group as defined before containing x to y carbon atoms. For example a $(C_1-C_4)$alkylsulfonyl group contains from one to four carbon atoms. Representative examples of alkylsulfonyl groups include methylsulfonyl, ethylsulfonyl, n-propylsulfonyl, iso-propylsulfonyl, n-butylsulfonyl, iso-butylsulfonyl, sec-butylsulfonyl and tert-butylsulfonyl.

In case "$R^1$" represents "$(C_1-C_4)$alkylsulfonyl" the term means $(C_1-C_4)$alkylsulfonyl groups as defined above. Examples of said groups are methylsulfonyl, ethylsulfonyl, n-propylsulfonyl, iso-propylsulfonyl, n-butylsulfonyl, iso-butylsulfonyl, sec-butylsulfonyl and tert-butylsulfonyl. Preferred is methylsulfonyl.

In case "$R^7$" represents "$(C_1-C_4)$alkylsulfonyl" the term means $(C_1-C_4)$alkylsulfonyl groups as defined above. Examples of said groups are methylsulfonyl, ethylsulfonyl, n-propylsulfonyl, iso-propylsulfonyl, n-butylsulfonyl, iso-butylsulfonyl, sec-butylsulfonyl and tert-butylsulfonyl. Preferred is methylsulfonyl.

The term "di-$[(C_1-C_2)$alkyl]-amino" refers to an amino group which is substituted by two $(C_1-C_2)$alkyl groups as defined above, wherein the two $(C_1-C_2)$alkyl groups may be the same or different. Examples of di-$[(C_1-C_2)$alkyl]-amino groups include dimethylamino, methyl-ethyl-amino and diethylamino. Preferred is dimethylamino.

The term "halogen" means fluoro, chloro, bromo or iodo.

In case "$R^1$" represents "halogen" the term means fluoro, chloro or bromo; and preferably fluoro or chloro.

In case "$R^2$" represents "halogen" the term means fluoro or chloro and preferably fluoro.

In case "$R^3$" represents "halogen" the term means fluoro or chloro and preferably fluoro.

In case "$R^4$" represents "halogen" the term means fluoro or chloro and preferably chloro.

In case "$R^5$" represents "halogen" the term means fluoro or chloro and preferably fluoro.

In case "$R^6$" represents "halogen" the term means fluoro, chloro or bromo; and preferably fluoro or chloro.

In case "$R^7$" represents "halogen" the term means fluoro, chloro or bromo; and preferably fluoro or chloro.

In case "halogen" is a substituent to a $(C_3-C_6)$cycloalkyl, an aryl, a heteroaryl, a heterocyclyl, an aryloxy, a heteroaryloxy or an aryl-$(C_1-C_2)$alkoxy group, the term means fluoro, chloro, bromo or iodo; and preferably fluoro or chloro.

The term "oxo" means an oxygen atom which is attached to a carbon atom via a double bond.

The term "cycloalkyl", used alone or in combination, refers to a cycloalkyl group containing three to six carbon atoms. The term "$(C_x-C_y)$cycloalkyl" (x and y each being an integer), refers to a cycloalkyl group as defined before containing x to y carbon atoms. For example a $(C_3-C_6)$cycloalkyl group contains from three to six carbon atoms. A cycloalkyl group containing four, five or six carbon atoms may optionally be annelated to a benzene or a pyridine ring, wherein the benzene ring is optionally mono-substituted with methoxy. Examples of $(C_3-C_6)$cycloalkyl groups are cyclopropyl, cyclobutyl, bicyclo[4.2.0]octa-1,3,5-trienyl, cyclopentyl, indanyl, cyclohexyl, 1,2,3,4-tetrahydronaphthyl, 5,6,7,8-tetrahydroquinolinyl and 5,6,7,8-tetrahydroisoquinolinyl. The cycloalkyl group may be unsubstituted or substituted as explicitly defined.

In case "$R^8$" represents "$(C_1-C_5)$alkyl which is substituted with optionally substituted $(C_3-C_6)$cycloalkyl" the term "$(C_3-C_6)$cycloalkyl" means $(C_3-C_6)$cycloalkyl groups as defined above. Representative examples of said groups are cyclopropyl, cyclobutyl, cyclopentyl, indanyl, cyclohexyl, 1,2,3,4-tetrahydronaphthyl, 5,6,7,8-tetrahydroquinolinyl and 5,6,7,8-tetrahydroisoquinolinyl. Preferred are cyclopropyl, cyclopentyl, indanyl, cyclohexyl, 1,2,3,4-tetrahydronaphthyl and 5,6,7,8-tetrahydroquinolinyl. The $(C_3-C_6)$cycloalkyl groups are unsubstituted or mono-substituted with $(C_1-C_4)$ alkyl; $(C_1-C_4)$alkoxy; hydroxy; or phenyl which is unsubstituted or mono-substituted with halogen (notably fluoro). Preferred examples of optionally substituted $(C_3-C_6)$cycloalkyl groups are cyclopropyl, 1-phenyl-cyclopropyl, 1-(2-fluoro-phenyl)-cyclopropyl, 1-(3-fluoro-phenyl)-cyclopropyl, 1-(4-fluoro-phenyl)-cyclopropyl, cyclopentyl, indan-1-yl, indan-2-yl, cyclohexyl, 1,2,3,4-tetrahydronaphth-1-yl, 1-methyl-1,2,3,4-tetrahydronaphth-1-yl, 1,2,3,4-tetrahydronaphth-2-yl and 5,6,7,8-tetrahydroquinolin-8-yl.

In case "$R^8$" represents "$(C_3-C_6)$cycloalkyl" the term means $(C_3-C_6)$cycloalkyl groups as defined above. Representative examples of said groups are cyclopropyl, cyclobutyl, bicyclo[4.2.0]octa-1,3,5-trienyl, cyclopentyl, indanyl, cyclohexyl and 1,2,3,4-tetrahydronaphthyl which is in the aromatic part unsubstituted or mono-substituted with methoxy. Preferred is cyclopropyl. The $(C_3-C_6)$cycloalkyl groups may be unsubstituted or substituted as explicitly defined.

The term "carboxy-cyclopropyl" refers to a cyclopropyl group in which one hydrogen atom has been replaced with —COOH. Examples of carboxy-cyclopropyl groups include 1-carboxy-cyclopropyl and 2-carboxy-cyclopropyl. Preferred is 1-carboxy-cyclopropyl.

The term "$(C_3-C_6)$cycloalkyl-methoxy" refers to a methoxy group in which one hydrogen atom has been replaced with a $(C_3-C_6)$cycloalkyl group as defined before. Representative examples of $(C_3-C_6)$cycloalkyl-methoxy groups are cyclopropyl-methoxy, cyclobutyl-methoxy, cyclopentyl-methoxy and cyclohexyl-methoxy. Preferred is cyclopropyl-methoxy.

The term "$(C_3-C_6)$cycloalkyloxy" refers to a $(C_3-C_6)$cycloalkyl-O— group wherein the $(C_3-C_6)$cycloalkyl group is as defined before. Examples of $(C_3-C_6)$cycloalkyloxy groups are cyclopropyloxy, cyclobutyloxy, cyclopentyloxy and cyclohexyloxy. Preferred is cyclopropyloxy.

The term "aryl", used alone or in any combination, means a phenyl or a naphthyl group. Preferred is a phenyl group. An "optionally substituted aryl" group means an aryl group as defined before which is unsubstituted or substituted as explicitly defined.

In case "$R^8$" represents "$(C_1-C_5)$alkyl which is substituted with optionally substituted aryl" the term "optionally substituted aryl" means the above-mentioned groups, which groups are independently unsubstituted, mono-, di- or tri-substituted, wherein the substituents are independently selected from the group consisting of halogen, $(C_1-C_4)$alkyl, $(C_1-C_4)$alkoxy, $(C_1-C_4)$fluoroalkyl and $(C_1-C_4)$fluoro-alkoxy. Preferred are phenyl groups which groups are independently unsubstituted, mono- or di-substituted, wherein the substituents are independently selected from the group consisting of halogen, $(C_1-C_4)$alkyl and $(C_1-C_4)$alkoxy.

Examples of such optionally substituted aryl groups are phenyl, 2-fluoro-phenyl, 3-fluoro-phenyl, 4-fluoro-phenyl, 2,3-difluoro-phenyl, 2,4-difluoro-phenyl, 2,5-difluoro-phenyl, 2-chloro-phenyl, 4-chloro-phenyl, 2-fluoro-5-chloro-phenyl, 2-methyl-phenyl and 2-methoxy-phenyl. In a preferred embodiment, in case Z represents —NH—, the term "optionally substituted aryl" preferably means a phenyl group which is unsubstituted or mono-substituted, wherein the substituent is selected from halogen or $(C_1-C_4)$alkoxy. In another preferred embodiment, in case Z represents —O—, the term "optionally substituted aryl" preferably means a phenyl group which is unsubstituted, mono-, di- or tri-substituted, wherein the substituents are independently selected from the group consisting of halogen, $(C_1-C_4)$alkyl, $(C_1-C_4)$ alkoxy and $(C_1-C_4)$fluoroalkyl (and preferably a phenyl group which is unsubstituted or mono- or di-substituted with halogen). In still another preferred embodiment, in case Z represents a bond, the term "optionally substituted aryl" means a phenyl group, which group is independently unsubstituted, mono- or di-substituted, wherein the substituents are independently selected from the group consisting of halogen, $(C_1-C_4)$alkyl, $(C_1-C_4)$alkoxy and $(C_1-C_4)$fluoroalkyl (and preferably a phenyl group, which group is unsubstituted or mono-substituted with halogen, $(C_1-C_4)$alkyl or $(C_1-C_4)$ alkoxy).

In case "$R^8$" represents "$(C_2-C_3)$alkenyl which is mono-substituted with optionally substituted aryl" the term "optionally substituted aryl" means the above-mentioned groups, which groups are independently unsubstituted, mono-, di- or tri-substituted, wherein the substituents are independently selected from the group consisting of halogen, $(C_1-C_4)$alkyl, $(C_1-C_4)$alkoxy and $(C_1-C_4)$fluoroalkyl. An example of such an optionally substituted aryl group is phenyl.

In case "$R^8$" represents "$(C_3-C_6)$cycloalkyl which is mono-substituted with optionally substituted aryl" the term "optionally substituted aryl" means the above-mentioned groups, which groups are independently unsubstituted, mono-, di- or tri-substituted, wherein the substituents are independently selected from the group consisting of halogen, $(C_1-C_4)$alkyl, $(C_1-C_4)$alkoxy and $(C_1-C_4)$fluoroalkyl. Preferred is a phenyl group which is unsubstituted, mono- or di-substituted, wherein the substituents are independently selected from the group consisting of halogen, $(C_1-C_4)$alkyl, $(C_1-C_4)$alkoxy and $(C_1-C_4)$fluoroalkyl. Examples of such optionally substituted aryl groups are phenyl, 2-fluoro-phenyl, 3-fluoro-phenyl, 4-fluoro-phenyl, 2-chloro-phenyl, 3-chloro-phenyl, 4-chloro-phenyl, 2,4-dichloro-phenyl, 2-methyl-phenyl, 4-methoxy-phenyl and 2-trifluoromethyl-phenyl.

The term "optionally substituted diphenylmethyl" refers to a methyl group which is substituted with two phenyl groups, which phenyl groups are independently unsubstituted or mono-substituted with halogen. An example is 1-(4-chloro-phenyl)-1-phenyl-methyl.

The term "aryloxy", used alone or in combination, refers to an aryl-O— group wherein the aryl group is as defined before. An "optionally substituted aryloxy" group means an aryloxy group as defined before which is unsubstituted or substituted as explicitly defined.

In case "$R^8$" represents "$(C_1-C_5)$alkyl which is substituted with optionally substituted aryloxy" the term "optionally substituted aryloxy" means a phenyloxy or naphthyloxy group, which groups are independently unsubstituted, mono-, di- or tri-substituted, wherein the substituents are independently selected from the group consisting of halogen, $(C_1-C_4)$alkyl, $(C_1-C_4)$alkoxy and $(C_1-C_4)$fluoroalkyl. Preferred is a phenyloxy group which is unsubstituted or mono-substituted with halogen. Examples of such optionally substituted aryloxy groups are phenoxy and 4-fluoro-phenoxy.

The term "optionally substituted aryl-$(C_1-C_2)$alkoxy", used alone or in combination, refers to an aryl-$(C_1-C_2)$alkoxy group as defined above wherein the aryl group is unsubstituted or substituted as explicitly defined.

In case "$R^8$" represents "$(C_1-C_5)$alkyl which is substituted with optionally substituted aryl-$(C_1-C_2)$alkoxy" the term "optionally substituted aryl-$(C_1-C_2)$alkoxy" means the above-mentioned groups, wherein the term "aryl" means a phenyl or a naphthyl group. The aryl groups are independently unsubstituted, mono-, di- or tri-substituted, wherein the substituents are independently selected from the group consisting of halogen, $(C_1-C_4)$alkyl, $(C_1-C_4)$alkoxy and $(C_1-C_4)$fluoroalkyl. A preferred aryl group is a phenyl group which is unsubstituted or mono-substituted with halogen. An example of such an aryl group is 2-chloro-phenyl.

The term "heteroaryl", used alone or in combination, means a 5- to 10-membered monocyclic or bicyclic aromatic ring containing 1, 2, 3 or 4 heteroatoms independently selected from oxygen, nitrogen and sulfur. Preferred is a 5- to 10-membered monocyclic or bicyclic aromatic ring containing a nitrogen atom and optionally one additional heteroatom selected from oxygen, nitrogen and sulfur. Examples of such heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzo[2,1,3]oxadiazolyl, benzo[2,1,3]thiadiazolyl, benzo[1,2,3]thiadiazolyl, quinolinyl, isoquinolinyl, cinnolinyl, quinazolinyl, quinoxalinyl and phthalazinyl. An "optionally substituted heteroaryl" group means an heteroaryl group as defined before which is unsubstituted or substituted as explicitly defined.

In case "$R^8$" represents "$(C_1-C_5)$alkyl which is substituted with optionally substituted heteroaryl" the term "heteroaryl" means the above-mentioned groups. Preferred examples of such heteroaryl groups are thiazolyl, pyrazolyl, pyridyl, pyrimidyl, pyrazinyl, indolyl, indazolyl and benzisoxazolyl. A preferred example, in case Z represents —N—, is pyridyl (notably pyridin-2-yl). Preferred examples, in case Z represents —O—, are thiazolyl (notably thiazol-4-yl and thiazol-5-yl), pyrazolyl (notably pyrazol-5-yl), pyridyl (notably pyridin-2-yl), pyrimidyl (notably pyrimidin-5-yl) and pyrazinyl (notably pyrazin-2-yl). Preferred examples, in case Z represents a bond, are thiazolyl (notably thiazol-2-yl), pyridyl (notably pyridin-2-yl, pyridin-3-yl and pyridin-4-yl), pyrimidyl (notably pyrimidin-2-yl), pyrazinyl (notably pyrazin-2-yl), indolyl (notably indol-1-yl and indol-3-yl), indazolyl (notably indazol-1-yl and indazol-3-yl) and benzisoxazolyl (notably benzisoxazol-3-yl). The heteroaryl groups are independently unsubstituted, mono-, di- or tri-substituted, wherein the substituents are independently selected from the group consisting of halogen, $(C_1-C_4)$alkyl, $(C_1-C_4)$alkoxy and $(C_1-C_4)$fluoroalkyl. Preferably the heteroaryl groups are independently unsubstituted, mono- or di-substituted wherein the substituents are independently selected from the group consisting of halogen, $(C_1-C_4)$alkyl and $(C_1-C_4)$alkoxy. Examples of such optionally substituted heteroaryl groups are thiazol-2-yl, 2-methyl-thiazol-4-yl, 2-methyl-thiazol-5-yl, 4-methyl-thiazol-5-yl, 1-methyl-pyrazol-5-yl, 1,3-dimethyl-pyrazol-5-yl, pyridin-2-yl, 6-methyl-pyridin-2-yl, 3-methoxy-pyridin-2-yl, 6-methoxy-pyridin-2-yl, 3-fluoro-5-methyl-pyridin-2-yl, pyridin-3-yl, pyridin-4-yl, pyrimidin-2-yl, pyrimidin-5-yl, pyrazin-2-yl, 3-methyl-indol-1-yl, 1-methyl-indol-3-yl, 2-methyl-indol-3-yl, 5-methoxy-indol-3-yl, indazol-1-yl, 3-methyl-indazol-1-yl, 5-fluoro-indazol-1-yl, indazol-3-yl, benzisoxazol-3-yl and 5-methoxy-benzisoxazol-3-yl.

In case "$R^8$" represents "$(C_2-C_3)$alkenyl which is mono-substituted with optionally substituted heteroaryl" the term "heteroaryl" means the above-mentioned groups. Preferred examples of such heteroaryl groups are thiazolyl (notably thiazol-5-yl), pyrazolyl (notably pyrazol-3-yl, pyrazol-4-yl and pyrazol-5-yl), pyridyl (notably pyridin-2-yl and pyridin-3-yl) and benzothiazolyl (notably benzothiazol-2-yl). The heteroaryl groups are independently unsubstituted, mono-, di- or tri-substituted, wherein the substituents are independently selected from the group consisting of halogen, $(C_1-C_4)$alkyl, $(C_1-C_4)$alkoxy and $(C_1-C_4)$fluoroalkyl. Preferred heteroaryl groups are independently unsubstituted, mono- or di-substituted, wherein the substituents are independently selected from the group consisting of $(C_1-C_4)$alkyl and $(C_1-C_4)$alkoxy. Examples of such optionally substituted heteroaryl groups are 2,4-dimethyl-thiazol-5-yl, 1-methyl-pyrazol-3-yl, 1-methyl-pyrazol-4-yl, 1,3-dimethyl-pyrazol-5-yl, pyridin-2-yl, pyridin-3-yl, 6-methoxy-pyridin-3-yl and benzothiazol-2-yl.

In case "$R^8$" represents "$(C_3-C_6)$cycloalkyl which is mono-substituted with optionally substituted heteroaryl" the term "heteroaryl" means the above-mentioned groups. A preferred example of such a heteroaryl group is pyridyl (notably pyridin-2-yl). The heteroaryl groups are independently unsubstituted, mono-, di- or tri-substituted, wherein the substituents are independently selected from the group consisting of halogen, $(C_1-C_4)$alkyl, $(C_1-C_4)$alkoxy and $(C_1-C_4)$fluoroalkyl. A preferred heteroaryl group is unsubstituted. An example of such a optionally substituted heteroaryl group is pyridin-2-yl.

The term "heteroaryloxy", used alone or in combination, refers to an heteroaryl-O— group wherein the heteroaryl group is as defined before. An "optionally substituted heteroaryloxy" group means a heteroaryloxy group as defined before which is unsubstituted or substituted as explicitly defined.

In case "$R^8$" represents "$(C_1-C_5)$alkyl which is substituted with optionally substituted heteroaryloxy" the term "optionally substituted heteroaryloxy" means the above-mentioned groups. Preferred are 5- or 6-membered monocyclic heteroaryloxy groups containing in the heteroaryl moiety 1, 2 or 3 heteroatoms independently selected from oxygen, nitrogen and sulfur. Examples of such heteroaryloxy groups are furanyloxy, oxazolyloxy, isoxazolyloxy, oxadiazolyloxy, thienyloxy, thiazolyloxy, isothiazolyloxy, thiadiazolyloxy, pyrrolyloxy, imidazolyloxy, pyrazolyloxy, triazolyloxy, pyridyloxy, pyrimidyloxy, pyridazinyloxy and pyrazinyloxy. A preferred example of such a heteroaryloxy group is pyridyloxy (notably pyridin-3-yloxy). The heteroaryloxy groups are independently unsubstituted, mono-, di- or tri-substituted, wherein the substituents are independently selected from the group consisting of halogen, $(C_1-C_4)$alkyl, $(C_1-C_4)$alkoxy and $(C_1-C_4)$fluoroalkyl. A preferred heteroaryl group is unsubstituted. An example of such an optionally substituted heteroaryloxy group is pyridin-3-yloxy.

The term "heterocyclyl", used alone or in combination, refers to a saturated monocyclic moiety of 5 to 7 ring members containing 1 or 2 heteroatoms selected from nitrogen, oxygen and sulfur, it being understood that a heterocyclyl group does not contain 2 sulfur atoms. The sulfur atom of a heterocyclyl group may be in an oxidised form, i.e. as a sulfoxide or sulfonyl. A heterocyclyl group may optionally be annelated to a benzene ring or a pyridine ring, wherein the benzene ring is optionally mono-substituted with fluoro. An "optionally substituted heterocyclyl" group means a heterocyclyl group as defined before which is unsubstituted or substituted as explicitly defined.

In case "$R^8$" represents "heterocyclyl" the term means the above-mentioned groups. Preferred are heterocyclyl groups with 5 or 6 ring members containing 1 heteroatom selected from nitrogen and oxygen (preferred) which are annelated to a benzene ring.

Examples of such heterocyclyl groups are pyrrolidinyl, imidazolidinyl, oxazolidinyl, thiazolidinyl, tetrahydrofuranyl, piperidinyl, piperazinyl, morpholinyl, thiomorpholinyl, tetrahydropyranyl, dioxanyl, indolinyl, isoindolinyl, dihydrobenzofuranyl, dihydroisobenzofuranyl, tetrahydroquinolinyl, tetrahydroisoquinolinyl, tetrahydroquinoxalinyl, chromanyl, isochromanyl, dihydrobenzooxazinyl, dihydrobenzothiazinyl, dihydrobenzodioxinyl and 3,4-dihydro-2H-pyrano[2,3-b]pyridinyl. Preferred examples are chromanyl (notably chroman-2-yl, chroman-3-yl and chroman-4-yl) and isochromanyl (notably isochroman-1-yl and isochroman-3-yl). The heterocyclyl groups are independently unsubstituted, mono-, di- or tri-substituted, wherein the substituents are independently selected from the group consisting of halogen, oxo and $(C_1-C_4)$alkyl. Preferred heterocyclyl groups are unsubstituted. Examples of such optionally substituted heterocyclyl groups are chroman-2-yl, chroman-3-yl, chroman-4-yl, isochroman-1-yl and isochroman-3-yl.

In case "$R^8$" represents "$(C_1-C_5)$alkyl which is substituted with optionally substituted heterocyclyl" the term "heterocyclyl" means the above-mentioned groups. Preferred are heterocyclyl groups with 5 or 6 ring members containing 1 heteroatom selected from nitrogen and oxygen which are annelated to a benzene ring or a pyridine ring, wherein the benzene ring is optionally mono-substituted with fluoro. Examples of such heterocyclyl groups are pyrrolidinyl, imidazolidinyl, oxazolidinyl, thiazolidinyl, tetrahydrofuranyl, piperidinyl, piperazinyl, morpholinyl, thiomorpholinyl, tetrahydropyranyl, dioxanyl, indolinyl, isoindolinyl, dihydrobenzofuranyl, dihydroisobenzofuranyl, tetrahydroquinolinyl, tetrahydroisoquinolinyl, tetrahydroquinoxalinyl, chromanyl, isochromanyl, dihydrobenzooxazinyl, dihydrobenzothiazinyl, dihydrobenzodioxinyl and 3,4-dihydro-2H-pyrano[2,3-b]pyridinyl. Preferred examples are tetrahydrofuranyl (tetrahydrofuran-2-yl), indolinyl (notably indolin-1-yl), dihydrobenzofuranyl (notably dihydrobenzofuran-3-yl), dihydroisobenzofuranyl (notably dihydroisobenzofuran-1-yl), chromanyl (notably chroman-3-yl and chroman-4-yl), isochromanyl (notably isochroman-1-yl and isochroman-4-yl), tetrahydroquinolinyl (notably 1,2,3,4-tetrahydroquinolin-1-yl), tetrahydroisoquinolinyl (notably 1,2,3,4-tetrahydroisoquinolin-1-yl) and 3,4-dihydro-2H-pyrano[2,3-b]pyridinyl (notably 3,4-dihydro-2H-pyrano[2,3-b]pyridin-4-yl). The heterocyclyl groups are independently unsubstituted, mono-, di- or tri-substituted, wherein the substituents are independently selected from the group consisting of halogen, oxo and $(C_1-C_4)$alkyl. Examples of such optionally substituted heterocyclyl groups are tetrahydrofuran-2-yl, indolin-1-yl, dihydrobenzofuran-3-yl, dihydroisobenzofuran-1-yl, chroman-3-yl, chroman-4-yl, 6-fluoro-chroman-4-yl, 7-fluoro-chroman-4-yl, 8-fluoro-chroman-4-yl, 2,2-dimethyl-chroman-4-yl, isochroman-1-yl, isochroman-4-yl, 1,2,3,4-tetrahydroquinolin-1-yl, 2-methyl-1,2,3,4-tetrahydroisoquinolin-1-yl and 2,2-dimethyl-3,4-dihydro-2H-pyrano[2,3-b]pyridin-4-yl.

The following paragraphs provide definitions of the various chemical moieties for the compounds of formula $I_P$ and are intended to apply to those compounds unless an otherwise expressly set out definition provides a broader or narrower definition.

The term "alkyl", used alone or in combination, refers to a straight or branched chain alkyl group containing one to five carbon atoms. The term "$(C_x-C_y)$alkyl" (x and y each being an integer), refers to an alkyl group as defined before containing x to y carbon atoms. For example a $(C_1-C_4)$alkyl group contains from one to four carbon atoms. Representative examples of $(C_1-C_4)$alkyl groups include methyl, ethyl, n-propyl, iso-propyl, n-butyl, iso-butyl, sec-butyl and tert-butyl. Representative examples of $(C_2-C_5)$alkyl groups include ethyl, n-propyl, iso-propyl, n-butyl, iso-butyl, sec-butyl, tert-butyl, pent-1-yl, pent-2-yl, pent-3-yl, 2-methyl-but-1-yl, 3-methyl-but-1-yl, 2-methyl-but-2-yl, 3-methyl-but-2-yl and 2,2-dimethyl-prop-1-yl. The alkyl group may be unsubstituted or substituted as explicitly defined.

In case "$R^1$" represents "$(C_1-C_4)$alkyl" the term means $(C_1-C_4)$alkyl groups as defined above. Examples of said groups are methyl, ethyl, n-propyl, iso-propyl, n-butyl, iso-butyl, sec-butyl and tert-butyl. Preferred are methyl and ethyl and most preferred is methyl.

In case "$R^7$" represents "$(C_1-C_4)$alkyl" the term means $(C_1-C_4)$alkyl groups as defined above. Examples of said groups are methyl, ethyl, n-propyl, iso-propyl, n-butyl, iso-butyl, sec-butyl and tert-butyl. Preferred are methyl and ethyl and most preferred is methyl.

In case "$R^8$" represents "$(C_2-C_5)$alkyl" the term means $(C_2-C_5)$alkyl groups as defined above. Examples of said groups are ethyl, n-propyl, iso-propyl, n-butyl, iso-butyl, sec-butyl, tert-butyl, pent-1-yl, pent-2-yl, pent-3-yl, 2-methyl-but-1-yl, 3-methyl-but-1-yl, 2-methyl-but-2-yl, 3-methyl-but-2-yl and 2,2-dimethyl-prop-1-yl. Preferred are ethyl, n-propyl, iso-propyl, iso-butyl, tert-butyl and 2,2-dimethyl-prop-1-yl.

In case "$R^8$" represents mono- or di-substituted $(C_1-C_4)$alkyl the term "$(C_1-C_4)$alkyl" means $(C_1-C_4)$alkyl groups as defined above. Examples of said groups are methyl, ethyl, n-propyl, iso-propyl, n-butyl, iso-butyl, sec-butyl and tert-butyl. Preferred are methyl, ethyl, n-propyl, iso-propyl and sec-butyl; most preferred are methyl and ethyl. The $(C_1-C_4)$alkyl group is substituted as explicitly defined.

In case "$(C_1-C_4)$alkyl" is a substituent to a $(C_3-C_6)$cycloalkyl, an aryl, a heteroaryl, a heterocyclyl, an aryloxy, a heteroaryloxy or an aryl-$(C_1-C_2)$alkoxy group, the term "$(C_1-C_4)$alkyl" means $(C_1-C_4)$alkyl groups as defined above. Examples of said groups are methyl, ethyl, n-propyl, iso-propyl, n-butyl, iso-butyl, sec-butyl and tert-butyl. Preferred are methyl and ethyl; most preferred is methyl.

The term "carboxy-$(C_x-C_y)$alkyl" (x and y each being an integer) refers to an alkyl group as defined before containing x to y carbon atoms in which one hydrogen atom has been replaced with —COOH. For example a carboxy-$(C_1-C_3)$alkyl group contains from one to three carbon atoms in which one hydrogen atom has been replaced with —COOH. Representative examples of carboxy-$(C_1-C_3)$alkyl groups include carboxy-methyl, 1-carboxy-ethyl, 2-carboxy-ethyl, 1-carboxy-propyl, 2-carboxy-propyl and 3-carboxy-propyl. Preferred are carboxy-methyl and 1-carboxy-ethyl and most preferred is carboxy-methyl.

The term "$(C_x-C_y)$fluoroalkyl" (x and y each being an integer) refers to an alkyl group as defined before containing x to y carbon atoms in which one or more (and possibly all) hydrogen atoms have been replaced with fluoro. For example a $(C_1-C_4)$fluoroalkyl group contains from one to four carbon atoms in which one to nine hydrogen atoms have been replaced with fluoro.

In case "$R^1$" represents "$(C_1-C_4)$fluoroalkyl" the term means a $(C_1-C_4)$fluoroalkyl group as defined above. Examples of said groups are difluoromethyl, trifluoromethyl, 2,2-difluoroethyl and 2,2,2-trifluoroethyl. Preferred is trifluoromethyl.

In case "$R^7$" represents "$(C_1-C_4)$fluoroalkyl" the term means a $(C_1-C_4)$fluoroalkyl group as defined above. Examples of said groups are difluoromethyl, trifluoromethyl, 2,2-difluoroethyl and 2,2,2-trifluoroethyl. Preferred is trifluoromethyl.

In case "$(C_1-C_4)$fluoroalkyl" is a substituent to a $(C_3-C_6)$cycloalkyl, an aryl, a heteroaryl, a heterocyclyl, an aryloxy, a heteroaryloxy or an aryl-$(C_1-C_2)$alkoxy group, the term "$(C_1-C_4)$fluoroalkyl" means $(C_1-C_4)$fluoroalkyl groups as defined above. Examples of said groups are difluoromethyl, trifluoromethyl, 2,2-difluoroethyl and 2,2,2-trifluoroethyl. Preferred is trifluoromethyl.

The term "alkenyl", used alone or in combination, refers to a straight or branched chain alkenyl group containing two to three carbon atoms. The term "$(C_x$-$C_y)$alkenyl" (x and y each being an integer), refers to an alkenyl group as defined before containing x to y carbon atoms. For example a $(C_2$-$C_3)$alkenyl group contains from two to three carbon atoms. Representative examples of $(C_2$-$C_3)$alkenyl groups include ethenyl and propenyl. Preferred is ethenyl. The $(C_2$-$C_3)$alkenyl group is substituted as explicitly defined.

The term "alkoxy", used alone or in combination, refers to an alkyl-O— group wherein the alkyl group is as defined before. The term "$(C_x$-$C_y)$alkoxy" (x and y each being an integer) refers to an alkoxy group as defined before containing x to y carbon atoms. For example a $(C_1$-$C_4)$alkoxy group contains from one to four carbon atoms. Representative examples of alkoxy groups include methoxy, ethoxy, n-propoxy, iso-propoxy, n-butoxy, iso-butoxy, sec-butoxy and tert-butoxy.

In case "$R^1$" represents "$(C_1$-$C_4)$alkoxy" the term means $(C_1$-$C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

In case "$R^3$" represents "$(C_1$-$C_4)$alkoxy" the term means $(C_1$-$C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

In case "$R^4$" represents "$(C_1$-$C_4)$alkoxy" the term means $(C_1$-$C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

In case "$R^5$" represents "$(C_1$-$C_4)$alkoxy" the term means $(C_1$-$C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

In case "$R^6$" represents "$(C_1$-$C_4)$alkoxy" the term means $(C_1$-$C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

In case "$R^7$" represents "$(C_1$-$C_4)$alkoxy" the term means $(C_1$-$C_4)$alkoxy groups as defined above. Examples of said groups are methoxy, ethoxy, n-propoxy, iso-propoxy, n-butoxy, iso-butoxy, sec-butoxy and tert-butoxy. Preferred are methoxy, ethoxy, n-propoxy, iso-propoxy and iso-butoxy. More preferred are methoxy, ethoxy and n-propoxy and most preferred is methoxy.

In case "$R^8$" represents "$(C_1$-$C_4)$alkyl which is substituted with $(C_1$-$C_4)$alkoxy" the term "$(C_1$-$C_4)$alkoxy" means $(C_1$-$C_4)$alkoxy groups as defined above. Examples of said groups are methoxy, ethoxy, n-propoxy, iso-propoxy, n-butoxy, iso-butoxy, sec-butoxy and tert-butoxy. Preferred are methoxy and ethoxy. Most preferred is ethoxy.

In case "$(C_1$-$C_4)$alkoxy" is a substituent to a $(C_3$-$C_6)$cycloalkyl, an aryl, a heteroaryl, a heterocyclyl, an aryloxy, a heteroaryloxy or an aryl-$(C_1$-$C_2)$alkoxy group, the term "$(C_1$-$C_4)$alkoxy" means $(C_1$-$C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

The term "aryl-$(C_1$-$C_2)$alkoxy" refers to an $(C_1$-$C_2)$alkoxy group as defined above in which one hydrogen atom has been replaced with an aryl group as defined below. Examples of aryl-$(C_1$-$C_2)$alkoxy groups are aryl-methoxy, 1-aryl-ethoxy and 2-aryl-ethoxy. Preferred is aryl-methoxy.

The term "carboxy-$(C_x$-$C_y)$alkoxy" (x and y each being an integer) refers to an alkoxy group as defined before containing x to y carbon atoms in which one hydrogen atom has been replaced with —COOH. For example a carboxy-$(C_1$-$C_3)$alkoxy group contains from one to three carbon atoms in which one hydrogen atom has been replaced with —COOH. Representative examples of carboxy-$(C_1$-$C_3)$alkoxy groups include carboxy-methoxy, 1-carboxy-ethoxy, 2-carboxy-ethoxy, 1-carboxy-propoxy, 2-carboxy-propoxy and 3-carboxy-propoxy. Preferred are carboxy-methoxy and 3-carboxy-propoxy and most preferred is carboxy-methoxy.

The term "$(C_x$-$C_y)$fluoroalkoxy" (x and y each being an integer) refers to an alkoxy group as defined before containing x to y carbon atoms in which one or more (and possibly all) hydrogen atoms have been replaced with fluoro. For example a $(C_1$-$C_4)$fluoroalkoxy group contains from one to four carbon atoms in which one to nine hydrogen atoms have been replaced with fluoro.

In case "$R^7$" represents "$(C_1$-$C_4)$fluoroalkoxy" the term means a $(C_1$-$C_4)$fluoroalkoxy group as defined above. Examples of said groups are difluoromethoxy, trifluoromethoxy, 2,2-difluoroethoxy and 2,2,2-trifluoroethoxy. Preferred is trifluoromethoxy.

In case "$(C_1$-$C_4)$fluoroalkoxy" is a substituent to a $(C_3$-$C_6)$cycloalkyl, an aryl, a heteroaryl, a heterocyclyl, an aryloxy, a heteroaryloxy or an aryl-$(C_1$-$C_2)$alkoxy group, the term "$(C_1$-$C_4)$fluoroalkoxy" means $(C_1$-$C_4)$fluoroalkoxy groups as defined above. Examples of said groups are difluoromethoxy, trifluoromethoxy, 2,2-difluoroethoxy and 2,2,2-trifluoroethoxy. Preferred is trifluoromethoxy.

The term "$(C_1$-$C_4)$alkylsulfonyl", used alone or in combination, refers to an alkyl-$S(O)_2$— group wherein the alkyl group is as defined before, which is attached to the rest of the molecule via the sulfur-atom. The term "$(C_x$-$C_y)$alkylsulfonyl" (x and y each being an integer) refers to an alkylsulfonyl group as defined before containing x to y carbon atoms. For example a $(C_1$-$C_4)$alkylsulfonyl group contains from one to four carbon atoms. Representative examples of alkylsulfonyl groups include methylsulfonyl, ethylsulfonyl, n-propylsulfonyl, iso-propylsulfonyl, n-butylsulfonyl, iso-butylsulfonyl, sec-butylsulfonyl and tert-butylsulfonyl.

In case "$R^1$" represents "$(C_1$-$C_4)$alkylsulfonyl" the term means $(C_1$-$C_4)$alkylsulfonyl groups as defined above. Examples of said groups are methylsulfonyl, ethylsulfonyl, n-propylsulfonyl, iso-propylsulfonyl, n-butylsulfonyl, iso-butylsulfonyl, sec-butylsulfonyl and tert-butylsulfonyl. Preferred is methylsulfonyl.

In case "$R^7$" represents "$(C_1$-$C_4)$alkylsulfonyl" the term means $(C_1$-$C_4)$alkylsulfonyl groups as defined above. Examples of said groups are methylsulfonyl, ethylsulfonyl, n-propylsulfonyl, iso-propylsulfonyl, n-butylsulfonyl, iso-butylsulfonyl, sec-butylsulfonyl and tert-butylsulfonyl. Preferred are methylsulfonyl and ethylsulfonyl; most preferred is methylsulfonyl.

The term "halogen" means fluoro, chloro, bromo or iodo.

In case "$R^1$" represents "halogen" the term means preferably fluoro, chloro or bromo; more preferably fluoro or chloro; and most preferably fluoro.

In case "$R^2$" represents "halogen" the term means preferably fluoro or chloro and most preferably fluoro.

In case "$R^3$" represents "halogen" the term means preferably fluoro or chloro and most preferably fluoro.

In case "$R^4$" represents "halogen" the term means preferably fluoro or chloro and most preferably chloro.

In case "$R^5$" represents "halogen" the term means preferably fluoro or chloro and most preferably fluoro.

In case "$R^6$" represents "halogen" the term means preferably fluoro, chloro or bromo; more preferably fluoro or chloro; and most preferably fluoro.

In case "$R^7$" represents "halogen" the term means preferably fluoro, chloro or bromo; more preferably fluoro or chloro; and most preferably chloro.

In case "halogen" is a substituent to a ($C_3$-$C_6$)cycloalkyl, an aryl, a heteroaryl, a heterocyclyl, an aryloxy, a heteroaryloxy or an aryl-($C_1$-$C_2$)alkoxy group, the term means fluoro, chloro, bromo or iodo; preferably fluoro or chloro; and most preferably fluoro.

The term "oxo" means an oxygen atom which is attached to a carbon atom via a double bond.

The term "cycloalkyl", used alone or in combination, refers to a cycloalkyl group containing three to six carbon atoms. The term "($C_x$-$C_y$)cycloalkyl" (x and y each being an integer), refers to a cycloalkyl group as defined before containing x to y carbon atoms. For example a ($C_3$-$C_6$)cycloalkyl group contains from three to six carbon atoms. A cycloalkyl group containing four, five or six carbon atoms may optionally be annelated to a benzene ring. Examples of ($C_3$-$C_6$)cycloalkyl groups are cyclopropyl, cyclobutyl, bicyclo[4.2.0]octa-1,3,5-trienyl, cyclopentyl, indanyl, cyclohexyl and 1,2,3,4-tetrahydronaphthyl. Preferred are cyclopropyl, cyclopentyl, indanyl, cyclohexyl and 1,2,3,4-tetrahydronaphthyl. The cycloalkyl group may be unsubstituted or substituted as explicitly defined.

In case "$R^8$" represents "($C_1$-$C_4$)alkyl which is substituted with optionally substituted ($C_3$-$C_6$)cycloalkyl" the term "($C_3$-$C_6$)cycloalkyl" means ($C_3$-$C_6$)cycloalkyl groups as defined above. Examples of said groups are cyclopropyl, cyclobutyl, cyclopentyl, indanyl, cyclohexyl and 1,2,3,4-tetrahydronaphthyl. Preferred are indanyl, cyclohexyl and 1,2,3,4-tetrahydronaphthyl; more preferred are indanyl and cyclohexyl; and most preferred is indanyl (especially indan-2-yl). The ($C_3$-$C_6$)cycloalkyl groups are unsubstituted or mono-substituted with ($C_1$-$C_4$)alkyl, ($C_1$-$C_4$)alkoxy or hydroxy (preferably hydroxy).

In case "$R^8$" represents "($C_3$-$C_6$)cycloalkyl" the term means ($C_3$-$C_6$)cycloalkyl groups as defined above. Examples of said groups are cyclopropyl, cyclobutyl, bicyclo[4.2.0]octa-1,3,5-trienyl, cyclopentyl, indanyl, cyclohexyl and 1,2,3,4-tetrahydronaphthyl. Preferred are cyclopropyl, bicyclo[4.2.0]octa-1,3,5-trienyl, indanyl and 1,2,3,4-tetrahydronaphthyl; more preferred are cyclopropyl, indanyl and 1,2,3,4-tetrahydronaphthyl; and most preferred is cyclopropyl. The ($C_3$-$C_6$)cycloalkyl groups may be unsubstituted or substituted as explicitly defined.

The term "aryl", used alone or in any combination, means a phenyl or a naphthyl group. Preferred is a phenyl group. An "optionally substituted aryl" group means an aryl group as defined before which is unsubstituted or substituted as explicitly defined.

In case "$R^8$" represents "($C_1$-$C_4$)alkyl which is substituted with optionally substituted aryl" the term "optionally substituted aryl" means the above-mentioned groups (preferably phenyl), which groups are independently unsubstituted, mono-, di- or tri-substituted (preferably unsubstituted, mono- or di-substituted and most preferably unsubstituted or mono-substituted), wherein the substituents are independently selected from the group consisting of halogen, ($C_1$-$C_4$)alkyl, ($C_1$-$C_4$)alkoxy, ($C_1$-$C_4$)fluoroalkyl and ($C_1$-$C_4$)fluoroalkoxy. Preferably the substituents are independently selected from the group consisting of halogen, ($C_1$-$C_4$)alkyl, ($C_1$-$C_4$)alkoxy and ($C_1$-$C_4$)fluoroalkyl. More preferably the substituents are independently selected from the group consisting of halogen and ($C_1$-$C_4$)alkoxy and most preferably from halogen. Examples of such optionally substituted aryl groups are phenyl, 2-fluoro-phenyl, 3-fluoro-phenyl, 4-fluoro-phenyl, 2,3-difluoro-phenyl, 2-chloro-phenyl, 4-chloro-phenyl, 2-methyl-phenyl and 2-methoxy-phenyl. In a preferred embodiment, in case Z represents —NH—, the term "optionally substituted aryl" preferably means a phenyl group which is unsubstituted or mono-substituted, wherein the substituent is selected from halogen or ($C_1$-$C_4$)alkoxy (especially from fluoro, chloro or methoxy). In another preferred embodiment, in case Z represents —O—, the term "optionally substituted aryl" preferably means a phenyl group which is unsubstituted, mono-, di- or tri-substituted (preferably unsubstituted, mono- or di-substituted), wherein the substituents are independently selected from the group consisting of halogen, ($C_1$-$C_4$)alkyl, ($C_1$-$C_4$)alkoxy and ($C_1$-$C_4$)fluoroalkyl and preferably from halogen (especially fluoro). In still another preferred embodiment, in case Z represents a bond, the term "optionally substituted aryl" means a phenyl group, which group is independently unsubstituted, mono- or di-substituted (preferably unsubstituted or mono-substituted), wherein the substituents are independently selected from the group consisting of halogen, ($C_1$-$C_4$)alkyl, ($C_1$-$C_4$)alkoxy and ($C_1$-$C_4$)fluoroalkyl and preferably from halogen and ($C_1$-$C_4$)alkyl (especially from fluoro, chloro and methyl).

In case "$R^8$" represents "($C_2$-$C_3$)alkenyl which is mono-substituted with optionally substituted aryl" the term "optionally substituted aryl" means the above-mentioned groups (preferably phenyl), which groups are independently unsubstituted, mono-, di- or tri-substituted (preferably unsubstituted or mono-substituted and most preferably unsubstituted), wherein the substituents are independently selected from the group consisting of halogen, ($C_1$-$C_4$)alkyl, ($C_1$-$C_4$)alkoxy and ($C_1$-$C_4$)fluoroalkyl. Preferably the substituents are independently selected from the group consisting of halogen and ($C_1$-$C_4$)alkyl. An examples of such an optionally substituted aryl group is phenyl.

In case "$R^8$" represents "($C_3$-$C_6$)cycloalkyl which is mono-substituted with optionally substituted aryl" the term "optionally substituted aryl" means the above-mentioned groups (preferably phenyl), which groups are independently unsubstituted, mono-, di- or tri-substituted (preferably unsubstituted, mono- or di-substituted and most preferably unsubstituted or mono-substituted), wherein the substituents are independently selected from the group consisting of halogen, ($C_1$-$C_4$)alkyl, ($C_1$-$C_4$)alkoxy and ($C_1$-$C_4$)fluoroalkyl. Preferably the substituents are independently selected from the group consisting of halogen, ($C_1$-$C_4$)alkyl and ($C_1$-$C_4$)fluoroalkyl. Examples of such optionally substituted aryl groups are phenyl, 2-fluoro-phenyl, 3-fluoro-phenyl, 4-fluoro-phenyl, 2-chloro-phenyl, 3-chloro-phenyl, 4-chloro-phenyl, 2,4-dichloro-phenyl, 2-methyl-phenyl, 4-methoxy-phenyl and 2-trifluoromethyl-phenyl, (and especially phenyl, 2-fluoro-phenyl, 3-fluoro-phenyl, 4-fluoro-phenyl, 2-chloro-phenyl, 3-chloro-phenyl, 4-chloro-phenyl, 2-methyl-phenyl and 2-trifluoromethyl-phenyl).

The term "aryloxy", used alone or in combination, refers to an aryl-O— group wherein the aryl group is as defined before. An "optionally substituted aryloxy" group means an aryloxy group as defined before which is unsubstituted or substituted as explicitly defined.

In case "$R^8$" represents "($C_1$-$C_4$)alkyl which is substituted with optionally substituted aryloxy" the term "optionally substituted aryloxy" means the above-mentioned groups (preferably phenoxy), which groups are independently unsubstituted, mono-, di- or tri-substituted (preferably unsubstituted or mono-substituted and most preferably mono-substituted), wherein the substituents are independently selected from the group consisting of halogen, $(C_1-C_4)$alkyl, $(C_1-C_4)$alkoxy and $(C_1-C_4)$fluoroalkyl. Preferably the substituents are independently selected from halogen (especially fluoro). Examples of such optionally substituted aryloxy groups are phenoxy and 4-fluoro-phenoxy.

The term "optionally substituted aryl-$(C_1-C_2)$alkoxy", used alone or in combination, refers to an aryl-$(C_1-C_2)$alkoxy group as defined above wherein the aryl group is unsubstituted or substituted as explicitly defined.

In case "$R^8$" represents "$(C_1-C_4)$alkyl which is substituted with optionally substituted aryl-$(C_1-C_2)$alkoxy" the term "optionally substituted aryl-$(C_1-C_2)$alkoxy" means the above-mentioned groups, wherein the term "aryl" means a phenyl or a naphthyl group (preferably a phenyl group). The aryl groups are independently unsubstituted, mono-, di- or tri-substituted (preferably unsubstituted or mono-substituted and most preferably mono-substituted), wherein the substituents are independently selected from the group consisting of halogen, $(C_1-C_4)$alkyl, $(C_1-C_4)$alkoxy and $(C_1-C_4)$fluoroalkyl. Preferably the substituents are independently selected from halogen (especially chloro). An example of such an aryl group is 2-chloro-phenyl.

The term "heteroaryl", used alone or in combination, means a 5- to 10-membered monocyclic or bicyclic aromatic ring containing 1, 2, 3 or 4 heteroatoms (preferably 1, 2 or 3 heteroatoms, more preferably 1 or 2 heteroatoms) independently selected from oxygen, nitrogen and sulfur. Examples of such heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzo[2,1,3]oxadiazolyl, benzo[2,1,3]thiadiazolyl, benzo[1,2,3]thiadiazolyl, quinolinyl, isoquinolinyl, cinnolinyl, quinazolinyl, quinoxalinyl and phthalazinyl. Preferred examples of such heteroaryl groups are thiazolyl (notably thiazol-4-yl and thiazol-5-yl), pyrazolyl (notably pyrazol-5-yl), pyridyl (notably pyridin-2-yl and pyridin-3-yl), pyrimidyl (notably pyrimidin-2-yl and pyrimidin-5-yl), indolyl (notably indol-1-yl and indol-3-yl), indazolyl (notably indazol-1-yl and indazol-3-yl), benzisoxazolyl (notably benzisoxazol-3-yl) and benzothiazolyl (notably benzothiazol-2-yl). An "optionally substituted heteroaryl" group means an heteroaryl group as defined before which is unsubstituted or substituted as explicitly defined.

In case "$R^8$" represents "$(C_1-C_4)$alkyl which is substituted with optionally substituted heteroaryl" the term "heteroaryl" means the above-mentioned groups. Preferred examples of such heteroaryl groups are thiazolyl (notably thiazol-4-yl and thiazol-5-yl), pyrazolyl (notably pyrazol-5-yl), pyridyl (notably pyridin-2-yl and pyridin-3-yl), pyrimidyl (notably pyrimidin-2-yl and pyrimidin-5-yl), indolyl (notably indol-1-yl and indol-3-yl), indazolyl (notably indazol-1-yl and indazol-3-yl) and benzisoxazolyl (notably benzisoxazol-3-yl). Most preferred examples are thiazolyl (notably thiazol-4-yl and thiazol-5-yl), pyrazolyl (notably pyrazol-5-yl), indolyl (notably indol-1-yl and indol-3-yl) and indazolyl (notably indazol-1-yl and indazol-3-yl). Preferred examples, in case X represents —O—, are thiazolyl (notably thiazol-4-yl and thiazol-5-yl), pyrazolyl (notably pyrazol-5-yl) and pyrimidyl (notably pyrimidin-5-yl). Preferred examples, in case X represents a bond, are pyridyl (notably pyridin-2-yl and pyridin-3-yl), pyrimidyl (notably pyrimidin-2-yl), indolyl (notably indol-1-yl and indol-3-yl), indazolyl (notably indazol-1-yl and indazol-3-yl) and benzisoxazolyl (notably benzisoxazol-3-yl); most preferred, in case X represents a bond, are indolyl (notably indol-1-yl and indol-3-yl) and indazolyl (notably indazol-1-yl and indazol-3-yl). The heteroaryl groups are independently unsubstituted, mono-, di- or tri-substituted (preferably unsubstituted, mono- or di-substituted and most preferably unsubstituted or mono-substituted), wherein the substituents are independently selected from the group consisting of halogen, $(C_1-C_4)$alkyl, $(C_1-C_4)$alkoxy and $(C_1-C_4)$fluoroalkyl. Preferably the substituents are independently selected from the group consisting of halogen, $(C_1-C_4)$alkyl and $(C_1-C_4)$alkoxy. Most preferably the substituents are independently selected from the group consisting of halogen and $(C_1-C_4)$alkyl. Examples of such optionally substituted heteroaryl groups are 2-methyl-thiazol-4-yl (preferred), 2-methyl-thiazol-5-yl (preferred), 4-methyl-thiazol-5-yl, 1-methyl-pyrazol-5-yl, 1,3-dimethyl-pyrazol-5-yl (preferred), pyridin-2-yl, 6-methyl-pyridin-2-yl, pyridin-3-yl, pyrimidin-2-yl, pyrimidin-5-yl, 3-methyl-indol-1-yl, 1-methyl-indol-3-yl (preferred), 2-methyl-indol-3-yl (preferred), 5-methoxy-indol-3-yl, indazol-1-yl, 3-methyl-indazol-1-yl, 5-fluoro-indazol-1-yl (preferred), indazol-3-yl, benzisoxazol-3-yl and 5-methoxy-benzisoxazol-3-yl.

In case "$R^8$" represents "$(C_2-C_3)$alkenyl which is mono-substituted with optionally substituted heteroaryl" the term "heteroaryl" means the above-mentioned groups. Preferred examples of such heteroaryl groups are thiazolyl (notably thiazol-5-yl), pyrazolyl (notably pyrazol-5-yl), pyridyl (notably pyridin-3-yl) and benzothiazolyl (notably benzothiazol-2-yl). A most preferred example is benzothiazolyl (notably benzothiazol-2-yl). The heteroaryl groups are independently unsubstituted, mono-, di- or tri-substituted (preferably unsubstituted, mono- or di-substituted and most preferably unsubstituted), wherein the substituents are independently selected from the group consisting of halogen, $(C_1-C_4)$alkyl, $(C_1-C_4)$alkoxy and $(C_1-C_4)$fluoroalkyl. Preferably the substituents are independently selected from the group consisting of $(C_1-C_4)$alkyl and $(C_1-C_4)$alkoxy. Examples of such optionally substituted heteroaryl groups are 2,4-dimethyl-thiazol-5-yl, 1,3-dimethyl-pyrazol-5-yl, pyridin-3-yl, 6-methoxy-pyridin-3-yl and benzothiazol-2-yl (preferred).

The term "heteroaryloxy", used alone or in combination, refers to an heteroaryl-O— group wherein the heteroaryl group is as defined before. An "optionally substituted heteroaryloxy" group means a heteroaryloxy group as defined before which is unsubstituted or substituted as explicitly defined.

In case "$R^8$" represents "$(C_1-C_4)$alkyl which is substituted with optionally substituted heteroaryloxy" the term "optionally substituted heteroaryloxy" means the above-mentioned groups. Preferred are 5- or 6-membered monocyclic heteroaryloxy groups containing in the heteroaryl moiety 1, 2 or 3 heteroatoms (preferably 1 or 2 heteroatoms) independently selected from oxygen, nitrogen and sulfur. Examples of such 5- or 6-membered monocyclic heteroaryloxy groups are furanyloxy, oxazolyloxy, isoxazolyloxy, oxadiazolyloxy, thienyloxy, thiazolyloxy, isothiazolyloxy, thiadiazolyloxy, pyrrolyloxy, imidazolyloxy, pyrazolyloxy, triazolyloxy, pyridyloxy, pyrimidyloxy, pyridazinyloxy and pyrazinyloxy. A preferred example of such heteroaryloxy group is pyridyloxy (notably pyridin-3-yloxy). The heteroaryloxy groups are independently unsubstituted, mono-, di- or tri-substituted (preferably unsubstituted, mono- or di-substituted and most preferably unsubstituted), wherein the substituents are independently selected from the group consisting of halogen, $(C_1-C_4)$alkyl, $(C_1-C_4)$alkoxy and $(C_1-C_4)$fluoroalkyl. Preferably the substituents are independently selected from the group consisting of $(C_1-C_4)$alkyl and $(C_1-C_4)$alkoxy. An example of such an optionally substituted heteroaryloxy group is pyridin-3-yloxy.

The term "heterocyclyl", used alone or in combination, refers to a saturated monocyclic moiety of 5 to 7 ring members containing 1 or 2 heteroatoms selected from nitrogen, oxygen and sulfur, it being understood that a heterocyclyl group does not contain 2 sulfur atoms. The sulfur atom of a heterocyclyl group may be in an oxidised form, i.e. as a sulfoxide or sulfonyl. A heterocyclyl group may optionally be annelated to a benzene ring. An "optionally substituted heterocyclyl" group means a heterocyclyl group as defined before which is unsubstituted or substituted as explicitly defined.

In case "$R^8$" represents "heterocyclyl" the term means the above-mentioned groups. Preferred are heterocyclyl groups with 5 or 6 ring members containing 1 heteroatom selected from nitrogen and oxygen (preferred) which are annelated to a benzene ring. Examples of such heterocyclyl groups are pyrrolidinyl, imidazolidinyl, oxazolidinyl, thiazolidinyl, piperidinyl, piperazinyl, morpholinyl, thiomorpholinyl, dioxanyl, indolinyl, isoindolinyl, dihydrobenzofuranyl, tetrahydroquinolinyl, tetrahydroisoquinolinyl, tetrahydroquinoxalinyl, chromanyl, dihydrobenzooxazinyl, dihydrobenzothiazinyl and dihydrobenzodioxinyl. A preferred example is chromanyl (notably chroman-2-yl and chroman-3-yl). The heterocyclyl groups are independently unsubstituted, mono-, di- or tri-substituted (preferably unsubstituted, mono- or di-substituted and most preferably unsubstituted), wherein the substituents are independently selected from the group consisting of halogen, oxo and $(C_1-C_4)$alkyl. Examples of such optionally substituted heterocyclyl groups are chroman-2-yl and chroman-3-yl.

In case "$R^8$" represents "$(C_1-C_4)$alkyl which is substituted with optionally substituted heterocyclyl" the term "heterocyclyl" means the above-mentioned groups. Preferred are heterocyclyl groups with 5 or 6 ring members containing 1 heteroatom selected from nitrogen (preferred) and oxygen which are annelated to a benzene ring. Examples of such heterocyclyl groups are pyrrolidinyl, imidazolidinyl, oxazolidinyl, thiazolidinyl, piperidinyl, piperazinyl, morpholinyl, thiomorpholinyl, dioxanyl, indolinyl, isoindolinyl, dihydrobenzofuranyl, tetrahydroquinolinyl, tetrahydroisoquinolinyl, tetrahydroquinoxalinyl, chromanyl, dihydrobenzooxazinyl, dihydrobenzothiazinyl and dihydrobenzodioxinyl. Preferred examples are indolinyl (notably indolin-1-yl) and tetrahydroquinolinyl (notably 1,2,3,4-tetrahydroquinolin-1-yl). The heterocyclyl groups are independently unsubstituted, mono-, di- or tri-substituted (preferably unsubstituted, mono- or di-substituted and most preferably unsubstituted), wherein the substituents are independently selected from the group consisting of halogen, oxo and $(C_1-C_4)$alkyl. Examples of such optionally substituted heterocyclyl groups are indolin-1-yl and 1,2,3,4-tetrahydroquinolin-1-yl.

2) A further embodiment of the invention relates to compounds of formula (I) according to embodiment 1), which are also compounds of formula ($I_P$)

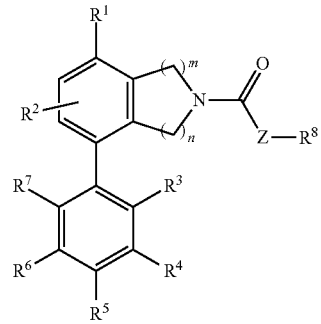

($I_P$)

wherein $R^1$ represents hydrogen, $(C_1-C_4)$alkyl, $(C_1-C_4)$alkoxy, $(C_1-C_4)$fluoroalkyl, $(C_1-C_4)$alkylsulfonyl, halogen or cyano;

$R^2$ represents hydrogen or halogen;

one of $R^3$, $R^4$ and $R^5$ represents carboxy-$(C_1-C_3)$alkyl or carboxy-$(C_1-C_3)$alkoxy and the other two represent independently of each other hydrogen, $(C_1-C_4)$alkoxy or halogen;

$R^6$ represents hydrogen, $(C_1-C_4)$alkoxy or halogen;

$R^7$ represents hydrogen, $(C_1-C_4)$alkyl, $(C_1-C_4)$alkoxy, cyclopropylmethoxy, methoxy-ethoxy, $(C_1-C_4)$fluoroalkyl, $(C_1-C_4)$fluoroalkoxy, halogen or $(C_1-C_4)$alkylsulfonyl;

or $R^6$ and $R^7$ together represent methylendioxy or ethylendioxy;

$R^8$ represents $(C_2-C_5)$alkyl;

$(C_1-C_4)$alkyl which is mono- or di-substituted wherein the substituents are independently selected from the group consisting of $(C_1-C_4)$alkoxy, oxo, optionally substituted $(C_3-C_6)$cycloalkyl, optionally substituted aryl, optionally substituted heteroaryl, optionally substituted heterocyclyl, optionally substituted aryloxy, optionally substituted heteroaryloxy or optionally substituted aryl-$(C_1-C_2)$alkoxy;

$(C_2-C_3)$alkenyl which is mono-substituted with optionally substituted aryl or optionally substituted heteroaryl;

$(C_3-C_6)$cycloalkyl which is unsubstituted, mono-, di-, tri- or tetra-substituted with methyl; mono-substituted with oxo; or mono-substituted with optionally substituted aryl; or heterocyclyl which is optionally mono-substituted with oxo;

n represents 1 or 2;

m represents 1 or 2; and

Z represents —NH—, —O— or a bond;

and to the salts (in particular pharmaceutically acceptable salts) of such compounds.

3) A further embodiment of the invention relates to compounds according to any one of embodiments 1) or 2), wherein $R^1$ represents hydrogen, methyl, trifluoromethyl, halogen or cyano;

$R^2$ represents hydrogen or halogen;

one of $R^3$, $R^4$ and $R^5$ represents carboxy-$(C_1-C_3)$alkyl or carboxy-$(C_1-C_3)$alkoxy, another one of $R^3$, $R^4$ and $R^5$ represents hydrogen, $(C_1-C_4)$alkoxy or halogen and the third one of $R^3$, $R^4$ and $R^5$ represents hydrogen;

$R^6$ represents hydrogen, methoxy or halogen;

$R^7$ represents hydrogen, $(C_1-C_4)$alkoxy, trifluoromethyl, trifluoromethoxy, halogen or methylsulfonyl;

or $R^6$ and $R^7$ together represent methylendioxy or ethylendioxy;

$R^8$ represents
- $(C_1-C_4)$alkyl which is mono-substituted with optionally substituted $(C_5-C_6)$cycloalkyl, optionally substituted aryl, optionally substituted heteroaryl, optionally substituted heterocyclyl, optionally substituted aryloxy or optionally substituted aryl-$(C_1-C_2)$alkoxy;
- $(C_2-C_3)$alkenyl which is mono-substituted with optionally substituted aryl or optionally substituted heteroaryl; or
- cyclopropyl which is mono-substituted with optionally substituted aryl;

n represents 1 or 2;
m represents 1 or 2; and
Z represents —NH—, —O— or a bond;
and to the salts (in particular pharmaceutically acceptable salts) of such compounds.

4) A further embodiment of the invention relates to compounds according to any one of embodiments 1) or 2), wherein
$R^1$ represents hydrogen or halogen;
$R^2$ represents hydrogen or halogen (preferably hydrogen or fluoro);
one of $R^3$, $R^4$ and $R^5$ represents carboxy-$(C_1-C_3)$alkyl or carboxy-$(C_1-C_3)$alkoxy (preferably carboxy-methyl, 1-carboxy-ethyl or carboxy-methoxy) and the other two represent hydrogen;
$R^6$ represents hydrogen, methoxy or halogen (preferably hydrogen, fluoro or chloro);
$R^7$ represents hydrogen, $(C_1-C_4)$alkoxy, trifluoromethyl, trifluoromethoxy, halogen or methylsulfonyl (preferably hydrogen, $(C_1-C_4)$alkoxy or halogen);
$R^8$ represents
- $(C_1-C_4)$alkyl which is mono-substituted with optionally substituted aryl, optionally substituted heteroaryl or optionally substituted aryl-$(C_1-C_2)$alkoxy; or
- cyclopropyl which is mono-substituted with optionally substituted aryl;

n represents 1 or 2;
m represents 1 or 2; and
Z represents —NH—, —O— or a bond;
and to the salts (in particular pharmaceutically acceptable salts) of such compounds.

5) A further embodiment of the invention relates to compounds according to embodiment 1), wherein
$R^1$ represents hydrogen, fluoro, chloro or cyano;
$R^2$ represents hydrogen or fluoro;
one of $R^3$, $R^4$ and $R^5$ represents carboxy-methyl, 1-carboxy-ethyl or carboxy-methoxy and the other two represent hydrogen;
$R^6$ represents hydrogen;
$R^7$ represents $(C_1-C_4)$alkoxy, cyclopropyl-methoxy, cyclopropyloxy, methoxy-ethoxy or $(C_1-C_4)$fluoroalkoxy;
$R^8$ represents
- $(C_1-C_4)$alkyl which is mono-substituted with optionally substituted $(C_3-C_6)$cycloalkyl, optionally substituted aryl, optionally substituted heteroaryl, optionally substituted heterocyclyl, optionally substituted aryloxy or optionally substituted aryl-$(C_1-C_2)$alkoxy; or
- cyclopropyl which is mono-substituted with optionally substituted aryl; or mono-substituted with optionally substituted heteroaryl;

n represents 1;
m represents 1 or 2; and
Z represents —NH—, —O— or a bond;
and to the salts (in particular pharmaceutically acceptable salts) of such compounds.

6) A further embodiment of the invention relates to compounds according to embodiment 1), wherein
$R^1$ represents fluoro;
$R^2$, $R^3$ and $R^6$ represent hydrogen;
one of $R^4$ and $R^5$ represents carboxy-methyl and the other represents hydrogen;
$R^7$ represents methoxy, ethoxy, n-propoxy, iso-propoxy, iso-butoxy, tert-butoxy, cyclopropyl-methoxy, difluoromethoxy, trifluoromethoxy, 2-fluoroethoxy, 2,2-difluoroethoxy or 2,2,2-trifluoroethoxy;
$R^8$ represents a methyl, ethyl or n-propyl group, which groups are independently mono-substituted with
- phenyl, wherein the phenyl is unsubstituted or mono-substituted with fluoro, chloro or methoxy; or
- pyridin-2-yl, wherein the pyridin-2-yl is unsubstituted, mono-substituted with methyl, or di-substituted with methyl and fluoro;

n represents 1;
m represents 2; and
Z represents —O— or a bond;
and to the salts (in particular pharmaceutically acceptable salts) of such compounds.

7) A further embodiment of the invention relates to compounds according to any one of embodiments 1) or 2), wherein
$R^1$ represents hydrogen or halogen (preferably hydrogen or fluoro);
$R^2$ represents hydrogen;
$R^3$ represents carboxy-$(C_1-C_3)$alkyl or carboxy-$(C_1-C_3)$alkoxy (preferably carboxy-methyl, carboxy-methoxy or carboxy-propoxy);
$R^4$ represents hydrogen;
$R^5$ represents hydrogen;
$R^6$ represents hydrogen or halogen (preferably fluoro or chloro);
$R^7$ represents hydrogen or methoxy (notably hydrogen);
$R^8$ represents $(C_1-C_4)$alkyl (preferably methyl) which is mono-substituted with optionally substituted aryl;

n represents 1;
m represents 2; and
Z represents —NH—, —O— or a bond (preferably —O—);
and to the salts (in particular pharmaceutically acceptable salts) of such compounds.

8) A further embodiment of the invention relates to compounds according to embodiment 1), wherein
$R^1$ represents fluoro;
$R^2$, $R^4$ and $R^6$ represent hydrogen;
$R^3$ represents hydrogen or $(C_1-C_4)$alkoxy;
$R^5$ represents carboxy-methyl or 1-carboxy-ethyl;
$R^7$ represents $(C_1-C_4)$alkoxy or $(C_1-C_4)$fluoroalkoxy;
$R^8$ represents
- $(C_1-C_4)$alkyl which is mono-substituted with optionally substituted $(C_3-C_6)$cycloalkyl, optionally substituted aryl, optionally substituted heteroaryl, optionally substituted heterocyclyl, optionally substituted aryloxy or optionally substituted aryl-$(C_1-C_2)$alkoxy; or
- cyclopropyl which is mono-substituted with phenyl or pyridyl;

n represents 1;
m represents 2; and
Z represents —NH—, —O— or a bond;
and to the salts (in particular pharmaceutically acceptable salts) of such compounds.

9) A further embodiment of the invention relates to compounds according to any one of embodiments 1) or 2), wherein
$R^1$ represents hydrogen or halogen;
$R^2$ represents hydrogen or fluoro (preferably hydrogen);

R³ represents hydrogen;
R⁴ represents hydrogen;
R⁵ represents carboxy-($C_1$-$C_3$)alkyl or carboxy-($C_1$-$C_3$)alkoxy (preferably carboxy-methyl or carboxy-methoxy);
R⁶ represents hydrogen or halogen;
R⁷ represents hydrogen, ($C_1$-$C_4$)alkoxy or halogen (preferably hydrogen, methoxy or halogen);
R⁸ represents
($C_1$-$C_4$)alkyl which is mono-substituted with optionally substituted aryl, optionally substituted heteroaryl, optionally substituted aryloxy or optionally substituted aryl-($C_1$-$C_2$)alkoxy; or
cyclopropyl which is mono-substituted with optionally substituted aryl;
n represents 1 or 2 (preferably 1);
m represents 1 or 2 (preferably 2); and
Z represents —NH—, —O— or a bond;
and to the salts (in particular pharmaceutically acceptable salts) of such compounds.

10) A further embodiment of the invention relates to compounds according to any one of embodiments 1) or 2), wherein
R¹ represents hydrogen or halogen (preferably fluoro);
R² represents hydrogen;
R³ represents hydrogen;
R⁴ represents hydrogen;
R⁵ represents carboxy-($C_1$-$C_3$)alkyl or carboxy-($C_1$-$C_3$)alkoxy (preferably carboxy-methyl or carboxy-methoxy);
R⁶ represents hydrogen, fluoro or chloro (preferably hydrogen or chloro);
R⁷ represents hydrogen, methoxy or halogen (preferably hydrogen, methoxy, fluoro or chloro);
R⁸ represents ($C_1$-$C_4$)alkyl (preferably methyl) which is mono-substituted with optionally substituted aryl;
n represents 1;
m represents 2; and
Z represents —O— or a bond (preferably —O—);
and to the salts (in particular pharmaceutically acceptable salts) of such compounds.

11) A further embodiment of the invention relates to compounds according to any one of embodiments 1) or 2), wherein
R¹ represents fluoro;
R², R³, R⁴ and R⁶ represent hydrogen;
R⁵ represents carboxy-methyl or 1-carboxy-ethyl;
R⁷ represents methoxy, ethoxy, isopropoxy or 2,2,2-trifluoroethoxy;
R⁸ represents a methyl, ethyl or n-propyl group, which groups are independently mono-substituted with
phenyl, wherein the phenyl is unsubstituted, mono-substituted with fluoro, chloro, methyl or methoxy, di-substituted with fluoro, or di-substituted with fluoro and chloro; or
pyridin-2-yl, wherein the pyridin-2-yl is unsubstituted, mono-substituted with methyl, or di-substituted with methyl and fluoro;
n represents 1;
m represents 2; and
Z represents —O— or a bond;
and to the salts (in particular pharmaceutically acceptable salts) of such compounds.

12) A further embodiment of the invention relates to compounds according to embodiment 1), wherein
R¹ represents hydrogen, fluoro, chloro or cyano;
R² represents hydrogen or fluoro;
R³ represents hydrogen or fluoro;
R⁴ represents carboxy-methyl, 1-carboxy-ethyl, carboxy-cyclopropyl or carboxy-methoxy;
R⁵ represents hydrogen, methoxy, fluoro or chloro;
R⁶ represents hydrogen, methoxy, fluoro or chloro;
R⁷ represents hydrogen, ($C_1$-$C_4$)alkyl, ($C_1$-$C_4$)alkoxy, cyclopropyl-methoxy, cyclopropyloxy, methoxy-ethoxy, dimethylamino, trifluoromethyl, difluoromethoxy, trifluoromethoxy, 2-fluoroethoxy, 2,2-difluoroethoxy, 2,2,2-trifluoroethoxy, fluoro, chloro or methyl-sulfonyl; or R⁶ and R⁷ together represent methylendioxy or ethylendioxy;
R⁸ represents
n-butyl, iso-butyl, 2-methyl-but-1-yl and 3-methyl-but-1-yl;
($C_1$-$C_5$)alkyl which is mono-substituted with hydroxy, methoxy, ethoxy, optionally substituted ($C_3$-$C_6$)cycloalkyl, optionally substituted aryl, optionally substituted heteroaryl, optionally substituted heterocyclyl, optionally substituted aryloxy, optionally substituted heteroaryloxy or optionally substituted aryl-($C_1$-$C_2$)alkoxy;
3-methyl-2-butenyl and 3-methyl-3-butenyl;
ethenyl which is mono-substituted with optionally substituted aryl or optionally substituted heteroaryl;
3-butynyl; or
cyclopropyl which is mono-substituted with optionally substituted aryl or optionally substituted heteroaryl;
n represents 1 or 2;
m represents 1 or 2; and
Z represents —NH—, —O— or a bond;
and to the salts (in particular pharmaceutically acceptable salts) of such compounds.

13) A further embodiment of the invention relates to compounds according to any one of embodiments 1) or 2), wherein
R¹ represents hydrogen, ($C_1$-$C_4$)alkyl, ($C_1$-$C_4$)alkoxy, ($C_1$-$C_4$)fluoroalkyl, ($C_1$-$C_4$)alkylsulfonyl, halogen or cyano;
R² represents hydrogen or halogen;
R³ represents hydrogen or halogen;
R⁴ represents carboxy-($C_1$-$C_3$)alkyl or carboxy-($C_1$-$C_3$)alkoxy;
R⁵ represents hydrogen, ($C_1$-$C_4$)alkoxy or halogen;
R⁶ represents hydrogen, ($C_1$-$C_4$)alkoxy or halogen;
R⁷ represents hydrogen, ($C_1$-$C_4$)alkyl, ($C_1$-$C_4$)alkoxy, cyclopropylmethoxy, methoxy-ethoxy, ($C_1$-$C_4$)fluoroalkyl, ($C_1$-$C_4$)fluoroalkoxy, halogen or ($C_1$-$C_4$)alkylsulfonyl; or R⁶ and R⁷ together represent methylendioxy or ethylendioxy;
R⁸ represents
($C_1$-$C_4$)alkyl which is mono-substituted with optionally substituted ($C_3$-$C_6$)cycloalkyl, optionally substituted aryl, optionally substituted heteroaryl, optionally substituted heterocyclyl, optionally substituted aryloxy, optionally substituted heteroaryloxy or optionally substituted aryl-($C_1$-$C_2$)alkoxy;
($C_2$-$C_3$)alkenyl which is mono-substituted with optionally substituted aryl or optionally substituted heteroaryl;
($C_3$-$C_6$)cycloalkyl which is unsubstituted, mono-, di-, tri- or tetra-substituted with methyl; mono-substituted with oxo; or mono-substituted with optionally substituted aryl; or
heterocyclyl;
n represents 1 or 2;
m represents 1 or 2; and
Z represents —NH—, —O— or a bond;
and to the salts (in particular pharmaceutically acceptable salts) of such compounds.

14) A further embodiment of the invention relates to compounds according to any one of embodiments 1) or 2), wherein $R^1$ represents hydrogen, methyl, methoxy, trifluoromethyl, halogen or cyano (preferably hydrogen, fluoro or chloro);
$R^2$ represents hydrogen or fluoro;
$R^3$ represents hydrogen or fluoro;
$R^4$ represents carboxy-methyl, 1-carboxy-ethyl or carboxy-methoxy;
$R^5$ represents hydrogen, methoxy, fluoro or chloro;
$R^6$ represents hydrogen, methoxy, fluoro or chloro;
$R^7$ represents hydrogen, methyl, $(C_1-C_4)$alkoxy, cyclopropylmethoxy, methoxy-ethoxy, trifluoromethyl, trifluoromethoxy, fluoro, chloro or methylsulfonyl;
or $R^6$ and $R^7$ together represent methylendioxy or ethylendioxy;
$R^8$ represents
  $(C_1-C_4)$alkyl which is mono-substituted with optionally substituted $(C_5-C_6)$cycloalkyl, optionally substituted aryl, optionally substituted heteroaryl, optionally substituted heterocyclyl, optionally substituted aryloxy or optionally substituted aryl-$(C_1-C_2)$alkoxy;
  $(C_2-C_3)$alkenyl which is mono-substituted with optionally substituted aryl or optionally substituted heteroaryl; or
  cyclopropyl which is mono-substituted with optionally substituted aryl;
n represents 1 or 2;
m represents 1 or 2; and
Z represents —NH—, —O— or a bond;
and to the salts (in particular pharmaceutically acceptable salts) of such compounds.

15) A further embodiment of the invention relates to compounds according to any one of embodiments 1) or 2), wherein $R^1$ represents fluoro, chloro or cyano;
$R^2$, $R^3$, $R^5$ and $R^6$ represent hydrogen;
$R^4$ represents carboxy-methyl or 1-carboxy-ethyl;
$R^7$ represents methoxy, ethoxy, n-propoxy, iso-propoxy, iso-butoxy, tert-butoxy, cyclopropyl-methoxy, methoxy-ethoxy, difluoromethoxy, trifluoromethoxy, 2-fluoroethoxy, 2,2-difluoroethoxy or 2,2,2-trifluoroethoxy;
$R^8$ represents a methyl, ethyl or n-propyl group, which groups are independently mono-substituted with
  phenyl, wherein the phenyl is unsubstituted, mono-substituted with fluoro, chloro or methoxy, di-substituted with fluoro, or di-substituted with fluoro and chloro; or
  pyridin-2-yl, wherein the pyridin-2-yl is unsubstituted, mono-substituted with methyl, or di-substituted with methyl and fluoro;
n represents 1;
m represents 2; and
Z represents —O— or a bond;
and to the salts (in particular pharmaceutically acceptable salts) of such compounds.

16) A further embodiment of the invention relates to compounds according to any one of embodiments 1), 2), 13 or 14), wherein $R^1$ represents hydrogen, methyl, trifluoromethyl, halogen or cyano;
and to the salts (in particular pharmaceutically acceptable salts) of such compounds.

17) A further embodiment of the invention relates to compounds according to any one of embodiments 1) to 5), 7), 9), 10) or 12) to 14), wherein $R^1$ represents hydrogen, fluoro or chloro;
and to the salts (in particular pharmaceutically acceptable salts) of such compounds.

18) A further embodiment of the invention relates to compounds according to any one of embodiments 1) to 15), wherein $R^1$ represents fluoro;
and to the salts (in particular pharmaceutically acceptable salts) of such compounds.

19) A further embodiment of the invention relates to compounds according to any one of embodiments 1) to 5), 13) or 16) to 18), wherein $R^2$ represents hydrogen or fluoro;
and to the salts (in particular pharmaceutically acceptable salts) of such compounds.

20) A further embodiment of the invention relates to compounds according to any one of embodiments 1) to 18), wherein $R^2$ represents hydrogen;
and to the salts (in particular pharmaceutically acceptable salts) of such compounds.

21) A further embodiment of the invention relates to compounds according to any one of embodiments 1) to 20), wherein one of $R^3$, $R^4$ and $R^5$ represents carboxy-$(C_1-C_3)$alkyl (preferably carboxy-methyl or 1-carboxy-ethyl and most preferably carboxy-methyl);
and to the salts (in particular pharmaceutically acceptable salts) of such compounds.

22) A further embodiment of the invention relates to compounds according to any one of embodiments 1) to 20), wherein $R^4$ represents carboxy-methyl;
and to the salts (in particular pharmaceutically acceptable salts) of such compounds.

23) A further embodiment of the invention relates to compounds according to any one of embodiments 1) to 20), wherein $R^5$ represents carboxy-methyl;
and to the salts (in particular pharmaceutically acceptable salts) of such compounds.

24) A further embodiment of the invention relates to compounds according to any one of embodiments 1) to 20), wherein one of $R^3$, $R^4$ and $R^5$ represents carboxy-$(C_1-C_3)$alkoxy (preferably carboxy-methoxy or 3-carboxy-propoxy and most preferably carboxy-methoxy);
and to the salts (in particular pharmaceutically acceptable salts) of such compounds.

25) A further embodiment of the invention relates to compounds according to any one of embodiments 1) to 20), wherein $R^4$ represents carboxy-methoxy;
and to the salts (in particular pharmaceutically acceptable salts) of such compounds.

26) A further embodiment of the invention relates to compounds according to any one of embodiments 1) to 5), 7), 9), 10), 12) to 14) or 16) to 20), wherein one of $R^3$, $R^4$ and $R^5$ represents carboxy-methyl, 1-carboxy-ethyl or carboxy-methoxy; and to the salts (in particular pharmaceutically acceptable salts) of such compounds.

27) A further embodiment of the invention relates to compounds according to any one of embodiments 1) to 5) or 16) to 20), wherein $R^3$ represents carboxy-$(C_1-C_3)$alkyl or carboxy-$(C_1-C_3)$alkoxy (preferably carboxy-methyl, carboxy-methoxy or 3-carboxy-propoxy);
and to the salts (in particular pharmaceutically acceptable salts) of such compounds.

28) A further embodiment of the invention relates to compounds according to any one of embodiments 1) to 5) or 16) to 20), wherein $R^4$ represents carboxy-$(C_1-C_3)$alkyl or carboxy-$(C_1-C_3)$alkoxy (preferably carboxy-methyl, 1-carboxy-ethyl or carboxy-methoxy);

and to the salts (in particular pharmaceutically acceptable salts) of such compounds.

29) A further embodiment of the invention relates to compounds according to any one of embodiments 1) to 5) or 16 to 20), wherein $R^5$ represents carboxy-$(C_1-C_3)$alkyl or carboxy-$(C_1-C_3)$alkoxy (preferably carboxy-methyl or carboxy-methoxy and most preferably carboxy-methyl);

and to the salts (in particular pharmaceutically acceptable salts) of such compounds.

30) A further embodiment of the invention relates to compounds according to any one of embodiments 1) to 29), wherein one or two of $R^3$, $R^4$ and $R^5$ represent hydrogen;

and to the salts (in particular pharmaceutically acceptable salts) of such compounds.

31) A further embodiment of the invention relates to compounds according to any one of embodiments 1) to 3), 13) or 16) to 30), wherein one of $R^3$, $R^4$ and $R^5$ represents $(C_1-C_4)$alkoxy or halogen (preferably methoxy, fluoro or chloro);

and to the salts (in particular pharmaceutically acceptable salts) of such compounds.

32) A further embodiment of the invention relates to compounds according to any one of embodiments 1) to 4), 13) or 16) to 31), wherein $R^6$ represents hydrogen, methoxy, fluoro or chloro (and preferably methoxy);

and to the salts (in particular pharmaceutically acceptable salts) of such compounds.

33) A further embodiment of the invention relates to compounds according to any one of embodiments 1) to 31), wherein $R^6$ represents hydrogen;

and to the salts (in particular pharmaceutically acceptable salts) of such compounds.

34) A further embodiment of the invention relates to compounds according to any one of embodiments 1) to 4), 13) or 16) to 33), wherein $R^7$ represents hydrogen, $(C_1-C_4)$alkoxy, trifluoromethyl, trifluoromethoxy, halogen or methylsulfonyl;

and to the salts (in particular pharmaceutically acceptable salts) of such compounds.

35) A further embodiment of the invention relates to compounds according to any one of embodiments 1) to 5), 8), 12) to 14) or 16) to 33), wherein $R^7$ represents $(C_1-C_4)$alkoxy or trifluoromethoxy (preferably methoxy, iso-propoxy or trifluoromethoxy);

and to the salts (in particular pharmaceutically acceptable salts) of such compounds.

36) A further embodiment of the invention relates to compounds according to any one of embodiments 1) to 4), 9), 12) to 14) or 16) to 33), wherein $R^7$ represents hydrogen, $(C_1-C_4)$alkoxy or halogen (preferably hydrogen, methoxy, fluoro or chloro);

and to the salts (in particular pharmaceutically acceptable salts) of such compounds.

37) A further embodiment of the invention relates to compounds according to any one of embodiments 1) to 4), 7), 9), 10), 12) to 14) or 16) to 22), wherein $R^7$ represents hydrogen;

and to the salts (in particular pharmaceutically acceptable salts) of such compounds.

38) A further embodiment of the invention relates to compounds according to any one of embodiments 1), 2), 13) or 16) to 37), wherein Z represents —NH— and $R^8$ represents $(C_1-C_4)$alkyl (preferably $(C_1-C_2)$alkyl) which is mono-substituted with optionally substituted aryl; or Z represents —O— and $R^8$ represents $(C_1-C_4)$alkyl (preferably methyl) which is mono-substituted with optionally substituted aryl or optionally substituted heteroaryl; or Z represents a bond and $R^8$ represents
  $(C_1-C_4)$alkyl which is mono-substituted with optionally substituted $(C_3-C_6)$cycloalkyl, optionally substituted aryl, optionally substituted heteroaryl, optionally substituted heterocyclyl, optionally substituted aryloxy or optionally substituted aryl-$(C_1-C_2)$alkoxy;
  $(C_2-C_3)$alkenyl which is mono-substituted with optionally substituted aryl or optionally substituted heteroaryl; or
  $(C_3-C_6)$cycloalkyl which is unsubstituted or mono-substituted with optionally substituted aryl;

and to the salts (in particular pharmaceutically acceptable salts) of such compounds.

39) A further embodiment of the invention relates to compounds according to any one of embodiments 1) to 3), 5), 9), 12) to 14) or 16) to 37), wherein Z represents —O— and $R^8$ represents $(C_1-C_4)$alkyl (preferably methyl) which is mono-substituted with optionally substituted aryl or optionally substituted heteroaryl; or Z represents a bond and $R^8$ represents
  $(C_1-C_4)$alkyl which is mono-substituted with optionally substituted aryl, optionally substituted heteroaryl, optionally substituted aryloxy or optionally substituted aryl-methoxy; or
  cyclopropyl which is mono-substituted with optionally substituted aryl;

and to the salts (in particular pharmaceutically acceptable salts) of such compounds.

40) A further embodiment of the invention relates to compounds according to any one of embodiments 1) to 3), 13), 14) or 16) to 37), wherein $R^8$ represents
  $(C_1-C_4)$alkyl which is mono-substituted with optionally substituted $(C_5-C_6)$cycloalkyl, optionally substituted aryl, optionally substituted heteroaryl, optionally substituted heterocyclyl, optionally substituted aryloxy or optionally substituted aryl-$(C_1-C_2)$alkoxy;
  $(C_2-C_3)$alkenyl which is mono-substituted with optionally substituted aryl or optionally substituted heteroaryl; or
  cyclopropyl which is mono-substituted with optionally substituted aryl;

and to the salts (in particular pharmaceutically acceptable salts) of such compounds.

41) A further embodiment of the invention relates to compounds according to any one of embodiments 1) to 5), 9), 12) to 14) or 16) to 37), wherein $R^8$ represents
  $(C_1-C_4)$alkyl which is mono-substituted with optionally substituted aryl, optionally substituted heteroaryl or optionally substituted aryl-$(C_1-C_2)$alkoxy; or
  cyclopropyl which is mono-substituted with optionally substituted aryl;

and to the salts (in particular pharmaceutically acceptable salts) of such compounds.

42) A further embodiment of the invention relates to compounds according to any one of embodiments 1) to 5), 9), 12) to 14) or 16) to 37), wherein R⁸ represents
(C₁-C₄)alkyl which is mono-substituted with optionally substituted aryl or optionally substituted heteroaryl; or
cyclopropyl which is mono-substituted with optionally substituted aryl;
and to the salts (in particular pharmaceutically acceptable salts) of such compounds.

43) A further embodiment of the invention relates to compounds according to any one of embodiments 1) to 5), 8), 9), 12) to 14) or 16) to 39), wherein
R⁸ represents (C₁-C₄)alkyl which is mono-substituted with optionally substituted aryl or optionally substituted heteroaryl (preferably mono-substituted with optionally substituted aryl);
and to the salts (in particular pharmaceutically acceptable salts) of such compounds.

44) A further embodiment of the invention relates to compounds according to any one of embodiments 1) to 5), 9), 12) to 14) or 16) to 37), wherein
R⁸ represents cyclopropyl which is mono-substituted with optionally substituted aryl; and to the salts (in particular pharmaceutically acceptable salts) of such compounds.

45) A further embodiment of the invention relates to compounds according to any one of embodiments 1) to 3), 5), 8), 12) to 14) or 16) to 37), wherein
R⁸ represents methyl which is mono-substituted with a 2,3-dihydrobenzofuranyl, a chromanyl or an isochromanyl group, which groups are in the aromatic portion optionally mono-substituted with fluorine and in the non-aromatic portion optionally di-substituted with methyl;
and to the salts (in particular pharmaceutically acceptable salts) of such compounds.

46) A further embodiment of the invention relates to compounds according to any one of embodiments 1) to 45), wherein
n represents 1;
and to the salts (in particular pharmaceutically acceptable salts) of such compounds.

47) A further embodiment of the invention relates to compounds according to any one of embodiments 1) to 4), 9), 12) to 14) or 16) to 45), wherein
n represents 2;
and to the salts (in particular pharmaceutically acceptable salts) of such compounds.

48) A further embodiment of the invention relates to compounds according to any one of embodiments 1) to 5), 9), 12) to 14) or 16) to 47), wherein
m represents 1;
and to the salts (in particular pharmaceutically acceptable salts) of such compounds.

49) A further embodiment of the invention relates to compounds according to any one of embodiments 1) to 47), wherein
m represents 2;
and to the salts (in particular pharmaceutically acceptable salts) of such compounds.

50) A further embodiment of the invention relates to compounds according to any one of embodiments 1) to 5), 7) to 9), 12) to 14), 16) to 38) or 40) to 49), wherein
Z represents —NH— or —O—;
and to the salts (in particular pharmaceutically acceptable salts) of such compounds.

51) A further embodiment of the invention relates to compounds according to any one of embodiments 1) to 49), wherein
Z represents —O— or a bond;
and to the salts (in particular pharmaceutically acceptable salts) of such compounds.

52) A further embodiment of the invention relates to compounds according to any one of embodiments 1) to 5), 7) to 9), 12) to 14), 16) to 38) or 40) to 49), wherein
Z represents —NH—;
and to the salts (in particular pharmaceutically acceptable salts) of such compounds.

53) A further embodiment of the invention relates to compounds according to any one of embodiments 1) to 49), wherein
Z represents —O—;
and to the salts (in particular pharmaceutically acceptable salts) of such compounds.

54) A further embodiment of the invention relates to compounds according to any one of embodiments 1) to 49), wherein
Z represents a bond;
and to the salts (in particular pharmaceutically acceptable salts) of such compounds.

55) Preferred compounds of formula (I) as defined in embodiment 1) are selected from the group consisting of:
(3-{5-Fluoro-2-[trans-2-(4-fluoro-phenyl)-cyclopropanecarbonyl]-1,2,3,4-tetrahydro-isoquinolin-8-yl}-4-methoxy-phenyl)-acetic acid;
(3-{2-[trans-2-(4-Chloro-phenyl)-cyclopropanecarbonyl]-5-fluoro-1,2,3,4-tetrahydro-isoquinolin-8-yl}-4-methoxy-phenyl)-acetic acid;
(3-{2-[trans-2-(2-Chloro-phenyl)-cyclopropanecarbonyl]-5-fluoro-1,2,3,4-tetrahydro-isoquinolin-8-yl}-4-methoxy-phenyl)-acetic acid;
(3-{2-[trans-2-(3-Chloro-phenyl)-cyclopropanecarbonyl]-5-fluoro-1,2,3,4-tetrahydro-isoquinolin-8-yl}-4-methoxy-phenyl)-acetic acid;
(3-{5-Fluoro-2-[trans-2-(2-fluoro-phenyl)-cyclopropanecarbonyl]-1,2,3,4-tetrahydro-isoquinolin-8-yl}-4-methoxy-phenyl)-acetic acid;
{3-[5-Fluoro-2-(trans-2-o-tolyl-cyclopropanecarbonyl)-1,2,3,4-tetrahydro-isoquinolin-8-yl]-4-methoxy-phenyl}-acetic acid;
8-(5-Carboxymethyl-2-methyl-phenyl)-5-fluoro-3,4-dihydro-1H-isoquinoline-2-carboxylic acid benzyl ester;
8-(5-Carboxymethyl-2-trifluoromethyl-phenyl)-5-fluoro-3,4-dihydro-1H-isoquinoline-2-carboxylic acid benzyl ester;
8-(5-Carboxymethyl-2-chloro-phenyl)-5-fluoro-3,4-dihydro-1H-isoquinoline-2-carboxylic acid benzyl ester;
8-(5-Carboxymethyl-2-fluoro-phenyl)-5-fluoro-3,4-dihydro-1H-isoquinoline-2-carboxylic acid benzyl ester;
8-(3-Carboxymethyl-4-chloro-phenyl)-5-fluoro-3,4-dihydro-1H-isoquinoline-2-carboxylic acid benzyl ester;
8-(3-Carboxymethyl-4-fluoro-phenyl)-5-fluoro-3,4-dihydro-1H-isoquinoline-2-carboxylic acid benzyl ester;
8-(3-Carboxymethyl-4-methoxy-phenyl)-5-fluoro-3,4-dihydro-1H-isoquinoline-2-carboxylic acid benzyl ester;
8-(3-Carboxymethyl-5-fluoro-phenyl)-5-fluoro-3,4-dihydro-1H-isoquinoline-2-carboxylic acid benzyl ester;
8-(3-Carboxymethyl-5-methoxy-phenyl)-5-fluoro-3,4-dihydro-1H-isoquinoline-2-carboxylic acid benzyl ester;
8-(3-Carboxymethyl-2-fluoro-phenyl)-5-fluoro-3,4-dihydro-1H-isoquinoline-2-carboxylic acid benzyl ester;
6-(5-Carboxymethyl-2-methoxy-phenyl)-9-fluoro-1,2,4,5-tetrahydro-benzo[d]azepine-3-carboxylic acid benzyl ester;
4-(5-Carboxymethyl-2-methoxy-phenyl)-7-fluoro-1,3-dihydro-isoindole-2-carboxylic acid benzyl ester;

8-(3-Carboxymethyl-5-chloro-phenyl)-5-fluoro-3,4-dihydro-1H-isoquinoline-2-carboxylic acid benzyl ester;

8-(5-Carboxymethyl-2-methanesulfonyl-phenyl)-5-fluoro-3,4-dihydro-1H-isoquinoline-2-carboxylic acid benzyl ester;

8-(5-Carboxymethyl-2-trifluoromethoxy-phenyl)-5-fluoro-3,4-dihydro-1H-isoquinoline-2-carboxylic acid benzyl ester;

8-(5-Carboxymethyl-2-isopropoxy-phenyl)-5-fluoro-3,4-dihydro-1H-isoquinoline-2-carboxylic acid benzyl ester;

8-(5-Carboxymethyl-2-fluoro-phenyl)-3,4-dihydro-1H-isoquinoline-2-carboxylic acid benzyl ester;

8-(3-Carboxymethyl-phenyl)-5-fluoro-3,4-dihydro-1H-isoquinoline-2-carboxylic acid benzyl ester;

8-(5-Carboxymethyl-2-methoxy-phenyl)-5-methanesulfonyl-3,4-dihydro-1H-isoquinoline-2-carboxylic acid benzyl ester;

{3-[5-Fluoro-2-((1R,2R)-2-phenyl-cyclopropanecarbonyl)-1,2,3,4-tetrahydro-isoquinolin-8-yl]-4-trifluoromethoxy-phenyl}-acetic acid;

{3-[5-Fluoro-2-((1R,2R)-2-phenyl-cyclopropanecarbonyl)-1,2,3,4-tetrahydro-isoquinolin-8-yl]-4-isopropoxy-phenyl}-acetic acid;

{4-Chloro-3-[5-fluoro-2-((1R,2R)-2-phenyl-cyclopropanecarbonyl)-1,2,3,4-tetrahydro-isoquinolin-8-yl]-phenyl}-acetic acid;

{3-[5-Fluoro-2-((1R,2R)-2-phenyl-cyclopropanecarbonyl)-1,2,3,4-tetrahydro-isoquinolin-8-yl]-4-methanesulfonyl-phenyl}-acetic acid;

8-(2-Carboxymethyl-phenyl)-5-fluoro-3,4-dihydro-1H-isoquinoline-2-carboxylic acid benzyl ester;

8-(5-Carboxymethyl-2-methoxy-phenyl)-5,6-difluoro-3,4-dihydro-1H-isoquinoline-2-carboxylic acid benzyl ester;

8-(5-Carboxymethyl-2-methoxy-phenyl)-6-fluoro-3,4-dihydro-1H-isoquinoline-2-carboxylic acid benzyl ester;

8-(5-Carboxymethyl-2-methoxy-phenyl)-7-fluoro-3,4-dihydro-1H-isoquinoline-2-carboxylic acid benzyl ester;

{3-[6-Fluoro-2-((1R,2R)-2-phenyl-cyclopropanecarbonyl)-1,2,3,4-tetrahydro-isoquinolin-8-yl]-4-methoxy-phenyl}-acetic acid;

{3-[7-Fluoro-2-((1R,2R)-2-phenyl-cyclopropanecarbonyl)-1,2,3,4-tetrahydro-isoquinolin-8-yl]-4-methoxy-phenyl}-acetic acid;

{3-[9-Fluoro-3-(trans-2-phenyl-cyclopropanecarbonyl)-2,3,4,5-tetrahydro-1H-benzo[d]azepin-6-yl]-4-methoxy-phenyl}-acetic acid;

{3-[7-Fluoro-2-(trans-2-phenyl-cyclopropanecarbonyl)-2,3-dihydro-1H-isoindol-4-yl]-4-methoxy-phenyl}-acetic acid;

{3-[5,7-Difluoro-2-((1R,2R)-2-phenyl-cyclopropanecarbonyl)-1,2,3,4-tetrahydro-isoquinolin-8-yl]-4-methoxy-phenyl}-acetic acid;

8-(5-Carboxymethyl-2-methoxy-phenyl)-5,7-difluoro-3,4-dihydro-1H-isoquinoline-2-carboxylic acid benzyl ester;

8-(4-Carboxymethyl-3-chloro-phenyl)-5-fluoro-3,4-dihydro-1H-isoquinoline-2-carboxylic acid benzyl ester;

8-(4-Carboxymethyl-phenyl)-5-fluoro-3,4-dihydro-1H-isoquinoline-2-carboxylic acid benzyl ester;

(3-{5-Fluoro-2-[3-(4-fluoro-phenoxy)-propionyl]-1,2,3,4-tetrahydro-isoquinolin-8-yl}-4-methoxy-phenyl)-acetic acid;

{3-[5-Fluoro-2-(2-phenoxy-acetyl)-1,2,3,4-tetrahydro-isoquinolin-8-yl]-4-methoxy-phenyl}-acetic acid;

(3-{5-Fluoro-2-[2-(4-fluoro-phenoxy)-acetyl]-1,2,3,4-tetrahydro-isoquinolin-8-yl}-4-methoxy-phenyl)-acetic acid;

(3-{5-Fluoro-2-[4-(2-fluoro-phenyl)-butyryl]-1,2,3,4-tetrahydro-isoquinolin-8-yl}-4-methoxy-phenyl)-acetic acid;

{3-[2-(2-Ethoxy-acetyl)-5-fluoro-1,2,3,4-tetrahydro-isoquinolin-8-yl]-4-methoxy-phenyl}-acetic acid;

{3-[2-(2-tert-Butoxy-acetyl)-5-fluoro-1,2,3,4-tetrahydro-isoquinolin-8-yl]-4-methoxy-phenyl}-acetic acid;

(3-{5-Fluoro-2-[trans-2-(3-fluoro-phenyl)-cyclopropanecarbonyl]-1,2,3,4-tetrahydro-isoquinolin-8-yl}-4-methoxy-phenyl)-acetic acid;

(3-{5-Fluoro-2-[2-(5-methoxy-benzo[d]isoxazol-3-yl)-acetyl]-1,2,3,4-tetrahydro-isoquinolin-8-yl}-4-methoxy-phenyl)-acetic acid;

{3-[5-Fluoro-2-(2,2,3,3-tetramethyl-cyclopropanecarbonyl)-1,2,3,4-tetrahydro-isoquinolin-8-yl]-4-methoxy-phenyl}-acetic acid;

{3-[5-Fluoro-2-(3-pyridin-3-yl-propionyl)-1,2,3,4-tetrahydro-isoquinolin-8-yl]-4-methoxy-phenyl}-acetic acid;

[3-(2-Cyclopropanecarbonyl-5-fluoro-1,2,3,4-tetrahydro-isoquinolin-8-yl)-4-methoxy-phenyl]-acetic acid;

{3-[2-(3-3,4-Dihydro-2H-quinolin-1-yl-propionyl)-5-fluoro-1,2,3,4-tetrahydro-isoquinolin-8-yl]-4-methoxy-phenyl}-acetic acid;

{3-[5-Fluoro-2-(3-phenyl-propionyl)-1,2,3,4-tetrahydro-isoquinolin-8-yl]-4-methoxy-phenyl}-acetic acid;

{3-[2-(2,2-Dimethyl-cyclopropanecarbonyl)-5-fluoro-1,2,3,4-tetrahydro-isoquinolin-8-yl]-4-methoxy-phenyl}-acetic acid;

{3-[5-Fluoro-2-(3-o-tolyl-propionyl)-1,2,3,4-tetrahydro-isoquinolin-8-yl]-4-methoxy-phenyl}-acetic acid;

(3-{5-Fluoro-2-[3-(3-methyl-indol-1-yl)-propionyl]-1,2,3,4-tetrahydro-isoquinolin-8-yl}-4-methoxy-phenyl)-acetic acid;

(3-{2-[2-(2-Chloro-benzyloxy)-acetyl]-5-fluoro-1,2,3,4-tetrahydro-isoquinolin-8-yl}-4-methoxy-phenyl)-acetic acid;

{3-[2-(3-2,3-Dihydro-indol-1-yl-propionyl)-5-fluoro-1,2,3,4-tetrahydro-isoquinolin-8-yl]-4-methoxy-phenyl}-acetic acid;

{3-[5-Fluoro-2-(trans-2-phenyl-cyclopropanecarbonyl)-1,2,3,4-tetrahydro-isoquinolin-8-yl]-4-methoxy-phenyl}-acetic acid;

(3-{5-Fluoro-2-[3-(2-methyl-1H-indol-3-yl)-propionyl]-1,2,3,4-tetrahydro-isoquinolin-8-yl}-4-methoxy-phenyl)-acetic acid;

(3-{5-Fluoro-2-[3-(1-methyl-1H-indol-3-yl)-propionyl]-1,2,3,4-tetrahydro-isoquinolin-8-yl}-4-methoxy-phenyl)-acetic acid;

(3-{5-Fluoro-2-[3-(5-methoxy-1H-indol-3-yl)-propionyl]-1,2,3,4-tetrahydro-isoquinolin-8-yl}-4-methoxy-phenyl)-acetic acid;

(3-{2-[(1R,2R)-2-(4-Chloro-phenyl)-cyclopropanecarbonyl]-5-fluoro-1,2,3,4-tetrahydro-isoquinolin-8-yl}-4-methoxy-phenyl)-acetic acid;

(3-{5-Fluoro-2-[(1R,2R)-2-(3-fluoro-phenyl)-cyclopropanecarbonyl]-1,2,3,4-tetrahydro-isoquinolin-8-yl}-4-methoxy-phenyl)-acetic acid;

(3-{5-Fluoro-2-[(1R,2R)-2-(2-fluoro-phenyl)-cyclopropanecarbonyl]-1,2,3,4-tetrahydro-isoquinolin-8-yl}-4-methoxy-phenyl)-acetic acid;

{3-[5-Fluoro-2-(3-indazol-1-yl-propionyl)-1,2,3,4-tetrahydro-isoquinolin-8-yl]-4-methoxy-phenyl}-acetic acid;

(3-{5-Chloro-2-[(1R,2R)-2-(4-chloro-phenyl)-cyclopropanecarbonyl]-1,2,3,4-tetrahydro-isoquinolin-8-yl}-4-methoxy-phenyl)-acetic acid;

(3-{5-Chloro-2-[(1R,2R)-2-(3-fluoro-phenyl)-cyclopropanecarbonyl]-1,2,3,4-tetrahydro-isoquinolin-8-yl}-4-methoxy-phenyl)-acetic acid;

(3-{5-Chloro-2-[(1R,2R)-2-(2-fluoro-phenyl)-cyclopropanecarbonyl]-1,2,3,4-tetrahydro-isoquinolin-8-yl}-4-methoxy-phenyl)-acetic acid;

{3-[5-Chloro-2-((1R,2R)-2-phenyl-cyclopropanecarbonyl)-1,2,3,4-tetrahydro-isoquinolin-8-yl]-4-methoxy-phenyl}-acetic acid;

{3-[5-Chloro-2-(3-indazol-1-yl-propionyl)-1,2,3,4-tetrahydro-isoquinolin-8-yl]-4-methoxy-phenyl}-acetic acid;

(3-{5-Chloro-2-[2-(2-chloro-benzyloxy)-acetyl]-1,2,3,4-tetrahydro-isoquinolin-8-yl}-4-methoxy-phenyl)-acetic acid;

(3-{5-Chloro-2-[4-(2-fluoro-phenyl)-butyryl]-1,2,3,4-tetrahydro-isoquinolin-8-yl}-4-methoxy-phenyl)-acetic acid;

(3-{5-Chloro-2-[3-(1-methyl-1H-indol-3-yl)-propionyl]-1,2,3,4-tetrahydro-isoquinolin-8-yl}-4-methoxy-phenyl)-acetic acid;

{3-[5-Chloro-2-(3-phenyl-propionyl)-1,2,3,4-tetrahydro-isoquinolin-8-yl]-4-methoxy-phenyl}-acetic acid;

{3-[5-Chloro-2-(3-3,4-dihydro-2H-quinolin-1-yl-propionyl)-1,2,3,4-tetrahydro-isoquinolin-8-yl]-4-methoxy-phenyl}-acetic acid;

{3-[5-Chloro-2-(3-2,3-dihydro-indol-1-yl-propionyl)-1,2,3,4-tetrahydro-isoquinolin-8-yl]-4-methoxy-phenyl}-acetic acid;

(3-{5-Chloro-2-[3-(2-methyl-1H-indol-3-yl)-propionyl]-1,2,3,4-tetrahydro-isoquinolin-8-yl}-4-methoxy-phenyl)-acetic acid;

{3-[5-Fluoro-2-((1R,2R)-2-phenyl-cyclopropanecarbonyl)-1,2,3,4-tetrahydro-isoquinolin-8-yl]-4-methoxy-phenyl}-acetic acid;

{3-[5-Fluoro-2-((1S,2S)-2-phenyl-cyclopropanecarbonyl)-1,2,3,4-tetrahydro-isoquinolin-8-yl]-4-methoxy-phenyl}-acetic acid;

[3-(2-Cyclopropanecarbonyl-5-trifluoromethyl-1,2,3,4-tetrahydro-isoquinolin-8-yl)-4-methoxy-phenyl]-acetic acid;

{4-Methoxy-3-[2-(trans-2-phenyl-cyclopropanecarbonyl)-5-trifluoromethyl-1,2,3,4-tetrahydro-isoquinolin-8-yl]-phenyl}-acetic acid;

{3-[5,6-Difluoro-2-((1R,2R)-2-phenyl-cyclopropanecarbonyl)-1,2,3,4-tetrahydro-isoquinolin-8-yl]-4-methoxy-phenyl}-acetic acid;

(3-{5-Fluoro-2-[(E)-(3-phenyl-acryloyl)]-1,2,3,4-tetrahydro-isoquinolin-8-yl}-4-methoxy-phenyl)-acetic acid;

(3-{5-Fluoro-2-[(E)-3-(6-methoxy-pyridin-3-yl)-acryloyl]-1,2,3,4-tetrahydro-isoquinolin-8-yl}-4-methoxy-phenyl)-acetic acid;

(3-{2-[(E)-3-(2,4-Dimethyl-thiazol-5-yl)-acryloyl]-5-fluoro-1,2,3,4-tetrahydro-isoquinolin-8-yl}-4-methoxy-phenyl)-acetic acid;

{3-[2-((E)-3-Benzothiazol-2-yl-acryloyl)-5-fluoro-1,2,3,4-tetrahydro-isoquinolin-8-yl]-4-methoxy-phenyl}-acetic acid;

{3-[5-Fluoro-2-((E)-3-pyridin-3-yl-acryloyl)-1,2,3,4-tetrahydro-isoquinolin-8-yl]-4-methoxy-phenyl}-acetic acid;

(3-{2-[(E)-3-(2,5-Dimethyl-2H-pyrazol-3-yl)-acryloyl]-5-fluoro-1,2,3,4-tetrahydro-isoquinolin-8-yl}-4-methoxy-phenyl)-acetic acid;

{3-[5-Fluoro-2-(3-pyridin-2-yl-propionyl)-1,2,3,4-tetrahydro-isoquinolin-8-yl]-4-methoxy-phenyl}-acetic acid;

(3-{5-Fluoro-2-[3-(6-methyl-pyridin-2-yl)-propionyl]-1,2,3,4-tetrahydro-isoquinolin-8-yl}-4-methoxy-phenyl)-acetic acid;

{3-[5-Fluoro-2-(3-pyrimidin-2-yl-propionyl)-1,2,3,4-tetrahydro-isoquinolin-8-yl]-4-methoxy-phenyl}-acetic acid;

(3-{5-Fluoro-2-[2-(pyridin-3-yloxy)-acetyl]-1,2,3,4-tetrahydro-isoquinolin-8-yl}-4-methoxy-phenyl)-acetic acid;

(3-{5-Fluoro-2-[trans-2-(2-trifluoromethyl-phenyl)-cyclopropanecarbonyl]-1,2,3,4-tetrahydro-isoquinolin-8-yl}-4-methoxy-phenyl)-acetic acid;

(3-{5-Fluoro-2-[trans-2-(4-methoxy-phenyl)-cyclopropanecarbonyl]-1,2,3,4-tetrahydro-isoquinolin-8-yl}-4-methoxy-phenyl)-acetic acid;

(3-{2-[3-(4-Chloro-phenyl)-3-phenyl-propionyl]-5-fluoro-1,2,3,4-tetrahydro-isoquinolin-8-yl}-4-methoxy-phenyl)-acetic acid;

(3-{2-[trans-2-(2,4-Dichloro-phenyl)-cyclopropanecarbonyl]-5-fluoro-1,2,3,4-tetrahydro-isoquinolin-8-yl}-4-methoxy-phenyl)-acetic acid;

{3-[8-Fluoro-2-((1R,2R)-2-phenyl-cyclopropanecarbonyl)-1,2,3,4-tetrahydro-isoquinolin-5-yl]-4-methoxy-phenyl}-acetic acid;

{3-[8-Fluoro-2-(4-phenyl-butyryl)-1,2,3,4-tetrahydro-isoquinolin-5-yl]-4-methoxy-phenyl}-acetic acid;

{3-[8-Fluoro-2-(3-phenyl-propionyl)-1,2,3,4-tetrahydro-isoquinolin-5-yl]-4-methoxy-phenyl}-acetic acid;

{3-[8-Fluoro-2-(3-phenoxy-propionyl)-1,2,3,4-tetrahydro-isoquinolin-5-yl]-4-methoxy-phenyl}-acetic acid;

(3-{2-[2-(2-Chloro-benzyloxy)-acetyl]-8-fluoro-1,2,3,4-tetrahydro-isoquinolin-5-yl}-4-methoxy-phenyl)-acetic acid;

{3-[2-(3-3,4-Dihydro-2H-quinolin-1-yl-propionyl)-8-fluoro-1,2,3,4-tetrahydro-isoquinolin-5-yl]-4-methoxy-phenyl}-acetic acid;

(3-{8-Fluoro-2-[3-(1-methyl-1H-indol-3-yl)-propionyl]-1,2,3,4-tetrahydro-isoquinolin-5-yl}-4-methoxy-phenyl)-acetic acid;

{3-[5-Fluoro-2-((R)-3-phenyl-butyryl)-1,2,3,4-tetrahydro-isoquinolin-8-yl]-4-methoxy-phenyl}-acetic acid;

{3-[5-Fluoro-2-((S)-3-phenyl-butyryl)-1,2,3,4-tetrahydro-isoquinolin-8-yl]-4-methoxy-phenyl}-acetic acid;

{3-[5-Fluoro-2-(3-methyl-3-phenyl-butyryl)-1,2,3,4-tetrahydro-isoquinolin-8-yl]-4-methoxy-phenyl}-acetic acid;

{3-[5-Fluoro-2-(2-methyl-3-phenyl-propionyl)-1,2,3,4-tetrahydro-isoquinolin-8-yl]-4-methoxy-phenyl}-acetic acid;

{3-[5-Fluoro-2-(indane-2-carbonyl)-1,2,3,4-tetrahydro-isoquinolin-8-yl]-4-methoxy-phenyl}-acetic acid;

{3-[5-Fluoro-2-(2-indan-2-yl-acetyl)-1,2,3,4-tetrahydro-isoquinolin-8-yl]-4-methoxy-phenyl}-acetic acid;

{3-[5-Fluoro-2-(indane-1-carbonyl)-1,2,3,4-tetrahydro-isoquinolin-8-yl]-4-methoxy-phenyl}-acetic acid;

{3-[2-(Chroman-3-carbonyl)-5-fluoro-1,2,3,4-tetrahydro-isoquinolin-8-yl]-4-methoxy-phenyl}-acetic acid;

{3-[5-Fluoro-2-(4-oxo-1,2,3,4-tetrahydro-naphthalene-2-carbonyl)-1,2,3,4-tetrahydro-isoquinolin-8-yl]-4-methoxy-phenyl}-acetic acid;

{3-[2-(Chroman-2-carbonyl)-5-fluoro-1,2,3,4-tetrahydro-isoquinolin-8-yl]-4-methoxy-phenyl}-acetic acid;

{3-[2-(Bicyclo[4.2.0]octa-1(6),2,4-triene-7-carbonyl)-5-fluoro-1,2,3,4-tetrahydro-isoquinolin-8-yl]-4-methoxy-phenyl}-acetic acid;

{3-[5-Fluoro-2-(4-phenyl-butyryl)-1,2,3,4-tetrahydro-isoquinolin-8-yl]-4-methoxy-phenyl}-acetic acid;

{3-[5-Fluoro-2-(4-oxo-4-phenyl-butyryl)-1,2,3,4-tetrahydro-isoquinolin-8-yl]-4-methoxy-phenyl}-acetic acid;

(3-{5-Fluoro-2-[2-(1-methyl-1H-indol-3-yl)-acetyl]-1,2,3,4-tetrahydro-isoquinolin-8-yl}-4-methoxy-phenyl)-acetic acid;

2-{3-[5-Fluoro-2-((1R,2R)-2-phenyl-cyclopropanecarbonyl]-1,2,3,4-tetrahydro-isoquinolin-8-yl]-4-methoxy-phenyl}-propionic acid;

{3-[2-(2-Benzo[d]isoxazol-3-yl-acetyl)-5-fluoro-1,2,3,4-tetrahydro-isoquinolin-8-yl]-4-methoxy-phenyl}-acetic acid;

{3-[5-Fluoro-2-(3-oxo-indane-1-carbonyl)-1,2,3,4-tetrahydro-isoquinolin-8-yl]-4-methoxy-phenyl}-acetic acid;

{3-[5-Fluoro-2-(1,2,3,4-tetrahydro-naphthalene-2-carbonyl)-1,2,3,4-tetrahydro-isoquinolin-8-yl]-4-methoxy-phenyl}-acetic acid;

{3-[5-Fluoro-2-(2-1H-indazol-3-yl-acetyl)-1,2,3,4-tetrahydro-isoquinolin-8-yl]-4-methoxy-phenyl}-acetic acid;

(3-{5-Fluoro-2-[3-(3-methyl-indazol-1-yl)-propionyl]-1,2,3,4-tetrahydro-isoquinolin-8-yl}-4-methoxy-phenyl)-acetic acid;

(3-{5-Fluoro-2-[3-(5-fluoro-indazol-1-yl)-propionyl]-1,2,3,4-tetrahydro-isoquinolin-8-yl}-4-methoxy-phenyl)-acetic acid;

{3-[2-(2-Cyclohexyl-acetyl)-5-fluoro-1,2,3,4-tetrahydro-isoquinolin-8-yl]-4-methoxy-phenyl}-acetic acid;

(3-{5-Fluoro-2-[2-(1-hydroxy-cyclohexyl)-acetyl]-1,2,3,4-tetrahydro-isoquinolin-8-yl}-4-methoxy-phenyl)-acetic acid;

{3-[2-(3,3-Dimethyl-butyryl)-5-fluoro-1,2,3,4-tetrahydro-isoquinolin-8-yl]-4-methoxy-phenyl}-acetic acid;

{3-[5-Fluoro-2-(2-fluoro-benzylcarbamoyl)-1,2,3,4-tetrahydro-isoquinolin-8-yl]-4-methoxy-phenyl}-acetic acid;

{3-[5-Fluoro-2-(3-fluoro-benzylcarbamoyl)-1,2,3,4-tetrahydro-isoquinolin-8-yl]-4-methoxy-phenyl}-acetic acid;

{3-[5-Fluoro-2-(4-fluoro-benzylcarbamoyl)-1,2,3,4-tetrahydro-isoquinolin-8-yl]-4-methoxy-phenyl}-acetic acid;

[3-(5-Fluoro-2-phenethylcarbamoyl-1,2,3,4-tetrahydro-isoquinolin-8-yl)-4-methoxy-phenyl]-acetic acid;

{3-[2-(2-Chloro-benzylcarbamoyl)-5-fluoro-1,2,3,4-tetrahydro-isoquinolin-8-yl]-4-methoxy-phenyl}-acetic acid;

{3-[5-Fluoro-2-(2-methoxy-benzylcarbamoyl)-1,2,3,4-tetrahydro-isoquinolin-8-yl]-4-methoxy-phenyl}-acetic acid;

[3-(2-Benzylcarbamoyl-5-fluoro-1,2,3,4-tetrahydro-isoquinolin-8-yl)-4-methoxy-phenyl]-acetic acid;

[3-(5-Fluoro-2-propylcarbamoyl-1,2,3,4-tetrahydro-isoquinolin-8-yl)-4-methoxy-phenyl]-acetic acid;

8-(5-Carboxymethyl-2-methoxy-phenyl)-5-fluoro-3,4-dihydro-1H-isoquinoline-2-carboxylic acid 3-fluoro-benzyl ester;

8-(5-Carboxymethyl-2-methoxy-phenyl)-5-fluoro-3,4-dihydro-1H-isoquinoline-2-carboxylic acid 4-fluoro-benzyl ester;

8-[5-(1-Carboxy-ethyl)-2-methoxy-phenyl]-5-fluoro-3,4-dihydro-1H-isoquinoline-2-carboxylic acid 2-fluoro-benzyl ester;

8-(5-Carboxymethyl-2-methoxy-phenyl)-5-fluoro-3,4-dihydro-1H-isoquinoline-2-carboxylic acid ethyl ester;

8-(5-Carboxymethyl-2-methoxy-phenyl)-5-fluoro-3,4-dihydro-1H-isoquinoline-2-carboxylic acid isobutyl ester;

8-(5-Carboxymethyl-2-methoxy-phenyl)-5-fluoro-3,4-dihydro-1H-isoquinoline-2-carboxylic acid isopropyl ester;

8-(3-Carboxymethoxy-5-chloro-phenyl)-5-fluoro-3,4-dihydro-1H-isoquinoline-2-carboxylic acid benzyl ester;

8-(2-Carboxymethoxy-5-chloro-phenyl)-5-fluoro-3,4-dihydro-1H-isoquinoline-2-carboxylic acid benzyl ester;

8-(5-Carboxymethyl-2-methoxy-phenyl)-5-fluoro-3,4-dihydro-1H-isoquinoline-2-carboxylic acid 2-fluoro-benzyl ester;

8-(5-Carboxymethyl-2-methoxy-phenyl)-5-fluoro-3,4-dihydro-1H-isoquinoline-2-carboxylic acid 2,3-difluoro-benzyl ester;

8-(5-Carboxymethyl-2-methoxy-phenyl)-5-fluoro-3,4-dihydro-1H-isoquinoline-2-carboxylic acid 2-methyl-2H-pyrazol-3-ylmethyl ester;

8-(5-Carboxymethyl-2-methoxy-phenyl)-5-fluoro-3,4-dihydro-1H-isoquinoline-2-carboxylic acid 2,5-dimethyl-2H-pyrazol-3-ylmethyl ester;

8-(5-Carboxymethyl-2-methoxy-phenyl)-5-fluoro-3,4-dihydro-1H-isoquinoline-2-carboxylic acid 2-methyl-thiazol-4-ylmethyl ester;

8-(5-Carboxymethyl-2-methoxy-phenyl)-5-fluoro-3,4-dihydro-1H-isoquinoline-2-carboxylic acid 2-methyl-thiazol-5-ylmethyl ester;

8-(5-Carboxymethyl-2-methoxy-phenyl)-5-fluoro-3,4-dihydro-1H-isoquinoline-2-carboxylic acid pyrimidin-5-ylmethyl ester;

8-(5-Carboxymethyl-2-methoxy-phenyl)-5-fluoro-3,4-dihydro-1H-isoquinoline-2-carboxylic acid 2-(4-methyl-thiazol-5-yl)-ethyl ester;

8-(5-Carboxymethyl-2-methoxy-phenyl)-5-chloro-3,4-dihydro-1H-isoquinoline-2-carboxylic acid benzyl ester;

8-(5-Carboxymethyl-2-methoxy-phenyl)-5-methyl-3,4-dihydro-1H-isoquinoline-2-carboxylic acid benzyl ester;

8-(5-Carboxymethyl-2-methoxy-phenyl)-5-methoxy-3,4-dihydro-1H-isoquinoline-2-carboxylic acid benzyl ester;

8-(5-Carboxymethyl-2-methoxy-phenyl)-5-fluoro-3,4-dihydro-1H-isoquinoline-2-carboxylic acid benzyl ester;

8-(5-Carboxymethyl-2-methoxy-phenyl)-5-trifluoromethyl-3,4-dihydro-1H-isoquinoline-2-carboxylic acid benzyl ester;

5-(5-Carboxymethyl-2-methoxy-phenyl)-8-fluoro-3,4-dihydro-1H-isoquinoline-2-carboxylic acid benzyl ester;

{3-[5-Fluoro-2-((1R,2R)-2-phenyl-cyclopropanecarbonyl)-1,2,3,4-tetrahydro-isoquinolin-8-yl]-4-trifluoromethoxy-phenoxy}-acetic acid;

{3-[5-Fluoro-2-((1R,2R)-2-phenyl-cyclopropanecarbonyl)-1,2,3,4-tetrahydro-isoquinolin-8-yl]-4-isopropoxy-phenoxy}-acetic acid;

8-(5-Carboxymethoxy-2-trifluoromethoxy-phenyl)-5-fluoro-3,4-dihydro-1H-isoquinoline-2-carboxylic acid benzyl ester;

8-(5-Carboxymethoxy-2-isopropoxy-phenyl)-5-fluoro-3,4-dihydro-1H-isoquinoline-2-carboxylic acid benzyl ester;

8-(4-Carboxymethyl-2-fluoro-phenyl)-5-fluoro-3,4-dihydro-1H-isoquinoline-2-carboxylic acid benzyl ester;

8-(4-Carboxymethyl-2-chloro-phenyl)-5-fluoro-3,4-dihydro-1H-isoquinoline-2-carboxylic acid benzyl ester;

8-(4-Carboxymethyl-2-methoxy-phenyl)-5-fluoro-3,4-dihydro-1H-isoquinoline-2-carboxylic acid benzyl ester;

8-(6-Carboxymethyl-benzo[1,3]dioxol-4-yl)-5-fluoro-3,4-dihydro-1H-isoquinoline-2-carboxylic acid benzyl ester;

8-(7-Carboxymethyl-2,3-dihydro-benzo[1,4]dioxin-5-yl)-5-fluoro-3,4-dihydro-1H-isoquinoline-2-carboxylic acid benzyl ester;

8-(5-Carboxymethyl-2-methoxy-phenyl)-5-cyano-3,4-dihydro-1H-isoquinoline-2-carboxylic acid benzyl ester;

8-(5-Carboxymethyl-2-methoxy-phenyl)-3,4-dihydro-1H-isoquinoline-2-carboxylic acid benzyl ester;

8-[5-(1-Carboxy-ethyl)-2-methoxy-phenyl]-5-fluoro-3,4-dihydro-1H-isoquinoline-2-carboxylic acid benzyl ester;

8-(4-Carboxymethoxy-phenyl)-5-fluoro-3,4-dihydro-1H-isoquinoline-2-carboxylic acid benzyl ester;
8-(2-Carboxymethoxy-5-fluoro-phenyl)-3,4-dihydro-1H-isoquinoline-2-carboxylic acid benzyl ester;
8-[2-(3-Carboxy-propoxy)-5-fluoro-phenyl]-3,4-dihydro-1H-isoquinoline-2-carboxylic acid benzyl ester;
8-(3-Carboxymethoxy-phenyl)-5-fluoro-3,4-dihydro-1H-isoquinoline-2-carboxylic acid benzyl ester;
8-(5-Carboxymethoxy-2-chloro-phenyl)-5-fluoro-3,4-dihydro-1H-isoquinoline-2-carboxylic acid benzyl ester;
8-(5-Carboxymethoxy-2-methoxy-phenyl)-5-fluoro-3,4-dihydro-1H-isoquinoline-2-carboxylic acid benzyl ester;
8-(5-Carboxymethoxy-2-chloro-phenyl)-5-chloro-3,4-dihydro-1H-isoquinoline-2-carboxylic acid benzyl ester;
8-(5-Carboxymethoxy-2-chloro-phenyl)-5-methyl-3,4-dihydro-1H-isoquinoline-2-carboxylic acid benzyl ester;
8-(5-Carboxymethoxy-2-chloro-phenyl)-5-trifluoromethyl-3,4-dihydro-1H-isoquinoline-2-carboxylic acid benzyl ester;
8-(5-Carboxymethoxy-2-chloro-phenyl)-3,4-dihydro-1H-isoquinoline-2-carboxylic acid benzyl ester;
{3-[5-Fluoro-2-((1R,2R)-2-phenyl-cyclopropanecarbonyl)-1,2,3,4-tetrahydro-isoquinolin-8-yl]-4-methoxy-phenoxy}-acetic acid;
(4-{5-Fluoro-2-[3-(1-methyl-1H-indol-3-yl)-propionyl]-1,2,3,4-tetrahydro-isoquinolin-8-yl}-3-methoxy-phenyl)-acetic acid;
{4-[5-Fluoro-2-((1R,2R)-2-phenyl-cyclopropanecarbonyl)-1,2,3,4-tetrahydro-isoquinolin-8-yl]-3-methoxy-phenyl}-acetic acid;
(4-{5-Fluoro-2-[4-(2-fluoro-phenyl)-butyryl]-1,2,3,4-tetrahydro-isoquinolin-8-yl}-3-methoxy-phenyl)-acetic acid;
(4-{5-Fluoro-2-[3-(2-methyl-1H-indol-3-yl)-propionyl]-1,2,3,4-tetrahydro-isoquinolin-8-yl}-3-methoxy-phenyl)-acetic acid;
{4-[5-Fluoro-2-(4-phenyl-butyryl)-1,2,3,4-tetrahydro-isoquinolin-8-yl]-3-methoxy-phenyl}-acetic acid;
{4-[5-Fluoro-2-(3-methyl-3-phenyl-butyryl)-1,2,3,4-tetrahydro-isoquinolin-8-yl]-3-methoxy-phenyl}-acetic acid;
{4-[5-Fluoro-2-((R)-3-phenyl-butyryl)-1,2,3,4-tetrahydro-isoquinolin-8-yl]-3-methoxy-phenyl}-acetic acid;
(4-{5-Fluoro-2-[3-(5-fluoro-indazol-1-yl)-propionyl]-1,2,3,4-tetrahydro-isoquinolin-8-yl}-3-methoxy-phenyl)-acetic acid;
{4-[2-(3-2,3-Dihydro-indol-1-yl-propionyl)-5-fluoro-1,2,3,4-tetrahydro-isoquinolin-8-yl]-3-methoxy-phenyl}-acetic acid;
(4-{5-Fluoro-2-[3-(4-fluoro-phenoxy)-propionyl]-1,2,3,4-tetrahydro-isoquinolin-8-yl}-3-methoxy-phenyl)-acetic acid;
(4-{2-[2-(2-Chloro-benzyloxy)-acetyl]-5-fluoro-1,2,3,4-tetrahydro-isoquinolin-8-yl}-3-methoxy-phenyl)-acetic acid;
{4-[5-Fluoro-2-(3-o-tolyl-propionyl)-1,2,3,4-tetrahydro-isoquinolin-8-yl]-3-methoxy-phenyl}-acetic acid;
8-(5-Carboxymethyl-2-ethoxy-phenyl)-5-fluoro-3,4-dihydro-1H-isoquinoline-2-carboxylic acid benzyl ester;
8-(5-Carboxymethyl-2-cyclopropylmethoxy-phenyl)-5-fluoro-3,4-dihydro-1H-isoquinoline-2-carboxylic acid benzyl ester;
8-(5-Carboxymethyl-2-propoxy-phenyl)-5-fluoro-3,4-dihydro-1H-isoquinoline-2-carboxylic acid benzyl ester;
8-(5-Carboxymethyl-2-isobutoxy-phenyl)-5-fluoro-3,4-dihydro-1H-isoquinoline-2-carboxylic acid benzyl ester; and
8-[5-Carboxymethyl-2-(2-methoxy-ethoxy)-phenyl]-5-fluoro-3,4-dihydro-1H-isoquinoline-2-carboxylic acid benzyl ester;
or salts (in particular pharmaceutically acceptable salts) of such compounds;

it is to be understood for any of the above listed compounds, that a stereogenic center, which is not specifically assigned, may be in absolute (R)- or absolute (S)-configuration and that a double bond, which is not specifically assigned, may be in (E)- or (Z)-configuration; notably it is to be understood for any compound listed above which can be separated into atropisomers, that the compound may be a respective atropisomer of formula ($I_{St1}$), a respective atropisomer of formula ($I_{St2}$) or any mixture thereof.

56) Further preferred compounds of formula (I) as defined in embodiment 1) are selected from the group consisting of:
{4-[2-((S)-2-Chroman-4-yl-acetyl)-5-fluoro-1,2,3,4-tetrahydro-isoquinolin-8-yl]-3-methoxy-phenyl}-acetic acid;
{4-[2-((R)-2-Chroman-4-yl-acetyl)-5-fluoro-1,2,3,4-tetrahydro-isoquinolin-8-yl]-3-methoxy-phenyl}-acetic acid;
8-[4-(1-Carboxy-ethoxy)-2-methoxy-phenyl]-5-fluoro-3,4-dihydro-1H-isoquinoline-2-carboxylic acid benzyl ester;
{4-Ethoxy-3-[5-fluoro-2-((S)-3-pyridin-2-yl-butyryl)-1,2,3,4-tetrahydro-isoquinolin-8-yl]-phenyl}-acetic acid;
{4-Ethoxy-3-[5-fluoro-2-((R)-3-pyridin-2-yl-butyryl)-1,2,3,4-tetrahydro-isoquinolin-8-yl]-phenyl}-acetic acid;
{3-Ethoxy-4-[5-fluoro-2-((S)-2-isochroman-1-yl-acetyl)-1,2,3,4-tetrahydro-isoquinolin-8-yl]-phenyl}-acetic acid;
{3-Ethoxy-4-[5-fluoro-2-((R)-2-isochroman-1-yl-acetyl)-1,2,3,4-tetrahydro-isoquinolin-8-yl]-phenyl}-acetic acid;
{3-[2-(2-[(S)-2,3-Dihydro-benzofuran-3-yl]-acetyl)-5-fluoro-1,2,3,4-tetrahydro-isoquinolin-8-yl]-4-ethoxy-phenyl}-acetic acid;
{3-[2-(2-[(R)-2,3-Dihydro-benzofuran-3-yl]-acetyl)-5-fluoro-1,2,3,4-tetrahydro-isoquinolin-8-yl]-4-ethoxy-phenyl}-acetic acid;
{4-Ethoxy-3-[5-fluoro-2-((S)-2-isochroman-4-yl-acetyl)-1,2,3,4-tetrahydro-isoquinolin-8-yl]-phenyl}-acetic acid;
{4-Ethoxy-3-[5-fluoro-2-((R)-2-isochroman-4-yl-acetyl)-1,2,3,4-tetrahydro-isoquinolin-8-yl]-phenyl}-acetic acid;
(4-Ethoxy-3-{5-fluoro-2-[(S)-3-(4-fluoro-phenyl)-butyryl]-1,2,3,4-tetrahydro-isoquinolin-8-yl}-phenyl)-acetic acid;
(4-Ethoxy-3-{5-fluoro-2-[(R)-3-(4-fluoro-phenyl)-butyryl]-1,2,3,4-tetrahydro-isoquinolin-8-yl}-phenyl)-acetic acid;
{4-Ethoxy-3-[5-fluoro-2-((S)-2-methyl-3-phenyl-propionyl)-1,2,3,4-tetrahydro-isoquinolin-8-yl]-phenyl}-acetic acid;
{4-Ethoxy-3-[5-fluoro-2-((R)-2-methyl-3-phenyl-propionyl)-1,2,3,4-tetrahydro-isoquinolin-8-yl]-phenyl}-acetic acid;
8-(5-Carboxymethyl-2-propyl-phenyl)-5-fluoro-3,4-dihydro-1H-isoquinoline-2-carboxylic acid benzyl ester;
8-(4-Carboxymethyl-2-isopropyl-phenyl)-5-fluoro-3,4-dihydro-1H-isoquinoline-2-carboxylic acid benzyl ester;
8-(4-Carboxymethyl-2-isopropoxy-phenyl)-5-fluoro-3,4-dihydro-1H-isoquinoline-2-carboxylic acid benzyl ester;
8-(4-Carboxymethyl-2,6-dimethoxy-phenyl)-5-fluoro-3,4-dihydro-1H-isoquinoline-2-carboxylic acid benzyl ester;
{4-Ethoxy-3-[5-fluoro-2-(2-indan-1-yl-acetyl)-1,2,3,4-tetrahydro-isoquinolin-8-yl]-phenyl}-acetic acid;
{4-Ethoxy-3-[5-fluoro-2-((1R,2R)-2-phenyl-cyclopropanecarbonyl)-1,2,3,4-tetrahydro-isoquinolin-8-yl]-phenyl}-acetic acid;
{4-Ethoxy-3-[5-fluoro-2-((R)-3-phenyl-butyryl)-1,2,3,4-tetrahydro-isoquinolin-8-yl]-phenyl}-acetic acid;

(4-Ethoxy-3-{5-fluoro-2-[2-(1-phenyl-cyclopropyl)-acetyl]-1,2,3,4-tetrahydro-isoquinolin-8-yl}-phenyl)-acetic acid;
(4-Ethoxy-3-{5-fluoro-2-[3-(4-fluoro-phenyl)-3-methyl-butyryl]-1,2,3,4-tetrahydro-isoquinolin-8-yl}-phenyl)-acetic acid;
{4-Ethoxy-3-[5-fluoro-2-(2-isochroman-1-yl-acetyl)-1,2,3,4-tetrahydro-isoquinolin-8-yl]-phenyl}-acetic acid;
{4-Ethoxy-3-[5-fluoro-2-(3-methyl-3-phenyl-butyryl)-1,2,3,4-tetrahydro-isoquinolin-8-yl]-phenyl}-acetic acid;
{3-[2-(2-Chroman-4-yl-acetyl)-5-fluoro-1,2,3,4-tetrahydro-isoquinolin-8-yl]-4-ethoxy-phenyl}-acetic acid;
{3-[2-(2-2,3-Dihydro-benzofuran-3-yl-acetyl)-5-fluoro-1,2,3,4-tetrahydro-isoquinolin-8-yl]-4-ethoxy-phenyl}-acetic acid;
{4-Ethoxy-3-[5-fluoro-2-(2-isochroman-4-yl-acetyl)-1,2,3,4-tetrahydro-isoquinolin-8-yl]-phenyl}-acetic acid;
{3-Ethoxy-4-[5-fluoro-2-(2-isochroman-1-yl-acetyl)-1,2,3,4-tetrahydro-isoquinolin-8-yl]-phenyl}-acetic acid;
(3-Ethoxy-4-{5-fluoro-2-[2-(1-phenyl-cyclopropyl)-acetyl]-1,2,3,4-tetrahydro-isoquinolin-8-yl}-phenyl)-acetic acid;
{3-Ethoxy-4-[5-fluoro-2-((1R,2R)-2-phenyl-cyclopropanecarbonyl)-1,2,3,4-tetrahydro-isoquinolin-8-yl]-phenyl}-acetic acid;
{3-Ethoxy-4-[5-fluoro-2-(2-isochroman-4-yl-acetyl)-1,2,3,4-tetrahydro-isoquinolin-8-yl]-phenyl}-acetic acid;
{3-Ethoxy-4-[5-fluoro-2-(2-indan-1-yl-acetyl)-1,2,3,4-tetrahydro-isoquinolin-8-yl]-phenyl}-acetic acid;
{3-Ethoxy-4-[5-fluoro-2-((R)-3-phenyl-butyryl)-1,2,3,4-tetrahydro-isoquinolin-8-yl]-phenyl}-acetic acid;
{4-[2-(2-2,3-Dihydro-benzofuran-3-yl-acetyl)-5-fluoro-1,2,3,4-tetrahydro-isoquinolin-8-yl]-3-ethoxy-phenyl}-acetic acid;
{4-[2-(2-Chroman-4-yl-acetyl)-5-fluoro-1,2,3,4-tetrahydro-isoquinolin-8-yl]-3-ethoxy-phenyl}-acetic acid;
(3-Ethoxy-4-{5-fluoro-2-[3-(4-fluoro-phenyl)-3-methyl-butyryl]-1,2,3,4-tetrahydro-isoquinolin-8-yl}-phenyl)-acetic acid;
{3-Ethoxy-4-[5-fluoro-2-(3-methyl-3-phenyl-butyryl)-1,2,3,4-tetrahydro-isoquinolin-8-yl]-phenyl}-acetic acid;
(3-{5-Fluoro-2-[2-(1-methyl-1,2,3,4-tetrahydro-naphthalen-1-yl)-acetyl]-1,2,3,4-tetrahydro-isoquinolin-8-yl}-4-methoxy-phenyl)-acetic acid;
(3-{2-[2-(2,2-Dimethyl-chroman-4-yl)-acetyl]-5-fluoro-1,2,3,4-tetrahydro-isoquinolin-8-yl}-4-methoxy-phenyl)-acetic acid;
{3-[5-Fluoro-2-(8-methoxy-1,2,3,4-tetrahydro-naphthalene-2-carbonyl)-1,2,3,4-tetrahydro-isoquinolin-8-yl]-4-methoxy-phenyl}-acetic acid;
{3-[2-(2-Chroman-3-yl-acetyl)-5-fluoro-1,2,3,4-tetrahydro-isoquinolin-8-yl]-4-methoxy-phenyl}-acetic acid;
(3-{5-Fluoro-2-[2-(7-fluoro-chroman-4-yl)-acetyl]-1,2,3,4-tetrahydro-isoquinolin-8-yl}-4-methoxy-phenyl)-acetic acid;
(3-{5-Fluoro-2-[2-(6-fluoro-chroman-4-yl)-acetyl]-1,2,3,4-tetrahydro-isoquinolin-8-yl}-4-methoxy-phenyl)-acetic acid;
{3-[2-(3-Cyclopropyl-butyryl)-5-fluoro-1,2,3,4-tetrahydro-isoquinolin-8-yl]-4-methoxy-phenyl}-acetic acid;
(3-{5-Fluoro-2-[2-(8-fluoro-chroman-4-yl)-acetyl]-1,2,3,4-tetrahydro-isoquinolin-8-yl}-4-methoxy-phenyl)-acetic acid;
{3-[5-Fluoro-2-(5,6,7,8-tetrahydro-isoquinolin-8-yl-acetyl)-1,2,3,4-tetrahydro-isoquinolin-8-yl]-4-methoxy-phenyl}-acetic acid;
(3-{5-Fluoro-2-[3-(6-methoxy-pyridin-2-yl)-butyryl]-1,2,3,4-tetrahydro-isoquinolin-8-yl}-4-methoxy-phenyl)-acetic acid;
(3-{5-Fluoro-2-[3-(6-methyl-pyridin-2-yl)-butyryl]-1,2,3,4-tetrahydro-isoquinolin-8-yl}-4-methoxy-phenyl)-acetic acid;
(3-{5-Fluoro-2-[2-(1-phenyl-cyclobutyl)-acetyl]-1,2,3,4-tetrahydro-isoquinolin-8-yl}-4-methoxy-phenyl)-acetic acid;
[3-(5-Fluoro-2-{2-[1-(4-fluoro-phenyl)-cyclobutyl]-acetyl}-1,2,3,4-tetrahydro-isoquinolin-8-yl)-4-methoxy-phenyl]-acetic acid;
(3-{5-Fluoro-2-[3-(3-fluoro-phenyl)-3-methyl-butyryl]-1,2,3,4-tetrahydro-isoquinolin-8-yl}-4-methoxy-phenyl)-acetic acid;
{3-[2-(2-{[(4-Chloro-phenyl)-phenyl-methyl]-methyl-amino}-acetyl)-5-fluoro-1,2,3,4-tetrahydro-isoquinolin-8-yl]-4-methoxy-phenyl}-acetic acid;
{3-[2-(2-Cyclopropyl-acetyl)-5-fluoro-1,2,3,4-tetrahydro-isoquinolin-8-yl]-4-methoxy-phenyl}-acetic acid;
{3-[5-Fluoro-2-((R)-2-phenyl-propionyl)-1,2,3,4-tetrahydro-isoquinolin-8-yl]-4-methoxy-phenyl}-acetic acid;
{3-[5-Fluoro-2-(3-hydroxy-3-phenyl-butyryl)-1,2,3,4-tetrahydro-isoquinolin-8-yl]-4-methoxy-phenyl}-acetic acid;
{3-[5-Fluoro-2-(2-isochroman-1-yl-acetyl)-1,2,3,4-tetrahydro-isoquinolin-8-yl]-4-methoxy-phenyl}-acetic acid;
(3-{5-Fluoro-2-[2-(1-phenyl-cyclopropyl)-acetyl]-1,2,3,4-tetrahydro-isoquinolin-8-yl}-4-methoxy-phenyl)-acetic acid;
(3-{5-Fluoro-2-[2-(2-methyl-1,2,3,4-tetrahydro-isoquinolin-1-yl)-acetyl]-1,2,3,4-tetrahydro-isoquinolin-8-yl}-4-methoxy-phenyl)-acetic acid;
{3-[5-Fluoro-2-(2-1,2,3,4-tetrahydro-naphthalen-2-yl-acetyl)-1,2,3,4-tetrahydro-isoquinolin-8-yl]-4-methoxy-phenyl}-acetic acid;
{3-[5-Fluoro-2-(2-indan-1-yl-acetyl)-1,2,3,4-tetrahydro-isoquinolin-8-yl]-4-methoxy-phenyl}-acetic acid;
{3-[2-(2-Chroman-4-yl-acetyl)-5-fluoro-1,2,3,4-tetrahydro-isoquinolin-8-yl]-4-methoxy-phenyl}-acetic acid;
{3-[5-Fluoro-2-(2-1,2,3,4-tetrahydro-naphthalen-1-yl-acetyl)-1,2,3,4-tetrahydro-isoquinolin-8-yl]-4-methoxy-phenyl}-acetic acid;
{3-[5-Fluoro-2-(4-methyl-3-phenyl-pentanoyl)-1,2,3,4-tetrahydro-isoquinolin-8-yl]-4-methoxy-phenyl}-acetic acid;
{3-[5-Fluoro-2-(3-pyridin-2-yl-butyryl)-1,2,3,4-tetrahydro-isoquinolin-8-yl]-4-methoxy-phenyl}-acetic acid;
{3-[5-Fluoro-2-(3-pyridin-3-yl-butyryl)-1,2,3,4-tetrahydro-isoquinolin-8-yl]-4-methoxy-phenyl}-acetic acid;
{3-[5-Fluoro-2-(3-pyridin-4-yl-butyryl)-1,2,3,4-tetrahydro-isoquinolin-8-yl]-4-methoxy-phenyl}-acetic acid;
{3-[5-Fluoro-2-(3-phenyl-pentanoyl)-1,2,3,4-tetrahydro-isoquinolin-8-yl]-4-methoxy-phenyl}-acetic acid;
{3-[5-Fluoro-2-((R)-1,2,3,4-tetrahydro-naphthalene-1-carbonyl)-1,2,3,4-tetrahydro-isoquinolin-8-yl]-4-methoxy-phenyl}-acetic acid;
{3-[2-(2-2,3-Dihydro-benzofuran-3-yl-acetyl)-5-fluoro-1,2,3,4-tetrahydro-isoquinolin-8-yl]-4-methoxy-phenyl}-acetic acid;
{3-[5-Fluoro-2-(2-isochroman-4-yl-acetyl)-1,2,3,4-tetrahydro-isoquinolin-8-yl]-4-methoxy-phenyl}-acetic acid;
{3-[2-(Chroman-4-carbonyl)-5-fluoro-1,2,3,4-tetrahydro-isoquinolin-8-yl]-4-methoxy-phenyl}-acetic acid;
{3-[5-Fluoro-2-(isochroman-1-carbonyl)-1,2,3,4-tetrahydro-isoquinolin-8-yl]-4-methoxy-phenyl}-acetic acid;
{3-[5-Fluoro-2-(isochroman-3-carbonyl)-1,2,3,4-tetrahydro-isoquinolin-8-yl]-4-methoxy-phenyl}-acetic acid;

[4-Ethoxy-3-(5-fluoro-2-{2-[1-(3-fluoro-phenyl)-cyclopropyl]-acetyl}-1,2,3,4-tetrahydro-isoquinolin-8-yl)-phenyl]-acetic acid;
[4-Ethoxy-3-(5-fluoro-2-{2-[1-(2-fluoro-phenyl)-cyclopropyl]-acetyl}-1,2,3,4-tetrahydro-isoquinolin-8-yl)-phenyl]-acetic acid;
[4-Ethoxy-3-(5-fluoro-2-{2-[1-(4-fluoro-phenyl)-cyclopropyl]-acetyl}-1,2,3,4-tetrahydro-isoquinolin-8-yl)-phenyl]-acetic acid;
(4-Ethoxy-3-{5-fluoro-2-[3-(4-fluoro-phenyl)-butyryl]-1,2,3,4-tetrahydro-isoquinolin-8-yl}-phenyl)-acetic acid;
(4-Ethoxy-3-{5-fluoro-2-[3-(3-fluoro-phenyl)-butyryl]-1,2,3,4-tetrahydro-isoquinolin-8-yl}-phenyl)-acetic acid;
(4-Ethoxy-3-{5-fluoro-2-[3-(2-fluoro-phenyl)-butyryl]-1,2,3,4-tetrahydro-isoquinolin-8-yl}-phenyl)-acetic acid;
{4-Ethoxy-3-[5-fluoro-2-(3-pyrazin-2-yl-butyryl)-1,2,3,4-tetrahydro-isoquinolin-8-yl]-phenyl}-acetic acid;
(4-Ethoxy-3-{5-fluoro-2-[3-(2-methoxy-phenyl)-butyryl]-1,2,3,4-tetrahydro-isoquinolin-8-yl}-phenyl)-acetic acid;
{4-Ethoxy-3-[5-fluoro-2-(3-thiazol-2-yl-butyryl)-1,2,3,4-tetrahydro-isoquinolin-8-yl]-phenyl}-acetic acid;
(3-{2-[2-(2,2-Dimethyl-3,4-dihydro-2H-pyrano[2,3-b]pyridin-4-yl)-acetyl]-5-fluoro-1,2,3,4-tetrahydro-isoquinolin-8-yl}-4-ethoxy-phenyl)-acetic acid;
[4-[2-(2-Chroman-4-yl-acetyl)-5-fluoro-1,2,3,4-tetrahydro-isoquinolin-8-yl]-3-(2,2,2-trifluoro-ethoxy)-phenyl]-acetic acid;
[4-[5-Fluoro-2-(3-methyl-3-phenyl-butyryl)-1,2,3,4-tetrahydro-isoquinolin-8-yl]-3-(2,2,2-trifluoro-ethoxy)-phenyl]-acetic acid;
[4-[5-Fluoro-2-((S)-3-phenyl-butyryl)-1,2,3,4-tetrahydro-isoquinolin-8-yl]-3-(2,2,2-trifluoro-ethoxy)-phenyl]-acetic acid;
[4-[5-Fluoro-2-(3-pyridin-2-yl-butyryl)-1,2,3,4-tetrahydro-isoquinolin-8-yl]-3-(2,2,2-trifluoro-ethoxy)-phenyl]-acetic acid;
[4-[5-Fluoro-2-((1R,2R)-2-phenyl-cyclopropanecarbonyl)-1,2,3,4-tetrahydro-isoquinolin-8-yl]-3-(2,2,2-trifluoro-ethoxy)-phenyl]-acetic acid;
{3-[2-(2-Chroman-4-yl-acetyl)-5-fluoro-1,2,3,4-tetrahydro-isoquinolin-8-yl]-4-isopropoxy-phenyl}-acetic acid;
{3-[5-Fluoro-2-(3-methyl-3-phenyl-butyryl)-1,2,3,4-tetrahydro-isoquinolin-8-yl]-4-isopropoxy-phenyl}-acetic acid;
{3-[5-Fluoro-2-((R)-3-phenyl-butyryl)-1,2,3,4-tetrahydro-isoquinolin-8-yl]-4-isopropoxy-phenyl}-acetic acid;
{3-[5-Fluoro-2-(3-pyridin-2-yl-butyryl)-1,2,3,4-tetrahydro-isoquinolin-8-yl]-4-isopropoxy-phenyl}-acetic acid;
(3-{5-Fluoro-2-[3-(6-methyl-pyridin-2-yl)-butyryl]-1,2,3,4-tetrahydro-isoquinolin-8-yl}-4-isopropoxy-phenyl)-acetic acid;
(3-{5-Fluoro-2-[3-(6-methyl-pyridin-2-yl)-propionyl]-1,2,3,4-tetrahydro-isoquinolin-8-yl}-4-isopropoxy-phenyl)-acetic acid;
{3-[5-Fluoro-2-(2-isochroman-4-yl-acetyl)-1,2,3,4-tetrahydro-isoquinolin-8-yl]-4-isopropoxy-phenyl}-acetic acid;
{3-[5-Fluoro-2-(2-isochroman-1-yl-acetyl)-1,2,3,4-tetrahydro-isoquinolin-8-yl]-4-isopropoxy-phenyl}-acetic acid;
{3-[2-(2-2,3-Dihydro-benzofuran-3-yl-acetyl)-5-fluoro-1,2,3,4-tetrahydro-isoquinolin-8-yl]-4-isopropoxy-phenyl}-acetic acid;
[3-[2-(2-Chroman-4-yl-acetyl)-5-fluoro-1,2,3,4-tetrahydro-isoquinolin-8-yl]-4-(2,2,2-trifluoro-ethoxy)-phenyl]-acetic acid;
[3-[5-Fluoro-2-(3-methyl-3-phenyl-butyryl)-1,2,3,4-tetrahydro-isoquinolin-8-yl]-4-(2,2,2-trifluoro-ethoxy)-phenyl]-acetic acid;
[3-[5-Fluoro-2-((R)-3-phenyl-butyryl)-1,2,3,4-tetrahydro-isoquinolin-8-yl]-4-(2,2,2-trifluoro-ethoxy)-phenyl]-acetic acid;
[3-[5-Fluoro-2-(3-pyridin-2-yl-butyryl)-1,2,3,4-tetrahydro-isoquinolin-8-yl]-4-(2,2,2-trifluoro-ethoxy)-phenyl]-acetic acid;
[3-{5-Fluoro-2-[3-(6-methyl-pyridin-2-yl)-butyryl]-1,2,3,4-tetrahydro-isoquinolin-8-yl}-4-(2,2,2-trifluoro-ethoxy)-phenyl]-acetic acid;
[3-{5-Fluoro-2-[3-(6-methyl-pyridin-2-yl)-propionyl]-1,2,3,4-tetrahydro-isoquinolin-8-yl}-4-(2,2,2-trifluoro-ethoxy)-phenyl]-acetic acid;
[3-[5-Fluoro-2-(2-isochroman-4-yl-acetyl)-1,2,3,4-tetrahydro-isoquinolin-8-yl]-4-(2,2,2-trifluoro-ethoxy)-phenyl]-acetic acid;
[3-[5-Fluoro-2-(2-isochroman-1-yl-acetyl)-1,2,3,4-tetrahydro-isoquinolin-8-yl]-4-(2,2,2-trifluoro-ethoxy)-phenyl]-acetic acid;
[3-[2-(2-2,3-Dihydro-benzofuran-3-yl-acetyl)-5-fluoro-1,2,3,4-tetrahydro-isoquinolin-8-yl]-4-(2,2,2-trifluoro-ethoxy)-phenyl]-acetic acid;
{4-Ethoxy-3-[5-fluoro-2-(3-pyridin-2-yl-pentanoyl)-1,2,3,4-tetrahydro-isoquinolin-8-yl]-phenyl}-acetic acid;
(4-Ethoxy-3-{5-fluoro-2-[3-(3-methoxy-pyridin-2-yl)-propionyl]-1,2,3,4-tetrahydro-isoquinolin-8-yl}-phenyl)-acetic acid;
(4-Ethoxy-3-{5-fluoro-2-[3-(4-fluoro-phenyl)-propionyl]-1,2,3,4-tetrahydro-isoquinolin-8-yl}-phenyl)-acetic acid;
(4-Ethoxy-3-{5-fluoro-2-[3-(3-fluoro-phenyl)-propionyl]-1,2,3,4-tetrahydro-isoquinolin-8-yl}-phenyl)-acetic acid;
(4-Ethoxy-3-{5-fluoro-2-[3-(2-fluoro-phenyl)-propionyl]-1,2,3,4-tetrahydro-isoquinolin-8-yl}-phenyl)-acetic acid;
{3-Ethoxy-4-[5-fluoro-2-(3-pyridin-2-yl-pentanoyl)-1,2,3,4-tetrahydro-isoquinolin-8-yl]-phenyl}-acetic acid;
(3-Ethoxy-4-{5-fluoro-2-[3-(3-methoxy-pyridin-2-yl)-propionyl]-1,2,3,4-tetrahydro-isoquinolin-8-yl}-phenyl)-acetic acid;
(3-Ethoxy-4-{5-fluoro-2-[3-(4-fluoro-phenyl)-propionyl]-1,2,3,4-tetrahydro-isoquinolin-8-yl}-phenyl)-acetic acid;
(3-Ethoxy-4-{5-fluoro-2-[3-(3-fluoro-phenyl)-propionyl]-1,2,3,4-tetrahydro-isoquinolin-8-yl}-phenyl)-acetic acid;
(3-Ethoxy-4-{5-fluoro-2-[3-(2-fluoro-phenyl)-propionyl]-1,2,3,4-tetrahydro-isoquinolin-8-yl}-phenyl)-acetic acid;
{3-[2-(3-Cyclopropyl-3-pyridin-2-yl-propionyl)-5-fluoro-1,2,3,4-tetrahydro-isoquinolin-8-yl]-4-ethoxy-phenyl}-acetic acid;
{4-[2-(3-Cyclopropyl-3-pyridin-2-yl-propionyl)-5-fluoro-1,2,3,4-tetrahydro-isoquinolin-8-yl]-3-ethoxy-phenyl}-acetic acid;
(3-Ethoxy-4-{5-fluoro-2-[3-(6-methyl-pyridin-2-yl)-butyryl]-1,2,3,4-tetrahydro-isoquinolin-8-yl}-phenyl)-acetic acid;
(3-Ethoxy-4-{5-fluoro-2-[3-(6-methyl-pyridin-2-yl)-propionyl]-1,2,3,4-tetrahydro-isoquinolin-8-yl}-phenyl)-acetic acid;
{3-Ethoxy-4-[5-fluoro-2-(trans-2-pyridin-2-yl-cyclopropanecarbonyl)-1,2,3,4-tetrahydro-isoquinolin-8-yl]-phenyl}-acetic acid;
(4-{2-[2-(2,2-Dimethyl-chroman-4-yl)-acetyl]-5-fluoro-1,2,3,4-tetrahydro-isoquinolin-8-yl}-3-ethoxy-phenyl)-acetic acid;
{4-[2-(2-Chroman-3-yl-acetyl)-5-fluoro-1,2,3,4-tetrahydro-isoquinolin-8-yl]-3-ethoxy-phenyl}-acetic acid;
{3-Ethoxy-4-[5-fluoro-2-(8-methoxy-1,2,3,4-tetrahydro-naphthalene-2-carbonyl)-1,2,3,4-tetrahydro-isoquinolin-8-yl]-phenyl}-acetic acid;

(3-Ethoxy-4-{5-fluoro-2-[2-(1-methyl-1,2,3,4-tetrahydro-naphthalen-1-yl)-acetyl]-1,2,3,4-tetrahydro-isoquinolin-8-yl}-phenyl)-acetic acid;

(3-Ethoxy-4-{5-fluoro-2-[2-(7-fluoro-chroman-4-yl)-acetyl]-1,2,3,4-tetrahydro-isoquinolin-8-yl}-phenyl)-acetic acid;

(4-Ethoxy-3-{5-fluoro-2-[3-(6-methyl-pyridin-2-yl)-butyryl]-1,2,3,4-tetrahydro-isoquinolin-8-yl}-phenyl)-acetic acid;

(4-Ethoxy-3-{5-fluoro-2-[3-(6-methyl-pyridin-2-yl)-propionyl]-1,2,3,4-tetrahydro-isoquinolin-8-yl}-phenyl)-acetic acid;

{4-Ethoxy-3-[5-fluoro-2-(trans-2-pyridin-2-yl-cyclopropanecarbonyl)-1,2,3,4-tetrahydro-isoquinolin-8-yl]-phenyl}-acetic acid;

(3-{2-[2-(2,2-Dimethyl-chroman-4-yl)-acetyl]-5-fluoro-1,2,3,4-tetrahydro-isoquinolin-8-yl}-4-ethoxy-phenyl)-acetic acid;

{3-[2-(2-Chroman-3-yl-acetyl)-5-fluoro-1,2,3,4-tetrahydro-isoquinolin-8-yl]-4-ethoxy-phenyl}-acetic acid;

{4-Ethoxy-3-[5-fluoro-2-(8-methoxy-1,2,3,4-tetrahydro-naphthalene-2-carbonyl)-1,2,3,4-tetrahydro-isoquinolin-8-yl]-phenyl}-acetic acid;

(4-Ethoxy-3-{5-fluoro-2-[2-(1-methyl-1,2,3,4-tetrahydro-naphthalen-1-yl)-acetyl]-1,2,3,4-tetrahydro-isoquinolin-8-yl}-phenyl)-acetic acid;

(4-Ethoxy-3-{5-fluoro-2-[2-(7-fluoro-chroman-4-yl)-acetyl]-1,2,3,4-tetrahydro-isoquinolin-8-yl}-phenyl)-acetic acid;

{4-Ethoxy-3-[5-fluoro-2-((E)-3-pyridin-2-yl-acryloyl)-1,2,3,4-tetrahydro-isoquinolin-8-yl]-phenyl}-acetic acid;

(4-Ethoxy-3-{5-fluoro-2-[(E)-3-(1-methyl-1H-pyrazol-3-yl)-acryloyl]-1,2,3,4-tetrahydro-isoquinolin-8-yl}-phenyl)-acetic acid;

{3-Ethoxy-4-[5-fluoro-2-((E)-3-pyridin-2-yl-acryloyl)-1,2,3,4-tetrahydro-isoquinolin-8-yl]-phenyl}-acetic acid;

(3-Ethoxy-4-{5-fluoro-2-[(E)-3-(1-methyl-1H-pyrazol-4-yl)-acryloyl]-1,2,3,4-tetrahydro-isoquinolin-8-yl}-phenyl)-acetic acid;

{4-Ethoxy-3-[5-fluoro-2-(2-pyridin-2-yl-acetyl)-1,2,3,4-tetrahydro-isoquinolin-8-yl]-phenyl}-acetic acid;

(4-Ethoxy-3-{5-fluoro-2-[(E)-3-(1-methyl-1H-pyrazol-4-yl)-acryloyl]-1,2,3,4-tetrahydro-isoquinolin-8-yl}-phenyl)-acetic acid;

{3-Ethoxy-4-[5-fluoro-2-(2-pyridin-2-yl-acetyl)-1,2,3,4-tetrahydro-isoquinolin-8-yl]-phenyl}-acetic acid;

{3-[5-Fluoro-2-(2-methyl-3-pyridin-3-yl-propionyl)-1,2,3,4-tetrahydro-isoquinolin-8-yl]-4-methoxy-phenyl}-acetic acid;

{3-Ethoxy-4-[5-fluoro-2-(3-pyridin-2-yl-butyryl)-1,2,3,4-tetrahydro-isoquinolin-8-yl]-phenyl}-acetic acid;

{4-Ethoxy-3-[5-fluoro-2-(3-pyridin-2-yl-butyryl)-1,2,3,4-tetrahydro-isoquinolin-8-yl]-phenyl}-acetic acid;

{4-[5-Fluoro-2-(3-pyridin-2-yl-butyryl)-1,2,3,4-tetrahydro-isoquinolin-8-yl]-3-isopropoxy-phenyl}-acetic acid;

[4-[5-Fluoro-2-((R)-3-phenyl-butyryl)-1,2,3,4-tetrahydro-isoquinolin-8-yl]-3-(2,2,2-trifluoro-ethoxy)-phenyl]-acetic acid;

{4-Ethoxy-3-[5-fluoro-2-(3-pyridin-2-yl-propionyl)-1,2,3,4-tetrahydro-isoquinolin-8-yl]-phenyl}-acetic acid;

{3-Ethoxy-4-[5-fluoro-2-(3-pyridin-2-yl-propionyl)-1,2,3,4-tetrahydro-isoquinolin-8-yl]-phenyl}-acetic acid;

{4-Ethoxy-3-[5-fluoro-2-(2-5,6,7,8-tetrahydro-quinolin-8-yl-acetyl)-1,2,3,4-tetrahydro-isoquinolin-8-yl]-phenyl}-acetic acid;

{4-Ethoxy-3-[5-fluoro-2-(2-methyl-3-pyridin-2-yl-propionyl)-1,2,3,4-tetrahydro-isoquinolin-8-yl]-phenyl}-acetic acid;

{3-Ethoxy-4-[5-fluoro-2-(2-methyl-3-pyridin-2-yl-propionyl)-1,2,3,4-tetrahydro-isoquinolin-8-yl]-phenyl}-acetic acid;

{4-[2-(2-Chroman-4-yl-acetyl)-5-fluoro-1,2,3,4-tetrahydro-isoquinolin-8-yl]-3-isopropoxy-phenyl}-acetic acid;

{4-[5-Fluoro-2-(3-methyl-3-phenyl-butyryl)-1,2,3,4-tetrahydro-isoquinolin-8-yl]-3-isopropoxy-phenyl}-acetic acid;

{4-[5-Fluoro-2-((S)-3-phenyl-butyryl)-1,2,3,4-tetrahydro-isoquinolin-8-yl]-3-isopropoxy-phenyl}-acetic acid;

{4-[5-Fluoro-2-((R)-3-phenyl-butyryl)-1,2,3,4-tetrahydro-isoquinolin-8-yl]-3-isopropoxy-phenyl}-acetic acid;

{4-[5-Fluoro-2-((1R,2R)-2-phenyl-cyclopropanecarbonyl)-1,2,3,4-tetrahydro-isoquinolin-8-yl]-3-isopropoxy-phenyl}-acetic acid;

(4-{5-Fluoro-2-[3-(4-fluoro-phenyl)-3-methyl-butyryl]-1,2,3,4-tetrahydro-isoquinolin-8-yl}-3-methoxy-phenyl)-acetic acid;

{4-[2-(2-Chroman-4-yl-acetyl)-5-fluoro-1,2,3,4-tetrahydro-isoquinolin-8-yl]-3-methoxy-phenyl}-acetic acid;

{4-[5-Fluoro-2-(2-indan-1-yl-acetyl)-1,2,3,4-tetrahydro-isoquinolin-8-yl]-3-methoxy-phenyl}-acetic acid;

{3-[5-Fluoro-2-(trans-2-pyridin-2-yl-cyclopropanecarbonyl)-1,2,3,4-tetrahydro-isoquinolin-8-yl]-4-methoxy-phenyl}-acetic acid;

{3-[2-(2-1,3-Dihydro-isobenzofuran-1-yl-acetyl)-5-fluoro-1,2,3,4-tetrahydro-isoquinolin-8-yl]-4-methoxy-phenyl}-acetic acid;

(3-{5-Fluoro-2-[3-(4-fluoro-phenyl)-3-methyl-butyryl]-1,2,3,4-tetrahydro-isoquinolin-8-yl}-4-methoxy-phenyl)-acetic acid;

8-(5-Carboxymethyl-2-ethoxy-phenyl)-5-fluoro-3,4-dihydro-1H-isoquinoline-2-carboxylic acid (R)-1-phenyl-ethyl ester;

8-(5-Carboxymethyl-2-ethoxy-phenyl)-5-fluoro-3,4-dihydro-1H-isoquinoline-2-carboxylic acid pyrazin-2-ylmethyl ester;

8-(5-Carboxymethyl-2-ethoxy-phenyl)-5-fluoro-3,4-dihydro-1H-isoquinoline-2-carboxylic acid 3-fluoro-5-methyl-pyridin-2-ylmethyl ester;

8-(5-Carboxymethyl-2-ethoxy-phenyl)-5-fluoro-3,4-dihydro-1H-isoquinoline-2-carboxylic acid 2-methyl-2H-pyrazol-3-ylmethyl ester;

8-(5-Carboxymethyl-2-ethoxy-phenyl)-5-fluoro-3,4-dihydro-1H-isoquinoline-2-carboxylic acid (S)-1-phenyl-ethyl ester;

8-(5-Carboxymethyl-2-ethoxy-phenyl)-5-fluoro-3,4-dihydro-1H-isoquinoline-2-carboxylic acid cyclopentylmethyl ester;

8-(5-Carboxymethyl-2-ethoxy-phenyl)-5-fluoro-3,4-dihydro-1H-isoquinoline-2-carboxylic acid 3-methyl-butyl ester;

8-(5-Carboxymethyl-2-ethoxy-phenyl)-5-fluoro-3,4-dihydro-1H-isoquinoline-2-carboxylic acid 6-methyl-pyridin-2-ylmethyl ester;

8-(5-Carboxymethyl-2-ethoxy-phenyl)-5-fluoro-3,4-dihydro-1H-isoquinoline-2-carboxylic acid cyclopropylmethyl ester;

8-(5-Carboxymethyl-2-ethoxy-phenyl)-5-fluoro-3,4-dihydro-1H-isoquinoline-2-carboxylic acid phenethyl ester;

8-(5-Carboxymethyl-2-ethoxy-phenyl)-5-fluoro-3,4-dihydro-1H-isoquinoline-2-carboxylic acid (R)-2-phenyl-propyl ester;

8-(5-Carboxymethyl-2-ethoxy-phenyl)-5-fluoro-3,4-dihydro-1H-isoquinoline-2-carboxylic acid 3-methyl-but-2-enyl ester;
8-(5-Carboxymethyl-2-ethoxy-phenyl)-5-fluoro-3,4-dihydro-1H-isoquinoline-2-carboxylic acid butyl ester;
8-(5-Carboxymethyl-2-ethoxy-phenyl)-5-fluoro-3,4-dihydro-1H-isoquinoline-2-carboxylic acid isobutyl ester;
8-(5-Carboxymethyl-2-ethoxy-phenyl)-5-fluoro-3,4-dihydro-1H-isoquinoline-2-carboxylic acid 2-methoxy-ethyl ester;
8-(5-Carboxymethyl-2-ethoxy-phenyl)-5-fluoro-3,4-dihydro-1H-isoquinoline-2-carboxylic acid 3-methyl-but-3-enyl ester;
8-(5-Carboxymethyl-2-ethoxy-phenyl)-5-fluoro-3,4-dihydro-1H-isoquinoline-2-carboxylic acid 2-methyl-butyl ester;
8-(5-Carboxymethyl-2-ethoxy-phenyl)-5-fluoro-3,4-dihydro-1H-isoquinoline-2-carboxylic acid but-3-ynyl ester;
8-(5-Carboxymethyl-2-ethoxy-phenyl)-5-fluoro-3,4-dihydro-1H-isoquinoline-2-carboxylic acid 3-hydroxy-3-methyl-butyl ester;
8-(5-Carboxymethyl-2-ethoxy-phenyl)-5-fluoro-3,4-dihydro-1H-isoquinoline-2-carboxylic acid 3-methoxy-3-methyl-butyl ester;
8-(5-Carboxymethyl-2-ethoxy-phenyl)-5-fluoro-3,4-dihydro-1H-isoquinoline-2-carboxylic acid tetrahydro-furan-2-ylmethyl ester;
8-(4-Carboxymethyl-2-ethoxy-phenyl)-5-fluoro-3,4-dihydro-1H-isoquinoline-2-carboxylic acid (R)-1-phenyl-ethyl ester;
8-(4-Carboxymethyl-2-ethoxy-phenyl)-5-fluoro-3,4-dihydro-1H-isoquinoline-2-carboxylic acid pyrazin-2-ylmethyl ester;
8-(4-Carboxymethyl-2-ethoxy-phenyl)-5-fluoro-3,4-dihydro-1H-isoquinoline-2-carboxylic acid 3-fluoro-5-methyl-pyridin-2-ylmethyl ester;
8-(4-Carboxymethyl-2-ethoxy-phenyl)-5-fluoro-3,4-dihydro-1H-isoquinoline-2-carboxylic acid 2-methyl-2H-pyrazol-3-ylmethyl ester;
8-(4-Carboxymethyl-2-ethoxy-phenyl)-5-fluoro-3,4-dihydro-1H-isoquinoline-2-carboxylic acid (S)-1-phenyl-ethyl ester;
8-(4-Carboxymethyl-2-ethoxy-phenyl)-5-fluoro-3,4-dihydro-1H-isoquinoline-2-carboxylic acid 6-methyl-pyridin-2-ylmethyl ester;
8-(4-Carboxymethyl-2-ethoxy-phenyl)-5-fluoro-3,4-dihydro-1H-isoquinoline-2-carboxylic acid cyclopropylmethyl ester;
8-(4-Carboxymethyl-2-ethoxy-phenyl)-5-fluoro-3,4-dihydro-1H-isoquinoline-2-carboxylic acid cyclopentylmethyl ester;
8-(4-Carboxymethyl-2-ethoxy-phenyl)-5-fluoro-3,4-dihydro-1H-isoquinoline-2-carboxylic acid 3-methyl-butyl ester;
8-(5-Carboxymethyl-2-ethoxy-phenyl)-5-fluoro-3,4-dihydro-1H-isoquinoline-2-carboxylic acid pyridin-2-ylmethyl ester;
8-(4-Carboxymethyl-2-ethoxy-phenyl)-5-fluoro-3,4-dihydro-1H-isoquinoline-2-carboxylic acid pyridin-2-ylmethyl ester;
8-(5-Carboxymethyl-2-ethoxy-phenyl)-5-fluoro-3,4-dihydro-1H-isoquinoline-2-carboxylic acid cyclohexylmethyl ester;
8-(4-Carboxymethyl-2-ethoxy-phenyl)-5-fluoro-3,4-dihydro-1H-isoquinoline-2-carboxylic acid cyclohexylmethyl ester;
8-(5-Carboxymethyl-2-ethoxy-phenyl)-5-fluoro-3,4-dihydro-1H-isoquinoline-2-carboxylic acid 4-fluoro-benzyl ester;
8-(5-Carboxymethyl-2-ethoxy-phenyl)-5-fluoro-3,4-dihydro-1H-isoquinoline-2-carboxylic acid 3-fluoro-benzyl ester;
8-(5-Carboxymethyl-2-ethoxy-phenyl)-5-fluoro-3,4-dihydro-1H-isoquinoline-2-carboxylic acid 2-fluoro-benzyl ester;
8-(5-Carboxymethyl-2-ethoxy-phenyl)-5-fluoro-3,4-dihydro-1H-isoquinoline-2-carboxylic acid 2,5-difluoro-benzyl ester;
8-(5-Carboxymethyl-2-ethoxy-phenyl)-5-fluoro-3,4-dihydro-1H-isoquinoline-2-carboxylic acid 5-chloro-2-fluoro-benzyl ester;
8-(5-Carboxymethyl-2-ethoxy-phenyl)-5-fluoro-3,4-dihydro-1H-isoquinoline-2-carboxylic acid 2,4-difluoro-benzyl ester;
8-(4-Carboxymethyl-2-ethoxy-phenyl)-5-fluoro-3,4-dihydro-1H-isoquinoline-2-carboxylic acid 4-fluoro-benzyl ester;
8-(4-Carboxymethyl-2-ethoxy-phenyl)-5-fluoro-3,4-dihydro-1H-isoquinoline-2-carboxylic acid 3-fluoro-benzyl ester;
8-(4-Carboxymethyl-2-ethoxy-phenyl)-5-fluoro-3,4-dihydro-1H-isoquinoline-2-carboxylic acid 2-fluoro-benzyl ester;
8-(4-Carboxymethyl-2-ethoxy-phenyl)-5-fluoro-3,4-dihydro-1H-isoquinoline-2-carboxylic acid 2,5-difluoro-benzyl ester;
8-(4-Carboxymethyl-2-ethoxy-phenyl)-5-fluoro-3,4-dihydro-1H-isoquinoline-2-carboxylic acid 5-chloro-2-fluoro-benzyl ester;
8-(4-Carboxymethyl-2-ethoxy-phenyl)-5-fluoro-3,4-dihydro-1H-isoquinoline-2-carboxylic acid 2,4-difluoro-benzyl ester;
8-(4-Carboxymethyl-2-ethoxy-phenyl)-5-fluoro-3,4-dihydro-1H-isoquinoline-2-carboxylic acid benzyl ester;
8-[4-Carboxymethyl-2-(2,2,2-trifluoro-ethoxy)-phenyl]-5-fluoro-3,4-dihydro-1H-isoquinoline-2-carboxylic acid benzyl ester;
8-(5-Carboxymethyl-2-difluoromethoxy-phenyl)-5-fluoro-3,4-dihydro-1H-isoquinoline-2-carboxylic acid benzyl ester;
8-[5-Carboxymethyl-2-(2,2-difluoro-ethoxy)-phenyl]-5-fluoro-3,4-dihydro-1H-isoquinoline-2-carboxylic acid benzyl ester;
8-[5-(1-Carboxy-ethoxy)-2-methoxy-phenyl]-5-fluoro-3,4-dihydro-1H-isoquinoline-2-carboxylic acid benzyl ester;
8-[5-(1-Carboxy-propoxy)-2-methoxy-phenyl]-5-fluoro-3,4-dihydro-1H-isoquinoline-2-carboxylic acid benzyl ester;
8-(2-Carboxymethyl-5-chloro-phenyl)-5-fluoro-3,4-dihydro-1H-isoquinoline-2-carboxylic acid benzyl ester;
8-(2-Carboxymethoxy-6-methoxy-phenyl)-5-fluoro-3,4-dihydro-1H-isoquinoline-2-carboxylic acid benzyl ester;
8-(2-Carboxymethyl-6-methoxy-phenyl)-5-fluoro-3,4-dihydro-1H-isoquinoline-2-carboxylic acid benzyl ester;
8-(2-tert-Butoxy-5-carboxymethyl-phenyl)-5-fluoro-3,4-dihydro-1H-isoquinoline-2-carboxylic acid benzyl ester;
8-(5-Carboxymethyl-2-dimethylamino-phenyl)-5-fluoro-3,4-dihydro-1H-isoquinoline-2-carboxylic acid benzyl ester;
8-[5-Carboxymethyl-2-(2,2,2-trifluoro-ethoxy)-phenyl]-5-fluoro-3,4-dihydro-1H-isoquinoline-2-carboxylic acid benzyl ester;

8-[5-Carboxymethyl-2-(2-fluoro-ethoxy)-phenyl]-5-fluoro-3,4-dihydro-1H-isoquinoline-2-carboxylic acid benzyl ester;
8-(3-Carboxymethyl-2-methoxy-phenyl)-5-fluoro-3,4-dihydro-1H-isoquinoline-2-carboxylic acid benzyl ester;
8-(4-Carboxymethoxy-2-methoxy-phenyl)-5-fluoro-3,4-dihydro-1H-isoquinoline-2-carboxylic acid benzyl ester;
8-[4-(1-Carboxy-ethyl)-2-ethoxy-phenyl]-5-fluoro-3,4-dihydro-1H-isoquinoline-2-carboxylic acid benzyl ester;
[3-[5-Fluoro-2-((1R,2R)-2-phenyl-cyclopropanecarbonyl)-1,2,3,4-tetrahydro-isoquinolin-8-yl]-4-(2,2,2-trifluoro-ethoxy)-phenyl]-acetic acid;
{4-(2-Fluoro-ethoxy)-3-[5-fluoro-2-((1R,2R)-2-phenyl-cyclopropanecarbonyl)-1,2,3,4-tetrahydro-isoquinolin-8-yl]-phenyl}-acetic acid;
{4-tert-Butoxy-3-[5-fluoro-2-((1R,2R)-2-phenyl-cyclopropanecarbonyl)-1,2,3,4-tetrahydro-isoquinolin-8-yl]-phenyl}-acetic acid;
1-{3-[5-Fluoro-2-((1R,2R)-2-phenyl-cyclopropanecarbonyl)-1,2,3,4-tetrahydro-isoquinolin-8-yl]-4-methoxy-phenyl}-cyclopropanecarboxylic acid;
8-(5-Carboxymethyl-2-cyclopropoxy-phenyl)-5-fluoro-3,4-dihydro-1H-isoquinoline-2-carboxylic acid benzyl ester;
8-(5-Carboxymethyl-2-isopropoxy-phenyl)-5-cyano-3,4-dihydro-1H-isoquinoline-2-carboxylic acid benzyl ester;
{4-Ethoxy-3-[5-fluoro-2-(2-fluoro-benzylcarbamoyl)-1,2,3,4-tetrahydro-isoquinolin-8-yl]-phenyl}-acetic acid;
{4-Ethoxy-3-[5-fluoro-2-(3-fluoro-benzylcarbamoyl)-1,2,3,4-tetrahydro-isoquinolin-8-yl]-phenyl}-acetic acid;
{4-Ethoxy-3-[5-fluoro-2-(4-fluoro-benzylcarbamoyl)-1,2,3,4-tetrahydro-isoquinolin-8-yl]-phenyl}-acetic acid;
[4-Ethoxy-3-(5-fluoro-2-phenethylcarbamoyl-1,2,3,4-tetrahydro-isoquinolin-8-yl)-phenyl]-acetic acid;
{3-[2-(2-Chloro-benzylcarbamoyl)-5-fluoro-1,2,3,4-tetrahydro-isoquinolin-8-yl]-4-ethoxy-phenyl}-acetic acid;
{4-Ethoxy-3-[5-fluoro-2-(2-methoxy-benzylcarbamoyl)-1,2,3,4-tetrahydro-isoquinolin-8-yl]-phenyl}-acetic acid;
[3-(2-Benzylcarbamoyl-5-fluoro-1,2,3,4-tetrahydro-isoquinolin-8-yl)-4-ethoxy-phenyl]-acetic acid;
[4-Ethoxy-3-(5-fluoro-2-propylcarbamoyl-1,2,3,4-tetrahydro-isoquinolin-8-yl)-phenyl]-acetic acid;
{3-Ethoxy-4-[5-fluoro-2-(2-fluoro-benzylcarbamoyl)-1,2,3,4-tetrahydro-isoquinolin-8-yl]-phenyl}-acetic acid;
{3-Ethoxy-4-[5-fluoro-2-(3-fluoro-benzylcarbamoyl)-1,2,3,4-tetrahydro-isoquinolin-8-yl]-phenyl}-acetic acid;
{3-Ethoxy-4-[5-fluoro-2-(4-fluoro-benzylcarbamoyl)-1,2,3,4-tetrahydro-isoquinolin-8-yl]-phenyl}-acetic acid;
[3-Ethoxy-4-(5-fluoro-2-phenethylcarbamoyl-1,2,3,4-tetrahydro-isoquinolin-8-yl)-phenyl]-acetic acid;
{4-[2-(2-Chloro-benzylcarbamoyl)-5-fluoro-1,2,3,4-tetrahydro-isoquinolin-8-yl]-3-ethoxy-phenyl}-acetic acid;
{3-Ethoxy-4-[5-fluoro-2-(2-methoxy-benzylcarbamoyl)-1,2,3,4-tetrahydro-isoquinolin-8-yl]-phenyl}-acetic acid;
[4-(2-Benzylcarbamoyl-5-fluoro-1,2,3,4-tetrahydro-isoquinolin-8-yl)-3-ethoxy-phenyl]-acetic acid;
[3-Ethoxy-4-(5-fluoro-2-propylcarbamoyl-1,2,3,4-tetrahydro-isoquinolin-8-yl)-phenyl]-acetic acid;
(3-Ethoxy-4-{5-fluoro-2-[(pyridin-2-ylmethyl)-carbamoyl]-1,2,3,4-tetrahydro-isoquinolin-8-yl}-phenyl)-acetic acid; and
(4-Ethoxy-3-{5-fluoro-2-[(pyridin-2-ylmethyl)-carbamoyl]-1,2,3,4-tetrahydro-isoquinolin-8-yl}-phenyl)-acetic acid;
or salts (in particular pharmaceutically acceptable salts) of such compounds;

it is to be understood for any of the above listed compounds, that a stereogenic center, which is not specifically assigned, may be in absolute (R)- or absolute (S)-configuration and that a double bond, which is not specifically assigned, may be in (E)- or (Z)-configuration; notably it is to be understood for any compound listed above which can be separated into atropisomers, that the compound may be a respective atropisomer of formula ($I_{Sr1}$), a respective atropisomer of formula ($I_{Sr2}$) or any mixture thereof.

It is well understood that the invention relates to compounds according to embodiment 1); or according to embodiment 1) limited by the features of an embodiment dependent on embodiment 1; or according to embodiment 1) limited by the features of a cascade of dependent embodiments e.g. in the form of "embodiment 9) depending on embodiment 2) depending on embodiment 1)". In case of an embodiment depending on more than one other embodiment, it is understood that each combination is specifically disclosed. Also, in case an embodiment is dependent on more than one other embodiment and one or more of said other embodiments are themselves dependent on one or more further embodiments, it is understood that each combination is specifically disclosed if obtainable with regard to the given dependencies and multiple dependencies. Notably, embodiments resulting from cascades of more than three embodiments depending on each other may be construed under observance of the given dependencies and multiple dependencies and are thus intended to be specifically disclosed. Representative examples of embodiments which are possible based on the dependencies of the embodiments 1) to 56) as disclosed hereinabove and which are therefore intended and herewith specifically disclosed in individualized form are:

1, 2+1, 3+1, 3+2+1, 4+1, 4+2+1, 5+1, 6+1, 7+1, 7+2+1, 8+1, 9+1, 9+2+1, 10+1, 10+2+1, 11+1, 11+2+1, 12+1, 13+1, 13+2+1, 14+1, 14+2+1, 15+1, 15+2+1, 16+1, 16+2+1, 17+1, 17+2+1, 17+14+1, 17+14+2+1, 18+1, 18+2+1, 18+3+1, 18+3+2+1, 18+4+1, 18+4+2+1, 18+5+1, 18+9+1, 18+9+2+1, 18+10+1, 18+10+2+1, 18+12+1, 18+13+1, 18+13+2+1, 18+14+1, 18+14+2+1, 18+15+1, 18+15+2+1, 19+1, 20+1, 20+2+1, 20+14+1, 20+14+2+1, 20+18+1, 20+18+2+1, 20+18+3+1, 20+18+3+2+1, 20+18+4+1, 20+18+4+2+1, 20+18+5+1, 20+18+9+1, 20+18+9+2+1, 20+18+10+1, 20+18+10+2+1, 20+18+12+1, 20+18+13+1, 20+18+13+2+1, 20+18+14+1, 20+18+14+2+1, 20+18+15+1, 20+18+15+2+1, 21+1, 21+2+1, 21+3+1, 21+3+2+1, 21+4+1, 21+4+2+1, 21+5+1, 22+1, 22+2+1, 22+3+1, 22+3+2+1, 22+4+1, 22+4+2+1, 22+5+1, 22+6+1, 22+12+1, 22+13+1, 22+13+2+1, 22+14+1, 22+14+2+1, 22+15+1, 22+15+2+1, 22+18+1, 22+18+2+1, 22+18+3+1, 22+18+3+2+1, 22+18+4+1, 22+18+4+2+1, 22+18+5+1, 22+18+9+1, 22+18+9+2+1, 22+18+10+1, 22+18+10+2+1, 22+18+12+1, 22+18+13+1, 22+18+13+2+1, 22+18+14+1, 22+18+14+2+1, 22+18+15+1, 22+18+15+2+1, 22+20+1, 22+20+2+1, 22+20+14+1, 22+20+14+2+1, 22+20+18+1, 22+20+18+2+1, 22+20+18+3+1, 22+20+18+3+2+1, 22+20+18+4+1, 22+20+18+4+2+1, 22+20+18+5+1, 22+20+18+9+1, 22+20+18+9+2+1, 22+20+18+10+1, 22+20+18+10+2+1, 22+20+18+12+1, 22+20+18+13+1, 22+20+18+13+2+1, 22+20+18+14+1, 22+20+18+14+2+1, 22+20+18+15+1, 22+20+18+15+2+1, 23+1, 23+2+1, 23+3+1, 23+3+2+1, 23+4+1, 23+4+2+1, 23+5+1, 23+6+1, 23+8+1, 23+9+1, 23+9+2+1, 23+10+1, 23+10+2+1, 23+11+1, 23+11+2+1, 23+18+1, 23+18+2+1, 23+18+3+1, 23+18+3+2+1, 23+18+4+1, 23+18+4+2+1, 23+18+5+1, 23+18+9+1, 23+18+9+2+1, 23+18+10+1, 23+18+10+2+1, 23+18+12+1, 23+18+13+1, 23+18+13+2+1, 23+18+14+1, 23+18+14+2+1, 23+18+15+1, 23+18+15+2+1, 23+20+1, 23+20+2+1, 23+20+14+1, 23+20+14+2+1, 23+20+18+1, 23+20+18+2+1, 23+20+18+3+1, 23+20+18+3+2+1, 23+20+18+4+1, 23+20+18+4+2+1, 23+20+18+5+1, 23+20+18+9+1, 23+20+18+9+2+1, 23+20+18+10+1, 23+20+18+10+2+1,

23+20+18+12+1, 23+20+18+13+1, 23+20+18+13+2+1, 23+20+18+14+1, 23+20+18+14+2+1, 23+20+18+15+1, 23+20+18+15+2+1, 24+1, 24+2+1, 24+3+1, 24+3+2+1, 24+4+1, 24+4+2+1, 24+5+1, 25+1, 25+2+1, 25+3+1, 25+3+2+1, 25+4+1, 25+4+2+1, 25+5+1, 25+12+1, 25+13+1, 25+13+2+1, 25+14+1, 25+14+2+1, 26+1, 27+1, 28+1, 28+2+1, 28+3+1, 28+3+2+1, 28+4+1, 28+4+2+1, 28+5+1, 29+1, 29+2+1, 29+3+1, 29+3+2+1, 29+4+1, 29+4+2+1, 29+5+1, 30+1, 31+1, 32+1, 33+1, 33+2+1, 33+3+1, 33+3+2+1, 33+4+1, 33+4+2+1, 33+9+1, 33+9+2+1, 33+10+1, 33+10+2+1, 33+11+1, 33+11+2+1, 33+12+1, 33+13+1, 33+13+2+1, 33+14+1, 33+14+2+1, 33+20+1, 33+20+2+1, 33+20+14+1, 33+20+14+2+1, 33+20+18+1, 33+20+18+2+1, 33+20+18+3+1, 33+20+18+3+2+1, 33+20+18+4+1, 33+20+18+4+2+1, 33+20+18+5+1, 33+20+18+9+1, 33+20+18+9+2+1, 33+20+18+10+1, 33+20+18+10+2+1, 33+20+18+12+1, 33+20+18+13+1, 33+20+18+13+2+1, 33+20+18+14+1, 33+20+18+14+2+1, 33+20+18+15+1, 33+20+18+15+2+1, 34+1, 35+33+1, 35+33+2+1, 35+33+3+1, 35+33+3+2+1, 35+33+4+1, 35+33+4+2+1, 35+33+9+1, 35+33+9+2+1, 35+33+10+1, 35+33+10+2+1, 35+33+11+1, 35+33+11+2+1, 35+33+12+1, 35+33+13+1, 35+33+13+2+1, 35+33+14+1, 35+33+14+2+1, 35+33+20+1, 35+33+20+2+1, 35+33+20+14+1, 35+33+20+14+2+1, 35+33+20+18+1, 35+33+20+18+2+1, 35+33+20+18+3+1, 35+33+20+18+3+2+1, 35+33+20+18+4+1, 35+33+20+18+4+2+1, 35+33+20+18+5+1, 35+33+20+18+9+1, 35+33+20+18+9+2+1, 35+33+20+18+10+1, 35+33+20+18+10+2+1, 35+33+20+18+12+1, 35+33+20+18+13+1, 35+33+20+18+13+2+1, 35+33+20+18+14+1, 35+33+20+18+14+2+1, 35+33+20+18+15+1, 35+33+20+18+15+2+1, 36+1, 37+1, 38+1, 39+1, 39+2+1, 39+3+1, 39+3+2+1, 39+5+1, 39+9+1, 39+9+2+1, 39+12+1, 39+13+1, 39+13+2+1, 39+14+1, 39+14+2+1, 39+35+33+1, 39+35+33+2+1, 39+35+33+3+1, 39+35+33+3+2+1, 39+35+33+4+1, 39+35+33+4+2+1, 39+35+33+9+1, 39+35+33+9+2+1, 39+35+33+10+1, 39+35+33+10+2+1, 39+35+33+11+1, 39+35+33+11+2+1, 39+35+33+12+1, 39+35+33+13+1, 39+35+33+13+2+1, 39+35+33+14+1, 39+35+33+14+2+1, 39+35+33+20+1, 39+35+33+20+2+1, 39+35+33+20+14+1, 39+35+33+20+14+2+1, 39+35+33+20+18+1, 39+35+33+20+18+2+1, 39+35+33+20+18+3+1, 39+35+33+20+18+3+2+1, 39+35+33+20+18+4+1, 39+35+33+20+18+4+2+1, 39+35+33+20+18+5+1, 39+35+33+20+18+9+1, 39+35+33+20+18+9+2+1, 39+35+33+20+18+10+1, 39+35+33+20+18+10+2+1, 39+35+33+20+18+12+1, 39+35+33+20+18+13+1, 39+35+33+20+18+13+2+1, 39+35+33+20+18+14+1, 39+35+33+20+18+14+2+1, 39+35+33+20+18+15+1, 39+35+33+20+18+15+2+1, 40+1, 41+1, 42+1, 43+1, 43+2+1, 43+3+1, 43+3+2+1, 43+4+1, 43+4+2+1, 43+5+1, 43+8+1, 43+9+1, 43+9+2+1, 43+12+1, 43+13+1, 43+13+2+1, 43+14+1, 43+14+2+1, 43+35+33+1, 43+35+33+2+1, 43+35+33+3+1, 43+35+33+3+2+1, 43+35+33+4+1, 43+35+33+4+2+1, 43+35+33+9+1, 43+35+33+9+2+1, 43+35+33+10+1, 43+35+33+10+2+1, 43+35+33+11+1, 43+35+33+11+2+1, 43+35+33+12+1, 43+35+33+13+1, 43+35+33+13+2+1, 43+35+33+14+1, 43+35+33+14+2+1, 43+35+33+20+1, 43+35+33+20+2+1, 43+35+33+20+14+1, 43+35+33+20+14+2+1, 43+35+33+20+18+1, 43+35+33+20+18+2+1, 43+35+33+20+18+3+1, 43+35+33+20+18+3+2+1, 43+35+33+20+18+4+1, 43+35+33+20+18+4+2+1, 43+35+33+20+18+5+1, 43+35+33+20+18+9+1, 43+35+33+20+18+9+2+1, 43+35+33+20+18+10+1, 43+35+33+20+18+10+2+1, 43+35+33+20+18+12+1, 43+35+33+20+18+13+1, 43+35+33+20+18+13+2+1, 43+35+33+20+18+14+1, 43+35+33+20+18+14+2+1, 43+35+33+20+18+15+1, 43+35+33+20+18+15+2+1, 44+1, 44+2+1, 44+3+1, 44+3+2+1, 44+4+1, 44+4+2+1, 44+5+1, 44+9+1, 44+9+2+1, 44+12+1, 44+13+1, 44+13+2+1, 44+14+1, 44+14+2+1, 45+1, 45+2+1, 45+3+1, 45+3+2+1, 45+4+1, 45+4+2+1, 45+5+1, 45+5+2+1, 45+8+1, 45+12+1, 45+13+1, 45+13+2+1, 45+14+1, 45+14+2+1, 45+35+33+1, 45+35+33+2+1, 45+35+33+3+1, 45+35+33+3+2+1, 45+35+33+4+1, 45+35+33+4+2+1, 45+35+33+9+1, 45+35+33+9+2+1, 45+35+33+10+1, 45+35+33+10+2+1, 45+35+33+11+1, 45+35+33+11+2+1, 45+35+33+12+1, 45+35+33+13+1, 45+35+33+13+2+1, 45+35+33+14+1, 45+35+33+14+2+1, 45+35+33+20+1, 45+35+33+20+2+1, 45+35+33+20+14+1, 45+35+33+20+14+2+1, 45+35+33+20+18+1, 45+35+33+20+18+2+1, 45+35+33+20+18+3+1, 45+35+33+20+18+3+2+1, 45+35+33+20+18+4+1, 45+35+33+20+18+4+2+1, 45+35+33+20+18+5+1, 45+35+33+20+18+9+1, 45+35+33+20+18+9+2+1, 45+35+33+20+18+10+1, 45+35+33+20+18+10+2+1, 45+35+33+20+18+12+1, 45+35+33+20+18+13+1, 45+35+33+20+18+13+2+1, 45+35+33+20+18+14+1, 45+35+33+20+18+14+2+1, 45+35+33+20+18+15+1, 45+35+33+20+18+15+2+1, 46+1, 47+1, 48+1, 49+1, 50+1, 51+1, 51+2+1, 51+3+1, 51+3+2+1, 51+4+1, 51+4+2+1, 51+5+1, 51+7+1, 51+7+2+1, 51+8+1, 51+9+1, 51+9+2+1, 51+12+1, 51+13+1, 51+13+2+1, 51+14+1, 51+14+2+1, 52+1, 53+1, 53+2+1, 53+3+1, 53+3+2+1, 53+4+1, 53+4+2+1, 53+5+1, 53+6+1, 53+7+1, 53+7+2+1, 53+8+1, 53+9+1, 53+9+2+1, 53+10+1, 53+10+2+1, 53+11+1, 53+11+2+1, 53+12+1, 53+13+1, 53+13+2+1, 53+14+1, 53+14+2+1, 53+15+1, 53+15+2+1, 53+22+1, 53+22+2+1, 53+22+3+1, 53+22+3+2+1, 53+22+4+1, 53+22+4+2+1, 53+22+5+1, 53+22+6+1, 53+22+12+1, 53+22+13+1, 53+22+13+2+1, 53+22+14+1, 53+22+14+2+1, 53+22+15+1, 53+22+15+2+1, 53+22+18+1, 53+22+18+2+1, 53+22+18+3+1, 53+22+18+3+2+1, 53+22+18+4+1, 53+22+18+4+2+1, 53+22+18+5+1, 53+22+18+9+1, 53+22+18+9+2+1, 53+22+18+10+1, 53+22+18+10+2+1, 53+22+18+12+1, 53+22+18+13+1, 53+22+18+13+2+1, 53+22+18+14+1, 53+22+18+14+2+1, 53+22+18+15+1, 53+22+18+15+2+1, 53+22+20+1, 53+22+20+2+1, 53+22+20+14+1, 53+22+20+14+2+1, 53+22+20+18+1, 53+22+20+18+2+1, 53+22+20+18+3+1, 53+22+20+18+3+2+1, 53+22+20+18+4+1, 53+22+20+18+4+2+1, 53+22+20+18+5+1, 53+22+20+18+9+1, 53+22+20+18+9+2+1, 53+22+20+18+10+1, 53+22+20+18+10+2+1, 53+22+20+18+12+1, 53+22+20+18+13+1, 53+22+20+18+13+2+1, 53+22+20+18+14+1, 53+22+20+18+14+2+1, 53+22+20+18+15+1, 53+22+20+18+15+2+1, 53+23+1, 53+23+2+1, 53+23+3+1, 53+23+3+2+1, 53+23+4+1, 53+23+4+2+1, 53+23+5+1, 53+23+6+1, 53+23+8+1, 53+23+9+1, 53+23+9+2+1, 53+23+10+1, 53+23+10+2+1, 53+23+11+1, 53+23+11+2+1, 53+23+18+1, 53+23+18+2+1, 53+23+18+3+1, 53+23+18+3+2+1, 53+23+18+4+1, 53+23+18+4+2+1, 53+23+18+5+1, 53+23+18+9+1, 53+23+18+9+2+1, 53+23+18+10+1, 53+23+18+10+2+1, 53+23+18+12+1, 53+23+18+13+1, 53+23+18+13+2+1, 53+23+18+14+1, 53+23+18+14+2+1, 53+23+18+15+1, 53+23+18+15+2+1, 53+23+20+1, 53+23+20+2+1, 53+23+20+14+1, 53+23+20+14+2+1, 53+23+20+18+1, 53+23+20+18+2+1, 53+23+20+18+3+1, 53+23+20+18+3+2+1, 53+23+20+18+4+1, 53+23+20+18+4+2+1, 53+23+20+18+5+1, 53+23+20+18+9+1, 53+23+20+18+9+2+1, 53+23+20+18+10+1, 53+23+20+18+10+2+1, 53+23+20+18+12+1, 53+23+20+18+13+1, 53+23+20+18+13+2+1, 53+23+20+18+14+1, 53+23+20+18+14+2+1, 53+23+20+18+15+1, 53+23+20+18+15+2+1, 53+43+1, 53+43+2+1, 53+43+3+1, 53+43+3+2+1, 53+43+4+1, 53+43+4+2+1, 53+43+5+1, 53+43+8+1, 53+43+9+1, 53+43+9+2+1, 53+43+12+1, 53+43+13+1, 53+43+13+2+1, 53+43+14+1, 53+43+14+2+1, 53+43+35+33+1, 53+43+35+

33+2+1, 53+43+35+33+3+1, 53+43+35+33+3+2+1, 53+43+ 35+33+4+1, 53+43+35+33+4+2+1, 53+43+35+33+9+1, 53+43+35+33+9+2+1, 53+43+35+33+10+1, 53+43+35+33+10+2+1, 53+43+35+33+11+1, 53+43+35+33+11+2+1, 53+43+35+33+12+1, 53+43+35+33+13+1, 53+43+35+33+13+2+1, 53+43+35+33+14+1, 53+43+35+33+14+2+1, 53+43+35+33+20+1, 53+43+35+33+20+2+1, 53+43+35+33+20+14+1, 53+43+35+33+20+14+2+1, 53+43+35+33+20+18+1, 53+43+35+33+20+18+2+1, 53+43+35+33+20+18+3+1, 53+43+35+33+20+18+3+2+1, 53+43+35+33+20+18+4+1, 53+43+35+33+20+18+4+2+1, 53+43+35+33+20+18+5+1, 53+43+35+33+20+18+9+1, 53+43+35+33+20+18+9+2+1, 53+43+35+33+20+18+10+1, 53+43+35+33+20+18+10+2+1, 53+43+35+33+20+18+12+1, 53+43+35+33+20+18+13+1, 53+43+35+33+20+18+13+2+1, 53+43+35+33+20+18+14+1, 53+43+35+33+20+18+14+2+1, 53+43+35+33+20+18+15+1, 53+43+35+33+20+18+15+2+1, 54+1, 54+2+1, 54+3+1, 54+3+2+1, 54+4+1, 54+4+2+1, 54+5+1, 54+6+1, 54+7+1, 54+7+2+1, 54+8+1, 54+9+1, 54+9+2+1, 54+10+1, 54+10+ 2+1, 54+11+1, 54+11+2+1, 54+12+1, 54+13+1, 54+13+2+1, 54+14+1, 54+14+2+1, 54+15+1, 54+15+2+1, 54+22+1, 54+22+2+1, 54+22+3+1, 54+22+3+2+1, 54+22+4+1, 54+22+4+2+1, 54+22+5+1, 54+22+6+1, 54+22+12+1, 54+22+13+1, 54+22+13+2+1, 54+22+14+1, 54+22+14+2+ 1, 54+22+15+1, 54+22+15+2+1, 54+22+18+1, 54+22+18+ 2+1, 54+22+18+3+1, 54+22+18+3+2+1, 54+22+18+4+1, 54+22+18+4+2+1, 54+22+18+5+1, 54+22+18+9+1, 54+22+ 18+9+2+1, 54+22+18+10+1, 54+22+18+10+2+1, 54+22+18+12+1, 54+22+18+13+1, 54+22+18+13+2+1, 54+22+18+14+1, 54+22+18+14+2+1, 54+22+18+15+1, 54+22+18+15+2+1, 54+22+20+1, 54+22+20+2+1, 54+22+ 20+14+1, 54+22+20+14+2+1, 54+22+20+18+1, 54+22+20+ 18+2+1, 54+22+20+18+3+1, 54+22+20+18+3+2+1, 54+22+ 20+18+4+1, 54+22+20+18+4+2+1, 54+22+20+18+5+1, 54+22+20+18+9+1, 54+22+20+18+9+2+1, 54+22+20+18+ 10+1, 54+22+20+18+10+2+1, 54+22+20+18+12+1, 54+22+ 20+18+13+1, 54+22+20+18+13+2+1, 54+22+20+18+14+1, 54+22+20+18+14+2+1, 54+22+20+18+15+1, 54+22+20+18+15+2+1, 54+23+1, 54+23+2+1, 54+23+3+1, 54+23+3+2+1, 54+23+4+1, 54+23+4+2+1, 54+23+5+1, 54+23+6+1, 54+23+8+1, 54+23+9+1, 54+23+9+2+1, 54+23+10+1, 54+23+10+2+1, 54+23+11+1, 54+23+11+2+ 1, 54+23+18+1, 54+23+18+2+1, 54+23+18+3+1, 54+23+18+3+2+1, 54+23+18+4+1, 54+23+18+4+2+1, 54+23+18+5+1, 54+23+18+9+1, 54+23+18+9+2+1, 54+23+ 18+10+1, 54+23+18+10+2+1, 54+23+18+12+1, 54+23+18+ 13+1, 54+23+18+13+2+1, 54+23+18+14+1, 54+23+18+14+ 2+1, 54+23+18+15+1, 54+23+18+15+2+1, 54+23+20+1, 54+23+20+2+1, 54+23+20+14+1, 54+23+20+14+2+1, 54+23+20+18+1, 54+23+20+18+2+1, 54+23+20+18+3+1, 54+23+20+18+3+2+1, 54+23+20+18+4+1, 54+23+20+18+ 4+2+1, 54+23+20+18+5+1, 54+23+20+18+9+1, 54+23+20+ 18+9+2+1, 54+23+20+18+10+1, 54+23+20+18+10+2+1, 54+23+20+18+12+1, 54+23+20+18+13+1, 54+23+20+18+ 13+2+1, 54+23+20+18+14+1, 54+23+20+18+14+2+1, 54+23+20+18+15+1, 54+23+20+18+15+2+1, 54+43+1, 54+43+2+1, 54+43+3+1, 54+43+3+2+1, 54+43+4+1, 54+43+4+2+1, 54+43+5+1, 54+43+8+1, 54+43+9+1, 54+43+9+2+1, 54+43+12+1, 54+43+13+1, 54+43+13+2+1, 54+43+14+1, 54+43+14+2+1, 54+43+35+33+1, 54+43+35+ 33+2+1, 54+43+35+33+3+1, 54+43+35+33+3+2+1, 54+43+ 35+33+4+1, 54+43+35+33+4+2+1, 54+43+35+33+9+1, 54+43+35+33+9+2+1, 54+43+35+33+10+1, 54+43+35+33+10+2+1, 54+43+35+33+11+1, 54+43+35+33+11+2+1, 54+43+35+33+12+1, 54+43+35+33+13+1, 54+43+35+33+13+2+1, 54+43+35+33+14+1, 54+43+35+33+14+2+1, 54+43+35+33+20+1, 54+43+35+33+20+2+1, 54+43+35+33+20+14+1, 54+43+35+33+20+14+2+1, 54+43+35+33+20+18+1, 54+43+35+33+20+18+2+1, 54+43+35+33+20+18+3+1, 54+43+35+33+20+18+3+2+1, 54+43+35+33+20+18+4+1, 54+43+35+33+20+18+4+2+1, 54+43+35+33+20+18+5+1, 54+43+35+33+20+18+9+1, 54+43+35+33+20+18+9+2+1, 54+43+35+33+20+18+10+1, 54+43+35+33+20+18+10+2+1, 54+43+35+33+20+18+12+1, 54+43+35+33+20+18+13+1, 54+43+35+33+20+18+13+2+1, 54+43+35+33+20+18+14+1, 54+43+35+33+20+18+14+2+1, 54+43+35+33+20+18+15+1, 54+43+35+33+20+18+15+2+1, 54+44+1, 54+44+2+1, 54+44+3+1, 54+44+3+2+1, 54+44+4+1, 54+44+4+2+1, 54+44+5+1, 54+44+9+1, 54+44+9+2+1, 54+44+12+1, 54+44+13+1, 54+44+13+2+1, 54+44+14+1, 54+44+14+2+ 1, 54+45+1, 54+45+2+1, 54+45+3+1, 54+45+3+2+1, 54+45+5+1, 54+45+8+1, 54+45+12+1, 54+45+13+1, 54+45+13+2+1, 54+45+14+1, 54+45+14+2+1, 54+45+35+ 33+1, 54+45+35+33+2+1, 54+45+35+33+3+1, 54+45+35+ 33+3+2+1, 54+45+35+33+4+1, 54+45+35+33+4+2+1, 54+45+35+33+9+1, 54+45+35+33+9+2+1, 54+45+35+33+ 10+1, 54+45+35+33+10+2+1, 54+45+35+33+11+1, 54+45+ 35+33+11+2+1, 54+45+35+33+12+1, 54+45+35+33+13+1, 54+45+35+33+13+2+1, 54+45+35+33+14+1, 54+45+35+33+14+2+1, 54+45+35+33+20+1, 54+45+35+33+20+2+1, 54+45+35+33+20+14+1, 54+45+35+33+20+14+2+1, 54+45+35+33+20+18+1, 54+45+35+33+20+18+2+1, 54+45+35+33+20+18+3+1, 54+45+35+33+20+18+3+2+1, 54+45+35+33+20+18+4+1, 54+45+35+33+20+18+4+2+1, 54+45+35+33+20+18+5+1, 54+45+35+33+20+18+9+1, 54+45+35+33+20+18+9+2+1, 54+45+35+33+20+18+10+1, 54+45+35+33+20+18+10+2+1, 54+45+35+33+20+18+12+1, 54+45+35+33+20+18+13+1, 54+45+35+33+20+18+13+2+1, 54+45+35+33+20+18+14+1, 54+45+35+33+20+18+14+2+1, 54+45+35+33+20+18+15+1, 54+45+35+33+20+18+15+2+1, 55+1, 56+1;

wherein the list above is not to be construed as limiting with respect to further embodiments which are also possible based on the dependencies of the embodiments 1) to 56) as disclosed hereinabove and which are also intended. In the list above the numbers refer to the embodiments according to their numbering provided hereinabove whereas "+" indicates the dependency from another embodiment. The different individualized embodiments are separated by commas. In other words, "9+2+1" for example refers to embodiment 9) depending on embodiment 2) depending on embodiment 1), i.e. embodiment "9+2+1" corresponds to embodiment 1) further limited by the features of embodiments 2) and 9).

Unless explicitly stated otherwise, the general terms and names used hereinbefore and hereinafter preferably have within the context of this disclosure the following meanings: Where the plural form is used for compounds, salts, pharmaceutical compositions, diseases and the like, this is intended to mean also a single compound, salt, pharmaceutical composition, disease or the like.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

The compounds of formula (I) according to any one of embodiments 1) to 56), or pharmaceutically acceptable salts thereof, may be used for the preparation of a medicament, and are suitable for the prevention and/or treatment of diseases selected from the group consisting of chronic and acute allergic/immune diseases/disorders, comprising asthma, allergic asthma, eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, systemic mast cell disorders, anaphylactic shock, urticaria, eczema, ulcerative colitis, chronic obstructive pulmonary disease (COPD), inflammatory bowel disease and rheumatoid arthritis; eosinophil-related diseases comprising small vessel vasculitides like Churg-Strauss syndrome, Wegener's granulomatosis, microscopic polyangiitis (and organ-specific subsets of the latter), hypereosinophilic syndromes like eosinophilic pneumonia, eosinophilic esophagitis, reflux esophagitis, eosinophilic endocarditis (Loeffler's endocarditis), eosinophilia-myalgia syndrome, eosinophilic fasciitis, eosinophilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia and DRESS syndrome (Drug Rash with Eosinophilia and Systemic Symptoms); and basophil-related diseases, comprising basophilic leukemia and basophilic leukocytosis.

In a preferred embodiment, the compounds of formula (I) according to any one of embodiments 1) to 56), or pharmaceutically acceptable salts thereof, may be used for the preparation of a medicament, and are suitable for the prevention and/or treatment of diseases selected from the group consisting of asthma, allergic asthma, eosinophilic asthma, severe asthma, allergic rhinitis, angioedema, insect venom allergy, drug allergies, allergic sinusitis, allergic nephritis, allergic conjunctivitis, atopic dermatitis, food allergy, systemic mast cell disorders, anaphylactic shock, urticaria and eczema.

In another preferred embodiment, the compounds of formula (I) according to any one of embodiments 1) to 56), or pharmaceutically acceptable salts thereof, may be used for the preparation of a medicament, and are suitable for the prevention and/or treatment of diseases selected from the group consisting of eosinophil-related diseases comprising small vessel vasculitides like Churg-Strauss syndrome, Wegener's granulomatosis, microscopic polyangiitis (and organ-specific subsets of the latter), hypereosinophilic syndromes like eosinophilic pneumonia, eosinophilic esophagitis, reflux esophagitis, eosinophilic endocarditis (Loeffler's endocarditis), eosinophilia-myalgia syndrome, eosinophilic fasciitis, eosinophilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia and DRESS syndrome (Drug Rash with Eosinophilia and Systemic Symptoms).

In yet another preferred embodiment, the compounds of formula (I) according to any one of embodiments 1) to 56), or pharmaceutically acceptable salts thereof, may be used for the preparation of a medicament, and are suitable for the prevention and/or treatment of diseases selected from the group consisting of basophil-related diseases, comprising basophilic leukemia and basophilic leukocytosis.

In a more preferred embodiment, the compounds of formula (I) according to any one of embodiments 1) to 56), or pharmaceutically acceptable salts thereof, may be used for the preparation of a medicament, and are suitable for the prevention and/or treatment of diseases selected from the group consisting of asthma, allergic asthma, eosinophilic asthma, severe asthma and allergic rhinitis.

In another more preferred embodiment, the compounds of formula (I) according to any one of embodiments 1) to 56), or pharmaceutically acceptable salts thereof, may be used for the preparation of a medicament, and are suitable for the prevention and/or treatment of eosinophilic esophagitis.

In still another more preferred embodiment, the compounds of formula (I) according to any one of embodiments 1) to 56), or pharmaceutically acceptable salts thereof, may be used for the preparation of a medicament, and are suitable for the prevention and/or treatment of atopic dermatitis.

The invention also relates to the use of a compound of formula (I) according to any one of embodiments 1) to 56) for the preparation of pharmaceutical compositions for the treatment and/or prophylaxis of the above-mentioned diseases.

The present invention also relates to pharmaceutically acceptable salts and to pharmaceutical compositions and formulations of compounds of formula (I) according to any one of embodiments 1) to 56).

A pharmaceutical composition according to the present invention contains at least one compound of formula (I) according to any one of embodiments 1) to 56) (or a pharmaceutically acceptable salt thereof) as the active agent and optionally carriers and/or diluents and/or adjuvants.

The compounds of formula (I) according to any one of embodiments 1) to 56) and their pharmaceutically acceptable salts can be used as medicaments, e.g. in the form of pharmaceutical compositions for enteral (such as especially oral) or parenteral (including topical application or inhalation) administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to any one of embodiments 1) to 56), or a pharmaceutically acceptable salt thereof.

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

Any reference to a compound of formula (I), $(I_P)$, $(I_{St1})$, $(I_{St2})$, (I-1) or (I-2) in this text is to be understood as referring also to the salts (and especially the pharmaceutically acceptable salts) of such compounds, as appropriate and expedient. The preferences indicated for the compounds of formula (I) of course apply mutatis mutandis to the compounds of formula $(I_P)$, the compounds of formula $(I_{St1})$, the compounds of formula $(I_{St2})$, the compounds of formula (I-1) and the compounds of formula (I-2) as well as to the salts and pharmaceutically acceptable salts of the compounds of formula (I), of formula $(I_P)$, of formula $(I_{St1})$, of formula $(I_{St2})$, of formula (I-1) and of formula (I-2). The same applies to these compounds as medicaments, to pharmaceutical compositions containing these compounds as active principles or to the uses of these compounds for the manufacture of a medicament for the treatment of the diseases according to this invention.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (r.t.) as used herein refers to a temperature of about 25° C.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range or if a variable is defined as being an integer between 1 and 4, this means that the variable is the integer 1, 2, 3, or 4.

As mentioned earlier, compounds of formula (I) modulate the PGD$_2$ activation of the CRTH2 receptor. The biological effect of such compounds may be tested in a variety of in vitro, ex vivo and in vivo assays. The ability of the compounds of formula (I) to bind to the CRTH2 receptor may be measured by methods similar to those described in the literature (Arimura A. et al., *J. Pharmacol. Exp. Ther.* 2001, 298(2), 411-419; and Sawyer N. et al., *Br. J. Pharmacol,* 2002, 137, 1163-1172, respectively) and by the assays described below in the experimental part.

A further aspect of the invention is a process for the preparation of compounds of Formula (I). Compounds according to Formula (I) of the present invention can be prepared according to the sequence of reactions outlined in the schemes below wherein Z, n, m, $R^1$, $R^2$, $R^3$, $R^4$, $R^5$, $R^6$, $R^7$ and $R^8$ are as defined for Formula (I). Other abbreviations used are defined in the experimental section. In some instances the generic groups Z, n, m, $R^1$, $R^2$, $R^3$, $R^4$, $R^5$, $R^6$, $R^7$ and $R^8$ might be incompatible with the assembly illustrated in the schemes below and, therefore, will require the use of protecting groups (PG). For example it may be necessary to protect reactive functional groups such as hydroxy, amino, imino, thio or carboxy groups, where these are desired in the final product, to avoid their unwanted participation in the reactions. The use of protecting groups is well known in the art (see for example "Protective Groups in Organic Synthesis", T. W. Greene, P. G. M. Wuts, Wiley-Interscience, 1999). It will be assumed that such protecting groups are as necessary in place. In the following description, for example, "PG", when used as amino-protecting group, preferably refers to a group such as tert-butoxycarbonyl, benzyloxycarbonyl, allyloxycarbonyl or benzyl, most preferably benzyloxycarbonyl. Further, "L" refers to a leaving group, such as an activated hydroxy group (for examples as mesylate, tosylate, active ester etc.), an in-situ activated hydroxy group (as used, for instance, in Mitsunobu reactions), or a halogen, in particular chloro or bromo. Further, "R" refers to a ($C_1$-$C_4$)alkyl group, preferably methyl, ethyl or tert-butyl.

In general, all chemical transformations can be performed according to well-known standard methodologies as described in the literature or as described in the procedures below. The compounds obtained may also be converted into pharmaceutically acceptable salts thereof in a manner known per se.

Generally, compounds of Formula (I) (or of Formula (I$_P$)), are obtained from an ester of Structure 1, wherein one of $R^A$, $R^B$ and $R^C$ represents ($C_1$-$C_4$)alkoxy-carbonyl-cyclopropyl, ($C_1$-$C_4$)alkoxy-carbonyl-($C_1$-$C_3$)alkyl or ($C_1$-$C_4$)alkoxy-carbonyl-($C_1$-$C_3$)alkoxy and the other two represent independently of each other hydrogen, ($C_1$-$C_4$)alkoxy or halogen, by hydrolysis of the ester group using routine procedures. For example, a methyl- or ethyl-ester derivative of Structure 1 can be saponified with an aqueous solution of LiOH, NaOH, or KOH in an organic co-solvent such as an alcohol (like MeOH or EtOH), THF, acetone, MeCN, or DMF; alternatively a tert.-butyl-ester derivative of Structure 1 can be cleaved with an acid like TFA.

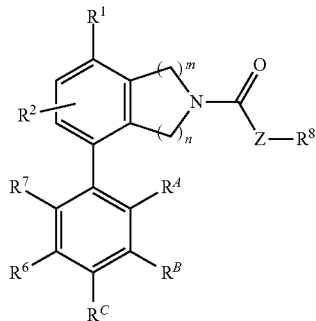

Ester of Structure 1

An intermediate of Structure 1 is for instance obtained by reacting an intermediate of Structure 2, or a salt thereof, such as a hydrochloride salt, with a reagent of Formula L-C(O)Z—$R^8$, wherein Z and $R^8$ are as defined for Formula (I) (or for Formula (I$_P$)) and L is a leaving group such as an halogen (in particular chloro), in the presence of a base like NEt$_3$, DIPEA, N-ethyl-morpholine, N-methylpiperidine, or pyridine, in a suitable solvent, such as THF, or DCM. The starting material L-C(O)Z—$R^8$ may be a chloroformate; an acyl anhydride; or an acyl halide like an acid chloride or an acid bromide. The acyl halide may be commercially available, known in the art or obtainable in situ from the corresponding commercially available or well known carboxylic acid in a reaction with a halogenating reagent like oxalyl chloride or phosphorous oxychloride under conditions known to a skilled person.

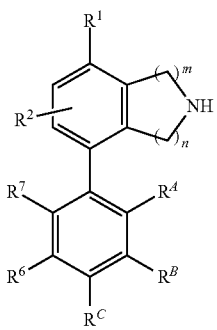

Structure 2

In another aspect, an intermediate of Structure 2 is reacted with a commercially available or well known isocyanate in the presence of a base like NEt$_3$ or DIPEA to form an intermediate of Structure 1.

In a further aspect, an intermediate of Structure 2 is condensed with a commercially available or well known carboxylic acid in the presence of a coupling reagent, such as EDC, TBTU, diisopropylcarbodiimide, HATU, DCC, Ghosez's reagent or the like, in the presence of a base like NEt$_3$, DIPEA, or pyridine to form an intermediate of Structure 1.

In another aspect an intermediate of Structure 2 is reacted with a carbonate 3, wherein $R^D$ represents optionally substituted aryl, in the presence of a base like NEt$_3$ or DIPEA to give an intermediate of Structure 1-A (Scheme 1). A carbonate 3 is prepared by reaction of a benzyl alcohol 4 with N,N'-disuccinimidyl carbonate in the presence of a base like DMAP.

Scheme 1. Synthesis of an intermediate of Structure 1-A.

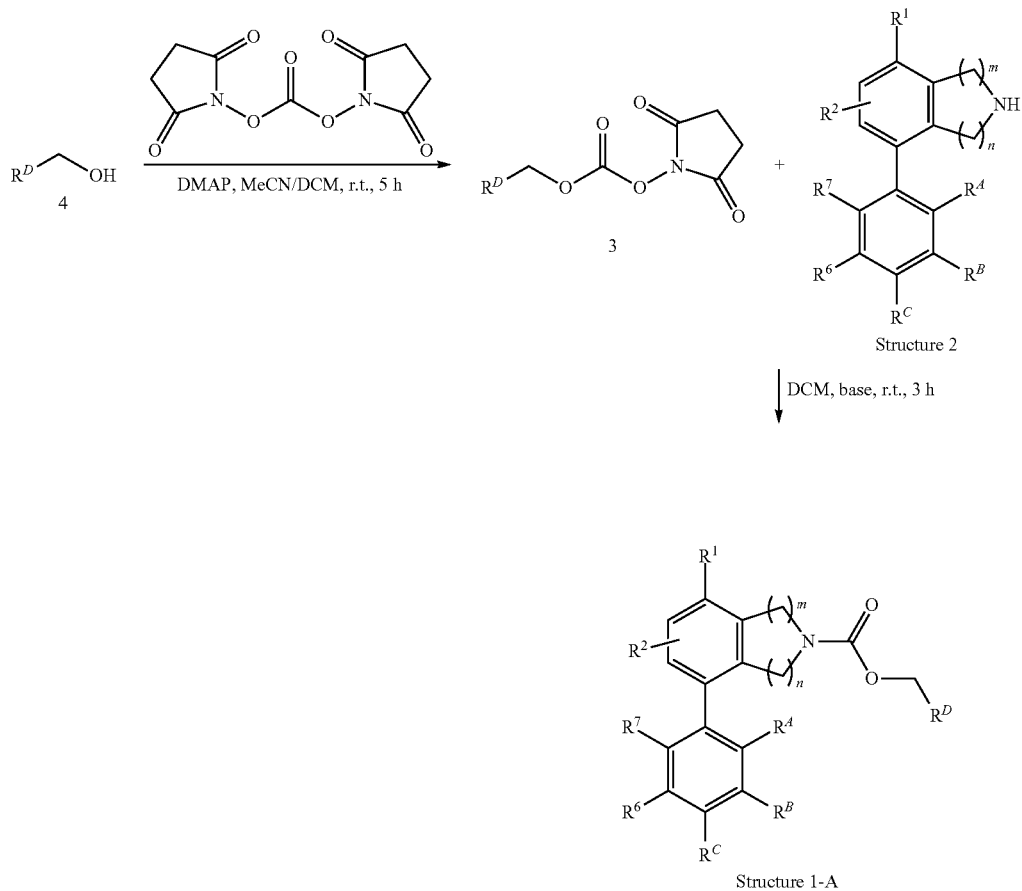

Alternatively an intermediate of Structure 2 is condensed with 4-nitrophenyl chloroformate in the presence of a base like $NEt_3$ or DIPEA to give a carbamate 5 (Scheme 2). The carbamate 5 is then treated with an alcohol $R^E OH$, wherein $R^E$ represents $(C_2-C_5)$alkyl; $(C_1-C_5)$alkyl which is mono-substituted with $(C_3-C_6)$cycloalkyl, optionally substituted heterocyclyl, optionally substituted aryl or optionally substituted heteroaryl; $(C_3-C_5)$alkenyl; or $(C_3-C_5)$alkynyl in the presence of potassium tert-butoxide to give a compound of Formula (I-A). Under these specific conditions, the saponification of the ester group of $R^A$, $R^B$, or $R^C$ and the substitution take place during the same reaction.

Scheme 2. Synthesis of a compound of Formula 1-A.

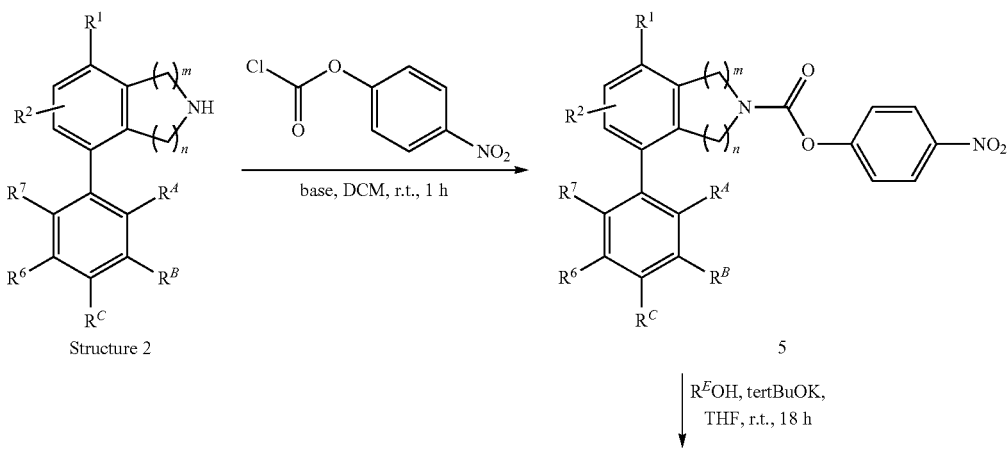

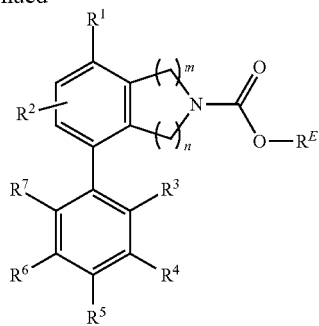

Formula (1-A)

An intermediate of Structure 2 is obtained after removal of a protecting group (PG) from an intermediate of Structure 6, applying reaction conditions known to a skilled person. Preferably, PG is a group such as tert-butoxycarbonyl or benzyloxycarbonyl. A benzyloxycarbonyl protecting group is removed by hydrogenolysis or treatment with an acid; a tert-butoxycarbonyl group is cleaved under acidic conditions. PG can also be a benzyl protecting group, which can be cleaved by hydrogenolysis.

An intermediate of Structure 6 is obtained by one of the synthetic pathways described below. For example, an intermediate of Structure 6 is obtained via Suzuki cross-coupling reaction between a compound of Structure 7, wherein $R^F$ represents bromo, chloro, or triflate and a boronic acid or boronic ester derivative 8, wherein $R^G$ represents hydroxy or pinacol in the presence of a base like $Na_2CO_3$ or $K_3PO_4$, and a palladium catalyst like $Pd(PPh_3)_4$, or $Pd(OAc)_2$ and (S)-Phos (Scheme 3). If not commercially available, the boronic ester derivatives 8 can be obtained from the corresponding compounds 9, wherein $R^H$ represents chloro, bromo or triflate (preferably bromo) by treatment with bis(pinacolato)diboron 10 in the presence of a base like potassium acetate and a palladium catalyst like $Pd(PPh_3)_4$ or $Pd(dppf)Cl_2$. Alternatively, a compound of Structure 7 can be converted in a boronic ester derivative 11 by treatment with bis(pinacolato)diboron 10 in the presence of a base like potassium acetate and a palladium catalyst like $Pd(PPh_3)_4$ or $Pd(dppf)Cl_2$. The resulting boronic ester 11 can undergo a Suzuki cross-coupling reaction with compound 9, wherein $R^H$ represents chloro, bromo or triflate (preferably bromo) in the presence of a base like $Na_2CO_3$ or $K_3PO_4$, and a palladium catalyst like $Pd(PPh_3)_4$, or $Pd(OAc)_2$ and (S)-Phos to give a compound of Structure 6.

Structure 6

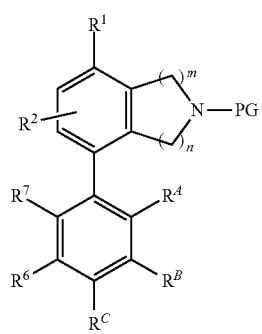

Scheme 3. Synthesis of a compound of Structure 6.

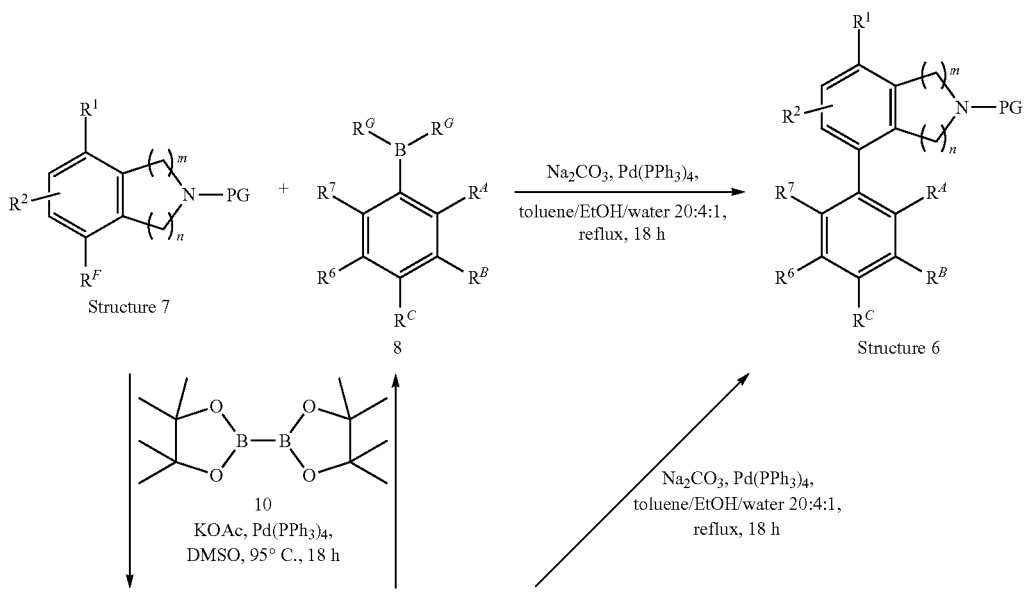

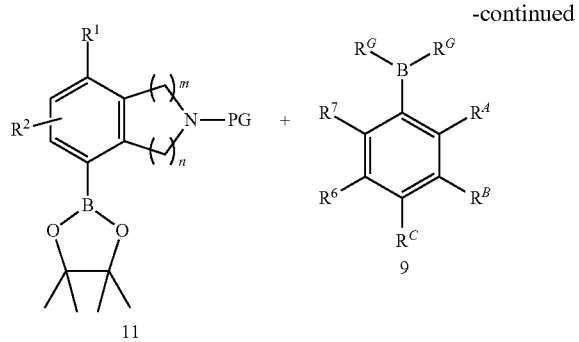

Alternatively, a compound of Structure 7 can be reacted in a Suzuki cross-coupling reaction with a boronic acid 12, wherein one of $R^I$, $R^J$ and $R^K$ represents hydroxy and the other two represent independently of each other hydrogen, $(C_1-C_4)$ alkoxy or halogen, in the presence of a base like $Na_2CO_3$ or $K_3PO_4$, and a palladium catalyst like $Pd(PPh_3)_4$, or $Pd(OAc)_2$ and (S)-Phos. The resulting phenol 13 can then be alkylated with an electrophile L-$(C_1-C_3)$alkyl-$CO_2R$, wherein R represents $(C_1-C_4)$alkyl and L is a leaving group such as bromide or tosyl which is attached to any carbon atom of the $(C_1-C_3)$ alkyl group, in the presence of a base like $Cs_2CO_3$ or $K_2CO_3$ to give an intermediate of Structure 6-A (Scheme 4).

In another aspect, a compound of Structure 2-A, wherein n represents 1 and m represents 2 (a tetrahydroisoquinoline) can be obtained by catalytic hydrogenation of an isoquinoline 14 in the presence of a platinum catalyst under an hydrogen atmosphere (Scheme 5). An isoquinoline 14 is obtained by a Suzuki cross-coupling reaction between an isoquinoline 15 and a boronic acid or boronic ester 8 in the presence of a base like $Na_2CO_3$ or $K_3PO_4$, and a palladium catalyst like $Pd(PPh_3)_4$, or $Pd(OAc)_2$ and (S)-Phos.

Scheme 4. Synthesis of a compound of Structure 6-A.

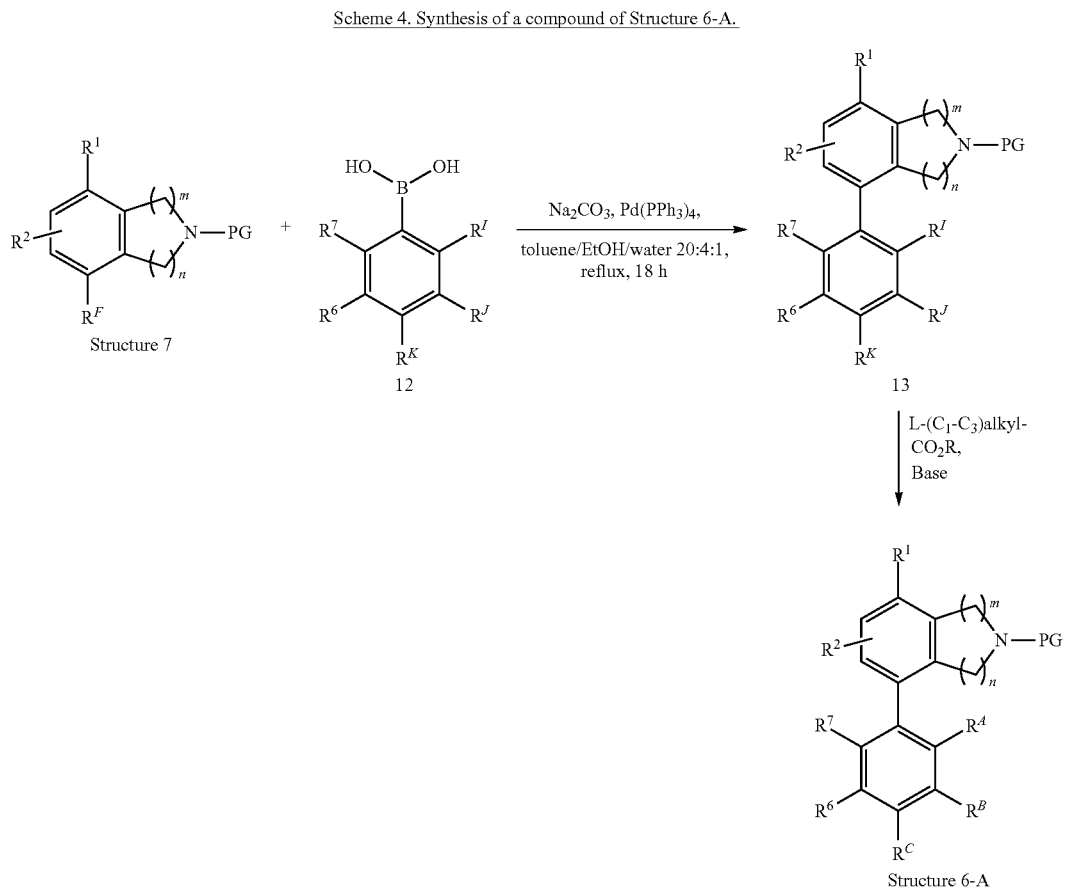

Scheme 5. Synthesis of a compound of Structure 2-A.

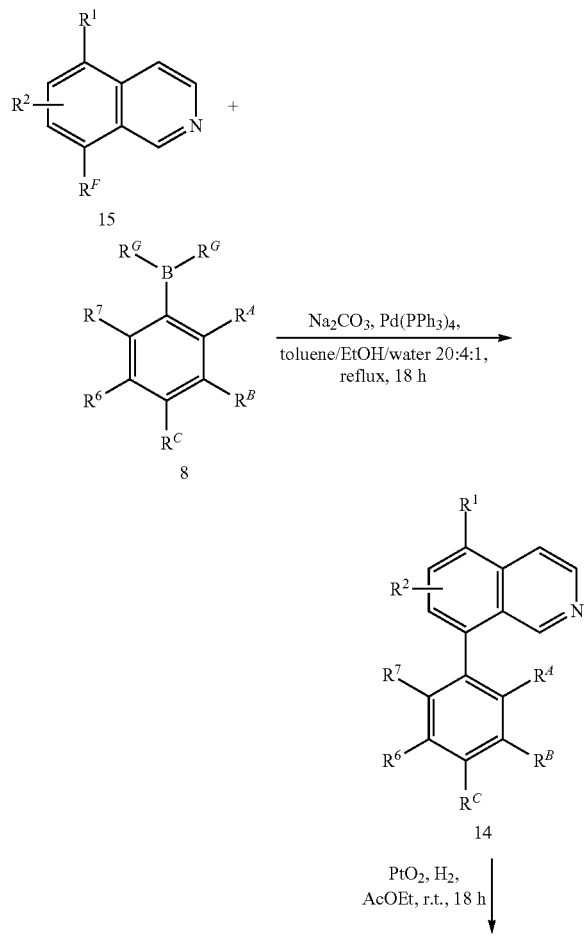

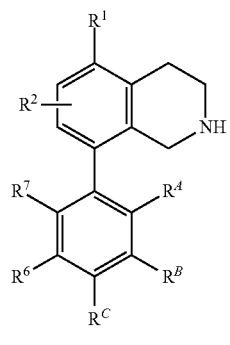

Structure 2-A

An intermediate of Structure 7, wherein n represents 1 and m represents 2 or n represents 2 and m represents 1 (a tetrahydroisoquinoline) is obtained by one of the synthetic pathways described below (Schemes 6 to 9). For example, a 3,4-dihydroisoquinoline 16, wherein $R^L$ represents chloro or bromo, can be reduced using for example $NaBH_4$ to afford the tetrahydroisoquinoline 17, which can be treated with a protecting group precursor PGL such as di-tert-butyl dicarbonate or a chloroformate (like benzyl chloroformate) in the presence of a base like $NEt_3$ or DIPEA to give a compound of Structure 7-A. The required 3,4-dihydroisoquinolines 16, are prepared from the corresponding phenethylamines 18 (or the corresponding hydrochloride salts) using a modified Bischler-Napieralski reaction. Thus, reaction of a phenethylamine 18 with ethyl formiate affords the corresponding formamide, which is transformed into an oxazolo intermediate upon treatment with oxalyl chloride and iron(III) chloride. Treatment of the oxazolo derivative with methanol in the presence of an acid like sulphuric acid yields the desired 3,4-dihydroisoquinoline 16. If not commercially available, the phenethylamines 18 may be synthesized by reduction of the corresponding α,β-unsaturated nitro derivatives 19, which are prepared from the aldehydes 20 via an Henry reaction (Scheme 6).

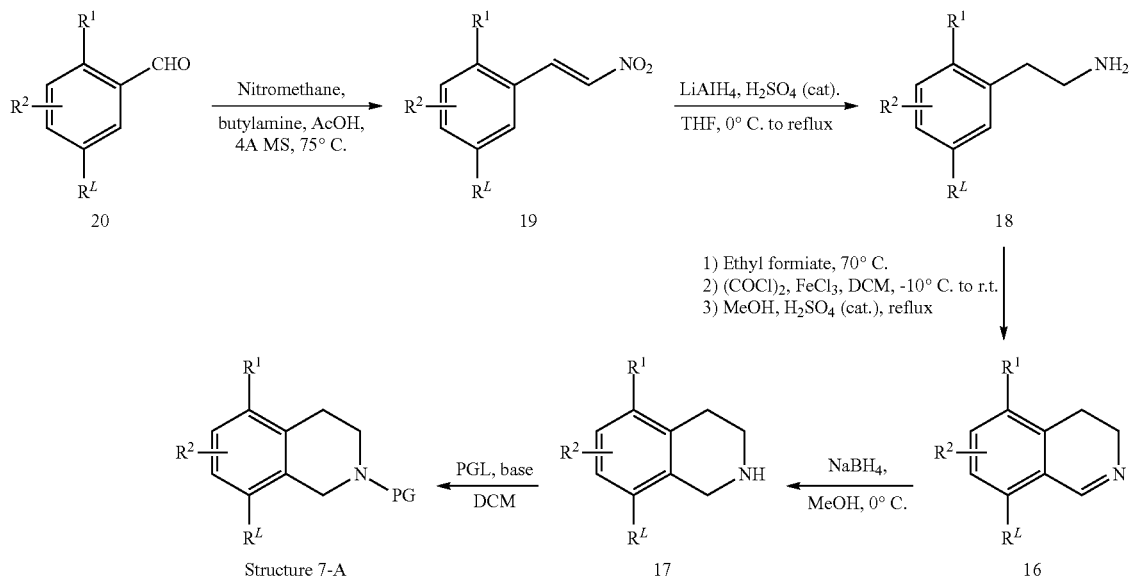

Alternatively, a phenethylamine 21, prepared from the corresponding aldehyde 22 following the sequence depicted in Scheme 6, is transformed into a formamide, which is then heated in a strong acid like PPA to give the 3,4-dihydroisoquinoline 23 (Scheme 7). Compound 23 can then be demethylated in the presence of aluminum trichloride, followed by reduction with NaBH$_4$ and treatment with a protecting group precursor PGL such as di-tert-butyl dicarbonate or a chloroformate (like benzyl chloroformate) in the presence of a base like NEt$_3$ or DIPEA to give a tetrahydroisoquinoline 24. Upon treatment with zinc cyanide in the presence of a palladium catalyst and poly(methylhydrosiloxane), the bromide 24 can be transformed into a nitrile, which can then be transformed into a triflate of Structure 7-B upon treatment with trifluoromethanesulfonic anhydride in the presence of a base like NEt$_3$.

Following the synthetic pathway depicted in Scheme 6, but starting from the corresponding aldehyde 26 an intermediate of Structure 7-D, wherein n represents 2 and m represents 1 (a tetrahydroisoquinoline) can be prepared (Scheme 9).

Scheme 9. Synthesis of the tetrahydroisoquinolines 7-D.

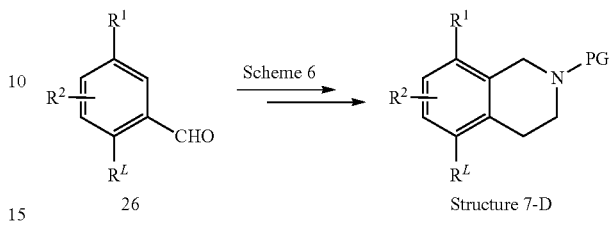

Scheme 7. Synthesis of a compound of Structure 7-B.

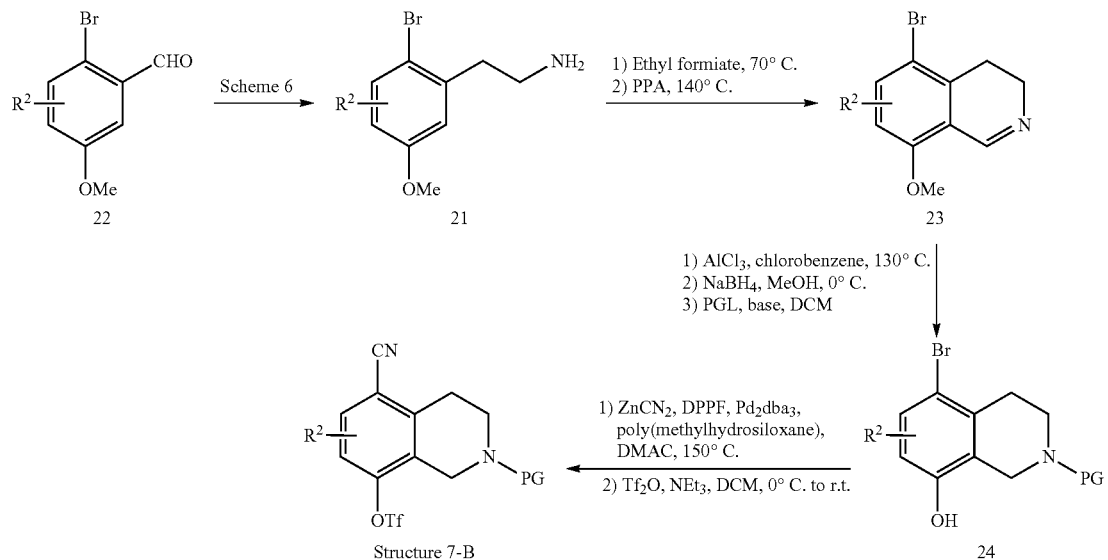

In another aspect, a bromide 25, prepared following the synthetic sequence depicted in Scheme 6, can be transformed in the corresponding sulfone of Structure 7-C using the sulfinate derivative MeS(O)ONa in the presence of a copper catalyst like CuI and a ligand like prolinate (Scheme 8).

Scheme 8. Synthesis of a compound of Structure 7-C.

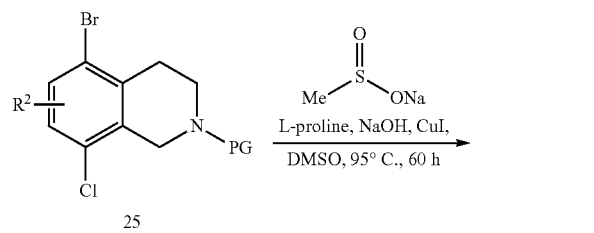

An intermediate of Structure 7-E, wherein n represents 1 and m represents 1 (an isoindoline) can be obtained by the synthetic pathway described in Scheme 10. Thus a dimethylbenzene derivative 27, wherein $R^M$ represents bromo or chloro, is brominated with for example NBS in the presence of a radical initiator like benzoyl peroxide to give the dibromide 28. The dibromide 28 can then react with a protected primary amine, like benzylamine, in the presence of a base like potassium carbonate, to give an isoindoline of Structure 7-E, wherein PG represents benzyl.

Scheme 10. Synthesis of the isoindolines of Structure 7-E.

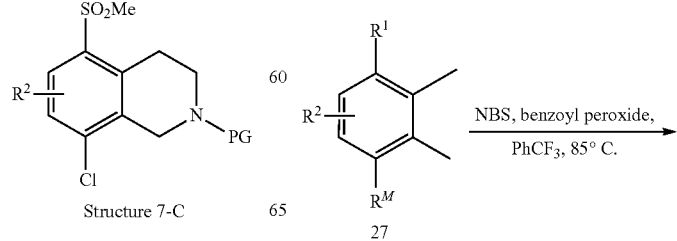

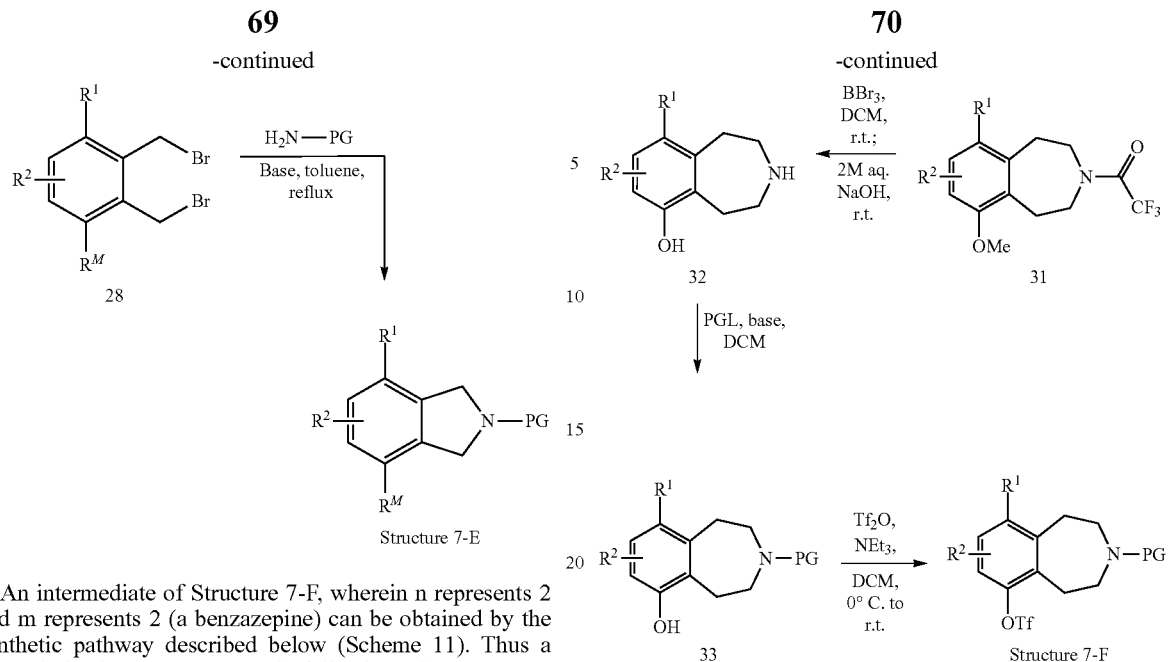

An intermediate of Structure 7-F, wherein n represents 2 and m represents 2 (a benzazepine) can be obtained by the synthetic pathway described below (Scheme 11). Thus a phenethylamine 29, prepared following the sequence depicted in Scheme 6, undergoes a condensation with glyoxal dimethyl acetal in a solvent like MeOH. The resulting imine is then reduced in the presence of NaBH$_4$ to give the amine 30. Protection of the amine 30 with trifluoroacetic anhydride, TFA mediated cyclization, and subsequent catalytic hydrogenation lead to the benzazepine 31. Demethylation using for example BBr$_3$ followed by cleavage of the trifluoroacetamide moiety with a base like NaOH gives the benzazepine 32, which can be treated with a protecting group precursor PGL such as di-tert-butyl dicarbonate or a chloroformate like benzyl chloroformate in the presence of a base like NEt$_3$ or DIPEA to give the benzazepine 33. The resulting phenol 33 can be converted into a triflate of Structure 7-F by treatment with trifluoromethanesulfonic anhydride in the presence of a base like NEt$_3$.

The isoquinolines 15 are prepared as described in Scheme 12. The aldehydes 34, wherein $R^N$ represents bromo, chloro, or methoxy, undergo a reductive amination with the amine 35 to give the secondary amine 36, which can be converted with tosyl chloride into a sulfonamide 37 in the presence of a base like NEt$_3$. In case $R^N$ represents bromo or chloro, the sulfonamide 37 is converted into the isoquinoline 15-A by treatment with aluminum trichloride. In case $R^N$ represents methoxy, an isoquinoline 38 is obtained by treatment of 37 with aluminum trichloride. The isoquinoline 38 is then converted into the triflate 15-B upon treatment with trifluoromethanesulfonic anhydride in the presence of a base like NEt$_3$.

Scheme 11. Synthesis of the benzazepines of Structure 7-F.

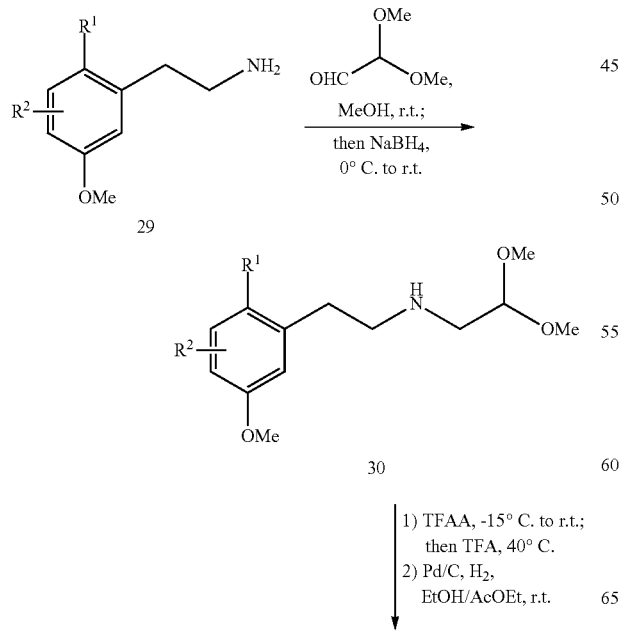

Scheme 12. Synthesis of the isoquinolines 15-A and 15-B.

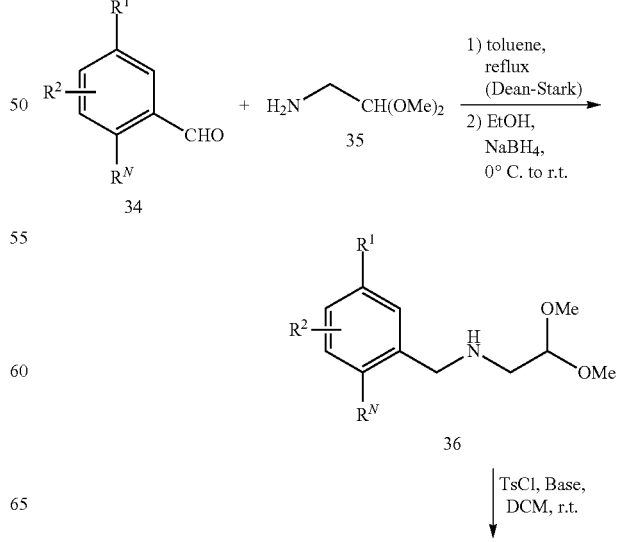

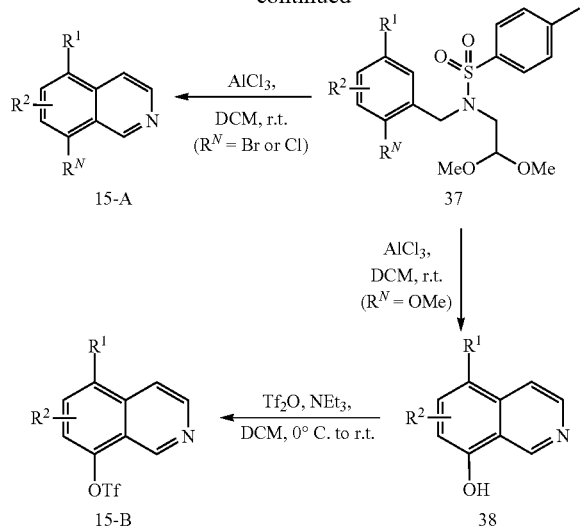

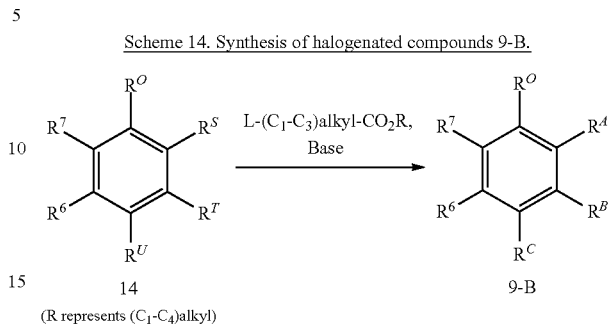

If not commercially available, halogenated derivatives 9-A wherein $R^O$ represents chloro or bromo can be prepared from the corresponding benzoic acid 39, wherein one of $R^P$, $R^Q$ and $R^R$ represents carboxy and the other two represent independently of each other hydrogen, $(C_1-C_4)$alkoxy or halogen, via an Arndt-Eistert homologation. The benzoic acid derivatives 39 are first converted into acyl chlorides, for example by treatment with oxalyl chloride in the presence of a catalytic amount of DMF (Scheme 13). The resulting acyl chlorides are then converted into diazoethanone derivatives upon treatment with trimethylsilyl diazomethane. The diazoethanone derivatives can then undergo a Wolff rearrangement in the presence of an alcohol like EtOH, a base like $NEt_3$, and a silver salt like silver benzoate to give the halogenated compounds 9-A, wherein one of $R^A$, $R^B$ or $R^C$ represents the respective alkoxy-carbonyl-methyl moiety.

Scheme 13. Synthesis of halogenated compounds 9-A.

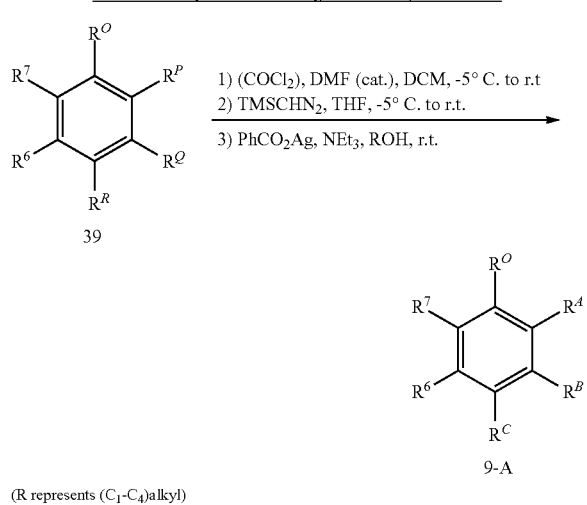

(R represents $(C_1-C_4)$alkyl)

Alternatively, halogenated derivatives 9-B can be prepared by alkylation of phenols 40, wherein one of $R^S$, $R^T$ and $R^U$ represents hydroxy and the other two represent independently of each other hydrogen, $(C_1-C_4)$alkoxy or halogen, with an electrophile L-$(C_1-C_3)$alkyl-$CO_2R$, wherein R represents $(C_1-C_4)$alkyl and L is a leaving group such as bromide or tosyl which is attached to any carbon atom of the $(C_1-C_3)$alkyl group, in the presence of a base like $Cs_2CO_3$ or $K_2CO_3$ (Scheme 14).

Scheme 14. Synthesis of halogenated compounds 9-B.

(R represents $(C_1-C_4)$alkyl)

In another aspect, a compound 9-C can be prepared by alkylation of a phenol 41 with L-$R^V$, wherein L represents a leaving group like iodide, bromide, chloride or triflate and $R^V$ represents $(C_1-C_4)$alkyl, $(C_1-C_4)$fluoroalkyl, or methoxyethyl in the presence of a base like potassium carbonate (Scheme 15). In analogy, alkylation of both, the hydroxy and the carboxy group of phenol 42 with L-$R^V$ in the presence of a base like potassium carbonate and subsequent saponification of the obtained ester with an aqueous solution of NaOH, KOH, or LiOH in the presence of a co-solvent like THF or EtOH gives a benzoic acid 39-A. Alternatively, the acid 42 may be selectively esterified by, for example, treatment with HCl in a solvent like EtOH. The resulting phenol can then be alkylated with L-$R^V$ in the presence of a base like potassium carbonate. A final saponification with an aqueous solution of NaOH, KOH, or LiOH in the presence of a co-solvent like THF or EtOH yields a benzoic acid 39-A.

Scheme 15. Alkylation of phenols 41 or 42.

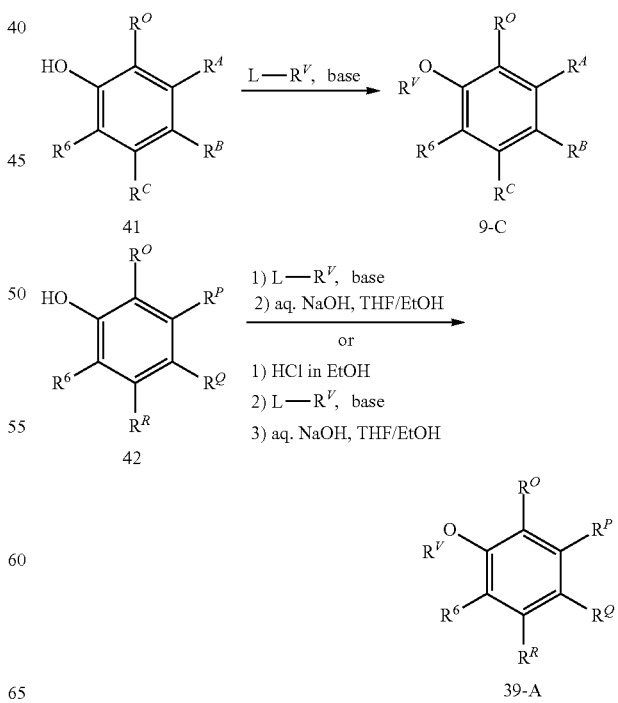

Acid derivatives used in the amide coupling with compounds of Structure 2 are commercially available, known in the art, or obtainable according to Schemes 16, 17, 18 or 19. A cinnamic acid 43, wherein $R^W$ and $R^X$ independently represent hydrogen, $(C_1-C_4)$alkyl, $(C_1-C_4)$alkoxy, $(C_1-C_4)$fluoroalkyl, or halogen, is converted to the Weinreb amide 44 using standard amide coupling conditions such as EDC in the presence of a base like DMAP in a solvent like DMF. Corey-Chaykovsky cyclopropanation gives the cyclopropane (±)-45, which is hydrolyzed to the corresponding carboxylic acid (±)-46 with a base like potassium tert-butoxide (Scheme 16).

Pyridine carboxylic acid (±)-52 can be prepared following the synthetic Scheme 18. An Horner-Emmons olefination between a pyridine derivative 53 (wherein $R^Y$ represents hydrogen, $(C_1-C_3)$alkyl or $(C_3-C_6)$cycloalkyl, and $R^Z$ and $R^{AA}$ independently represent hydrogen, halogen, $(C_1-C_3)$alkyl or $(C_1-C_2)$alkoxy) and dimethyl(benzyloxycarbonyl)methyl phosphonate, in the presence of a base like NaH, gives the α,β-unsaturated ester 54. The cis- and trans-isomer may be

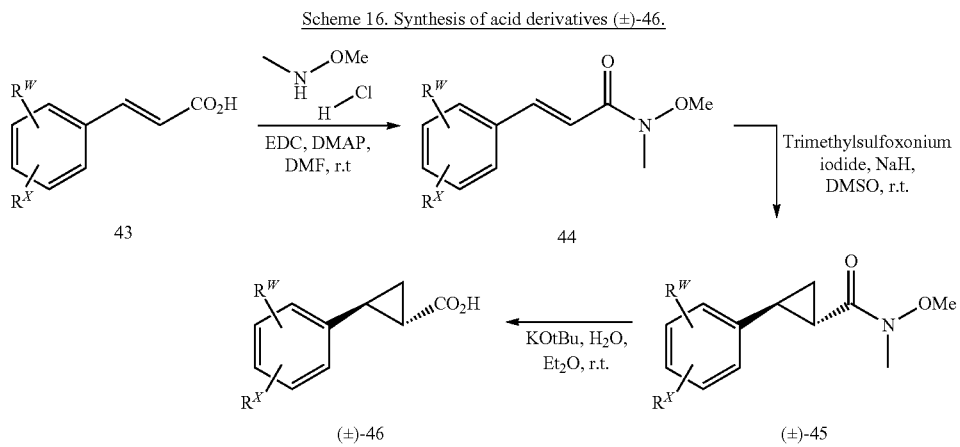

Scheme 16. Synthesis of acid derivatives (±)-46.

Optically pure phenylcyclopropyl carboxylic acid (R,R)-47 can be prepared following the synthetic sequence depicted in Scheme 17. A styrene derivative 48, wherein $R^W$ and $R^X$ independently represent hydrogen, $(C_1-C_4)$alkyl, $(C_1-C_4)$alkoxy, $(C_1-C_4)$fluoroalkyl, or halogen, is converted into epoxide (S)-49 via Sharpless-dihydroxylation using AD-mix-α (J. Org. Chem. 1992, 57, 2768-2771), followed by transformation of the resulting diol into the respective epoxide using a protocol developed by Sharpless et al. (Tetrahedron 1992, 48, 10515-10530). The epoxide (S)-49 undergoes an Horner-Emmons cyclopropanation in the presence of triethyl phosphonoacetate and a base like nBuLi to give the ester (R,R)-50, which is hydrolyzed to the corresponding phenylcyclopropyl carboxylic acid (R,R)-47 (Scheme 17).

separated by column chromatography or may be used as a mixture in the next catalytic hydrogenation. Thus, upon treatment with Pd/C under an $H_2$-atmosphere in a solvent like THF, the α,β-unsaturated ester 54 is transformed into the racemic carboxylic acid (±)-52 (Scheme 18). In analogy, starting from a substituted pyridine anneleted to a cyclohexanone, like for example 6,7-dihydro-5H-quinolin-8-one, the corresponding carboxylic acid derivative, like for example (±)-2-(5,6,7,8-tetrahydroquinolin-8-yl)acetic acid, may be obtained.

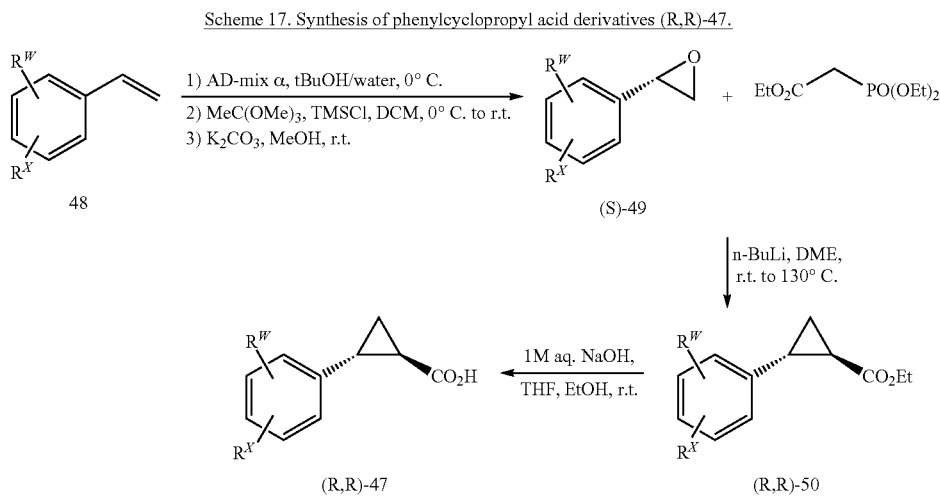

Scheme 17. Synthesis of phenylcyclopropyl acid derivatives (R,R)-47.

Scheme 18. Synthesis of pyridinecarboxylic acid derivatives (±)-52.

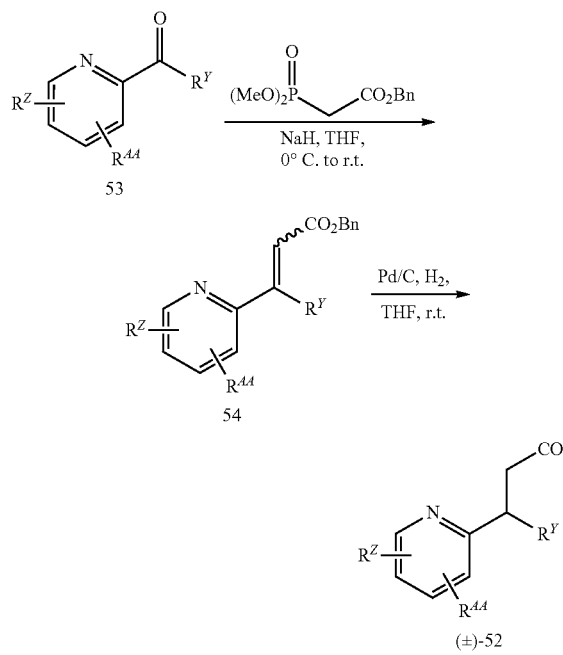

The synthesis of carboxylic acid derivatives (±)-55 is depicted in Scheme 19. An Horner-Emmons olefination between a ketone 56 (wherein $R^{AB}$ and $R^{AC}$ independently represent hydrogen or halogen, one of Q and T represents —O— or —CH$_2$— and the other one is absent or represents —CH$_2$— or —C(Me)$_2$-) and a phosphonoacetate, like triethyl phosphonoacetate, in the presence of a base like NaH affords the α,β-unsaturated ester 57. The cis- and trans-isomer may be separated by column chromatography or may be used as a mixture in the next catalytic hydrogenation. The racemic acid (±)-55 is obtained through catalytic hydrogenation of the α,β-unsaturated ester 57 in the presence of Pd/C under an H$_2$-atmosphere in a solvent like EtOH and a subsequent ester hydrolysis with an aqueous solution of NaOH in a co-solvent like THF or EtOH (Scheme 19).

Scheme 19. Synthesis of the carboxylic acid derivatives (±)-55.

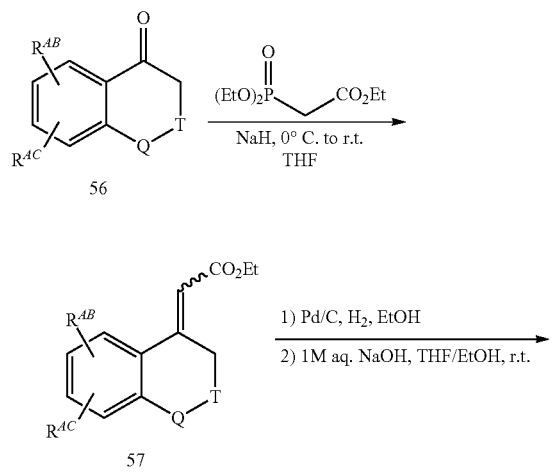

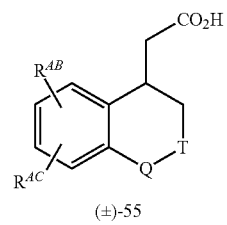

Whenever the compounds of Formula (I) are obtained in the form of mixtures of enantiomers or diastereoisomers, the enantiomers or diastereoisomers can be separated using methods known to one skilled in the art: e.g. by formation and separation of diastereomeric salts or by HPLC over a chiral stationary phase such as a ChiralPak AD-H (5 μm) column, ChiralPak AY-H (5 μm) column, a ChiralPak IA (5 μm) column, a ChiralPak IB (5 μm) column, or a Regis (R,R)-Whelk-O1 (5 μm). Typical conditions of chiral HPLC are an isocratic mixture of eluent A (EtOH or DCM, in presence or absence of a base like NEt$_3$ and/or diethylamine or of an acid like TFA) and eluent B (heptane).

Experimental Section:
Abbreviations (as Used Herein):
AcOEt Ethyl acetate
AcOH Acetic acid
aq. aqueous
Bdg Binding
BSA Bovine Serum Albumin
Bu n-butyl
ca. circa (latin)—approximately
Cbz Benzyloxycarbonyl
CC Column chromatography on silica gel
CDI Carbonyldiimidazole
comb. combined
conc. Concentrated
dba Dibenzylidenaceton
DBU 1,8-Diazabicyclo[5.4.0]undec-7-ene
DCC 1,3-Dicyclohexylcarbodiimide
DCM Dichloromethane
DIPEA N,N-Diisopropylethylamine
DMAC Dimethylacetamide
DMAP N,N-Dimethyl-4-aminopyridine
DME 1,2-Dimethoxyethane
DMF Dimethylformamide
DMSO Dimethylsulfoxide
dpm decays per minute
DPPF 1,1'-Bis(diphenylphosphino)ferrocen
EDTA Ethylene Diamine Tetraacetic Acid
EDC 1-Ethyl-3-(3-dimethylaminopropyl)carbodiimide
ee enantiomeric excess
eq. Equivalent
EtOH ethanol
ESI-MS Electrospray Ionization Mass Spectroscopy
Ghosez's reagent 1-Chloro-N,N,2-trimethyl-1-propenylamine
h hour(s)
HATU O-(7-Aza-1H-benzotriazole-1-yl)-1,1,3,3-tetramethyluronium hexafluorophosphate
Hept Heptane
HPLC High Performance Liquid Chromatography
HSA human serum albumin
h.v. high vacuum
iPr isopropyl
L liter(s)
LAH lithium aluminum hydride LC-MS Liquid Chromatography-Mass Spectroscopy
M molarity [mol L$^{-1}$]
Me Methyl
MeCN Acetonitrile
MeI Methyl iodide
MeOH Methanol
mesyl Methanesulfonyl
Meth. Method
min minute(s)
MS Mass Spectroscopy or Molecular Sieves
MW Molecular Weight
N Normality of solution
NBS N-bromo-succinimide
NEt$_3$ Triethylamine
NMR Nuclear magnetic resonance
org. organic
PBS Phosphate Buffered Saline
PG Protecting Group
Ph Phenyl
PGD$_2$ Prostaglandin D$_2$
(S)-Phos 2-Dicyclohexylphosphino-2',6'-dimethoxybiphenyl
PMSF Phenylmethylsulfonyl fluoride
PPA Polyphosphoric acid
prep. preparative
r.t. room temperature
s second(s)
sat. saturated
Si-carbonate Polymer supported carbonate
Si-DEA Polymer supported diethyl amine
soln. solution
subst. Substituted
TBTU O-(Benzotriazol-1-yl)-N,N,N',N'-tetramethyluronium
tBu tert-Butyl
tert. Tertiary
Tf Triflate
TFA Trifluoroacetic acid
TFAA Trifluoroacetic anhydride
THF Tetrahydrofuran
TMS Trimethylsilyl
tosyl Toluenesulfonyl
t$_R$ retention time
Tris Tris-(hydroxymethyl)aminomethane buffer
Ts Tosyl
Chemistry
General Remarks All solvents and reagents are used as obtained from commercial sources unless otherwise indicated.

Temperatures are indicated in degrees Celsius (° C.). Unless otherwise indicated, the reactions take place at room temperature (r.t.).

In mixtures, relations of parts of solvent or eluent or reagent mixtures in liquid form are given as volume relations (v/v), unless indicated otherwise.

Analytical HPLC conditions as used in the Examples below:

LC-MS 1

LC-MS-conditions: Analytical. Pump: Waters Acquity Binary Solvent Manager, MS: Waters SQ Detector, DAD: Acquity UPLC PDA Detector, ELSD: Acquity UPLC ELSD. Column: Acquity UPLC BEH C18 1.7 mm 2.1×50 mm ID from Waters, thermostated in the Acquity UPLC Column Manager at 60° C. Eluents: A: H$_2$O+0.05% formic acid or TFA; B: MeCN+0.05% formic acid or TFA. Method: Gradient: 2% B to 98% B over 2.00 min. Flow: 1.2 mL/min. Detection: UV/Vis and/or ELSD, and MS, t$_R$ is given in min LC-MS 1 FA: Eluents: A: H$_2$O+0.05% formic acid; B: MeCN+0.045% formic acid LC-MS 1TFA: Eluents: A: H$_2$O+0.05% TFA; B: MeCN+0.045% TFA LC-MS 2 to LC-MS 4

HPLC/MS analyses are performed on a Ultimate 3000RS Dionex HPLC instrument, equipped with a Dionex Ultimate 3000 RS Photodiode Array Detector, a Dionex Ultimate 3000RS pump and a Dionex MSQ$^+$ mass spectrometer.

The LC retention times are obtained using the following elution conditions:

LC-MS 2: Analytical HPLC on a Waters X-Bridge C18 column (4.6×30 mm, 2.5 µm, Waters); Linear gradient of water/0.04% TFA (A) and MeCN (B) from 5% to 95% B over 1.5 min; flow rate 4.5 mL/min, detection at 215 nm.

LC-MS 3: Analytical HPLC on a Zorbax® SB-AQ column (4.6×50 mm, 3.5 µm, Agilent); Linear gradient of water/0.04% TFA (A) and MeCN (B) from 5% to 95% B over 1.5 min; flow rate 4.5 mL/min, detection at 215 nm.

LC-MS 4: Analytical HPLC on a Waters Atlantis T3 column (4.6×30 mm, 5 µm, Waters); Linear gradient of water/0.04% TFA (A) and MeCN (B) from 5% to 95% B over 1.5 min; flow rate 4.5 mL/min, detection at 215 nm.

LC-MS 5 to LC-MS 12 (Chiral Analysis)

LC-MS 5: Analytical HPLC, column ChiralPak AD-H (4.6×250 mm, 5 µm), eluent A 80% Heptane and eluent B 20% EtOH+0.1% TFA, flow 0.8 mL/min. Detection at 210 nm.

LC-MS 6: Analytical HPLC, column ChiralPak AD-H (4.6×250 mm, 5 µm), eluent A 50% Heptane and eluent B 50% EtOH+0.1% TFA, flow 0.8 mL/min. Detection at 210 nm.

LC-MS 7: Analytical HPLC, column (R,R) Whelk-O1 (4.6×250 mm, 5 µm), eluent A 70% Heptane and eluent B 30% EtOH+0.1% TFA, flow 1.6 mL/min. Detection at 210 nm.

LC-MS 8: Analytical HPLC, column (R,R) Whelk-O1 (4.6×250 mm, 5 µm), eluent A 50% Heptane and eluent B 50% EtOH+0.1% TFA, flow 0.8 mL/min. Detection at 210 nm.

LC-MS 9: Analytical HPLC, column ChiralPak AS-H (4.6×250 mm, 5 µm), eluent A 80% Heptane and eluent B 20% EtOH+0.1% TFA, flow 1.0 mL/min. Detection at 210 nm.

LC-MS 10: Analytical HPLC, column ChiralPak AY-H (4.6×250 mm, 5 µm), eluent A 80% Heptane and eluent B 20% EtOH+0.1% TFA, flow 1.0 mL/min. Detection at 210 nm.

LC-MS 11: Analytical HPLC, column (R,R) Whelk-O1 (4.6×250 mm, 5 µm), eluent A 80% Heptane and eluent B 20% EtOH+0.1% TFA, flow 0.8 mL/min. Detection at 210 nm.

LC-MS 12: Analytical HPLC, column ChiralPak IC (4.6×250 mm, 5 µm), eluent A 95% Heptane and eluent B 5% EtOH+0.1% TFA, flow 1.0 mL/min. Detection at 210 nm.

LC-MS 13

Analytical HPLC on a Supelco Ascentis Express C18 column (5×2.1 mm, 2.7 µm, Supelco); Linear gradient of water/0.05% formic acid (A) and MeCN (B) from 5% to 95% B over 2.5 min; flow rate 1.8 mL/min, detection at 214 and 254 nm.

Preparative HPLC/MS purifications are performed on a Gilson HPLC system, equipped with a Gilson 215 autosampler, Gilson 333/334 pumps, Finnigan AQA MS detector system, and a Dionex UV detector, using a Waters Xbridge C18 or an Waters Atlantis T3 column, with a linear gradient of water/formic acid 0.02% (A) and MeCN (B) (acidic conditions) or water/ammonia 0.02% (A) and MeCN (B) (basic conditions).

Synthesis of Compounds of Formula (I):

The following examples illustrate the preparation of compounds of the invention but do not at all limit the scope thereof. Whenever used in the experimental part, generic Structures 1, 2, 3 etc. Refer to the respective Structures described in preceeding general description of the preparation of compounds of Formula (I).

General Method for the Preparation of Compounds of Formula (I):

Saponification

To a solution of (±)-(3-{5-fluoro-2-[trans-2-(4-fluoro-phenyl)-cyclopropanecarbonyl]-1,2,3,4- tetrahydro-isoquinolin-8-yl}-4-methoxy-phenyl)-acetic acid ethyl ester in DMF (1 mL), 2M aq. NaOH (1 mL) was added. The mixture was stirred at r.t. for 18 hours. The solution was neutralized with formic acid (ca. 1 mL), purified by prep. HPLC (column: Atlantis, 18×50 mm, 10 um, UV/MS, acidic conditions) and concentrated in vacuo to give the desired acid as a white solid.

Listed in Table 1 below are examples of compounds of Formula (I), prepared according to the above-mentioned method with the corresponding compound of Structure 1 as starting material.

TABLE 1

| Example | Compound of Formula (I) | Formula MW | $t_R$ [min] LC-MS Method | MS-data m/z $[M + H]^+$ |
|---|---|---|---|---|
| 1 | (±)-(3-{5-Fluoro-2-[trans-2-(4-fluoro-phenyl)-cyclopropanecarbonyl]-1,2,3,4-tetrahydro-isoquinolin-8-yl}-4-methoxy-phenyl)-acetic acid | C28H25NO4F2 477.18 | 1.04 LC-MS 1FA | 478.3 |
| 2 | (±)-(3-{2-[trans-2-(4-Chloro-phenyl)-cyclopropanecarbonyl]-5-fluoro-1,2,3,4-tetrahydro-isoquinolin-8-yl}-4-methoxy-phenyl)-acetic acid | C28H25NO4ClF 493.15 | 1.10 LC-MS 1FA | 494.3 |
| 3 | (±)-(3-{2-[trans-2-(2-Chloro-phenyl)-cyclopropanecarbonyl]-5-fluoro-1,2,3,4-tetrahydro-isoquinolin-8-yl}-4-methoxy-phenyl)-acetic acid | C28H25NO4ClF 493.15 | 1.07 LC-MS 1FA | 494.3 |
| 4 | (±)-(3-{2-[trans-2-(3-Chloro-phenyl)-cyclopropanecarbonyl]-5-fluoro-1,2,3,4-tetrahydro-isoquinolin-8-yl}-4-methoxy-phenyl)-acetic acid | C28H25NO4ClF 493.15 | 1.10 LC-MS 1FA | 494.3 |
| 5 | (±)-(3-{5-Fluoro-2-[trans-2-(2-fluoro-phenyl)-cyclopropanecarbonyl]-1,2,3,4-tetrahydro-isoquinolin-8-yl}-4-methoxy-phenyl)-acetic acid | C28H25NO4F2 477.18 | 1.04 LC-MS 1FA | 478.3 |
| 6 | (±)-{3-[5-Fluoro-2-(trans-2-o-tolyl-cyclopropanecarbonyl)-1,2,3,4-tetrahydro-isoquinolin-8-yl]-4-methoxy-phenyl}-acetic acid | C29H28NO4F 473.20 | 1.08 LC-MS 1FA | 474.4 |
| 7 | 8-(5-Carboxymethyl-2-methyl-phenyl)-5-fluoro-3,4-dihydro-1H-isoquinoline-2-carboxylic acid benzyl ester | C26H24NO4F 433.17 | 1.14 LC-MS 1FA | 434.3 |
| 8 | 8-(5-Carboxymethyl-2-trifluoromethyl-phenyl)-5-fluoro-3,4-dihydro-1H-isoquinoline-2-carboxylic acid benzyl ester | C26H21NO4F4 487.14 | 1.15 LC-MS 1FA | 488.3 |
| 9 | 8-(5-Carboxymethyl-2-chloro-phenyl)-5-fluoro-3,4-dihydro-1H-isoquinoline-2-carboxylic acid benzyl ester | C25H21NO4ClF 453.11 | 1.13 LC-MS 1FA | 454.2 |
| 10 | 8-(5-Carboxymethyl-2-fluoro-phenyl)-5-fluoro-3,4-dihydro-1H-isoquinoline-2-carboxylic acid benzyl ester | C25H21NO4F2 437.14 | 1.09 LC-MS 1FA | 438.2 |
| 11 | 8-(3-Carboxymethyl-4-chloro-phenyl)-5-fluoro-3,4-dihydro-1H-isoquinoline-2-carboxylic acid benzyl ester | C25H21NO4ClF 453.11 | 1.14 LC-MS 1FA | 454.3 |
| 12 | 8-(3-Carboxymethyl-4-fluoro-phenyl)-5-fluoro-3,4-dihydro-1H-isoquinoline-2-carboxylic acid benzyl ester | C25H21NO4F2 437.14 | 1.10 LC-MS 1FA | 438.2 |
| 13 | 8-(3-Carboxymethyl-4-methoxy-phenyl)-5-fluoro-3,4-dihydro-1H-isoquinoline-2-carboxylic acid benzyl ester | C26H24NO5F 449.16 | 1.10 LC-MS 1FA | 450.3 |
| 14 | 8-(3-Carboxymethyl-5-fluoro-phenyl)-5-fluoro-3,4-dihydro-1H-isoquinoline-2-carboxylic acid benzyl ester | C25H21NO4F2 437.14 | 1.12 LC-MS 1FA | 438.3 |
| 15 | 8-(3-Carboxymethyl-5-methoxy-phenyl)-5-fluoro-3,4-dihydro-1H-isoquinoline-2-carboxylic acid benzyl ester | C26H24NO5F 449.16 | 1.10 LC-MS 1FA | 450.3 |
| 16 | 8-(3-Carboxymethyl-2-fluoro-phenyl)-5-fluoro-3,4-dihydro-1H-isoquinoline-2-carboxylic acid benzyl ester | C25H21NO4F2 437.14 | 1.09 LC-MS 1FA | 438.3 |
| 17 | 6-(5-Carboxymethyl-2-methoxy-phenyl)-9-fluoro-1,2,4,5-tetrahydro-benzo[d]azepine-3-carboxylic acid benzyl ester | C27H26NO5F 463.18 | 1.08 LC-MS 1FA | 464.3 |

TABLE 1-continued

| Example | Compound of Formula (I) | Formula MW | $t_R$ [min] LC-MS Method | MS-data m/z [M + H]⁺ |
|---|---|---|---|---|
| 18 | 4-(5-Carboxymethyl-2-methoxy-phenyl)-7-fluoro-1,3-dihydro-isoindole-2-carboxylic acid benzyl ester | C25H22NO5F 435.15 | 1.06 LC-MS 1FA | 436.2 |
| 19 | 8-(3-Carboxymethyl-5-chloro-phenyl)-5-fluoro-3,4-dihydro-1H-isoquinoline-2-carboxylic acid benzyl ester | C25H21NO4ClF 453.11 | 1.17 LC-MS 1FA | 454.2 |
| 20 | 8-(5-Carboxymethyl-2-methanesulfonyl-phenyl)-5-fluoro-3,4-dihydro-1H-isoquinoline-2-carboxylic acid benzyl ester | C26H24NO6FS 497.13 | 0.94 LC-MS 1FA | 498.3 |
| 21 | 8-(5-Carboxymethyl-2-trifluoromethoxy-phenyl)-5-fluoro-3,4-dihydro-1H-isoquinoline-2-carboxylic acid benzyl ester | C26H21NO5F4 503.14 | 1.17 LC-MS 1FA | 504.3 |
| 22 | 8-(5-Carboxymethyl-2-isopropoxy-phenyl)-5-fluoro-3,4-dihydro-1H-isoquinoline-2-carboxylic acid benzyl ester | C28H28NO5F 477.20 | 1.16 LC-MS 1FA | 478.3 |
| 23 | 8-(5-Carboxymethyl-2-fluoro-phenyl)-3,4-dihydro-1H-isoquinoline-2-carboxylic acid benzyl ester | C25H22NO4F 419.15 | 1.06 LC-MS 1FA | 420.2 |
| 24 | 8-(3-Carboxymethyl-phenyl)-5-fluoro-3,4-dihydro-1H-isoquinoline-2-carboxylic acid benzyl ester | C25H22NO4F 419.15 | 1.10 LC-MS 1FA | 420.2 |
| 25 | 8-(5-Carboxymethyl-2-methoxy-phenyl)-5-methanesulfonyl-3,4-dihydro-1H-isoquinoline-2-carboxylic acid benzyl ester | C27H27NO7S 509.15 | 0.90 LC-MS 1FA | 510.3 |
| 26 | {3-[5-Fluoro-2-((1R,2R)-2-phenyl-cyclopropanecarbonyl)-1,2,3,4-tetrahydro-isoquinolin-8-yl]-4-trifluoromethoxy-phenyl}-acetic acid | C28H23NO4F4 513.16 | 1.15 LC-MS 1FA | 514.3 |
| 27 | {3-[5-Fluoro-2-((1R,2R)-2-phenyl-cyclopropanecarbonyl)-1,2,3,4-tetrahydro-isoquinolin-8-yl]-4-isopropoxy-phenyl}-acetic acid | C30H30NO4F 487.22 | 1.14 LC-MS 1FA | 488.4 |
| 28 | {4-Chloro-3-[5-fluoro-2-((1R,2R)-2-phenyl-cyclopropanecarbonyl)-1,2,3,4-tetrahydro-isoquinolin-8-yl]-phenyl}-acetic acid | C27H23NO3ClF 463.14 | 1.11 LC-MS 1FA | 464.2 |
| 29 | {3-[5-Fluoro-2-((1R,2R)-2-phenyl-cyclopropanecarbonyl)-1,2,3,4-tetrahydro-isoquinolin-8-yl]-4-methanesulfonyl-phenyl}-acetic acid | C28H26NO5FS 507.15 | 0.91 LC-MS 1FA | 508.3 |
| 30 | 8-(2-Carboxymethyl-phenyl)-5-fluoro-3,4-dihydro-1H-isoquinoline-2-carboxylic acid benzyl ester | C25H22NO4F 419.15 | 1.08 LC-MS 1FA | 420.2 |
| 31 | 8-(5-Carboxymethyl-2-methoxy-phenyl)-5,6-difluoro-3,4-dihydro-1H-isoquinoline-2-carboxylic acid benzyl ester | C26H23NO5F2 467.15 | 1.09 LC-MS 1FA | 468.3 |
| 32 | 8-(5-Carboxymethyl-2-methoxy-phenyl)-6-fluoro-3,4-dihydro-1H-isoquinoline-2-carboxylic acid benzyl ester | C26H24NO5F 449.16 | 1.05 LC-MS 1FA | 450.1 |
| 33 | 8-(5-Carboxymethyl-2-methoxy-phenyl)-7-fluoro-3,4-dihydro-1H-isoquinoline-2-carboxylic acid benzyl ester | C26H24NO5F 449.16 | 1.03 LC-MS 1FA | 450.3 |
| 34 | {3-[6-Fluoro-2-((1R,2R)-2-phenyl-cyclopropanecarbonyl)-1,2,3,4-tetrahydro-isoquinolin-8-yl]-4-methoxy-phenyl}-acetic acid | C28H26NO4F 459.19 | 1.03 LC-MS 1FA | 460.3 |
| 35 | {3-[7-Fluoro-2-((1R,2R)-2-phenyl-cyclopropanecarbonyl)-1,2,3,4-tetrahydro-isoquinolin-8-yl]-4-methoxy-phenyl}-acetic acid | C28H26NO4F 459.19 | 1.00 LC-MS 1FA | 460.3 |
| 36 | (±)-{3-[9-Fluoro-3-(trans-2-phenyl-cyclopropanecarbonyl)-2,3,4,5-tetrahydro-1H-benzo[d]azepin-6-yl]-4-methoxy-phenyl}-acetic acid | C29H28NO4F 473.20 | 1.04 LC-MS 1FA | 474.4 |
| 37 | (±)-{3-[7-Fluoro-2-(trans-2-phenyl-cyclopropanecarbonyl)-2,3-dihydro-1H-isoindol-4-yl]-4-methoxy-phenyl}-acetic acid | C27H24NO4F 445.17 | 1.02 LC-MS 1FA | 446.3 |

TABLE 1-continued

| Example | Compound of Formula (I) | Formula MW | $t_R$ [min] LC-MS Method | MS-data m/z [M + H]+ |
|---|---|---|---|---|
| 38 | {3-[5,7-Difluoro-2-((1R,2R)-2-phenyl-cyclopropanecarbonyl)-1,2,3,4-tetrahydro-isoquinolin-8-yl]-4-methoxy-phenyl}-acetic acid | C28H25NO4F2 477.18 | 1.05 LC-MS 1FA | 478.3 |
| 39 | 8-(5-Carboxymethyl-2-methoxy-phenyl)-5,7-difluoro-3,4-dihydro-1H-isoquinoline-2-carboxylic acid benzyl ester | C26H23NO5F2 467.15 | 1.07 LC-MS 1FA | 468.3 |
| 40 | 8-(4-Carboxymethyl-3-chloro-phenyl)-5-fluoro-3,4-dihydro-1H-isoquinoline-2-carboxylic acid benzyl ester | C25H21NO4ClF 453.11 | 1.16 LC-MS 1FA | 454.1 |
| 41 | 8-(4-Carboxymethyl-phenyl)-5-fluoro-3,4-dihydro-1H-isoquinoline-2-carboxylic acid benzyl ester | C25H22NO4F 419.15 | 1.10 LC-MS 1FA | 420.3 |

Amide Coupling and Subsequent Saponification

Method A: To a solution of 3-(4-fluorophenoxy)propionic acid (22 mg, 0.12 mmol, 1.2 eq.) in DCM/DMF 1:1 (1.00 mL), TBTU (39 mg, 0.12 mmol, 1.2 eq.) and Si-DEA (238 mg, 0.30 mmol, 3.0 eq.) were added in sequence. The mixture was stirred at r.t. for 30 min. A solution of [3-(5-fluoro-1,2,3,4-tetrahydro-isoquinolin-8-yl)-4-methoxy-phenyl]-acetic acid ethyl ester hydrochloride (38 mg, 0.10 mmol, 1.0 eq.) in DMF (0.25 mL) was added and the resulting mixture was stirred at r.t. for 1 hour. The mixture was filtered, the solid rinsed with DCM (3 mL), and the filtrate was concentrated in vacuo. To a solution of the residue in THF (1.0 mL), 1M aq. NaOH (1.0 mL) was added. The mixture was stirred at r.t. for 1 hour. The reaction mixture was concentrated in vacuo and the residue was purified by prep. HPLC (column: Waters X-Bridge, 30×75 mm, 10 um, UV/MS, acidic conditions) and evaporated to give the desired acid as a white solid.

Listed in Table 2 below are examples of compounds of Formula (I), prepared according to the above-mentioned method with the corresponding compound of Structure 2 and the corresponding acid as starting materials.

TABLE 2

| Example | Compound of Formula (I) | Formula MW | $t_R$ [min] LC-MS Method | MS-data m/z [M + H]+ |
|---|---|---|---|---|
| 42 | (3-{5-Fluoro-2-[3-(4-fluoro-phenoxy)-propionyl]-1,2,3,4-tetrahydro-isoquinolin-8-yl}-4-methoxy-phenyl)-acetic acid | C27H25NO5F2 481.17 | 1.01 LC-MS 1FA | 482.3 |
| 43 | {3-[5-Fluoro-2-(2-phenoxy-acetyl)-1,2,3,4-tetrahydro-isoquinolin-8-yl]-4-methoxy-phenyl}-acetic acid | C26H24NO5F 449.16 | 0.97 LC-MS 1FA | 450.3 |
| 44 | (3-{5-Fluoro-2-[2-(4-fluoro-phenoxy)-acetyl]-1,2,3,4-tetrahydro-isoquinolin-8-yl}-4-methoxy-phenyl)-acetic acid | C26H23NO5F2 467.15 | 0.98 LC-MS 1FA | 468.3 |
| 45 | (3-{5-Fluoro-2-[4-(2-fluoro-phenyl)-butyryl]-1,2,3,4-tetrahydro-isoquinolin-8-yl}-4-methoxy-phenyl)-acetic acid | C28H27NO4F2 479.19 | 1.06 LC-MS 1FA | 480.3 |
| 46 | {3-[2-(2-Ethoxy-acetyl)-5-fluoro-1,2,3,4-tetrahydro-isoquinolin-8-yl]-4-methoxy-phenyl}-acetic acid | C22H24NO5F 401.16 | 0.85 LC-MS 1FA | 402.3 |
| 47 | {3-[2-(2-tert-Butoxy-acetyl)-5-fluoro-1,2,3,4-tetrahydro-isoquinolin-8-yl]-4-methoxy-phenyl}-acetic acid | C24H28NO5F 429.20 | 0.94 LC-MS 1FA | 430.3 |
| 48 | (±)-(3-{5-Fluoro-2-[trans-2-(3-fluoro-phenyl)-cyclopropanecarbonyl]-1,2,3,4-tetrahydro-isoquinolin-8-yl}-4-methoxy-phenyl)-acetic acid | C28H25NO4F2 477.18 | 1.05 LC-MS 1FA | 478.3 |
| 49 | (3-{5-Fluoro-2-[2-(5-methoxy-benzo[d]isoxazol-3-yl)-acetyl]-1,2,3,4-tetrahydro-isoquinolin-8-yl}-4-methoxy-phenyl)-acetic acid | C28H25N2O6F 504.17 | 0.96 LC-MS 1FA | 505.3 |
| 50 | {3-[5-Fluoro-2-(2,2,3,3-tetramethyl-cyclopropanecarbonyl)-1,2,3,4-tetrahydro-isoquinolin-8-yl]-4-methoxy-phenyl}-acetic acid | C26H30NO4F 439.22 | 1.05 LC-MS 1FA | 440.4 |

TABLE 2-continued

| Example | Compound of Formula (I) | Formula MW | $t_R$ [min] LC-MS Method | MS-data m/z [M + H]+ |
|---|---|---|---|---|
| 51 | {3-[5-Fluoro-2-(3-pyridin-3-yl-propionyl)-1,2,3,4-tetrahydro-isoquinolin-8-yl]-4-methoxy-phenyl}-acetic acid | C26H25N2O4F 448.18 | 0.66 LC-MS 1FA | 449.3 |
| 52 | [3-(2-Cyclopropanecarbonyl-5-fluoro-1,2,3,4-tetrahydro-isoquinolin-8-yl)-4-methoxy-phenyl]-acetic acid | C22H22NO4F 383.15 | 0.88 LC-MS 1FA | 384.2 |
| 53 | {3-[2-(3-3,4-Dihydro-2H-quinolin-1-yl-propionyl)-5-fluoro-1,2,3,4-tetrahydro-isoquinolin-8-yl]-4-methoxy-phenyl}-acetic acid | C30H31N2O4F 502.23 | 1.08 LC-MS 1FA | 503.4 |
| 54 | {3-[5-Fluoro-2-(3-phenyl-propionyl)-1,2,3,4-tetrahydro-isoquinolin-8-yl]-4-methoxy-phenyl}-acetic acid | C27H26NO4F 447.19 | 1.00 LC-MS 1FA | 448.3 |
| 55 | (±)-{3-[2-(2,2-Dimethyl-cyclopropanecarbonyl)-5-fluoro-1,2,3,4-tetrahydro-isoquinolin-8-yl]-4-methoxy-phenyl}-acetic acid | C24H26NO4F 411.19 | 0.95 LC-MS 1FA | 412.3 |
| 56 | {3-[5-Fluoro-2-(3-o-tolyl-propionyl)-1,2,3,4-tetrahydro-isoquinolin-8-yl]-4-methoxy-phenyl}-acetic acid | C28H28NO4F 461.20 | 1.04 LC-MS 1FA | 462.3 |
| 57 | (3-{5-Fluoro-2-[3-(3-methyl-indol-1-yl)-propionyl]-1,2,3,4-tetrahydro-isoquinolin-8-yl}-4-methoxy-phenyl)-acetic acid | C30H29N2O4F 500.21 | 1.09 LC-MS 1FA | 501.4 |
| 58 | (3-{2-[2-(2-Chloro-benzyloxy)-acetyl]-5-fluoro-1,2,3,4-tetrahydro-isoquinolin-8-yl}-4-methoxy-phenyl)-acetic acid | C27H25NO5ClF 497.14 | 1.03 LC-MS 1FA | 498.3 |
| 59 | {3-[2-(3-2,3-Dihydro-indol-1-yl-propionyl)-5-fluoro-1,2,3,4-tetrahydro-isoquinolin-8-yl]-4-methoxy-phenyl}-acetic acid | C29H29N2O4F 488.21 | 1.02 LC-MS 1FA | 489.4 |
| 60 | (±)-{3-[5-Fluoro-2-(trans-2-phenyl-cyclopropanecarbonyl)-1,2,3,4-tetrahydro-isoquinolin-8-yl]-4-methoxy-phenyl}-acetic acid | C28H26NO4F 459.19 | 1.04 LC-MS 1FA | 460.3 |
| 61 | (3-{5-Fluoro-2-[3-(2-methyl-1H-indol-3-yl)-propionyl]-1,2,3,4-tetrahydro-isoquinolin-8-yl}-4-methoxy-phenyl)-acetic acid | C30H29N2O4F 500.21 | 0.98 LC-MS 1FA | 501.4 |
| 62 | (3-{5-Fluoro-2-[3-(1-methyl-1H-indol-3-yl)-propionyl]-1,2,3,4-tetrahydro-isoquinolin-8-yl}-4-methoxy-phenyl)-acetic acid | C30H29N2O4F 500.21 | 1.04 LC-MS 1FA | 501.4 |
| 63 | (3-{5-Fluoro-2-[3-(5-methoxy-1H-indol-3-yl)-propionyl]-1,2,3,4-tetrahydro-isoquinolin-8-yl}-4-methoxy-phenyl)-acetic acid | C30H29N2O5F 516.21 | 0.94 LC-MS 1FA | 517.4 |

Method B: A solution of (1R,2R)-2-(4-chloro-phenyl)-cyclopropanecarboxylic acid (20 mg, 0.10 mmol, 1.0 eq.) and [3-(5-fluoro-1,2,3,4-tetrahydro-isoquinolin-8-yl)-4-methoxy-phenyl]-acetic acid ethyl ester hydrochloride (38 mg, 0.10 mmol, 1.0 eq.) in DMF (1.2 mL) was treated with 4-(dimethylamino)pyridine (37 mg, 0.30 mmol, 3.0 eq) and N-(3-dimethylaminopropyl)-N'-ethylcarbodiimide hydrochloride (29 mg, 0.15 mmol, 1.5 eq) and the resulting solution was stirred at r.t. for 18 hours. 1M aq. NaOH soln. (0.6 mL) was added. The solution was stirred at r.t. during 1 hour. Formic acid (0.2 mL) was added. The crude mixture was purified by prep. HPLC (column: Waters Xbridge, 30×75 mm, 10 um, UV/MS, acidic conditions) and concentrated in vacuo to give the desired acid as a white foam.

Listed in Table 3 below are examples of compounds of Formula (I), prepared according to the above-mentioned method with the corresponding compound of Structure 2 and the corresponding acid as starting materials.

TABLE 3

| Example | Compound of Formula (I) | Formula MW | $t_R$ [min] LC-MS Method | MS-data m/z [M + H]+ |
|---|---|---|---|---|
| 64 | (3-{2-[(1R,2R)-2-(4-Chloro-phenyl)-cyclopropanecarbonyl]-5-fluoro-1,2,3,4-tetrahydro-isoquinolin-8-yl}-4-methoxy-phenyl)-acetic acid | C28H25NO4ClF 493.15 | 1.10 LC-MS 1FA | 494.3 |

TABLE 3-continued

| Example | Compound of Formula (I) | Formula MW | $t_R$ [min] LC-MS Method | MS-data m/z [M + H]⁺ |
|---|---|---|---|---|
| 65 | (3-{5-Fluoro-2-[(1R,2R)-2-(3-fluoro-phenyl)-cyclopropanecarbonyl]-1,2,3,4-tetrahydro-isoquinolin-8-yl}-4-methoxy-phenyl)-acetic acid | C28H25NO4F2 477.18 | 1.05 LC-MS 1FA | 478.3 |
| 66 | (3-{5-Fluoro-2-[(1R,2R)-2-(2-fluoro-phenyl)-cyclopropanecarbonyl]-1,2,3,4-tetrahydro-isoquinolin-8-yl}-4-methoxy-phenyl)-acetic acid | C28H25NO4F2 477.18 | 1.04 LC-MS 1FA | 478.4 |
| 67 | {3-[5-Fluoro-2-(3-indazol-1-yl-propionyl)-1,2,3,4-tetrahydro-isoquinolin-8-yl]-4-methoxy-phenyl}-acetic acid | C28H26N3O4F 487.19 | 0.95 LC-MS 1FA | 488.3 |
| 68 | (3-{5-Chloro-2-[(1R,2R)-2-(4-chloro-phenyl)-cyclopropanecarbonyl]-1,2,3,4-tetrahydro-isoquinolin-8-yl}-4-methoxy-phenyl)-acetic acid | C28H25NO4Cl2 509.12 | 1.16 LC-MS 1FA | 510.2 |
| 69 | (3-{5-Chloro-2-[(1R,2R)-2-(3-fluoro-phenyl)-cyclopropanecarbonyl]-1,2,3,4-tetrahydro-isoquinolin-8-yl}-4-methoxy-phenyl)-acetic acid | C28H25NO4ClF 493.15 | 1.11 LC-MS 1FA | 494.3 |
| 70 | (3-{5-Chloro-2-[(1R,2R)-2-(2-fluoro-phenyl)-cyclopropanecarbonyl]-1,2,3,4-tetrahydro-isoquinolin-8-yl}-4-methoxy-phenyl)-acetic acid | C28H25NO4ClF 493.15 | 1.10 LC-MS 1FA | 494.3 |
| 71 | {3-[5-Chloro-2-((1R,2R)-2-phenyl-cyclopropanecarbonyl)-1,2,3,4-tetrahydro-isoquinolin-8-yl]-4-methoxy-phenyl}-acetic acid | C28H26NO4Cl 475.16 | 1.10 LC-MS 1FA | 476.3 |
| 72 | {3-[5-Chloro-2-(3-indazol-1-yl-propionyl)-1,2,3,4-tetrahydro-isoquinolin-8-yl]-4-methoxy-phenyl}-acetic acid | C28H26N3O4Cl 503.16 | 1.02 LC-MS 1FA | 504.3 |
| 73 | (3-{5-Chloro-2-[2-(2-chloro-benzyloxy)-acetyl]-1,2,3,4-tetrahydro-isoquinolin-8-yl}-4-methoxy-phenyl)-acetic acid | C27H25NO5Cl2 513.11 | 1.09 LC-MS 1FA | 514.3 |
| 74 | (3-{5-Chloro-2-[4-(2-fluoro-phenyl)-butyryl]-1,2,3,4-tetrahydro-isoquinolin-8-yl}-4-methoxy-phenyl)-acetic acid | C28H27NO4ClF 495.16 | 1.12 LC-MS 1FA | 496.3 |
| 75 | (3-{5-Chloro-2-[3-(1-methyl-1H-indol-3-yl)-propionyl]-1,2,3,4-tetrahydro-isoquinolin-8-yl}-4-methoxy-phenyl)-acetic acid | C30H29N2O4Cl 516.18 | 1.10 LC-MS 1FA | 517.4 |
| 76 | {3-[5-Chloro-2-(3-phenyl-propionyl)-1,2,3,4-tetrahydro-isoquinolin-8-yl]-4-methoxy-phenyl}-acetic acid | C27H26NO4Cl 463.16 | 1.07 LC-MS 1FA | 464.3 |
| 77 | {3-[5-Chloro-2-(3-3,4-dihydro-2H-quinolin-1-yl-propionyl)-1,2,3,4-tetrahydro-isoquinolin-8-yl]-4-methoxy-phenyl}-acetic acid | C30H31N2O4Cl 518.20 | 1.14 LC-MS 1FA | 519.4 |
| 78 | {3-[5-Chloro-2-(3-2,3-dihydro-indol-1-yl-propionyl)-1,2,3,4-tetrahydro-isoquinolin-8-yl]-4-methoxy-phenyl}-acetic acid | C29H29N2O4Cl 504.18 | 1.09 LC-MS 1FA | 505.0 |
| 79 | (3-{5-Chloro-2-[3-(2-methyl-1H-indol-3-yl)-propionyl]-1,2,3,4-tetrahydro-isoquinolin-8-yl}-4-methoxy-phenyl)-acetic acid | C30H29N2O4Cl 516.18 | 1.04 LC-MS 1FA | 517.3 |
| 80 | {3-[5-Fluoro-2-((1R,2R)-2-phenyl-cyclopropanecarbonyl)-1,2,3,4-tetrahydro-isoquinolin-8-yl]-4-methoxy-phenyl}-acetic acid | C28H26NO4F 459.19 | 1.04 LC-MS 1FA | 460.3 |
| 81 | {3-[5-Fluoro-2-((1S,2S)-2-phenyl-cyclopropanecarbonyl)-1,2,3,4-tetrahydro-isoquinolin-8-yl]-4-methoxy-phenyl}-acetic acid | C28H26NO4F 459.19 | 1.04 LC-MS 1FA | 460.1 |
| 82 | [3-(2-Cyclopropanecarbonyl-5-trifluoromethyl-1,2,3,4-tetrahydro-isoquinolin-8-yl)-4-methoxy-phenyl]-acetic acid | C23H22NO4F3 433.15 | 0.98 LC-MS 1FA | 434.2 |
| 83 | (±)-{4-Methoxy-3-[2-(trans-2-phenyl-cyclopropanecarbonyl)-5-trifluoromethyl-1,2,3,4-tetrahydro-isoquinolin-8-yl]-phenyl}-acetic acid | C29H26NO4F3 509.18 | 1.12 LC-MS 1FA | 510.3 |

TABLE 3-continued

| Example | Compound of Formula (I) | Formula MW | $t_R$ [min] LC-MS Method | MS-data m/z [M + H]+ |
|---|---|---|---|---|
| 84 | {3-[5,6-Difluoro-2-((1R,2R)-2-phenyl-cyclopropanecarbonyl)-1,2,3,4-tetrahydro-isoquinolin-8-yl]-4-methoxy-phenyl}-acetic acid | C28H25NO4F2 477.18 | 1.07 LC-MS 1FA | 478.3 |
| 85 | (3-{5-Fluoro-2-[(E)-(3-phenyl-acryloyl)]-1,2,3,4-tetrahydro-isoquinolin-8-yl}-4-methoxy-phenyl)-acetic acid | C27H24NO4F 445.17 | 1.01 LC-MS 1FA | 446.3 |
| 86 | (3-{5-Fluoro-2-[(E)-3-(6-methoxy-pyridin-3-yl)-acryloyl]-1,2,3,4-tetrahydro-isoquinolin-8-yl}-4-methoxy-phenyl)-acetic acid | C27H25N2O5F 476.18 | 0.95 LC-MS 1FA | 477.3 |
| 87 | (3-{2-[(E)-3-(2,4-Dimethyl-thiazol-5-yl)-acryloyl]-5-fluoro-1,2,3,4-tetrahydro-isoquinolin-8-yl}-4-methoxy-phenyl)-acetic acid | C26H25N2O4FS 480.15 | 0.92 LC-MS 1FA | 481.3 |
| 88 | {3-[2-((E)-3-Benzothiazol-2-yl-acryloyl)-5-fluoro-1,2,3,4-tetrahydro-isoquinolin-8-yl]-4-methoxy-phenyl}-acetic acid | C28H23N2O4FS 502.13 | 1.03 LC-MS 1FA | 503.2 |
| 89 | {3-[5-Fluoro-2-((E)-3-pyridin-3-yl-acryloyl)-1,2,3,4-tetrahydro-isoquinolin-8-yl]-4-methoxy-phenyl}-acetic acid | C26H23N2O4F 446.16 | 0.78 LC-MS 1FA | 447.3 |
| 90 | (3-{2-[(E)-3-(2,5-Dimethyl-2H-pyrazol-3-yl)-acryloyl]-5-fluoro-1,2,3,4-tetrahydro-isoquinolin-8-yl}-4-methoxy-phenyl)-acetic acid | C26H26N3O4F 463.19 | 0.89 LC-MS 1FA | 464.3 |
| 91 | {3-[5-Fluoro-2-(3-pyridin-2-yl-propionyl)-1,2,3,4-tetrahydro-isoquinolin-8-yl]-4-methoxy-phenyl}-acetic acid | C26H25N2O4F 448.18 | 0.66 LC-MS 1FA | 449.3 |
| 92 | (3-{5-Fluoro-2-[3-(6-methyl-pyridin-2-yl)-propionyl]-1,2,3,4-tetrahydro-isoquinolin-8-yl}-4-methoxy-phenyl)-acetic acid | C27H27N2O4F 462.20 | 0.65 LC-MS 1FA | 463.4 |
| 93 | {3-[5-Fluoro-2-(3-pyrimidin-2-yl-propionyl)-1,2,3,4-tetrahydro-isoquinolin-8-yl]-4-methoxy-phenyl}-acetic acid | C25H24N3O4F 449.18 | 0.80 LC-MS 1FA | 450.3 |
| 94 | (3-{5-Fluoro-2-[2-(pyridin-3-yloxy)-acetyl]-1,2,3,4-tetrahydro-isoquinolin-8-yl}-4-methoxy-phenyl)-acetic acid | C25H23N2O5F 450.16 | 0.71 LC-MS 1FA | 451.3 |
| 95 | (±)-(3-{5-Fluoro-2-[trans-2-(2-trifluoromethyl-phenyl)-cyclopropanecarbonyl]-1,2,3,4-tetrahydro-isoquinolin-8-yl}-4-methoxy-phenyl)-acetic acid | C29H25NO4F4 527.17 | 1.08 LC-MS 1FA | 528.3 |
| 96 | (±)-(3-{5-Fluoro-2-[trans-2-(4-methoxy-phenyl)-cyclopropanecarbonyl]-1,2,3,4-tetrahydro-isoquinolin-8-yl}-4-methoxy-phenyl)-acetic acid | C29H28NO5F 489.20 | 1.02 LC-MS 1FA | 490.4 |
| 97 | (±)-(3-{2-[3-(4-Chloro-phenyl)-3-phenyl-propionyl]-5-fluoro-1,2,3,4-tetrahydro-isoquinolin-8-yl}-4-methoxy-phenyl)-acetic acid | C33H29NO4ClF 557.18 | 1.16 LC-MS 1FA | 558.3 |
| 98 | (±)-(3-{2-[trans-2-(2,4-Dichloro-phenyl)-cyclopropanecarbonyl]-5-fluoro-1,2,3,4-tetrahydro-isoquinolin-8-yl}-4-methoxy-phenyl)-acetic acid | C28H24NO4Cl2F 527.11 | 1.14 LC-MS 1FA | 528.3 |
| 99 | {3-[8-Fluoro-2-((1R,2R)-2-phenyl-cyclopropanecarbonyl)-1,2,3,4-tetrahydro-isoquinolin-5-yl]-4-methoxy-phenyl}-acetic acid | C28H26NO4F 459.19 | 1.04 LC-MS 1FA | 460.3 |
| 100 | {3-[8-Fluoro-2-(4-phenyl-butyryl)-1,2,3,4-tetrahydro-isoquinolin-5-yl]-4-methoxy-phenyl}-acetic acid | C28H28NO4F 461.20 | 1.06 LC-MS 1FA | 462.3 |
| 101 | {3-[8-Fluoro-2-(3-phenyl-propionyl)-1,2,3,4-tetrahydro-isoquinolin-5-yl]-4-methoxy-phenyl}-acetic acid | C27H26NO4F 447.19 | 1.01 LC-MS 1FA | 448.3 |

TABLE 3-continued

| Example | Compound of Formula (I) | Formula MW | $t_R$ [min] LC-MS Method | MS-data m/z [M + H]+ |
|---|---|---|---|---|
| 102 | {3-[8-Fluoro-2-(3-phenoxy-propionyl)-1,2,3,4-tetrahydro-isoquinolin-5-yl]-4-methoxy-phenyl}-acetic acid | C27H26NO5F 463.18 | 1.00 LC-MS 1FA | 464.3 |
| 103 | (3-{2-[2-(2-Chloro-benzyloxy)-acetyl]-8-fluoro-1,2,3,4-tetrahydro-isoquinolin-5-yl}-4-methoxy-phenyl)-acetic acid | C27H25NO5ClF 497.14 | 1.03 LC-MS 1FA | 498.3 |
| 104 | {3-[2-(3-3,4-Dihydro-2H-quinolin-1-yl-propionyl)-8-fluoro-1,2,3,4-tetrahydro-isoquinolin-5-yl]-4-methoxy-phenyl}-acetic acid | C30H31N2O4F 502.23 | 1.08 LC-MS 1FA | 503.4 |
| 105 | (3-{8-Fluoro-2-[3-(1-methyl-1H-indol-3-yl)-propionyl]-1,2,3,4-tetrahydro-isoquinolin-5-yl}-4-methoxy-phenyl)-acetic acid | C30H29N2O4F 500.21 | 1.04 LC-MS 1FA | 501.4 |

Method C: To a solution of (R)-3-phenylbutyric acid (19 mg, 0.12 mmol, 1 eq.) in DCM (2 mL), DIPEA (0.1 mL, 0.58 mmol, 5 eq.) and TBTU (37 mg, 0.12 mmol, 1 eq.) were added in sequence. The resulting solution was stirred at r.t. for 30 minutes. Then [3-(5-fluoro-1,2,3,4-tetrahydro-isoquinolin-8-yl)-4-methoxy-phenyl]-acetic acid ethyl ester (40 mg, 0.12 mmol, 1 eq.) was added and the resulting mixture was stirred at r.t. for 18 hours. The mixture was concentrated in vacuo. The residue was dissolved in DMF (0.8 mL). 1 M aq. NaOH (1 mL) was added. The mixture was stirred at r.t. for 3 hours. The solution was carefully neutralized with formic acid (0.5 mL), purified by prep. HPLC (column: Atlantis, 30×75 mm, 10 um, UV/MS, acidic conditions) and concentrated in vacuo to give the desired acid.

Listed in Table 4 below are examples of compounds of Formula (I), prepared according to the above-mentioned method with the corresponding compound of Structure 2 and the corresponding acid as starting materials.

TABLE 4

| Example | Compound of Formula (I) | Formula MW | $t_R$ [min] LC-MS Method | MS-data m/z [M + H]+ |
|---|---|---|---|---|
| 106 | {3-[5-Fluoro-2-((R)-3-phenyl-butyryl)-1,2,3,4-tetrahydro-isoquinolin-8-yl]-4-methoxy-phenyl}-acetic acid | C28H28NO4F 461.20 | 1.04 LC-MS 1FA | 462.3 |
| 107 | {3-[5-Fluoro-2-((S)-3-phenyl-butyryl)-1,2,3,4-tetrahydro-isoquinolin-8-yl]-4-methoxy-phenyl}-acetic acid | C28H28NO4F 461.20 | 1.04 LC-MS 1FA | 462.3 |
| 108 | {3-[5-Fluoro-2-(3-methyl-3-phenyl-butyryl)-1,2,3,4-tetrahydro-isoquinolin-8-yl]-4-methoxy-phenyl}-acetic acid | C29H30NO4F 475.22 | 1.08 LC-MS 1FA | 476.3 |
| 109 | (±)-{3-[5-Fluoro-2-(2-methyl-3-phenyl-propionyl)-1,2,3,4-tetrahydro-isoquinolin-8-yl]-4-methoxy-phenyl}-acetic acid | C28H28NO4F 461.20 | 1.05 LC-MS 1FA | 462.3 |
| 110 | {3-[5-Fluoro-2-(indane-2-carbonyl)-1,2,3,4-tetrahydro-isoquinolin-8-yl]-4-methoxy-phenyl}-acetic acid | C28H26NO4F 459.19 | 1.06 LC-MS 1FA | 460.3 |
| 111 | {3-[5-Fluoro-2-(2-indan-2-yl-acetyl)-1,2,3,4-tetrahydro-isoquinolin-8-yl]-4-methoxy-phenyl}-acetic acid | C29H28NO4F 473.20 | 1.08 LC-MS 1FA | 474.4 |
| 112 | (±)-{3-[5-Fluoro-2-(indane-1-carbonyl)-1,2,3,4-tetrahydro-isoquinolin-8-yl]-4-methoxy-phenyl}-acetic acid | C28H26NO4F 459.19 | 1.03 LC-MS 1FA | 460.3 |
| 113 | (±)-{3-[2-(Chroman-3-carbonyl)-5-fluoro-1,2,3,4-tetrahydro-isoquinolin-8-yl]-4-methoxy-phenyl}-acetic acid | C28H26NO5F 475.18 | 1.04 LC-MS 1FA | 476.3 |
| 114 | (±)-{3-[5-Fluoro-2-(4-oxo-1,2,3,4-tetrahydro-naphthalene-2-carbonyl)-1,2,3,4-tetrahydro-isoquinolin-8-yl]-4-methoxy-phenyl}-acetic acid | C29H26NO5F 487.18 | 0.96 LC-MS 1FA | 488.3 |
| 115 | (±)-{3-[2-(Chroman-2-carbonyl)-5-fluoro-1,2,3,4-tetrahydro-isoquinolin-8-yl]-4-methoxy-phenyl}-acetic acid | C28H26NO5F 475.18 | 1.04 LC-MS 1FA | 476.3 |

TABLE 4-continued

| Example | Compound of Formula (I) | Formula MW | $t_R$ [min] LC-MS Method | MS-data m/z [M + H]$^+$ |
|---------|------------------------|------------|--------------------------|-------------------------|
| 116 | (±)-{3-[2-(Bicyclo[4.2.0]octa-1(6),2,4-triene-7-carbonyl)-5-fluoro-1,2,3,4-tetrahydro-isoquinolin-8-yl]-4-methoxy-phenyl}-acetic acid | C27H24NO4F 445.17 | 1.01 LC-MS 1FA | 446.3 |
| 117 | {3-[5-Fluoro-2-(4-phenyl-butyryl)-1,2,3,4-tetrahydro-isoquinolin-8-yl]-4-methoxy-phenyl}-acetic acid | C28H28NO4F 461.20 | 1.07 LC-MS 1FA | 462.3 |
| 118 | {3-[5-Fluoro-2-(4-oxo-4-phenyl-butyryl)-1,2,3,4-tetrahydro-isoquinolin-8-yl]-4-methoxy-phenyl}-acetic acid | C28H26NO5F 475.18 | 0.99 LC-MS 1FA | 476.3 |
| 119 | (3-{5-Fluoro-2-[2-(1-methyl-1H-indol-3-yl)-acetyl]-1,2,3,4-tetrahydro-isoquinolin-8-yl}-4-methoxy-phenyl)-acetic acid | C29H27N2O4F 486.20 | 1.01 LC-MS 1FA | 487.3 |
| 120 | (±)-2-{3-[5-Fluoro-2-((1R,2R)-2-phenyl-cyclopropanecarbonyl)-1,2,3,4-tetrahydro-isoquinolin-8-yl]-4-methoxy-phenyl}-propionic acid | C29H28NO4F 473.20 | 1.10 LC-MS 1FA | 474.3 |

Method D: To a solution of 2-(1,2-benzisoxazol-3-yl)acetic acid (24 mg, 0.13 mmol, 1 eq.) in DCM (1 mL), 1-hydroxybenzotriazole hydrate (18 mg, 0.13 mmol, 1 eq.) and N-(3-dimethylaminopropyl-N'-ethylcarbodiimide hydrochloride (26 mg, 0.13 mmol, 1 eq.) were added in sequence. The resulting solution was stirred at r.t. for 2 min. Then a solution of [3-(5-fluoro-1,2,3,4-tetrahydro-isoquinolin-8-yl)-4-methoxy-phenyl]-acetic acid ethyl ester (46 mg, 0.13 mmol, 1 eq.) and NEt$_3$ (37 µL, 0.27 mmol, 2 eq.) in DCM (1 mL) was added and the resulting mixture was stirred at r.t. for 18 hours. The mixture was concentrated in vacuo. The residue was dissolved in DMF (0.8 mL). 1M aq. NaOH (1 mL) was added. The mixture was stirred at r.t. for 3 hours. The solution was carefully neutralized with formic acid (0.5 mL), purified by prep. HPLC (column: Atlantis, 30×75 mm, 10 um, UV/MS, acidic conditions) and concentrated in vacuo to give the desired acid.

Listed in Table 5 below are examples of compounds of Formula (I), prepared according to the above-mentioned method with the corresponding compound of Structure 2 and the corresponding acid as starting materials.

TABLE 5

| Example | Compound of Formula (I) | Formula MW | $t_R$ [min] LC-MS Method | MS-data m/z [M + H]$^+$ |
|---------|------------------------|------------|--------------------------|-------------------------|
| 121 | {3-[2-(2-Benzo[d]isoxazol-3-yl-acetyl)-5-fluoro-1,2,3,4-tetrahydro-isoquinolin-8-yl]-4-methoxy-phenyl}-acetic acid | C27H23N2O5F 474.16 | 0.97 LC-MS 1FA | 475.3 |
| 122 | (±)-{3-[5-Fluoro-2-(3-oxo-indane-1-carbonyl)-1,2,3,4-tetrahydro-isoquinolin-8-yl]-4-methoxy-phenyl}-acetic acid | C28H24NO5F 473.16 | 0.91 LC-MS 1FA | 474.3 |
| 123 | (±)-{3-[5-Fluoro-2-(1,2,3,4-tetrahydro-naphthalene-2-carbonyl)-1,2,3,4-tetrahydro-isoquinolin-8-yl]-4-methoxy-phenyl}-acetic acid | C29H28NO4F 473.20 | 1.08 LC-MS 1FA | 474.3 |
| 124 | {3-[5-Fluoro-2-(2-1H-indazol-3-yl-acetyl)-1,2,3,4-tetrahydro-isoquinolin-8-yl]-4-methoxy-phenyl}-acetic acid | C27H24N3O4F 473.18 | 0.88 LC-MS 1FA | 474.3 |
| 125 | (3-{5-Fluoro-2-[3-(3-methyl-indazol-1-yl)-propionyl]-1,2,3,4-tetrahydro-isoquinolin-8-yl}-4-methoxy-phenyl)-acetic acid | C29H28N3O4F 501.21 | 1.01 LC-MS 1FA | 502.3 |
| 126 | (3-{5-Fluoro-2-[3-(5-fluoro-indazol-1-yl)-propionyl]-1,2,3,4-tetrahydro-isoquinolin-8-yl}-4-methoxy-phenyl)-acetic acid | C28H25N3O4F2 505.18 | 0.98 LC-MS 1FA | 506.3 |
| 127 | {3-[2-(2-Cyclohexyl-acetyl)-5-fluoro-1,2,3,4-tetrahydro-isoquinolin-8-yl]-4-methoxy-phenyl}-acetic acid | C26H30NO4F 439.22 | 1.08 LC-MS 1FA | 440.3 |
| 128 | (3-{5-Fluoro-2-[2-(1-hydroxy-cyclohexyl)-acetyl]-1,2,3,4-tetrahydro-isoquinolin-8-yl}-4-methoxy-phenyl)-acetic acid | C26H30NO5F 455.21 | 0.98 LC-MS 1FA | 456.3 |

TABLE 5-continued

| Example | Compound of Formula (I) | Formula MW | $t_R$ [min] LC-MS Method | MS-data m/z [M + H]$^+$ |
|---|---|---|---|---|
| 129 | {3-[2-(3,3-Dimethyl-butyryl)-5-fluoro-1,2,3,4-tetrahydro-isoquinolin-8-yl]-4-methoxy-phenyl}-acetic acid | C24H28NO4F 413.20 | 1.01 LC-MS 1FA | 414.3 |

Urea Formation and Subsequent Saponification

To a solution of [3-(5-fluoro-1,2,3,4-tetrahydro-isoquinolin-8-yl)-4-methoxy-phenyl]-acetic acid ethyl ester hydrochloride (57 mg, 0.15 mmol, 1.00 eq) and triethylamine (63 μl, 0.45 mmol, 3.00 eq) in MeCN (1.0 mL), a solution of 2-fluorobenzyl isocyanate (25 mg, 0.16 mmol, 1.05 eq.) in MeCN (1.0 mL) was added. The mixture was stirred at r.t. for 18 hours. 1M aq. NaOH (0.8 mL) was added. The mixture was stirred at r.t. for 18 hours. Formic acid (0.2 mL) was added. The mixture was then purified by prep. HPLC (column: Waters Xbridge, 30×75 mm, 10 um, UV/MS, acidic conditions) and concentrated in vacuo to give the desired acid as a white foam.

Listed in Table 6 below are examples of compounds of Formula (I), prepared according to the above-mentioned method with the corresponding compound of Structure 2 and the corresponding isocyanate as starting materials.

Carbamate Formation and Subsequent Saponification

Method A: To a solution of [3-(5-fluoro-1,2,3,4-tetrahydro-isoquinolin-8-yl)-4-methoxy-phenyl]-acetic acid ethyl ester hydrochloride (38 mg, 0.10 mmol, 1.0 eq.) and DIPEA (42 μL, 0.25 mmol, 2.5 eq.) in DCM (1.5 mL), carbonic acid 2,5-dioxo-pyrrolidin-1-yl ester 3-fluoro-benzyl ester (32 mg, 0.12 mmol, 1.2 eq.) was added. The mixture was stirred at r.t. for 1 hour. The reaction was quenched with 1M aq. citric acid soln. (1.5 mL). The layers were separated over phase separators. The aq. phase was extracted with DCM (3×). The comb. org. phases were concentrated in vacuo. To a solution of the residue in DMF (0.4 mL), 1M aq. NaOH (0.5 mL) was added. The solution was stirred at r.t. for 18 hours. Formic acid (0.2 mL) was added. The resulting solution was purified by prep. HPLC (column: Waters Xbridge, 30×75 mm, 10 um, UV/MS, acidic conditions) and concentrated in vacuo to give the desired acid as a white foam.

Listed in Table 7 below are examples of compounds of Formula (I), prepared according to the above-mentioned method with the corresponding compound of Structure 2 and the corresponding carbonate 3 as starting materials.

TABLE 6

| Example | Compound of Formula (I) | Formula MW | $t_R$ [min] LC-MS Method | MS-data m/z [M + H]$^+$ |
|---|---|---|---|---|
| 130 | {3-[5-Fluoro-2-(2-fluoro-benzylcarbamoyl)-1,2,3,4-tetrahydro-isoquinolin-8-yl]-4-methoxy-phenyl}-acetic acid | C26H24N2O4F2 466.17 | 0.95 LC-MS 1FA | 467.3 |
| 131 | {3-[5-Fluoro-2-(3-fluoro-benzylcarbamoyl)-1,2,3,4-tetrahydro-isoquinolin-8-yl]-4-methoxy-phenyl}-acetic acid | C26H24N2O4F2 466.17 | 0.95 LC-MS 1FA | 467.3 |
| 132 | {3-[5-Fluoro-2-(4-fluoro-benzylcarbamoyl)-1,2,3,4-tetrahydro-isoquinolin-8-yl]-4-methoxy-phenyl}-acetic acid | C26H24N2O4F2 466.17 | 0.95 LC-MS 1FA | 467.3 |
| 133 | [3-(5-Fluoro-2-phenethylcarbamoyl-1,2,3,4-tetrahydro-isoquinolin-8-yl)-4-methoxy-phenyl]-acetic acid | C27H27N2O4F 462.20 | 0.97 LC-MS 1FA | 463.3 |
| 134 | {3-[2-(2-Chloro-benzylcarbamoyl)-5-fluoro-1,2,3,4-tetrahydro-isoquinolin-8-yl]-4-methoxy-phenyl}-acetic acid | C26H24N2O4ClF 482.14 | 0.98 LC-MS 1FA | 483.0 |
| 135 | {3-[5-Fluoro-2-(2-methoxy-benzylcarbamoyl)-1,2,3,4-tetrahydro-isoquinolin-8-yl]-4-methoxy-phenyl}-acetic acid | C27H27N2O5F 478.19 | 0.95 LC-MS 1FA | 479.3 |
| 136 | [3-(2-Benzylcarbamoyl-5-fluoro-1,2,3,4-tetrahydro-isoquinolin-8-yl)-4-methoxy-phenyl]-acetic acid | C26H25N2O4F 448.18 | 0.94 LC-MS 1FA | 449.3 |
| 137 | [3-(5-Fluoro-2-propylcarbamoyl-1,2,3,4-tetrahydro-isoquinolin-8-yl)-4-methoxy-phenyl]-acetic acid | C22H25N2O4F 400.18 | 0.87 LC-MS 1FA | 401.3 |

TABLE 7

| Example | Compound of Formula (I) | Formula MW | $t_R$ [min] LC-MS Method | MS-data m/z $[M + H]^+$ |
|---|---|---|---|---|
| 138 | 8-(5-Carboxymethyl-2-methoxy-phenyl)-5-fluoro-3,4-dihydro-1H-isoquinoline-2-carboxylic acid 3-fluoro-benzyl ester | C26H23NO5F2 467.15 | 1.07 LC-MS 1FA | 468.3 |
| 139 | 8-(5-Carboxymethyl-2-methoxy-phenyl)-5-fluoro-3,4-dihydro-1H-isoquinoline-2-carboxylic acid 4-fluoro-benzyl ester | C26H23NO5F2 467.15 | 1.07 LC-MS 1FA | 468.3 |
| 140 | (±)-8-[5-(1-Carboxy-ethyl)-2-methoxy-phenyl]-5-fluoro-3,4-dihydro-1H-isoquinoline-2-carboxylic acid 2-fluoro-benzyl ester | C27H25NO5F2 481.17 | 1.13 LC-MS 1FA | 482.2 |

Method B: To a solution of [3-(5-fluoro-1,2,3,4-tetrahydro-isoquinolin-8-yl)-4-methoxy-phenyl]-acetic acid ethyl ester hydrochloride (38 mg, 0.10 mmol, 1.0 eq) and DIPEA (42 µL, 0.25 mmol, 2.5 eq) in DCM (1.5 mL), ethyl chloroformate (12 µL, 0.12 mmol, 1.2 eq.) was added. The mixture was stirred at r.t. for 1 hour. The reaction was quenched with 1M aq. citric acid soln. (1.5 mL). The layers were separated over phase separators. The aq. phase was extracted with DCM (3×). The comb. org. phases were concentrated in vacuo. To a solution of the residue in DMF (0.4 mL), 1M aq. NaOH (0.5 mL) was added. The solution was stirred at r.t. for 18 hours. Formic acid (0.2 mL) was added. The resulting solution was purified by prep. HPLC (column: Waters Xbridge, 30×75 mm, 10 um, UV/MS, acidic conditions) and concentrated in vacuo to give the desired acid as a white foam.

Listed in Table 8 below are examples of compounds of Formula (I), prepared according to the above-mentioned method with the corresponding compound of Structure 2 and the corresponding chloroformate as starting materials.

Carbamate Formation and Concomitant Saponification

To a solution of 8-(5-ethoxycarbonylmethyl-2-methoxy-phenyl)-5-fluoro-3,4-dihydro-1H-isoquinoline-2-carboxylic acid 4-nitro-phenyl ester (56 mg, 0.1 mmol, 1 eq.) and 2-fluorobenzyl alcohol (38 mg, 0.3 mmol, 3 eq.) in THF (1.7 mL), potassium tert-butoxide (33.7 mg, 0.3 mmol, 3 eq.) was added. The mixture was stirred at r.t. for 2 hours. The solvent was removed in vacuo. The residue was dissolved in MeCN/H₂O 1:1 (1.0 mL), formic acid (0.2 mL) was added followed by DMF (0.5 mL). The resulting solution was purified by prep. HPLC (column: Waters Xbridge, 30×75 mm, 10 um, UV/MS, acidic conditions) and concentrated in vacuo to give the desired acid as pale yellow foam.

Listed in Table 9 below are examples of compounds of Formula (I), prepared according to the above-mentioned method with the corresponding nitrophenyl carbamate 5 and the corresponding alcohol as starting materials.

TABLE 8

| Example | Compound of Formula (I) | Formula MW | $t_R$ [min] LC-MS Method | MS-data m/z $[M + H]^+$ |
|---|---|---|---|---|
| 141 | 8-(5-Carboxymethyl-2-methoxy-phenyl)-5-fluoro-3,4-dihydro-1H-isoquinoline-2-carboxylic acid ethyl ester | C21H22NO5F 387.15 | 0.95 LC-MS 1FA | 388.2 |
| 142 | 8-(5-Carboxymethyl-2-methoxy-phenyl)-5-fluoro-3,4-dihydro-1H-isoquinoline-2-carboxylic acid isobutyl ester | C23H26NO5F 415.18 | 1.06 LC-MS 1FA | 416.3 |
| 143 | 8-(5-Carboxymethyl-2-methoxy-phenyl)-5-fluoro-3,4-dihydro-1H-isoquinoline-2-carboxylic acid isopropyl ester | C22H24NO5F 401.16 | 1.01 LC-MS 1FA | 402.2 |
| 144 | 8-(3-Carboxymethoxy-5-chloro-phenyl)-5-fluoro-3,4-dihydro-1H-isoquinoline-2-carboxylic acid benzyl ester | C25H21NO5ClF 469.11 | 1.16 LC-MS 1FA | 470.2 |
| 145 | 8-(2-Carboxymethoxy-5-chloro-phenyl)-5-fluoro-3,4-dihydro-1H-isoquinoline-2-carboxylic acid benzyl ester | C25H21NO5ClF 469.11 | 1.16 LC-MS 1FA | 470.2 |

TABLE 9

| Example | Compound of Formula (I) | Formula MW | $t_R$ [min] LC-MS Method | MS-data m/z [M + H]$^+$ |
|---|---|---|---|---|
| 146 | 8-(5-Carboxymethyl-2-methoxy-phenyl)-5-fluoro-3,4-dihydro-1H-isoquinoline-2-carboxylic acid 2-fluoro-benzyl ester | C26H23NO5F2 467.15 | 1.07 LC-MS 1FA | 468.3 |
| 147 | 8-(5-Carboxymethyl-2-methoxy-phenyl)-5-fluoro-3,4-dihydro-1H-isoquinoline-2-carboxylic acid 2,3-difluoro-benzyl ester | C26H22NO5F3 485.15 | 1.08 LC-MS 1FA | 486.3 |
| 148 | 8-(5-Carboxymethyl-2-methoxy-phenyl)-5-fluoro-3,4-dihydro-1H-isoquinoline-2-carboxylic acid 2-methyl-2H-pyrazol-3-ylmethyl ester | C24H24N3O5F 453.17 | 0.89 LC-MS 1FA | 454.3 |
| 149 | 8-(5-Carboxymethyl-2-methoxy-phenyl)-5-fluoro-3,4-dihydro-1H-isoquinoline-2-carboxylic acid 2,5-dimethyl-2H-pyrazol-3-ylmethyl ester | C25H26N3O5F 467.19 | 0.91 LC-MS 1FA | 468.4 |
| 150 | 8-(5-Carboxymethyl-2-methoxy-phenyl)-5-fluoro-3,4-dihydro-1H-isoquinoline-2-carboxylic acid 2-methyl-thiazol-4-ylmethyl ester | C24H23N2O5FS 470.13 | 0.95 LC-MS 1FA | 471.3 |
| 151 | 8-(5-Carboxymethyl-2-methoxy-phenyl)-5-fluoro-3,4-dihydro-1H-isoquinoline-2-carboxylic acid 2-methyl-thiazol-5-ylmethyl ester | C24H23N2O5FS 470.13 | 0.93 LC-MS 1FA | 471.3 |
| 152 | 8-(5-Carboxymethyl-2-methoxy-phenyl)-5-fluoro-3,4-dihydro-1H-isoquinoline-2-carboxylic acid pyrimidin-5-ylmethyl ester | C24H22N3O5F 451.15 | 0.84 LC-MS 1FA | 452.3 |
| 153 | 8-(5-Carboxymethyl-2-methoxy-phenyl)-5-fluoro-3,4-dihydro-1H-isoquinoline-2-carboxylic acid 2-(4-methyl-thiazol-5-yl)-ethyl ester | C25H25N2O5FS 484.15 | 0.92 LC-MS 1FA | 485.3 |

Suzuki Cross-coupling and Subsequent Saponification

Method A: To a mixture under $N_2$ of 8-bromo-5-chloro-3,4-dihydro-1H-isoquinoline-2-carboxylic acid benzyl ester (214 mg, 0.50 mmol, 1.00 eq.), [4-methoxy-3-(4,4,5,5-tetramethyl-[1,3,2]dioxaborolan-2-yl)-phenyl]-acetic acid ethyl ester (203 mg, 0.50 mmol, 1.00 eq.) and sodium carbonate (212 mg, 2.00 mmol, 4.00 eq.) in toluene/MeOH/water 20:4:1 (10.0 mL), tetrakis(triphenylphosphine) palladium (0) (29 mg, 0.03 mmol, 0.05 eq.) was added and the mixture was stirred at 100° C. for 18 hours. The mixture was allowed to cool to r.t. and concentrated in vacuo. The residue was partitioned between AcOEt (20 mL) and water (20 mL). The layers were separated. The org. phase was washed with sat. aq. NaCl soln. (1×10 mL), dried over MgSO$_4$, and filtered through Celite. The filtrate was concentrated in vacuo. To a solution of the residue in DMF (2.2 mL), 1M aq. NaOH soln. (0.6 mL) was added. The solution was stirred at r.t. for 18 hours. Formic acid was added (0.2 mL). The resulting solution was purified by prep. HPLC (column: Waters Xbridge, 30×75 mm, 10 um, UV/MS, acidic conditions) and concentrated in vacuo to give the desired acid as a white foam.

Listed in Table 10 below are examples of compounds of Formula (I), prepared according to the above-mentioned method with the corresponding compound of Structure 7 as starting material.

TABLE 10

| Example | Compound of Formula (I) | Formula MW | $t_R$ [min] LC-MS Method | MS-data m/z [M + H]$^+$ |
|---|---|---|---|---|
| 154 | 8-(5-Carboxymethyl-2-methoxy-phenyl)-5-chloro-3,4-dihydro-1H-isoquinoline-2-carboxylic acid benzyl ester | C26H24NO5Cl 465.13 | 1.13 LC-MS 1FA | 466.3 |
| 155 | 8-(5-Carboxymethyl-2-methoxy-phenyl)-5-methyl-3,4-dihydro-1H-isoquinoline-2-carboxylic acid benzyl ester | C27H27NO5 445.19 | 1.08 LC-MS 1FA | 446.3 |
| 156 | 8-(5-Carboxymethyl-2-methoxy-phenyl)-5-methoxy-3,4-dihydro-1H-isoquinoline-2-carboxylic acid benzyl ester | C27H27NO6 461.18 | 1.05 LC-MS 1FA | 462.3 |
| 157 | 8-(5-Carboxymethyl-2-methoxy-phenyl)-5-fluoro-3,4-dihydro-1H-isoquinoline-2-carboxylic acid benzyl ester | C26H24NO5F 449.16 | 1.06 LC-MS 1FA | 450.2 |

TABLE 10-continued

| Example | Compound of Formula (I) | Formula MW | $t_R$ [min] LC-MS Method | MS-data m/z [M + H]$^+$ |
|---|---|---|---|---|
| 158 | 8-(5-Carboxymethyl-2-methoxy-phenyl)-5-trifluoromethyl-3,4-dihydro-1H-isoquinoline-2-carboxylic acid benzyl ester | C27H24NO5F3 499.16 | 1.15 LC-MS 1FA | 500.3 |
| 159 | 5-(5-Carboxymethyl-2-methoxy-phenyl)-8-fluoro-3,4-dihydro-1H-isoquinoline-2-carboxylic acid benzyl ester | C26H24NO5F 449.16 | 1.07 LC-MS 1FA | 450.1 |

Method B: To a mixture under $N_2$ of [5-fluoro-8-(4,4,5,5-tetramethyl-[1,3,2]dioxaborolan-2-yl)-3,4-dihydro-1H-isoquinolin-2-yl]-((1R,2R)-2-phenyl-cyclopropyl)-methanone (53 mg, 0.125 mmol, 1.00 eq.), (3-bromo-4-trifluoromethoxy-phenoxy)-acetic acid ethyl ester (43 mg, 0.125 mmol, 1.00 eq.) and sodium carbonate (66 mg, 0.63 mmol, 5.00 eq.) in toluene/EtOH/water 20:4:1 (1.9 mL), tetrakis (triphenylphosphine) palladium (0) (7.2 mg, 0.006 mmol, 0.05 eq.) was added and the mixture was stirred at 100° C. for 18 hours. The mixture was allowed to cool to r.t., filtered through celite, and concentrated in vacuo. The residue was redissolved in DMF (0.6 mL) and 1M aq. NaOH (0.25 mL) was added. The resulting mixture was stirred at r.t. for 30 min. Formic acid (0.2 mL) was added. The crude mixture was purified by prep. HPLC (column: Waters Xbridge, 30×75 mm, 10 um, UV/MS, acidic conditions) and concentrated in vacuo to give the desired acid.

Listed in Table 11 below are examples of compounds of Formula (I), prepared according to the above-mentioned method with the corresponding halogenated compound 9 as starting material.

TABLE 11

| Example | Compound of Formula (I) | Formula MW | $t_R$ [min] LC-MS Method | MS-data m/z [M + H]$^+$ |
|---|---|---|---|---|
| 160 | {3-[5-Fluoro-2-((1R,2R)-2-phenyl-cyclopropanecarbonyl)-1,2,3,4-tetrahydro-isoquinolin-8-yl]-4-trifluoromethoxy-phenoxy}-acetic acid | C28H23NO5F4 529.15 | 1.14 LC-MS 1FA | 530.3 |
| 161 | {3-[5-Fluoro-2-((1R,2R)-2-phenyl-cyclopropanecarbonyl)-1,2,3,4-tetrahydro-isoquinolin-8-yl]-4-isopropoxy-phenoxy}-acetic acid | C30H30NO5F 503.21 | 1.13 LC-MS 1FA | 504.4 |

Method C: To a mixture under $N_2$ of 5-fluoro-8-(4,4,5,5-tetramethyl-[1,3,2]dioxaborolan-2-yl)-3,4-dihydro-1H-isoquinoline-2-carboxylic acid benzyl ester (52 mg, 0.125 mmol, 1.00 eq.), (3-bromo-4-trifluoromethoxy-phenoxy)-acetic acid ethyl ester (43 mg, 0.125 mmol, 1.00 eq.) and sodium carbonate (66 mg, 0.63 mmol, 5.00 eq.) in toluene/EtOH/water 20:4:1 (1.9 mL), tetrakis(triphenylphosphine) palladium (0) (7.2 mg, 0.006 mmol, 0.05 eq.) was added and the mixture was stirred at 100° C. for 18 hours. The mixture was allowed to cool to r.t., filtered over celite, and concentrated in vacuo. The residue was redissolved in DMF (0.6 mL) and 1M aq. NaOH (0.25 mL) was added. The resulting mixture was stirred at r.t. for 30 min. Formic acid (0.2 mL) was added. The crude mixture was purified by prep. HPLC (column: Waters Xbridge, 30×75 mm, 10 um, UV/MS, acidic conditions) and concentrated in vacuo to give the desired acid.

Listed in Table 12 below are examples of compounds of Formula (I), prepared according to the above-mentioned method with the corresponding halogenated compound 9 as starting material.

TABLE 12

| Example | Compound of Formula (I) | Formula MW | $t_R$ [min] LC-MS Method | MS-data m/z [M + H]$^+$ |
|---|---|---|---|---|
| 162 | 8-(5-Carboxymethoxy-2-trifluoromethoxy-phenyl)-5-fluoro-3,4-dihydro-1H-isoquinoline-2-carboxylic acid benzyl ester | C26H21NO6F4 519.13 | 1.16 LC-MS 1FA | 520.3 |

TABLE 12-continued

| Example | Compound of Formula (I) | Formula MW | $t_R$ [min] LC-MS Method | MS-data m/z [M + H]$^+$ |
|---|---|---|---|---|
| 163 | 8-(5-Carboxymethoxy-2-isopropoxy-phenyl)-5-fluoro-3,4-dihydro-1H-isoquinoline-2-carboxylic acid benzyl ester | C28H28NO6F 493.19 | 1.15 LC-MS 1FA | 494.3 |
| 164 | 8-(4-Carboxymethyl-2-fluoro-phenyl)-5-fluoro-3,4-dihydro-1H-isoquinoline-2-carboxylic acid benzyl ester | C25H21NO4F2 437.14 | 1.11 LC-MS 1FA | 438.2 |
| 165 | 8-(4-Carboxymethyl-2-chloro-phenyl)-5-fluoro-3,4-dihydro-1H-isoquinoline-2-carboxylic acid benzyl ester | C25H21NO4ClF 453.11 | 1.14 LC-MS 1FA | 454.3 |
| 166 | 8-(4-Carboxymethyl-2-methoxy-phenyl)-5-fluoro-3,4-dihydro-1H-isoquinoline-2-carboxylic acid benzyl ester | C26H24NO5F 449.16 | 1.10 LC-MS 1FA | 450.2 |

Method D: A mixture under $N_2$ of palladium(II)acetate (0.2 mg, 0.001 mmol, 0.01 eq.), 2-dicyclohexylphosphino-2',6'-dimethoxybiphenyl (0.8 mg, 0.002 mmol, 0.02 eq.), 5-fluoro-8-(4,4,5,5-tetramethyl-[1,3,2]dioxaborolan-2-yl)-3,4-dihydro-1H-isoquinoline-2-carboxylic acid benzyl ester (86.4 mg, 0.150 mmol, 1.50 eq.) and potassium phosphate (42.5 mg, 0.200 mmol, 2.00 eq.) in toluene (0.3 mL) and water (20 was stirred at r.t. for 2 min. A solution of (7-chloro-benzo[1,3]dioxol-5-yl)-acetic acid ethyl ester (24.3 mg, 0.100 mmol, 1.00 eq.) in toluene (0.3 mL) was added and the mixture was stirred at 100° C. for 66 hours. The mixture was allowed to cool to r.t., filtered through celite and concentrated in vacuo. The residue was dissolved in DMF (0.5 mL) and 2M aq. NaOH (0.2 mL) was added. The resulting mixture was stirred at r.t. for 18 hours. Formic acid (0.2 mL) was added. The crude mixture was purified by prep. HPLC (column: Waters Xbridge, 30×75 mm, 10 um, UV/MS, acidic conditions) and concentrated in vacuo.

Listed in Table 13 below are examples of compounds of Formula (I), prepared according to the above-mentioned method with the corresponding halogenated compound 9 as starting material.

TABLE 13

| Example | Compound of Formula (I) | Formula MW | $t_R$ [min] LC-MS Method | MS-data m/z [M + H]$^+$ |
|---|---|---|---|---|
| 167 | 8-(6-Carboxymethyl-benzo[1,3]dioxol-4-yl)-5-fluoro-3,4-dihydro-1H-isoquinoline-2-carboxylic acid benzyl ester | C26H22NO6F 463.14 | 1.07 LC-MS 1FA | 464.3 |
| 168 | 8-(7-Carboxymethyl-2,3-dihydro-benzo[1,4]dioxin-5-yl)-5-fluoro-3,4-dihydro-1H-isoquinoline-2-carboxylic acid benzyl ester | C27H24NO6F 477.16 | 1.05 LC-MS 1FA | 478.3 |

EXAMPLE 169

8-(5-Carboxymethyl-2-methoxy-phenyl)-5-cyano-3,4-dihydro-1H-isoquinoline-2-carboxylic acid benzyl ester (C27H24N2O5, MW=456.17)

To an ice-cooled suspension of 5-cyano-8-hydroxy-3,4-dihydro-1H-isoquinoline-2-5 carboxylic acid benzyl ester (73 mg, 0.24 mmol, 1.0 eq.) in DCM (4.4 mL), triethylamine (99 μL, 0.71 mmol, 3.0 eq.) and trifluoromethanesulfonic anhydride (61 μL, 0.355 mmol, 1.5 eq.) were added in sequence. The reaction mixture was stirred at 0° C. for 30 min and further at r.t. for 45 min. The mixture was diluted with DCM (10 mL) and washed with sat. aq. $NaHCO_3$ soln. (2×). The org. layer was dried over $MgSO_4$, filtered, and concentrated in vacuo. To a mixture under $N_2$ of the triflate, [4-methoxy-3-(4,4,5,5-tetramethyl-[1,3,2]dioxaborolan-2-yl)-phenyl]-acetic acid ethyl ester (97 mg, 0.24 mmol, 1.0 eq.), and sodium carbonate (100 mg, 0.95 mmol, 4.0 eq.) in toluene/EtOH/water 20:4:1 (4.8 mL), tetrakis(triphenylphosphine) palladium (0) (14 mg, 12 μmol, 0.05 eq.) was added. The mixture was stirred at 100° C. for 18 hours. The mixture was allowed to cool to r.t. and concentrated in vacuo. The residue was partitioned between AcOEt (10 mL) and water (10 mL). The layers were separated. The org. phase was washed with sat. aq. NaCl soln. (1×5 mL), dried over $MgSO_4$ and filtered through Celite. The filtrate was concentrated in vacuo. The residue was purified by flashmaster (column: 25 g, flow: 30 mL/min, 27 fractions of 30 mL, Heptane+10% AcOEt to Heptane+40% AcOEt). To a solution of the residue in DMF (1 mL), 1M aq. NaOH soln. (0.5 mL) was added. The mixture was stirred at r.t. for 18 hours. Formic acid was added (0.2 mL). The mixture was purified by prep. HPLC (column: Waters Xbridge, 30×75 mm, 10 um, UV/MS, acidic conditions) and concentrated in vacuo to give the title compound as a white foam.

LC-MS 1FA: $t_R$=1.00 min; [M+H]$^+$=457.3

EXAMPLE 170

8-(5-Carboxymethyl-2-methoxy-phenyl)-3,4-dihydro-1H-isoquinoline-2-carboxylic acid benzyl ester (C26H25NO5, MW=431.17)

To an ice-cooled solution of 8-hydroxy-3,4-dihydro-1H-isoquinoline-2-carboxylic acid benzyl ester (113 mg, 0.40 mmol, 1.00 eq.) in DCM (1 mL), $NEt_3$ (0.17 mL, 1.20 mmol, 3.00 eq.) and trifluoromethanesulfonic anhydride (0.10 mL, 0.60 mmol, 1.50 eq.) were added in sequence. The reaction mixture was stirred at 0° C. for 30 min and further at r.t. for 45 min. The mixture was diluted with DCM (50 mL) and washed with sat. aq. $NaHCO_3$ soln. (2×25 mL). The org. layer was dried over $MgSO_4$ and concentrated in vacuo. To a mixture under $N_2$ of the triflate, [4-methoxy-3-(4,4,5,5-tetramethyl-[1,3,2]dioxaborolan-2-yl)-phenyl]-acetic acid ethyl ester (128 mg, 0.40 mmol, 1.00 eq.), and sodium carbonate (170 mg, 1.60 mmol, 4.00 eq.) in toluene/EtOH/water 20:4:1 (2.5 mL), tetrakis(triphenylphosphine)palladium(0) (23 mg, 0.02 mmol, 0.05 eq.) was added. The mixture was stirred at 100° C. for 17 hours. The mixture was allowed to cool to r.t. and concentrated in vacuo. The residue was partitioned between AcOEt (20 mL) and water (10 mL). The layers were separated. The org. phase was washed with sat. aq. NaCl soln. (1×10 mL), dried over $MgSO_4$, and concentrated in vacuo. The residue was partially purified by CC ($SiO_2$, Hept/AcOEt 8:2 to 7:3) to give an yellow oil. The residue was dissolved in THF (3 mL) and 1M aq. NaOH (0.6 mL) was added. The resulting solution was stirred at r.t. for 68 hours. The org. solvent was removed in vacuo. The residue was diluted with water (10 mL) and acidified with 1M aq. HCl. The mixture was extracted with DCM/THF 3:1 (3×5 mL). The comb. org. phases were concentrated in vacuo. The crude product was purified by prep. HPLC (column: Waters X-Bridge, 30×75 mm, 10 um, UV/MS, acidic conditions) and concentrated in vacuo to give the desired acid as a white solid.

LC-MS 1FA: $t_R$=1.03 min; $[M+H]^+$=432.3

EXAMPLE 171

(±)-8-[5-(1-Carboxy-ethyl)-2-methoxy-phenyl]-5-fluoro-3,4-dihydro-1H-isoquinoline-2-carboxylic acid benzyl ester (C27H26NO5F, MW=463.18)

To a mixture under $N_2$ of 5-fluoro-8-(4,4,5,5-tetramethyl-[1,3,2]dioxaborolan-2-yl)-3,4-dihydro-1H-isoquinoline-2-carboxylic acid benzyl ester (82 mg, 0.20 mmol, 1.00 eq.), (±)-2-(3-bromo-4-methoxy-phenyl)-propionic acid ethyl ester (63 mg, 0.20 mmol, 1.00 eq.) and sodium carbonate (85 mg, 0.80 mmol, 4.00 eq.) in toluene/MeOH/water 20:4:1 (4 mL), tetrakis(triphenylphosphine)palladium(0) (12 mg, 0.01 mmol, 0.05 eq.) was added and the mixture was stirred at 100° C. for 18 hours. The mixture was allowed to cool to r.t. and concentrated in vacuo. The residue was partitioned between AcOEt (10 mL) and water (10 mL). The layers were separated. The org. phase was washed with sat. aq. NaCl soln. (1×5 mL), dried over $MgSO_4$ and filtered through Celite. The filtrate was concentrated in vacuo. To a solution of the previous residue in DMF (0.9 mL), 1M aq. NaOH soln. (1.3 mL) was added. The mixture was stirred at 50° C. for 18 hours. The reaction mixture was concentrated in vacuo. The residue was redissolved in THF (2 mL) and water (2 mL). Lithiumhydroxide monohydrate (23 mg, 0.54 mmol, 2.71 eq.) was added and the mixture was stirred at 50° C. for 18 hours. Formic acid was added (0.2 mL). The solution was diluted with DCM. The layers were separated and the aq. phase was extracted with DCM (2×). The comb. org. layers were dried over $MgSO_4$, filtered and concentrated in vacuo.

The residue was purified by prep. HPLC (column: Waters Xbridge, 19×30 mm, 5 um, UV/MS, acidic conditions) and concentrated in vacuo to give the acid as a pale yellow solid.

LC-MS 1FA: $t_R$=1.11 min; $[M+H]^+$=464.3

EXAMPLE 172

8-(4-Carboxymethoxy-phenyl)-5-fluoro-3,4-dihydro-1H-isoquinoline-2-carboxylic acid benzyl ester (C25H22NO5F, MW=435.15)

To a mixture under $N_2$ of 8-bromo-5-fluoro-3,4-dihydro-1H-isoquinoline-2-carboxylic acid benzyl ester (72.8 mg, 0.2 mmol, 1.0 eq.), 4-hydroxybenzeneboronic acid (41.4 mg, 0.3 mmol, 1.5 eq.) and sodium carbonate (127.2 mg, 1.2 mmol, 6.0 eq.) in toluene/MeOH/water 20:4:1 (4 mL), tetrakis(triphenylphosphine)palladium(0) (17.4 mg, 0.015 mmol, 0.08 eq) was added and the mixture was stirred under reflux at 100° C. for 72 hours. The mixture was allowed to cool to r.t. and concentrated in vacuo. The residue was partitioned between AcOEt (10 mL) and water (10 mL). The layers were separated. The org. phase was washed with sat. aq. NaCl soln. (1×5 mL), dried over $MgSO_4$ and filtered through Celite. The filtrate was concentrated in vacuo. The residue was purified by flashmaster (column: 25 g, flow: 30 mL/min, 30 fractions of 30 mL, Heptane 100% to Heptane+40% AcOEt) to yield a colorless oil. To a solution of the colorless oil and $K_2CO_3$ (82.9 mg, 0.6 mmol, 3.0 eq.) in DMF (0.7 mL), ethyl bromoacetate (66 pt, 0.6 mmol, 3.0 eq.) was added. The mixture was stirred at r.t. for 2 hours. 1M aq. NaOH soln. (0.54 mL) was added and the mixture stirred at r.t. for 18 hours. Formic acid was added (0.2 mL). The resulting acidic mixture was purified by prep. HPLC (column: Waters Xbridge, 30×75 mm, 10 um, UV/MS, acidic conditions) and concentrated in vacuo to give the title compound as a yellow oil.

LC-MS 1FA: $t_R$=1.10 min; $[M+H]^+$=436.2

Alkylation and Subsequent Saponification

Method A: To a solution of 8-(5-fluoro-2-hydroxy-phenyl)-3,4-dihydro-1H-isoquinoline-2-carboxylic acid benzyl ester (50 mg, 0.13 mmol, 1.0 eq.) and potassium carbonate anhydrous (55 mg, 0.40 mmol, 3.0 eq.) in DMF (1.5 mL), ethyl bromoacetate (22 μL, 0.20 mmol, 1.5 eq.) was added. The reaction mixture was stirred at r.t. for 18 hours. The reaction mixture was diluted with water (10 mL) and AcOEt (20 mL). The layers were separated. The aq. phase was extracted with AcOEt (2×10 mL). The comb. org. phases were washed with water (1×10 mL), sat. aq. NaCl soln. (1×10 mL), dried over $MgSO_4$, and concentrated in vacuo. To a solution of the residue in THF (1 mL), 1M aq. NaOH (0.2 mL) was added. The resulting solution was stirred at r.t. for 4 hours. The org. solvent was removed in vacuo. The residue was diluted with water (2 mL) and acidified with 1M aq. HCl.

The mixture was extracted with DCM/THF 2:1 (3×6 mL). The comb. org. phases were concentrated in vacuo. The crude product was purified by prep. HPLC (column: Waters X-Bridge, 30×75 mm, 10 um, UV/MS, acidic conditions) and concentrated in vacuo to give the desired acid as a white foam.

Listed in Table 14 below are examples of compounds of Formula (I), prepared according to the above-mentioned method with the corresponding phenols 13 as starting material.

TABLE 14

| Example | Compound of Formula (I) | Formula MW | $t_R$ [min] LC-MS Method | MS-data m/z [M + H]+ |
|---|---|---|---|---|
| 173 | 8-(2-Carboxymethoxy-5-fluoro-phenyl)-3,4-dihydro-1H-isoquinoline-2-carboxylic acid benzyl ester | C25H22NO5F 435.15 | 1.08 LC-MS 1FA | 436.2 |
| 174 | 8-[2-(3-Carboxy-propoxy)-5-fluoro-phenyl]-3,4-dihydro-1H-isoquinoline-2-carboxylic acid benzyl ester | C27H26NO5F 463.18 | 1.13 LC-MS 1FA | 464.3 |

Method B: To a solution of 5-fluoro-8-(3-hydroxy-phenyl)-3,4-dihydro-1H-isoquinoline-2-carboxylic acid benzyl ester (84 mg, 0.22 mmol, 1.0 eq.) and potassium carbonate (91 mg, 0.66 mmol, 3.0 eq.) in DMF (0.7 mL), ethyl bromoacetate (36 μL, 0.33 mmol, 3.0 eq.) was added. The mixture was stirred at r.t. for 2 hours. The reaction mixture was diluted with AcOEt and water. The layers were separated and the aq. phase was extracted with AcOEt (2×). The comb. org. phases were washed with water, sat. aq. NaCl soln., dried over MgSO4, filtered, and concentrated in vacuo. To a solution of the residue in DMF (1.0 mL), 1M aq. NaOH soln. (0.3 mL) was added. The solution was stirred at r.t. for 18 hours. Formic acid was added (0.2 mL). The resulting solution was purified by prep. HPLC (column: Waters Xbridge, 19×30 mm, 5 um, UV/MS, acidic conditions) and concentrated in vacuo to give the desired acid as a white foam.

Listed in Table 15 below are examples of compounds of Formula (I), prepared according to the above-mentioned method with the corresponding phenol 13 as starting material.

Amide Coupling and Subsequent Saponification

To a solution of 3-(1-methyl-1H-indol-3-yl)-propionic acid (26 mg, 0.13 mmol, 1.1 eq.) in DCM (2 mL), DIPEA (80 μL, 0.47 mmol, 4.0 eq.) and TBTU (41 mg, 0.13 mmol, 1.1 eq.) were added in sequence. The resulting solution was stirred at r.t. for 30 min. Then ethyl 2-(4-(5-fluoro-1,2,3,4-tetrahydroisoquinolin-8-yl)-3-methoxyphenyl)acetate (40 mg, 0.12 mmol, 1.0 eq.) was added and the resulting mixture was stirred at r.t. for 18 hours. The mixture was concentrated in vacuo. The residue was dissolved in DMF (0.8 mL). 1M aq. NaOH (1 mL) was added. The mixture was stirred at r.t. for 3 hours. The solution was carefully neutralized with formic acid (0.5 mL), and purified by prep. HPLC (column: Atlantis, 30×75 mm, 10 um, UV/MS, acidic conditions) and concentrated in vacuo to give the desired acid.

Listed in Table 16 below are examples of compounds of Formula (I), prepared according to the above-mentioned method with the corresponding acid as starting material.

TABLE 15

| Example | Compound of Formula (I) | Formula MW | $t_R$ [min] LC-MS Method | MS-data m/z [M + H]+ |
|---|---|---|---|---|
| 175 | 8-(3-Carboxymethoxy-phenyl)-5-fluoro-3,4-dihydro-1H-isoquinoline-2-carboxylic acid benzyl ester | C25H22NO5F 435.15 | 1.09 LC-MS 1FA | 436.2 |
| 176 | 8-(5-Carboxymethoxy-2-chloro-phenyl)-5-fluoro-3,4-dihydro-1H-isoquinoline-2-carboxylic acid benzyl ester | C25H21NO5ClF 469.11 | 1.13 LC-MS 1FA | 470.2 |
| 177 | 8-(5-Carboxymethoxy-2-methoxy-phenyl)-5-fluoro-3,4-dihydro-1H-isoquinoline-2-carboxylic acid benzyl ester | C26H24NO6F 465.16 | 1.05 LC-MS 1FA | 466.2 |
| 178 | 8-(5-Carboxymethoxy-2-chloro-phenyl)-5-chloro-3,4-dihydro-1H-isoquinoline-2-carboxylic acid benzyl ester | C25H21NO5Cl2 485.08 | 1.19 LC-MS 1FA | 486.0 |
| 179 | 8-(5-Carboxymethoxy-2-chloro-phenyl)-5-methyl-3,4-dihydro-1H-isoquinoline-2-carboxylic acid benzyl ester | C26H24NO5Cl 465.13 | 1.14 LC-MS 1FA | 466.1 |
| 180 | 8-(5-Carboxymethoxy-2-chloro-phenyl)-5-trifluoromethyl-3,4-dihydro-1H-isoquinoline-2-carboxylic acid benzyl ester | C26H21NO5ClF3 519.11 | 1.20 LC-MS 1FA | 520.2 |
| 181 | 8-(5-Carboxymethoxy-2-chloro-phenyl)-3,4-dihydro-1H-isoquinoline-2-carboxylic acid benzyl ester | C25H22NO5Cl 451.12 | 1.09 LC-MS 1FA | 452.2 |
| 182 | {3-[5-Fluoro-2-((1R,2R)-2-phenyl-cyclopropanecarbonyl)-1,2,3,4-tetrahydro-isoquinolin-8-yl]-4-methoxy-phenoxy}-acetic acid | C28H26NO5F 475.18 | 1.02 LC-MS 1FA | 476.3 |

TABLE 16

| Example | Compound of Formula (I) | Formula MW | $t_R$ [min] LC-MS Method | MS-data m/z $[M + H]^+$ |
|---|---|---|---|---|
| 183 | (4-{5-Fluoro-2-[3-(1-methyl-1H-indol-3-yl)-propionyl]-1,2,3,4-tetrahydro-isoquinolin-8-yl}-3-methoxy-phenyl)-acetic acid | C30H29N2O4F 500.21 | 1.06 LC-MS 1FA | 501.3 |
| 184 | {4-[5-Fluoro-2-((1R,2R)-2-phenyl-cyclopropanecarbonyl)-1,2,3,4-tetrahydro-isoquinolin-8-yl]-3-methoxy-phenyl}-acetic acid | C28H26NO4F 459.19 | 1.06 LC-MS 1FA | 460.2 |
| 185 | (4-{5-Fluoro-2-[4-(2-fluoro-phenyl)-butyryl]-1,2,3,4-tetrahydro-isoquinolin-8-yl}-3-methoxy-phenyl)-acetic acid | C28H27NO4F2 479.19 | 1.08 LC-MS 1FA | 480.2 |
| 186 | (4-{5-Fluoro-2-[3-(2-methyl-1H-indol-3-yl)-propionyl]-1,2,3,4-tetrahydro-isoquinolin-8-yl}-3-methoxy-phenyl)-acetic acid | C30H29N2O4F 500.21 | 1.00 LC-MS 1FA | 501.3 |
| 187 | {4-[5-Fluoro-2-(4-phenyl-butyryl)-1,2,3,4-tetrahydro-isoquinolin-8-yl]-3-methoxy-phenyl}-acetic acid | C28H28NO4F 461.20 | 1.07 LC-MS 1FA | 462.3 |
| 188 | {4-[5-Fluoro-2-(3-methyl-3-phenyl-butyryl)-1,2,3,4-tetrahydro-isoquinolin-8-yl]-3-methoxy-phenyl}-acetic acid | C29H30NO4F 475.22 | 1.09 LC-MS 1FA | 476.3 |
| 189 | {4-[5-Fluoro-2-((R)-3-phenyl-butyryl)-1,2,3,4-tetrahydro-isoquinolin-8-yl]-3-methoxy-phenyl}-acetic acid | C28H28NO4F 461.20 | 1.05 LC-MS 1FA | 462.3 |
| 190 | (4-{5-Fluoro-2-[3-(5-fluoro-indazol-1-yl)-propionyl]-1,2,3,4-tetrahydro-isoquinolin-8-yl}-3-methoxy-phenyl)-acetic acid | C28H25N3O4F2 505.18 | 0.99 LC-MS 1FA | 506.2 |
| 191 | {4-[2-(3-2,3-Dihydro-indol-1-yl-propionyl)-5-fluoro-1,2,3,4-tetrahydro-isoquinolin-8-yl]-3-methoxy-phenyl}-acetic acid | C29H29N2O4F 488.21 | 1.04 LC-MS 1FA | 489.3 |
| 192 | (4-{5-Fluoro-2-[3-(4-fluoro-phenoxy)-propionyl]-1,2,3,4-tetrahydro-isoquinolin-8-yl}-3-methoxy-phenyl)-acetic acid | C27H25NO5F2 481.17 | 1.03 LC-MS 1FA | 482.2 |
| 193 | (4-{2-[2-(2-Chloro-benzyloxy)-acetyl]-5-fluoro-1,2,3,4-tetrahydro-isoquinolin-8-yl}-3-methoxy-phenyl)-acetic acid | C27H25NO5ClF 497.14 | 1.05 LC-MS 1FA | 498.2 |
| 194 | {4-[5-Fluoro-2-(3-o-tolyl-propionyl)-1,2,3,4-tetrahydro-isoquinolin-8-yl]-3-methoxy-phenyl}-acetic acid | C28H28NO4F 461.20 | 1.06 LC-MS 1FA | 462.3 |

Suzuki Cross-coupling and Subsequent Saponification

To a mixture under $N_2$ of 5-fluoro-8-(4,4,5,5-tetramethyl-[1,3,2]dioxaborolan-2-yl)-3,4-dihydro-1H-isoquinoline-2-carboxylic acid benzyl ester (97 mg, 0.20 mmol, 1.00 eq.), (3-bromo-4-ethoxy-phenyl)-acetic acid ethyl ester (57 mg, 0.20 mmol, 1.00 eq.) and sodium carbonate (106 mg, 1.00 mmol, 5.00 eq.) in toluene/EtOH/Water 20:4:1 (3 mL), tetrakis(triphenylphosphine) palladium (0) (11.6 mg, 0.01 mmol, 0.05 eq.) was added and the mixture was stirred at 100° C. for 18 hours. The mixture was allowed to cool to r.t., filtered over celite, and concentrated in vacuo. The residue, redissolved in MeCN/H$_2$O 1:1 (2 mL) and formic acid (0.2 mL), was purified by prep. HPLC (column: Waters Xbridge, 30×75 mm, 10 um, UV/MS, acidic conditions) and concentrated in vacuo. The residue was redissolved in DMF (1 mL) and 2M aq. NaOH (0.4 ml) was added. The resulting mixture was stirred at r.t. for 18 hours. Formic acid (0.2 mL) was added. The crude mixture was purified by prep. HPLC (column: Waters Xbridge, 30×75 mm, 10 um, UV/MS, acidic conditions) and concentrated in vacuo to yield the desired acid.

Listed in Table 17 below are examples of compounds of Formula (I), prepared according to the above-mentioned method with the corresponding compound 9 as starting material.

TABLE 17

| Example | Compound of Formula (I) | Formula MW | $t_R$ [min] LC-MS Method | MS-data m/z $[M + H]^+$ |
|---|---|---|---|---|
| 195 | 8-(5-Carboxymethyl-2-ethoxy-phenyl)-5-fluoro-3,4-dihydro-1H-isoquinoline-2-carboxylic acid benzyl ester | C27H26NO5F 463.18 | 1.12 LC-MS 1FA | 464.3 |

TABLE 17-continued

| Example | Compound of Formula (I) | Formula MW | $t_R$ [min] LC-MS Method | MS-data m/z $[M + H]^+$ |
|---|---|---|---|---|
| 196 | 8-(5-Carboxymethyl-2-cyclopropylmethoxy-phenyl)-5-fluoro-3,4-dihydro-1H-isoquinoline-2-carboxylic acid benzyl ester | C29H28NO5F 489.20 | 1.16 LC-MS 1FA | 490.2 |
| 197 | 8-(5-Carboxymethyl-2-propoxy-phenyl)-5-fluoro-3,4-dihydro-1H-isoquinoline-2-carboxylic acid benzyl ester | C28H28NO5F 477.20 | 1.18 LC-MS 1FA | 478.3 |
| 198 | 8-(5-Carboxymethyl-2-isobutoxy-phenyl)-5-fluoro-3,4-dihydro-1H-isoquinoline-2-carboxylic acid benzyl ester | C29H30NO5F 491.21 | 1.24 LC-MS 1FA | 492.3 |
| 199 | 8-[5-Carboxymethyl-2-(2-methoxy-ethoxy)-phenyl]-5-fluoro-3,4-dihydro-1H-isoquinoline-2-carboxylic acid benzyl ester | C28H28NO6F 493.19 | 1.06 LC-MS 1FA | 494.3 |

Saponification

Method A: To a solution of {4-[2-(2-Chroman-4-yl-acetyl)-5-fluoro-1,2,3,4-tetrahydro-isoquinolin-8-yl]-3-methoxy-phenyl}-acetic acid ethyl ester (enantiomer 1) (73 mg, 0.14 mmol, 1 eq.) in DMF (0.5 mL), 2M aq. NaOH soln. (0.5 mL) was added. The mixture was stirred at r.t. for 18 hours. The solution was neutralized with formic acid (0.3 mL) and then purified by prep. HPLC (column: Atlantis, 18×50 mm, 10 um, UV/MS, acidic conditions) and concentrated in vacuo to give the desired acid as a white solid.

Listed in Table 18 below are examples of compounds of Formula (I), prepared according to the above-mentioned method with the corresponding compound of Structure 1 as starting material.

TABLE 18

| Example | Compound of Formula (I) | Starting ester of Structure 1 | Formula MW LC-MS Method $t_R$ [min] | $t_R$ [min] LC-MS Method MS-data m/z $[M + H]^+$ |
|---|---|---|---|---|
| 200 | {4-[2-(2-Chroman-4-yl-acetyl)-5-fluoro-1,2,3,4-tetrahydro-isoquinolin-8-yl]-3-methoxy-phenyl}-acetic acid (enantiomer 1) | {4-[2-(2-Chroman-4-yl-acetyl)-5-fluoro-1,2,3,4-tetrahydro-isoquinolin-8-yl]-3-methoxy-phenyl}-acetic acid ethyl ester (enantiomer 1) | C29H28NO5F 489.20 LC-MS 5 12.26 | 1.09 LC-MS 1FA 490.4 |
| 201 | {4-[2-(2-Chroman-4-yl-acetyl)-5-fluoro-1,2,3,4-tetrahydro-isoquinolin-8-yl]-3-methoxy-phenyl}-acetic acid (enantiomer 2) | {4-[2-(2-Chroman-4-yl-acetyl)-5-fluoro-1,2,3,4-tetrahydro-isoquinolin-8-yl]-3-methoxy-phenyl}-acetic acid ethyl ester (enantiomer 2) | C29H28NO5F 489.20 LC-MS 5 15.02 | 1.09 LC-MS 1FA 490.3 |
| 202 | 8-[4-(1-Carboxy-ethoxy)-2-methoxy-phenyl]-5-fluoro-3,4-dihydro-1H-isoquinoline-2-carboxylic acid benzyl ester (enantiomer 2) | 5-Fluoro-8-[2-methoxy-4-(1-methoxycarbonyl-ethoxy)-phenyl]-3,4-dihydro-1H-isoquinoline-2-carboxylic acid benzyl ester (enantiomer 2) | C27H26NO6F 479.17 LC-MS 6 7.59 | 1.19 LC-MS 1FA 480.4 |
| 203 | {4-Ethoxy-3-[5-fluoro-2-(3-pyridin-2-yl-butyryl)-1,2,3,4-tetrahydro-isoquinolin-8-yl]-phenyl}-acetic acid (enantiomer 1) | {4-Ethoxy-3-[5-fluoro-2-(3-pyridin-2-yl-butyryl)-1,2,3,4-tetrahydro-isoquinolin-8-yl]-phenyl}-acetic acid ethyl ester (enantiomer 1) | C28H29N2O4F 476.21 LC-MS 7 11.68 | 0.82 LC-MS 1FA 477.4 |
| 204 | {4-Ethoxy-3-[5-fluoro-2-(3-pyridin-2-yl-butyryl)-1,2,3,4-tetrahydro-isoquinolin-8-yl]-phenyl}-acetic acid (enantiomer 2) | {4-Ethoxy-3-[5-fluoro-2-(3-pyridin-2-yl-butyryl)-1,2,3,4-tetrahydro-isoquinolin-8-yl]-phenyl}-acetic acid ethyl ester (enantiomer 2) | C28H29N2O4F 476.21 LC-MS 7 14.51 | 0.82 LC-MS 1FA 477.4 |

TABLE 18-continued

| Example | Compound of Formula (I) | Starting ester of Structure 1 | Formula MW LC-MS Method $t_R$ [min] | $t_R$ [min] LC-MS Method MS-data m/z [M + H]$^+$ |
|---|---|---|---|---|
| 205 | {3-Ethoxy-4-[5-fluoro-2-(2-isochroman-1-yl-acetyl)-1,2,3,4-tetrahydro-isoquinolin-8-yl]-phenyl}-acetic acid (enantiomer 1) | {3-Ethoxy-4-[5-fluoro-2-(2-isochroman-1-yl-acetyl)-1,2,3,4-tetrahydro-isoquinolin-8-yl]-phenyl}-acetic acid ethyl ester (enantiomer 1) | C30H30NO5F 503.21 LC-MS 8 11.99 | 1.13 LC-MS 1FA 504.4 |
| 206 | {3-Ethoxy-4-[5-fluoro-2-(2-isochroman-1-yl-acetyl)-1,2,3,4-tetrahydro-isoquinolin-8-yl]-phenyl}-acetic acid (enantiomer 2) | {3-Ethoxy-4-[5-fluoro-2-(2-isochroman-1-yl-acetyl)-1,2,3,4-tetrahydro-isoquinolin-8-yl]-phenyl}-acetic acid ethyl ester (enantiomer 2) | C30H30NO5F 503.21 LC-MS 8 14.04 | 1.13 LC-MS 1FA 504.4 |
| 207 | {3-[2-(2-2,3-Dihydro-benzofuran-3-yl-acetyl)-5-fluoro-1,2,3,4-tetrahydro-isoquinolin-8-yl]-4-ethoxy-phenyl}-acetic acid (enantiomer 1) | {3-[2-(2-2,3-Dihydro-benzofuran-3-yl-acetyl)-5-fluoro-1,2,3,4-tetrahydro-isoquinolin-8-yl]-4-ethoxy-phenyl}-acetic acid ethyl ester (enantiomer 1) | C29H28NO5F 489.20 LC-MS 9 10.37 | 1.13 LC-MS 1FA 490.4 |
| 208 | {3-[2-(2-2,3-Dihydro-benzofuran-3-yl-acetyl)-5-fluoro-1,2,3,4-tetrahydro-isoquinolin-8-yl]-4-ethoxy-phenyl}-acetic acid (enantiomer 2) | {3-[2-(2-2,3-Dihydro-benzofuran-3-yl-acetyl)-5-fluoro-1,2,3,4-tetrahydro-isoquinolin-8-yl]-4-ethoxy-phenyl}-acetic acid ethyl ester (enantiomer 2) | C29H28NO5F 489.20 LC-MS 9 16.38 | 1.13 LC-MS 1FA 490.4 |
| 209 | {4-Ethoxy-3-[5-fluoro-2-(2-isochroman-4-yl-acetyl)-1,2,3,4-tetrahydro-isoquinolin-8-yl]-phenyl}-acetic acid (enantiomer 1) | {4-Ethoxy-3-[5-fluoro-2-(2-isochroman-4-yl-acetyl)-1,2,3,4-tetrahydro-isoquinolin-8-yl]-phenyl}-acetic acid ethyl ester (enantiomer 1) | C30H30NO5F 503.21 LC-MS 10 10.74 | 1.10 LC-MS 1FA 504.4 |
| 210 | {4-Ethoxy-3-[5-fluoro-2-(2-isochroman-4-yl-acetyl)-1,2,3,4-tetrahydro-isoquinolin-8-yl]-phenyl}-acetic acid (enantiomer 2) | {4-Ethoxy-3-[5-fluoro-2-(2-isochroman-4-yl-acetyl)-1,2,3,4-tetrahydro-isoquinolin-8-yl]-phenyl}-acetic acid ethyl ester (enantiomer 2) | C30H30NO5F 503.21 LC-MS 10 16.09 | 1.10 LC-MS 1FA 504.4 |
| 211 | (4-Ethoxy-3-{5-fluoro-2-[3-(4-fluoro-phenyl)-butyryl]-1,2,3,4-tetrahydro-isoquinolin-8-yl}-phenyl)-acetic acid (enantiomer 1) | (4-Ethoxy-3-{5-fluoro-2-[3-(4-fluoro-phenyl)-butyryl]-1,2,3,4-tetrahydro-isoquinolin-8-yl}-phenyl)-acetic acid ethyl ester (enantiomer 1) | C29H29NO4F2 493.21 LC-MS 11 25.22 | 1.17 LC-MS 1FA 494.3 |
| 212 | (4-Ethoxy-3-{5-fluoro-2-[3-(4-fluoro-phenyl)-butyryl]-1,2,3,4-tetrahydro-isoquinolin-8-yl}-phenyl)-acetic acid (enantiomer 2) | (4-Ethoxy-3-{5-fluoro-2-[3-(4-fluoro-phenyl)-butyryl]-1,2,3,4-tetrahydro-isoquinolin-8-yl}-phenyl)-acetic acid ethyl ester (enantiomer 2) | C29H29NO4F2 493.21 LC-MS 11 27.93 | 1.17 LC-MS 1FA 494.3 |
| 213 | {4-Ethoxy-3-[5-fluoro-2-(2-methyl-3-phenyl-propionyl)-1,2,3,4-tetrahydro-isoquinolin-8-yl]-phenyl}-acetic acid (enantiomer 1) | {4-Ethoxy-3-[5-fluoro-2-(2-methyl-3-phenyl-propionyl)-1,2,3,4-tetrahydro-isoquinolin-8-yl]-phenyl}-acetic acid ethyl ester (enantiomer 1) | C29H30NO4F 475.22 LC-MS 12 27.19 | 1.17 LC-MS 1FA 476.4 |
| 214 | {4-Ethoxy-3-[5-fluoro-2-(2-methyl-3-phenyl-propionyl)-1,2,3,4-tetrahydro-isoquinolin-8-yl]-phenyl}-acetic acid (enantiomer 2) | {4-Ethoxy-3-[5-fluoro-2-(2-methyl-3-phenyl-propionyl)-1,2,3,4-tetrahydro-isoquinolin-8-yl]-phenyl}-acetic acid ethyl ester (enantiomer 2) | C29H30NO4F 475.22 LC-MS 12 31.51 | 1.17 LC-MS 1FA 476.3 |

Method B: TFA (0.49 mL) was slowly added to an ice-cooled solution of 8-(5-tert-butoxycarbonylmethyl-2-propyl-phenyl)-5-fluoro-3,4-dihydro-1H-isoquinoline-2-carboxylic acid benzyl ester (110 mg, 0.21 mmol, 1 eq.) in DCM (0.55 mL). The reaction mixture was stirred at r.t. for 30 min. The mixture was concentrated in vacuo without heating and the residue was redissolved in MeCN (0.8 mL). The crude mixture was purified by prep. HPLC (column: Waters XBridge, 30×75 mm, 10 um, UV/MS, acidic conditions) and evaporated to give the desired acid as a pale yellow oil.

Listed in Table 19 below are examples of compounds of Formula (I), prepared according to the above-mentioned method with the corresponding compound of Structure 1 as starting material.

TABLE 19

| Example | Compound of Formula (I) | Formula MW | $t_R$ [min] LC-MS Method | MS-data m/z $[M + H]^+$ |
|---|---|---|---|---|
| 215 | 8-(5-Carboxymethyl-2-propyl-phenyl)-5-fluoro-3,4-dihydro-1H-isoquinoline-2-carboxylic acid benzyl ester | C28H28NO4F 461.20 | 1.31 LC-MS 1FA | 462.4 |
| 216 | 8-(4-Carboxymethyl-2-isopropyl-phenyl)-5-fluoro-3,4-dihydro-1H-isoquinoline-2-carboxylic acid benzyl ester | C28H28NO4F 461.20 | 1.29 LC-MS 1FA | 462.3 |
| 217 | 8-(4-Carboxymethyl-2-isopropoxy-phenyl)-5-fluoro-3,4-dihydro-1H-isoquinoline-2-carboxylic acid benzyl ester | C28H28NO5F 477.20 | 1.24 LC-MS 1FA | 478.4 |

EXAMPLE 218

8-(4-Carboxymethyl-2,6-dimethoxy-phenyl)-5-fluoro-3,4-dihydro-1H-isoquinoline-2-carboxylic acid benzyl ester (C27H26NO6F, MW=479.17)

To a solution of 8-(4-ethoxycarbonylmethyl-2,6-dimethoxy-phenyl)-5-fluoro-3,4-dihydro-1H-isoquinoline-2-carboxylic acid benzyl ester (9.5 mg, 0.02 mmol, 1 eq.) in DMF (0.1 mL), 2M aq. NaOH soln. (68 µL) was added. The solution was stirred at r.t. for 18 hours. Formic acid was added (0.1 mL). The resulting acidic solution was purified by prep. HPLC (column: Waters XBridge, 19×30 mm, 10 um, UV/MS, acidic conditions) and evaporated to give the desired acid as a white solid.

LC-MS 1TFA: $t_R$=1.13 min; $[M+H]^+$=480.3

Amide Coupling and Subsequent Saponification

Method A: To a solution of (±)-indan-1-yl-acetic acid (22 mg, 0.12 mmol, 1.2 eq.) in DCM/DMF 1:1 (1.00 mL), TBTU (39 mg, 0.12 mmol, 1.2 eq.) and Si-DEA (238 mg, 0.30 mmol, 3.0 eq.) were added in sequence. The mixture was stirred at r.t. for 1 hour. A solution of [4-ethoxy-3-(5-fluoro-1,2,3,4-tetrahydro-isoquinolin-8-yl)-phenyl]-acetic acid ethyl ester (36 mg, 0.10 mmol, 1.0 eq.) in DMF (0.25 mL) was added and the resulting mixture was stirred at r.t. for 1 hour. The mixture was filtered, the solid rinsed with DCM (3 mL), and the filtrate was concentrated in vacuo. To a solution of the residue in THF (0.5 mL), 1M aq. NaOH (1.0 mL) was added. The mixture was stirred at r.t. for 4 hours. The reaction mixture was concentrated in vacuo and the residue was purified by prep. HPLC (column: Waters X-Bridge, 30×75 mm, 10 um, UV/MS, acidic conditions) and evaporated to give the desired acid as a white solid.

Listed in Table 20 below are examples of compounds of Formula (I), prepared according to the above-mentioned method with the corresponding compound of Structure 2 and the corresponding acid as starting materials.

TABLE 20

| Example | Compound of Formula (I) | Formula MW | $t_R$ [min] LC-MS Method | MS-data m/z $[M + H]^+$ |
|---|---|---|---|---|
| 219 | (±)-{4-Ethoxy-3-[5-fluoro-2-(2-indan-1-yl-acetyl)-1,2,3,4-tetrahydro-isoquinolin-8-yl]-phenyl}-acetic acid | C30H30NO4F 487.22 | 1.19 LC-MS 1FA | 488.4 |

TABLE 20-continued

| Example | Compound of Formula (I) | Formula MW | $t_R$ [min] LC-MS Method | MS-data m/z [M + H]+ |
|---|---|---|---|---|
| 220 | {4-Ethoxy-3-[5-fluoro-2-((1R,2R)-2-phenyl-cyclopropanecarbonyl)-1,2,3,4-tetrahydro-isoquinolin-8-yl]-phenyl}-acetic acid | C29H28NO4F 473.20 | 1.16 LC-MS 1FA | 474.4 |
| 221 | {4-Ethoxy-3-[5-fluoro-2-((R)-3-phenyl-butyryl)-1,2,3,4-tetrahydro-isoquinolin-8-yl]-phenyl}-acetic acid | C29H30NO4F 475.22 | 1.16 LC-MS 1FA | 476.4 |
| 222 | (4-Ethoxy-3-{5-fluoro-2-[2-(1-phenyl-cyclopropyl)-acetyl]-1,2,3,4-tetrahydro-isoquinolin-8-yl}-phenyl)-acetic acid | C30H30NO4F 487.22 | 1.16 LC-MS 1FA | 488.4 |
| 223 | (4-Ethoxy-3-{5-fluoro-2-[3-(4-fluoro-phenyl)-3-methyl-butyryl]-1,2,3,4-tetrahydro-isoquinolin-8-yl}-phenyl)-acetic acid | C30H31NO4F2 507.22 | 1.19 LC-MS 1FA | 508.4 |
| 224 | (±)-{4-Ethoxy-3-[5-fluoro-2-(2-isochroman-1-yl-acetyl)-1,2,3,4-tetrahydro-isoquinolin-8-yl]-phenyl}-acetic acid | C30H30NO5F 503.21 | 1.12 LC-MS 1FA | 504.4 |
| 225 | {4-Ethoxy-3-[5-fluoro-2-(3-methyl-3-phenyl-butyryl)-1,2,3,4-tetrahydro-isoquinolin-8-yl]-phenyl}-acetic acid | C30H32NO4F 489.23 | 1.19 LC-MS 1FA | 490.4 |
| 226 | (±)-{3-[2-(2-Chroman-4-yl-acetyl)-5-fluoro-1,2,3,4-tetrahydro-isoquinolin-8-yl]-4-ethoxy-phenyl}-acetic acid | C30H30NO5F 503.21 | 1.13 LC-MS 1FA | 504.4 |
| 227 | (±)-{3-[2-(2-2,3-Dihydro-benzofuran-3-yl-acetyl)-5-fluoro-1,2,3,4-tetrahydro-isoquinolin-8-yl]-4-ethoxy-phenyl}-acetic acid | C29H28NO5F 489.20 | 1.13 LC-MS 1FA | 490.4 |
| 228 | (±)-{4-Ethoxy-3-[5-fluoro-2-(2-isochroman-4-yl-acetyl)-1,2,3,4-tetrahydro-isoquinolin-8-yl]-phenyl}-acetic acid | C30H30NO5F 503.21 | 1.29 LC-MS 13 | 504.3 |
| 229 | (±)-{3-Ethoxy-4-[5-fluoro-2-(2-isochroman-1-yl-acetyl)-1,2,3,4-tetrahydro-isoquinolin-8-yl]-phenyl}-acetic acid | C30H30NO5F 503.21 | 1.13 LC-MS 1FA | 504.4 |
| 230 | (3-Ethoxy-4-{5-fluoro-2-[2-(1-phenyl-cyclopropyl)-acetyl]-1,2,3,4-tetrahydro-isoquinolin-8-yl}-phenyl)-acetic acid | C30H30NO4F 487.22 | 1.18 LC-MS 1FA | 488.4 |
| 231 | {3-Ethoxy-4-[5-fluoro-2-((1R,2R)-2-phenyl-cyclopropanecarbonyl)-1,2,3,4-tetrahydro-isoquinolin-8-yl]-phenyl}-acetic acid | C29H28NO4F 473.20 | 1.17 LC-MS 1FA | 474.4 |
| 232 | (±)-{3-Ethoxy-4-[5-fluoro-2-(2-isochroman-4-yl-acetyl)-1,2,3,4-tetrahydro-isoquinolin-8-yl]-phenyl}-acetic acid | C30H30NO5F 503.21 | 1.11 LC-MS 1FA | 504.4 |
| 233 | (±)-{3-Ethoxy-4-[5-fluoro-2-(2-indan-1-yl-acetyl)-1,2,3,4-tetrahydro-isoquinolin-8-yl]-phenyl}-acetic acid | C30H30NO4F 487.22 | 1.20 LC-MS 1FA | 488.4 |
| 234 | {3-Ethoxy-4-[5-fluoro-2-((R)-3-phenyl-butyryl)-1,2,3,4-tetrahydro-isoquinolin-8-yl]-phenyl}-acetic acid | C29H30NO4F 475.22 | 1.17 LC-MS 1FA | 476.4 |
| 235 | (±)-{4-[2-(2-2,3-Dihydro-benzofuran-3-yl-acetyl)-5-fluoro-1,2,3,4-tetrahydro-isoquinolin-8-yl]-3-ethoxy-phenyl}-acetic acid | C29H28NO5F 489.20 | 1.14 LC-MS 1FA | 490.4 |
| 236 | (±)-{4-[2-(2-Chroman-4-yl-acetyl)-5-fluoro-1,2,3,4-tetrahydro-isoquinolin-8-yl]-3-ethoxy-phenyl}-acetic acid | C30H30NO5F 503.21 | 1.14 LC-MS 1FA | 504.3 |
| 237 | (3-Ethoxy-4-{5-fluoro-2-[3-(4-fluoro-phenyl)-3-methyl-butyryl]-1,2,3,4-tetrahydro-isoquinolin-8-yl}-phenyl)-acetic acid | C30H31NO4F2 507.22 | 1.20 LC-MS 1FA | 508.4 |

TABLE 20-continued

| Example | Compound of Formula (I) | Formula MW | $t_R$ [min] LC-MS Method | MS-data m/z [M + H]$^+$ |
|---|---|---|---|---|
| 238 | {3-Ethoxy-4-[5-fluoro-2-(3-methyl-3-phenyl-butyryl)-1,2,3,4-tetrahydro-isoquinolin-8-yl]-phenyl}-acetic acid | C30H32NO4F 489.23 | 1.21 LC-MS 1FA | 490.4 |

Method B: A solution of (±)-(1-methyl-1,2,3,4-tetrahydro-naphthalen-1-yl)-acetic acid (22 mg, 0.12 mmol, 1.2 eq.) and [3-(5-fluoro-1,2,3,4-tetrahydro-isoquinolin-8-yl)-4-methoxy-phenyl]-acetic acid ethyl ester (34 mg, 0.10 mmol, 1.0 eq.) in DMF (1.2 mL) was treated with 4-(dimethylamino) pyridine (37 mg, 0.30 mmol, 3.0 eq) and N-(3-dimethylaminopropyl)-N'-ethylcarbodiimide hydrochloride (29 mg, 0.15 mmol, 1.5 eq) and the resulting solution was stirred at r.t. for 18 hours. 1M aq. NaOH soln. (1.0 mL) was added. The solution was stirred at r.t. during 2 hours. Formic acid (0.2 mL) was added. The crude mixture was purified by prep. HPLC (column: Waters XBridge, 30×75 mm, 10 um, UV/MS, acidic conditions) and concentrated in vacuo to give the desired acid as a white foam.

Listed in Table 21 below are examples of compounds of Formula (I), prepared according to the above-mentioned method with the corresponding compound of Structure 2 and the corresponding acid as starting materials.

TABLE 21

| Example | Compound of Formula (I) | Formula MW | $t_R$ [min] LC-MS Method | MS-data m/z [M + H]$^+$ |
|---|---|---|---|---|
| 239 | (±)-(3-{5-Fluoro-2-[2-(1-methyl-1,2,3,4-tetrahydro-naphthalen-1-yl)-acetyl]-1,2,3,4-tetrahydro-isoquinolin-8-yl}-4-methoxy-phenyl)-acetic acid | C31H32NO4F 501.23 | 1.18 LC-MS 1FA | 502.4 |
| 240 | (±)-(3-{2-[2-(2,2-Dimethyl-chroman-4-yl)-acetyl]-5-fluoro-1,2,3,4-tetrahydro-isoquinolin-8-yl}-4-methoxy-phenyl)-acetic acid | C31H32NO5F 517.23 | 1.16 LC-MS 1FA | 518.4 |
| 241 | (±)-{3-[5-Fluoro-2-(8-methoxy-1,2,3,4-tetrahydro-naphthalene-2-carbonyl)-1,2,3,4-tetrahydro-isoquinolin-8-yl]-4-methoxy-phenyl}-acetic acid | C30H30NO5F 503.21 | 1.14 LC-MS 1FA | 504.4 |
| 242 | (±)-{3-[2-(2-Chroman-3-yl-acetyl)-5-fluoro-1,2,3,4-tetrahydro-isoquinolin-8-yl]-4-methoxy-phenyl}-acetic acid | C29H28NO5F 489.20 | 1.10 LC-MS 1FA | 490.3 |
| 243 | (±)-(3-{5-Fluoro-2-[2-(7-fluoro-chroman-4-yl)-acetyl]-1,2,3,4-tetrahydro-isoquinolin-8-yl}-4-methoxy-phenyl)-acetic acid | C29H27NO5F2 507.19 | 1.10 LC-MS 1FA | 508.4 |
| 244 | (±)-(3-{5-Fluoro-2-[2-(6-fluoro-chroman-4-yl)-acetyl]-1,2,3,4-tetrahydro-isoquinolin-8-yl}-4-methoxy-phenyl)-acetic acid | C29H27NO5F2 507.19 | 1.09 LC-MS 1FA | 508.3 |
| 245 | (±)-{3-[2-(3-Cyclopropyl-butyryl)-5-fluoro-1,2,3,4-tetrahydro-isoquinolin-8-yl]-4-methoxy-phenyl}-acetic acid | C25H28NO4F 425.20 | 1.06 LC-MS 1FA | 426.4 |
| 246 | (±)-(3-{5-Fluoro-2-[2-(8-fluoro-chroman-4-yl)-acetyl]-1,2,3,4-tetrahydro-isoquinolin-8-yl}-4-methoxy-phenyl)-acetic acid | C29H27NO5F2 507.19 | 1.08 LC-MS 1FA | 508.3 |
| 247 | (±)-{3-[5-Fluoro-2-(2-5,6,7,8-tetrahydro-isoquinolin-8-yl-acetyl)-1,2,3,4-tetrahydro-isoquinolin-8-yl]-4-methoxy-phenyl}-acetic acid hydrochloride | C29H29N2O4F 488.21 | 0.74 LC-MS 1FA | 489.4 |
| 248 | (±)-(3-{5-Fluoro-2-[3-(6-methoxy-pyridin-2-yl)-butyryl]-1,2,3,4-tetrahydro-isoquinolin-8-yl}-4-methoxy-phenyl)-acetic acid hydrochloride | C28H29N2O5F 492.21 | 1.08 LC-MS 1FA | 493.4 |
| 249 | (±)-(3-{5-Fluoro-2-[3-(6-methyl-pyridin-2-yl)-butyryl]-1,2,3,4-tetrahydro-isoquinolin-8-yl}-4-methoxy-phenyl)-acetic acid hydrochloride | C28H29N2O4F 476.21 | 0.74 LC-MS 1FA | 477.4 |

TABLE 21-continued

| Example | Compound of Formula (I) | Formula MW | $t_R$ [min] LC-MS Method | MS-data m/z [M + H]+ |
|---|---|---|---|---|
| 250 | (3-{5-Fluoro-2-[2-(1-phenyl-cyclobutyl)-acetyl]-1,2,3,4-tetrahydro-isoquinolin-8-yl}-4-methoxy-phenyl)-acetic acid | C30H30NO4F 487.22 | 1.16 LC-MS 1FA | 488.4 |
| 251 | [3-(5-Fluoro-2-{2-[1-(4-fluoro-phenyl)-cyclobutyl]-acetyl}-1,2,3,4-tetrahydro-isoquinolin-8-yl)-4-methoxy-phenyl]-acetic acid | C30H29NO4F2 505.21 | 1.16 LC-MS 1FA | 506.4 |
| 252 | (3-{5-Fluoro-2-[3-(3-fluoro-phenyl)-3-methyl-butyryl]-1,2,3,4-tetrahydro-isoquinolin-8-yl}-4-methoxy-phenyl)-acetic acid | C29H29NO4F2 493.21 | 1.14 LC-MS 1FA | 494.4 |
| 253 | (±)-{3-[2-(2-{[(4-Chloro-phenyl)-phenyl-methyl]-methyl-amino}-acetyl)-5-fluoro-1,2,3,4-tetrahydro-isoquinolin-8-yl]-4-methoxy-phenyl}-acetic acid | C34H32N2O4ClF 586.20 | 1.00 LC-MS 1TFA | 587.3 |
| 254 | {3-[2-(2-Cyclopropyl-acetyl)-5-fluoro-1,2,3,4-tetrahydro-isoquinolin-8-yl]-4-methoxy-phenyl}-acetic acid | C23H24NO4F 397.17 | 0.97 LC-MS 1FA | 398.4 |
| 255 | {3-[5-Fluoro-2-((R)-2-phenyl-propionyl)-1,2,3,4-tetrahydro-isoquinolin-8-yl]-4-methoxy-phenyl}-acetic acid | C27H26NO4F 447.19 | 1.07 LC-MS 1FA | 448.4 |
| 256 | (±)-{3-[5-Fluoro-2-(3-hydroxy-3-phenyl-butyryl)-1,2,3,4-tetrahydro-isoquinolin-8-yl]-4-methoxy-phenyl}-acetic acid | C28H28NO5F 477.20 | 1.04 LC-MS 1FA | 478.4 |
| 257 | (±)-{3-[5-Fluoro-2-(2-isochroman-1-yl-acetyl)-1,2,3,4-tetrahydro-isoquinolin-8-yl]-4-methoxy-phenyl}-acetic acid | C29H28NO5F 489.20 | 1.06 LC-MS 1FA | 490.4 |
| 258 | (3-{5-Fluoro-2-[2-(1-phenyl-cyclopropyl)-acetyl]-1,2,3,4-tetrahydro-isoquinolin-8-yl}-4-methoxy-phenyl)-acetic acid | C29H28NO4F 473.20 | 1.11 LC-MS 1FA | 474.4 |
| 259 | (±)-(3-{5-Fluoro-2-[2-(2-methyl-1,2,3,4-tetrahydro-isoquinolin-1-yl)-acetyl]-1,2,3,4-tetrahydro-isoquinolin-8-yl}-4-methoxy-phenyl)-acetic acid | C30H31N2O4F 502.23 | 0.84 LC-MS 1TFA | 503.4 |
| 260 | (±)-{3-[5-Fluoro-2-(2-1,2,3,4-tetrahydro-naphthalen-2-yl-acetyl)-1,2,3,4-tetrahydro-isoquinolin-8-yl]-4-methoxy-phenyl}-acetic acid | C30H30NO4F 487.22 | 1.17 LC-MS 1FA | 488.4 |
| 261 | (±)-{3-[5-Fluoro-2-(2-indan-1-yl-acetyl)-1,2,3,4-tetrahydro-isoquinolin-8-yl]-4-methoxy-phenyl}-acetic acid | C29H28NO4F 473.20 | 1.13 LC-MS 1FA | 474.4 |
| 262 | (±)-{3-[2-(2-Chroman-4-yl-acetyl)-5-fluoro-1,2,3,4-tetrahydro-isoquinolin-8-yl]-4-methoxy-phenyl}-acetic acid | C29H28NO5F 489.20 | 1.07 LC-MS 1FA | 490.4 |
| 263 | (±)-{3-[5-Fluoro-2-(2-1,2,3,4-tetrahydro-naphthalen-1-yl-acetyl)-1,2,3,4-tetrahydro-isoquinolin-8-yl]-4-methoxy-phenyl}-acetic acid | C30H30NO4F 487.22 | 1.16 LC-MS 1FA | 488.4 |
| 264 | (±)-{3-[5-Fluoro-2-(4-methyl-3-phenyl-pentanoyl)-1,2,3,4-tetrahydro-isoquinolin-8-yl]-4-methoxy-phenyl}-acetic acid | C30H32NO4F 489.23 | 1.18 LC-MS 1FA | 490.4 |
| 265 | (±)-{3-[5-Fluoro-2-(3-pyridin-2-yl-butyryl)-1,2,3,4-tetrahydro-isoquinolin-8-yl]-4-methoxy-phenyl}-acetic acid | C27H27N2O4F 462.20 | 0.76 LC-MS 1FA | 463.4 |
| 266 | (±)-{3-[5-Fluoro-2-(3-pyridin-3-yl-butyryl)-1,2,3,4-tetrahydro-isoquinolin-8-yl]-4-methoxy-phenyl}-acetic acid formiate | C27H27N2O4F 462.20 | 0.73 LC-MS 1FA | 463.4 |
| 267 | (±)-{3-[5-Fluoro-2-(3-pyridin-4-yl-butyryl)-1,2,3,4-tetrahydro-isoquinolin-8-yl]-4-methoxy-phenyl}-acetic acid formiate | C27H27N2O4F 462.20 | 0.71 LC-MS 1FA | 463.4 |

TABLE 21-continued

| Example | Compound of Formula (I) | Formula MW | $t_R$ [min] LC-MS Method | MS-data m/z [M + H]+ |
|---|---|---|---|---|
| 268 | (±)-{3-[5-Fluoro-2-(3-phenyl-pentanoyl)-1,2,3,4-tetrahydro-isoquinolin-8-yl]-4-methoxy-phenyl}-acetic acid | C29H30NO4F 475.22 | 1.14 LC-MS 1FA | 476.4 |
| 269 | {3-[5-Fluoro-2-((R)-1,2,3,4-tetrahydro-naphthalene-1-carbonyl)-1,2,3,4-tetrahydro-isoquinolin-8-yl]-4-methoxy-phenyl}-acetic acid | C29H28NO4F 473.20 | 1.11 LC-MS 1FA | 474.4 |
| 270 | (±)-{3-[2-(2-2,3-Dihydro-benzofuran-3-yl-acetyl)-5-fluoro-1,2,3,4-tetrahydro-isoquinolin-8-yl]-4-methoxy-phenyl}-acetic acid | C28H26NO5F 475.18 | 1.07 LC-MS 1FA | 476.4 |
| 271 | (±)-{3-[5-Fluoro-2-(2-isochroman-4-yl-acetyl)-1,2,3,4-tetrahydro-isoquinolin-8-yl]-4-methoxy-phenyl}-acetic acid | C29H28NO5F 489.20 | 1.04 LC-MS 1FA | 490.4 |
| 272 | (±)-{3-[2-(Chroman-4-carbonyl)-5-fluoro-1,2,3,4-tetrahydro-isoquinolin-8-yl]-4-methoxy-phenyl}-acetic acid | C28H26NO5F 475.18 | 1.04 LC-MS 1FA | 476.4 |
| 273 | (±)-{3-[5-Fluoro-2-(isochroman-1-carbonyl)-1,2,3,4-tetrahydro-isoquinolin-8-yl]-4-methoxy-phenyl}-acetic acid | C28H26NO5F 475.18 | 1.04 LC-MS 1FA | 476.4 |
| 274 | (±)-{3-[5-Fluoro-2-(isochroman-3-carbonyl)-1,2,3,4-tetrahydro-isoquinolin-8-yl]-4-methoxy-phenyl}-acetic acid | C28H26NO5F 475.18 | 1.07 LC-MS 1FA | 476.4 |
| 275 | [4-Ethoxy-3-(5-fluoro-2-{2-[1-(3-fluoro-phenyl)-cyclopropyl]-acetyl}-1,2,3,4-tetrahydro-isoquinolin-8-yl)-phenyl]-acetic acid | C30H29NO4F2 505.21 | 1.17 LC-MS 1FA | 506.4 |
| 276 | [4-Ethoxy-3-(5-fluoro-2-{2-[1-(2-fluoro-phenyl)-cyclopropyl]-acetyl}-1,2,3,4-tetrahydro-isoquinolin-8-yl)-phenyl]-acetic acid | C30H29NO4F2 505.21 | 1.16 LC-MS 1FA | 506.4 |
| 277 | [4-Ethoxy-3-(5-fluoro-2-{2-[1-(4-fluoro-phenyl)-cyclopropyl]-acetyl}-1,2,3,4-tetrahydro-isoquinolin-8-yl)-phenyl]-acetic acid | C30H29NO4F2 505.21 | 1.16 LC-MS 1FA | 506.4 |
| 278 | (±)-(4-Ethoxy-3-{5-fluoro-2-[3-(4-fluoro-phenyl)-butyryl]-1,2,3,4-tetrahydro-isoquinolin-8-yl}-phenyl)-acetic acid | C29H29NO4F2 493.21 | 1.16 LC-MS 1FA | 494.4 |
| 279 | (±)-(4-Ethoxy-3-{5-fluoro-2-[3-(3-fluoro-phenyl)-butyryl]-1,2,3,4-tetrahydro-isoquinolin-8-yl}-phenyl)-acetic acid | C29H29NO4F2 493.21 | 1.16 LC-MS 1FA | 494.4 |
| 280 | (±)-(4-Ethoxy-3-{5-fluoro-2-[3-(2-fluoro-phenyl)-butyryl]-1,2,3,4-tetrahydro-isoquinolin-8-yl}-phenyl)-acetic acid | C29H29NO4F2 493.21 | 1.17 LC-MS 1FA | 494.4 |
| 281 | (±)-{4-Ethoxy-3-[5-fluoro-2-(3-pyrazin-2-yl-butyryl)-1,2,3,4-tetrahydro-isoquinolin-8-yl]-phenyl}-acetic acid | C27H28N3O4F 477.21 | 0.98 LC-MS 1FA | 478.4 |
| 282 | (±)-(4-Ethoxy-3-{5-fluoro-2-[3-(2-methoxy-phenyl)-butyryl]-1,2,3,4-tetrahydro-isoquinolin-8-yl}-phenyl)-acetic acid | C30H32NO5F 505.23 | 1.18 LC-MS 1FA | 506.4 |
| 283 | (±)-{4-Ethoxy-3-[5-fluoro-2-(3-thiazol-2-yl-butyryl)-1,2,3,4-tetrahydro-isoquinolin-8-yl]-phenyl}-acetic acid | C26H27N2O4FS 482.17 | 1.03 LC-MS 1FA | 483.3 |
| 284 | (±)-(3-{2-[2-(2,2-Dimethyl-3,4-dihydro-2H-pyrano[2,3-b]pyridin-4-yl)-acetyl]-5-fluoro-1,2,3,4-tetrahydro-isoquinolin-8-yl}-4-ethoxy-phenyl)-acetic acid | C31H33N2O5F 532.24 | 0.95 LC-MS 1FA | 533.4 |
| 285 | (±)-[4-[2-(2-Chroman-4-yl-acetyl)-5-fluoro-1,2,3,4-tetrahydro-isoquinolin-8-yl]-3-(2,2,2-trifluoro-ethoxy)-phenyl]-acetic acid | C30H27NO5F4 557.18 | 1.17 LC-MS 1FA | 558.3 |

TABLE 21-continued

| Example | Compound of Formula (I) | Formula MW | $t_R$ [min] LC-MS Method | MS-data m/z [M + H]+ |
|---|---|---|---|---|
| 286 | [4-[5-Fluoro-2-(3-methyl-3-phenyl-butyryl)-1,2,3,4-tetrahydro-isoquinolin-8-yl]-3-(2,2,2-trifluoro-ethoxy)-phenyl]-acetic acid | C30H29NO4F4 543.20 | 1.23 LC-MS 1FA | 544.4 |
| 287 | [4-[5-Fluoro-2-((S)-3-phenyl-butyryl)-1,2,3,4-tetrahydro-isoquinolin-8-yl]-3-(2,2,2-trifluoro-ethoxy)-phenyl]-acetic acid | C29H27NO4F4 529.19 | 1.19 LC-MS 1FA | 530.3 |
| 288 | (±)-[4-[5-Fluoro-2-(3-pyridin-2-yl-butyryl)-1,2,3,4-tetrahydro-isoquinolin-8-yl]-3-(2,2,2-trifluoro-ethoxy)-phenyl]-acetic acid | C28H26N2O4F4 530.18 | 0.86 LC-MS 1FA | 531.4 |
| 289 | [4-[5-Fluoro-2-((1R,2R)-2-phenyl-cyclopropanecarbonyl)-1,2,3,4-tetrahydro-isoquinolin-8-yl]-3-(2,2,2-trifluoro-ethoxy)-phenyl]-acetic acid | C29H25NO4F4 527.17 | 1.19 LC-MS 1FA | 528.3 |
| 290 | (±)-{3-[2-(2-Chroman-4-yl-acetyl)-5-fluoro-1,2,3,4-tetrahydro-isoquinolin-8-yl]-4-isopropoxy-phenyl}-acetic acid | C31H32NO5F 517.23 | 1.18 LC-MS 1FA | 518.4 |
| 291 | {3-[5-Fluoro-2-(3-methyl-3-phenyl-butyryl)-1,2,3,4-tetrahydro-isoquinolin-8-yl]-4-isopropoxy-phenyl}-acetic acid | C31H34NO4F 503.25 | 1.25 LC-MS 1FA | 504.4 |
| 292 | {3-[5-Fluoro-2-((R)-3-phenyl-butyryl)-1,2,3,4-tetrahydro-isoquinolin-8-yl]-4-isopropoxy-phenyl}-acetic acid | C30H32NO4F 489.23 | 1.21 LC-MS 1FA | 490.4 |
| 293 | (±)-{3-[5-Fluoro-2-(3-pyridin-2-yl-butyryl)-1,2,3,4-tetrahydro-isoquinolin-8-yl]-4-isopropoxy-phenyl}-acetic acid | C29H31N2O4F 490.23 | 0.88 LC-MS 1FA | 491.4 |
| 294 | (±)-(3-{5-Fluoro-2-[3-(6-methyl-pyridin-2-yl)-butyryl]-1,2,3,4-tetrahydro-isoquinolin-8-yl}-4-isopropoxy-phenyl)-acetic acid | C30H33N2O4F 504.24 | 0.83 LC-MS 1FA | 505.4 |
| 295 | (3-{5-Fluoro-2-[3-(6-methyl-pyridin-2-yl)-propionyl]-1,2,3,4-tetrahydro-isoquinolin-8-yl}-4-isopropoxy-phenyl)-acetic acid | C29H31N2O4F 490.23 | 0.81 LC-MS 1FA | 491.4 |
| 296 | (±)-{3-[5-Fluoro-2-(2-isochroman-4-yl-acetyl)-1,2,3,4-tetrahydro-isoquinolin-8-yl]-4-isopropoxy-phenyl}-acetic acid | C31H32NO5F 517.23 | 1.15 LC-MS 1FA | 518.4 |
| 297 | (±)-{3-[5-Fluoro-2-(2-isochroman-1-yl-acetyl)-1,2,3,4-tetrahydro-isoquinolin-8-yl]-4-isopropoxy-phenyl}-acetic acid | C31H32NO5F 517.23 | 1.17 LC-MS 1FA | 518.4 |
| 298 | (±)-{3-[2-(2-2,3-Dihydro-benzofuran-3-yl-acetyl)-5-fluoro-1,2,3,4-tetrahydro-isoquinolin-8-yl]-4-isopropoxy-phenyl}-acetic acid | C30H30NO5F 503.21 | 1.18 LC-MS 1FA | 504.4 |
| 299 | (±)-[3-[2-(2-Chroman-4-yl-acetyl)-5-fluoro-1,2,3,4-tetrahydro-isoquinolin-8-yl]-4-(2,2,2-trifluoro-ethoxy)-phenyl]-acetic acid | C30H27NO5F4 557.18 | 1.15 LC-MS 1FA | 558.4 |
| 300 | [3-[5-Fluoro-2-(3-methyl-3-phenyl-butyryl)-1,2,3,4-tetrahydro-isoquinolin-8-yl]-4-(2,2,2-trifluoro-ethoxy)-phenyl]-acetic acid | C30H29NO4F4 543.20 | 1.21 LC-MS 1FA | 544.4 |
| 301 | [3-[5-Fluoro-2-((R)-3-phenyl-butyryl)-1,2,3,4-tetrahydro-isoquinolin-8-yl]-4-(2,2,2-trifluoro-ethoxy)-phenyl]-acetic acid | C29H27NO4F4 529.19 | 1.17 LC-MS 1FA | 530.4 |
| 302 | (±)-[3-[5-Fluoro-2-(3-pyridin-2-yl-butyryl)-1,2,3,4-tetrahydro-isoquinolin-8-yl]-4-(2,2,2-trifluoro-ethoxy)-phenyl]-acetic acid | C28H26N2O4F4 530.18 | 0.86 LC-MS 1FA | 531.3 |
| 303 | (±)-[3-{5-Fluoro-2-[3-(6-methyl-pyridin-2-yl)-butyryl]-1,2,3,4-tetrahydro-isoquinolin-8-yl}-4-(2,2,2-trifluoro-ethoxy)-phenyl]-acetic acid | C29H28N2O4F4 544.20 | 0.82 LC-MS 1FA | 545.4 |
| 304 | [3-{5-Fluoro-2-[3-(6-methyl-pyridin-2-yl)-propionyl]-1,2,3,4-tetrahydro-isoquinolin-8-yl}-4-(2,2,2-trifluoro-ethoxy)-phenyl]-acetic acid | C28H26N2O4F4 530.18 | 0.79 LC-MS 1FA | 531.4 |

TABLE 21-continued

| Example | Compound of Formula (I) | Formula MW | $t_R$ [min] LC-MS Method | MS-data m/z [M + H]+ |
|---|---|---|---|---|
| 305 | (±)-[3-[5-Fluoro-2-(2-isochroman-4-yl-acetyl)-1,2,3,4-tetrahydro-isoquinolin-8-yl]-4-(2,2,2-trifluoro-ethoxy)-phenyl]-acetic acid | C30H27NO5F4 557.18 | 1.12 LC-MS 1FA | 558.3 |
| 306 | (±)-[3-[5-Fluoro-2-(2-isochroman-1-yl-acetyl)-1,2,3,4-tetrahydro-isoquinolin-8-yl]-4-(2,2,2-trifluoro-ethoxy)-phenyl]-acetic acid | C30H27NO5F4 557.18 | 1.14 LC-MS 1FA | 558.3 |
| 307 | (±)-[3-[2-(2-2,3-Dihydro-benzofuran-3-yl-acetyl)-5-fluoro-1,2,3,4-tetrahydro-isoquinolin-8-yl]-4-(2,2,2-trifluoro-ethoxy)-phenyl]-acetic acid | C29H25NO5F4 543.17 | 1.15 LC-MS 1FA | 544.3 |
| 308 | (±)-{4-Ethoxy-3-[5-fluoro-2-(3-pyridin-2-yl-pentanoyl)-1,2,3,4-tetrahydro-isoquinolin-8-yl]-phenyl}-acetic acid | C29H31N2O4F 490.23 | 0.86 LC-MS 1FA | 491.4 |
| 309 | (4-Ethoxy-3-{5-fluoro-2-[3-(3-methoxy-pyridin-2-yl)-propionyl]-1,2,3,4-tetrahydro-isoquinolin-8-yl}-phenyl)-acetic acid | C28H29N2O5F 492.21 | 0.83 LC-MS 1FA | 493.4 |
| 310 | (4-Ethoxy-3-{5-fluoro-2-[3-(4-fluoro-phenyl)-propionyl]-1,2,3,4-tetrahydro-isoquinolin-8-yl}-phenyl)-acetic acid | C28H27NO4F2 479.19 | 1.13 LC-MS 1FA | 480.4 |
| 311 | (4-Ethoxy-3-{5-fluoro-2-[3-(3-fluoro-phenyl)-propionyl]-1,2,3,4-tetrahydro-isoquinolin-8-yl}-phenyl)-acetic acid | C28H27NO4F2 479.19 | 1.14 LC-MS 1FA | 480.4 |
| 312 | (4-Ethoxy-3-{5-fluoro-2-[3-(2-fluoro-phenyl)-propionyl]-1,2,3,4-tetrahydro-isoquinolin-8-yl}-phenyl)-acetic acid | C28H27NO4F2 479.19 | 1.14 LC-MS 1FA | 480.4 |
| 313 | (±)-{3-Ethoxy-4-[5-fluoro-2-(3-pyridin-2-yl-pentanoyl)-1,2,3,4-tetrahydro-isoquinolin-8-yl]-phenyl}-acetic acid | C29H31N2O4F 490.23 | 0.85 LC-MS 1FA | 491.4 |
| 314 | (3-Ethoxy-4-{5-fluoro-2-[3-(3-methoxy-pyridin-2-yl)-propionyl]-1,2,3,4-tetrahydro-isoquinolin-8-yl}-phenyl)-acetic acid | C28H29N2O5F 492.21 | 0.83 LC-MS 1FA | 493.4 |
| 315 | (3-Ethoxy-4-{5-fluoro-2-[3-(4-fluoro-phenyl)-propionyl]-1,2,3,4-tetrahydro-isoquinolin-8-yl}-phenyl)-acetic acid | C28H27NO4F2 479.19 | 1.14 LC-MS 1FA | 480.4 |
| 316 | (3-Ethoxy-4-{5-fluoro-2-[3-(3-fluoro-phenyl)-propionyl]-1,2,3,4-tetrahydro-isoquinolin-8-yl}-phenyl)-acetic acid | C28H27NO4F2 479.19 | 1.15 LC-MS 1FA | 480.3 |
| 317 | (3-Ethoxy-4-{5-fluoro-2-[3-(2-fluoro-phenyl)-propionyl]-1,2,3,4-tetrahydro-isoquinolin-8-yl}-phenyl)-acetic acid | C28H27NO4F2 479.19 | 1.15 LC-MS 1FA | 480.4 |
| 318 | (±)-{3-[2-(3-Cyclopropyl-3-pyridin-2-yl-propionyl)-5-fluoro-1,2,3,4-tetrahydro-isoquinolin-8-yl]-4-ethoxy-phenyl}-acetic acid | C30H31N2O4F 502.23 | 0.89 LC-MS 1FA | 503.4 |
| 319 | (±)-{4-[2-(3-Cyclopropyl-3-pyridin-2-yl-propionyl)-5-fluoro-1,2,3,4-tetrahydro-isoquinolin-8-yl]-3-ethoxy-phenyl}-acetic acid | C30H31N2O4F 502.23 | 0.88 LC-MS 1FA | 503.4 |
| 320 | (±)-(3-Ethoxy-4-{5-fluoro-2-[3-(6-methyl-pyridin-2-yl)-butyryl]-1,2,3,4-tetrahydro-isoquinolin-8-yl}-phenyl)-acetic acid | C29H31N2O4F 490.23 | 0.79 LC-MS 1FA | 491.4 |
| 321 | (3-Ethoxy-4-{5-fluoro-2-[3-(6-methyl-pyridin-2-yl)-propionyl]-1,2,3,4-tetrahydro-isoquinolin-8-yl}-phenyl)-acetic acid | C28H29N2O4F 476.21 | 0.76 LC-MS 1FA | 477.4 |
| 322 | (±)-{3-Ethoxy-4-[5-fluoro-2-(trans-2-pyridin-2-yl-cyclopropanecarbonyl)-1,2,3,4-tetrahydro-isoquinolin-8-yl]-phenyl}-acetic acid | C28H27N2O4F 474.20 | 0.93 LC-MS 1FA | 475.4 |
| 323 | (±)-(4-{2-[2-(2,2-Dimethyl-chroman-4-yl)-acetyl]-5-fluoro-1,2,3,4-tetrahydro-isoquinolin-8-yl}-3-ethoxy-phenyl)-acetic acid | C32H34NO5F 531.24 | 1.23 LC-MS 1FA | 532.4 |

TABLE 21-continued

| Example | Compound of Formula (I) | Formula MW | $t_R$ [min] LC-MS Method | MS-data m/z [M + H]$^+$ |
|---|---|---|---|---|
| 324 | (±)-{4-[2-(2-Chroman-3-yl-acetyl)-5-fluoro-1,2,3,4-tetrahydro-isoquinolin-8-yl]-3-ethoxy-phenyl}-acetic acid | C30H30NO5F 503.21 | 1.17 LC-MS 1FA | 504.4 |
| 325 | (±)-{3-Ethoxy-4-[5-fluoro-2-(8-methoxy-1,2,3,4-tetrahydro-naphthalene-2-carbonyl)-1,2,3,4-tetrahydro-isoquinolin-8-yl]-phenyl}-acetic acid | C31H32NO5F 517.23 | 1.21 LC-MS 1FA | 518.4 |
| 326 | (±)-(3-Ethoxy-4-{5-fluoro-2-[2-(1-methyl-1,2,3,4-tetrahydro-naphthalen-1-yl)-acetyl]-1,2,3,4-tetrahydro-isoquinolin-8-yl}-phenyl)-acetic acid | C32H34NO4F 515.25 | 1.25 LC-MS 1FA | 516.5 |
| 327 | (±)-(3-Ethoxy-4-{5-fluoro-2-[2-(7-fluoro-chroman-4-yl)-acetyl]-1,2,3,4-tetrahydro-isoquinolin-8-yl}-phenyl)-acetic acid | C30H29NO5F2 521.20 | 1.16 LC-MS 1FA | 522.3 |
| 328 | (±)-(4-Ethoxy-3-{5-fluoro-2-[3-(6-methyl-pyridin-2-yl)-butyryl]-1,2,3,4-tetrahydro-isoquinolin-8-yl}-phenyl)-acetic acid | C29H31N2O4F 490.23 | 0.79 LC-MS 1FA | 491.4 |
| 329 | (4-Ethoxy-3-{5-fluoro-2-[3-(6-methyl-pyridin-2-yl)-propionyl]-1,2,3,4-tetrahydro-isoquinolin-8-yl}-phenyl)-acetic acid | C28H29N2O4F 476.21 | 0.76 LC-MS 1FA | 477.4 |
| 330 | (±)-{4-Ethoxy-3-[5-fluoro-2-(trans-2-pyridin-2-yl-cyclopropanecarbonyl)-1,2,3,4-tetrahydro-isoquinolin-8-yl]-phenyl}-acetic acid | C28H27N2O4F 474.20 | 0.95 LC-MS 1FA | 475.4 |
| 331 | (±)-(3-{2-[2-(2,2-Dimethyl-chroman-4-yl)-acetyl]-5-fluoro-1,2,3,4-tetrahydro-isoquinolin-8-yl}-4-ethoxy-phenyl)-acetic acid | C32H34NO5F 531.24 | 1.22 LC-MS 1FA | 532.4 |
| 332 | (±)-{3-[2-(2-Chroman-3-yl-acetyl)-5-fluoro-1,2,3,4-tetrahydro-isoquinolin-8-yl]-4-ethoxy-phenyl}-acetic acid | C30H30NO5F 503.21 | 1.16 LC-MS 1FA | 504.3 |
| 333 | (±)-{4-Ethoxy-3-[5-fluoro-2-(8-methoxy-1,2,3,4-tetrahydro-naphthalene-2-carbonyl)-1,2,3,4-tetrahydro-isoquinolin-8-yl]-phenyl}-acetic acid | C31H32NO5F 517.23 | 1.20 LC-MS 1FA | 518.4 |
| 334 | (±)-(4-Ethoxy-3-{5-fluoro-2-[2-(1-methyl-1,2,3,4-tetrahydro-naphthalen-1-yl)-acetyl]-1,2,3,4-tetrahydro-isoquinolin-8-yl}-phenyl)-acetic acid | C32H34NO4F 515.25 | 1.24 LC-MS 1FA | 516.4 |
| 335 | (±)-(4-Ethoxy-3-{5-fluoro-2-[2-(7-fluoro-chroman-4-yl)-acetyl]-1,2,3,4-tetrahydro-isoquinolin-8-yl}-phenyl)-acetic acid | C30H29NO5F2 521.20 | 1.15 LC-MS 1FA | 522.4 |
| 336 | {4-Ethoxy-3-[5-fluoro-2-((E)-3-pyridin-2-yl-acryloyl)-1,2,3,4-tetrahydro-isoquinolin-8-yl]-phenyl}-acetic acid | C27H25N2O4F 460.18 | 1.01 LC-MS 1FA | 461.4 |
| 337 | (4-Ethoxy-3-{5-fluoro-2-[(E)-3-(1-methyl-1H-pyrazol-3-yl)-acryloyl]-1,2,3,4-tetrahydro-isoquinolin-8-yl}-phenyl)-acetic acid | C26H26N3O4F 463.19 | 0.98 LC-MS 1FA | 464.4 |
| 338 | {3-Ethoxy-4-[5-fluoro-2-((E)-3-pyridin-2-yl-acryloyl)-1,2,3,4-tetrahydro-isoquinolin-8-yl]-phenyl}-acetic acid | C27H25N2O4F 460.18 | 0.99 LC-MS 1FA | 461.4 |
| 339 | (3-Ethoxy-4-{5-fluoro-2-[(E)-3-(1-methyl-1H-pyrazol-4-yl)-acryloyl]-1,2,3,4-tetrahydro-isoquinolin-8-yl}-phenyl)-acetic acid | C26H26N3O4F 463.19 | 0.98 LC-MS 1FA | 464.4 |
| 340 | {4-Ethoxy-3-[5-fluoro-2-(2-pyridin-2-yl-acetyl)-1,2,3,4-tetrahydro-isoquinolin-8-yl]-phenyl}-acetic acid | C26H25N2O4F 448.18 | 0.83 LC-MS 1FA | 449.4 |
| 341 | (4-Ethoxy-3-{5-fluoro-2-[(E)-3-(1-methyl-1H-pyrazol-4-yl)-acryloyl]-1,2,3,4-tetrahydro-isoquinolin-8-yl}-phenyl)-acetic acid | C26H26N3O4F 463.19 | 0.98 LC-MS 1FA | 464.4 |

TABLE 21-continued

| Example | Compound of Formula (I) | Formula MW | $t_R$ [min] LC-MS Method | MS-data m/z $[M + H]^+$ |
|---|---|---|---|---|
| 342 | {3-Ethoxy-4-[5-fluoro-2-(2-pyridin-2-yl-acetyl)-1,2,3,4-tetrahydro-isoquinolin-8-yl]-phenyl}-acetic acid | C26H25N2O4F 448.18 | 0.84 LC-MS 1FA | 449.4 |
| 343 | (±)-{3-[5-Fluoro-2-(2-methyl-3-pyridin-3-yl-propionyl)-1,2,3,4-tetrahydro-isoquinolin-8-yl]-4-methoxy-phenyl}-acetic acid | C27H27N2O4F 462.20 | 0.73 LC-MS 1FA | 463.4 |
| 344 | (±)-{3-Ethoxy-4-[5-fluoro-2-(3-pyridin-2-yl-butyryl)-1,2,3,4-tetrahydro-isoquinolin-8-yl]-phenyl}-acetic acid | C28H29N2O4F 476.21 | 0.82 LC-MS 1FA | 477.4 |
| 345 | (±)-{4-Ethoxy-3-[5-fluoro-2-(3-pyridin-2-yl-butyryl)-1,2,3,4-tetrahydro-isoquinolin-8-yl]-phenyl}-acetic acid | C28H29N2O4F 476.21 | 0.82 LC-MS 1FA | 477.4 |
| 346 | (±)-{4-[5-Fluoro-2-(3-pyridin-2-yl-butyryl)-1,2,3,4-tetrahydro-isoquinolin-8-yl]-3-isopropoxy-phenyl}-acetic acid | C29H31N2O4F 490.23 | 0.87 LC-MS 1FA | 491.4 |
| 347 | [4-[5-Fluoro-2-((R)-3-phenyl-butyryl)-1,2,3,4-tetrahydro-isoquinolin-8-yl]-3-(2,2,2-trifluoro-ethoxy)-phenyl]-acetic acid | C29H27NO4F4 529.19 | 1.19 LC-MS 1FA | 530.4 |
| 348 | {4-Ethoxy-3-[5-fluoro-2-(3-pyridin-2-yl-propionyl)-1,2,3,4-tetrahydro-isoquinolin-8-yl]-phenyl}-acetic acid | C27H27N2O4F 462.20 | 0.78 LC-MS 1FA | 463.4 |
| 349 | {3-Ethoxy-4-[5-fluoro-2-(3-pyridin-2-yl-propionyl)-1,2,3,4-tetrahydro-isoquinolin-8-yl]-phenyl}-acetic acid | C27H27N2O4F 462.20 | 0.78 LC-MS 1FA | 463.4 |
| 350 | (±)-{4-Ethoxy-3-[5-fluoro-2-(2-5,6,7,8-tetrahydro-quinolin-8-yl-acetyl)-1,2,3,4-tetrahydro-isoquinolin-8-yl]-phenyl}-acetic acid | C30H31N2O4F 502.23 | 0.77 LC-MS 1FA | 503.4 |
| 351 | (±)-{4-Ethoxy-3-[5-fluoro-2-(2-methyl-3-pyridin-2-yl-propionyl)-1,2,3,4-tetrahydro-isoquinolin-8-yl]-phenyl}-acetic acid | C28H29N2O4F 476.21 | 0.82 LC-MS 1FA | 477.4 |
| 352 | (±)-{3-Ethoxy-4-[5-fluoro-2-(2-methyl-3-pyridin-2-yl-propionyl)-1,2,3,4-tetrahydro-isoquinolin-8-yl]-phenyl}-acetic acid | C28H29N2O4F 476.21 | 0.82 LC-MS 1FA | 477.4 |

Method C: A solution of (±)-chroman-4-yl-acetic acid (7.5 mg, 39 μmol, 1.0 eq.) and [4-(5-fluoro-1,2,3,4-tetrahydro-isoquinolin-8-yl)-3-isopropoxy-phenyl]-acetic acid tert-butyl ester (16 mg, 39 μmol, 1.0 eq.) in MeCN (0.5 mL) was treated with 4-(dimethylamino)pyridine (7.2 mg, 59 μmol, 1.5 eq.) and N-(3-dimethylaminopropyl)-N'-ethylcarbodiimide hydrochloride (11.3 mg, 59 μmol, 1.5 eq.) and the resulting solution was stirred at r.t. for 18 hours. The crude mixture was concentrated in vacuo. To an ice-cooled solution of the residue in DCM (0.1 mL), TFA (0.13 mL) was added slowly. The mixture was stirred at r.t. for 2 hours. The mixture was concentrated in vacuo without heating. The residue was redissolved in MeCN (1 mL) and purified by prep. HPLC (column: Waters XBridge, 30×75 mm, 10 um, UV/MS, acidic conditions) and evaporated to give the desired acid as a white foam.

Listed in Table 22 below are examples of compounds of Formula (I), prepared according to the above-mentioned method with the corresponding compound of Structure 2 and the corresponding acid as starting materials.

TABLE 22

| Example | Compound of Formula (I) | Formula MW | $t_R$ [min] LC-MS Method | MS-data m/z $[M + H]^+$ |
|---|---|---|---|---|
| 353 | (±)-{4-[2-(2-Chroman-4-yl-acetyl)-5-fluoro-1,2,3,4-tetrahydro-isoquinolin-8-yl]-3-isopropoxy-phenyl}-acetic acid | C31H32NO5F 517.23 | 1.19 LC-MS 1FA | 518.4 |
| 354 | {4-[5-Fluoro-2-(3-methyl-3-phenyl-butyryl)-1,2,3,4-tetrahydro-isoquinolin-8-yl]-3-isopropoxy-phenyl}-acetic acid | C31H34NO4F 503.25 | 1.25 LC-MS 1FA | 504.4 |
| 355 | {4-[5-Fluoro-2-((S)-3-phenyl-butyryl)-1,2,3,4-tetrahydro-isoquinolin-8-yl]-3-isopropoxy-phenyl}-acetic acid | C30H32NO4F 489.23 | 1.21 LC-MS 1FA | 490.4 |

TABLE 22-continued

| Example | Compound of Formula (I) | Formula MW | $t_R$ [min] LC-MS Method | MS-data m/z [M + H]⁺ |
|---|---|---|---|---|
| 356 | {4-[5-Fluoro-2-((R)-3-phenyl-butyryl)-1,2,3,4-tetrahydro-isoquinolin-8-yl]-3-isopropoxy-phenyl}-acetic acid | C30H32NO4F 489.23 | 1.21 LC-MS 1FA | 490.4 |
| 357 | {4-[5-Fluoro-2-((1R,2R)-2-phenyl-cyclopropanecarbonyl)-1,2,3,4-tetrahydro-isoquinolin-8-yl]-3-isopropoxy-phenyl}-acetic acid | C30H30NO4F 487.22 | 1.21 LC-MS 1FA | 488.4 |

Method D: To a solution of 3-(4-fluoro-phenyl)-3-methyl-butyric acid (22 mg, 0.11 mmol, 1.1 eq.) in DCM (2 mL), DIPEA (70 μL, 0.41 mmol, 4 eq.) and TBTU (36 mg, 0.11 mmol, 1.1 eq.) were added in sequence. The resulting solutions were stirred at room temperature for 30 minutes. Then [4-(5-fluoro-1,2,3,4-tetrahydro-isoquinolin-8-yl)-3-methoxy-phenyl]-acetic acid ethyl ester (35 mg, 0.10 mmol, 1.0 eq.) was added and the resulting mixture was stirred at r.t. for 18 hours. The mixture was concentrated in vacuo. The residue was dissolved in DMF (0.8 mL). 1M aq. NaOH (1 mL) was added. The mixture was stirred at r.t. for 3 hours. The solution was carefully neutralized with formic acid (0.5 mL), purified by prep. HPLC (column: Atlantis, 30×75 mm, 10 um, UV/MS, acidic conditions) and concentrated in vacuo to give the desired acid as a white solid.

Listed in Table 23 below are examples of compounds of Formula (I), prepared according to the above-mentioned method with the corresponding compound of Structure 2 and the corresponding acid as starting materials.

N-(3-dimethylaminopropyl)-N'-ethylcarbodiimide hydrochloride (19 mg, 0.1 mmol, 1.0 eq.) were added in sequence. The resulting solution was stirred at r.t. for 2 minutes. Then a solution of [3-(5-fluoro-1,2,3,4-tetrahydro-isoquinolin-8-yl)-4-methoxy-phenyl]-acetic acid ethyl ester (34 mg, 0.1 mmol, 1.0 eq.) and triethylamine (42 μL, 0.3 mmol, 3.0 eq.) in DCM (1 mL) was added and the resulting mixture was stirred at r.t. for 18 hours. The mixture was concentrated in vacuo. The residue was dissolved in DMF (0.8 mL). 1M aq. NaOH (1 mL) was added. The mixture was stirred at r.t. for 3 hours. The solution was carefully neutralized with formic acid (0.5 mL), and purified by prep. HPLC (column: Atlantis, 30×75 mm, 10 um, UV/MS, acidic conditions) and concentrated in vacuo to give the title compound as a white solid.

LC-MS 3: $t_R$=0.92 min; [M+H]⁺=494.3

Carbamate Formation and Concomitant Saponification

To a solution of 8-(2-ethoxy-5-ethoxycarbonylmethyl-phenyl)-5-fluoro-3,4-dihydro-1H-isoquinoline-2-carboxylic acid 4-nitro-phenyl ester (40 mg, 0.08 mmol, 1 eq.) and

TABLE 23

| Example | Compound of Formula (I) | Formula MW | $t_R$ [min] LC-MS Method | MS-data m/z [M + H]⁺ |
|---|---|---|---|---|
| 358 | (4-{5-Fluoro-2-[3-(4-fluoro-phenyl)-3-methyl-butyryl]-1,2,3,4-tetrahydro-isoquinolin-8-yl}-3-methoxy-phenyl)-acetic acid | C29H29NO4F2 493.21 | 1.16 LC-MS 1FA | 494.4 |
| 359 | (±)-{4-[2-(2-Chroman-4-yl-acetyl)-5-fluoro-1,2,3,4-tetrahydro-isoquinolin-8-yl]-3-methoxy-phenyl}-acetic acid | C29H28NO5F 489.20 | 1.09 LC-MS 1FA | 490.4 |
| 360 | (±)-{4-[5-Fluoro-2-(2-indan-1-yl-acetyl)-1,2,3,4-tetrahydro-isoquinolin-8-yl]-3-methoxy-phenyl}-acetic acid | C29H28NO4F 473.20 | 1.15 LC-MS 1FA | 474.4 |
| 361 | (±)-{3-[5-Fluoro-2-(trans-2-pyridin-2-yl-cyclopropanecarbonyl)-1,2,3,4-tetrahydro-isoquinolin-8-yl]-4-methoxy-phenyl}-acetic acid | C27H25N2O4F 460.18 | 0.87 LC-MS 1FA | 461.4 |
| 362 | (±)-{3-[2-(2-1,3-Dihydro-isobenzofuran-1-yl-acetyl)-5-fluoro-1,2,3,4-tetrahydro-isoquinolin-8-yl]-4-methoxy-phenyl}-acetic acid | C28H26NO5F 475.18 | 1.02 LC-MS 1FA | 476.4 |

EXAMPLE 363

(3-{5-Fluoro-2-[3-(4-fluoro-phenyl)-3-methyl-butyryl]-1,2,3,4-tetrahydro-isoquinolin-8-yl}-4-methoxy-phenyl)-acetic acid (C29H29NO4F2, MW=493.21)

To a solution of 3-(4-fluoro-phenyl)-3-methyl-butyric acid (20 mg, 0.1 mmol, 1.0 eq.) in DCM (1 mL), 1-hydroxybenzotriazole hydrate (HOBt) (14 mg, 0.1 mmol, 1.0 eq.) and (R)-(+)-sec-phenethyl alcohol (28 mg. 0.23 mmol, 3 eq.) in THF (2 mL), potassium tert-butoxide (27 mg, 0.23 mmol, 3 eq.) was added. The mixture was stirred at r.t. for 3 hours. The reaction mixture was quenched with formic acid (6 eq.) and the flask was opened and let stand at r.t. to allow solvent evaporation (2 days). The residue was dissolved in MeCN/H₂O 1:1 (1 mL) and DMF (0.2 mL). The resulting solution was purified by prep. HPLC (column: Atlantis, 18×50 mm, 10 um, UV/MS, acidic conditions) and concentrated in vacuo to give the desired acid as a white solid.

Listed in Table 24 below are examples of compounds of Formula (I), prepared according to the above-mentioned method with the corresponding nitrophenyl carbamate 5 and the corresponding alcohol as starting materials.

TABLE 24

| Example | Compound of Formula (I) | Formula MW | $t_R$ [min] LC-MS Method | MS-data m/z $[M + H]^+$ |
|---|---|---|---|---|
| 364 | 8-(5-Carboxymethyl-2-ethoxy-phenyl)-5-fluoro-3,4-dihydro-1H-isoquinoline-2-carboxylic acid (R)-1-phenyl-ethyl ester | C28H28NO5F 477.20 | 1.23 LC-MS 1FA | 478.4 |
| 365 | 8-(5-Carboxymethyl-2-ethoxy-phenyl)-5-fluoro-3,4-dihydro-1H-isoquinoline-2-carboxylic acid pyrazin-2-ylmethyl ester | C25H24N3O5F 465.17 | 1.00 LC-MS 1FA | 466.4 |
| 366 | 8-(5-Carboxymethyl-2-ethoxy-phenyl)-5-fluoro-3,4-dihydro-1H-isoquinoline-2-carboxylic acid 3-fluoro-5-methyl-pyridin-2-ylmethyl ester | C27H26N2O5F2 496.18 | 1.12 LC-MS 1FA | 497.3 |
| 367 | 8-(5-Carboxymethyl-2-ethoxy-phenyl)-5-fluoro-3,4-dihydro-1H-isoquinoline-2-carboxylic acid 2-methyl-2H-pyrazol-3-ylmethyl ester | C25H26N3O5F 467.19 | 1.01 LC-MS 1FA | 468.4 |
| 368 | 8-(5-Carboxymethyl-2-ethoxy-phenyl)-5-fluoro-3,4-dihydro-1H-isoquinoline-2-carboxylic acid (S)-1-phenyl-ethyl ester | C28H28NO5F 477.20 | 1.23 LC-MS 1FA | 478.4 |
| 369 | 8-(5-Carboxymethyl-2-ethoxy-phenyl)-5-fluoro-3,4-dihydro-1H-isoquinoline-2-carboxylic acid cyclopentylmethyl ester | C26H30NO5F 455.21 | 1.26 LC-MS 1FA | 456.4 |
| 370 | 8-(5-Carboxymethyl-2-ethoxy-phenyl)-5-fluoro-3,4-dihydro-1H-isoquinoline-2-carboxylic acid 3-methyl-butyl ester | C25H30NO5F 443.21 | 1.25 LC-MS 1FA | 444.4 |
| 371 | 8-(5-Carboxymethyl-2-ethoxy-phenyl)-5-fluoro-3,4-dihydro-1H-isoquinoline-2-carboxylic acid 6-methyl-pyridin-2-ylmethyl ester | C27H27N2O5F 478.19 | 0.97 LC-MS 1FA | 479.4 |
| 372 | 8-(5-Carboxymethyl-2-ethoxy-phenyl)-5-fluoro-3,4-dihydro-1H-isoquinoline-2-carboxylic acid cyclopropylmethyl ester | C24H26NO5F 427.18 | 1.15 LC-MS 1FA | 428.4 |
| 373 | 8-(5-Carboxymethyl-2-ethoxy-phenyl)-5-fluoro-3,4-dihydro-1H-isoquinoline-2-carboxylic acid phenethyl ester | C28H28NO5F 477.20 | 1.21 LC-MS 1FA | 478.4 |
| 374 | 8-(5-Carboxymethyl-2-ethoxy-phenyl)-5-fluoro-3,4-dihydro-1H-isoquinoline-2-carboxylic acid (R)-2-phenyl-propyl ester | C29H30NO5F 491.21 | 1.25 LC-MS 1FA | 492.4 |
| 375 | 8-(5-Carboxymethyl-2-ethoxy-phenyl)-5-fluoro-3,4-dihydro-1H-isoquinoline-2-carboxylic acid 3-methyl-but-2-enyl ester | C25H28NO5F 441.20 | 1.21 LC-MS 1FA | 442.4 |
| 376 | 8-(5-Carboxymethyl-2-ethoxy-phenyl)-5-fluoro-3,4-dihydro-1H-isoquinoline-2-carboxylic acid butyl ester | C24H28NO5F 429.20 | 1.20 LC-MS 1FA | 430.4 |
| 377 | 8-(5-Carboxymethyl-2-ethoxy-phenyl)-5-fluoro-3,4-dihydro-1H-isoquinoline-2-carboxylic acid isobutyl ester | C24H28NO5F 429.20 | 1.20 LC-MS 1FA | 430.4 |
| 378 | 8-(5-Carboxymethyl-2-ethoxy-phenyl)-5-fluoro-3,4-dihydro-1H-isoquinoline-2-carboxylic acid 2-methoxy-ethyl ester | C23H26NO6F 431.17 | 1.03 LC-MS 1FA | 432.4 |
| 379 | 8-(5-Carboxymethyl-2-ethoxy-phenyl)-5-fluoro-3,4-dihydro-1H-isoquinoline-2-carboxylic acid 3-methyl-but-3-enyl ester | C25H28NO5F 441.20 | 1.20 LC-MS 1FA | 442.4 |
| 380 | (±)-8-(5-Carboxymethyl-2-ethoxy-phenyl)-5-fluoro-3,4-dihydro-1H-isoquinoline-2-carboxylic acid 2-methyl-butyl ester | C25H30NO5F 443.20 | 1.25 LC-MS 1FA | 444.4 |
| 381 | 8-(5-Carboxymethyl-2-ethoxy-phenyl)-5-fluoro-3,4-dihydro-1H-isoquinoline-2-carboxylic acid but-3-ynyl ester | C24H24NO5F 425.16 | 1.09 LC-MS 1FA | 426.4 |

TABLE 24-continued

| Example | Compound of Formula (I) | Formula MW | $t_R$ [min] LC-MS Method | MS-data m/z $[M + H]^+$ |
|---|---|---|---|---|
| 382 | 8-(5-Carboxymethyl-2-ethoxy-phenyl)-5-fluoro-3,4-dihydro-1H-isoquinoline-2-carboxylic acid 3-hydroxy-3-methyl-butyl ester | C25H30NO6F 459.21 | 1.02 LC-MS 1FA | 460.4 |
| 383 | 8-(5-Carboxymethyl-2-ethoxy-phenyl)-5-fluoro-3,4-dihydro-1H-isoquinoline-2-carboxylic acid 3-methoxy-3-methyl-butyl ester | C26H32NO6F 473.22 | 1.14 LC-MS 1FA | 474.4 |
| 384 | (±)-8-(5-Carboxymethyl-2-ethoxy-phenyl)-5-fluoro-3,4-dihydro-1H-isoquinoline-2-carboxylic acid tetrahydro-furan-2-ylmethyl ester | C25H28NO6F 457.19 | 1.06 LC-MS 1FA | 458.4 |
| 385 | 8-(4-Carboxymethyl-2-ethoxy-phenyl)-5-fluoro-3,4-dihydro-1H-isoquinoline-2-carboxylic acid (R)-1-phenyl-ethyl ester | C28H28NO5F 477.20 | 1.24 LC-MS 1FA | 478.4 |
| 386 | 8-(4-Carboxymethyl-2-ethoxy-phenyl)-5-fluoro-3,4-dihydro-1H-isoquinoline-2-carboxylic acid pyrazin-2-ylmethyl ester | C25H24N3O5F 465.17 | 1.01 LC-MS 1FA | 466.4 |
| 387 | 8-(4-Carboxymethyl-2-ethoxy-phenyl)-5-fluoro-3,4-dihydro-1H-isoquinoline-2-carboxylic acid 3-fluoro-5-methyl-pyridin-2-ylmethyl ester | C27H26N2O5F2 496.18 | 1.12 LC-MS 1FA | 497.4 |
| 388 | 8-(4-Carboxymethyl-2-ethoxy-phenyl)-5-fluoro-3,4-dihydro-1H-isoquinoline-2-carboxylic acid 2-methyl-2H-pyrazol-3-ylmethyl ester | C25H26N3O5F 467.19 | 1.03 LC-MS 1FA | 468.4 |
| 389 | 8-(4-Carboxymethyl-2-ethoxy-phenyl)-5-fluoro-3,4-dihydro-1H-isoquinoline-2-carboxylic acid (S)-1-phenyl-ethyl ester | C28H28NO5F 477.20 | 1.24 LC-MS 1FA | 478.3 |
| 390 | 8-(4-Carboxymethyl-2-ethoxy-phenyl)-5-fluoro-3,4-dihydro-1H-isoquinoline-2-carboxylic acid 6-methyl-pyridin-2-ylmethyl ester | C27H27N2O5F 478.19 | 0.98 LC-MS 1FA | 479.4 |
| 391 | 8-(4-Carboxymethyl-2-ethoxy-phenyl)-5-fluoro-3,4-dihydro-1H-isoquinoline-2-carboxylic acid cyclopropylmethyl ester | C24H26NO5F 427.18 | 1.16 LC-MS 1FA | 428.4 |
| 392 | 8-(4-Carboxymethyl-2-ethoxy-phenyl)-5-fluoro-3,4-dihydro-1H-isoquinoline-2-carboxylic acid cyclopentylmethyl ester | C26H30NO5F 455.21 | 1.28 LC-MS 1FA | 456.3 |
| 393 | 8-(4-Carboxymethyl-2-ethoxy-phenyl)-5-fluoro-3,4-dihydro-1H-isoquinoline-2-carboxylic acid 3-methyl-butyl ester | C25H30NO5F 443.21 | 1.26 LC-MS 1FA | 444.4 |
| 394 | 8-(5-Carboxymethyl-2-ethoxy-phenyl)-5-fluoro-3,4-dihydro-1H-isoquinoline-2-carboxylic acid pyridin-2-ylmethyl ester | C26H25N2O5F 464.18 | 1.01 LC-MS 1FA | 465.4 |
| 395 | 8-(4-Carboxymethyl-2-ethoxy-phenyl)-5-fluoro-3,4-dihydro-1H-isoquinoline-2-carboxylic acid pyridin-2-ylmethyl ester | C26H25N2O5F 464.18 | 1.01 LC-MS 1FA | 465.4 |
| 396 | 8-(5-Carboxymethyl-2-ethoxy-phenyl)-5-fluoro-3,4-dihydro-1H-isoquinoline-2-carboxylic acid cyclohexylmethyl ester | C27H32NO5F 469.23 | 1.31 LC-MS 1FA | 470.4 |
| 397 | 8-(4-Carboxymethyl-2-ethoxy-phenyl)-5-fluoro-3,4-dihydro-1H-isoquinoline-2-carboxylic acid cyclohexylmethyl ester | C27H32NO5F 469.23 | 1.32 LC-MS 1FA | 470.4 |

Carbamate Formation and Subsequent Saponification

Method A: To a solution of [4-ethoxy-3-(5-fluoro-1,2,3,4-tetrahydro-isoquinolin-8-yl)-phenyl]-acetic acid ethyl ester (72 mg, 0.20 mmol, 1.0 eq.) and DIPEA (46 µL, 0.50 mmol, 2.5 eq.) in DCM (3 mL), carbonic acid 2,5-dioxo-pyrrolidin-1-yl ester 4-fluoro-benzyl ester (65 mg, 0.24 mmol, 1.2 eq.) was added. The mixture was stirred at r.t. for 1 hour. The reaction was quenched with 1M aq. citric acid soln. (3 mL). The layers were separated over phase separators. The aq. phase was extracted with DCM (3×). The comb. org. phases were concentrated in vacuo. To a solution of the residue in DMF (0.9 mL), 2M aq. NaOH (0.5 mL) was added. The solution was stirred at r.t. for 2 hours. Formic acid (0.2 mL) was added. The resulting solution was purified by prep. HPLC (column: Waters Xbridge, 30×75 mm, 10 um, UV/MS, acidic conditions) and concentrated in vacuo to give the desired acid as a white foam.

Listed in Table 25 below are examples of compounds of Formula (I), prepared according to the above-mentioned method with the corresponding compound of Structure 2 and the corresponding carbonate 3 as starting materials.

TABLE 25

| Example | Compound of Formula (I) | Formula MW | $t_R$ [min] LC-MS Method | MS-data m/z $[M + H]^+$ |
|---|---|---|---|---|
| 398 | 8-(5-Carboxymethyl-2-ethoxy-phenyl)-5-fluoro-3,4-dihydro-1H-isoquinoline-2-carboxylic acid 4-fluoro-benzyl ester | C27H25NO5F2 481.17 | 1.20 LC-MS 1FA | 482.4 |
| 399 | 8-(5-Carboxymethyl-2-ethoxy-phenyl)-5-fluoro-3,4-dihydro-1H-isoquinoline-2-carboxylic acid 3-fluoro-benzyl ester | C27H25NO5F2 481.17 | 1.20 LC-MS 1FA | 482.4 |
| 400 | 8-(5-Carboxymethyl-2-ethoxy-phenyl)-5-fluoro-3,4-dihydro-1H-isoquinoline-2-carboxylic acid 2-fluoro-benzyl ester | C27H25NO5F2 481.17 | 1.19 LC-MS 1FA | 482.3 |
| 401 | 8-(5-Carboxymethyl-2-ethoxy-phenyl)-5-fluoro-3,4-dihydro-1H-isoquinoline-2-carboxylic acid 2,5-difluoro-benzyl ester | C27H24NO5F3 499.16 | 1.21 LC-MS 1FA | 500.3 |
| 402 | 8-(5-Carboxymethyl-2-ethoxy-phenyl)-5-fluoro-3,4-dihydro-1H-isoquinoline-2-carboxylic acid 5-chloro-2-fluoro-benzyl ester | C27H24NO5ClF2 515.13 | 1.25 LC-MS 1FA | 516.3 |
| 403 | 8-(5-Carboxymethyl-2-ethoxy-phenyl)-5-fluoro-3,4-dihydro-1H-isoquinoline-2-carboxylic acid 2,4-difluoro-benzyl ester | C27H24NO5F3 499.16 | 1.21 LC-MS 1FA | 500.3 |
| 404 | 8-(4-Carboxymethyl-2-ethoxy-phenyl)-5-fluoro-3,4-dihydro-1H-isoquinoline-2-carboxylic acid 4-fluoro-benzyl ester | C27H25NO5F2 481.17 | 1.21 LC-MS 1FA | 482.4 |
| 405 | 8-(4-Carboxymethyl-2-ethoxy-phenyl)-5-fluoro-3,4-dihydro-1H-isoquinoline-2-carboxylic acid 3-fluoro-benzyl ester | C27H25NO5F2 481.17 | 1.21 LC-MS 1FA | 482.4 |
| 406 | 8-(4-Carboxymethyl-2-ethoxy-phenyl)-5-fluoro-3,4-dihydro-1H-isoquinoline-2-carboxylic acid 2-fluoro-benzyl ester | C27H25NO5F2 481.17 | 1.21 LC-MS 1FA | 482.4 |
| 407 | 8-(4-Carboxymethyl-2-ethoxy-phenyl)-5-fluoro-3,4-dihydro-1H-isoquinoline-2-carboxylic acid 2,5-difluoro-benzyl ester | C27H24NO5F3 499.16 | 1.22 LC-MS 1FA | 500.3 |
| 408 | 8-(4-Carboxymethyl-2-ethoxy-phenyl)-5-fluoro-3,4-dihydro-1H-isoquinoline-2-carboxylic acid 5-chloro-2-fluoro-benzyl ester | C27H24NO5ClF2 515.13 | 1.27 LC-MS 1FA | 516.3 |
| 409 | 8-(4-Carboxymethyl-2-ethoxy-phenyl)-5-fluoro-3,4-dihydro-1H-isoquinoline-2-carboxylic acid 2,4-difluoro-benzyl ester | C27H24NO5F3 499.16 | 1.22 LC-MS 1FA | 500.3 |

Method B: To an ice-cooled solution of [3-ethoxy-4-(5-fluoro-1,2,3,4-tetrahydro-isoquinolin-8-yl)-phenyl]-acetic acid ethyl ester (112 mg, 0.3 mmol, 1.0 eq.) and DIPEA (0.15 mL, 0.9 mmol, 3.0 eq.) in DMF (3.6 mL), benzyl chloroformate (50 µL, 0.33 mmol, 1.1 eq.) was added dropwise. Upon completion of the addition, the cooling bath was removed and the suspension was stirred at r.t. for 48 hours. Formic acid was added (0.2 mL). The resulting acidic solution was purified by prep. HPLC (column: Waters XBridge, 30×75 mm, 10 um, UV/MS, acidic conditions) and evaporated. To a solution of the previous ester in DMF (3.6 mL), 2M aq. NaOH soln. (1.8 mL) was added. The solution was stirred at r.t. for 1 hour. Formic acid was added (0.2 mL). The resulting acidic solution was purified by prep. HPLC (column: Waters XBridge, 30×75 mm, 10 um, UV/MS, acidic conditions) and evaporated (genevac) to give the desired acid as a white foam.

Listed in Table 26 below are examples of compounds of Formula (I), prepared according to the above-mentioned method with the corresponding compound of Structure 2 as starting material.

TABLE 26

| Example | Compound of Formula (I) | Formula MW | $t_R$ [min] LC-MS Method | MS-data m/z [M + H]$^+$ |
|---|---|---|---|---|
| 410 | 8-(4-Carboxymethyl-2-ethoxy-phenyl)-5-fluoro-3,4-dihydro-1H-isoquinoline-2-carboxylic acid benzyl ester | C27H26NO5F 463.18 | 1.20 LC-MS 1FA | 464.4 |
| 411 | 8-[4-Carboxymethyl-2-(2,2,2-trifluoro-ethoxy)-phenyl]-5-fluoro-3,4-dihydro-1H-isoquinoline-2-carboxylic acid benzyl ester | C27H23NO5F4 517.15 | 1.22 LC-MS 1FA | 518.3 |

Suzuki Cross-Coupling and Subsequent Saponification

Method A: To a mixture under $N_2$ of (3-bromo-4-difluoromethoxy-phenyl)-acetic acid ethyl ester (32 mg, 0.10 mmol, 1.00 eq.), 5-fluoro-8-(4,4,5,5-tetramethyl-[1,3,2]dioxaborolan-2-yl)-3,4-dihydro-1H-isoquinoline-2-carboxylic acid benzyl ester (49 mg, 0.10 mmol, 1.00 eq.) and sodium carbonate (42 mg, 0.40 mmol, 4.00 eq) in toluene/MeOH/water 20:4:1 (2.0 mL), tetrakis(triphenylphosphine) palladium (0) (5.8 mg, 5 μmol, 0.05 eq.) was added and the mixture was stirred at 100° C. for 18 hours. The mixture was allowed to cool to r.t., filtered over celite, and concentrated in vacuo. The residue, redissolved in DMF (1 mL) and formic acid (0.2 mL) was purified by prep. HPLC (column: Waters XBridge, 30×75 mm, 10 um, UV/MS, acidic conditions) and evaporated. The resulting ester was redissolved in DMF (0.5 mL) and 2M aq. NaOH soln. (0.2 mL) was added. The mixture was stirred at r.t. for 1 hour. Formic acid (0.2 mL) was added and the resulting acidic solution was purified by prep. HPLC (column: Waters XBridge, 30×75 mm, 10 um, UV/MS, acidic conditions) and evaporated to give the desired acid as a white foam.

Listed in Table 27 below are examples of compounds of Formula (I), prepared according to the above-mentioned method with the corresponding halogenated compound 9 as starting material.

Method B: A mixture under $N_2$ of palladium (II) acetate (0.4 mg, 2 μmol, 0.01 eq.), 2-dicyclohexylphosphino-2',6'-dimethoxybiphenyl (1.7 mg, 4 μmol, 0.02 eq.), 5-fluoro-8-(4,4,5,5-tetramethyl-[1,3,2]dioxaborolan-2-yl)-3,4-dihydro-1H-isoquinoline-2-carboxylic acid benzyl ester (82.3 mg, 0.2 mmol, 1.00 eq.) and potassium phosphate (84.9 mg, 0.4 mmol, 2.00 eq.) in toluene (0.6 mL) and water (35 was stirred at r.t. during 2 min. A solution of (2-bromo-3-methoxy-phenoxy)-acetic acid ethyl ester (64 mg, 0.2 mmol, 1.00 eq.) in toluene (0.6 mL) was added and the mixture was stirred at 100° C. for 18 hours. The mixture was allowed to cool to r.t., filtered through celite, and concentrated in vacuo. The residue, redissolved in MeCN/H$_2$O (1.8 mL) and formic acid (0.2 mL), was purified by prep. HPLC (column: Waters XBridge, 30×75 mm, 10 um, UV/MS, acidic conditions) and evaporated. The residue was redissolved in DMF (1.0 mL) and 2M aq. NaOH soln. (0.4 mL) was added. The resulting mixture was stirred at r.t. for 60 hours. Formic acid (0.2 mL) was added. The crude mixture was purified by prep. HPLC (column: Waters XBridge, 30×75 mm, 10 um, UV/MS, acidic conditions) and evaporated to give the desired acid as a white foam.

Listed in Table 28 below are examples of compounds of Formula (I), prepared according to the above-mentioned method with the corresponding halogenated compound 9 as starting material.

TABLE 27

| Example | Compound of Formula (I) | Formula MW | $t_R$ [min] LC-MS Method | MS-data m/z [M + H]$^+$ |
|---|---|---|---|---|
| 412 | 8-(5-Carboxymethyl-2-difluoromethoxy-phenyl)-5-fluoro-3,4-dihydro-1H-isoquinoline-2-carboxylic acid benzyl ester | C26H22NO5F3 485.15 | 1.16 LC-MS 1FA | 486.3 |
| 413 | 8-[5-Carboxymethyl-2-(2,2-difluoro-ethoxy)-phenyl]-5-fluoro-3,4-dihydro-1H-isoquinoline-2-carboxylic acid benzyl ester | C27H24NO5F3 499.16 | 1.15 LC-MS 1FA | 500.3 |
| 414 | (±)-8-[5-(1-Carboxy-ethoxy)-2-methoxy-phenyl]-5-fluoro-3,4-dihydro-1H-isoquinoline-2-carboxylic acid benzyl ester | C27H26NO6F 479.17 | 1.17 LC-MS 1FA | 480.3 |
| 415 | (±)-8-[5-(1-Carboxy-propoxy)-2-methoxy-phenyl]-5-fluoro-3,4-dihydro-1H-isoquinoline-2-carboxylic acid benzyl ester | C28H28NO6F 493.19 | 1.22 LC-MS 1FA | 494.4 |
| 416 | 8-(2-Carboxymethyl-5-chloro-phenyl)-5-fluoro-3,4-dihydro-1H-isoquinoline-2-carboxylic acid benzyl ester | C25H21NO4ClF 453.11 | 1.23 LC-MS 1FA | 454.3 |

TABLE 28

| Example | Compound of Formula (I) | Formula MW | $t_R$ [min] LC-MS Method | MS-data m/z [M + H]$^+$ |
|---|---|---|---|---|
| 417 | 8-(2-Carboxymethoxy-6-methoxy-phenyl)-5-fluoro-3,4-dihydro-1H-isoquinoline-2-carboxylic acid benzyl ester | C26H24NO6F 465.16 | 1.11 LC-MS 1FA | 466.4 |
| 418 | 8-(2-Carboxymethyl-6-methoxy-phenyl)-5-fluoro-3,4-dihydro-1H-isoquinoline-2-carboxylic acid benzyl ester | C26H24NO5F 449.16 | 1.11 LC-MS 1FA | 450.4 |
| 419 | 8-(2-tert-Butoxy-5-carboxymethyl-phenyl)-5-fluoro-3,4-dihydro-1H-isoquinoline-2-carboxylic acid benzyl ester | C29H30NO5F 491.21 | 1.29 LC-MS 1FA | 492.4 |
| 420 | 8-(5-Carboxymethyl-2-dimethylamino-phenyl)-5-fluoro-3,4-dihydro-1H-isoquinoline-2-carboxylic acid benzyl ester | C27H27N2O4F 462.20 | 1.11 LC-MS 1FA | 463.4 |
| 421 | 8-[5-Carboxymethyl-2-(2,2,2-trifluoro-ethoxy)-phenyl]-5-fluoro-3,4-dihydro-1H-isoquinoline-2-carboxylic acid benzyl ester | C27H23NO5F4 517.15 | 1.20 LC-MS 1FA | 518.3 |
| 422 | 8-[5-Carboxymethyl-2-(2-fluoro-ethoxy)-phenyl]-5-fluoro-3,4-dihydro-1H-isoquinoline-2-carboxylic acid benzyl ester | C27H25NO5F2 481.17 | 1.12 LC-MS 1FA | 482.3 |
| 423 | 8-(3-Carboxymethyl-2-methoxy-phenyl)-5-fluoro-3,4-dihydro-1H-isoquinoline-2-carboxylic acid benzyl ester | C26H24NO5F 449.16 | 1.17 LC-MS 1FA | 450.4 |
| 424 | 8-(4-Carboxymethoxy-2-methoxy-phenyl)-5-fluoro-3,4-dihydro-1H-isoquinoline-2-carboxylic acid benzyl ester | C26H24NO6F 465.16 | 1.15 LC-MS 1FA | 466.3 |
| 425 | (±)-8-[4-(1-Carboxy-ethyl)-2-ethoxy-phenyl]-5-fluoro-3,4-dihydro-1H-isoquinoline-2-carboxylic acid benzyl ester | C28H28NO5F 477.20 | 1.24 LC-MS 1FA | 478.4 |

Method C: A mixture under $N_2$ of palladium (II) acetate (0.44 mg, 2 μmol, 0.01 eq.), 2-dicyclohexylphosphino-2',6'-dimethoxybiphenyl (1.64 mg, 4 μmol, 0.02 eq.), [5-fluoro-8-(4,4,5,5-tetramethyl-[1,3,2]dioxaborolan-2-yl)-3,4-dihydro-1H-isoquinolin-2-yl]-((1R,2R)-2-phenyl-cyclopropyl)-methanone (95.4 mg, 0.2 mmol, 1.00 eq.) and potassium phosphate (85 mg, 0.4 mmol, 2.00 eq.) in toluene (0.6 mL) and water was stirred at r.t. for 2 min. A solution of [3-bromo-4-(2,2,2-trifluoro-ethoxy)-phenyl]-acetic acid ethyl ester (68.2 mg, 0.2 mmol, 1.00 eq.) in toluene (0.6 mL) was added and the mixture was stirred at 100° C. for 48 hours. The mixture was allowed to cool to r.t., filtered through celite, and concentrated in vacuo. The crude residue, redissolved in MeCN (1.3 mL) and formic acid (0.2 mL), was purified by prep. HPLC (column: Waters XBridge, 30×75 mm, 10 um, UV/MS, acidic conditions) and evaporated. To a solution of the previous ester in DMF (1 mL), 2M aq. NaOH soln. (0.4 mL) was added. The resulting solution was stirred at r.t. for 18 hours.

Formic acid (0.2 mL) was added. The mixture was purified by prep. HPLC (column: Waters XBridge, 19×30 mm, 5 um, UV/MS, acidic conditions) and evaporated to give the desired acid as a colorless oil.

Listed in Table 29 below are examples of compounds of Formula (I), prepared according to the above-mentioned method with the corresponding halogenated compound 9 as starting material.

TABLE 29

| Example | Compound of Formula (I) | Formula MW | $t_R$ [min] LC-MS Method | MS-data m/z [M + H]$^+$ |
|---|---|---|---|---|
| 426 | [3-[5-Fluoro-2-((1R,2R)-2-phenyl-cyclopropanecarbonyl)-1,2,3,4-tetrahydro-isoquinolin-8-yl]-4-(2,2,2-trifluoro-ethoxy)-phenyl]-acetic acid | C29H25NO4F4 527.17 | 1.18 LC-MS 1FA | 528.3 |
| 427 | {4-(2-Fluoro-ethoxy)-3-[5-fluoro-2-((1R,2R)-2-phenyl-cyclopropanecarbonyl)-1,2,3,4-tetrahydro-isoquinolin-8-yl]-phenyl}-acetic acid | C29H27NO4F2 491.19 | 1.10 LC-MS 1FA | 492.4 |

TABLE 29-continued

| Example | Compound of Formula (I) | Formula MW | $t_R$ [min] LC-MS Method | MS-data m/z [M + H]$^+$ |
|---|---|---|---|---|
| 428 | {4-tert-Butoxy-3-[5-fluoro-2-((1R,2R)-2-phenyl-cyclopropanecarbonyl)-1,2,3,4-tetrahydro-isoquinolin-8-yl]-phenyl}-acetic acid | C31H32NO4F 501.23 | 1.25 LC-MS 1FA | 502.4 |
| 429 | 1-{3-[5-Fluoro-2-((1R,2R)-2-phenyl-cyclopropanecarbonyl)-1,2,3,4-tetrahydro-isoquinolin-8-yl]-4-methoxy-phenyl}-cyclopropanecarboxylic acid | C30H28NO4F 485.20 | 1.17 LC-MS 1FA | 486.4 |

EXAMPLE 430

8-(5-Carboxymethyl-2-cyclopropoxy-phenyl)-5-fluoro-3,4-dihydro-1H-isoquinoline-2-carboxylic acid benzyl ester (C28H26NO5F, MW=475.18)

A mixture under N$_2$ of palladium (II) acetate (0.4 mg, 2 µmol, 0.01 eq.), 2-dicyclohexylphosphino-2',6'-dimethoxybiphenyl (1.7 mg, 4 µmol, 0.02 eq.), 5-fluoro-8-(4,4,5,5-tetramethyl-[1,3,2]dioxaborolan-2-yl)-3,4-dihydro-1H-isoquinoline-2-carboxylic acid benzyl ester (82.3 mg, 0.2 mmol, 1.00 eq.) and potassium phosphate (84.9 mg, 0.4 mmol, 2.00 eq.) in toluene (0.6 mL) and water (35 µL) was stirred at r.t. during 2 min. A solution of (3-chloro-4-cyclopropoxy-phenyl)-acetic acid tert-butyl ester (57 mg, 0.2 mmol, 1.00 eq.) in toluene (0.6 mL) was added and the mixture was stirred at 100° C. for 18 hours. The mixture was allowed to cool to r.t., filtered through celite, and concentrated in vacuo. The residue, redissolved in MeCN (1.8 mL) and formic acid (0.2 mL), was purified by prep. HPLC (column: Waters XBridge, 30×75 mm, 10 um, UV/MS, acidic conditions) and evaporated. Trifluoroacetic acid (0.23 mL) was slowly added to an ice-cooled solution of the previous tert-butyl ester in DCM (0.23 mL). The reaction mixture was stirred at r.t. for 1.5 hours. The mixture was concentrated in vacuo without heating and the residue was redissolved in DMF (1.3 mL). Formic acid (0.2 mL) was added. The crude mixture was purified by prep. HPLC (column: Waters XBridge, 30×75 mm, 10 um, UV/MS, acidic conditions) and evaporated to give the title compound as a white foam.

LC-MS 1FA: $t_R$=1.20 min; [M+H]$^+$=476.4

EXAMPLE 431

8-(5-Carboxymethyl-2-isopropoxy-phenyl)-5-cyano-3,4-dihydro-1H-isoquinoline-2-carboxylic acid benzyl ester (C29H28N2O5, MW=484.20)

A mixture under N$_2$ of palladium(II) acetate (0.21 mg, 0.9 µmol, 0.01 eq.), 2-dicyclohexylphosphino-2',6'-dimethoxybiphenyl (0.78 mg, 1.9 mmol, 0.02 eq.), [4-isopropoxy-3-(4,4,5,5-tetramethyl-[1,3,2]dioxaborolan-2-yl)-phenyl]-acetic acid ethyl ester (34 mg, 94.3 µmol, 1.00 eq.) and potassium phosphate (40 mg, 0.19 mmol, 2.00 eq.) in toluene (0.3 mL) and water (0.04 mL) was stirred at r.t. for 2 min. A solution of 8-chloro-5-cyano-3,4-dihydro-1H-isoquinoline-2-carboxylic acid benzyl ester (32.1 mg, 94.3 µmol, 1.00 eq.) in toluene (0.3 mL) was added and the mixture was stirred at 100° C. for 48 hours. The mixture was allowed to cool to r.t., filtered through celite, and concentrated in vacuo. The residue, redissolved in MeCN/H$_2$O (1.6 mL) and formic acid (0.2 mL), was purified by prep. HPLC (column: Waters XBridge, 30×75 mm, 10 um, UV/MS, acidic conditions) and evaporated. The residue was redissolved in DMF (0.45 mL) and 2M aq. NaOH soln. (0.2 mL) was added. The resulting mixture was stirred at r.t. for 1 hour. Formic acid (0.2 mL) was added. The crude mixture was purified by prep. HPLC (column: Waters XBridge, 30×75 mm, 10 um, UV/MS, acidic conditions) and evaporated to give the title compound as a milky oil.

LC-MS 1FA: $t_R$=1.17 min; [M+H]$^+$=485.4

Urea Formation and Subsequent Saponification

Method A: To a solution of [4-ethoxy-3-(5-fluoro-1,2,3,4-tetrahydro-isoquinolin-8-yl)-phenyl]-acetic acid ethyl ester (40 mg, 0.11 mmol, 1.00 eq.) and NEt$_3$ (47 µL, 0.34 mmol, 3.00 eq.) in MeCN (1 mL), 2-fluorobenzyl isocyanate (18 mg, 0.12 mmol, 1.05 eq.) in MeCN (1 mL) was added. The mixture was stirred at r.t. for 18 hours. 2M aq. NaOH soln. (0.50 mL) was added. The mixture was stirred at r.t. for 18 hours. The solution was neutralized with formic acid (1 mL) and then purified by prep. HPLC (column: Atlantis, 30×75 mm, 10 um, UV/MS, acidic conditions) and concentrated in vacuo to give the desired acid as a white solid.

Listed in Table 30 below are examples of compounds of Formula (I), prepared according to the above-mentioned method with the corresponding compound of Structure 2 and the corresponding isocyanate as starting materials.

TABLE 30

| Example | Compound of Formula (I) | Formula MW | $t_R$ [min] LC-MS Method | MS-data m/z [M + H]$^+$ |
|---|---|---|---|---|
| 432 | {4-Ethoxy-3-[5-fluoro-2-(2-fluoro-benzylcarbamoyl)-1,2,3,4-tetrahydro-isoquinolin-8-yl]-phenyl}-acetic acid | C27H26N2O4F2 480.19 | 1.08 LC-MS 1FA | 481.3 |

TABLE 30-continued

| Example | Compound of Formula (I) | Formula MW | $t_R$ [min] LC-MS Method | MS-data m/z [M + H]$^+$ |
|---|---|---|---|---|
| 433 | {4-Ethoxy-3-[5-fluoro-2-(3-fluoro-benzylcarbamoyl)-1,2,3,4-tetrahydro-isoquinolin-8-yl]-phenyl}-acetic acid | C27H26N2O4F2 480.19 | 1.08 LC-MS 1FA | 481.3 |
| 434 | {4-Ethoxy-3-[5-fluoro-2-(4-fluoro-benzylcarbamoyl)-1,2,3,4-tetrahydro-isoquinolin-8-yl]-phenyl}-acetic acid | C27H26N2O4F2 480.19 | 1.08 LC-MS 1TFA | 481.3 |
| 435 | [4-Ethoxy-3-(5-fluoro-2-phenethylcarbamoyl-1,2,3,4-tetrahydro-isoquinolin-8-yl)-phenyl]-acetic acid | C28H29N2O4F 476.21 | 1.10 LC-MS 1FA | 477.4 |
| 436 | {3-[2-(2-Chloro-benzylcarbamoyl)-5-fluoro-1,2,3,4-tetrahydro-isoquinolin-8-yl]-4-ethoxy-phenyl}-acetic acid | C27H26N2O4ClF 496.16 | 1.12 LC-MS 1FA | 497.3 |
| 437 | {4-Ethoxy-3-[5-fluoro-2-(2-methoxy-benzylcarbamoyl)-1,2,3,4-tetrahydro-isoquinolin-8-yl]-phenyl}-acetic acid | C28H29N2O5F 492.21 | 1.08 LC-MS 1FA | 493.3 |
| 438 | [3-(2-Benzylcarbamoyl-5-fluoro-1,2,3,4-tetrahydro-isoquinolin-8-yl)-4-ethoxy-phenyl]-acetic acid | C27H27N2O4F 462.20 | 1.07 LC-MS 1TFA | 463.3 |
| 439 | [4-Ethoxy-3-(5-fluoro-2-propylcarbamoyl-1,2,3,4-tetrahydro-isoquinolin-8-yl)-phenyl]-acetic acid | C23H27N2O4F 414.20 | 1.00 LC-MS 1FA | 415.4 |
| 440 | {3-Ethoxy-4-[5-fluoro-2-(2-fluoro-benzylcarbamoyl)-1,2,3,4-tetrahydro-isoquinolin-8-yl]-phenyl}-acetic acid | C27H26N2O4F2 480.19 | 1.08 LC-MS 1FA | 481.3 |
| 441 | {3-Ethoxy-4-[5-fluoro-2-(3-fluoro-benzylcarbamoyl)-1,2,3,4-tetrahydro-isoquinolin-8-yl]-phenyl}-acetic acid | C27H26N2O4F2 480.19 | 1.08 LC-MS 1FA | 481.3 |
| 442 | {3-Ethoxy-4-[5-fluoro-2-(4-fluoro-benzylcarbamoyl)-1,2,3,4-tetrahydro-isoquinolin-8-yl]-phenyl}-acetic acid | C27H26N2O4F2 480.19 | 1.08 LC-MS 1FA | 481.4 |
| 443 | [3-Ethoxy-4-(5-fluoro-2-phenethylcarbamoyl-1,2,3,4-tetrahydro-isoquinolin-8-yl)-phenyl]-acetic acid | C28H29N2O4F 476.21 | 1.10 LC-MS 1FA | 477.4 |
| 444 | {4-[2-(2-Chloro-benzylcarbamoyl)-5-fluoro-1,2,3,4-tetrahydro-isoquinolin-8-yl]-3-ethoxy-phenyl}-acetic acid | C27H26N2O4ClF 496.16 | 1.12 LC-MS 1FA | 497.3 |
| 445 | {3-Ethoxy-4-[5-fluoro-2-(2-methoxy-benzylcarbamoyl)-1,2,3,4-tetrahydro-isoquinolin-8-yl]-phenyl}-acetic acid | C28H29N2O5F 492.21 | 1.09 LC-MS 1FA | 493.3 |
| 446 | [4-(2-Benzylcarbamoyl-5-fluoro-1,2,3,4-tetrahydro-isoquinolin-8-yl)-3-ethoxy-phenyl]-acetic acid | C27H27N2O4F 462.20 | 1.07 LC-MS 1FA | 463.4 |
| 447 | [3-Ethoxy-4-(5-fluoro-2-propylcarbamoyl-1,2,3,4-tetrahydro-isoquinolin-8-yl)-phenyl]-acetic acid | C23H27N2O4F 414.20 | 1.01 LC-MS 1FA | 415.4 |

Method B: 2-(Aminomethyl)pyridine (15 µL, 0.14 mmol, 1.00 eq.) was dissolved in MeCN (1 mL). N-Ethyldiisopropylamine (72 µL, 0.42 mmol, 3.00 eq.) was added followed by 1,1'-carbonyldiimidazole (24 mg, 0.15 mmol, 1.05 eq.). The resulting mixture was stirred at 45° C. for 3 hours. [3-Ethoxy-4-(5-fluoro-1,2,3,4-tetrahydro-isoquinolin-8-yl)-phenyl]-acetic acid ethyl ester (50 mg, 0.14 mmol, 1.00 eq.) was added and the mixture was heated to 70° C. for 18 hours. The reaction mixture was partially purified by prep. HPLC (column: Water X-Bridge, 30×75 mm, 10 um, UV/MS, basic conditions) and concentrated in vacuo. To a solution of the residue in DMF (0.50 mL), 2M aq. NaOH soln. (0.50 mL) was added. The resulting solution was stirred at r.t. for 18 hours. The solution was neutralized with formic acid (1.00 mL), filtered and then purified by prep. HPLC (column: Atlantis, 30×75 mm, 10 um, UV/MS, acidic conditions) and concentrated in vacuo to give the desired acid as a white solid.

Listed in Table 31 below are examples of compounds of Formula (I), prepared according to the above-mentioned method with the corresponding compound of Structure 2 as starting material.

TABLE 31

| Example | Compound of Formula (I) | Formula MW | $t_R$ [min] LC-MS Method | MS-data m/z [M + H]$^+$ |
|---|---|---|---|---|
| 448 | (3-Ethoxy-4-{5-fluoro-2-[(pyridin-2-ylmethyl)-carbamoyl]-1,2,3,4-tetrahydro-isoquinolin-8-yl}-phenyl)-acetic acid | C26H26N3O4F 463.19 | 0.80 LC-MS 1FA | 464.4 |
| 449 | (4-Ethoxy-3-{5-fluoro-2-[(pyridin-2-ylmethyl)-carbamoyl]-1,2,3,4-tetrahydro-isoquinolin-8-yl}-phenyl)-acetic acid | C26H26N3O4F 463.19 | 0.80 LC-MS 1FA | 464.4 |

Synthesis of Precursors and Intermediates
General Method for the Synthesis of the Nitrostyrenes 19

5-Chloro-2-(trifluoromethyl)benzaldehyde (10.75 g, 50.0 mmol, 1.00 eq.) was dissolved in nitromethane (30 mL). Molecular sieves (4 A 961 mg), butylamine (0.59 mL, 5.9 mmol, 0.12 eq.) and acetic acid (0.58 mL, 10.2 mmol, 0.20 eq.) were added and the mixture was stirred at 95° C. for 1 hour. The mixture was transferred into a new flask to remove the mol. sieves. The solvent was removed in vacuo. The residue was purified by flashmaster (column: 100 g, flow: 40 mL/min, 30 fractions of 40 mL, Heptane to Heptane+12% AcOEt) to yield the desired nitrostyrene as a brown oil.

Listed in Table 32 below are nitrostyrenes 19, prepared according to the above-mentioned method, with corresponding benzaldehyde 20, 22, or 26 as starting material.

TABLE 32

| Nitrostyrenes 19 | Formula MW | $t_R$ [min] LC-MS Method | MS-data m/z [M + H]$^+$ |
|---|---|---|---|
| 4-Chloro-2-((E)-2-nitro-vinyl)-1-trifluoromethyl-benzene | C9H5NO2ClF3 251.00 | 0.94 LC-MS 3 | no ionization |
| 4-Bromo-1-fluoro-2-((E)-2-nitro-vinyl)-benzene | C8H5NO2BrF 244.95 | 0.89 LC-MS 3 | no ionization |
| 4-Bromo-1-chloro-2-((E)-2-nitro-vinyl)-benzene | C8H5NO2BrCl 260.92 | 0.94 LC-MS 3 | no ionization |
| 4-Bromo-1-methyl-2-((E)-2-nitro-vinyl)-benzene | C9H8NO2Br 240.97 | 0.92 LC-MS 3 | no ionization |
| 1-Bromo-4-chloro-2-((E)-2-nitro-vinyl)-benzene | C8H5NO2BrCl 260.92 | 0.93 LC-MS 3 | no ionization |
| 1-Bromo-4-methoxy-2-((E)-2-nitro-vinyl)-benzene | C9H8NO3Br 260.92 | 0.92 LC-MS 3 | no ionization |
| 1-Bromo-4-fluoro-2-((E)-2-nitro-vinyl)-benzene | C8H5NO2BrF 244.95 | 0.89 LC-MS 3 | no ionization |
| 1-Fluoro-4-methoxy-2-((E)-2-nitro-vinyl)-benzene | C9H8NO3F 197.05 | 0.86 LC-MS 3 | no ionization |

General Method for the Preparation of the Phenethylamines (or the Corresponding Hydrochloride Salt) 18

Sulfuric acid (1.78 mL) was added dropwise to a stirred suspension of LiAlH$_4$ (2.66 g, 66.55 mmol, 4.46 eq.) in THF (100 mL) under ice-cooling. After stirring for 20 min, a solution of 4-chloro-2-((E)-2-nitro-vinyl)-1-trifluoromethyl-benzene (4.02 g, 14.91 mmol, 1.00 eq.) in THF (10.5 mL) was added dropwise within 20 min under ice-cooling. After 10 min, the cooling bath was removed and the mixture was warmed up gently by using a heat gun until the mixture gently boiled. After 5 min the mixture was again cooled to 0° C. and carefully hydrolyzed by the dropwise addition of iPrOH (11 mL) and then 2M aq. NaOH soln. (8.2 mL). The resulting suspension was filtered off and the filter cake was rinsed with THF. The filtrate was concentrated in vacuo to give the desired phenethylamine.

The free amine was dissolved in Et$_2$O (54 mL) and iPrOH (2.1 mL) and acidified with 2M HCl in Et$_2$O soln. (29 mL). The suspension was filtered off and the filter cake was rinsed with Et$_2$O. The resulting white solid was dried under h.v. The HCl salt was used without further purification.

Listed in Table 33 below are phenethylamines 18 or phenethylamine hydrochlorides 18, prepared according to the above-mentioned method, with corresponding nitrostyrenes 19 as starting material.

TABLE 33

| Intermediates 18 | Formula MW | $t_R$ [min] LC-MS Method | MS-data m/z [M + H]$^+$ |
|---|---|---|---|
| 2-(5-Chloro-2-trifluoromethyl-phenyl)-ethylamine hydrochloride | C9H9NClF3 223.04 | 0.59 LC-MS 3 | no ionization |
| 2-(5-Bromo-2-fluoro-phenyl)-ethylamine hydrochloride | C8H9NBrF 216.99 | 0.50 LC-MS 3 | 218.2 |
| 2-(5-Bromo-2-chloro-phenyl)-ethylamine hydrochloride | C8H9NBrCl 232.96 | 0.55 LC-MS 3 | 234.2 |

TABLE 33-continued

| Intermediates 18 | Formula MW | $t_R$ [min] LC-MS Method | MS-data m/z [M + H]+ |
|---|---|---|---|
| 2-(5-Bromo-2-methyl-phenyl)-ethylamine hydrochloride | C9H12NBr 213.02 | 0.56 LC-MS 3 | no ionization |
| 2-(2-Bromo-5-chloro-phenyl)-ethylamine hydrochloride | C8H9NBrCl 232.96 | 0.55 LC-MS 3 | 234.1 |
| 2-(2-Bromo-5-methoxy-phenyl)-ethylamine hydrochloride | C9H12NOBr 229.01 | 0.53 LC-MS 3 | 230.3 |
| 2-(2-Bromo-5-fluoro-phenyl)-ethylamine hydrochloride | C8H9NBrF 216.99 | 0.50 LC-MS 3 | 218.2 |
| 2-(2-Fluoro-5-methoxy-phenyl)-ethylamine | C9H12NOF 169.09 | 0.45 LC-MS 3 | 170.2 |

General Method for the Synthesis of the 3,4-Dihydroisoquinolines 16

A mixture of 2-(5-bromo-2-fluoro-phenyl)-ethylamine hydrochloride (7.65 g, 27.2 mmol, 1.0 eq.), and ethyl formiate (2.91 mL, 36.2 mmol, 1.1 eq.) was stirred at 70° C. for 6 hours. The reaction mixture was allowed to cool to r.t. and partitioned between AcOEt (150 mL) and water (150 mL). The layers were separated. The org. phase was washed with water (1×150 mL), sat. aq. NaCl soln. (1×150 mL), dried over MgSO$_4$, filtered, and concentrated in vacuo to give the corresponding formamide.

The formamide was dissolved in DCM (272 mL). Oxalyl chloride (2.59 mL, 30.0 mmol, 1.1 eq.) was added. The mixture was stirred at r.t. for 30 min, then cooled to −10° C. Iron-(III)-chlorid anhydrous (5.3 g, 32.7 mmol, 1.2 eq.) was added to the cold mixture. The resulting mixture was allowed to slowly warm to r.t. and stirred at r.t. for 4 hours. The reaction was quenched with 2M aq. HCl soln. (272 mL) and the biphasic system was stirred at r.t. for 1 hour. The layers were separated. The aq. phase was extracted with DCM (1×150 mL). The comb. org. phases were washed with sat. aq. NaCl soln. (1×150 mL), dried over MgSO$_4$, filtered, and concentrated in vacuo to give the oxazolo intermediate.

The oxazolo intermediate was dissolved in MeOH (310 mL) and conc. H$_2$SO$_4$ (16.4 mL). The resulting mixture was refluxed for 18 hours. The mixture was allowed to cool to r.t. and concentrated in vacuo. The residue was partitioned between water (150 mL) and AcOEt (150 mL). The layers were separated. The org. phase was extracted with 2M aq. HCl soln. (2×70 mL). The comb. 3 acidic aq. phases were basified with 25% NH$_3$ and extracted with DCM (3×150 mL). The comb. org. phases were washed with sat. aq. NaCl soln. (1×150 mL), dried over MgSO$_4$, filtered, and concentrated in vacuo. The residue was purified by flashmaster (column: 100 g, flow: 45 mL/min, 30 fractions of 45 mL, Heptane+5% AcOEt to Heptane+30% AcOEt) to yield the desired 3,4-dihydroisoquinoline as a yellow oil.

Listed in Table 34 below are 3,4-dihydroisoquinolines 16, prepared according to the above-mentioned method, with corresponding phenethylamines 18 or phenethylamines hydrochloride salt 18 as starting material.

TABLE 34

| 3,4-Dihydroisoquinolines 16 | Formula MW | $t_R$ [min] LC-MS Method | MS-data m/z [M + H]+ |
|---|---|---|---|
| 8-Bromo-5-fluoro-3,4-dihydro-isoquinoline | C9H7NBrF 226.98 | 0.41 LC-MS 3 | 228.1 |
| 8-Chloro-5-trifluoromethyl-3,4-dihydro-isoquinoline | C10H7NClF3 233.02 | 0.53 LC-MS 3 | 233.9 |
| 8-Bromo-5-chloro-3,4-dihydro-isoquinoline | C9H7NBrCl 242.95 | 0.48 LC-MS 3 | 244.1 |
| 8-Bromo-5-methoxy-3,4-dihydro-isoquinoline | C10H10NOBr 239.00 | 0.48 LC-MS 3 | 240.1 |
| 8-Bromo-5-methyl-3,4-dihydro-isoquinoline | C10H10NBr 223.00 | 0.48 LC-MS 3 | 224.2 |
| 5-Bromo-8-chloro-3,4-dihydro-isoquinoline | C9H7NBrCl 242.95 | 0.49 LC-MS 3 | 244.1 |
| 5-Bromo-8-fluoro-3,4-dihydro-isoquinoline | C9H7NBrF 226.98 | 0.43 LC-MS 3 | 228.2 |

Synthesis of 5-bromo-8-methoxy-3,4-dihydro-isoquinoline (C10H10NOBr, MW=239.00)

A mixture of 2-(2-bromo-5-methoxy-phenyl)-ethylamine hydrochloride (1.50 g, 4.07 mmol, 1.00 eq.) and triethylamine (1.14 mL, 8.16 mmol, 2.01 eq.) in ethyl formiate (28 mL) was refluxed for 2 hours. The solvent was removed in vacuo and the residue was partitioned between AcOEt (20 mL) and water (20 mL). The layers were separated. The org. phase was washed with water (1×20 mL), sat. aq. NaCl soln. (1×20 mL), dried over MgSO$_4$, filtered, and concentrated in vacuo to give the desired formamide. The residue was stirred at 140° C. in polyphosphoric acid (22 g) for 3 hours. After cooling to r.t. the mixture was basified with 2M aq. NaOH soln. and extracted with DCM. The org. layer was then dried over MgSO$_4$, filtered, and concentrated in vacuo. The residue was purified by flashmaster (column: 100 g, flow: 45 mL/min, 23 fractions of 45 mL, Heptane+50% AcOEt to Heptane+70% AcOEt) to yield the title compound as an orange oil that solidified upon standing. LC-MS 3: $t_R$=0.50 min; [M+H]+=240.2

General Method for the Synthesis of the Tetrahydroisoquinoline (or the Corresponding Hydrochloride Salt) 17

To an ice-cooled solution of 8-bromo-5-fluoro-3,4-dihydro-isoquinoline (3.56 g, 15.5 mmol, 1 eq.) in MeOH (156 mL), NaBH$_4$ (1.22 g, 31.0 mmol, 2 eq.) was added. The mixture was stirred at 0° C. for 20 min. The reaction mixture was concentrated in vacuo. The residue was partitioned between water and AcOEt. The layers were separated and the aq. phase was extracted with AcOEt (2×). The comb. org. phases were dried over MgSO$_4$, filtered, and concentrated in vacuo to give the desired tetrahydroisoquinoline.

The free amine was dissolved in 4M HCl in dioxane (60 mL). The resulting solid precipitate was filtered, washed with Et$_2$O, and dried under h.v to afford the tetrahydroisoquinoline salt as a white solid.

Listed in Table 35 below are tetrahydroisoquinolines 17 and tetrahydroisoquinoline hydrochlorides 17, prepared according to the above-mentioned method, with corresponding 3,4-dihydroisoquinolines 16 as starting material.

TABLE 35

| Intermediates 17 | Formula MW | $t_R$ [min] LC-MS Method | MS-data m/z [M + H]$^+$ |
|---|---|---|---|
| 8-Bromo-5-fluoro-1,2,3,4-tetrahydro-isoquinoline | C9H9NBrF 228.99 | 0.47 LC-MS 3 | 230.2 |
| 8-Bromo-5-methoxy-1,2,3,4-tetrahydro-isoquinoline | C10H12NOBr 241.01 | 0.52 LC-MS 3 | 241.9 |
| 8-Bromo-5-chloro-1,2,3,4-tetrahydro-isoquinoline | C9H9NBrCl 244.96 | 0.52 LC-MS 3 | 246.1 |
| 8-Chloro-5-trifluoromethyl-1,2,3,4-tetrahydro-isoquinoline | C10H9NClF3 235.04 | 0.55 LC-MS 3 | 235.3 |
| 8-Bromo-5-methyl-1,2,3,4-tetrahydro-isoquinoline | C10H12NBr 225.02 | 0.52 LC-MS 3 | 226.2 |
| 8-Bromo-5-chloro-1,2,3,4-tetrahydro-isoquinoline hydrochloride | C9H9NBrCl 244.96 | 0.52 LC-MS 3 | 246.1 |
| 5-Bromo-8-chloro-1,2,3,4-tetrahydro-isoquinoline hydrochloride | C9H9NBrCl 244.96 | 0.54 LC-MS 3 | no ionization |
| 8-Bromo-5-fluoro-1,2,3,4-tetrahydro-isoquinoline hydrochloride | C9H9NBrF 228.99 | 0.48 LC-MS 3 | 230.1 |
| 5-Bromo-8-fluoro-1,2,3,4-tetrahydro-isoquinoline | C9H9NBrF 228.99 | 0.48 LC-MS 3 | 230.2 |

General Method for the Synthesis of Boc-protected Tetrahydroisoquinolines 7-A

To a solution of 8-chloro-5-trifluoromethyl-1,2,3,4-tetrahydro-isoquinoline (908 mg, 3.69 mmol, 1.00 eq.) and triethylamine (0.51 mL, 3.69 mmol, 1.00 eq.) in DCM (11.5 mL), a solution of di-tert-butyl dicarbonate (821 mg, 3.76 mmol, 1.02 eq.) in DCM (11.5 mL) was added under N$_2$. The resulting mixture was stirred at r.t. for 18 hours. The solvent was removed in vacuo and the residue was partitioned between AcOEt and water. The org. layer was washed once with water, dried over MgSO$_4$, filtered, and concentrated in vacuo to give the Boc-protected tetrahydroisoquinoline as a yellow oil that solidifies upon standing. The product was used without further purification.

Listed in Table 36 below are Boc-protected tetrahydroisoquinolines 7-A, prepared according to the above-mentioned method, with corresponding tetrahydroisoquinolines 17 (or the corresponding hydrochloride salt) as starting material.

TABLE 36

| Intermediates 7-A | Formula MW | $t_R$ [min] LC-MS Method | MS-data m/z [M + H]$^+$ |
|---|---|---|---|
| 8-Chloro-5-trifluoromethyl-3,4-dihydro-1H-isoquinoline-2-carboxylic acid tert-butyl ester | C15H17NO2ClF3 335.09 | 1.03 LC-MS 3 | no ionization |
| 8-Bromo-5-fluoro-3,4-dihydro-1H-isoquinoline-2-carboxylic acid tert-butyl ester | C14H17NO2BrF 329.04 | 0.99 LC-MS 3 | no ionization |

General Method for the Synthesis of Cbz-protected Tetrahydroisoquinolines 7-A

To an ice-cooled solution of 8-bromo-5-fluoro-1,2,3,4-tetrahydro-isoquinoline (2.53 g, 10.6 mmol, 1.0 eq.) and triethylamine (4.43 mL, 31.8 mmol, 3.0 eq.) in DCM (284 mL), benzyl chloroformate (1.75 mL, 11.7 mmol, 1.1 eq.) was added dropwise. Upon completion of the addition, the cooling bath was removed and the suspension was stirred at r.t. for 2 hours. The reaction was quenched with 1M aq. citric acid soln. (265 mL). The layers were separated. The aq. phase was extracted with DCM (3×). The comb. org. phases were dried over $MgSO_4$, filtered and concentrated in vacuo. The residue was purified by flashmaster (column: 100 g, flow: 45 mL/min, 25 fractions of 45 mL, Heptane 100% to Heptane+15% AcOEt) to yield the Cbz-protected tetrahydroisoquinoline as a pale yellow oil.

Listed in Table 37 below are Cbz-protected tetrahydroisoquinolines 7-A, prepared according to the above-mentioned method, with corresponding tetrahydroisoquinolines (or the corresponding hydrochloride salt) 17 as starting material.

TABLE 37

| Intermediates 7-A | Formula MW | $t_R$ [min] LC-MS Method | MS-data m/z $[M + H]^+$ |
|---|---|---|---|
| 8-Bromo-5-fluoro-3,4-dihydro-1H-isoquinoline-2-carboxylic acid benzyl ester | C17H15NO2BrF 363.03 | 0.98 LC-MS 3 | 364.1 |
| 8-Bromo-5-methoxy-3,4-dihydro-1H-isoquinoline-2-carboxylic acid benzyl ester | C18H18NO3Br 375.05 | 1.00 LC-MS 3 | 376.1 |
| 8-Bromo-5-chloro-3,4-dihydro-1H-isoquinoline-2-carboxylic acid benzyl ester | C17H15NO2BrCl 379.00 | 1.02 LC-MS 3 | 380.0 |
| 8-Bromo-5-methyl-3,4-dihydro-1H-isoquinoline-2-carboxylic acid benzyl ester | C18H18NO2Br 359.05 | 1.01 LC-MS 3 | 360.1 |
| 8-Chloro-5-trifluoromethyl-3,4-dihydro-1H-isoquinoline-2-carboxylic acid benzyl ester | C18H15NO2ClF3 369.07 | 1.03 LC-MS 3 | 369.8 |
| 5-Bromo-8-chloro-3,4-dihydro-1H-isoquinoline-2-carboxylic acid benzyl ester | C17H15NO2BrCl 379.00 | 1.02 LC-MS 3 | 380.0 |
| 5-Bromo-8-fluoro-3,4-dihydro-1H-isoquinoline-2-carboxylic acid benzyl ester | C17H15NO2BrF 363.03 | 0.99 LC-MS 3 | 364.1 |

Synthesis of 8-hydroxy-3,4-dihydro-1H-isoquinoline-2-carboxylic acid benzyl ester (C17H17NO3, MW=283.1)

To an-ice cooled suspension of 8-hydroxy-1,2,3,4-tetrahydroisoquinoline hydrochloride (746 mg, 5.0 mmol, 1.0 eq.) and triethylamine (2.13 mL, 15.0 mmol, 3.0 eq.) in DCM (25 mL), benzyl chloroformate (0.83 mL, 5.5 mmol, 1.1 eq.) was added dropwise. The solution was stirred at 0° C. for 1 hour and further at r.t. for 4 hours. The reaction was quenched with 1M aq. citric acid soln. (50 mL). The layers were separated. The aq. phase was extracted with DCM (3×50 mL). The comb. org. phases were dried over $Na_2SO_4$ and concentrated in vacuo. The residue was dissolved in THF (20 mL) and 1M aq. NaOH soln. (6 mL) was added. The mixture was stirred at r.t. for 68 hours. The org. solvent was removed in vacuo. The resulting aq. layer was acidified with 2N aq. HCl soln. and extracted with DCM (3×25 ml). The comb. org. phases were dried over $MgSO_4$ and concentrated in vacuo. The residue was purified by CC ($SiO_2$, Hept/AcOEt 8:2 to 7:3) to give the title compound as a white solid.

LC-MS 2: $t_R$=0.78 min; $[M+H]^+$=284.1

Synthesis of 5-bromo-8-hydroxy-3,4-dihydro-1H-isoquinoline-2-carboxylic acid benzyl ester (C17H16NO3Br, MW=361.03)

A solution of 5-bromo-8-methoxy-3,4-dihydro-isoquinoline (312 mg, 1.3 mmol, 1.0 eq.) in chlorobenzene (18.4 mL) was treated with aluminium chloride (520 mg, 3.9 mmol, 3.0 eq.) and stirred at 130° C. for 1 hour. After cooling to r.t., sat. aq. $NaHCO_3$ soln. was added and the mixture was extracted with AcOEt (2×). The combined org. layers were dried over $MgSO_4$, filtered, and concentrated in vacuo. The residue was partially purified by flashmaster (column: 25 g, flow: 30 mL/min, 25 fractions of 30 mL, AcOEt+10% MeOH) to yield a yellow oil. To an ice-cooled solution of the residue in MeOH (13.1 mL), $NaBH_4$ (98 mg, 2.6 mmol, 2.0 eq.) was added. The mixture was stirred at 0° C. for 30 min. The reaction mixture was concentrated in vacuo. The residue was partitioned between water and AcOEt. The layers were separated and the aq. phase was extracted with AcOEt (2×). The comb. org. phases were dried over $MgSO_4$, filtered, and concentrated in vacuo. To an ice-cooled solution of the residue and triethylamine (0.54 mL, 3.9 mmol, 3.0 eq.) in DCM (36 mL), benzyl chloroformate (0.21 mL, 1.43 mmol, 1.1 eq.) was added dropwise. Upon completion of the addition, the cooling bath was removed and the suspension was stirred at r.t. for 4 hours. The reaction was quenched with 1M aq. citric acid soln. (36 mL). The layers were separated. The aq. phase was extracted with DCM (3×). The comb. org. phases were dried over $MgSO_4$, filtered and concentrated in vacuo. The residue was purified by flashmaster (column: 25 g, flow: 30 mL/min, 27 fractions of 30 mL, Heptane 100% to Heptane+20% AcOEt). The residue was dissolved in THF (5 mL) and 1M aq. NaOH soln. (5 mL) was added. The mixture was stirred at r.t. for 18 hours. The org. solvent was removed in vacuo. The resulting aq. layer was acidified with 2N aq. HCl soln. and extracted with DCM (3×10 ml). The comb. org. phases were dried over $MgSO_4$ and concentrated in vacuo to give the title compound as a beige solid.

LC-MS 3: $t_R$=0.90 min; $[M+H]^+$=362.2

Synthesis of 5-cyano-8-hydroxy-3,4-dihydro-1H-isoquinoline-2-carboxylic acid benzyl ester (C18H16N2O3, MW=308.12)

To a solution of 5-bromo-8-hydroxy-3,4-dihydro-1H-isoquinoline-2-carboxylic acid benzyl ester (123 mg, 0.31 mmol, 1.0 eq.) in DMAC (0.62 mL), zinc cyanide (18 mg, 0.16 mmol, 0.5 eq.), tris(dibenzylideneacetone)dipalladium (0) (6.2 mg, 7 µmol, 0.02 eq.), 1,1'-bis-(diphenylphosphino)-ferrocene (4.7 mg, 8 µmol, 0.03 eq.) and poly(methylhydrosiloxane) (6 µL) were added. The resulting mixture was stirred at 150° C. under microwave irradiation for 30 min. The reaction mixture was diluted with AcOEt and water was added. The layers were separated and the org. layer was dried over MgSO$_4$, filtered over celite, and concentrated in vacuo. The residue was purified by flashmaster (column: 10 g, flow: 15 mL/min, 25 fractions of 15 mL, Heptane+5% AcOEt to Heptane+40% AcOEt) to yield the title compound as a beige solid.

LC-MS 3: t$_R$=0.84 min; [M+H]$^+$=309.1

Synthesis of 8-chloro-5-cyano-3,4-dihydro-1H-isoquinoline-2-carboxylic acid benzyl ester (C18H15N2O2Cl, MW=326.08)

To a solution of 5-bromo-8-chloro-3,4-dihydro-1H-isoquinoline-2-carboxylic acid benzyl ester (381 mg, 1.00 mmol, 1.00 eq.) in DMAC (2 mL), zinc cyanide (59 mg, 0.50 mmol, 0.50 eq.), tris(dibenzylideneacetone)dipalladium(O) (20 mg, 0.02 mmol, 0.02 eq.), 1,1'-bis-(diphenylphosphino)-ferrocene (15 mg, 0.03 mmol, 0.03 eq.) and poly(methylhydrosiloxane) (20 µL) were added. The resulting mixture was stirred at 150° C. under microwave irradiation for 30 min. The mixture was allowed to cool to r.t. To the previous mixture, zinc cyanide (59 mg, 0.50 mmol, 0.50 eq.), tris(dibenzylideneacetone)dipalladium(O) (20 mg, 0.02 mmol, 0.02 eq.), 1,1'-bis-(diphenylphosphino)-ferrocene (15 mg, 0.03 mmol, 0.03 eq.) and poly(methylhydrosiloxane) (20 µL) were added. The resulting mixture was stirred at 150° C. under microwave irradiation for 30 min. The reaction mixture was diluted with AcOEt and water was added. The layers were separated and the org. layer was dried over MgSO$_4$, filtered over celite, and concentrated in vacuo. The residue was purified by flashmaster (column: 25 g, flow: 30 mL/min, 40 fractions of 30 mL, Heptane+5% AcOEt to Heptane+30% AcOEt) to yield the title compound as a yellow oil.

LC-MS 3: t$_R$=0.95 min; [M+H]$^+$=327.0

Synthesis of 8-chloro-5-methanesulfonyl-3,4-dihydro-1H-isoquinoline-2-carboxylic acid benzyl ester (C18H18NO4ClS, MW=379.07)

A mixture under Ar of 5-bromo-8-chloro-3,4-dihydro-1H-isoquinoline-2-carboxylic acid benzyl ester (190 mg, 0.5 mmol, 1.0 eq.), sodium methanesulfinate (72 mg, 0.6 mmol, 1.2 eq.), L-proline (12 mg, 0.1 mmol, 0.2 eq.), 1M aq. NaOH soln. (0.1 mL, 0.1 mmol, 0.2 eq.), and copper (I) iodide (10 mg, 0.05 mmol, 0.1 eq.) in DMSO (5 mL) was stirred at 150° C. under microwave irradiations for 1 hour. The mixture was allowed to cool to r.t. and partitioned between AcOEt (125 mL), and H$_2$O (125 mL). The layers were separated and the aq. phase was extracted with AcOEt (2×125 mL). The comb. org. phases were dried over MgSO$_4$ and concentrated in vacuo. The residue was purified by prep. HPLC (column: Waters Xbridge, 30×75 mm, 10 um, UV/MS, acidic conditions) and evaporated to give the title compound as a colorless oil.

LC-MS 3: t$_R$=0.89 min; [M+H]$^+$=380.1

Synthesis of (8-Bromo-5-fluoro-3,4-dihydro-1H-isoquinolin-2-yl)-((1R,2R)-2-phenyl-cyclopropyl)-methanone (C19H17NOBrF, MW=373.05)

To a solution of (1R,2R)-2-phenyl-cyclopropanecarboxylic acid (389 mg, 2.4 mmol, 1.2 eq.) in DCM (10 mL), DIPEA (1.37 ml, 8 mmol, 4.0 eq.) and TBTU (771 mg, 2.4 mmol, 1.2 eq.) were added in sequence. The resulting solution was stirred at r.t. for 30 minutes. Then 8-bromo-5-fluoro-1,2,3,4-tetrahydro-isoquinoline hydrochloride (533 mg, 2.0 mmol, 1.0 eq.) was added and the resulting mixture was stirred at r.t. for 18 hours. The reaction mixture was poured in water (50 mL). The mixture was extracted with DCM (2×30 mL). The comb. org. phases were dried over MgSO$_4$ and concentrated in vacuo. The residue was purified by flashmaster (column: 100 g, flow: 45 mL/min, 30 fractions of 45 mL, Heptane to Heptane+50% AcOEt) to yield the title compound as a yellow oil.

LC-MS 3: t$_R$=0.96 min; [M+H]$^+$=374.0

General Method for the Synthesis of Sulfonamides 37

Step 1: A mixture of 2-chloro-4-fluorobenzaldehyde (3.17 g, 20 mmol, 1.0 eq.) and aminoacetaldehyde dimethyl acetal (2.18 mL, 20 mmol, 1.0 eq.) in toluene (50 mL) was stirred at 130° C. with concomitant removal of H$_2$O (Dean-Stark) for 2.5 hours. The mixture was concentrated in vacuo and dried under h.v. The residue was dissolved in EtOH (100 mL). The solution was cooled to 0° C. and NaBH$_4$ (1.14 g, 30 mmol, 1.5 eq.) was added portionwise. The cooling bath was removed and the solution was stirred at r.t. for 18 hours. The resulting reaction mixture was quenched with sat. aq. NaHCO$_3$ soln. (150 mL). The mixture was extracted with DCM (3×50 mL). The comb. org. phases were washed with sat. aq. NaCl soln. (1×50 mL), dried over MgSO$_4$, and concentrated in vacuo to give (2-chloro-4-fluoro-benzyl)-(2,2-dimethoxy-ethyl)-amine as a yellow oil. The product was used without further purification.

LC-MS 3: t$_R$=0.52 min; [M+H]$^+$=248.2

Step 2: To a suspension of (2-chloro-4-fluoro-benzyl)-(2,2-dimethoxy-ethyl)-amine (4.90 g, 19.8 mmol, 1.0 eq.) and NEt$_3$ (8.3 mL, 59.3 mmol, 3.0 eq.) in DCM (100 mL), a solution of p-toluenesulfonyl chloride (4.15 g, 21.8 mmol, 1.1 eq) in DCM (25 mL) was added dropwise. The solution was stirred at r.t. for 18 hours. The reaction was quenched with sat. aq. NaHCO$_3$ soln. (150 mL). The layers were separated. The aq. phase was extracted with DCM (3×50 mL). The comb. org. phases were dried over Na$_2$SO$_4$ and concentrated in vacuo. The residue was purified by flashmaster (column: 100 g, flow: 45 mL/min, 40 fractions of 45 mL, Heptane to Heptane+45% AcOEt) to yield the desired sulfonamide as a colorless oil.

Listed in Table 38 below are sulfonamides 37, prepared according to the above-mentioned method, with corresponding aldehyde 34 as starting material.

TABLE 38

| Sulfonamides 37 | Formula MW | $t_R$ [min] LC-MS Method | MS-data m/z [M + H]$^+$ |
|---|---|---|---|
| N-(2-Chloro-4-fluoro-benzyl)-N-(2,2-dimethoxy-ethyl)-4-methyl-benzenesulfonamide | C18H21NO4ClFS 401.09 | 0.98 LC-MS 3 | No ionization |
| N-(2-Chloro-4,5-difluoro-benzyl)-N-(2,2-dimethoxy-ethyl)-4-methyl-benzenesulfonamide | C18H20NO4ClF2S 419.08 | 0.99 LC-MS 3 | No ionization |
| N-(3,5-Difluoro-2-methoxy-benzyl)-N-(2,2-dimethoxy-ethyl)-4-methyl-benzenesulfonamide | C19H23NO5F2S 415.13 | 0.97 LC-MS 3 | No ionization |

General Method for the Synthesis of Isoquinolines 15-A

To a suspension of aluminiumchloride (3.32 g, 24.9 mmol, 5 eq.) in DCM (40 mL), a solution of N-(2-chloro-4-fluoro-benzyl)-N-(2,2-dimethoxy-ethyl)-4-methyl-benzene-sulfonamide (2.00 g, 4.98 mmol, 1 eq.) in DCM (15 mL) was added dropwise at r.t. The reaction mixture was stirred at r.t. for 18 hours. The reaction mixture was poured on ice (300 g). The mixture was extracted with DCM (3×200 mL). The comb. org. phases were washed with sat. aq. NaHCO$_3$ soln. (150 mL) and sat. aq. NaCl soln. (1×100 mL), dried over MgSO$_4$, and concentrated in vacuo. The residue was purified by flashmaster (column: 50 g, flow: 40 mL/min, 30 fractions of 40 mL, Heptane to Heptane+50% AcOEt) to yield the desired isoquinoline as a brown solid.

Listed in Table 39 below are isoquinolines 15-A, prepared according to the above-mentioned method, with corresponding sulfonamide 37 as starting material.

TABLE 39

| Isoquinolines 15-A | Formula MW | $t_R$ [min] LC-MS Method | MS-data m/z [M + H]$^+$ |
|---|---|---|---|
| 8-Chloro-6-fluoro-isoquinoline | C9H5NClF 181.01 | 0.52 LC-MS 3 | 182.2 |
| 8-Chloro-5,6-difluoro-isoquinoline | C9H4NClF2 199.00 | 0.74 LC-MS 3 | 200.1 |

Synthesis of 5,7-Difluoro-isoquinolin-8-ol (C9H5NOF2, MW=181.03)

To a suspension of aluminiumchlorid (3.85 g, 28.9 mmol, 5 eq.) in DCM (40 mL), N-(3,5-difluoro-2-methoxy-benzyl)-N-(2,2-dimethoxy-ethyl)-4-methyl-benzenesulfonamide (2.40 g, 5.78 mmol, 1 eq.) in DCM (15 mL) was added dropwise at r.t. The reaction mixture was stirred at r.t. for 18 hours. The reaction mixture was poured on ice (300 g). The mixture was extracted with DCM (3×200 mL). The comb. org. phases were washed with sat. aq. NaHCO$_3$ soln. (150 mL) and sat. aq. NaCl soln. (1×100 mL). The resulting suspension was filtered and the solid was rinsed with DCM (20 mL). The solid was dried at h.v. to give the title compound as a yellow solid. The product was used without further purification.

LC-MS 3: $t_R$=0.42 min; [M+H]$^+$=182.2

Synthesis of 8-bromo-7-fluoro-isoquinoline (C9H5NBrF, MW=224.96)

A mixture of 2-bromo-3-fluorobenzaldehyde (4.06 g, 20 mmol, 1 eq.) and aminoacetaldehyde dimethyl acetal (2.18 mL, 20 mmol, 1 eq.) in toluene (50 mL) was stirred at 130° C. with concomitant removal of H$_2$O (Dean-Stark) for 1 hour. The mixture was concentrated in vacuo and dried under h.v. The resulting imine was added dropwise over 20 min to hot H$_2$SO$_4$ (20 mL) at 140° C. After addition completion, the mixture was stirred at 130° C. for another 30 min. The mixture was allowed to cool to r.t., poured on ice (1 kg). Some black tar was removed by filtration over Celite. The filtrate was basified by addition of 32% aq. NaOH soln. The mixture was extracted with AcOEt (3×200 mL). The comb. org. phases were dried over MgSO$_4$ and concentrated in vacuo. The residue was purified by prep. HPLC (column: Water X-Bridge, 30×75 mm, 10 um, UV/MS, acidic conditions) and concentrated in vacuo to give the title compound.

LC-MS 3: $t_R$=0.58 min; [M+H]$^+$=226.1

Synthesis of 3-Bromo-4-isopropoxy-benzoic acid (C10H11O3Br, MW=257.99)

Step 1: To a mixture of 3-bromo-4-hydroxybenzoic acid (4.00 g, 18.1 mmol, 1.0 eq.) and potassium carbonate anhydrous (5.49 g, 39.7 mmol, 2.2 eq.) in DMF (50 mL), 2-iodopropane (4.05 mL, 39.7 mmol, 2.2 eq.) was added. The mixture was heated at 80° C. for 18 hours. The reaction mixture was poured in water (150 mL). The mixture was extracted with AcOEt (2×200 mL). The comb. org. phases were dried over MgSO$_4$ and concentrated in vacuo to give 3-bromo-4-isopropoxy-benzoic acid isopropyl ester. The product was used without further purification Step 2: To a solution of 3-bromo-4-isopropoxy-benzoic acid isopropyl ester (5.32 g, 17.7 mmol, 1 eq.) in EtOH (100 mL), 1M aq. NaOH soln. (80 mL) was added. The resulting solution was heated at 80° C. for 18 hours, then concentrated in vacuo. The resulting aq. layer was carefully acidified with 2N aq. HCl soln. The mixture was extracted with DCM (3×100 mL). The comb. org. phases were dried over MgSO$_4$ and concentrated in vacuo to give 3-bromo-4-isopropoxy-benzoic acid. The product was used without further purification.

LC-MS 3: $t_R$=0.80 min; [M+H]$^+$=259.3

Synthesis of 3-Bromo-4-trifluoromethyl-benzoic acid (C8H4O2BrF3, MW=267.94)

3-Amino-4-(trifluoromethyl)benzoic acid (1.70 g, 8.29 mmol, 1.0 eq.) was added portionwise to a mixture of copper (II) bromide (2.78 g, 12.43 mmol, 1.5 eq.) and tert-butyl nitrite (1.48 mL, 12.43 mmol, 1.5 eq.) in MeCN (100 mL) under N$_2$ at r.t. A slow gas evolution started. The reaction mixture was stirred at r.t. for 1 hour. The reaction mixture was quenched with 1M aq. NaOH soln. (150 mL) and the reaction mixture was stirred at r.t. for 10 min. The blue suspension was filtered through Celite, the Celite rinsed with water. The filtrate was acidified with 2M aq. HCl soln. (150 mL) and extracted with DCM (3×100 mL). The comb. org. phases were washed with sat. aq. NaCl soln. (1×50 mL), dried over $Na_2SO_4$ and concentrated in vacuo to give the title compound. The residue was used without further purification.

LC-MS 3: $t_R$=0.80 min; no ionization

Synthesis of 3-Bromo-4-trifluoromethoxy-benzoic acid (C8H4O3BrF3, MW=283.93)

To an ice-cooled solution of 3-bromo-4-(trifluoromethoxy)benzaldehyde (3.00 g, 11.2 mmol, 1 eq.) in MeOH (14 mL), a solution of hydrogen peroxide (30% wt solution in water, 14 mL, 11.2 mmol, 1 eq.) in 15% aq. NaOH soln. (14 mL) was added dropwise. The reaction mixture was stirred at 0° C. for 1 hour and further at r.t. for 18 hours. The reaction mixture was acidified by addition of conc. HCl. The suspension was filtered off and the filter cake was rinsed with $H_2O$. The resulting white solid was dried under h.v. to give the title compound. The product was used without further purification.

LC-MS 3: $t_R$=0.82 min; no ionization

General Method for the Arndt-Eistert Homologation of an Acid 39

Step 1: To a mixture of 3-bromo-4-chlorobenzoic acid (1.51 g, 6.4 mmol, 1.00 eq.) in DCM (25 mL) cooled at −5° C., oxalylchlorid (0.8 mL, 9.6 mmol, 1.50 eq.) and 4 drops of DMF were added. The reaction mixture was warmed to r.t. over 20 hours. The mixture was concentrated in vacuo. The resulting oil was dissolved in THF (50 mL) and cooled to −5° C. (Trimethylsilyl)diazomethane solution (2.0 M in hexanes, 7.2 mL, 14.4 mmol, 2.25 eq.) was added and the mixture was allowed to warm to r.t. over 18 hours. The mixture was concentrated in vacuo. The residue was purified by flashmaster (column: 100 g, flow: 45 mL/min, 60 fractions of 45 mL, Heptane to Heptane+20% AcOEt) to yield 1-(3-bromo-4-chloro-phenyl)-2-diazo-ethanone as a yellow solid.

Step 2: To a solution of 1-(3-bromo-4-chloro-phenyl)-2-diazo-ethanone (877 mg, 3.38 mmol, 1.0 eq.) in MeOH (30 mL), a solution of silver benzoate (464 mg, 2.03 mmol, 0.6 eq.) in triethylamine (7.0 mL) was added dropwise. The resulting black solution was stirred at r.t. for 19 hours. The reaction mixture was concentrated in vacuo. The residue was dissolved in AcOEt (100 mL) and washed with sat. aq. $NH_4Cl$ soln. (3×50 mL), sat. aq. NaCl soln. (2×50 mL), dried over $MgSO_4$, and concentrated in vacuo. The product was purified by flashmaster (column: 100 g, flow: 45 mL/min, 60 fractions of 45 mL, Heptane to Heptane+20% AcOEt) to yield (3-bromo-4-chloro-phenyl)-acetic acid methyl ester as a yellow solid.

Listed in Table 40 below are phenylacetic acid ester 9-A, prepared according to the above-mentioned method, with corresponding acid 39 and the corresponding alcohol (step 2) as starting materials.

TABLE 40

| Phenylacetic acid ester 9-A | Formula MW | $t_R$ [min] LC-MS Method | MS-data m/z [M + H]$^+$ |
|---|---|---|---|
| (3-Bromo-4-chloro-phenyl)-acetic acid methyl ester | C9H8O2BrCl 261.94 | 0.84 LC-MS 2 | no ionization |
| (3-Bromo-5-chloro-phenyl)-acetic acid ethyl ester | C10H10O2BrCl 275.96 | 0.92 LC-MS 3 | no ionization |
| (3-Bromo-4-trifluoromethyl-phenyl)-acetic acid methyl ester | C10H8O2BrF3 295.97 | 0.90 LC-MS 3 | no ionization |
| (3-Bromo-4-methyl-phenyl)-acetic acid methyl ester | C10H11O2Br 241.99 | 0.88 LC-MS 3 | no ionization |
| (3-Bromo-2-fluoro-phenyl)-acetic acid ethyl ester | C10H10O2BrF 259.99 | 0.87 LC-MS 3 | no ionization |
| (3-Bromo-5-methoxy-phenyl)-acetic acid ethyl ester | C11H13O3Br 272.01 | 0.89 LC-MS 3 | no ionization |
| (5-Bromo-2-chloro-phenyl)-acetic acid methyl ester | C9H8O2BrCl 261.94 | 0.83 LC-MS 2 | no ionization |
| (5-Bromo-2-fluoro-phenyl)-acetic acid methyl ester | C9H8O2BrF 245.97 | 0.78 LC-MS 2 | no ionization |
| (3-Bromo-4-trifluoromethoxy-phenyl)-acetic acid ethyl ester | C11H10O3BrF3 325.98 | 0.96 LC-MS 3 | no ionization |
| (3-Bromo-4-methanesulfonyl-phenyl)-acetic acid ethyl ester | C11H13O4BrS 319.97 | 0.76 LC-MS 3 | no ionization |
| (3-Bromo-4-isopropoxy-phenyl)-acetic acid ethyl ester | C13H17O3Br 300.04 | 0.95 LC-MS 3 | no ionization |
| (8-Chloro-2,3-dihydro-benzo[1,4]dioxin-6-yl)-acetic acid ethyl ester | C12H13O4Cl 256.05 | 0.85 LC-MS 3 | no ionization |
| (7-Chloro-benzo[1,3]dioxol-5-yl)-acetic acid ethyl ester | C11H11O4Cl 242.04 | 0.86 LC-MS 3 | no ionization |
| (4-Bromo-3-fluoro-phenyl)-acetic acid ethyl ester | C10H10O2BrF 259.99 | 0.88 LC-MS 3 | no ionization |
| (4-Bromo-2-chloro-phenyl)-acetic acid ethyl ester | C10H10O2BrCl 275.96 | 0.92 LC-MS 3 | no ionization |
| (4-Bromo-3-chloro-phenyl)-acetic acid ethyl ester | C10H10O2BrCl 275.96 | 0.91 LC-MS 3 | no ionization |
| (4-Bromo-3-methoxy-phenyl)-acetic acid ethyl ester | C11H13O3Br 272.01 | 0.87 LC-MS 3 | no ionization |
| (3-Bromo-4-tert-butoxy-phenyl)-acetic acid ethyl ester | C14H19O3Br 314.05 | 0.97 LC-MS 3 | no ionization |
| (3-Bromo-4-difluoromethoxy-phenyl)-acetic acid ethyl ester | C11H11O3BrF2 307.99 | 0.90 LC-MS 3 | no ionization |

TABLE 40-continued

| Phenylacetic acid ester 9-A | Formula MW | $t_R$ [min] LC-MS Method | MS-data m/z [M + H]$^+$ |
|---|---|---|---|
| (4-Bromo-3-ethoxy-phenyl)-acetic acid ethyl ester | C12H15O3Br 286.02 | 0.91 LC-MS 3 | no ionization |
| [4-Bromo-3-(2,2,2-trifluoro-ethoxy)-phenyl]-acetic acid ethyl ester | C12H12O3BrF3 339.99 | 0.95 LC-MS 3 | no ionization |

General Method for the Esterification of an Acid

A solution of (3-bromo-4-methoxy-phenyl)-acetic acid (2.5 g, 10 mmol, 1 eq) in 1.25M HCl in ethanol (13 mL) was stirred at r.t. for 18 hours. The reaction mixture was concentrated in vacuo. The residue was partitioned between DCM (25 mL) and 1M aq. NaOH (25 mL). The layers were separated. The aq. phase was extracted with DCM (2×25 mL). The comb. org. phases were washed with water (1×25 mL), dried over MgSO$_4$, and concentrated in vacuo to give the desired ester as a pale yellow oil. The product was used without further purification.

Listed in Table 41 below are phenylacetic acid ester 9, prepared according to the above-mentioned method, with corresponding acid as starting material.

TABLE 41

| Phenylacetic acid ester 9 | Formula MW | $t_R$ [min] LC-MS Method | MS-data m/z [M + H]$^+$ |
|---|---|---|---|
| (3-Bromo-4-methoxy-phenyl)-acetic acid ethyl ester | C11H13O3Br 272.01 | 0.81 LC-MS 2 | no ionization |
| (3-Bromo-4-fluoro-phenyl)-acetic acid ethyl ester | C10H10O2BrF 259.99 | 0.85 LC-MS 2 | no ionization |
| (3-Bromo-5-fluoro-phenyl)-acetic acid ethyl ester | C10H10O2BrF 259.99 | 0.89 LC-MS 3 | no ionization |
| (5-Bromo-2-methoxy-phenyl)-acetic acid ethyl ester | C11H13O3Br 272.01 | 0.88 LC-MS 3 | 273.2 |
| (2-Bromo-phenyl)-acetic acid ethyl ester | C10H11O2Br 241.99 | 0.86 LC-MS 3 | no ionization |
| (2-Bromo-4-chloro-phenyl)-acetic acid ethyl ester | C10H10O2BrCl 275.96 | 0.91 LC-MS 3 | no ionization |
| (2-Bromo-4-methoxy-phenyl)-acetic acid ethyl ester | C11H13O3Br 272.01 | 0.87 LC-MS 3 | no ionization |

General Method for the Transesterification of an Ester

A solution of (5-bromo-2-chloro-phenyl)-acetic acid methyl ester (1.04 g, 3.93 mmol, 1 eq.) in 1.25M HCl in ethanol (30 mL) was stirred at r.t. for 18 hours. The mixture was concentrated in vacuo. The product was used without further purification.

Listed in Table 42 below are phenylacetic acid ester 9, prepared according to the above-mentioned method, with corresponding ester as starting material.

TABLE 42

| Phenylacetic acid ester 9 | Formula MW | $t_R$ [min] LC-MS Method | MS-data m/z [M + H]$^+$ |
|---|---|---|---|
| (5-Bromo-2-chloro-phenyl)-acetic acid ethyl ester | C10H10O2BrCl 275.96 | 0.89 LC-MS 2 | no ionization |
| (5-Bromo-2-fluoro-phenyl)-acetic acid ethyl ester | C10H10O2BrF 259.99 | 0.84 LC-MS 2 | no ionization |

Synthesis of 1-(3-chloro-4-methoxy-phenyl)-cyclopropanecarboxylic acid ethyl ester (C13H15O3Cl, MW=254.07)

Step 1: To a suspension of potassium tert-butoxide (2.36 g, 20 mmol, 4 eq.) in THF (15 mL), a solution of tosylmethyl isocyanide (1.95 g, 10 mmol, 2 eq.) in THF (5 mL) was added at −78° C. The mixture was stirred at −78° C. for 15 min. A solution of 3-chloro-4-methoxybenzaldehyde (879 mg, 5 mmol, 1 eq.) in THF (5 mL) was added dropwise. The resulting mixture was stirred for 1.5 hours at −78° C. To the cooled reaction mixture, methanol (5 mL) was added. The mixture was then heated at reflux for 30 min. The solvent was removed in vacuo. The residue was partitioned between water (20 mL) and AcOEt (10 mL). The aq. phase was extracted with AcOEt (2×10 mL). The comb. org. layers were dried over MgSO$_4$, filtered, and concentrated in vacuo. The residue was purified by flashmaster (column: 100 g, flow: 45 mL/min, 50 fractions of 45 mL, Heptane to Heptane+25% AcOEt) to yield (3-chloro-4-methoxy-phenyl)-acetonitrile as a pale yellow oil that solidified upon standing.

LC-MS 3: $t_R$=0.78 min; [M+H]$^+$=no ionization

Step 2: A mixture of (3-chloro-4-methoxy-phenyl)-acetonitrile (320 mg, 1.76 mmol, 1.00 eq.), 1-bromo-2-chloro ethane (0.51 mL, 6.05 mmol, 3.40 eq.) and benzyltriethylammonium chloride (10 mg, 0.04 mmol, 0.02 eq.) was heated at 70° C. 50% aq. NaOH soln (1.5 mL) was slowly added and the reaction mixture was stirred at 70° C. for 18 hours. 1-Bromo-2-chloro ethane (0.26 mL, 3.03 mmol, 1.72 eq.) and a spatula tip of benzyltriethylammonium chloride were added again and the mixture was stirred at 70° C. for 3 hours. 50% aq. NaOH soln. (1.5 mL) and water (5 mL) were added and the mixture was then heated up to 130° C. and stirred at that temperature for 18 hours. The reaction mixture was allowed to cool to r.t., diluted with water (20 mL) and extracted once with AcOEt (20 mL) and once with DCM (20 mL). The basic aq. layer was acidified with conc. HCl (pH<1). The resulting precipitate was filtered and washed with 1M aq. HCl soln. The filter cake was then redissolved in DCM (20 mL) and washed with 1M HCl soln (2×20 mL) and sat. aq. NaCl soln (1×20 mL). The org. layer was dried over MgSO$_4$, filtered, and concentrated in vacuo to give 1-(3-chloro-4-methoxy-phenyl)-cyclopropanecarboxylic acid as a yellow solid. The product was used without further purification.

LC-MS 3: $t_R$=0.75 min; [M+H]$^+$=no ionization

Step 3: A solution of 1-(3-chloro-4-methoxy-phenyl)-cyclopropanecarboxylic acid (250 mg, 0.96 mmol, 1 eq.) in 1.25M HCl in EtOH (2.4 mL) was stirred at r.t. for 2 hours and further at 50° C. for 18 hours. The mixture was allowed to cool to r.t. and concentrated in vacuo. The residue was purified by flashmaster (column: 25 g, flow: 30 mL/min, 30 fractions of 30 mL, Heptane 100% to Heptane+20% AcOEt) to yield the title compound as a colorless oil. LC-MS 3: $t_R$=0.91 min; [M+H]$^+$=255.2

Synthesis of (±)-2-(3-Bromo-4-methoxy-phenyl)-propionic acid ethyl ester (C12H15O3Br, MW=286.02)

To an ice-cooled solution of (3-bromo-4-methoxy-phenyl)-acetic acid ethyl ester (1.45 g, 5.12 mmol, 1.00 eq.) in THF (18 mL), sodium hydride (60% dispersion in mineral oil, 225 mg, 5.63 mmol, 1.10 eq.) was added. The reaction mixture was stirred at r.t. for 30 min. Iodomethane (0.34 mL, 5.38 mmol, 1.05 eq.) was added and the resulting mixture was stirred at r.t. for 18 hours. Water was carefully added. THF was removed in vacuo. The residue was extracted with AcOEt (2×). The org. layer was dried over MgSO$_4$, filtered and concentrated in vacuo. The residue was purified by flashmaster (column: 50 g, flow: 40 mL/min, 25 fractions of 40 mL, Heptane 100% to Heptane+15% AcOEt) to yield the title compound as a yellow oil.

LC-MS 3: $t_R$=0.90 min; [M+H]$^+$=287.2

Synthesis of (8-Bromo-5-fluoro-3,4-dihydro-1H-isoquinolin-2-yl)-((1R,2R)-2-phenyl-cyclopropyl)-methanone (C19H17NOBrF, MW=373.05)

A solution of 8-bromo-5-fluoro-1,2,3,4-tetrahydro-isoquinoline hydrochloride (200 mg, 0.75 mmol, 1.0 eq.) and the acid (1R,2R)-2-phenyl-cyclopropanecarboxylic acid (122 mg, 0.75 mmol, 1.0 eq.) in DMF (9 mL) was treated with 4-(dimethylamino)pyridine (367 mg, 3.00 mmol, 4.0 eq.) and N-(3-dimethylaminopropyl)-N'-ethylcarbodiimide hydrochloride (216 mg, 1.13 mmol, 1.5 eq.) and the resulting solution was stirred at r.t. for 18 hours. The reaction mixture was diluted with AcOEt (70 mL). The diluted solution was washed with 1N aq. HCl (3×30 mL), sat. aq. NaCl soln. (1×30 mL), dried over MgSO$_4$, filtered, and concentrated in vacuo to give the desired compound as a pale yellow oil. The product was used without further purification.

LC-MS 3: $t_R$=0.97 min; [M+H]$^+$=374.0

Synthesis of 3-Bromo-4-isopropoxy-phenol (C9H11O2Br, MW=229.99)

Step 1: To a solution of hydroquinone (3.37 g, 30.0 mmol, 1.00 eq.) and 2-iodopropane (2 mL, 19.8 mmol, 0.66 eq.) in EtOH (12 mL), a solution of KOH (1.68 g, 30.0 mmol, 1.00 eq.) in water (6 mL) was added. The dark brown solution was refluxed for 18 hours. The solvent was removed in vacuo and the remaining aq. phase was acidified with 2M aq. HCl soln. and extracted with AcOEt (3×15 mL). The comb. org. layers were washed with sat. aq. NaCl soln., dried over MgSO$_4$, filtered, and concentrated in vacuo. The residue was purified by flashmaster (column: 340 g, flow: 90 mL/min, 100 fractions of 45 mL, Heptane to Heptane+35% AcOEt) to yield 4-isopropoxy-phenol as an orange oil.

LC-MS 3: $t_R$=0.67 min; [M+H]$^+$=No ionization

Step 2: To a solution of 4-isopropoxy-phenol (800 mg, 5.26 mmol, 1.0 eq.) and triethylamine (1.47 mL, 10.5 mmol, 2.0 eq.) in DCM (22 mL), acetyl chloride (0.45 mL, 6.36 mmol, 1.2 eq.) was added dropwise. The reaction mixture was stirred at r.t. for 4 days. Sat. aq. NaHCO$_3$ soln. was added and the layers were separated. The org. phase was dried over MgSO$_4$, filtered, and concentrated in vacuo to give acetic acid 4-isopropoxy-phenyl ester as a yellow oil. The product was used without further purification.

LC-MS 3: $t_R$=0.83 min; [M+H]$^+$=No ionization

Step 3: To a solution of acetic acid 4-isopropoxy-phenyl ester (1.04 g, 5.35 mmol, 1 eq.) in MeCN (22 mL), N-bromsuccinimide (953 mg, 5.35 mmol, 1 eq.) was added. The resulting mixture was stirred at r.t. for 18 hours. The solvent was removed in vacuo. The residue was partitioned between water and Et$_2$O. The org. layer was dried over MgSO$_4$, filtered, and concentrated in vacuo to give acetic acid 3-bromo-4-isopropoxy-phenyl ester as an orange oil. The product was used without further purification.

LC-MS 3: $t_R$=0.90 min; [M+H]$^+$=No ionization

Step 4: To a solution of acetic acid 3-bromo-4-isopropoxy-phenyl ester (1.44 g, 4.98 mmol, 1.00 eq.) in MeOH (20 mL), a solution of KOH (303 mg, 5.39 mmol, 1.08 eq.) in H$_2$O (3 mL) was added. The resulting mixture was stirred at r.t. for 45 min. Water (5 mL) was added and the mixture was acidified with 2N aq. HCl soln. then extracted with DCM (3×). The comb. org. layers were dried over MgSO$_4$, filtered, and concentrated in vacuo to give the title compound as a brown oil. The product was used without purification.

LC-MS 3: $t_R$=0.79 min; [M+H]$^+$=230.1

General Method for the Alkylation of a Phenol 40

To a mixture of 3-bromo-4-isopropoxy-phenol (1.22 g, 4.86 mmol, 1.0 eq.) and K$_2$CO$_3$ (2.01 g, 14.6 mmol, 3.0 eq.) in DMF (17.5 mL), ethyl bromoacetate (0.81 mL, 7.29 mmol, 1.5 eq.) was added. The mixture was stirred at r.t. for 18 hours. The reaction mixture was partitioned between AcOEt and water. The layers were separated and the aq. phase was extracted with AcOEt (2×). The comb. org. extracts were washed with water and sat. aq. NaCl, dried over MgSO$_4$, filtered, and concentrated in vacuo. The residue was purified by flashmaster (column: 100 g, flow: 45 mL/min, 30 fractions of 45 mL, Heptane 100% to Heptane+20% AcOEt) to give the desired product as a colorless oil.

Listed in Table 43 below are phenoxyacetic acid ester 9-B, prepared according to the above-mentioned method, with corresponding phenol 40 and the corresponding bromide as starting material.

TABLE 43

| Phenoxyacetic acid ester 9-B | Formula MW | $t_R$ [min] LC-MS Method | MS-data m/z [M + H]$^+$ |
|---|---|---|---|
| (3-Bromo-4-isopropoxy-phenoxy)-acetic acid ethyl ester | C13H17O4Br 316.03 | 0.93 LC-MS 3 | no ionization |
| (3-Bromo-4-trifluoromethoxy-phenoxy)-acetic acid ethyl ester | C11H10O4BrF3 341.97 | 0.95 LC-MS 3 | no ionization |
| 2-(3-Bromo-4-methoxy-phenoxy)-propionic acid ethyl ester | C12H15O4Br 302.02 | 0.89 LC-MS 3 | 303.1 |
| 2-(3-Bromo-4-methoxy-phenoxy)-butyric acid ethyl ester | C13H17O4Br 316.03 | 0.93 LC-MS 3 | 316.9 |
| 2-(3-Bromo-4-methoxy-phenoxy)-2-methyl-propionic acid ethyl ester | C13H17O4Br 316.03 | 0.92 LC-MS 3 | 316.9 |
| (2-Bromo-3-methoxy-phenoxy)-acetic acid ethyl ester | C11H13O4Br 288.00 | 0.84 LC-MS 3 | 288.9 |

Synthesis of (3-Bromo-4-hydroxy-phenyl)-acetic acid ethyl ester (C10H11O3Br, MW=257.90)

To a solution of 3-bromo-4-hydroxyphenylacetic acid (1.19 g, 5 mmol, 1 eq.) in EtOH (15 mL), thionyl chloride (0.73 mL, 10 mmol, 2 eq.) was added. The reaction mixture was stirred at r.t. during 1 h 30. The mixture was concentrated in vacuo. The residue was partitioned between DCM (50 mL) and sat. aq. NaHCO$_3$ soln. (50 mL). The layers were separated and the aq. phase was extracted with DCM (2×50 mL). The comb. org. phases were dried over MgSO$_4$, filtered, and concentrated in vacuo to give the title compound as a pale yellow oil. The product was used without further purification.

LC-MS 3: $t_R$=0.76 min; [M+H]$^+$=259.3

General Method for the Alkylation of a Phenol

Method A: To a solution of (3-bromo-4-hydroxy-phenyl)-acetic acid ethyl ester (135 mg, 0.5 mmol, 1.0 eq.) and K$_2$CO$_3$ (207 mg, 1.5 mmol, 3.0 eq.) in DMF (1.8 mL), iodoethane (61 µL, 0.8 mmol, 1.5 eq.) was added. The mixture was stirred at 60° C. for 18 hours. The reaction mixture was partitioned between DCM and water. The layers were separated and the aq. phase was extracted with DCM (2×). The comb. org. extracts were concentrated in vacuo. The residue was purified by prep. HPLC (column: Waters XBridge, 30×75 mm, 10 um, UV/MS, acidic conditions) and concentrated in vacuo.

Listed in Table 44 below are compound 9-C, prepared according to the above-mentioned method, with corresponding halogen as starting material.

Method B: Synthesis of [3-Bromo-4-(2,2-difluoro-ethoxy)-phenyl]acetic acid ethyl ester (C12H13O3BrF2, MW=322.00): Sodium hydride 60% dispersion in mineral oil (80 mg, 2.0 mmol, 1.0 eq.) was added portionwise to an ice-cooled solution of (3-bromo-4-hydroxy-phenyl)-acetic acid ethyl ester (564 mg, 2.0 mmol, 1.0 eq.) in THF (9.4 mL). The ice bath was removed and the mixture was allowed to warm to r.t. and stirred for 30 min. A solution of 2,2-difluoroethyl trifluoromethanesulfonate (961 mg, 4.4 mmol, 2.2 eq.) in THF (1 mL) was added and the resulting mixture was stirred at r.t. for 18 hours. The mixture was concentrated in vacuo. The residue was taken up in DCM and water was added. The layers were separated and the aq. phase was extracted with DCM (3×). The comb. org. layers were washed with sat. aq. NaCl soln., dried over MgSO$_4$, filtered and concentrated in vacuo to give the title compound as a yellow oil. The product was used without further purification.

LC-MS 3: $t_R$=0.90 min; [M+H]$^+$=no ionization

Method C: Synthesis of [3-bromo-4-(2,2,2-trifluoro-ethoxy)-phenyl]-acetic acid ethyl ester (C12H12O3BrF3, MW=339.99): 1,1,1-Trifluoro-2-iodoethane (0.15 mL, 1.5 mmol, 1 eq.) was added to a solution of (3-bromo-4-hydroxy-phenyl)-acetic acid ethyl ester (456 mg, 1.5 mmol, 1 eq.) and potassium carbonate (622 mg, 4.5 mmol, 3 eq.) in DMF (1.5 mL). The resulting mixture was stirred at 150° C. under microwave irradiation for 30 min. The reaction mixture was diluted with DCM and water. The layers were separated and the aq. phase was extracted with DCM (2×). The comb. org. layers were dried over MgSO$_4$, filtered, and concentrated in vacuo. The residue was purified by flashmaster (column: 50 g, flow: 30 mL/min, 30 fractions of 30 mL, Heptane 100% to Heptane+AcOEt 20%) to yield the title compound as a colorless oil.

LC-MS 3: $t_R$=0.94 min; [M+H]$^+$=no ionization

TABLE 44

| Compound 9 | Formula MW | $t_R$ [min] LC-MS Method | MS-data m/z [M + H]$^+$ |
|---|---|---|---|
| (3-Bromo-4-ethoxy-phenyl)-acetic acid ethyl ester | C12H15O3Br 286.02 | 0.91 LC-MS 3 | 286.9 |
| (3-Bromo-4-cyclopropylmethoxy-phenyl)-acetic acid ethyl ester | C14H17O3Br 312.04 | 0.95 LC-MS 3 | 312.9 |
| (3-Bromo-4-propoxy-phenyl)-acetic acid ethyl ester | C13H17O3Br 300.04 | 0.96 LC-MS 3 | 300.9 |
| (3-Bromo-4-isobutoxy-phenyl)-acetic acid ethyl ester | C14H19O3Br 314.05 | 1.00 LC-MS 3 | 314.9 |
| [3-Bromo-4-(2-methoxy-ethoxy)-phenyl]-acetic acid ethyl ester | C13H17O4Br 316.03 | 0.87 LC-MS 3 | 316.9 |
| [3-Bromo-4-(2-fluoro-ethoxy)-phenyl]-acetic acid ethyl ester | C12H14O3BrF 304.01 | 0.88 LC-MS 3 | no ionization |

Synthesis (±)-2-(4-Bromo-3-methoxy-phenoxy)-propionic acid methyl ester (C11H13O4Br, MW=288.00)

4-Bromo-3-methoxyphenol (209 mg, 1 mmol, 1 eq.) was dissolved in MeCN (4 mL). (±)-2-(Toluene-4-sulfonyloxy)-propionic acid methyl ester (258 mg, 1 mmol, 1 eq.) and $K_2CO_3$ (276 mg, 2 mmol, 2 eq.) were added and the mixture was stirred at 65° C. for 6 hours and further at r.t. for 4 days. The mixture was partitioned between water and $Et_2O$. The layers were separated and the aq. phase was extracted with $Et_2O$ (2×). The comb. org. phases were dried over $MgSO_4$, filtered, and concentrated in vacuo. The crude product was purified by flashmaster (column: 25 g, flow: 30 mL/min, 30 fractions of 30 mL, Heptane 100% to Heptane+20% AcOEt) to the title compound as a colorless oil.

LC-MS 3: $t_R$=0.87 min; $[M+H]^+$=289.0

Synthesis of (4-chloro-3-isopropoxy-phenyl)-acetic acid tert-butyl ester (C15H21O3Cl, MW=284.12)

Step 1: To a solution of 5-bromo-2-chlorophenol (2.08 g, 10 mmol, 1.0 eq.) and potassium carbonate (4.15 g, 30 mmol, 3.0 eq.) in MeCN (19 mL), 2-iodopropane (1.53 mL, 15 mmol, 1.5 eq.) was added. The mixture was stirred at r.t. for 18 hours. The mixture was heated up to 50° C. and stirred at that temperature for 2.5 hours. The reaction mixture was partitioned between AcOEt and water. The layers were separated and the aq. phase was extracted with AcOEt (2×). The comb. org. extracts were washed with water and sat. aq. NaCl soln., dried over $MgSO_4$, filtered, and concentrated in vacuo to give 4-bromo-1-chloro-2-isopropoxy-benzene as a yellow oil. The product was used without further purification. LC-MS 3: $t_R$=0.98 min; $[M+H]^+$=no ionization Step 2: To a solution of 4-bromo-1-chloro-2-isopropoxy-benzene (2.48 g, 9.8 mmol, 1.0 eq.) and bis(tri-tert-butylphosphine)palladium(0) (501 mg, 0.98 mmol, 0.1 eq.) in dioxane (84 mL), a 0.5M solution of 2-tert-butoxy-2-oxoethylzinc chloride in $Et_2O$ (35.3 mL, 17.6 mmol, 1.8 eq.) was added. The resulting mixture was stirred at r.t. for 2 days. The mixture was filtered over celite and concentrated in vacuo. The residue was purified by flashmaster (column: 100 g, flow: 45 mL/min, 30 fractions of 45 mL, Heptane 100% to Heptane+8% AcOEt) to yield the title compound as a colorless oil.

LC-MS 3: $t_R$=1.01 min; $[M+H]^+$=no ionization

Synthesis of (3-chloro-4-cyclopropoxy-phenyl)-acetic acid tert-butyl ester (C15H19O3Cl, MW=282.10)

Step 1: Potassium carbonate (8.29 g, 60 mmol, 3.0 eq.) and 2-chloroethyl p-toluenesulfonate (5.16 g, 22 mmol, 1.1 eq.) were added in sequence to a solution of 4-bromo-2-chlorophenol (4.19 g, 20 mmol, 1.0 eq.) in DMF (25 mL). The resulting mixture was heated up to 60° C. and stirred at that temperature for 4 hours. The mixture was allowed to cool down to r.t. and was partitioned between AcOEt (290 mL) and water (120 mL). The layers were separated. The org. phase was washed with water (4×120 mL), dried over $MgSO_4$, filtered, and concentrated in vacuo to give 4-bromo-2-chloro-1-(2-chloro-ethoxy)-benzene as a colorless oil that solidified upon standing. The product was used without further purification.

LC-MS 3: $t_R$=0.93 min; $[M+H]^+$=no ionization

Step 2: To a solution of 4-bromo-2-chloro-1-(2-chloro-ethoxy)-benzene (5.84 g, 17.4 mmol, 1 eq.) in DMF (22 mL), sodium hydride 60% dispersion in mineral oil (1.40 g, 34.9 mmol, 2 eq.) was added portionwise at r.t. The resulting mixture was stirred at r.t. for 18 hours. The mixture was partitioned between water (70 mL) and AcOEt (250 mL). The layers were separated and the org. layer was washed with water (4×100 mL), dried over $MgSO_4$, filtered, and concentrated in vacuo. To a solution of the residue in DMF (22 mL), sodium hydride 60% dispersion in mineral oil (1.40 g, 34.9 mmol, 2 eq.) was added portionwise at r.t. The resulting mixture was stirred at r.t. for 48 hours. The mixture was partitioned between water (70 mL) and AcOEt (250 mL). The layers were separated and the org. layer was washed with water (4×100 mL), dried over $MgSO_4$, filtered, and concentrated in vacuo. The residue was purified by flashmaster (column: 100 g, flow: 45 mL/min, 30 fractions of 45 mL, Heptane 100% to Heptane+5% AcOEt) to give 4-bromo-2-chloro-1-vinyloxy-benzene as a colorless oil.

LC-MS 3: $t_R$=0.93 min; $[M+H]^+$=no ionization

Step 3: To an ice-cooled solution of diethylzinc solution (1.0 M in hexanes) (8.25 mL, 8.25 mmol, 2.75 eq.) in DCM (15 mL), trifluoroacetic acid (0.6 mL, 7.80 mmol, 2.60 eq.) was added slowly (gas evolution). Upon addition completion, the mixture was stirred at 0° C. for 10 min. Methyleniodid (0.7 mL, 8.70 mmol, 2.90 eq.) was added dropwise and the mixture was stirred at 0° C. for 10 min. A solution of 4-bromo-2-chloro-1-vinyloxy-benzene (700 mg, 3.00 mmol, 1.00 eq.) in DCM (5 mL) was added dropwise. The reaction mixture was stirred at 0° C. for 30 min and further at r.t. for 1 hour, then quenched with 2N aq. HCl soln. (15 mL) and water (5 mL). The layers were separated. The aq. layer was extracted with DCM (1×25 mL). The comb. org. phases were dried over $MgSO_4$ and concentrated in vacuo. The residue was purified by flashmaster (column: 100 g, flow: 45 mL/min, 30 fractions of 45 mL, Heptane to Heptane+5% AcOEt) to yield 4-bromo-2-chloro-1-cyclopropoxy-benzene as a colorless oil.

LC-MS 3: $t_R$=0.95 min; $[M+H]^+$=no ionization

Step 4: To a solution of 4-bromo-2-chloro-1-cyclopropoxy-benzene (610 mg, 2.46 mmol, 1.00 eq.) in dioxane (20 mL), bis(tri-t-butylphosphine)palladium (0) (193 mg, 0.37 mmol, 0.15 eq.) and 2-tert-butoxy-2-oxoethylzinc chloride (0.5M in diethyl ether) (8.9 mL, 4.44 mmol, 1.80 eq.) were added in sequence. The resulting mixture was stirred at r.t. for 18 hours and further at 60° C. for 4 hours. The mixture was allowed to cool down to r.t. and filtered through Celite. The filtrate was concentrated in vacuo. The residue was purified by flashmaster (column: 100 g, flow: 45 mL/min, 40 fractions of 45 mL, Heptane to Heptane+5% AcOEt) to yield the title compound as a white solid.

LC-MS 3: $t_R$=0.98 min; $[M+H]^+$=no ionization

Synthesis of (3-bromo-4-dimethylamino-phenyl)-acetic acid ethyl ester (C12H16NO2Br, MW=285.04)

Step 1: To a solution of ethyl 4-aminophenylacetate (1.79 g, 10 mmol, 1 eq.) in MeCN (50 mL), N-bromsuccinimide (1.78 g, 10 mmol, 1 eq.) was added slowly. The mixture was stirred at r.t. for 72 hours. The reaction mixture was concentrated in vacuo. The residue was partitioned between water (50 mL) and $Et_2O$ (50 mL). The org. phase was washed with sat. aq. NaCl soln. (1×50 mL), dried over $MgSO_4$, and concentrated in vacuo to give (4-amino-3-bromo-phenyl)-acetic acid ethyl ester as an orange oil. The product was used without further purification.

LC-MS 3: $t_R$=0.77 min; $[M+H]^+$=257.9

Step 2: To a solution of (4-amino-3-bromo-phenyl)-acetic acid ethyl ester (2.56 g, 9.9 mmol, 1.0 eq.) in formic acid (1.89 mL, 49.6 mmol, 5.0 eq.), 37% wt aqueous formaldehyde solution (1.7 mL, 21.8 mmol, 2.2 eq.) was added. The mixture was stirred at 90° C. for 4 hours. The mixture was allowed to cool down to r.t. and partitioned between sat. aq. NaHCO$_3$ soln. (75 mL) and DCM (75 mL). The layers were separated. The aq. phase was extracted with DCM (2×50 mL). The comb. org. phases were dried over MgSO$_4$ and concentrated in vacuo. The residue was purified by flashmaster (column: 100 g, flow: 45 mL/min, 40 fractions of 45 mL, Hept/AcOEt-NEt$_3$ (10% NEt$_3$) 95:5 to Hept/AcOEt-NEt$_3$ (10% NEt$_3$) 8:2) to yield the title compound as an yellow oil.

LC-MS 3: $t_R$=0.68 min; [M+H]$^+$=286.1

Synthesis of (3-bromo-2-methoxy-phenyl)-acetic acid methyl ester (C10H11O3Br, MW=257.99)

Step 1: To a solution of tert-butylamine (1.74 mL, 16.4 mmol, 1.50 eq.) in toluene (54 mL), bromine (0.47 mL, 9.2 mmol, 0.84 eq.) was added dropwise at −30° C. The mixture was stirred at −30° C. for 1 hour then cooled down to −78° C. and a solution of methyl 2-(2-hydroxyphenyl)acetate (1.82 g, 11.0 mmol, 1.00 eq.) in DCM (10 mL) was slowly added. The resulting mixture was stirred at r.t. for 18 hours. Water was added and the layers were separated. The aq. phase was extracted with DCM (2×). The comb. org. layers were dried over MgSO$_4$, filtered, and concentrated in vacuo. The residue was purified by prep. HPLC (column: Waters XBridge, 30×75 mm, 10 um, UV/MS, acidic conditions) and evaporated to give (3-bromo-2-hydroxy-phenyl)-acetic acid methyl ester as a pale yellow oil that solidified upon standing.

LC-MS 3: $t_R$=0.74 min; [M+H]$^+$=no ionization

Step 2: To a solution of (3-bromo-2-hydroxy-phenyl)-acetic acid methyl ester (866 mg, 3.5 mmol, 1 eq.) and potassium carbonate (2.44 g, 17.7 mmol, 5 eq.) in MeCN (9 mL), iodomethane (0.67 mL, 10.6 mmol, 3 eq.) was added. The resulting mixture was stirred at 50° C. for 2 hours. The reaction mixture was diluted with AcOEt and water. The layers were separated and the aq. phase was extracted with AcOEt (2×). The comb. org. layers were dried over MgSO$_4$, filtered, and concentrated in vacuo to give the title compound as an orange oil. The product was used without further purification.

LC-MS 3: $t_R$=0.83 min; [M+H]$^+$=259.1

Synthesis of (2-chloro-3-methoxy-phenyl)-acetic acid ethyl ester (C11H13O3Cl, MW=228.06)

Step 1: To a solution of 2-chloro-3-methoxybenzaldehyde (1.74 g, 10.0 mmol, 1.0 eq.) and methyl(methylsulfinyl)methyl sulfide (1.72 mL, 16.1 mmol, 1.6 eq.) in THF (9 mL), benzyltrimethylammonium hydroxide solution in methanol (2.3 mL, 10.0 mmol, 1.0 eq.) was added. The resulting solution was refluxed for 18 hours. The solvent was removed in vacuo. The residue was taken up in AcOEt and washed with 1M aq. HCl soln., water, and sat. aq. NaCl soln. The org. layer was dried over MgSO$_4$, filtered, and concentrated in vacuo. The residue was purified by flashmaster (column: 100 g, flow: 45 mL/min, 30 fractions of 45 mL, Heptane+20% AcOEt to Heptane+65% AcOEt) to yield 2-chloro-1-((E)-2-methanesulfinyl-2-methylsulfanyl-vinyl)-3-methoxy-benzene as a pale orange oil.

LC-MS 3: $t_R$=0.79 min; [M+H]$^+$=277.1

Step 2: To a solution of 2-chloro-1-((E)-2-methanesulfinyl-2-methylsulfanyl-vinyl)-3-methoxy-benzene (400 mg, 1.26 mmol, 1 eq.) in EtOH (2 mL), 1.25M hydrogen chloride in ethanol (2 mL) was added and the resulting solution was refluxed for 2 hours. The solvent was removed in vacuo. The residue was purified by flashmaster (column: 50 g, flow: 40 mL/min, 35 fractions of 40 mL, Heptane 100% to Hept.+20% AcOEt) to yield the title compound as a colorless oil.

LC-MS 3: $t_R$=0.84 min; [M+H]$^+$=no ionization

Synthesis of (3-hydroxy-4-propyl-phenyl)-acetic acid tert-butyl ester (C15H22O3, MW=250.16)

Step 1: To a suspension of ethyltriphenylphosphonium bromide (8.44 g, 22 mmol, 2.2 eq.) in toluene (60 mL), a solution of potassium tert-butoxide (2.60 g, 22 mmol, 2.2 eq.) in THF (15 mL) was added dropwise. The resulting red mixture was stirred at r.t. for 4 hours. The mixture was then cooled to −78° C. and a solution of 4-bromo-2-hydroxybenzaldehyde (2.12 mg, 10 mmol, 1.0 eq.) in toluene (10 mL) was added dropwise. The resulting solution was allowed to slowly warm to r.t. and further stirred at r.t. for 20 hours. The reaction was quenched with sat. aq. NH$_4$Cl soln. (30 mL). The mixture was diluted with water (30 mL). The layers were separated and the aq. phase was extracted with Et$_2$O (3×30 mL). The comb. org. phases were dried over MgSO$_4$ and concentrated in vacuo. The residue was purified by flashmaster (column: 100 g, flow: 45 mL/min, 40 fractions of 45 mL, Heptane to Heptane/AcOEt 8:2) to yield 5-bromo-2-(propenyl)-phenol as a yellow oil as an unseparable mixture of E- and Z-isomer (ca. 85:15).

LC-MS 3: $t_R$=0.85 min; [M+H]$^+$=no ionization

Step 2: A solution of 5-bromo-2-(propenyl)-phenol (mixture of E- and Z-isomer ca. 85:15) (1.10 g, 4.99 mmol, 1.0 eq.) in DMF (15 mL) was slowly added to sodium hydride 60% dispersion in mineral oil (261 mg, 6.52 mmol, 1.3 eq.) at 0° C. under N$_2$. Upon completion of the addition, the mixture was allowed to warm to r.t. Benzyl bromide (0.61 mL, 4.99 mmol, 1.0 eq.) was added and the resulting mixture was stirred at r.t. for 18 hours. AcOEt was added and the reaction was stirred at r.t. for 30 min. Water was added to the mixture. The layers were separated and the org. phase was washed with water and sat. aq. NaCl soln., dried over MgSO$_4$, filtered, and concentrated in vacuo. The residue was purified by flashmaster (column: 100 g, flow: 45 mL/min, 30 fractions of 45 mL, Heptane 100% to Heptane+10% AcOEt) to yield 2-benzyloxy-4-bromo-1-(propenyl)-benzene as a pale yellow oil as an unseparable mixture of E- and Z-isomers (ca. 9/1).

LC-MS 3: $t_R$=1.05 min; [M+H]$^+$=no ionization

Step 3: A solution of 2-tert-butoxy-2-oxoethylzinc chloride (12.2 mL, 6.13 mmol, 1.8 eq.) was added to a solution of 2-benzyloxy-4-bromo-1-(propenyl)-benzene (mixture of E- and Z-isomers ca. 9:1) (1.17 g, 3.40 mmol, 1.00 eq.) and bis(tri-tert-butylphosphine)palladium(0) (266 mg, 0.51 mmol, 0.15 eq.) in dioxane (27 mL). The resulting mixture was stirred at r.t. for 18 hours. The mixture was filtered through Celite and the filter cake was rinsed with dioxane. The filtrate was concentrated in vacuo. The residue was purified by flashmaster (column: 100 g, flow: 45 mL/min, 30 fractions of 45 mL, Heptane 100% to Heptane+12% AcOEt) to yield [3-benzyloxy-4-(propenyl)-phenyl]-acetic acid tert-butyl ester as a pale yellow oil.

LC-MS 3: $t_R$=1.07 min; [M+H]$^+$=339.1

Step 4: To a solution of [3-benzyloxy-4-(propenyl)-phenyl]-acetic acid tert-butyl ester (1.21 g, 3.21 mmol, 1 eq.) in THF (39 mL) under N$_2$, palladium on activated carbon (10% wt., 121 mg) was added. The flask was carefully evacuated and refilled with H$_2$ (3×). The black suspension was stirred at r.t. under an H$_2$-atmosphere for 18 hours. The black suspension was filtered through Celite and the filter cake was rinsed with THF. The filtrate was concentrated in vacuo. The residue was purified by flashmaster (column: 100 g, flow: 45 mL/min, 50 fractions of 45 mL, Heptane 100% to Heptane+20% AcOEt) to yield the title compound as a colorless oil.

LC-MS 3: $t_R$=0.93 min; $[M+H]^+$=no ionization

Synthesis of (4-hydroxy-3-isopropyl-phenyl)-acetic acid tert-butyl ester (C15H22O3, MW=250.16)

Step 1: To a solution of 2-isopropylphenol (1.39 mL, 10 mmol, 1 eq.) in DCM (8 mL), bromine (0.52 mL, 10 mmol, 1 eq.) was added at r.t. over a period of 10 min. The reaction mixture was stirred at r.t. for 18 hours. The mixture was poured into a mixture of sat. aq. NaHCO$_3$ soln. (25 mL) and ice. The resulting mixture was extracted with AcOEt (2×25 mL). The comb. org. layers were washed successively with water (25 mL) and sat. aq. NaCl soln. (25 mL), then dried over MgSO$_4$, filtered, and concentrated in vacuo. The residue was purified by flashmaster (column: 100 g, flow: 45 mL/min, 30 fractions of 45 mL, Heptane 100% to Heptane+10% AcOEt) to yield 4-bromo-2-isopropyl-phenol as a pale yellow oil.

LC-MS 3: $t_R$=0.87 min; $[M+H]^+$=no ionization

Step 2: A solution of 4-bromo-2-isopropyl-phenol (1.98 g, 9.1 mmol, 1.0 eq.) in DMF (27 mL) was slowly added to sodium hydride 60% dispersion in mineral oil (476 mg, 11.9 mmol, 1.3 eq.) at 0° C. under N$_2$. Upon completion of the addition, the mixture was allowed to warm to r.t. Benzyl bromide (1.1 mL, 9.1 mmol, 1.0 eq.) was added and the resulting mixture was stirred at r.t. for 18 hours. AcOEt was added and the reaction was stirred for 30 min. Water was added to the mixture. The layers were separated and the org. phase was washed with water and sat. aq. NaCl soln., dried over MgSO$_4$, filtered, and concentrated in vacuo. To a solution of the residue in dioxane (75 mL), a solution of 2-tert-butoxy-2-oxoethylzinc chloride (33.9 mL, 17 mmol, 1.8 eq.) and bis(tri-tert-butylphosphine)palladium(0) (739 mg, 1.42 mmol, 0.15 eq) were added. The resulting mixture was stirred at r.t. for 18 hours. The mixture was filtered through Celite and the filter cake was rinsed with dioxane. The filtrate was concentrated in vacuo. The residue was purified by flashmaster (column: 100 g, flow: 45 mL/min, 30 fractions of 45 mL, Heptane 100% to Heptane+12% AcOEt) to yield (4-benzyloxy-3-isopropyl-phenyl)-acetic acid tert-butyl ester as a colorless oil.

LC-MS 3: $t_R$=1.08 min; $[M+H]^+$=no ionization

Step 3: To a solution of (4-benzyloxy-3-isopropyl-phenyl)-acetic acid tert-butyl ester (3.04 g, 8.16 mmol, 1 eq) in THF (99 mL) under N$_2$, palladium on activated carbon (10 wt. % 304 mg) was added. The flask was carefully evacuated and refilled with H$_2$ (3×). The black suspension was stirred at r.t. under an H$_2$-atmosphere for 2 days. The black suspension was filtered through Celite and the filter cake was rinsed with THF. The filtrate was concentrated in vacuo to give the title compound as a colorless oil. The product was used without further purification.

LC-MS 3: $t_R$=0.91 min; $[M+H]^+$=no ionization

General Method for the Synthesis of Pinacol Boronic Esters 8 or 11

To a solution under N$_2$ of (3-bromo-4-methoxy-phenyl)-acetic acid ethyl ester (10.90 g, 39.9 mmol, 1.00 eq.) in DMSO (100 mL), bis(pinacolato)diboron (12.41 g, 47.9 mmol, 1.20 eq.), potassium acetate (11.87 g, 120.0 mmol, 3.00 eq.), and tetrakis(triphenylphosphine) palladium (0) (2.31 g, 2.0 mmol, 0.05 eq.) were added in sequence. The reaction mixture was stirred at 95° C. for 18 hours. The mixture was allowed to cool to r.t. and partitioned between DCM (200 mL) and water (100 mL). The layers were separated. The org. phase was washed with sat. aq. NaCl soln. (2×50 mL), dried over MgSO$_4$, filtered over celite and concentrated in vacuo. The residue was purified by flashmaster (column: 340 g, flow: 90 mL/min, 90 fractions of 45 mL, Heptane to Heptane+40% AcOEt) to yield the desired pinacol boronic ester as a yellow oil.

Listed in Table 45 below are pinacol boronic ester 8 or 11, prepared according to the above-mentioned method, with corresponding bromides 9 or Structure 7 as starting material.

TABLE 45

| Pinacol boronic ester 8 or 11 | Formula MW | $t_R$ [min] LC-MS Method | MS-data m/z $[M + H]^+$ |
|---|---|---|---|
| [4-Methoxy-3-(4,4,5,5-tetramethyl-[1,3,2]dioxaborolan-2-yl)-phenyl]-acetic acid ethyl ester | C17H25O5B 320.18 | 0.90 LC-MS 3 | 321.2 |
| [4-Fluoro-3-(4,4,5,5-tetramethyl-[1,3,2]dioxaborolan-2-yl)-phenyl]-acetic acid ethyl ester | C16H22O4BF 308.16 | 0.95 LC-MS 3 | 309.4 |
| 5-Fluoro-8-(4,4,5,5-tetramethyl-[1,3,2]dioxaborolan-2-yl)-3,4-dihydro-1H-isoquinoline-2-carboxylic acid benzyl ester | C23H27NO4BF 411.20 | 1.07 LC-MS 3 | 412.1 |
| [5-Fluoro-8-(4,4,5,5-tetramethyl-[1,3,2]dioxaborolan-2-yl)-3,4-dihydro-1H-isoquinolin-2-yl]-((1R,2R)-2-phenyl-cyclopropyl)-methanone | C25H29NO3BF 421.22 | 1.05 LC-MS 3 | 422.1 |
| [4-Isopropoxy-3-(4,4,5,5-tetramethyl-[1,3,2]dioxaborolan-2-yl)-phenoxy]-acetic acid ethyl ester | C19H29O6B 364.21 | 0.97 LC-MS 3 | 365.2 |
| [4-Ethoxy-3-(4,4,5,5-tetramethyl-[1,3,2]dioxaborolan-2-yl)-phenyl]-acetic acid ethyl ester | C18H27O5B 334.20 | 0.96 LC-MS 3 | 335.3 |

General Method for the Synthesis of Esters of Structure 6

A mixture under N$_2$ of 5-fluoro-8-(4,4,5,5-tetramethyl-[1,3,2]dioxaborolan-2-yl)-3,4-dihydro-1H-isoquinoline-2-carboxylic acid benzyl ester (206 mg, 0.5 mmol, 1.00 eq.), (3-bromo-4-isopropoxy-phenyl)-acetic acid ethyl ester (151 mg, 0.5 mmol, 1.00 eq.), tetrakis(triphenylphosphine) palladium (0) (29 mg, 0.025 mmol, 0.05 eq.), and sodium carbonate (212 mg, 2.0 mmol, 4.00 eq.) in toluene/EtOH/water 20:4:1 (5 mL) was stirred at 100° C. for 48 hours. The mixture was allowed to cool to r.t. and concentrated in vacuo. The residue was partitioned between AcOEt (50 mL) and water (50 mL). The layers were separated. The org. phase was washed with sat. aq. NaCl soln. (1×50 mL), dried over MgSO$_4$, and concentrated in vacuo. The residue was purified by flashmaster (column: 100 g, flow: 45 mL/min, 50 fractions of 45 mL, Heptane to Heptane+30% AcOEt) to yield the desired compound as a colorless oil.

Listed in Table 46 below are esters of Structure 6, prepared according to the above-mentioned method, with corresponding halogenated compound 9 as starting material.

trifluoromethoxy-phenyl)-acetic acid ethyl ester (35 mg, 0.11 mmol, 1.10 eq.) and tetrakis(triphenylphosphine) palladium (0) (5.6 mg, 5 μmol, 0.05 eq) were added in sequence. The mixture was refluxed for 18 hours. The mixture was allowed to cool to r.t. and concentrated in vacuo. The residue was taken up in DMF, filtered, and purified by prep. HPLC (col-

TABLE 46

| Intermediates of Structure 6 | Formula MW | t$_R$ [min] LC-MS Method | MS-data m/z [M + H]$^+$ |
|---|---|---|---|
| 8-(5-Ethoxycarbonylmethyl-2-isopropoxy-phenyl)-5-fluoro-3,4-dihydro-1H-isoquinoline-2-carboxylic acid benzyl ester | C30H32NO5F 505.23 | 1.07 LC-MS 2 | 506.3 |
| 5-Fluoro-8-(5-methoxycarbonylmethyl-2-methyl-phenyl)-3,4-dihydro-1H-isoquinoline-2-carboxylic acid benzyl ester | C27H26NO4F 447.19 | 1.03 LC-MS 3 | 448.3 |
| 5-Fluoro-8-(5-methoxycarbonylmethyl-2-trifluoromethyl-phenyl)-3,4-dihydro-1H-isoquinoline-2-carboxylic acid benzyl ester | C27H23NO4F4 501.16 | 1.03 LC-MS 3 | 502.3 |
| 8-(2-Chloro-5-methoxycarbonylmethyl-phenyl)-5-fluoro-3,4-dihydro-1H-isoquinoline-2-carboxylic acid benzyl ester | C26H23NO4ClF 467.13 | 1.03 LC-MS 3 | 468.3 |
| 8-(5-Ethoxycarbonylmethyl-2-fluoro-phenyl)-5-fluoro-3,4-dihydro-1H-isoquinoline-2-carboxylic acid benzyl ester | C27H25NO4F2 465.18 | 1.03 LC-MS 3 | 466.2 |
| 8-(4-Chloro-3-ethoxycarbonylmethyl-phenyl)-5-fluoro-3,4-dihydro-1H-isoquinoline-2-carboxylic acid benzyl ester | C27H25NO4ClF 481.15 | 1.07 LC-MS 3 | 482.2 |
| 8-(3-Ethoxycarbonylmethyl-4-fluoro-phenyl)-5-fluoro-3,4-dihydro-1H-isoquinoline-2-carboxylic acid benzyl ester | C27H25NO4F2 465.18 | 1.05 LC-MS 3 | 466.3 |
| 8-(3-Ethoxycarbonylmethyl-4-methoxy-phenyl)-5-fluoro-3,4-dihydro-1H-isoquinoline-2-carboxylic acid benzyl ester | C28H28NO5F 477.20 | 1.05 LC-MS 3 | 478.4 |
| 8-(3-Ethoxycarbonylmethyl-5-fluoro-phenyl)-5-fluoro-3,4-dihydro-1H-isoquinoline-2-carboxylic acid benzyl ester | C27H25NO4F2 465.18 | 1.05 LC-MS 3 | 466.4 |
| 8-(3-Ethoxycarbonylmethyl-5-methoxy-phenyl)-5-fluoro-3,4-dihydro-1H-isoquinoline-2-carboxylic acid benzyl ester | C28H28NO5F 477.20 | 1.04 LC-MS 3 | 478.4 |
| 8-(3-Ethoxycarbonylmethyl-2-fluoro-phenyl)-5-fluoro-3,4-dihydro-1H-isoquinoline-2-carboxylic acid benzyl ester | C27H25NO4F2 465.18 | 1.01 LC-MS 3 | 466.4 |
| 8-(5-Ethoxycarbonylmethyl-2-methoxy-phenyl)-5-fluoro-3,4-dihydro-1H-isoquinoline-2-carboxylic acid benzyl ester | C28H28NO5F 477.20 | 1.02 LC-MS 3 | 478.4 |
| 8-(3-Chloro-5-ethoxycarbonylmethyl-phenyl)-5-fluoro-3,4-dihydro-1H-isoquinoline-2-carboxylic acid benzyl ester | C27H25NO4ClF 481.15 | 1.06 LC-MS 3 | 482.4 |
| 8-(5-Ethoxycarbonylmethyl-2-methanesulfonyl-phenyl)-5-fluoro-3,4-dihydro-1H-isoquinoline-2-carboxylic acid benzyl ester | C28H28NO6FS 525.16 | 0.97 LC-MS 3 | 526.2 |
| 8-(5-Ethoxycarbonylmethyl-2-trifluoromethoxy-phenyl)-5-fluoro-3,4-dihydro-1H-isoquinoline-2-carboxylic acid benzyl ester | C28H25NO5F4 531.17 | 1.07 LC-MS 3 | 532.2 |
| 8-(2-Ethoxycarbonylmethyl-phenyl)-5-fluoro-3,4-dihydro-1H-isoquinoline-2-carboxylic acid benzyl ester | C27H26NO4F 447.19 | 1.03 LC-MS 3 | 448.1 |
| 8-(3-Chloro-4-ethoxycarbonylmethyl-phenyl)-5-fluoro-3,4-dihydro-1H-isoquinoline-2-carboxylic acid benzyl ester | C27H25NO4ClF 481.15 | 1.07 LC-MS 3 | 482.0 |
| 8-(4-Ethoxycarbonylmethyl-phenyl)-5-fluoro-3,4-dihydro-1H-isoquinoline-2-carboxylic acid benzyl ester | C27H26NO4F 447.19 | 1.05 LC-MS 3 | 448.3 |

General Method for the Synthesis of Ester of Structure 1

To a mixture under N$_2$ of [5-fluoro-8-(4,4,5,5-tetramethyl-[1,3,2]dioxaborolan-2-yl)-3,4-dihydro-1H-isoquinolin-2-yl]-((1R,2R)-2-phenyl-cyclopropyl)-methanone (41 mg, 0.1 mmol, 1.00 eq.) and sodium carbonate (41 mg, 0.4 mmol, 4.00 eq.) in toluene/EtOH/water 20:4:1 (3 mL), (3-bromo-4- umn: Atlantis, 30×75 mm, 10 um, UV/MS, acidic conditions) and concentrated in vacuo to give the desired ester.

Listed in Table 47 below are esters of Structure 1, prepared according to the above-mentioned method, with corresponding halogenated compound 9 as starting material.

TABLE 47

| Intermediates of Structure 1 | Formula MW | $t_R$ [min] LC-MS Method | MS-data m/z [M + H]+ |
|---|---|---|---|
| {3-[5-Fluoro-2-((1R,2R)-2-phenyl-cyclopropanecarbonyl)-1,2,3,4-tetrahydro-isoquinolin-8-yl]-4-trifluoromethoxy-phenyl}-acetic acid ethyl ester | C30H27NO4F4 541.19 | 1.05 LC-MS 3 | 542.1 |
| {3-[5-Fluoro-2-((1R,2R)-2-phenyl-cyclopropanecarbonyl)-1,2,3,4-tetrahydro-isoquinolin-8-yl]-4-isopropoxy-phenyl}-acetic acid ethyl ester | C32H34NO4F 515.25 | 1.05 LC-MS 3 | 516.3 |
| {4-Chloro-3-[5-fluoro-2-((1R,2R)-2-phenyl-cyclopropanecarbonyl)-1,2,3,4-tetrahydro-isoquinolin-8-yl]-phenyl}-acetic acid methyl ester | C28H25NO3ClF 477.15 | 1.02 LC-MS 3 | 478.2 |
| {3-[5-Fluoro-2-((1R,2R)-2-phenyl-cyclopropanecarbonyl)-1,2,3,4-tetrahydro-isoquinolin-8-yl]-4-methanesulfonyl-phenyl}-acetic acid ethyl ester | C30H30NO5FS 535.18 | 0.95 LC-MS 3 | 536.2 |

General Method for the Formation of a Triflate and Subsequent Suzuki Cross-coupling Method A: To an ice-cooled solution of 8-hydroxy-3,4-dihydro-1H-isoquinoline-2-carboxylic acid benzyl ester (142 mg, 0.50 mmol, 1.00 eq.) in DCM (1 mL), NEt₃ (0.21 mL, 1.50 mmol, 3.00 eq.) and trifluoromethanesulfonic anhydride (0.13 mL, 0.75 mmol, 1.50 eq.) were added in sequence. The reaction mixture was stirred at 0° C. for 30 min and further at r.t. for 45 min. The mixture was diluted with DCM (50 mL) and washed with sat. aq. NaHCO₃ soln. (2×25 mL). The org. layer was dried over MgSO₄ and concentrated in vacuo. To a mixture under N₂ of the resulting triflate, 2-benzyloxy-5-fluorobenzeneboronic acid (123 mg, 0.50 mmol, 1.00 eq.), and sodium carbonate (212 mg, 2.00 mmol, 4.00 eq.) in toluene/EtOH/water 20:4:1 (2.5 mL), tetrakis(triphenylphosphine) palladium (0) (29 mg, 0.03 mmol, 0.05 eq.) was added. The mixture was stirred at 100° C. for 14 hours. The mixture was allowed to cool to r.t. and concentrated in vacuo. The residue was partitioned between AcOEt (20 mL) and water (10 mL). The layers were separated. The org. phase was washed with sat. aq. NaCl soln. (1×10 mL), dried over MgSO₄, and concentrated in vacuo. The residue was purified by CC (SiO₂, Hept/AcOEt 8:2) to give the product as an yellow oil.

Listed in Table 48 below are intermediates, prepared according to the above-mentioned method, with corresponding phenol and boronic acid or boronic ester as starting material.

Method B: To an ice-cooled solution of (3-hydroxy-4-propyl-phenyl)-acetic acid tert-butyl ester (66 mg, 0.26 mmol, 1.30 eq.) and triethylamine (0.11 mL, 0.78 mmol, 3.90 eq.) in DCM (1 mL), trifluoromethanesulfonic anhydride (68 µL, 0.39 mmol, 1.90 eq.) was added dropwise. The resulting solution was stirred at r.t. for 1 hour. The reaction mixture was concentrated in vacuo. A mixture under N₂ of 5-fluoro-8-(4,4,5,5-tetramethyl-[1,3,2]dioxaborolan-2-yl)-3,4-dihydro-1H-isoquinoline-2-carboxylic acid benzyl ester (91 mg, 0.20 mmol, 1.0 eq.), the previous triflate and tetrakis(triphenylphosphine) palladium (0) (12 mg, 0.01 mmol, 0.05 eq.) was dissolved in DME/EtOH/Toluene (9:1:1, 0.7 mL). 2M aq. Na₂CO₃ soln. (0.2 mL) was added and the mixture was stirred at 90° C. for 3 hours. The mixture was filtered over Celite and the filter cake was rinsed with EtOH. The filtrate was concentrated in vacuo. The residue was purified by prep. HPLC (column: Waters XBridge, 30×75 mm, 10 um, UV/MS, acidic conditions) and evaporated to give the desired product as a brown oil.

Listed in Table 49 below are intermediates, prepared according to the above-mentioned method, with corresponding phenol and boronic acid or boronic ester as starting material.

TABLE 48

| Intermediates | Formula MW | $t_R$ [min] LC-MS Method | MS-data m/z [M + H]+ |
|---|---|---|---|
| 8-(2-Benzyloxy-5-fluoro-phenyl)-3,4-dihydro-1H-isoquinoline-2-carboxylic acid benzyl ester | C30H26NO3F 467.19 | 1.07 LC-MS 2 | 468.2 |
| 8-(5-Ethoxycarbonylmethyl-2-fluoro-phenyl)-3,4-dihydro-1H-isoquinoline-2-carboxylic acid benzyl ester | C27H26NO4F 447.19 | 1.02 LC-MS 3 | 448.1 |
| 8-(2-Chloro-5-hydroxy-phenyl)-3,4-dihydro-1H-isoquinoline-2-carboxylic acid benzyl ester | C23H20NO3Cl 393.11 | 0.95 LC-MS 3 | 394.1 |

TABLE 49

| Intermediates | Formula MW | $t_R$ [min] LC-MS Method | MS-data m/z $[M + H]^+$ |
|---|---|---|---|
| 8-(5-tert-Butoxycarbonylmethyl-2-propyl-phenyl)-5-fluoro-3,4-dihydro-1H-isoquinoline-2-carboxylic acid benzyl ester | C32H36NO4F 517.26 | 1.13 LC-MS 3 | 518.2 |
| 8-(4-tert-Butoxycarbonylmethyl-2-isopropyl-phenyl)-5-fluoro-3,4-dihydro-1H-isoquinoline-2-carboxylic acid benzyl ester | C32H36NO4F 517.26 | 1.14 LC-MS 3 | 518.2 |
| 8-(4-Ethoxycarbonylmethyl-2,6-dimethoxy-phenyl)-5-fluoro-3,4-dihydro-1H-isoquinoline-2-carboxylic acid benzyl ester | C29H30NO6F 507.21 | 1.02 LC-MS 3 | 508.2 |

General Method for the Synthesis of Esters of Structure 6

A mixture under $N_2$ of palladium(II)acetate (2.1 mg, 9.4 μmol, 0.01 eq.), 2-dicyclohexylphosphino-2',6'-dimethoxy-biphenyl (7.9 mg, 0.02 mmol, 0.02 eq.), [4-methoxy-3-(4,4,5,5-tetramethyl-[1,3,2]dioxaborolan-2-yl)-phenyl]-acetic acid ethyl ester (525 mg, 1.44 mmol, 1.50 eq.) and potassium phosphate (408 mg, 1.92 mmol, 2.00 eq.) in toluene (1.9 mL) and water (0.2 mL) was stirred at r.t. for 2 min. 8-Chloro-5-trifluoromethyl-3,4-dihydro-1H-isoquinoline-2-carboxylic acid benzyl ester (355 mg, 0.96 mmol, 1.00 eq.) was added and the mixture was stirred at 100° C. for 18 hours. The mixture was allowed to cool to r.t., diluted with $Et_2O$ (10 mL), filtered through celite, washed with $Et_2O$, and concentrated in vacuo. The residue was purified by flashmaster (column: 50 g, flow: 40 mL/min, 30 fractions of 40 mL, Heptane+5% AcOEt to Heptane+30% AcOEt) to yield the desired product as a pale yellow oil.

Listed in Table 50 below are esters of Structure 6, prepared according to the above-mentioned method, with corresponding compound of Structure 7 as starting material.

TABLE 50

| Intermediates of Structure 6 | Formula MW | $t_R$ [min] LC-MS Method | MS-data m/z $[M + H]^+$ |
|---|---|---|---|
| 8-(5-Ethoxycarbonylmethyl-2-methoxy-phenyl)-5-trifluoromethyl-3,4-dihydro-1H-isoquinoline-2-carboxylic acid benzyl ester | C29H28NO5F3 527.19 | 1.05 LC-MS 3 | 528.4 |
| 8-(5-Ethoxycarbonylmethyl-2-methoxy-phenyl)-5-methanesulfonyl-3,4-dihydro-1H-isoquinoline-2-carboxylic acid benzyl ester | C29H31NO7S 537.18 | 0.94 LC-MS 3 | 538.1 |

General Method for the Synthesis of an Ester of Structure 6

To a mixture under $N_2$ of [3-bromo-4-(2-methoxy-ethoxy)-phenyl]-acetic acid ethyl ester (159 mg, 0.50 mmol, 1.00 eq.), 5-fluoro-8-(4,4,5,5-tetramethyl-[1,3,2]dioxaborolan-2-yl)-3,4-dihydro-1H-isoquinoline-2-carboxylic acid benzyl ester (243 mg, 0.50 mmol, 1.00 eq.) and sodium carbonate (212 mg, 2.00 mmol, 4.00 eq.) in toluene/MeOH/water 20:4:1 (10 mL), tetrakis(triphenylphosphine)palladium (0) (29 mg, 0.03 mmol, 0.05 eq.) was added and the mixture was stirred at 100° C. for 48 hours. The mixture was allowed to cool to r.t., filtered over celite, and concentrated in vacuo. The residue, redissolved in DMF (3 mL) and formic acid (0.2 mL), was purified by prep. HPLC (column: Waters XBridge, 30×75 mm, 10 um, UV/MS, acidic conditions) and evaporated to give the desired product as an orange oil.

Listed in Table 51 below are esters of Structure 6, prepared according to the above-mentioned method, with corresponding compound 9 as starting material.

TABLE 51

| Intermediates of Structure 6 | Formula MW | $t_R$ [min] LC-MS Method | MS-data m/z $[M + H]^+$ |
|---|---|---|---|
| 8-[5-Ethoxycarbonylmethyl-2-(2-methoxy-ethoxy)-phenyl]-5-fluoro-3,4-dihydro-1H-isoquinoline-2-carboxylic acid benzyl ester | C30H32NO6F 521.22 | 1.02 LC-MS 3 | 522.3 |
| 8-(2-Ethoxy-5-ethoxycarbonylmethyl-phenyl)-5-fluoro-3,4-dihydro-1H-isoquinoline-2-carboxylic acid benzyl ester | C29H30NO5F 491.21 | 1.05 LC-MS 3 | 492.4 |

TABLE 51-continued

| Intermediates of Structure 6 | Formula MW | $t_R$ [min] LC-MS Method | MS-data m/z $[M + H]^+$ |
|---|---|---|---|
| 8-(2-Ethoxy-4-ethoxycarbonylmethyl-phenyl)-5-fluoro-3,4-dihydro-1H-isoquinoline-2-carboxylic acid benzyl ester | C29H30NO5F 491.21 | 1.06 LC-MS 3 | 492.4 |
| 8-[4-Ethoxycarbonylmethyl-2-(2,2,2-trifluoro-ethoxy)-phenyl]-5-fluoro-3,4-dihydro-1H-isoquinoline-2-carboxylic acid benzyl ester | C29H27NO5F4 545.18 | 1.06 LC-MS 3 | 545.9 |

Synthesis of 8-(4-tert-Butoxycarbonylmethyl-2-isopropoxy-phenyl)-5-fluoro-3,4-dihydro-1H-isoquinoline-2-carboxylic acid benzyl ester (C32H36NO5F, MW=533.26)

A mixture under $N_2$ of (4-chloro-3-isopropoxy-phenyl)-acetic acid tert-butyl ester (142 mg, 0.50 mmol, 1.00 eq.), 5-fluoro-8-(4,4,5,5-tetramethyl-[1,3,2]dioxaborolan-2-yl)-3,4-dihydro-1H-isoquinoline-2-carboxylic acid benzyl ester (232 mg, 0.50 mmol, 1.00 eq.), bis(di-tert-butyl(4-dimethylaminophenyl)phosphine)dichloropalladium(II) (18 mg, 0.03 mmol, 0.05 eq.) and potassium carbonate (138 mg, 1.00 mmol, 2.00 eq.) in toluene (2.5 mL) and water (0.25 mL) was stirred at 110° C. for 2 days. The mixture was allowed to cool to r.t., filtered through celite, and concentrated in vacuo. The residue was purified by flashmaster (column: 25 g, flow: 30 mL/min, 30 fractions of 30 mL, Heptane 100% to Heptane+20% AcOEt) to yield the title compound as a pale yellow oil.
LC-MS 3: $t_R$=1.12 min; $[M+H]^+$=534.2

Synthesis of 8-(3-Ethoxycarbonylmethyl-phenyl)-5-fluoro-3,4-dihydro-1H-isoquinoline-2-carboxylic acid benzyl ester (C27H26NO4F, MW=447.19)

To a mixture under $N_2$ of 8-bromo-5-fluoro-3,4-dihydro-1H-isoquinoline-2-carboxylic acid benzyl ester (73 mg, 0.20 mmol, 1.00 eq.), (3-ethoxycarbonylmethyl)phenylboronic acid, pinacol ester (58 mg, 0.20 mmol, 1.00 eq.) and sodium carbonate (85 mg, 0.80 mmol, 4.00 eq.) in toluene/MeOH/water 20:4:1 (4 mL), tetrakis(triphenylphosphine) palladium (0) (12 mg, 0.01 mmol, 0.05 eq.) was added and the mixture was stirred at 100° C. for 18 hours.
The mixture was allowed to cool to r.t. and concentrated in vacuo. The residue was partitioned between AcOEt (10 mL) and water (10 mL). The layers were separated. The org. phase was washed with sat. aq. NaCl soln. (1×5 mL), dried over $MgSO_4$, and filtered through Celite. The filtrate was concentrated in vacuo. The residue was purified by CC ($SiO_2$, eluent: Hept./AcOEt 8:2) to give the desired product as a yellow oil.
LC-MS 3: $t_R$=1.05 min; $[M+H]^+$=448.1

Synthesis of 5-(5-Ethoxycarbonylmethyl-2-methoxy-phenyl)-8-fluoro-3,4-dihydro-1H-isoquinoline-2-carboxylic acid benzyl ester (C28H28NO5F, MW=477.20)

To a mixture under $N_2$ of 5-bromo-8-fluoro-3,4-dihydro-1H-isoquinoline-2-carboxylic acid benzyl ester (529 mg, 1.45 mmol, 1.00 eq.), [4-methoxy-3-(4,4,5,5-tetramethyl-[1,3,2]dioxaborolan-2-yl)-phenyl]-acetic acid ethyl ester (659 mg, 1.45 mmol, 1.00 eq.) and sodium carbonate (616 mg, 5.81 mmol, 4.00 eq.) in toluene/MeOH/water 20:4:1 (29 mL), tetrakis(triphenylphosphine) palladium (0) (84 mg, 0.07 mmol, 0.05 eq.) was added and the mixture was stirred at 100° C. for 18 hours. The mixture was allowed to cool to r.t. and concentrated in vacuo. The residue was partitioned between AcOEt (60 mL) and water (60 mL). The layers were separated. The org. phase was washed with sat. aq. NaCl soln. (1×60 mL), dried over $MgSO_4$ and filtered through Celite. The filtrate was concentrated in vacuo. The residue was purified by flashmaster (column: 50 g, flow: 40 mL/min, 40 fractions of 40 mL, Heptane 100% to Heptane+30% AcOEt) to yield the title compound as a yellow oil.
LC-MS 3: $t_R$=1.03 min; $[M+H]^+$=478.2

Synthesis of 8-(5-Ethoxycarbonylmethyl-2-methoxy-phenyl)-5-fluoro-3,4-dihydro-1H-isoquinoline-2-carboxylic acid tert-butyl ester (C25H30NO5F, MW=443.21)

To a mixture under $N_2$ of 8-bromo-5-fluoro-3,4-dihydro-1H-isoquinoline-2-carboxylic acid tert-butyl ester (1.24 g, 3.75 mmol, 1.00 eq.), [4-methoxy-3-(4,4,5,5-tetramethyl-[1,3,2]dioxaborolan-2-yl)-phenyl]-acetic acid ethyl ester (1.69 g, 3.75 mmol, 1.00 eq.) and sodium carbonate (1.59 g, 15.00 mmol, 4.00 eq.) in toluene/MeOH/water 20:4:1 (75 mL), tetrakis(triphenylphosphine) palladium (0) (217 mg, 0.19 mmol, 0.05 eq.) was added and the mixture was stirred under reflux at 100° C. for 70 hours. The mixture was allowed to cool to r.t. and concentrated in vacuo. The residue was partitioned between AcOEt (150 mL) and water (150 mL). The layers were separated. The org. phase was washed with sat. aq. NaCl soln. (1×75 mL), dried over $MgSO_4$ and filtered through Celite. The filtrate was concentrated in vacuo. The residue was purified by flashmaster (column: 100 g, flow: 45 mL/min, 30 fractions of 40 mL, Heptane+10% AcOEt to Heptane+25% AcOEt) to yield the desired ester as a pale yellow oil.
LC-MS 3: $t_R$=1.02 min; $[M+H]^+$=444.1

Synthesis of [3-(5-Chloro-1,2,3,4-tetrahydro-isoquinolin-8-yl)-4-methoxy-phenyl]-acetic acid ethyl ester (C20H22NO3Cl, MW=359.13)

To a mixture under $N_2$ of 8-bromo-5-chloro-1,2,3,4-tetrahydro-isoquinoline hydrochloride (566 mg, 2.00 mmol, 1 eq.), [4-methoxy-3-(4,4,5,5-tetramethyl-[1,3,2]dioxaborolan-2-yl)-phenyl]-acetic acid ethyl ester (901 mg, 2.0 mmol, 1.00 eq) and sodium carbonate (1.06 g, 10.0 mmol, 5.00 eq.) in toluene/MeOH/water 20:4:1 (40 mL), tetrakis(triphenylphosphine) palladium (0) (116 mg, 0.1 mmol, 0.05 eq.) was added and the mixture was stirred under reflux for 18 hours. The mixture was allowed to cool to r.t. and concentrated in vacuo. The residue was partitioned between AcOEt (75 mL) and water (75 mL). The layers were separated. The org. phase was washed with sat. aq. NaCl soln. (1×50 mL), dried over $MgSO_4$ and filtered through Celite. The filtrate was concentrated in vacuo. The residue was purified by flashmaster (column: 100 g, flow: 45 mL/min, 40 fractions of 45 mL, AcOEt+MeOH 10%) to yield the title product as an orange oil.

LC-MS 2: $t_R$=0.69 min; [M+H]$^+$=360.1

Synthesis of (±)-8-[5-(1-Ethoxycarbonyl-ethyl)-2-methoxy-phenyl]-5-fluoro-3,4-dihydro-1H-isoquinoline-2-carboxylic acid benzyl ester (C29H30NO5F, MW=491.21)

A mixture under N$_2$ of palladium(II)acetate (1.2 mg, 5 μmol, 0.02 eq.), 2-dicyclohexylphosphino-2',6'-dimethoxy-biphenyl (4.2 mg, 0.01 mmol, 0.04 eq.), (±)-2-(3-bromo-4-methoxy-phenyl)-propionic acid ethyl ester (80 mg, 0.26 mmol, 1 eq.) and potassium phosphate (109 mg, 0.51 mmol, 2 eq.) in toluene (1.9 mL) and water (0.2 mL) was stirred at r.t. during 2 min. 5-Fluoro-8-(4,4,5,5-tetramethyl-[1,3,2]dioxaborolan-2-yl)-3,4-dihydro-1H-isoquinoline-2-carboxylic acid benzyl ester (147 mg, 0.26 mmol, 1 eq.) was added and the mixture was stirred at 100° C. for 18 hours. The mixture was allowed to cool to r.t., diluted with Et$_2$O (10 mL), filtered through celite, washed with Et$_2$O, and the filtrate was concentrated in vacuo. The residue was purified by prep. HPLC (column: Atlantis, 30×75 mm, 10 um, UV/MS, acidic conditions) and concentrated in vacuo to give the title compound as a colorless oil.

LC-MS 3: $t_R$=1.04 min; [M+H]$^+$=492.2

Synthesis of 8-(5-Fluoro-2-hydroxy-phenyl)-3,4-dihydro-1H-isoquinoline-2-carboxylic acid benzyl ester (C23H20NO3F, MW=377.14)

To a solution under N$_2$ of 8-(2-benzyloxy-5-fluoro-phenyl)-3,4-dihydro-1H-isoquinoline-2-carboxylic acid benzyl ester (208 mg, 0.45 mmol, 1.0 eq.) in EtOH (10 mL), palladium on activated carbon (10 wt. %, 21 mg) was added. The flask was evacuated and refilled with H$_2$. The black suspension was stirred at r.t. under an H$_2$-atmosphere for 6 hours. The black suspension was filtered through Celite and the filtrate was concentrated in vacuo to give a beige foam. To an-ice cooled suspension of the residue and triethylamine (93 μL, 0.67 mmol, 1.5 eq.) in DCM (10 mL), benzyl chloroformate (67 μL, 0.45 mmol, 1.0 eq.) was added dropwise. Upon completion of the addition, the mixture was stirred at 0° C. for 1 hour and further at r.t. for 4 hours. The reaction was quenched with 1M aq. citric acid soln. (10 mL). The layers were separated. The aq. phase was extracted with DCM (3×10 mL). The comb. org. phases were dried over Na$_2$SO$_4$ and concentrated in vacuo. The residue was dissolved in THF (10 mL) and 1M aq. NaOH (2 mL) was added. The mixture was stirred at r.t. for 64 hours. The org. solvent was removed in vacuo and the aq. layer was acidified with 2N aq. HCl. The aq. layer was extracted with DCM (3×10 mL). The comb. org. phases were dried over MgSO$_4$ and concentrated in vacuo. The residue was purified by CC (SiO$_2$, Hept/AcOEt 7:3) to give the title compound as a white foam.

LC-MS 2: $t_R$=0.90 min; [M+H]$^+$=378.1

Synthesis of (±)-5-Fluoro-8-[2-methoxy-4-(1-methoxycarbonyl-ethoxy)-phenyl]-3,4-dihydro-1H-isoquinoline-2-carboxylic acid benzyl ester (C28H28NO6F, MW=493.19)

A mixture under N$_2$ of palladium (II) acetate (0.4 mg, 2 μmol, 0.01 eq.), 2-dicyclohexylphosphino-2',6'-dimethoxy-biphenyl (1.7 mg, 4 μmol, 0.02 eq.), 5-fluoro-8-(4,4,5,5-tetramethyl-[1,3,2]dioxaborolan-2-yl)-3,4-dihydro-1H-isoquinoline-2-carboxylic acid benzyl ester (95 mg, 0.20 mmol, 1.00 eq.) and potassium phosphate (85 mg, 0.40 mmol, 2.00 eq.) in toluene (0.6 mL) and water (0.035 mL) was stirred at r.t. for 2 min. A solution of (±)-2-(4-Bromo-3-methoxy-phenoxy)-propionic acid methyl ester (58 mg, 0.2 mmol, 1.00 eq.) in toluene (0.6 mL) was added and the mixture was stirred at 100° C. for 2 days. The mixture was allowed to cool to r.t., filtered through celite and concentrated in vacuo. The crude residue, redissolved in MeCN (1.5 mL) and formic acid (0.2 mL), was purified by prep. HPLC (column: Waters XBridge, 30×75 mm, 10 um, UV/MS, acidic conditions) and evaporated to give the title compound as a colorless oil.

LC-MS 3: $t_R$=1.03 min; [M+H]$^+$=494.3

General Method for the Synthesis of Phenols 13

To a mixture under N$_2$ of 8-bromo-5-fluoro-3,4-dihydro-1H-isoquinoline-2-carboxylic acid benzyl ester (146 mg, 0.40 mmol, 1.00 eq.), 5-hydroxy-2-methoxyphenylboronic acid (69 mg, 0.40 mmol, 1.00 eq.) and sodium carbonate (170 mg, 1.60 mmol, 4.00 eq.) in toluene/MeOH/Water 20:4:1 (8 mL), tetrakis(triphenylphosphine) palladium (0) (23 mg, 0.02 mmol, 0.05 eq.) was added and the mixture was stirred under reflux at 100° C. for 48 hours. The mixture was allowed to cool to r.t. and concentrated in vacuo. The residue was partitioned between AcOEt (20 mL) and water (20 mL). The layers were separated. The org. phase was washed with sat. aq. NaCl soln. (1×10 mL), dried over MgSO$_4$ and filtered through Celite. The filtrate was concentrated in vacuo. The residue was purified by flashmaster (column: 10 g, flow: 15 mL/min, 30 fractions of 15 mL, Heptane 100% to Heptane+32% AcOEt) to yield the desired phenol as a pale yellow foam.

Listed in Table 52 below are phenols 13, prepared according to the above-mentioned method, with corresponding compound of Structure 7 and the corresponding boronic acid derivative as starting materials.

TABLE 52

| Phenols 13 | Formula MW | $t_R$ [min] LC-MS Method | MS-data m/z [M + H]$^+$ |
|---|---|---|---|
| 5-Fluoro-8-(5-hydroxy-2-methoxy-phenyl)-3,4-dihydro-1H-isoquinoline-2-carboxylic acid benzyl ester | C24H22NO4F 407.15 | 0.94 LC-MS 3 | 407.7 |
| 5-Fluoro-8-(3-hydroxy-phenyl)-3,4-dihydro-1H-isoquinoline-2-carboxylic acid benzyl ester | C23H20NO3F 377.14 | 0.95 LC-MS 3 | 377.8 |
| 8-(2-Chloro-5-hydroxy-phenyl)-5-fluoro-3,4-dihydro-1H-isoquinoline-2-carboxylic acid benzyl ester | C23H19NO3ClF 411.10 | 0.97 LC-MS 3 | 412.0 |
| 8-(4-Chloro-3-hydroxy-phenyl)-5-fluoro-3,4-dihydro-1H-isoquinoline-2-carboxylic acid benzyl ester | C23H19NO3ClF 411.10 | 0.99 LC-MS 3 | 411.9 |

TABLE 52-continued

| Phenols 13 | Formula MW | $t_R$ [min] LC-MS Method | MS-data m/z [M + H]$^+$ |
|---|---|---|---|
| 8-(3-Chloro-5-hydroxy-phenyl)-5-fluoro-3,4-dihydro-1H-isoquinoline-2-carboxylic acid tert-butyl ester | C20H21NO3ClF 377.12 | 0.99 LC-MS 3 | 378.0 |
| 8-(5-Chloro-2-hydroxy-phenyl)-5-fluoro-3,4-dihydro-1H-isoquinoline-2-carboxylic acid tert-butyl ester | C20H21NO3ClF 377.12 | 0.99 LC-MS 3 | 378.0 |
| 8-(3-Chloro-5-hydroxy-phenyl)-5-trifluoromethyl-3,4-dihydro-1H-isoquinoline-2-carboxylic acid tert-butyl ester | C21H21NO3ClF3 427.12 | 1.03 LC-MS 3 | No ionization |
| 5-Chloro-8-(2-chloro-5-hydroxy-phenyl)-3,4-dihydro-1H-isoquinoline-2-carboxylic acid benzyl ester | C23H19NO3Cl2 427.07 | 0.99 LC-MS 3 | 428.1 |
| 8-(2-Chloro-5-hydroxy-phenyl)-5-methoxy-3,4-dihydro-1H-isoquinoline-2-carboxylic acid benzyl ester | C24H22NO4Cl 423.12 | 0.96 LC-MS 3 | 424.2 |
| 8-(2-Chloro-5-hydroxy-phenyl)-5-methyl-3,4-dihydro-1H-isoquinoline-2-carboxylic acid benzyl ester | C24H22NO3Cl 407.13 | 0.97 LC-MS 3 | 408.2 |
| 8-(2-Chloro-5-hydroxy-phenyl)-5-trifluoromethyl-3,4-dihydro-1H-isoquinoline-2-carboxylic acid benzyl ester | C24H19NO3ClF3 461.10 | 1.00 LC-MS 3 | 462.2 |

Synthesis of [5-Fluoro-8-(5-hydroxy-2-methoxy-phenyl)-3,4-dihydro-1H-isoquinolin-2-yl]-((1R,2R)-2-phenyl-cyclopropyl)-methanone (C26H24NO3F, MW=417.17)

To a mixture under N$_2$ of (8-bromo-5-fluoro-3,4-dihydro-1H-isoquinolin-2-yl)-((1R,2R)-2-phenyl-cyclopropyl)-methanone (289 mg, 0.76 mmol, 1.00 eq.), 5-hydroxy-2-methoxyphenylboronic acid (131 mg, 0.76 mmol, 1.00 eq.) and sodium carbonate (324 mg, 3.05 mmol, 4.00 eq.) in toluene/MeOH/water 20:4:1 (15 mL), tetrakis(triphenylphosphine) palladium (0) (44 mg, 0.04 mmol, 0.05 eq.) was added and the mixture was stirred at 100° C. for 62 hours. The mixture was allowed to cool to r.t. and concentrated in vacuo. The residue was partitioned between AcOEt (30 mL) and water (30 mL). The layers were separated. The org. phase was washed with sat. aq. NaCl soln. (1×15 mL), dried over MgSO$_4$ and filtered through Celite. The filtrate was concentrated in vacuo. The residue was purified by flashmaster (column: 50 g, flow: 40 mL/min, 28 fractions of 40 mL, Heptane+10% AcOEt to Heptane+50% AcOEt) to yield the title product as a colorless oil.

LC-MS 3: $t_R$=0.91 min; [M+H]$^+$=417.9

General Method for the Alkylation of a Phenol 13

Ethyl bromoacetate (54 µL, 0.49 mmol, 1.5 eq.) was added to a solution of 8-(3-chloro-5-hydroxy-phenyl)-5-fluoro-3,4-dihydro-1H-isoquinoline-2-carboxylic acid tert-butyl ester (124 mg, 0.33 mmol, 1.0 eq.) and K$_2$CO$_3$ (136 mg, 0.99 mmol, 3.0 eq.) in DMF (1 mL). The mixture was stirred at r.t. for 18 hours. The reaction mixture was partitioned between AcOEt and water. The layers were separated and the aq. phase was extracted with AcOEt (2×). The comb. org. extracts were washed with water and sat. aq. NaCl soln., dried over MgSO$_4$, filtered, and concentrated in vacuo to give the desired ester as a yellow oil. The product was used without further purification.

Listed in Table 53 below are esters of Structure 6-A, prepared according to the above-mentioned method, with corresponding phenols 13 as starting material.

TABLE 53

| Esters 6-A | Formula MW | $t_R$ [min] LC-MS Method | MS-data m/z [M + H]$^+$ |
|---|---|---|---|
| 8-(3-Chloro-5-ethoxycarbonylmethoxy-phenyl)-5-fluoro-3,4-dihydro-1H-isoquinoline-2-carboxylic acid tert-butyl ester | C24H27NO5ClF 463.16 | 1.07 LC-MS 3 | 464.0 |
| 8-(5-Chloro-2-ethoxycarbonylmethoxy-phenyl)-5-fluoro-3,4-dihydro-1H-isoquinoline-2-carboxylic acid tert-butyl ester | C24H27NO5ClF 463.16 | 1.05 LC-MS 3 | 464.0 |
| 8-(3-Chloro-5-ethoxycarbonylmethoxy-phenyl)-5-trifluoromethyl-3,4-dihydro-1H-isoquinoline-2-carboxylic acid tert-butyl ester | C25H27NO5ClF3 513.15 | 1.10 LC-MS 3 | 513.5 |

General Method for the Preparation of Intermediates of Structure 2

To an ice-cooled solution of 8-(3-chloro-5-ethoxycarbonylmethoxy-phenyl)-5-fluoro-3,4-dihydro-1H-isoquinoline-2-carboxylic acid tert-butyl ester (173 mg, 0.32 mmol, 1 eq.) in DCM (0.6 mL), 4M HCl in dioxane (1.4 mL) was added. The resulting solution was stirred at r.t. for 2 hours. The reaction mixture was concentrated in vacuo. The residue was coevaporated with EtOH (3×) to give the desired salt as a pale yellow solid. The product was used without further purification.

Listed in Table 54 below are compounds of Structure 2, prepared according to the above-mentioned method, with corresponding Boc-protected esters of Structure 6 as starting material.

TABLE 54

| Intermediates of Structure 2 | Formula MW | $t_R$ [min] LC-MS Method | MS-data m/z $[M + H]^+$ |
|---|---|---|---|
| [3-Chloro-5-(5-fluoro-1,2,3,4-tetrahydro-isoquinolin-8-yl)-phenoxy]-acetic acid ethyl ester hydrochloride | C19H19NO3ClF 363.10 | 0.73 LC-MS 3 | 364.0 |
| [4-Chloro-2-(5-fluoro-1,2,3,4-tetrahydro-isoquinolin-8-yl)-phenoxy]-acetic acid ethyl ester hydrochloride | C19H19NO3ClF 363.10 | 0.73 LC-MS 3 | 364.0 |
| [3-Chloro-5-(5-trifluoromethyl-1,2,3,4-tetrahydro-isoquinolin-8-yl)-phenoxy]-acetic acid ethyl ester hydrochloride | C20H19NO3ClF3 413.10 | 0.78 LC-MS 3 | 414.0 |
| [3-(5-Fluoro-1,2,3,4-tetrahydro-isoquinolin-8-yl)-4-methoxy-phenyl]-acetic acid ethyl ester hydrochloride | C20H22NO3F 343.16 | 0.69 LC-MS 3 | 344.3 |

General Method for the Preparation of Intermediates of Structure 2

Method A: A solution of 8-(4-tert-butoxycarbonylmethyl-2-isopropoxy-phenyl)-5-fluoro-3,4-dihydro-1H-isoquinoline-2-carboxylic acid benzyl ester (109 mg, 0.20 mmol, 1 eq.) in THF (4 mL, 0.05 M) was hydrogenated through H-Cube (settings: Cartridge Pd(OH)$_2$/C, Flow=1 mL/min, Mode Full H$_2$, r.t.). The solution was set in closed circuit for 18 hours. The solvent was removed in vacuo to give the intermediate of Structure 2 as a pale orange oil. The residue was used without further purification.

Listed in Table 55 below are compounds of Structure 2, prepared according to the above-mentioned method, with corresponding Cbz-protected esters of Structure 6 as starting material.

TABLE 55

| Intermediates of Structure 2 | Formula MW | $t_R$ [min] LC-MS Method | MS-data m/z $[M + H]^+$ |
|---|---|---|---|
| [4-(5-Fluoro-1,2,3,4-tetrahydro-isoquinolin-8-yl)-3-isopropoxy-phenyl]-acetic acid tert-butyl ester | C24H30NO3F 399.22 | 0.79 LC-MS 3 | 400.2 |
| [4-(5-Fluoro-1,2,3,4-tetrahydro-isoquinolin-8-yl)-3-(2,2,2-trifluoro-ethoxy)-phenyl]-acetic acid ethyl ester | C21H21NO3F4 411.15 | 0.74 LC-MS 3 | 412.1 |
| [3-(5-Fluoro-1,2,3,4-tetrahydro-isoquinolin-8-yl)-4-(2,2,2-trifluoro-ethoxy)-phenyl]-acetic acid ethyl ester | C21H21NO3F4 411.15 | 0.74 LC-MS 3 | 412.1 |

Method B: To a solution under N$_2$ of 8-(4-ethoxycarbonylmethyl-2-methoxy-phenyl)-5-fluoro-3,4-dihydro-1H-isoquinoline-2-carboxylic acid benzyl ester (770 mg, 1.61 mmol, 1 eq.) in AcOEt (60 mL), Pd on activated carbon (10 wt. %, 80 mg) was added. The flask was evacuated and backfilled with H$_2$ (3×). The black suspension was stirred at r.t. under an H$_2$-atmosphere for 18 hours. The suspension was filtered through Celite, the Celite rinsed with AcOEt. The filtrate was concentrated in vacuo to give the desired compound of Structure 2. The product was used without further purification.

Listed in Table 56 below are compounds of Structure 2, prepared according to the above-mentioned method, with corresponding Cbz-protected esters of Structure 6 as starting material.

TABLE 56

| Intermediates of Structure 2 | Formula MW | $t_R$ [min] LC-MS Method | MS-data m/z $[M + H]^+$ |
|---|---|---|---|
| [4-(5-Fluoro-1,2,3,4-tetrahydro-isoquinolin-8-yl)-3-methoxy-phenyl]-acetic acid ethyl ester | C20H22NO3F 343.16 | 0.68 LC-MS 3 | 344.1 |

TABLE 56-continued

| Intermediates of Structure 2 | Formula MW | $t_R$ [min] LC-MS Method | MS-data m/z $[M + H]^+$ |
|---|---|---|---|
| [3-Ethoxy-4-(5-fluoro-1,2,3,4-tetrahydro-isoquinolin-8-yl)-phenyl]-acetic acid ethyl ester | C21H24NO3F 357.17 | 0.71 LC-MS 3 | 358.1 |

Synthesis of [3-(5-Fluoro-1,2,3,4-tetrahydro-isoquinolin-8-yl)-4-isopropoxy-phenyl]-acetic acid ethyl ester (C22H26NO3F, MW=371.19)

To a solution of 8-(5-ethoxycarbonylmethyl-2-isopropoxy-phenyl)-5-fluoro-3,4-dihydro-1H-isoquinoline-2-carboxylic acid benzyl ester (1.65 g, 3.17 mmol, 1 eq.) in EtOH (15.5 mL) under $N_2$, palladium on activated carbon (10 wt. %, 165 mg) was added. The flask was carefully evacuated and refilled with $H_2$ (3×). The black suspension was stirred at r.t. under an $H_2$-atmosphere for 24 hours and further at 50° C. for 18 hours. The black suspension was filtered through Celite. The Celite was rinsed with EtOH. The filtrate was concentrated in vacuo. The residue was purified by flashmaster (column: 100 g, flow: 45 mL/min, 30 fractions of 45 mL, AcOEt to (AcOEt+10% NEt$_3$) to yield the title compound as a colorless oil.

LC-MS 3: $t_R$=0.74 min; $[M+H]^+$=372.1

Synthesis of [3-(8-Fluoro-1,2,3,4-tetrahydro-isoquinolin-5-yl)-4-methoxy-phenyl]-acetic acid ethyl ester hydrochloride (C20H22NO3F, MW=343.16)

To a solution of 5-(5-ethoxycarbonylmethyl-2-methoxy-phenyl)-8-fluoro-3,4-dihydro-1H-isoquinoline-2-carboxylic acid benzyl ester (760 mg, 1.39 mmol, 1 eq) in EtOH (7 mL) under $N_2$, palladium on activated carbon (10 wt. %, 76 mg) was added. The flask was carefully evacuated and refilled with $H_2$ (3×). The black suspension was stirred at r.t. under an $H_2$-atmosphere for 72 hours and further at 40° C. for 3 hours. The black suspension was filtered through Celite. The Celite was rinsed with EtOH. The filtrate was concentrated in vacuo. The residue was purified by flashmaster (column: 50 g, flow: 40 mL/min, 50 fractions of 45 mL, AcOEt to AcOEt+12% MeOH). The desired product was dissolved in 4M HCl in dioxane (10 mL). The resulting solution was stirred at r.t. for 30 min, then concentrated in vacuo. The salt was dissolved in EtOH and concentrated in vacuo (3 times) to afford the title salt as a yellow oil.

LC-MS 3: $t_R$=0.67 min; $[M+H]^+$=344.1

Synthesis of [4-Methoxy-3-(5-trifluoromethyl-1,2,3,4-tetrahydro-isoquinolin-8-yl)-phenyl]-acetic acid ethyl ester hydrochloride (C21H22NO3F3, MW=393.16)

To a solution of 8-(5-ethoxycarbonylmethyl-2-methoxy-phenyl)-5-trifluoromethyl-3,4-dihydro-1H-isoquinoline-2-carboxylic acid benzyl ester (426 mg, 0.79 mmol, 1 eq) in EtOH (4 mL) under $N_2$, palladium on activated carbon (10 wt. %, 43 mg) was added. The flask was carefully evacuated and refilled with $H_2$ (3×). The black suspension was stirred at r.t. under an $H_2$-atmosphere for 3 hours. The black suspension was filtered through Celite. The Celite was rinsed with EtOH. The filtrate was concentrated in vacuo. The residue was dissolved in 4M HCl in dioxane (5 mL). The resulting solution was stirred at r.t. for 18 hours, then concentrated in vacuo. The residue was dissolved in EtOH and concentrated in vacuo (3 times) to afford the title salt as a pale yellow solid.

LC-MS 3: $t_R$=0.74 min; $[M+H]^+$=394.3

Synthesis of (±)-Ethyl 2-(3-(5-fluoro-1,2,3,4-tetrahydroisoquinolin-8-yl)-4-methoxyphenyl)propanoate (C21H24NO3F, MW=357.17)

To a solution under $N_2$ of (±)-8-[5-(1-ethoxycarbonyl-ethyl)-2-methoxy-phenyl]-5-fluoro-3,4-dihydro-1H-isoquinoline-2-carboxylic acid benzyl ester (57 mg, 0.12 mmol, 1 eq.) in EtOH (40 mL), palladium on activated carbon (10 wt. %, 3.2 mg) was added. The flask was evacuated and backfilled with $H_2$ (3×). The black suspension was stirred at 50° C. under an $H_2$-atmosphere for 18 hours. The suspension was filtered through Celite, the Celite rinsed with EtOH. The filtrate was concentrated in vacuo to afford the title product as a yellow oil. The product was used without further purification.

LC-MS 3: $t_R$=0.72 min; $[M+H]^+$=358.1

Synthesis of ethyl 2-(4-(5-fluoro-1,2,3,4-tetrahydroisoquinolin-8-yl)-3-methoxyphenyl)acetate (C20H22NO3F, MW=343.16)

Step 1: A mixture under $N_2$ of palladium(II)acetate (13 mg, 0.06 mmol, 0.02 eq.), 2-dicyclohexylphosphino-2',6'-dimethoxybiphenyl (48 mg, 0.12 mmol, 0.04 eq.), 5-fluoro-8-(4,4,5,5-tetramethyl-[1,3,2]dioxaborolan-2-yl)-3,4-dihydro-1H-isoquinoline-2-carboxylic acid benzyl ester (1.20 g, 2.92 mmol, 1.00 eq.) and potassium phosphate (1.24 g, 5.84 mmol, 2.00 eq.) in toluene (8 mL) and water (0.8 mL) was stirred at r.t. during 2 min. (4-Bromo-3-methoxy-phenyl)-acetic acid ethyl ester (797 mg, 2.92 mmol, 1.00 eq) was added and the mixture was stirred at 100° C. for 18 hours. The mixture was allowed to cool to r.t., diluted with Et$_2$O (10 mL), filtered through celite, washed with Et$_2$O and concentrated in vacuo. The residue was purified by flashmaster (column: 100 g, flow: 45 mL/min, 30 fractions of 45 mL, Heptane to Heptane+50% AcOEt) to yield 8-(4-ethoxycarbonylmethyl-2-methoxy-phenyl)-5-fluoro-3,4-dihydro-1H-isoquinoline-2-carboxylic acid benzyl ester as a colorless oil.

LC-MS 3: $t_R$=1.03 min; $[M+H]^+$=478.3

Step 2: To a solution under $N_2$ of 8-(4-ethoxycarbonylmethyl-2-methoxy-phenyl)-5-fluoro-3,4-dihydro-1H-isoquinoline-2-carboxylic acid benzyl ester (770 mg, 1.61 mmol, 1 eq.) in AcOEt (60 mL), palladium on activated carbon (10 wt. %, 80 mg) was added. The flask was evacuated and backfilled with $H_2$ (3×). The black suspension was stirred at r.t. under an $H_2$-atmosphere for 18 hours. The suspension was filtered through Celite, the Celite rinsed with AcOEt. The filtrate was concentrated in vacuo to give ethyl 2-(4-(5-fluoro-1,2,3,4-tetrahydroisoquinolin-8-yl)-3-methoxyphenyl)acetate as an yellow oil. The product was used without further purification.

LC-MS 3: $t_R$=0.68 min; $[M+H]^+$=344.1

General Method for the Synthesis of Isoquinolines 14

A mixture under $N_2$ of palladium(II)acetate (11 mg, 51 μmol, 0.01 eq.), 2-dicyclohexylphosphino-2',6'-dimethoxybiphenyl (43 mg, 0.10 mmol, 0.02 eq.), [4-methoxy-3-(4,4,5,5-tetramethyl-[1,3,2]dioxaborolan-2-yl)-phenyl]-acetic acid ethyl ester (3.29 g, 7.78 mmol, 1.50 eq.) and potassium phosphate (2.20 g, 10.4 mmol, 2.00 eq.) in toluene (10 mL) and water (1 mL) was stirred at r.t. during 2 min. 8-Chloro-5,6-difluoro-isoquinoline (1.11 g, 5.19 mmol, 1.00 eq.) was added and the mixture was stirred at 100° C. for 18 hours. The mixture was allowed to cool to r.t., diluted with Et$_2$O (55 mL), filtered through celite, washed with $Et_2O$, and concentrated in vacuo. The residue was purified by flashmaster (column: 100 g, flow: 45 mL/min, 30 fractions of 45 mL, Heptane+5% AcOEt to Heptane+45% AcOEt) to yield the desired isoquinoline as a yellow oil.

Listed in Table 57 below are isoquinolines 14, prepared according to the above-mentioned method, with corresponding isoquinolines 15 as starting material.

TABLE 57

| Isoquinolines 14 | Formula MW | $t_R$ [min] LC-MS Method | MS-data m/z $[M + H]^+$ |
|---|---|---|---|
| [3-(5,6-Difluoro-isoquinolin-8-yl)-4-methoxy-phenyl]-acetic acid ethyl ester | C20H17NO3F2 357.12 | 0.81 LC-MS 3 | 358.1 |
| [3-(7-Fluoro-isoquinolin-8-yl)-4-methoxy-phenyl]-acetic acid ethyl ester | C20H18NO3F 339.13 | 0.70 LC-MS 3 | 340.1 |
| [3-(6-Fluoro-isoquinolin-8-yl)-4-methoxy-phenyl]-acetic acid ethyl ester | C20H18NO3F 339.13 | 0.72 LC-MS 3 | 340.2 |

Synthesis of [3-(5,7-Difluoro-isoquinolin-8-yl)-4-methoxy-phenyl]-acetic acid ethyl ester (C20H17NO3F2, MW=357.12)

To an ice-cooled suspension of 5,7-difluoro-isoquinolin-8-ol (200 mg, 1.10 mmol, 1.00 eq.) in DCM (10 mL), $NEt_3$ (0.46 mL, 3.31 mmol, 3.00 eq.) and trifluoromethanesulfonic anhydride (0.29 mL, 1.66 mmol, 1.50 eq.) were added in sequence. The reaction mixture was stirred at 0° C. for 30 min and further at r.t. for 45 min. The mixture was diluted with DCM (20 mL) and washed with sat. aq. $NaHCO_3$ soln. (2×10 mL). The org. layer was dried over $MgSO_4$ and concentrated in vacuo. To a mixture under $N_2$ of the resulting triflate, [4-methoxy-3-(4,4,5,5-tetramethyl-[1,3,2]dioxaborolan-2-yl)-phenyl]-acetic acid ethyl ester (354 mg, 1.10 mmol, 1.00 eq.), and sodium carbonate (468 mg, 4.42 mmol, 4.00 eq.) in toluene/EtOH/water 20:4:1 (10 mL), tetrakis(triphenylphosphine) palladium (0) (64 mg, 0.06 mmol, 0.05 eq.) was added. The mixture was stirred at 100° C. for 18 hours. The mixture was allowed to cool to r.t. and concentrated in vacuo. The residue was taken up in DMF, filtered, and purified by prep. HPLC (column Atlantis, 30×75 mm, 10 um, UV/MS, acidic conditions) and concentrated in vacuo to give the title compound as a brown oil.

LC-MS 3: $t_R$=0.83 min; $[M+H]^+$=358.0

General Method for the Catalytic Hydrogenation of Isoquinolines 14

To a solution under $N_2$ of [3-(7-fluoro-isoquinolin-8-yl)-4-methoxy-phenyl]-acetic acid ethyl ester (75 mg, 0.221 mmol, 1 eq) in AcOEt (20 mL), platinum(IV) oxide hydrate (80-82% Pt) (43 mg) was added. The flask was evacuated and backfilled with $H_2$ (3×). The black suspension was stirred at r.t. under an $H_2$-atmosphere for 18 hours. The suspension was filtered through Celite, the Celite rinsed with AcOEt. The filtrate was concentrated in vacuo to give the desired tetrahydroisoquinoline as a yellow oil. The product was used without further purification.

Listed in Table 58 below are tetrahydroisoquinolines 2-A, prepared according to the above-mentioned method, with corresponding isoquinolines 14 as starting material.

TABLE 58

| Tetrahydroisoquinolines 2-A | Formula MW | $t_R$ [min] LC-MS Method | MS-data m/z $[M + H]^+$ |
|---|---|---|---|
| [3-(7-Fluoro-1,2,3,4-tetrahydro-isoquinolin-8-yl)-4-methoxy-phenyl]-acetic acid ethyl ester | C20H22NO3F 343.16 | 0.68 LC-MS 3 | 344.1 |
| [3-(6-Fluoro-1,2,3,4-tetrahydro-isoquinolin-8-yl)-4-methoxy-phenyl]-acetic acid ethyl ester | C20H22NO3F 343.16 | 0.69 LC-MS 3 | 344.1 |
| [3-(5,7-Difluoro-1,2,3,4-tetrahydro-isoquinolin-8-yl)-4-methoxy-phenyl]-acetic acid ethyl ester | C20H21NO3F2 361.15 | 0.69 LC-MS 3 | 362.1 |
| [3-(5,6-Difluoro-1,2,3,4-tetrahydro-isoquinolin-8-yl)-4-methoxy-phenyl]-acetic acid ethyl ester | C20H21NO3F2 361.15 | 0.70 LC-MS 3 | 362.1 |

General Method for the Synthesis of a Nitrophenol Carbamate 5

To a solution of [3-(5-fluoro-1,2,3,4-tetrahydro-isoquinolin-8-yl)-4-methoxy-phenyl]-acetic acid ethyl ester hydrochloride (368 mg, 0.96 mmol, 1.0 eq.) in DCM (10 mL) and N-ethyldiisopropylamine (0.41 mL, 2.40 mmol, 2.5 eq), 4-nitrophenyl chloroformate (232 mg, 1.15 mmol, 1.2 eq.) was added. The mixture was stirred at r.t. for 1 hour. The reaction was quenched with 1M aq. citric acid soln. (10 mL). The layers were separated. The aq. phase was extracted with DCM (3×10 mL). The comb. org. phases were dried over $MgSO_4$, filtered, and concentrated in vacuo to give the title compound as a yellow foam. The product was used without further purification.

Listed in Table 59 below are examples of nitrophenol carbamate 5, prepared according to the above-mentioned method with the corresponding compound of Structure 2 (or the corresponding salt) as starting material.

TABLE 59

| Nitrophenol carbamate 5 | Formula MW | $t_R$ [min] LC-MS Method | MS-data m/z $[M + H]^+$ |
|---|---|---|---|
| 8-(5-Ethoxycarbonylmethyl-2-methoxy-phenyl)-5-fluoro-3,4-dihydro-1H-isoquinoline-2-carboxylic acid 4-nitro-phenyl ester | C27H25N2O7F 508.17 | 1.02 LC-MS 3 | 509.2 |
| 8-(2-Ethoxy-5-ethoxycarbonylmethyl-phenyl)-5-fluoro-3,4-dihydro-1H-isoquinoline-2-carboxylic acid 4-nitro-phenyl ester | C28H27N2O7F 522.18 | 1.05 LC-MS 3 | 523.2 |
| 8-(2-Ethoxy-4-ethoxycarbonylmethyl-phenyl)-5-fluoro-3,4-dihydro-1H-isoquinoline-2-carboxylic acid 4-nitro-phenyl ester | C28H27N2O7F 522.18 | 1.05 LC-MS 3 | 523.2 |

Synthesis of
1-Bromo-2,3-bis-bromomethyl-4-fluoro-benzene
(C8H6Br3F, MW=357.80)

To a solution of 6-bromo-3-fluoro-o-xylene (2.03 g, 10.00 mmol, 1.00 eq.) in trifluoromethylbenzene (40 mL), N-bromsuccinimide (3.56 g, 20.00 mmol, 2.00 eq.) and benzoyl peroxide (49 mg, 0.15 mmol, 0.015 eq.) were added in sequence. The reaction mixture was heated at 85° C. for 18 hours. The mixture was allowed to cool to r.t., filtered, and the solid rinsed with heptane. The filtrate was concentrated in vacuo. The residue was purified by flashmaster (column: 100 g, flow: 45 mL/min, 30 fractions of 45 mL, Heptane to Heptane+10% AcOEt) to yield the desired compound as a colorless oil LC-MS 3: $t_R$=0.94 min; $[M+H]^+$=no ionization Synthesis of [3-(2-Benzyl-7-fluoro-2,3-dihydro-1H-isoindol-4-yl)-4-methoxy-phenyl]-acetic acid ethyl ester (C26H26NO3F, MW=419.19)

To a mixture of 1-bromo-2,3-bis-bromomethyl-4-fluoro-benzene (3.06 g, 8.48 mmol, 1.0 eq.) and K$_2$CO$_3$ (2.58 g, 18.70 mmol, 2.2 eq.) in toluene (350 mL), benzylamine (0.94 mL, 8.48 mmol, 1.0 eq.) was added. The mixture was refluxed for 18 hours. The reaction mixture was allowed to cool to r.t. and was concentrated in vacuo. The residue was poured in water (150 mL). The mixture was extracted with DCM (2×100 mL). The comb. org. phases were dried over MgSO$_4$ and concentrated in vacuo. The residue was partially purified by flashmaster (column: 100 g, flow: 45 mL/min, 30 fractions of 45 mL, Heptane to Heptane+10% AcOEt).

To a solution under N$_2$ of the residue (306 mg, 1.00 mmol, 1.00 eq.) and sodium carbonate (424 mg, 4.00 mmol, 4.00 eq.) in toluene/EtOH/water 20:4:1 (10 mL), [4-methoxy-3-(4,4,5,5-tetramethyl-[1,3,2]dioxaborolan-2-yl)-phenyl]-acetic acid ethyl ester (320 mg, 1.00 mmol, 1.00 eq.) and tetrakis(triphenylphosphine) palladium (0) (58 mg, 0.05 mmol, 0.05 eq.) were added in sequence. The mixture was refluxed for 18 hours. The mixture was allowed to cool to r.t. and concentrated in vacuo. The residue was taken up in DMF, filtered, and then purified by prep. HPLC (column: Atlantis, 30×75 mm, 10 um, UV/MS, acidic conditions) and concentrated in vacuo to give the title compound.

LC-MS 3: $t_R$=0.79 min; $[M+H]^+$=420.3

Synthesis of [3-(7-Fluoro-2,3-dihydro-1H-isoindol-4-yl)-4-methoxy-phenyl]-acetic acid ethyl ester (C19H20NO3F, MW=329.14)

To a solution under N$_2$ of [3-(2-benzyl-7-fluoro-2,3-dihydro-1H-isoindol-4-yl)-4-methoxy-phenyl]-acetic acid ethyl ester (246 mg, 0.59 mmol, 1 eq.) in ethanol (40 mL), palladium on activated carbon (20 mg) was added. The flask was evacuated and backfilled with H$_2$ (3×). The black suspension was stirred at r.t. under an H$_2$-atmosphere for 18 hours. The suspension was filtered through Celite, the Celite rinsed with EtOH. The filtrate was concentrated in vacuo to give the desired product. The product was used without further purification.

LC-MS 2: $t_R$=0.59 min; $[M+H]^+$=330.3

Synthesis of 2,2,2-Trifluoro-1-(6-fluoro-9-methoxy-1,2,4,5-tetrahydro-benzo[d]azepin-3-yl)-ethanone
(C13H13NO2F4, MW=291.09)

Step 1: To a solution of 2-(2-fluoro-5-methoxy-phenyl)-ethylamine (4.30 g, 25.4 mmol, 1.0 eq.) in MeOH (100 mL), glyoxal dimethyl acetal (60% aqueous solution, 5.73 g, 33.0 mmol, 1.3 eq.) was added. The resulting yellow solution was stirred at r.t. for 18 hours. The yellow solution was cooled to 0° C. and sodium borohydride (1.44 g, 38.1 mmol, 1.5 eq.) was added portionwise. The cooling bath was removed and the yellow solution was stirred at r.t. for 2 hours. The reaction mixture was concentrated in vacuo. The residue was diluted with water (50 mL) and DCM (100 mL). The layers were separated. The aq. phase was extracted with DCM (2×50 mL). The comb. org. phases were washed with water (1×150 mL), sat. aq. NaCl soln. (1×50 mL), dried over MgSO$_4$, and concentrated in vacuo to give N-(2-fluoro-5-methoxyphenethyl)-2,2-dimethoxyethanamine. The product was used without further purification.

LC-MS 3: $t_R$=0.54 min; $[M+H]^+$=258.1

Step 2: N-(2-Fluoro-5-methoxyphenethyl)-2,2-dimethoxyethanamine (3.0 g, 11.7 mmol, 1.0 eq.) was added dropwise to trifluoacetic anhydride (5.2 mL, 37.3 mmol, 3.2 eq.) at −15° C. The reaction mixture was allowed to warm to r.t. and stirred for 25 min. Then, trifluoroacetic acid (9.2 mL, 120.0 mmol, 10.3 eq.) was added and the resulting solution was heated to 40° C. for 18 hours. The reaction mixture was poured in cold water (100 mL). The mixture was extracted with DCM (3×50 mL). The comb. org. phases were dried over MgSO$_4$ and concentrated in vacuo. To a solution under N$_2$ of the residue in AcOEt/EtOH 1:1 (60 mL), palladium on activated carbon (10 wt. %, 400 mg) was added. The flask was evacuated and backfilled with H$_2$ (3×). The black suspension was stirred at r.t. under an H$_2$-atmosphere for 18 hours. The suspension was filtered through Celite, the Celite rinsed with EtOH. The filtrate was concentrated in vacuo. The residue was purified by flashmaster (column: 100 g, flow: 45 mL/min, 30 fractions of 45 mL, Heptane to Heptane+50% AcOEt) to yield the title compound as a white solid.

LC-MS 3: $t_R$=0.90 min; $[M+H]^+$=292.2

Synthesis of 9-Fluoro-2,3,4,5-tetrahydro-1H-benzo[d]azepin-6-ol (C10H12NOF, MW=181.09)

To a solution of 2,2,2-trifluoro-1-(6-fluoro-9-methoxy-1,2,4,5-tetrahydro-benzo[d]azepin-3-yl)-ethanone (1.22 g, 4.19 mmol, 1 eq.) in DCM (50 mL), 1M boron tribromide solution in dichloromethane (8.38 mL) was added. The mixture was stirred at r.t. for 2 hours. The reaction was carefully quenched with 2N aq. NaOH soln. (50 mL) and stirred at r.t. for 30 min. The reaction mixture was washed with DCM (2×50 mL). The aq. layer was concentrated in vacuo. The residue was purified by prep. HPLC (column: Water X-Bridge, 30×75 mm, 10 um, UV/MS, basic conditions) and concentrated in vacuo to give the desired product.

LC-MS 3: $t_R$=0.41 min; $[M+H]^+$=182.4

Synthesis of 6-Fluoro-9-hydroxy-1,2,4,5-tetrahydro-benzo[d]azepine-3-carboxylic acid benzyl ester (C18H18NO3F, MW=315.13)

To an ice-cooled solution of 9-fluoro-2,3,4,5-tetrahydro-1H-benzo[d]azepin-6-ol (550 mg, 3.04 mmol, 1.0 eq.) and DIPEA (1.56 mL, 9.11 mmol, 3.0 eq.) in a mixture of DMF/DCM 1:2 (30 mL), benzyl chloroformate (0.50 mL, 3.34 mmol, 1.1 eq.) was added dropwise. Upon completion of the addition, the cooling bath was removed and the solution was stirred at r.t. for 3 hours. Then 1M aq. NaOH soln. (10 mL) was added ant the reaction mixture was stirred at r.t. for 1 hour. The mixture was extracted with DCM (3×50 mL). The comb. org. phases were dried over MgSO4 and concentrated in vacuo. The residue was purified by prep. HPLC (column: Atlantis, 30×75 mm, 10 um, UV/MS, acidic conditions) and concentrated in vacuo to give the title compound as a brown solid.

LC-MS 3: $t_R$=0.86 min; $[M+H]^+$=316.3

Synthesis of 6-(5-Ethoxycarbonylmethyl-2-methoxy-phenyl)-9-fluoro-1,2,4,5-tetrahydro-benzo[d]azepine-3-carboxylic acid benzyl ester (C29H30NO5F, MW=491.21)

To an ice-cooled suspension of 6-fluoro-9-hydroxy-1,2,4,5-tetrahydro-benzo[d]azepine-3-carboxylic acid benzyl ester (170 mg, 0.54 mmol, 1.00 eq) in DCM (10 mL), NEt3 (0.23 mL, 1.62 mmol, 3.00 eq) and trifluoromethanesulfonic anhydride (0.14 mL, 0.81 mmol, 1.50 eq.) were added in sequence. The reaction mixture was stirred at 0° C. for 30 min and further at r.t. for 45 min. The mixture was diluted with DCM (20 mL) and washed with sat. aq. NaHCO3 soln. (2×10 mL). The org. layer was dried over MgSO4 and concentrated in vacuo. To a mixture under N2 of the resulting triflate, [4-methoxy-3-(4,4,5,5-tetramethyl-[1,3,2]dioxaborolan-2-yl)-phenyl]-acetic acid ethyl ester (173 mg, 0.54 mmol, 1.00 eq.), and sodium carbonate (229 mg, 2.16 mmol, 4.00 eq.) in toluene/EtOH/water 20:4:1 (10 mL), tetrakis(triphenylphosphine)palladium (0) (31 mg, 0.03 mmol, 0.05 eq.) was added. The mixture was stirred at 100° C. for 17 hours. The mixture was allowed to cool to r.t. and concentrated in vacuo. The residue was taken up in DMF, filtered, and purified by prep. HPLC (column Atlantis, 30×75 mm, 10 um, UV/MS, acidic conditions) and concentrated in vacuo to give the title compound as a brown oil.

LC-MS 3: $t_R$=1.04 min; $[M+H]^+$=492.4

Synthesis of [3-(9-Fluoro-2,3,4,5-tetrahydro-1H-benzo[d]azepin-6-yl)-4-methoxy-phenyl]-acetic acid ethyl ester hydrochloride (C21H24NO3F, MW=357.17)

To a solution under N2 of 6-(5-carboxymethyl-2-methoxy-phenyl)-9-fluoro-1,2,4,5-tetrahydro-benzo[d]azepine-3-carboxylic acid benzyl ester (80 mg, 0.17 mmol, 1 eq.) in 1.25M hydrogen chloride in ethanol (15 ml), Pd on activated carbon (10 mg) was added. The flask was evacuated and backfilled with H2 (3×). The black suspension was stirred at r.t. under an H2-atmosphere for 18 hours. The suspension was filtered through Celite, the Celite rinsed with EtOH. The filtrate was concentrated in vacuo to give the desired salt as a colorless oil. The product was used without further purification.

LC-MS 3: $t_R$=0.70 min; $[M+H]^+$=358.3

General Method for the Synthesis of Cyclopropanecarboxylic Acid Derivatives (±)-46

Step 1: A solution of 2-chlorocinnamic acid (1.84 g, 10.0 mmol, 1.0 eq.) and N,O-dimethylhydroxylamine hydrochloride (995 mg, 10.0 mmol, 1.0 eq.) in DMF (60 mL) was treated with 4-(dimethylamino)pyridine (4.89 g, 40.0 mmol, 4.0 eq.) and N-(3-dimethylaminopropyl)-N'-ethylcarbodiimide hydrochloride (2.88 g, 15.0 mmol, 1.5 eq.) and the resulting solution was stirred at r.t. for 62 hours. The reaction mixture was diluted with AcOEt (1 L). The diluted solution was washed with 1N aq. HCl soln. (3×400 mL), sat. aq. NaHCO3 soln. (3×400 mL), sat. aq. NaCl soln. (1×400 mL), dried over MgSO4, and concentrated in vacuo to give the desired amide as a pale yellow oil. The product was used without further purification.

LC-MS 3: $t_R$=0.80 min; $[M+H]^+$=226.2

Step 2: To a solution under N2 of trimethylsulfoxonium (2.20 g, 10.0 mmol, 2.0 eq.) in DMSO (10 mL) maintained at r.t. with a water bath, sodium hydride (60% dispersion in mineral oil, 400 mg, 10.0 mmol, 2.0 eq.) was added portionwise over 10 min. The resulting mixture was stirred at r.t. for 1 hour. A solution of (E)-3-(2-chloro-phenyl)-N-methoxy-N-methyl-acrylamide (1.14 g, 5.0 mmol, 1.0 eq.) in DMSO (5 mL) was added and the reaction mixture was stirred at r.t. for 19 hours. The reaction mixture was poured in sat. aq. NH4Cl soln. (50 mL) and extracted with DCM (3×50 mL). The comb. org. phases were washed with sat. aq. NaCl soln. (1×50 mL), dried over MgSO4, and concentrated in vacuo. The residue was purified by CC (SiO2, Hept/AcOEt) to give the desired cyclopropyl as a colorless oil.

LC-MS 2: $t_R$=0.75 min; $[M+H]^+$=240.2

Step 3: To a solution of (±)-(trans)-2-(2-chloro-phenyl)-cyclopropanecarboxylic acid methoxy-methyl-amide (1.00 g, 4.20 mmol, 1.0 eq.) in Et2O (30 mL), tert-butoxide (2.54 g, 22.66 mmol, 5.4 eq.) and H2O (0.15 mL) were added. The mixture was stirred at r.t. for 18 hours. The reaction mixture was concentrated in vacuo. The residue was dissolved in H2O and the solution was carefully acidified with conc. HCl. The mixture was extracted with DCM (3×20 mL). The comb. org. phases were dried over MgSO4, filtered and concentrated in vacuo to give the desired acid as a colorless oil that solidifies upon standing. The residue was used without further purification.

Listed in Table 60 below are cyclopropyl acids (±)-46, prepared according to the above-mentioned method, with the corresponding α,β-unsaturated acid 43 as starting material.

TABLE 60

| Intermediates (±)-46 | Formula MW | $t_R$ [min] LC-MS Method | MS-data m/z [M + H]$^+$ |
| --- | --- | --- | --- |
| (±)-(trans)-2-(2-Chloro-phenyl)-cyclopropanecarboxylic acid | C10H9O2Cl 196.03 | 0.67 LC-MS 2 | No ionization |
| (±)-(trans)-2-(2-Fluoro-phenyl)-cyclopropanecarboxylic acid | C10H9O2F 180.06 | 0.71 LC-MS 3 | No ionization |
| (±)-(trans)-2-o-Tolyl-cyclopropanecarboxylic acid | C11H12O2 176.08 | 0.73 LC-MS 3 | No ionization |
| (±)-(trans)-2-(4-Chloro-phenyl)-cyclopropanecarboxylic acid | C10H9O2Cl 196.03 | 0.76 LC-MS 3 | No ionization |
| (±)-(trans)-2-(4-Fluoro-phenyl)-cyclopropanecarboxylic acid | C10H9O2F 180.06 | 0.63 LC-MS 2 | No ionization |
| (±)-(trans)-2-(3-Chloro-phenyl)-cyclopropanecarboxylic acid | C10H9O2Cl 196.03 | 0.76 LC-MS 3 | No ionization |
| (±)-(trans)-2-(3-Fluoro-phenyl)-cyclopropanecarboxylic acid | C10H9O2F 180.06 | 0.71 LC-MS 3 | No ionization |
| (±)-(trans)-2-(2,4-Dichloro-phenyl)-cyclopropanecarboxylic acid | C10H8O2Cl2 229.99 | 0.80 LC-MS 3 | No ionization |
| (±)-(trans)-2-(2-Trifluoromethyl-phenyl)-cyclopropanecarboxylic acid | C11H9O2F3 230.06 | 0.78 LC-MS 3 | No ionization |
| (±)-(trans)-2-(4-Methoxy-phenyl)-cyclopropanecarboxylic acid | C11H12O3 192.08 | 0.61 LC-MS 2 | No ionization |

Synthesis of (±)-(trans)-2-Pyridin-2-yl-cyclopropanecarboxylic acid (C9H9NO2, MW=163.06)

Step 1: To a suspension of (E)-3-(pyridin-2-yl)acrylic acid (1.49 g, 10 mmol, 1 eq.) and N,O-dimethylhydroxylamine hydrochloride (975 mg, 10 mmol, 1 eq.) in DMF (20 mL), 4-dimethylaminopyridine (4.89 mg, 40 mmol, 4 eq.) and N-(3-dimethylaminopropyl)-N'-ethylcarbodiimid hydrochloride (2.30 g, 12 mmol, 1.2 eq.) were added. The resulting mixture was stirred at r.t. for 18 hours. The reaction mixture was diluted with AcOEt (300 mL). The diluted solution was washed with sat. aq. NaHCO$_3$ soln. (2×150 mL), sat. aq. NaCl soln. (1×150 mL), dried over MgSO$_4$, and concentrated in vacuo. The resulting product was used without further purification.

LC-MS 3: $t_R$=0.45 min; 193.4

Step 2: To a solution under N$_2$ of trimethylsulfoxonium iodide (3.89 g, 17.7 mmol, 2 eq.) in DMSO (10 mL) cooled at r.t. with a water bath, sodium hydride 60% dispersion in mineral oil (707 mg, 17.7 mmol, 2 eq.) was added portionwise over 10 min. The resulting mixture was stirred at r.t. for 1 hour. A solution of (E)-N-methoxy-N-methyl-3-(pyridin-2-yl)acrylamide (1.70 g, 8.8 mmol, 1 eq.) in DMSO (5 mL) was added and the reaction mixture was stirred at r.t. for 18 hours. The reaction mixture was poured in sat. aq. NH$_4$Cl soln. (50 mL) and extracted with DCM (3×50 mL). The comb. org. phases were washed with sat. aq. NaCl soln. (1×50 mL), dried over MgSO4, filtered, and concentrated in vacuo. The residue was purified by flashmaster (column: 100 g, flow: 45 mL/min, 30 fractions of 45 mL, Heptane+20% AcOEt to Heptane+80% AcOEt) to yield (±)-(trans)-2-pyridin-2-yl-cyclopropanecarboxylic acid methoxy-methyl-amide as an yellow oil.

LC-MS 3: $t_R$=0.40 min; 207.4

Step 3: To a solution of (±)-(trans)-2-pyridin-2-yl-cyclopropanecarboxylic acid methoxy-methyl-amide (950 mg, 4.61 mmol, 1 eq) in Et$_2$O (30 mL), potassium tert-butoxide (569 mg, 5.07 mmol, 1.1 eq) and H$_2$O (0.4 mL) were added. The mixture was stirred at r.t. for 18 hours. Potassium tert-butoxide (1.86 g, 16.6 mmol, 3.6 eq.) was added again. The mixture was stirred at r.t. for 24 hours. The reaction mixture was concentrated in vacuo. The residue was dissolved in water (5 mL) and formic acid (3 mL). The solution was directly purified by prep. HPLC (column: Atlantis, 30×75 mm, 10 um, UV/MS, acidic conditions, extremely polar method) and concentrated in vacuo to give the title compound as a white solid.

LC-MS 3: $t_R$=0.27 min; 164.2

General Method for the Synthesis of Cyclopropanecarboxylic Acid Derivatives (R,R)-47

Step 1: A mixture of AD-mix-alpha (7.0 g) in tBuOH (23 mL) and water (23 mL) was stirred at r.t. during 15 min. The mixture was then cooled down to 0° C. and 4-chlorostyrene (0.64 mL, 5.0 mmol, 1.0 eq.) was added. The resulting heterogeneous slurry was stirred vigorously at 0° C. for 3 hours. Sodium sulfite (7.5 g, 59.5 mmol, 11.9 eq.) was added and the reaction mixture was allowed to warm to r.t. and stirred at that temperature for 1 hour. DCM (45 mL) was added and the layers were separated. The aq. phase was extracted with DCM (3×20 mL). The combined org. layers were dried over MgSO$_4$, filtered, and concentrated in vacuo. The residue was dissolved in DCM (12 mL). Trimethyl orthoacetate (0.85 ml, 6.5 mmol, 1.3 eq.) was added and the mixture was cooled down to 0° C. Chlorotrimethylsilane (0.83 mL, 6.5 mmol, 1.3 eq.) was added dropwise and the reaction mixture was stirred for 1.5 hour. The solvent was removed in vacuo and the residue was dissolved in MeOH, treated with K$_2$CO$_3$ (0.86 g) and stirred vigorously at r.t. for 18 hours. The suspension was filtered and the filter cake was washed with DCM. The filtrate was concentrated in vacuo. The resulting residue was dissolved in DCM and water was added. The layers were separated and the aq. phase was extracted once with DCM. The combined org. layers were dried over MgSO$_4$, filtered, and concentrated in vacuo. The residue was purified by flashmaster (column: 100 g, flow: 45 mL/min, 28 fractions of 45 mL, Heptane 100% to Heptane+10% AcOEt) to yield (S)-2-(4-chloro-phenyl)-oxirane as a colorless oil.

LC-MS 3: $t_R$=0.79 min; no ionization

Step 2: To a solution of triethyl phosphonoacetate (1.1 mL, 5.4 mmol, 2.0 eq.) in DME (11 mL) at r.t., 2.5M n-butyl-lithium solution in hexanes (2.2 mL, 23.9 mmol, 8.9 eq.) was added dropwise over 5 min (the internal temperature should remain under 30° C.). After 15 min a solution of (S)-2-(4-chloro-phenyl)-oxirane (560 mg, 2.7 mmol, 1.0 eq.) in DME (1 mL) was added in one portion. After 15 min the reaction mixture was heated up to 130° C. and stirred at that temperature for 18 hours. The mixture was allowed to cool to r.t. and sat. aq. NH₄Cl soln. was added (25 mL). The mixture was extracted with Et₂O (3×50 mL). The combined org. phases were dried over MgSO₄, filtered, and concentrated in vacuo. The residue was purified by flashmaster (column: 50 g, flow: 40 mL/min, 28 fractions of 40 mL, Heptane 100% to Heptane+10% AcOEt) to give (1R,2R)-2-(4-chloro-phenyl)-cyclopropanecarboxylic acid ethyl ester as a colorless oil.

LC-MS 3: $t_R$=0.92 min; no ionization

Step 3: To a solution of (1R,2R)-2-(4-chloro-phenyl)-cyclopropanecarboxylic acid ethyl ester (470 mg, 2.1 mmol, 1 eq.) in THF (6.3 mL) and EtOH (1.7 mL), 1M aq. NaOH soln. (3 mL) was added. The solution was stirred at r.t. for 18 hours. The organic solvents were removed in vacuo. The residue was diluted with water and washed with AcOEt. The aq. phase was acidified with 2N aq. HCl soln. The mixture was extracted with DCM (3×). The comb. org. phases were dried over MgSO₄, filtered, and concentrated in vacuo to give the desired acid as a white-off solid. The product was used without further purification.

Listed in Table 61 below are cyclopropyl acids (R,R)-47, prepared according to the above-mentioned method, with the corresponding styrene 48 as starting material.

TABLE 61

| Intermediates (R,R)-47 | Formula MW | $t_R$ [min] LC-MS Method | MS-data m/z [M + H]⁺ |
|---|---|---|---|
| (1R,2R)-2-(4-Chloro-phenyl)-cyclopropanecarboxylic acid | C10H9O2Cl 196.03 | 0.76 LC-MS 3 | No ionization |
| (1R,2R)-2-Phenyl-cyclopropane-carboxylic acid | C10H10O2 162.07 | 0.69 LC-MS 3 | No ionization |
| (1R,2R)-2-(2-Fluoro-phenyl)-cyclopropanecarboxylic acid | C10H9O2F 180.06 | 0.71 LC-MS 3 | No ionization |
| (1R,2R)-2-(3-Fluoro-phenyl)-cyclopropanecarboxylic acid | C10H9O2F 180.06 | 0.71 LC-MS 3 | No ionization |

Synthesis of
(1S,2S)-2-Phenyl-cyclopropanecarboxylic acid
(C10H10O2, MW=162.07)

Step 1: To a solution of triethyl phosphonoacetate (0.67 mL, 3.29 mmol, 2.0 eq.) in DME (6.6 mL) at r.t. was added 2.5M n-butyllithium solution in hexanes (1.35 mL, 14.6 mmol, 8.9 eq.) dropwise over 5 min (the internal temperature should remain under 30° C.). After 15 min (1R,2R)-(+)-styrenoxide (0.19 mL, 1.65 mmol, 1.0 eq.) was added in one portion. After 15 min the reaction mixture was heated up to 130° C. and stirred at that temperature for 18 hours. The mixture was allowed to cool to r.t. and sat. aq. NH₄Cl soln was added (15 mL). The mixture was extracted with Et₂O (3×30 mL). The combined org. phases were dried over MgSO₄, filtered, and concentrated in vacuo. The residue was purified by prep. HPLC (column: Atlantis, 30×75 mm, 10 um, UV/MS, acidic conditions) and concentrated in vacuo to give (1S,2S)-2-phenyl-cyclopropanecarboxylic acid ethyl ester as a colorless liquid.

LC-MS 3: $t_R$=0.87 min; no ionization

Step 2: To a solution of (1S,2S)-2-phenyl-cyclopropanecarboxylic acid ethyl ester (42 mg, 0.22 mmol, 1.0 eq.) in THF (0.68 mL) and EtOH (0.18 mL), 1M aq. NaOH (0.32 ml) was added. The solution was stirred at r.t. for 18 hours. The organic solvents were removed in vacuo. The residue was diluted with water and washed with AcOEt. The aq. phase was acidified with 2N aq. HCl soln. The mixture was extracted with DCM (3×). The comb. org. phases were dried over MgSO₄, filtered and concentrated in vacuo to give the title compound as a colorless oil. The product was used without further purification.

LC-MS 3: $t_R$=0.69 min; no ionization

General Synthesis of Carboxylic Acid (±)-55

Step 1: To a suspension of sodium hydride 60% dispersion in mineral oil (880 mg, 22 mmol, 2.2 eq.) in THF (30 mL) at 0° C., triethyl phosphonoacetate (4.4 mL, 22 mmol, 2.2 eq.) was added dropwise. The mixture was stirred at 0° C. for 15 min. 4-Chromanone (1.53 g, 10 mmol, 1.0 eq.) was added portionwise. The mixture was slowly warmed up to r.t. and stirred at r.t. for 18 hours (the ice bath was let expire). The reaction mixture was diluted with water (150 mL) and extracted with DCM (3×50 mL). The comb. org. phases were washed with sat. aq. NaCl soln (1×50 mL), dried over MgSO₄, filtered, and concentrated in vacuo. The residue was purified by flashmaster (column: 100 g, flow: 45 mL/min, 30 fractions of 45 mL, Heptane 100% to Heptane+AcOEt 20%) to yield chroman-(4E)-ylidene-acetic acid ethyl ester as a colorless oil (LC-MS 3: $t_R$=0.90 min; 219.2) and chroman-(4Z)-ylidene-acetic acid ethyl ester (LC-MS 3: $t_R$=0.86 min; 219.3) as a colorless oil (E/Z ratio ca. 3:1).

Step 2: To a solution of chroman-(4E)-ylidene-acetic acid ethyl ester and chroman-(4Z)-ylidene-acetic acid ethyl ester (1.68 g, 7.47 mmol, 1 eq.) in EtOH (91 mL) under N₂, palladium on activated carbon (10 wt. %, 168 mg) was added. The flask was carefully evacuated and refilled with H₂ (3×). The black suspension was stirred at 45° C. under an H₂-atmosphere for 18 hours. The black suspension was filtered through Celite. The Celite was rinsed with EtOH. The filtrate was concentrated in vacuo to give (±)-chroman-4-yl-acetic acid ethyl ester as a grey oil. The product was used without further purification.

LC-MS 3: $t_R$=0.86 min; 221.3

Step 3: To a solution of (±)-chroman-4-yl-acetic acid ethyl ester (1.74 g, 7.83 mmol, 1 eq.) in THF (24 mL) and EtOH (6.5 mL), 1M aq. NaOH (11.3 mL) was added. The solution was stirred at r.t. for 18 hours. The organic solvents were removed in vacuo. The resulting aq. phase was acidified with 6N aq. HCl soln. The resulting suspension was kept at 4° C. for 4 hours. The resulting suspension was filtered. The solids were rinsed with water and dried under h.v. to give the desired acid as a grey solid. The product was used without further purification.

Listed in Table 62 below are carboxylic acids (±)-55, prepared according to the above-mentioned method, with the corresponding carbonyl derivative 56 as starting material.

TABLE 62

| Carboxylic acid (±)-55 | Formula MW | $t_R$ [min] LC-MS Method | MS-data m/z [M + H]⁺ |
|---|---|---|---|
| (±)-Chroman-4-yl-acetic acid | C11H12O3 192.08 | 0.68 LC-MS 3 | No ionization |
| (±)-(1,2,3,4-Tetrahydro-naphthalen-1-yl)-acetic acid | C12H14O2 190.10 | 0.77 LC-MS 3 | No ionization |

TABLE 62-continued

| Carboxylic acid (±)-55 | Formula MW | $t_R$ [min] LC-MS Method | MS-data m/z [M + H]⁺ |
|---|---|---|---|
| (±)-Isochroman-4-yl-acetic acid | C11H12O3 192.08 | 0.63 LC-MS 3 | 193.2 |
| (±)-(8-Fluoro-chroman-4-yl)-acetic acid | C11H11O3F 210.07 | 0.70 LC-MS 3 | No ionization |
| (±)-(6-Fluoro-chroman-4-yl)-acetic acid | C11H11O3F 210.07 | 0.71 LC-MS 3 | No ionization |
| (±)-(7-Fluoro-chroman-4-yl)-acetic acid | C11H11O3F 210.07 | 0.72 LC-MS 3 | No ionization |
| (±)-(2,2-Dimethyl-chroman-4-yl)-acetic acid | C13H16O3 220.11 | 0.76 LC-MS 3 | No ionization |
| (±)-Indan-1-yl-acetic acid | C11H12O2 176.08 | 0.73 LC-MS 3 | No ionization |

Synthesis of (±)-Isochroman-1-yl-acetic acid
(C11H12O3, 192.08)

Step 1: To an ice-cooled solution of phenethyl alcohol (1.21 mL, 10 mmol, 1.0 eq.) and ethyl 3,3-diethoxy-propionate (2.59 mL, 12 mmol, 1.2 eq) in DCM (5 mL), 1N titantetrachloride solution in DCM (22 mL, 22 mmol, 2.2 eq) was added dropwise. The mixture was stirred at 0° C. for 1 hour and further at r.t. for 3 hours. The mixture was poured onto ice and 2N aq. HCl soln. (30 mL). The layers were separated. The aq. phase was extracted with DCM (2×50 mL). The comb. org. phases were washed with sat. aq. NaCl soln. (1×50 mL), dried over Na₂SO₄, and concentrated in vacuo. The residue was purified by flashmaster (column: 100 g, flow: 45 mL/min, 40 fractions of 45 mL, Heptane to Heptane/AcOEt 85:15) to yield (±)-isochroman-1-yl-acetic acid ethyl ester as a colorless oil.

LC-MS 3: $t_R$=0.81 min; 221.2

Step 2: To a solution of (±)-isochroman-1-yl-acetic acid ethyl ester (1.90 g, 8.63 mmol, 1 eq.) in THF (40 mL) and MeOH (10 mL), 1M aq. NaOH soln. (17.3 mL, 17.3 mmol, 2 eq.) was added. The pale yellow solution was stirred at r.t. for 2 hours, then the organic solvents were removed in vacuo. The aq. layer was washed with AcOEt (1×10 mL). The aq. layer was acidified with 1N aq. HCl (pH=1). The resulting emulsion was extracted with DCM (3×25 mL). The comb. org. phases were dried over MgSO₄ and concentrated in vacuo to give the title compound as a colorless oil that solidifies upon standing. The product was used without further purification.

LC-MS 3: $t_R$=0.63 min; no ionization

General Synthesis of Pyridinecarboxylic Acid (±)-52

Step 1: To a suspension of sodium hydride 60% dispersion in mineral oil (480 mg, 12 mmol, 1.2 eq.) in THF (20 mL) at 0° C., dimethyl(benzyloxycarbonyl)methyl phosphonate (2.14 ml, 10 mmol, 1.0 eq.) was added dropwise. The mixture was stirred at 0° C. for 15 min. 2-Acetyl pyridine (1.14 mL, 10 mmol, 1.0 eq.) was added dropwise. The mixture was slowly warmed up to r.t. and stirred at r.t. for 18 hours (the ice bath was let expire). The reaction mixture was quenched with sat. aq. NaHCO₃ soln. (50 mL). The mixture was extracted with DCM (3×50 mL). The comb. org. phases were washed with sat. aq. NaCl soln., dried over MgSO₄, and concentrated in vacuo. The residue was purified by flashmaster (column: 100 g, flow: 45 mL/min, 40 fractions of 45 mL, Heptane 100% to Heptane+40% AcOEt) to yield (E)-3-pyridin-2-yl-but-2-enoic acid benzyl ester as a white solid (LC-MS 3: $t_R$=0.84 min; 254.3) and (Z)-3-pyridin-2-yl-but-2-enoic acid benzyl ester (LC-MS 3: $t_R$=0.63 min; 254.3) as a colorless oil (E/Z ratio ca. 55:13).

Step 2: To a solution under N₂ of (E)-3-pyridin-2-yl-but-2-enoic acid benzyl ester (1.40 g, 5.53 mmol, 1.00 eq.) and (Z)-3-pyridin-2-yl-but-2-enoic acid benzyl ester (320 mg, 1.26 mmol, 0.23 eq.) in THF (50 mL), palladium on activated carbon (10 wt. %, 200 mg) was added. The flask was evacuated and refilled with H₂ (3×). The black suspension was stirred at 50° C. under an H₂-atmosphere for 16 hours. The black suspension was filtered through Celite. The Celite was rinsed with THF and the filtrate was concentrated in vacuo. The residue was dissolved in water (3 mL), MeCN (1 mL) and formic acid (0.5 mL). The solution was directly purified by prep. HPLC (column: Atlantis, 30×75 mm, 10 um, UV/MS, acidic conditions, extremely polar method) and concentrated in vacuo to give the desired acid as a white solid.

Listed in Table 63 below are pyridinecarboxylic acids (±)-52, prepared according to the above-mentioned method, with the corresponding carbonyl derivative 53 as starting material.

TABLE 63

| Pyridinecarboxylic acid (±)-52 | Formula MW | $t_R$ [min] LC-MS Method | MS-data m/z [M + H]⁺ |
|---|---|---|---|
| (±)-3-Pyridin-2-yl-butyric acid | C9H11NO2 165.08 | 0.27 LC-MS 3 | 166.2 |
| (±)-3-(6-Methoxy-pyridin-2-yl)-butyric acid | C10H13NO3 195.09 | 0.53 LC-MS 3 | 196.2 |
| (±)-3-(3-Fluoro-pyridin-2-yl)-butyric acid | C9H10NO2F 183.07 | 0.51 LC-MS 3 | 184.3 |
| (±)-3-(6-Methyl-pyridin-2-yl)-butyric acid | C10H13NO2 179.10 | 0.33 LC-MS 3 | 180.3 |

TABLE 63-continued

| Pyridinecarboxylic acid (±)-52 | Formula MW | $t_R$ [min] LC-MS Method | MS-data m/z [M + H]+ |
|---|---|---|---|
| (±)-3-Cyclopropyl-3-pyridin-2-yl-propionic acid | C11H13NO2 191.10 | 0.38 LC-MS 3 | 192.3 |
| 3-(3-Methoxy-pyridin-2-yl)-propionic acid | C9H11NO3 181.07 | 0.35 LC-MS 3 | 182.4 |
| (±)-3-Pyridin-2-yl-pentanoic acid | C10H13NO2 179.10 | 0.34 LC-MS 3 | 180.3 |
| (±)-2-(2,2-Dimethyl-3,4-dihydro-2H-pyrano[2,3-b]pyridin-4-yl)acetic acid | C12H15NO3 221.11 | 0.43 LC-MS 3 | 222.3 |
| (±)-2-(5,6,7,8-tetrahydroquinolin-8-yl)acetic acid | C11H13NO2 191.10 | 0.39 LC-MS 3 | 192.3 |

Synthesis of (±)-2-Methyl-3-pyridin-2-yl-propionic acid (C9H11NO2, MW=165.08)

Step 1: To a solution of 2-pyridinecarboxaldehyde (0.96 mL, 10 mmol, 1.0 eq.) in toluene (17 mL) was added a solution of (carbethoxyethylidene)triphenylphosphorane (6.50 g, 16.1 mmol, 1.6 eq.) in toluene (24 mL). The resulting mixture was stirred at 80° C. for 18 hours. The solvent was removed in vacuo. The residue was suspended in a minimum amount of water and DCM was added. The product was extracted with 5% HCl soln. The aq. phase was cooled down to 0° C. and was basified with solid $K_2CO_3$. The product was then extracted with DCM (2×) and the comb. org. layers were dried over $MgSO_4$, filtered, and concentrated in vacuo. The residue was purified by flashmaster (column: 100 g, flow: 45 mL/min, 45 fractions of 45 mL, Heptane 100% to Heptane+25% AcOEt). To a solution of the resulting α,β-unsaturated ester in THF (21 mL) under $N_2$, palladium on activated carbon (10 wt. %, 33 mg) was added. The flask was carefully evacuated and refilled with $H_2$ (3×). The black suspension was stirred at 45° C. under an $H_2$-atmosphere for 18 hours. The black suspension was filtered through Celite. The Celite was rinsed with THF. The filtrate was concentrated in vacuo. The residue was purified by flashmaster (column: 25 g, flow: 30 mL/min, 30 fractions of 30 mL, Heptane 100% to Heptane+AcOEt 30%) to yield (±)-2-methyl-3-pyridin-2-yl-propionic acid ethyl ester as a colorless oil.

LC-MS 3: $t_R$=0.44 min; 194.3

Step 2: To a solution of (±)-2-methyl-3-pyridin-2-yl-propionic acid ethyl ester (250 mg, 1.29 mmol, 1.0 eq.) in dioxane (8 mL), lithium hydroxide monohydrate (67 mg, 1.55 mmol, 1.2 eq.) in water (5 mL) was added in portions keeping the temperature below 30° C. The resulting solution was stirred at r.t. for 18 hours. The mixture was concentrated in vacuo The residue was dissolved in water (3 mL), MeCN (1 mL) and formic acid (0.5 mL). The solution was directly purified by prep. HPLC (column: Atlantis, 30×75 mm, 10 um, UV/MS, acidic conditions, extremely polar method) and concentrated in vacuo to give the title compound as a white solid.

LC-MS 3: $t_R$=0.27 min; 166.2

General Method for the Synthesis of Carbonate 3

To a solution of 4-fluorobenzyl alcohol (631 mg, 5.0 mmol, 1.0 eq.) and DMAP (305 mg, 2.5 mmol, 0.5 eq.) in MeCN/DCM 1:1 (15 mL) N',N'-disuccinimidyl carbonate (1.28 g, 5.0 mmol, 1.0 eq.) was added. The mixture was stirred at r.t. for 18 hours. The mixture was washed with $H_2O$ (1×15 mL), sat. aq. NaCl soln. (1×15 mL), dried over $MgSO_4$, filtered and concentrated in vacuo. The residue was recrystallized from iPrOH.

Listed in Table 64 below are carbonates 3, prepared according to the above-mentioned method, with corresponding benzyl alcohols 4 as starting materials.

TABLE 64

| Carbonates 3 | Formula MW | $t_R$ [min] LC-MS Method | MS-data m/z [M + H]+ |
|---|---|---|---|
| Carbonic acid 2,5-dioxo-pyrrolidin-1-yl ester 4-fluoro-benzyl ester | C12H10NO5F 267.05 | 0.69 LC-MS 2 | No ionization |
| Carbonic acid 2,5-dioxo-pyrrolidin-1-yl ester 3-fluoro-benzyl ester | C12H10NO5F 267.05 | 0.78 LC-MS 3 | No ionization |
| Carbonic acid 2,5-dioxo-pyrrolidin-1-yl ester 2-fluoro-benzyl ester | C12H10NO5F 267.05 | 0.78 LC-MS 3 | No ionization |

General Method for the Carbamate Formation to Give an Intermediate of Structure 1

To an ice-cooled solution of [3-(5,6-difluoro-1,2,3,4-tetrahydro-isoquinolin-8-yl)-4-methoxy-phenyl]-acetic acid ethyl ester (101 mg, 0.20 mmol, 1.0 eq.) and triethylamine (84 µL, 0.60 mmol, 3.0 eq.) in DCM (5.5 mL), benzyl chloroformate (33 µL, 0.22 mmol, 1.1 eq.) was added dropwise. Upon completion of the addition, the cooling bath was removed and the suspension was stirred at r.t. for 4 hours. The reaction was quenched with 1M aq. citric acid soln. (5.5 mL). The layers were separated. The aq. phase was extracted with DCM (3×). The comb. org. phases were dried over $MgSO_4$, filtered, and concentrated in vacuo. The residue was purified by prep. HPLC (column: Waters Xbridge, 30×75 mm, 10 um, UV/MS, acidic conditions) and evaporated to give the desired ester as a colorless oil.

Listed in Table 65 below are intermediates of Structure 1, prepared according to the above-mentioned method, with the corresponding intermediate of Structure 2 as starting material.

TABLE 65

| Intermediates of Structure 1 | Formula MW | $t_R$ [min] LC-MS Method | MS-data m/z [M + H]$^+$ |
|---|---|---|---|
| 8-(5-Ethoxycarbonylmethyl-2-methoxy-phenyl)-5,6-difluoro-3,4-dihydro-1H-isoquinoline-2-carboxylic acid benzyl ester | C28H27NO5F2 495.19 | 1.03 LC-MS 3 | 496.2 |
| 8-(5-Ethoxycarbonylmethyl-2-methoxy-phenyl)-6-fluoro-3,4-dihydro-1H-isoquinoline-2-carboxylic acid benzyl ester | C28H28NO5F 477.20 | 1.02 LC-MS 3 | 478.3 |
| 8-(5-Ethoxycarbonylmethyl-2-methoxy-phenyl)-7-fluoro-3,4-dihydro-1H-isoquinoline-2-carboxylic acid benzyl ester | C28H28NO5F 477.20 | 1.01 LC-MS 3 | 478.3 |
| 4-(5-Ethoxycarbonylmethyl-2-methoxy-phenyl)-7-fluoro-1,3-dihydro-isoindole-2-carboxylic acid benzyl ester | C27H26NO5F 463.18 | 1.02 LC-MS 3 | 464.4 |
| 8-(5-Ethoxycarbonylmethyl-2-methoxy-phenyl)-5,7-difluoro-3,4-dihydro-1H-isoquinoline-2-carboxylic acid benzyl ester | C28H27NO5F2 495.19 | 1.02 LC-MS 3 | 496.2 |

Synthesis of 8-(2-Ethoxy-4-ethoxycarbonylmethyl-phenyl)-5-fluoro-3,4-dihydro-1H-isoquinoline-2-carboxylic acid 4-fluoro-benzyl ester (C29H29NO5F2, MW=509.20)

To a solution of [3-ethoxy-4-(5-fluoro-1,2,3,4-tetrahydro-isoquinolin-8-yl)-phenyl]-acetic acid ethyl ester (1.49 g, 4.2 mmol, 1.00 eq.) and N-ethyldiisopropylamine (3.56 mL, 20.8 mmol, 5.00 eq.) in DCM (50 mL), carbonic acid 2,5-dioxo-pyrrolidin-1-yl ester 4-fluoro-benzyl ester (1.17 g, 4.4 mmol, 1.05 eq.) was added. The mixture was stirred at r.t. for 18 hours. The solution was diluted with sat. aq. NaHCO$_3$ soln. (100 mL). The layers were separated. The aq. phase was extracted with DCM (2×). The comb. org. phases were dried over MgSO$_4$, filtered, and concentrated in vacuo. The residue was purified by flashmaster (column: 100 g, flow: 45 mL/min, 100 fractions of 45 mL, Heptane 100% to Heptane+40% AcOEt) to yield the title compound as a colorless oil.

LC-MS 3: $t_R$=1.06 min; 510.2

General Method for the Amide Coupling to Give an Intermediate of Structure 1

Method A: To a solution of (1R,2R)-2-phenyl-cyclopropanecarboxylic acid (30 mg, 0.19 mmol, 1.2 eq.) in DMF (1 mL), DIPEA (79 µL, 0.46 mmol, 3.0 eq.) and TBTU (60 mg, 0.19 mmol, 1.2 eq.) were added in sequence. The resulting solution was stirred at r.t. for 30 minutes. Then [3-(6-fluoro-1,2,3,4-tetrahydro-isoquinolin-8-yl)-4-methoxy-phenyl]-acetic acid ethyl ester (53 mg, 0.15 mmol, 1.0 eq.) in DMF (1 mL) was added and the resulting mixture was stirred at r.t. for 18 hours. The reaction mixture was concentrated in vacuo. The residue was purified by prep. HPLC (column: Atlantis, 30×75 mm, 10 um, UV/MS, acidic conditions) and concentrated in vacuo to give the desired amide as a yellow oil.

Listed in Table 66 below are intermediates of Structure 1, prepared according to the above-mentioned method, with the corresponding intermediate of Structure 2 and the corresponding carboxylic acid as starting materials.

TABLE 66

| Intermediates of Structure 1 | Formula MW | $t_R$ [min] LC-MS Method | MS-data m/z [M + H]$^+$ |
|---|---|---|---|
| {3-[6-Fluoro-2-((1R,2R)-2-phenyl-cyclopropanecarbonyl)-1,2,3,4-tetrahydro-isoquinolin-8-yl]-4-methoxy-phenyl}-acetic acid ethyl ester | C30H30NO4F 487.22 | 1.01 LC-MS 3 | 488.3 |
| {3-[7-Fluoro-2-((1R,2R)-2-phenyl-cyclopropanecarbonyl)-1,2,3,4-tetrahydro-isoquinolin-8-yl]-4-methoxy-phenyl}-acetic acid ethyl ester | C30H30NO4F 487.22 | 1.00 LC-MS 3 | 488.3 |
| (±)-(3-{5-Fluoro-2-[trans-2-(4-fluoro-phenyl)-cyclopropanecarbonyl]-1,2,3,4-tetrahydro-isoquinolin-8-yl}-4-methoxy-phenyl)-acetic acid ethyl ester | C30H29NO4F2 505.21 | 1.02 LC-MS 3 | 506.2 |
| (±)-(3-{2-[trans-2-(4-Chloro-phenyl)-cyclopropanecarbonyl]-5-fluoro-1,2,3,4-tetrahydro-isoquinolin-8-yl}-4-methoxy-phenyl)-acetic acid ethyl ester | C30H29NO4ClF 521.18 | 1.05 LC-MS 3 | 522.2 |
| (±)-(3-{2-[trans-2-(2-Chloro-phenyl)-cyclopropanecarbonyl]-5-fluoro-1,2,3,4-tetrahydro-isoquinolin-8-yl}-4-methoxy-phenyl)-acetic acid ethyl ester | C30H29NO4ClF 521.18 | 1.04 LC-MS 3 | 522.2 |
| (±)-(3-{2-[trans-2-(3-Chloro-phenyl)-cyclopropanecarbonyl]-5-fluoro-1,2,3,4-tetrahydro-isoquinolin-8-yl}-4-methoxy-phenyl)-acetic acid ethyl ester | C30H29NO4ClF 521.18 | 1.05 LC-MS 3 | 522.2 |

TABLE 66-continued

| Intermediates of Structure 1 | Formula MW | $t_R$ [min] LC-MS Method | MS-data m/z [M + H]+ |
|---|---|---|---|
| (±)-(3-{5-Fluoro-2-[trans-2-(2-fluoro-phenyl)-cyclopropanecarbonyl]-1,2,3,4-tetrahydro-isoquinolin-8-yl}-4-methoxy-phenyl)-acetic acid ethyl ester | C30H29NO4F2 505.21 | 1.02 LC-MS 3 | 506.2 |
| (±)-{3-[5-Fluoro-2-(trans-2-o-tolyl-cyclopropanecarbonyl)-1,2,3,4-tetrahydro-isoquinolin-8-yl]-4-methoxy-phenyl}-acetic acid ethyl ester | C31H32NO4F 501.23 | 1.04 LC-MS 3 | 502.3 |
| {3-[5,7-Difluoro-2-((1R,2R)-2-phenyl-cyclopropanecarbonyl)-1,2,3,4-tetrahydro-isoquinolin-8-yl]-4-methoxy-phenyl}-acetic acid ethyl ester | C30H29NO4F2 505.21 | 1.01 LC-MS 3 | 506.2 |
| (±)-{3-[7-Fluoro-2-(trans-2-phenyl-cyclopropanecarbonyl)-2,3-dihydro-1H-isoindol-4-yl]-4-methoxy-phenyl}-acetic acid ethyl ester | C29H28NO4F 473.20 | 0.99 LC-MS 3 | 474.4 |
| (±)-{3-[9-Fluoro-3-(trans-2-phenyl-cyclopropanecarbonyl)-2,3,4,5-tetrahydro-1H-benzo[d]azepin-6-yl]-4-methoxy-phenyl}-acetic acid ethyl ester | C31H32NO4F 501.23 | 1.01 LC-MS 3 | 502.4 |
| (±)-{4-[2-(2-Chroman-4-yl-acetyl)-5-fluoro-1,2,3,4-tetrahydro-isoquinolin-8-yl]-3-methoxy-phenyl}-acetic acid ethyl ester | C31H32NO5F 517.23 | 1.01 LC-MS 3 | 518.3 |

Method B: A solution of the amine[4-ethoxy-3-(5-fluoro-1,2,3,4-tetrahydro-isoquinolin-8-yl)-phenyl]-acetic acid ethyl ester (185 mg, 0.51 mmol, 1.0 eq.) and (±)-isochroman-4-yl-acetic acid (103 mg, 0.51 mmol, 1.0 eq.) in DMF (6 mL) was treated with 4-(dimethylamino)pyridine (94 mg, 0.77 mmol, 1.5 eq.) and N-(3-dimethylaminopropyl)-N'-ethylcarbodiimide hydrochloride (147 mg, 0.77 mmol, 1.5 eq.) and the resulting solution was stirred at r.t. for 2.5 hours. Formic acid was added (0.2 mL). The resulting acidic solution was purified by prep. HPLC (column: Waters XBridge, 30×75 mm, 10 um, UV/MS, acidic conditions) and evaporated to give the desired intermediate of Structure 1 as a colorless oil.

Listed in Table 67 below are intermediates of Structure 1, prepared according to the above-mentioned method, with the corresponding intermediate of Structure 2 and the corresponding carboxylic acid as starting materials.

Chiral Separation

Listed in table 68 are mixtures of enantiomers which were separated by prep. HPLC over a chiral stationary phase. Conditions for the separation are:

Method CS1: Column ChiralPak AD-H (20×250 mm, 5 μm), eluent A 80% Heptane and eluent B 20% EtOH, flow 16 mL/min. Detection at 210 nm.

Method CS2: Column ChiralPak AY-H (20×250 mm, 5 μm), eluent A 80% Heptane and eluent B 20% EtOH, flow 20 mL/min. Detection at 210 nm.

Method CS3: Column ChiralPak IA (20×250 mm, 5 μm), eluent A 90% Heptane and eluent B 10% EtOH/DCM (1:2), flow 16 mL/min. Detection at 218 nm.

Method CS4: Column Regis (R,R) Whelk-O1 (21.1×250 mm, 5 μm), eluent A 50% Heptane and eluent B 50% EtOH, flow 20 mL/min. Detection at 210 nm.

Method CS5: Column Regis (R,R) Whelk-O1 (21.1×250 mm, 5 μm), eluent A 25% Heptane and eluent B 75% EtOH, flow 20 mL/min. Detection at 210 nm.

TABLE 67

| Intermediates of Structure 1 | Formula MW | $t_R$ [min] LC-MS Method | MS-data m/z [M + H]+ |
|---|---|---|---|
| (±)-{4-Ethoxy-3-[5-fluoro-2-(2-isochroman-4-yl-acetyl)-1,2,3,4-tetrahydro-isoquinolin-8-yl]-phenyl}-acetic acid ethyl ester | C32H34NO5F 531.24 | 1.02 LC-MS 3 | 531.9 |
| (±)-{3-[2-(2-2,3-Dihydro-benzofuran-3-yl-acetyl)-5-fluoro-1,2,3,4-tetrahydro-isoquinolin-8-yl]-4-ethoxy-phenyl}-acetic acid ethyl ester | C31H32NO5F 517.23 | 1.03 LC-MS 3 | 518.2 |
| (±)-{3-Ethoxy-4-[5-fluoro-2-(2-isochroman-1-yl-acetyl)-1,2,3,4-tetrahydro-isoquinolin-8-yl]-phenyl}-acetic acid ethyl ester | C32H34NO5F 531.24 | 1.03 LC-MS 3 | 532.3 |
| (±)-{4-Ethoxy-3-[5-fluoro-2-(2-methyl-3-phenyl-propionyl)-1,2,3,4-tetrahydro-isoquinolin-8-yl]-phenyl}-acetic acid ethyl ester | C31H34NO4F 503.25 | 1.04 LC-MS 3 | 504.2 |
| (±)-(4-Ethoxy-3-{5-fluoro-2-[3-(4-fluoro-phenyl)-butyryl]-1,2,3,4-tetrahydro-isoquinolin-8-yl}-phenyl)-acetic acid ethyl ester | C31H33NO4F2 521.24 | 1.04 LC-MS 3 | 522.2 |

Method CS6: Column Regis (R,R) Whelk-O1 (21.1×250 mm, 5 μm), eluent A 70% Heptane and eluent B 30% AcOEt+ 1% DEA, flow 16 mL/min. Detection at 273 nm.

Method CS7: Column ChiralPak IA (20×250 mm, 5 μm), eluent A 50% DCM and eluent B 50% heptane, flow 20 mL/min. Detection at 281 nm.

TABLE 68

| Mixture | Optically pure intermediates | Formula MW HPLC Method $t_R$ [min] | $t_R$ [min] LC-MS Method MS-data m/z [M + H]$^+$ |
|---|---|---|---|
| (±)-5-Fluoro-8-[2-methoxy-4-(1-methoxycarbonyl-ethoxy)-phenyl]-3,4-dihydro-1H-isoquinoline-2-carboxylic acid benzyl ester | 5-Fluoro-8-[2-methoxy-4-(1-methoxycarbonyl-ethoxy)-phenyl]-3,4-dihydro-1H-isoquinoline-2-carboxylic acid benzyl ester (enantiomer 1) | C28H28NO6F 493.19 CS1 10.83 | 1.03 LC-MS 3 494.3 |
| (±)-5-Fluoro-8-[2-methoxy-4-(1-methoxycarbonyl-ethoxy)-phenyl]-3,4-dihydro-1H-isoquinoline-2-carboxylic acid benzyl ester | 5-Fluoro-8-[2-methoxy-4-(1-methoxycarbonyl-ethoxy)-phenyl]-3,4-dihydro-1H-isoquinoline-2-carboxylic acid benzyl ester (enantiomer 2) | C28H28NO6F 493.19 CS1 13.59 | 1.03 LC-MS 3 494.3 |
| (±)-{4-[2-(2-Chroman-4-yl-acetyl)-5-fluoro-1,2,3,4-tetrahydro-isoquinolin-8-yl]-3-methoxy-phenyl}-acetic acid ethyl ester | {4-[2-(2-Chroman-4-yl-acetyl)-5-fluoro-1,2,3,4-tetrahydro-isoquinolin-8-yl]-3-methoxy-phenyl}-acetic acid ethyl ester (enantiomer 1) | C31H32NO5F 517.23 CS1 12.13 | 1.01 LC-MS 3 518.3 |
| (±)-{4-[2-(2-Chroman-4-yl-acetyl)-5-fluoro-1,2,3,4-tetrahydro-isoquinolin-8-yl]-3-methoxy-phenyl}-acetic acid ethyl ester | {4-[2-(2-Chroman-4-yl-acetyl)-5-fluoro-1,2,3,4-tetrahydro-isoquinolin-8-yl]-3-methoxy-phenyl}-acetic acid ethyl ester (enantiomer 2) | C31H32NO5F 517.23 CS1 14.44 | 1.01 LC-MS 3 518.3 |
| (±)-{4-Ethoxy-3-[5-fluoro-2-(2-isochroman-4-yl-acetyl)-1,2,3,4-tetrahydro-isoquinolin-8-yl]-phenyl}-acetic acid ethyl ester | {4-Ethoxy-3-[5-fluoro-2-(2-isochroman-4-yl-acetyl)-1,2,3,4-tetrahydro-isoquinolin-8-yl]-phenyl}-acetic acid ethyl ester (enantiomer 1) | C32H34NO5F 531.24 CS2 10.61 | 1.01 LC-MS 3 532.2 |
| (±)-{4-Ethoxy-3-[5-fluoro-2-(2-isochroman-4-yl-acetyl)-1,2,3,4-tetrahydro-isoquinolin-8-yl]-phenyl}-acetic acid ethyl ester | {4-Ethoxy-3-[5-fluoro-2-(2-isochroman-4-yl-acetyl)-1,2,3,4-tetrahydro-isoquinolin-8-yl]-phenyl}-acetic acid ethyl ester (enantiomer 2) | C32H34NO5F 531.24 CS2 14.98 | 1.01 LC-MS 3 532.2 |
| (±)-{3-[2-(2-2,3-Dihydro-benzofuran-3-yl-acetyl)-5-fluoro-1,2,3,4-tetrahydro-isoquinolin-8-yl]-4-ethoxy-phenyl}-acetic acid ethyl ester | {3-[2-(2-2,3-Dihydro-benzofuran-3-yl-acetyl)-5-fluoro-1,2,3,4-tetrahydro-isoquinolin-8-yl]-4-ethoxy-phenyl}-acetic acid ethyl ester (enantiomer 1) | C31H32NO5F 517.23 CS3 12.24 | 1.02 LC-MS 3 518.2 |
| (±)-{3-[2-(2-2,3-Dihydro-benzofuran-3-yl-acetyl)-5-fluoro-1,2,3,4-tetrahydro-isoquinolin-8-yl]-4-ethoxy-phenyl}-acetic acid ethyl ester | {3-[2-(2-2,3-Dihydro-benzofuran-3-yl-acetyl)-5-fluoro-1,2,3,4-tetrahydro-isoquinolin-8-yl]-4-ethoxy-phenyl}-acetic acid ethyl ester (enantiomer 2) | C31H32NO5F 517.23 CS3 14.07 | 1.02 LC-MS 3 518.2 |
| (±)-{3-Ethoxy-4-[5-fluoro-2-(2-isochroman-1-yl-acetyl)-1,2,3,4-tetrahydro-isoquinolin-8-yl]-phenyl}-acetic acid ethyl ester | {3-Ethoxy-4-[5-fluoro-2-(2-isochroman-1-yl-acetyl)-1,2,3,4-tetrahydro-isoquinolin-8-yl]-phenyl}-acetic acid ethyl ester (enantiomer 1) | C32H34NO5F 531.24 CS4 15.72 | 1.02 LC-MS 3 532.2 |
| (±)-{3-Ethoxy-4-[5-fluoro-2-(2-isochroman-1-yl-acetyl)-1,2,3,4-tetrahydro-isoquinolin-8-yl]-phenyl}-acetic acid ethyl ester | {3-Ethoxy-4-[5-fluoro-2-(2-isochroman-1-yl-acetyl)-1,2,3,4-tetrahydro-isoquinolin-8-yl]-phenyl}-acetic acid ethyl ester (enantiomer 2) | C32H34NO5F 531.24 CS4 19.20 | 1.02 LC-MS 3 532.2 |
| (±)-{4-Ethoxy-3-[5-fluoro-2-(3-pyridin-2-yl-butyryl)-1,2,3,4-tetrahydro-isoquinolin-8-yl]-phenyl}-acetic acid ethyl ester | {4-Ethoxy-3-[5-fluoro-2-(3-pyridin-2-yl-butyryl)-1,2,3,4-tetrahydro-isoquinolin-8-yl]-phenyl}-acetic acid ethyl ester (enantiomer 1) | C30H33N2O4F 504.24 CS5 8.93 | 0.80 LC-MS 3 505.3 |
| (±)-{4-Ethoxy-3-[5-fluoro-2-(3-pyridin-2-yl-butyryl)-1,2,3,4-tetrahydro-isoquinolin-8-yl]-phenyl}-acetic acid ethyl ester | {4-Ethoxy-3-[5-fluoro-2-(3-pyridin-2-yl-butyryl)-1,2,3,4-tetrahydro-isoquinolin-8-yl]-phenyl}-acetic acid ethyl ester (enantiomer 2) | C30H33N2O4F 504.24 CS5 11.66 | 0.80 LC-MS 3 505.3 |
| (±)-(4-Ethoxy-3-{5-fluoro-2-[3-(4-fluoro-phenyl)-butyryl]-1,2,3,4-tetrahydro- | (4-Ethoxy-3-{5-fluoro-2-[3-(4-fluoro-phenyl)-butyryl]-1,2,3,4-tetrahydro- | C31H33NO4F2 521.24 CS6 | 1.04 LC-MS 3 522.2 |

TABLE 68-continued

| Mixture | Optically pure intermediates | Formula MW HPLC Method $t_R$ [min] | $t_R$ [min] LC-MS Method MS-data m/z [M + H]+ |
|---|---|---|---|
| isoquinolin-8-yl}-phenyl)-acetic acid ethyl ester | isoquinolin-8-yl}-phenyl)-acetic acid ethyl ester (enantiomer 1) | 13.80 | |
| (±)-(4-Ethoxy-3-{5-fluoro-2-[3-(4-fluoro-phenyl)-butyryl]-1,2,3,4-tetrahydro-isoquinolin-8-yl}-phenyl)-acetic acid ethyl ester | (4-Ethoxy-3-{5-fluoro-2-[3-(4-fluoro-phenyl)-butyryl]-1,2,3,4-tetrahydro-isoquinolin-8-yl}-phenyl)-acetic acid ethyl ester (enantiomer 2) | C31H33NO4F2 521.24 CS6 16.07 | 1.04 LC-MS 3 522.2 |
| (±)-{4-Ethoxy-3-[5-fluoro-2-(2-methyl-3-phenyl-propionyl)-1,2,3,4-tetrahydro-isoquinolin-8-yl]-phenyl}-acetic acid ethyl ester | {4-Ethoxy-3-[5-fluoro-2-(2-methyl-3-phenyl-propionyl)-1,2,3,4-tetrahydro-isoquinolin-8-yl]-phenyl}-acetic acid ethyl ester (enantiomer 1) | C31H34NO4F 503.25 CS7 4.55 | 1.04 LC-MS 3 504.2 |
| (±)-{4-Ethoxy-3-[5-fluoro-2-(2-methyl-3-phenyl-propionyl)-1,2,3,4-tetrahydro-isoquinolin-8-yl]-phenyl}-acetic acid ethyl ester | {4-Ethoxy-3-[5-fluoro-2-(2-methyl-3-phenyl-propionyl)-1,2,3,4-tetrahydro-isoquinolin-8-yl]-phenyl}-acetic acid ethyl ester (enantiomer 2) | C31H34NO4F 503.25 CS7 7.04 | 1.04 LC-MS 3 504.2 |

Biological Assays:
Preparation of hCRTH2 Receptor Membranes and Radioligand Displacement Assay:

First, recombinant HEK293-hCRTH$_2$ cells were detached from culture plates into 5 ml buffer A/plate (Buffer A: 5 mM Tris, 1 mM MgCl$_2$-6H$_2$O pH=7.4) using a rubber policeman. Cells were then transferred into centrifugation tubes and centrifuged for 5 min at 400 g. The cell pellet was resuspended in the same buffer and tubes were frozen at −80° C. Cells were thawed and membrane fragments were generated by homogenization using a polytron homogenizer (30 seconds). The membrane fragments were then centrifuged at 3000 g for 20 minutes and resuspended in buffer C (Buffer C: 75 mM Tris, 25 mM MgCl$_2$, 250 mM Saccharose pH 7.4). Aliquots of membrane fragments were stored at −20° C.

Binding assay was performed in a final assay volume of 250 μl. First, 25 μl of test compound, previously diluted in Binding-Buffer (Binding-Buffer: 50 mM Tris-Base, 100 mM NaCl, 1 mM EDTA, 0.1% BSA (protease free), 0.01% NaN$_3$, 10 mM MnCl$_2$, pH 7.0) was placed into each well. After addition of 75 μl Binding-Buffer, 50 μl of the radioligand $^3$H-PGD$_2$ (at 2.5 nM (220.000 dpm/well) from ANAWA ART0662) was added to each well. Binding assay was started by addition of 100 μl CRTH$_2$ membrane fragments, reaching a final concentration of 20 μg/well. For non-specific binding, PGD$_2$ was added to the reaction mixture to 10 mM final concentration. This assay mix was incubated for 90 minutes at room temperature and then filtered through a GF/C filter 96-well plate which was pre-soaked for 3 hours in 0.5% polyethyleneimine (PEI). The filter-wells were washed three times with ice cold Binding-Buffer. Then, 40 μl of Microscint-40 (Packard) was added to each well and the retained radioactivity quantified in a Topcount (Packard).

Antagonistic activities of exemplified compounds are displayed in the following Table:

| Example | Name | IC$_{50}$ [nM] |
|---|---|---|
| 1 | (±)-(3-{5-Fluoro-2-[trans-2-(4-fluoro-phenyl)-cyclopropanecarbonyl]-1,2,3,4-tetrahydro-isoquinolin-8-yl}-4-methoxy-phenyl)-acetic acid | 1.99 |
| 2 | (±)-(3-{2-[trans-2-(4-Chloro-phenyl)-cyclopropanecarbonyl]-5-fluoro-1,2,3,4-tetrahydro-isoquinolin-8-yl}-4-methoxy-phenyl)-acetic acid | 1.93 |
| 3 | (±)-(3-{2-[trans-2-(2-Chloro-phenyl)-cyclopropanecarbonyl]-5-fluoro-1,2,3,4-tetrahydro-isoquinolin-8-yl}-4-methoxy-phenyl)-acetic acid | 2.11 |
| 4 | (±)-(3-{2-[trans-2-(3-Chloro-phenyl)-cyclopropanecarbonyl]-5-fluoro-1,2,3,4-tetrahydro-isoquinolin-8-yl}-4-methoxy-phenyl)-acetic acid | 5.39 |
| 5 | (±)-(3-{5-Fluoro-2-[trans-2-(2-fluoro-phenyl)-cyclopropanecarbonyl]-1,2,3,4-tetrahydro-isoquinolin-8-yl}-4-methoxy-phenyl)-acetic acid | 3.64 |
| 6 | (±)-{3-[5-Fluoro-2-(trans-2-o-tolyl-cyclopropanecarbonyl)-1,2,3,4-tetrahydro-isoquinolin-8-yl]-4-methoxy-phenyl}-acetic acid | 4.22 |
| 7 | 8-(5-Carboxymethyl-2-methyl-phenyl)-5-fluoro-3,4-dihydro-1H-isoquinoline-2-carboxylic acid benzyl ester | 25.6 |
| 8 | 8-(5-Carboxymethyl-2-trifluoromethyl-phenyl)-5-fluoro-3,4-dihydro-1H-isoquinoline-2-carboxylic acid benzyl ester | 7.31 |
| 9 | 8-(5-Carboxymethyl-2-chloro-phenyl)-5-fluoro-3,4-dihydro-1H-isoquinoline-2-carboxylic acid benzyl ester | 12.8 |

-continued

| Example | Name | IC$_{50}$ [nM] |
|---|---|---|
| 10 | 8-(5-Carboxymethyl-2-fluoro-phenyl)-5-fluoro-3,4-dihydro-1H-isoquinoline-2-carboxylic acid benzyl ester | 10.1 |
| 11 | 8-(3-Carboxymethyl-4-chloro-phenyl)-5-fluoro-3,4-dihydro-1H-isoquinoline-2-carboxylic acid benzyl ester | 69.1 |
| 12 | 8-(3-Carboxymethyl-4-fluoro-phenyl)-5-fluoro-3,4-dihydro-1H-isoquinoline-2-carboxylic acid benzyl ester | 21.8 |
| 13 | 8-(3-Carboxymethyl-4-methoxy-phenyl)-5-fluoro-3,4-dihydro-1H-isoquinoline-2-carboxylic acid benzyl ester | 72.3 |
| 14 | 8-(3-Carboxymethyl-5-fluoro-phenyl)-5-fluoro-3,4-dihydro-1H-isoquinoline-2-carboxylic acid benzyl ester | 14.8 |
| 15 | 8-(3-Carboxymethyl-5-methoxy-phenyl)-5-fluoro-3,4-dihydro-1H-isoquinoline-2-carboxylic acid benzyl ester | 18.5 |
| 16 | 8-(3-Carboxymethyl-2-fluoro-phenyl)-5-fluoro-3,4-dihydro-1H-isoquinoline-2-carboxylic acid benzyl ester | 25.2 |
| 17 | 6-(5-Carboxymethyl-2-methoxy-phenyl)-9-fluoro-1,2,4,5-tetrahydro-benzo[d]azepine-3-carboxylic acid benzyl ester | 141 |
| 18 | 4-(5-Carboxymethyl-2-methoxy-phenyl)-7-fluoro-1,3-dihydro-isoindole-2-carboxylic acid benzyl ester | 165 |
| 19 | 8-(3-Carboxymethyl-5-chloro-phenyl)-5-fluoro-3,4-dihydro-1H-isoquinoline-2-carboxylic acid benzyl ester | 20.2 |
| 20 | 8-(5-Carboxymethyl-2-methanesulfonyl-phenyl)-5-fluoro-3,4-dihydro-1H-isoquinoline-2-carboxylic acid benzyl ester | 16.3 |
| 21 | 8-(5-Carboxymethyl-2-trifluoromethoxy-phenyl)-5-fluoro-3,4-dihydro-1H-isoquinoline-2-carboxylic acid benzyl ester | 2.19 |
| 22 | 8-(5-Carboxymethyl-2-isopropoxy-phenyl)-5-fluoro-3,4-dihydro-1H-isoquinoline-2-carboxylic acid benzyl ester | 4.72 |
| 23 | 8-(5-Carboxymethyl-2-fluoro-phenyl)-3,4-dihydro-1H-isoquinoline-2-carboxylic acid benzyl ester | 192 |
| 24 | 8-(3-Carboxymethyl-phenyl)-5-fluoro-3,4-dihydro-1H-isoquinoline-2-carboxylic acid benzyl ester | 69.5 |
| 25 | 8-(5-Carboxymethyl-2-methoxy-phenyl)-5-methanesulfonyl-3,4-dihydro-1H-isoquinoline-2-carboxylic acid benzyl ester | 149 |
| 26 | {3-[5-Fluoro-2-((1R,2R)-2-phenyl-cyclopropanecarbonyl)-1,2,3,4-tetrahydro-isoquinolin-8-yl]-4-trifluoromethoxy-phenyl}-acetic acid | 3.07 |
| 27 | {3-[5-Fluoro-2-((1R,2R)-2-phenyl-cyclopropanecarbonyl)-1,2,3,4-tetrahydro-isoquinolin-8-yl]-4-isopropoxy-phenyl}-acetic acid | 12.9 |
| 28 | {4-Chloro-3-[5-fluoro-2-((1R,2R)-2-phenyl-cyclopropanecarbonyl)-1,2,3,4-tetrahydro-isoquinolin-8-yl]-phenyl}-acetic acid | 10.0 |
| 29 | {3-[5-Fluoro-2-((1R,2R)-2-phenyl-cyclopropanecarbonyl)-1,2,3,4-tetrahydro-isoquinolin-8-yl]-4-methanesulfonyl-phenyl}-acetic acid | 6.6 |
| 30 | 8-(2-Carboxymethyl-phenyl)-5-fluoro-3,4-dihydro-1H-isoquinoline-2-carboxylic acid benzyl ester | 875 |
| 31 | 8-(5-Carboxymethyl-2-methoxy-phenyl)-5,6-difluoro-3,4-dihydro-1H-isoquinoline-2-carboxylic acid benzyl ester | 12 |
| 32 | 8-(5-Carboxymethyl-2-methoxy-phenyl)-6-fluoro-3,4-dihydro-1H-isoquinoline-2-carboxylic acid benzyl ester | 10.5 |
| 33 | 8-(5-Carboxymethyl-2-methoxy-phenyl)-7-fluoro-3,4-dihydro-1H-isoquinoline-2-carboxylic acid benzyl ester | 113 |
| 34 | {3-[6-Fluoro-2-((1R,2R)-2-phenyl-cyclopropanecarbonyl)-1,2,3,4-tetrahydro-isoquinolin-8-yl]-4-methoxy-phenyl}-acetic acid | 2.7 |
| 35 | {3-[7-Fluoro-2-((1R,2R)-2-phenyl-cyclopropanecarbonyl)-1,2,3,4-tetrahydro-isoquinolin-8-yl]-4-methoxy-phenyl}-acetic acid | 3.19 |
| 36 | (±)-{3-[9-Fluoro-3-(trans-2-phenyl-cyclopropanecarbonyl)-2,3,4,5-tetrahydro-1H-benzo[d]azepin-6-yl]-4-methoxy-phenyl}-acetic acid | 19.9 |
| 37 | (±)-{3-[7-Fluoro-2-(trans-2-phenyl-cyclopropanecarbonyl)-2,3-dihydro-1H-isoindol-4-yl]-4-methoxy-phenyl}-acetic acid | 7.54 |
| 38 | {3-[5,7-Difluoro-2-((1R,2R)-2-phenyl-cyclopropanecarbonyl)-1,2,3,4-tetrahydro-isoquinolin-8-yl]-4-methoxy-phenyl}-acetic acid | 11.2 |
| 39 | 8-(5-Carboxymethyl-2-methoxy-phenyl)-5,7-difluoro-3,4-dihydro-1H-isoquinoline-2-carboxylic acid benzyl ester | 5.89 |
| 40 | 8-(4-Carboxymethyl-3-chloro-phenyl)-5-fluoro-3,4-dihydro-1H-isoquinoline-2-carboxylic acid benzyl ester | 29.1 |
| 41 | 8-(4-Carboxymethyl-phenyl)-5-fluoro-3,4-dihydro-1H-isoquinoline-2-carboxylic acid benzyl ester | 44.9 |
| 42 | (3-{5-Fluoro-2-[3-(4-fluoro-phenoxy)-propionyl]-1,2,3,4-tetrahydro-isoquinolin-8-yl}-4-methoxy-phenyl)-acetic acid | 8.76 |
| 43 | {3-[5-Fluoro-2-(2-phenoxy-acetyl)-1,2,3,4-tetrahydro-isoquinolin-8-yl]-4-methoxy-phenyl}-acetic acid | 30.2 |
| 44 | (3-{5-Fluoro-2-[2-(4-fluoro-phenoxy)-acetyl]-1,2,3,4-tetrahydro-isoquinolin-8-yl}-4-methoxy-phenyl)-acetic acid | 59.1 |

| Example | Name | IC$_{50}$ [nM] |
|---|---|---|
| 45 | (3-{5-Fluoro-2-[4-(2-fluoro-phenyl)-butyryl]-1,2,3,4-tetrahydro-isoquinolin-8-yl}-4-methoxy-phenyl)-acetic acid | 2.9 |
| 46 | {3-[2-(2-Ethoxy-acetyl)-5-fluoro-1,2,3,4-tetrahydro-isoquinolin-8-yl]-4-methoxy-phenyl}-acetic acid | 774 |
| 47 | {3-[2-(2-tert-Butoxy-acetyl)-5-fluoro-1,2,3,4-tetrahydro-isoquinolin-8-yl]-4-methoxy-phenyl}-acetic acid | 551 |
| 48 | (±)-(3-{5-Fluoro-2-[trans-2-(3-fluoro-phenyl)-cyclopropanecarbonyl]-1,2,3,4-tetrahydro-isoquinolin-8-yl}-4-methoxy-phenyl)-acetic acid | 12 |
| 49 | (3-{5-Fluoro-2-[2-(5-methoxy-benzo[d]isoxazol-3-yl)-acetyl]-1,2,3,4-tetrahydro-isoquinolin-8-yl}-4-methoxy-phenyl)-acetic acid | 54 |
| 50 | {3-[5-Fluoro-2-(2,2,3,3-tetramethyl-cyclopropanecarbonyl)-1,2,3,4-tetrahydro-isoquinolin-8-yl]-4-methoxy-phenyl}-acetic acid | 267 |
| 51 | {3-[5-Fluoro-2-(3-pyridin-3-yl-propionyl)-1,2,3,4-tetrahydro-isoquinolin-8-yl]-4-methoxy-phenyl}-acetic acid | 57.1 |
| 52 | [3-(2-Cyclopropanecarbonyl-5-fluoro-1,2,3,4-tetrahydro-isoquinolin-8-yl)-4-methoxy-phenyl]-acetic acid | 68.9 |
| 53 | {3-[2-(3-3,4-Dihydro-2H-quinolin-1-yl-propionyl)-5-fluoro-1,2,3,4-tetrahydro-isoquinolin-8-yl]-4-methoxy-phenyl}-acetic acid | 4.49 |
| 54 | {3-[5-Fluoro-2-(3-phenyl-propionyl)-1,2,3,4-tetrahydro-isoquinolin-8-yl]-4-methoxy-phenyl}-acetic acid | 5.83 |
| 55 | (±)-{3-[2-(2,2-Dimethyl-cyclopropanecarbonyl)-5-fluoro-1,2,3,4-tetrahydro-isoquinolin-8-yl]-4-methoxy-phenyl}-acetic acid | 45.7 |
| 56 | {3-[5-Fluoro-2-(3-o-tolyl-propionyl)-1,2,3,4-tetrahydro-isoquinolin-8-yl]-4-methoxy-phenyl}-acetic acid | 42.1 |
| 57 | (3-{5-Fluoro-2-[3-(3-methyl-indol-1-yl)-propionyl]-1,2,3,4-tetrahydro-isoquinolin-8-yl}-4-methoxy-phenyl)-acetic acid | 16.2 |
| 58 | (3-{2-[2-(2-Chloro-benzyloxy)-acetyl]-5-fluoro-1,2,3,4-tetrahydro-isoquinolin-8-yl}-4-methoxy-phenyl)-acetic acid | 3.57 |
| 59 | {3-[2-(3-2,3-Dihydro-indol-1-yl-propionyl)-5-fluoro-1,2,3,4-tetrahydro-isoquinolin-8-yl]-4-methoxy-phenyl}-acetic acid | 7.4 |
| 60 | (±)-{3-[5-Fluoro-2-(trans-2-phenyl-cyclopropanecarbonyl)-1,2,3,4-tetrahydro-isoquinolin-8-yl]-4-methoxy-phenyl}-acetic acid | 2.64 |
| 61 | (3-{5-Fluoro-2-[3-(2-methyl-1H-indol-3-yl)-propionyl]-1,2,3,4-tetrahydro-isoquinolin-8-yl}-4-methoxy-phenyl)-acetic acid | 8.0 |
| 62 | (3-{5-Fluoro-2-[3-(1-methyl-1H-indol-3-yl)-propionyl]-1,2,3,4-tetrahydro-isoquinolin-8-yl}-4-methoxy-phenyl)-acetic acid | 4.74 |
| 63 | (3-{5-Fluoro-2-[3-(5-methoxy-1H-indol-3-yl)-propionyl]-1,2,3,4-tetrahydro-isoquinolin-8-yl}-4-methoxy-phenyl)-acetic acid | 29.5 |
| 64 | (3-{2-[(1R,2R)-2-(4-Chloro-phenyl)-cyclopropanecarbonyl]-5-fluoro-1,2,3,4-tetrahydro-isoquinolin-8-yl}-4-methoxy-phenyl)-acetic acid | 1.12 |
| 65 | (3-{5-Fluoro-2-[(1R,2R)-2-(3-fluoro-phenyl)-cyclopropanecarbonyl]-1,2,3,4-tetrahydro-isoquinolin-8-yl}-4-methoxy-phenyl)-acetic acid | 1.85 |
| 66 | (3-{5-Fluoro-2-[(1R,2R)-2-(2-fluoro-phenyl)-cyclopropanecarbonyl]-1,2,3,4-tetrahydro-isoquinolin-8-yl}-4-methoxy-phenyl)-acetic acid | 1.77 |
| 67 | {3-[5-Fluoro-2-(3-indazol-1-yl-propionyl)-1,2,3,4-tetrahydro-isoquinolin-8-yl]-4-methoxy-phenyl}-acetic acid | 21.6 |
| 68 | (3-{5-Chloro-2-[(1R,2R)-2-(4-chloro-phenyl)-cyclopropanecarbonyl]-1,2,3,4-tetrahydro-isoquinolin-8-yl}-4-methoxy-phenyl)-acetic acid | 3.75 |
| 69 | (3-{5-Chloro-2-[(1R,2R)-2-(3-fluoro-phenyl)-cyclopropanecarbonyl]-1,2,3,4-tetrahydro-isoquinolin-8-yl}-4-methoxy-phenyl)-acetic acid | 9.58 |
| 70 | (3-{5-Chloro-2-[(1R,2R)-2-(2-fluoro-phenyl)-cyclopropanecarbonyl]-1,2,3,4-tetrahydro-isoquinolin-8-yl}-4-methoxy-phenyl)-acetic acid | 1.16 |
| 71 | {3-[5-Chloro-2-((1R,2R)-2-phenyl-cyclopropanecarbonyl)-1,2,3,4-tetrahydro-isoquinolin-8-yl]-4-methoxy-phenyl}-acetic acid | 1.68 |
| 72 | {3-[5-Chloro-2-(3-indazol-1-yl-propionyl)-1,2,3,4-tetrahydro-isoquinolin-8-yl]-4-methoxy-phenyl}-acetic acid | 37.8 |
| 73 | (3-{5-Chloro-2-[2-(2-chloro-benzyloxy)-acetyl]-1,2,3,4-tetrahydro-isoquinolin-8-yl}-4-methoxy-phenyl)-acetic acid | 30.2 |
| 74 | (3-{5-Chloro-2-[4-(2-fluoro-phenyl)-butyryl]-1,2,3,4-tetrahydro-isoquinolin-8-yl}-4-methoxy-phenyl)-acetic acid | 10.5 |
| 75 | (3-{5-Chloro-2-[3-(1-methyl-1H-indol-3-yl)-propionyl]-1,2,3,4-tetrahydro-isoquinolin-8-yl}-4-methoxy-phenyl)-acetic acid | 38.4 |
| 76 | {3-[5-Chloro-2-(3-phenyl-propionyl)-1,2,3,4-tetrahydro-isoquinolin-8-yl]-4-methoxy-phenyl}-acetic acid | 43.1 |
| 77 | {3-[5-Chloro-2-(3-3,4-dihydro-2H-quinolin-1-yl-propionyl)-1,2,3,4-tetrahydro-isoquinolin-8-yl]-4-methoxy-phenyl}-acetic acid | 24.0 |
| 78 | {3-[5-Chloro-2-(3-2,3-dihydro-indol-1-yl-propionyl)-1,2,3,4-tetrahydro-isoquinolin-8-yl]-4-methoxy-phenyl}-acetic acid | 61.5 |

-continued

| Example | Name | IC$_{50}$ [nM] |
|---|---|---|
| 79 | (3-{5-Chloro-2-[3-(2-methyl-1H-indol-3-yl)-propionyl]-1,2,3,4-tetrahydro-isoquinolin-8-yl}-4-methoxy-phenyl)-acetic acid | 37.8 |
| 80 | {3-[5-Fluoro-2-((1R,2R)-2-phenyl-cyclopropanecarbonyl)-1,2,3,4-tetrahydro-isoquinolin-8-yl]-4-methoxy-phenyl}-acetic acid | 1.89 |
| 81 | {3-[5-Fluoro-2-((1S,2S)-2-phenyl-cyclopropanecarbonyl)-1,2,3,4-tetrahydro-isoquinolin-8-yl]-4-methoxy-phenyl}-acetic acid | 33.1 |
| 82 | [3-(2-Cyclopropanecarbonyl-5-trifluoromethyl-1,2,3,4-tetrahydro-isoquinolin-8-yl)-4-methoxy-phenyl]-acetic acid | 250 |
| 83 | (±)-{4-Methoxy-3-[2-(trans-2-phenyl-cyclopropanecarbonyl)-5-trifluoromethyl-1,2,3,4-tetrahydro-isoquinolin-8-yl]-phenyl}-acetic acid | 26.1 |
| 84 | {3-[5,6-Difluoro-2-((1R,2R)-2-phenyl-cyclopropanecarbonyl)-1,2,3,4-tetrahydro-isoquinolin-8-yl]-4-methoxy-phenyl}-acetic acid | 4.82 |
| 85 | (3-{5-Fluoro-2-[(E)-(3-phenyl-acryloyl)]-1,2,3,4-tetrahydro-isoquinolin-8-yl}-4-methoxy-phenyl)-acetic acid | 35.8 |
| 86 | (3-{5-Fluoro-2-[(E)-3-(6-methoxy-pyridin-3-yl)-acryloyl]-1,2,3,4-tetrahydro-isoquinolin-8-yl}-4-methoxy-phenyl)-acetic acid | 70.5 |
| 87 | (3-{2-[(E)-3-(2,4-Dimethyl-thiazol-5-yl)-acryloyl]-5-fluoro-1,2,3,4-tetrahydro-isoquinolin-8-yl}-4-methoxy-phenyl)-acetic acid | 93.8 |
| 88 | {3-[2-((E)-3-Benzothiazol-2-yl-acryloyl)-5-fluoro-1,2,3,4-tetrahydro-isoquinolin-8-yl]-4-methoxy-phenyl}-acetic acid | 9.14 |
| 89 | {3-[5-Fluoro-2-((E)-3-pyridin-3-yl-acryloyl)-1,2,3,4-tetrahydro-isoquinolin-8-yl]-4-methoxy-phenyl}-acetic acid | 57.2 |
| 90 | (3-{2-[(E)-3-(2,5-Dimethyl-2H-pyrazol-3-yl)-acryloyl]-5-fluoro-1,2,3,4-tetrahydro-isoquinolin-8-yl}-4-methoxy-phenyl)-acetic acid | 49.1 |
| 91 | {3-[5-Fluoro-2-(3-pyridin-2-yl-propionyl)-1,2,3,4-tetrahydro-isoquinolin-8-yl]-4-methoxy-phenyl}-acetic acid | 32.1 |
| 92 | (3-{5-Fluoro-2-[3-(6-methyl-pyridin-2-yl)-propionyl]-1,2,3,4-tetrahydro-isoquinolin-8-yl}-4-methoxy-phenyl)-acetic acid | 15.7 |
| 93 | {3-[5-Fluoro-2-(3-pyrimidin-2-yl-propionyl)-1,2,3,4-tetrahydro-isoquinolin-8-yl]-4-methoxy-phenyl}-acetic acid | 690 |
| 94 | (3-{5-Fluoro-2-[2-(pyridin-3-yloxy)-acetyl]-1,2,3,4-tetrahydro-isoquinolin-8-yl}-4-methoxy-phenyl)-acetic acid | 418 |
| 95 | (±)-(3-{5-Fluoro-2-[trans-2-(2-trifluoromethyl-phenyl)-cyclopropanecarbonyl]-1,2,3,4-tetrahydro-isoquinolin-8-yl}-4-methoxy-phenyl)-acetic acid | 0.22 |
| 96 | (±)-(3-{5-Fluoro-2-[trans-2-(4-methoxy-phenyl)-cyclopropanecarbonyl]-1,2,3,4-tetrahydro-isoquinolin-8-yl}-4-methoxy-phenyl)-acetic acid | 21.2 |
| 97 | (±)-(3-{2-[3-(4-Chloro-phenyl)-3-phenyl-propionyl]-5-fluoro-1,2,3,4-tetrahydro-isoquinolin-8-yl}-4-methoxy-phenyl)-acetic acid | 48.1 |
| 98 | (±)-(3-{2-[trans-2-(2,4-Dichloro-phenyl)-cyclopropanecarbonyl]-5-fluoro-1,2,3,4-tetrahydro-isoquinolin-8-yl}-4-methoxy-phenyl)-acetic acid | 10.1 |
| 99 | {3-[8-Fluoro-2-((1R,2R)-2-phenyl-cyclopropanecarbonyl)-1,2,3,4-tetrahydro-isoquinolin-5-yl]-4-methoxy-phenyl}-acetic acid | 414 |
| 100 | {3-[8-Fluoro-2-(4-phenyl-butyryl)-1,2,3,4-tetrahydro-isoquinolin-5-yl]-4-methoxy-phenyl}-acetic acid | 105 |
| 101 | {3-[8-Fluoro-2-(3-phenyl-propionyl)-1,2,3,4-tetrahydro-isoquinolin-5-yl]-4-methoxy-phenyl}-acetic acid | 64.7 |
| 102 | {3-[8-Fluoro-2-(3-phenoxy-propionyl)-1,2,3,4-tetrahydro-isoquinolin-5-yl]-4-methoxy-phenyl}-acetic acid | 43 |
| 103 | (3-{2-[2-(2-Chloro-benzyloxy)-acetyl]-8-fluoro-1,2,3,4-tetrahydro-isoquinolin-5-yl}-4-methoxy-phenyl)-acetic acid | 69.2 |
| 104 | {3-[2-(3-3,4-Dihydro-2H-quinolin-1-yl-propionyl)-8-fluoro-1,2,3,4-tetrahydro-isoquinolin-5-yl]-4-methoxy-phenyl}-acetic acid | 21.3 |
| 105 | (3-{8-Fluoro-2-[3-(1-methyl-1H-indol-3-yl)-propionyl]-1,2,3,4-tetrahydro-isoquinolin-5-yl}-4-methoxy-phenyl)-acetic acid | 17.7 |
| 106 | {3-[5-Fluoro-2-((R)-3-phenyl-butyryl)-1,2,3,4-tetrahydro-isoquinolin-8-yl]-4-methoxy-phenyl}-acetic acid | 10.4 |
| 107 | {3-[5-Fluoro-2-((S)-3-phenyl-butyryl)-1,2,3,4-tetrahydro-isoquinolin-8-yl]-4-methoxy-phenyl}-acetic acid | 18.3 |
| 108 | {3-[5-Fluoro-2-(3-methyl-3-phenyl-butyryl)-1,2,3,4-tetrahydro-isoquinolin-8-yl]-4-methoxy-phenyl}-acetic acid | 10.1 |
| 109 | (±)-{3-[5-Fluoro-2-(2-methyl-3-phenyl-propionyl)-1,2,3,4-tetrahydro-isoquinolin-8-yl]-4-methoxy-phenyl}-acetic acid | 28.9 |
| 110 | {3-[5-Fluoro-2-(indane-2-carbonyl)-1,2,3,4-tetrahydro-isoquinolin-8-yl]-4-methoxy-phenyl}-acetic acid | 172 |
| 111 | {3-[5-Fluoro-2-(2-indan-2-yl-acetyl)-1,2,3,4-tetrahydro-isoquinolin-8-yl]-4-methoxy-phenyl}-acetic acid | 8.11 |
| 112 | (±)-{3-[5-Fluoro-2-(indane-1-carbonyl)-1,2,3,4-tetrahydro-isoquinolin-8-yl]-4-methoxy-phenyl}-acetic acid | 202 |
| 113 | (±)-{3-[2-(Chroman-3-carbonyl)-5-fluoro-1,2,3,4-tetrahydro-isoquinolin-8-yl]-4-methoxy-phenyl}-acetic acid | 18.6 |

| Example | Name | IC$_{50}$ [nM] |
|---|---|---|
| 114 | (±)-{3-[5-Fluoro-2-(4-oxo-1,2,3,4-tetrahydro-naphthalene-2-carbonyl)-1,2,3,4-tetrahydro-isoquinolin-8-yl]-4-methoxy-phenyl}-acetic acid | 21.2 |
| 115 | (±)-{3-[2-(Chroman-2-carbonyl)-5-fluoro-1,2,3,4-tetrahydro-isoquinolin-8-yl]-4-methoxy-phenyl}-acetic acid | 173 |
| 116 | (±)-{3-[2-(Bicyclo[4.2.0]octa-1(6),2,4-triene-7-carbonyl)-5-fluoro-1,2,3,4-tetrahydro-isoquinolin-8-yl]-4-methoxy-phenyl}-acetic acid | 211 |
| 117 | {3-[5-Fluoro-2-(4-phenyl-butyryl)-1,2,3,4-tetrahydro-isoquinolin-8-yl]-4-methoxy-phenyl}-acetic acid | 5.41 |
| 118 | {3-[5-Fluoro-2-(4-oxo-4-phenyl-butyryl)-1,2,3,4-tetrahydro-isoquinolin-8-yl]-4-methoxy-phenyl}-acetic acid | 38.6 |
| 119 | (3-{5-Fluoro-2-[2-(1-methyl-1H-indol-3-yl)-acetyl]-1,2,3,4-tetrahydro-isoquinolin-8-yl}-4-methoxy-phenyl)-acetic acid | 69.5 |
| 120 | (±)-2-{3-[5-Fluoro-2-((1R,2R)-2-phenyl-cyclopropanecarbonyl)-1,2,3,4-tetrahydro-isoquinolin-8-yl]-4-methoxy-phenyl}-propionic acid | 8.56 |
| 121 | {3-[2-(2-Benzo[d]isoxazol-3-yl-acetyl)-5-fluoro-1,2,3,4-tetrahydro-isoquinolin-8-yl]-4-methoxy-phenyl}-acetic acid | 47.2 |
| 122 | (±)-{3-[5-Fluoro-2-(3-oxo-indane-1-carbonyl)-1,2,3,4-tetrahydro-isoquinolin-8-yl]-4-methoxy-phenyl}-acetic acid | 862 |
| 123 | (±)-{3-[5-Fluoro-2-(1,2,3,4-tetrahydro-naphthalene-2-carbonyl)-1,2,3,4-tetrahydro-isoquinolin-8-yl]-4-methoxy-phenyl}-acetic acid | 37.7 |
| 124 | {3-[5-Fluoro-2-(2-1H-indazol-3-yl-acetyl)-1,2,3,4-tetrahydro-isoquinolin-8-yl]-4-methoxy-phenyl}-acetic acid | 10.5 |
| 125 | (3-{5-Fluoro-2-[3-(3-methyl-indazol-1-yl)-propionyl]-1,2,3,4-tetrahydro-isoquinolin-8-yl}-4-methoxy-phenyl)-acetic acid | 16.3 |
| 126 | (3-{5-Fluoro-2-[3-(5-fluoro-indazol-1-yl)-propionyl]-1,2,3,4-tetrahydro-isoquinolin-8-yl}-4-methoxy-phenyl)-acetic acid | 9.54 |
| 127 | {3-[2-(2-Cyclohexyl-acetyl)-5-fluoro-1,2,3,4-tetrahydro-isoquinolin-8-yl]-4-methoxy-phenyl}-acetic acid | 176 |
| 128 | (3-{5-Fluoro-2-[2-(1-hydroxy-cyclohexyl)-acetyl]-1,2,3,4-tetrahydro-isoquinolin-8-yl}-4-methoxy-phenyl)-acetic acid | 538 |
| 129 | {3-[2-(3,3-Dimethyl-butyryl)-5-fluoro-1,2,3,4-tetrahydro-isoquinolin-8-yl]-4-methoxy-phenyl}-acetic acid | 913 |
| 130 | {3-[5-Fluoro-2-(2-fluoro-benzylcarbamoyl)-1,2,3,4-tetrahydro-isoquinolin-8-yl]-4-methoxy-phenyl}-acetic acid | 17.7 |
| 131 | {3-[5-Fluoro-2-(3-fluoro-benzylcarbamoyl)-1,2,3,4-tetrahydro-isoquinolin-8-yl]-4-methoxy-phenyl}-acetic acid | 60.1 |
| 132 | {3-[5-Fluoro-2-(4-fluoro-benzylcarbamoyl)-1,2,3,4-tetrahydro-isoquinolin-8-yl]-4-methoxy-phenyl}-acetic acid | 15.1 |
| 133 | [3-(5-Fluoro-2-phenethylcarbamoyl-1,2,3,4-tetrahydro-isoquinolin-8-yl)-4-methoxy-phenyl]-acetic acid | 13 |
| 134 | {3-[2-(2-Chloro-benzylcarbamoyl)-5-fluoro-1,2,3,4-tetrahydro-isoquinolin-8-yl]-4-methoxy-phenyl}-acetic acid | 21.5 |
| 135 | {3-[5-Fluoro-2-(2-methoxy-benzylcarbamoyl)-1,2,3,4-tetrahydro-isoquinolin-8-yl]-4-methoxy-phenyl}-acetic acid | 19.6 |
| 136 | [3-(2-Benzylcarbamoyl-5-fluoro-1,2,3,4-tetrahydro-isoquinolin-8-yl)-4-methoxy-phenyl]-acetic acid | 30.6 |
| 137 | [3-(5-Fluoro-2-propylcarbamoyl-1,2,3,4-tetrahydro-isoquinolin-8-yl)-4-methoxy-phenyl]-acetic acid | 764 |
| 138 | 8-(5-Carboxymethyl-2-methoxy-phenyl)-5-fluoro-3,4-dihydro-1H-isoquinoline-2-carboxylic acid 3-fluoro-benzyl ester | 5.42 |
| 139 | 8-(5-Carboxymethyl-2-methoxy-phenyl)-5-fluoro-3,4-dihydro-1H-isoquinoline-2-carboxylic acid 4-fluoro-benzyl ester | 2.53 |
| 140 | (±)-8-[5-(1-Carboxy-ethyl)-2-methoxy-phenyl]-5-fluoro-3,4-dihydro-1H-isoquinoline-2-carboxylic acid 2-fluoro-benzyl ester | 62.6 |
| 141 | 8-(5-Carboxymethyl-2-methoxy-phenyl)-5-fluoro-3,4-dihydro-1H-isoquinoline-2-carboxylic acid ethyl ester | 187 |
| 142 | 8-(5-Carboxymethyl-2-methoxy-phenyl)-5-fluoro-3,4-dihydro-1H-isoquinoline-2-carboxylic acid isobutyl ester | 148 |
| 143 | 8-(5-Carboxymethyl-2-methoxy-phenyl)-5-fluoro-3,4-dihydro-1H-isoquinoline-2-carboxylic acid isopropyl ester | 348 |
| 144 | 8-(3-Carboxymethoxy-5-chloro-phenyl)-5-fluoro-3,4-dihydro-1H-isoquinoline-2-carboxylic acid benzyl ester | 86.2 |
| 145 | 8-(2-Carboxymethoxy-5-chloro-phenyl)-5-fluoro-3,4-dihydro-1H-isoquinoline-2-carboxylic acid benzyl ester | 430 |
| 146 | 8-(5-Carboxymethyl-2-methoxy-phenyl)-5-fluoro-3,4-dihydro-1H-isoquinoline-2-carboxylic acid 2-fluoro-benzyl ester | 3.06 |
| 147 | 8-(5-Carboxymethyl-2-methoxy-phenyl)-5-fluoro-3,4-dihydro-1H-isoquinoline-2-carboxylic acid 2,3-difluoro-benzyl ester | 2.51 |
| 148 | 8-(5-Carboxymethyl-2-methoxy-phenyl)-5-fluoro-3,4-dihydro-1H-isoquinoline-2-carboxylic acid 2-methyl-2H-pyrazol-3-ylmethyl ester | 51.6 |
| 149 | 8-(5-Carboxymethyl-2-methoxy-phenyl)-5-fluoro-3,4-dihydro-1H-isoquinoline-2-carboxylic acid 2,5-dimethyl-2H-pyrazol-3-ylmethyl ester | 6.87 |

-continued

| Example | Name | IC$_{50}$ [nM] |
|---|---|---|
| 150 | 8-(5-Carboxymethyl-2-methoxy-phenyl)-5-fluoro-3,4-dihydro-1H-isoquinoline-2-carboxylic acid 2-methyl-thiazol-4-ylmethyl ester | 7.12 |
| 151 | 8-(5-Carboxymethyl-2-methoxy-phenyl)-5-fluoro-3,4-dihydro-1H-isoquinoline-2-carboxylic acid 2-methyl-thiazol-5-ylmethyl ester | 5.73 |
| 152 | 8-(5-Carboxymethyl-2-methoxy-phenyl)-5-fluoro-3,4-dihydro-1H-isoquinoline-2-carboxylic acid pyrimidin-5-ylmethyl ester | 34.1 |
| 153 | 8-(5-Carboxymethyl-2-methoxy-phenyl)-5-fluoro-3,4-dihydro-1H-isoquinoline-2-carboxylic acid 2-(4-methyl-thiazol-5-yl)-ethyl ester | 40.7 |
| 154 | 8-(5-Carboxymethyl-2-methoxy-phenyl)-5-chloro-3,4-dihydro-1H-isoquinoline-2-carboxylic acid benzyl ester | 5.9 |
| 155 | 8-(5-Carboxymethyl-2-methoxy-phenyl)-5-methyl-3,4-dihydro-1H-isoquinoline-2-carboxylic acid benzyl ester | 46.8 |
| 156 | 8-(5-Carboxymethyl-2-methoxy-phenyl)-5-methoxy-3,4-dihydro-1H-isoquinoline-2-carboxylic acid benzyl ester | 251 |
| 157 | 8-(5-Carboxymethyl-2-methoxy-phenyl)-5-fluoro-3,4-dihydro-1H-isoquinoline-2-carboxylic acid benzyl ester | 11.7 |
| 158 | 8-(5-Carboxymethyl-2-methoxy-phenyl)-5-trifluoromethyl-3,4-dihydro-1H-isoquinoline-2-carboxylic acid benzyl ester | 67.8 |
| 159 | 5-(5-Carboxymethyl-2-methoxy-phenyl)-8-fluoro-3,4-dihydro-1H-isoquinoline-2-carboxylic acid benzyl ester | 594 |
| 160 | {3-[5-Fluoro-2-((1R,2R)-2-phenyl-cyclopropanecarbonyl)-1,2,3,4-tetrahydro-isoquinolin-8-yl]-4-trifluoromethoxy-phenoxy}-acetic acid | 0.67 |
| 161 | {3-[5-Fluoro-2-((1R,2R)-2-phenyl-cyclopropanecarbonyl)-1,2,3,4-tetrahydro-isoquinolin-8-yl]-4-isopropoxy-phenoxy}-acetic acid | 1.38 |
| 162 | 8-(5-Carboxymethoxy-2-trifluoromethoxy-phenyl)-5-fluoro-3,4-dihydro-1H-isoquinoline-2-carboxylic acid benzyl ester | 2.47 |
| 163 | 8-(5-Carboxymethoxy-2-isopropoxy-phenyl)-5-fluoro-3,4-dihydro-1H-isoquinoline-2-carboxylic acid benzyl ester | 7.94 |
| 164 | 8-(4-Carboxymethyl-2-fluoro-phenyl)-5-fluoro-3,4-dihydro-1H-isoquinoline-2-carboxylic acid benzyl ester | 47.3 |
| 165 | 8-(4-Carboxymethyl-2-chloro-phenyl)-5-fluoro-3,4-dihydro-1H-isoquinoline-2-carboxylic acid benzyl ester | 26.3 |
| 166 | 8-(4-Carboxymethyl-2-methoxy-phenyl)-5-fluoro-3,4-dihydro-1H-isoquinoline-2-carboxylic acid benzyl ester | 4.5 |
| 167 | 8-(6-Carboxymethyl-benzo[1,3]dioxol-4-yl)-5-fluoro-3,4-dihydro-1H-isoquinoline-2-carboxylic acid benzyl ester | 15.4 |
| 168 | 8-(7-Carboxymethyl-2,3-dihydro-benzo[1,4]dioxin-5-yl)-5-fluoro-3,4-dihydro-1H-isoquinoline-2-carboxylic acid benzyl ester | 17.9 |
| 169 | 8-(5-Carboxymethyl-2-methoxy-phenyl)-5-cyano-3,4-dihydro-1H-isoquinoline-2-carboxylic acid benzyl ester | 9.17 |
| 170 | 8-(5-Carboxymethyl-2-methoxy-phenyl)-3,4-dihydro-1H-isoquinoline-2-carboxylic acid benzyl ester | 110 |
| 171 | (±)-8-[5-(1-Carboxy-ethyl)-2-methoxy-phenyl]-5-fluoro-3,4-dihydro-1H-isoquinoline-2-carboxylic acid benzyl ester | 21.2 |
| 172 | 8-(4-Carboxymethoxy-phenyl)-5-fluoro-3,4-dihydro-1H-isoquinoline-2-carboxylic acid benzyl ester | 209 |
| 173 | 8-(2-Carboxymethoxy-5-fluoro-phenyl)-3,4-dihydro-1H-isoquinoline-2-carboxylic acid benzyl ester | 91.4 |
| 174 | 8-[2-(3-Carboxy-propoxy)-5-fluoro-phenyl]-3,4-dihydro-1H-isoquinoline-2-carboxylic acid benzyl ester | 289 |
| 175 | 8-(3-Carboxymethoxy-phenyl)-5-fluoro-3,4-dihydro-1H-isoquinoline-2-carboxylic acid benzyl ester | 117 |
| 176 | 8-(5-Carboxymethoxy-2-chloro-phenyl)-5-fluoro-3,4-dihydro-1H-isoquinoline-2-carboxylic acid benzyl ester | 13.6 |
| 177 | 8-(5-Carboxymethoxy-2-methoxy-phenyl)-5-fluoro-3,4-dihydro-1H-isoquinoline-2-carboxylic acid benzyl ester | 21.3 |
| 178 | 8-(5-Carboxymethoxy-2-chloro-phenyl)-5-chloro-3,4-dihydro-1H-isoquinoline-2-carboxylic acid benzyl ester | 17.5 |
| 179 | 8-(5-Carboxymethoxy-2-chloro-phenyl)-5-methyl-3,4-dihydro-1H-isoquinoline-2-carboxylic acid benzyl ester | 250 |
| 180 | 8-(5-Carboxymethoxy-2-chloro-phenyl)-5-trifluoromethyl-3,4-dihydro-1H-isoquinoline-2-carboxylic acid benzyl ester | 208 |
| 181 | 8-(5-Carboxymethoxy-2-chloro-phenyl)-3,4-dihydro-1H-isoquinoline-2-carboxylic acid benzyl ester | 123 |
| 182 | {3-[5-Fluoro-2-((1R,2R)-2-phenyl-cyclopropanecarbonyl)-1,2,3,4-tetrahydro-isoquinolin-8-yl]-4-methoxy-phenoxy}-acetic acid | 4.36 |
| 183 | (4-{5-Fluoro-2-[3-(1-methyl-1H-indol-3-yl)-propionyl]-1,2,3,4-tetrahydro-isoquinolin-8-yl}-3-methoxy-phenyl)-acetic acid | 0.46 |
| 184 | {4-[5-Fluoro-2-((1R,2R)-2-phenyl-cyclopropanecarbonyl)-1,2,3,4-tetrahydro-isoquinolin-8-yl]-3-methoxy-phenyl}-acetic acid | 0.90 |
| 185 | (4-{5-Fluoro-2-[4-(2-fluoro-phenyl)-butyryl]-1,2,3,4-tetrahydro-isoquinolin-8-yl}-3-methoxy-phenyl)-acetic acid | 1.28 |
| 186 | (4-{5-Fluoro-2-[3-(2-methyl-1H-indol-3-yl)-propionyl]-1,2,3,4-tetrahydro-isoquinolin-8-yl}-3-methoxy-phenyl)-acetic acid | 2.66 |

-continued

| Example | Name | IC$_{50}$ [nM] |
|---|---|---|
| 187 | {4-[5-Fluoro-2-(4-phenyl-butyryl)-1,2,3,4-tetrahydro-isoquinolin-8-yl]-3-methoxy-phenyl}-acetic acid | 0.89 |
| 188 | {4-[5-Fluoro-2-(3-methyl-3-phenyl-butyryl)-1,2,3,4-tetrahydro-isoquinolin-8-yl]-3-methoxy-phenyl}-acetic acid | 0.53 |
| 189 | {4-[5-Fluoro-2-((R)-3-phenyl-butyryl)-1,2,3,4-tetrahydro-isoquinolin-8-yl]-3-methoxy-phenyl}-acetic acid | 1.04 |
| 190 | (4-{5-Fluoro-2-[3-(5-fluoro-indazol-1-yl)-propionyl]-1,2,3,4-tetrahydro-isoquinolin-8-yl}-3-methoxy-phenyl)-acetic acid | 7.25 |
| 191 | {4-[2-(3-2,3-Dihydro-indol-1-yl-propionyl)-5-fluoro-1,2,3,4-tetrahydro-isoquinolin-8-yl]-3-methoxy-phenyl}-acetic acid | 2.42 |
| 192 | (4-{5-Fluoro-2-[3-(4-fluoro-phenoxy)-propionyl]-1,2,3,4-tetrahydro-isoquinolin-8-yl}-3-methoxy-phenyl)-acetic acid | 0.69 |
| 193 | (4-{2-[2-(2-Chloro-benzyloxy)-acetyl]-5-fluoro-1,2,3,4-tetrahydro-isoquinolin-8-yl}-3-methoxy-phenyl)-acetic acid | 1.38 |
| 194 | {4-[5-Fluoro-2-(3-o-tolyl-propionyl)-1,2,3,4-tetrahydro-isoquinolin-8-yl]-3-methoxy-phenyl}-acetic acid | 0.75 |
| 195 | 8-(5-Carboxymethyl-2-ethoxy-phenyl)-5-fluoro-3,4-dihydro-1H-isoquinoline-2-carboxylic acid benzyl ester | 1.06 |
| 196 | 8-(5-Carboxymethyl-2-cyclopropylmethoxy-phenyl)-5-fluoro-3,4-dihydro-1H-isoquinoline-2-carboxylic acid benzyl ester | 0.28 |
| 197 | 8-(5-Carboxymethyl-2-propoxy-phenyl)-5-fluoro-3,4-dihydro-1H-isoquinoline-2-carboxylic acid benzyl ester | 0.28 |
| 198 | 8-(5-Carboxymethyl-2-isobutoxy-phenyl)-5-fluoro-3,4-dihydro-1H-isoquinoline-2-carboxylic acid benzyl ester | 1.28 |
| 199 | 8-[5-Carboxymethyl-2-(2-methoxy-ethoxy)-phenyl]-5-fluoro-3,4-dihydro-1H-isoquinoline-2-carboxylic acid benzyl ester | 0.49 |
| 200 | {4-[2-(2-Chroman-4-yl-acetyl)-5-fluoro-1,2,3,4-tetrahydro-isoquinolin-8-yl]-3-methoxy-phenyl}-acetic acid (enantiomer 1) | 8.0 |
| 201 | {4-[2-(2-Chroman-4-yl-acetyl)-5-fluoro-1,2,3,4-tetrahydro-isoquinolin-8-yl]-3-methoxy-phenyl}-acetic acid (enantiomer 2) | 9.5 |
| 202 | 8-[4-(1-Carboxy-ethoxy)-2-methoxy-phenyl]-5-fluoro-3,4-dihydro-1H-isoquinoline-2-carboxylic acid benzyl ester (enantiomer 2) | 179 |
| 203 | {4-Ethoxy-3-[5-fluoro-2-(3-pyridin-2-yl-butyryl)-1,2,3,4-tetrahydro-isoquinolin-8-yl]-phenyl}-acetic acid (enantiomer 1) | 2.9 |
| 204 | {4-Ethoxy-3-[5-fluoro-2-(3-pyridin-2-yl-butyryl)-1,2,3,4-tetrahydro-isoquinolin-8-yl]-phenyl}-acetic acid (enantiomer 2) | 2.9 |
| 205 | {3-Ethoxy-4-[5-fluoro-2-(2-isochroman-1-yl-acetyl)-1,2,3,4-tetrahydro-isoquinolin-8-yl]-phenyl}-acetic acid (enantiomer 1) | 1.0 |
| 206 | {3-Ethoxy-4-[5-fluoro-2-(2-isochroman-1-yl-acetyl)-1,2,3,4-tetrahydro-isoquinolin-8-yl]-phenyl}-acetic acid (enantiomer 2) | 2.4 |
| 207 | {3-[2-(2-2,3-Dihydro-benzofuran-3-yl-acetyl)-5-fluoro-1,2,3,4-tetrahydro-isoquinolin-8-yl]-4-ethoxy-phenyl}-acetic acid (enantiomer 1) | 1.4 |
| 208 | {3-[2-(2-2,3-Dihydro-benzofuran-3-yl-acetyl)-5-fluoro-1,2,3,4-tetrahydro-isoquinolin-8-yl]-4-ethoxy-phenyl}-acetic acid (enantiomer 2) | 1.6 |
| 209 | {4-Ethoxy-3-[5-fluoro-2-(2-isochroman-4-yl-acetyl)-1,2,3,4-tetrahydro-isoquinolin-8-yl]-phenyl}-acetic acid (enantiomer 1) | 3.4 |
| 210 | {4-Ethoxy-3-[5-fluoro-2-(2-isochroman-4-yl-acetyl)-1,2,3,4-tetrahydro-isoquinolin-8-yl]-phenyl}-acetic acid (enantiomer 2) | 5.5 |
| 211 | (4-Ethoxy-3-{5-fluoro-2-[3-(4-fluoro-phenyl)-butyryl]-1,2,3,4-tetrahydro-isoquinolin-8-yl}-phenyl)-acetic acid (enantiomer 1) | 2.6 |
| 212 | (4-Ethoxy-3-{5-fluoro-2-[3-(4-fluoro-phenyl)-butyryl]-1,2,3,4-tetrahydro-isoquinolin-8-yl}-phenyl)-acetic acid (enantiomer 2) | 11.4 |
| 213 | {4-Ethoxy-3-[5-fluoro-2-(2-methyl-3-phenyl-propionyl)-1,2,3,4-tetrahydro-isoquinolin-8-yl]-phenyl}-acetic acid (enantiomer 1) | 111 |
| 214 | {4-Ethoxy-3-[5-fluoro-2-(2-methyl-3-phenyl-propionyl)-1,2,3,4-tetrahydro-isoquinolin-8-yl]-phenyl}-acetic acid (enantiomer 2) | 3.1 |
| 215 | 8-(5-Carboxymethyl-2-propyl-phenyl)-5-fluoro-3,4-dihydro-1H-isoquinoline-2-carboxylic acid benzyl ester | 3.6 |
| 216 | 8-(4-Carboxymethyl-2-isopropyl-phenyl)-5-fluoro-3,4-dihydro-1H-isoquinoline-2-carboxylic acid benzyl ester | 19.4 |
| 217 | 8-(4-Carboxymethyl-2-isopropoxy-phenyl)-5-fluoro-3,4-dihydro-1H-isoquinoline-2-carboxylic acid benzyl ester | 2.3 |
| 218 | 8-(4-Carboxymethyl-2,6-dimethoxy-phenyl)-5-fluoro-3,4-dihydro-1H-isoquinoline-2-carboxylic acid benzyl ester | 1.7 |
| 219 | (±)-{4-Ethoxy-3-[5-fluoro-2-(2-indan-1-yl-acetyl)-1,2,3,4-tetrahydro-isoquinolin-8-yl]-phenyl}-acetic acid | 9.1 |
| 220 | {4-Ethoxy-3-[5-fluoro-2-((1R,2R)-2-phenyl-cyclopropanecarbonyl)-1,2,3,4-tetrahydro-isoquinolin-8-yl]-phenyl}-acetic acid | 13.5 |
| 221 | {4-Ethoxy-3-[5-fluoro-2-((R)-3-phenyl-butyryl)-1,2,3,4-tetrahydro-isoquinolin-8-yl]-phenyl}-acetic acid | 1.2 |

-continued

| Example | Name | IC$_{50}$ [nM] |
|---|---|---|
| 222 | (4-Ethoxy-3-{5-fluoro-2-[2-(1-phenyl-cyclopropyl)-acetyl]-1,2,3,4-tetrahydro-isoquinolin-8-yl}-phenyl)-acetic acid | 26.4 |
| 223 | (4-Ethoxy-3-{5-fluoro-2-[3-(4-fluoro-phenyl)-3-methyl-butyryl]-1,2,3,4-tetrahydro-isoquinolin-8-yl}-phenyl)-acetic acid | 15 |
| 224 | (±)-{4-Ethoxy-3-[5-fluoro-2-(2-isochroman-1-yl-acetyl)-1,2,3,4-tetrahydro-isoquinolin-8-yl]-phenyl}-acetic acid | 8.2 |
| 225 | {4-Ethoxy-3-[5-fluoro-2-(3-methyl-3-phenyl-butyryl)-1,2,3,4-tetrahydro-isoquinolin-8-yl]-phenyl}-acetic acid | 11.7 |
| 226 | (±)-{3-[2-(2-Chroman-4-yl-acetyl)-5-fluoro-1,2,3,4-tetrahydro-isoquinolin-8-yl]-4-ethoxy-phenyl}-acetic acid | 12.9 |
| 227 | (±)-{3-[2-(2-2,3-Dihydro-benzofuran-3-yl-acetyl)-5-fluoro-1,2,3,4-tetrahydro-isoquinolin-8-yl]-4-ethoxy-phenyl}-acetic acid | 0.9 |
| 228 | (±)-{4-Ethoxy-3-[5-fluoro-2-(2-isochroman-4-yl-acetyl)-1,2,3,4-tetrahydro-isoquinolin-8-yl]-phenyl}-acetic acid | 6.8 |
| 229 | (±)-{3-Ethoxy-4-[5-fluoro-2-(2-isochroman-1-yl-acetyl)-1,2,3,4-tetrahydro-isoquinolin-8-yl]-phenyl}-acetic acid | 0.7 |
| 230 | (3-Ethoxy-4-{5-fluoro-2-[2-(1-phenyl-cyclopropyl)-acetyl]-1,2,3,4-tetrahydro-isoquinolin-8-yl}-phenyl)-acetic acid | 1.0 |
| 231 | {3-Ethoxy-4-[5-fluoro-2-((1R,2R)-2-phenyl-cyclopropanecarbonyl)-1,2,3,4-tetrahydro-isoquinolin-8-yl]-phenyl}-acetic acid | 10.5 |
| 232 | (±)-{3-Ethoxy-4-[5-fluoro-2-(2-isochroman-4-yl-acetyl)-1,2,3,4-tetrahydro-isoquinolin-8-yl]-phenyl}-acetic acid | 0.6 |
| 233 | (±)-{3-Ethoxy-4-[5-fluoro-2-(2-indan-1-yl-acetyl)-1,2,3,4-tetrahydro-isoquinolin-8-yl]-phenyl}-acetic acid | 1.1 |
| 234 | {3-Ethoxy-4-[5-fluoro-2-((R)-3-phenyl-butyryl)-1,2,3,4-tetrahydro-isoquinolin-8-yl]-phenyl}-acetic acid | 0.9 |
| 235 | (±)-{4-[2-(2-2,3-Dihydro-benzofuran-3-yl-acetyl)-5-fluoro-1,2,3,4-tetrahydro-isoquinolin-8-yl]-3-ethoxy-phenyl}-acetic acid | 0.3 |
| 236 | (±)-{4-[2-(2-Chroman-4-yl-acetyl)-5-fluoro-1,2,3,4-tetrahydro-isoquinolin-8-yl]-3-ethoxy-phenyl}-acetic acid | 0.8 |
| 237 | (3-Ethoxy-4-{5-fluoro-2-[3-(4-fluoro-phenyl)-3-methyl-butyryl]-1,2,3,4-tetrahydro-isoquinolin-8-yl}-phenyl)-acetic acid | 0.3 |
| 238 | {3-Ethoxy-4-[5-fluoro-2-(3-methyl-3-phenyl-butyryl)-1,2,3,4-tetrahydro-isoquinolin-8-yl]-phenyl}-acetic acid | 0.6 |
| 239 | (±)-(3-{5-Fluoro-2-[2-(1-methyl-1,2,3,4-tetrahydro-naphthalen-1-yl)-acetyl]-1,2,3,4-tetrahydro-isoquinolin-8-yl}-4-methoxy-phenyl)-acetic acid | 28.4 |
| 240 | (±)-(3-{2-[2-(2,2-Dimethyl-chroman-4-yl)-acetyl]-5-fluoro-1,2,3,4-tetrahydro-isoquinolin-8-yl}-4-methoxy-phenyl)-acetic acid | 3.6 |
| 241 | (±)-{3-[5-Fluoro-2-(8-methoxy-1,2,3,4-tetrahydro-naphthalene-2-carbonyl)-1,2,3,4-tetrahydro-isoquinolin-8-yl]-4-methoxy-phenyl}-acetic acid | 8.3 |
| 242 | (±)-{3-[2-(2-Chroman-3-yl-acetyl)-5-fluoro-1,2,3,4-tetrahydro-isoquinolin-8-yl]-4-methoxy-phenyl}-acetic acid | 2.7 |
| 243 | (±)-(3-{5-Fluoro-2-[2-(7-fluoro-chroman-4-yl)-acetyl]-1,2,3,4-tetrahydro-isoquinolin-8-yl}-4-methoxy-phenyl)-acetic acid | 20.6 |
| 244 | (±)-(3-{5-Fluoro-2-[2-(6-fluoro-chroman-4-yl)-acetyl]-1,2,3,4-tetrahydro-isoquinolin-8-yl}-4-methoxy-phenyl)-acetic acid | 158 |
| 245 | (±)-{3-[2-(3-Cyclopropyl-butyryl)-5-fluoro-1,2,3,4-tetrahydro-isoquinolin-8-yl]-4-methoxy-phenyl}-acetic acid | 399 |
| 246 | (±)-(3-{5-Fluoro-2-[2-(8-fluoro-chroman-4-yl)-acetyl]-1,2,3,4-tetrahydro-isoquinolin-8-yl}-4-methoxy-phenyl)-acetic acid | 22.3 |
| 247 | (±)-{3-[5-Fluoro-2-(2-5,6,7,8-tetrahydro-isoquinolin-8-yl-acetyl)-1,2,3,4-tetrahydro-isoquinolin-8-yl]-4-methoxy-phenyl}-acetic acid hydrochloride | 484 |
| 248 | (±)-(3-{5-Fluoro-2-[3-(6-methoxy-pyridin-2-yl)-butyryl]-1,2,3,4-tetrahydro-isoquinolin-8-yl}-4-methoxy-phenyl)-acetic acid hydrochloride | 77.9 |
| 249 | (±)-(3-{5-Fluoro-2-[3-(6-methyl-pyridin-2-yl)-butyryl]-1,2,3,4-tetrahydro-isoquinolin-8-yl}-4-methoxy-phenyl)-acetic acid hydrochloride | 40.4 |
| 250 | (3-{5-Fluoro-2-[2-(1-phenyl-cyclobutyl)-acetyl]-1,2,3,4-tetrahydro-isoquinolin-8-yl}-4-methoxy-phenyl)-acetic acid | 146 |
| 251 | [3-(5-Fluoro-2-{2-[1-(4-fluoro-phenyl)-cyclobutyl]-acetyl}-1,2,3,4-tetrahydro-isoquinolin-8-yl)-4-methoxy-phenyl]-acetic acid | 414 |
| 252 | (3-{5-Fluoro-2-[3-(3-fluoro-phenyl)-3-methyl-butyryl]-1,2,3,4-tetrahydro-isoquinolin-8-yl}-4-methoxy-phenyl)-acetic acid | 13.2 |
| 253 | (±)-{3-[2-(2-{[(4-Chloro-phenyl)-phenyl-methyl]-methyl-amino}-acetyl)-5-fluoro-1,2,3,4-tetrahydro-isoquinolin-8-yl]-4-methoxy-phenyl}-acetic acid | 10.6 |
| 254 | {3-[2-(2-Cyclopropyl-acetyl)-5-fluoro-1,2,3,4-tetrahydro-isoquinolin-8-yl]-4-methoxy-phenyl}-acetic acid | 614 |

-continued

| Example | Name | IC$_{50}$ [nM] |
|---|---|---|
| 255 | {3-[5-Fluoro-2-((R)-2-phenyl-propionyl)-1,2,3,4-tetrahydro-isoquinolin-8-yl]-4-methoxy-phenyl}-acetic acid | 981 |
| 256 | (±)-{3-[5-Fluoro-2-(3-hydroxy-3-phenyl-butyryl)-1,2,3,4-tetrahydro-isoquinolin-8-yl]-4-methoxy-phenyl}-acetic acid | 49.8 |
| 257 | (±)-{3-[5-Fluoro-2-(2-isochroman-1-yl-acetyl)-1,2,3,4-tetrahydro-isoquinolin-8-yl]-4-methoxy-phenyl}-acetic acid | 2.2 |
| 258 | (3-{5-Fluoro-2-[2-(1-phenyl-cyclopropyl)-acetyl]-1,2,3,4-tetrahydro-isoquinolin-8-yl}-4-methoxy-phenyl)-acetic acid | 2.8 |
| 259 | (±)-(3-{5-Fluoro-2-[2-(2-methyl-1,2,3,4-tetrahydro-isoquinolin-1-yl)-acetyl]-1,2,3,4-tetrahydro-isoquinolin-8-yl}-4-methoxy-phenyl)-acetic acid | 587 |
| 260 | (±)-{3-[5-Fluoro-2-(2-1,2,3,4-tetrahydro-naphthalen-2-yl-acetyl)-1,2,3,4-tetrahydro-isoquinolin-8-yl]-4-methoxy-phenyl}-acetic acid | 1.4 |
| 261 | (±)-{3-[5-Fluoro-2-(2-indan-1-yl-acetyl)-1,2,3,4-tetrahydro-isoquinolin-8-yl]-4-methoxy-phenyl}-acetic acid | 3.1 |
| 262 | (±)-{3-[2-(2-Chroman-4-yl-acetyl)-5-fluoro-1,2,3,4-tetrahydro-isoquinolin-8-yl]-4-methoxy-phenyl}-acetic acid | 8.4 |
| 263 | (±)-{3-[5-Fluoro-2-(2-1,2,3,4-tetrahydro-naphthalen-1-yl-acetyl)-1,2,3,4-tetrahydro-isoquinolin-8-yl]-4-methoxy-phenyl}-acetic acid | 4.9 |
| 264 | (±)-{3-[5-Fluoro-2-(4-methyl-3-phenyl-pentanoyl)-1,2,3,4-tetrahydro-isoquinolin-8-yl]-4-methoxy-phenyl}-acetic acid | 253 |
| 265 | (±)-{3-[5-Fluoro-2-(3-pyridin-2-yl-butyryl)-1,2,3,4-tetrahydro-isoquinolin-8-yl]-4-methoxy-phenyl}-acetic acid | 7.8 |
| 266 | (±)-{3-[5-Fluoro-2-(3-pyridin-3-yl-butyryl)-1,2,3,4-tetrahydro-isoquinolin-8-yl]-4-methoxy-phenyl}-acetic acid formiate | 32.7 |
| 267 | (±)-{3-[5-Fluoro-2-(3-pyridin-4-yl-butyryl)-1,2,3,4-tetrahydro-isoquinolin-8-yl]-4-methoxy-phenyl}-acetic acid formiate | 86.1 |
| 268 | (±)-{3-[5-Fluoro-2-(3-phenyl-pentanoyl)-1,2,3,4-tetrahydro-isoquinolin-8-yl]-4-methoxy-phenyl}-acetic acid | 63.6 |
| 269 | {3-[5-Fluoro-2-((R)-1,2,3,4-tetrahydro-naphthalene-1-carbonyl)-1,2,3,4-tetrahydro-isoquinolin-8-yl]-4-methoxy-phenyl}-acetic acid | 95.7 |
| 270 | (±)-{3-[2-(2-2,3-Dihydro-benzofuran-3-yl-acetyl)-5-fluoro-1,2,3,4-tetrahydro-isoquinolin-8-yl]-4-methoxy-phenyl}-acetic acid | 25.3 |
| 271 | (±)-{3-[5-Fluoro-2-(2-isochroman-4-yl-acetyl)-1,2,3,4-tetrahydro-isoquinolin-8-yl]-4-methoxy-phenyl}-acetic acid | 22.3 |
| 272 | (±)-{3-[2-(Chroman-4-carbonyl)-5-fluoro-1,2,3,4-tetrahydro-isoquinolin-8-yl]-4-methoxy-phenyl}-acetic acid | 262 |
| 273 | (±)-{3-[5-Fluoro-2-(isochroman-1-carbonyl)-1,2,3,4-tetrahydro-isoquinolin-8-yl]-4-methoxy-phenyl}-acetic acid | 683 |
| 274 | (±)-{3-[5-Fluoro-2-(isochroman-3-carbonyl)-1,2,3,4-tetrahydro-isoquinolin-8-yl]-4-methoxy-phenyl}-acetic acid | 58.2 |
| 275 | [4-Ethoxy-3-(5-fluoro-2-{2-[1-(3-fluoro-phenyl)-cyclopropyl]-acetyl}-1,2,3,4-tetrahydro-isoquinolin-8-yl)-phenyl]-acetic acid | 6.8 |
| 276 | [4-Ethoxy-3-(5-fluoro-2-{2-[1-(2-fluoro-phenyl)-cyclopropyl]-acetyl}-1,2,3,4-tetrahydro-isoquinolin-8-yl)-phenyl]-acetic acid | 35.9 |
| 277 | [4-Ethoxy-3-(5-fluoro-2-{2-[1-(4-fluoro-phenyl)-cyclopropyl]-acetyl}-1,2,3,4-tetrahydro-isoquinolin-8-yl)-phenyl]-acetic acid | 1.9 |
| 278 | (±)-(4-Ethoxy-3-{5-fluoro-2-[3-(4-fluoro-phenyl)-butyryl]-1,2,3,4-tetrahydro-isoquinolin-8-yl}-phenyl)-acetic acid | 3.9 |
| 279 | (±)-(4-Ethoxy-3-{5-fluoro-2-[3-(3-fluoro-phenyl)-butyryl]-1,2,3,4-tetrahydro-isoquinolin-8-yl}-phenyl)-acetic acid | 6.9 |
| 280 | (±)-(4-Ethoxy-3-{5-fluoro-2-[3-(2-fluoro-phenyl)-butyryl]-1,2,3,4-tetrahydro-isoquinolin-8-yl}-phenyl)-acetic acid | 3.4 |
| 281 | (±)-{4-Ethoxy-3-[5-fluoro-2-(3-pyrazin-2-yl-butyryl)-1,2,3,4-tetrahydro-isoquinolin-8-yl]-phenyl}-acetic acid | 27.5 |
| 282 | (±)-(4-Ethoxy-3-{5-fluoro-2-[3-(2-methoxy-phenyl)-butyryl]-1,2,3,4-tetrahydro-isoquinolin-8-yl}-phenyl)-acetic acid | 2.2 |
| 283 | (±)-{4-Ethoxy-3-[5-fluoro-2-(3-thiazol-2-yl-butyryl)-1,2,3,4-tetrahydro-isoquinolin-8-yl]-phenyl}-acetic acid | 7.2 |
| 284 | (±)-(3-{2-[2-(2,2-Dimethyl-3,4-dihydro-2H-pyrano[2,3-b]pyridin-4-yl)-acetyl]-5-fluoro-1,2,3,4-tetrahydro-isoquinolin-8-yl}-4-ethoxy-phenyl)-acetic acid | 2.4 |
| 285 | (±)-[4-[2-(2-Chroman-4-yl-acetyl)-5-fluoro-1,2,3,4-tetrahydro-isoquinolin-8-yl]-3-(2,2,2-trifluoro-ethoxy)-phenyl]-acetic acid | 3.5 |
| 286 | [4-[5-Fluoro-2-(3-methyl-3-phenyl-butyryl)-1,2,3,4-tetrahydro-isoquinolin-8-yl]-3-(2,2,2-trifluoro-ethoxy)-phenyl]-acetic acid | 8.9 |
| 287 | [4-[5-Fluoro-2-((S)-3-phenyl-butyryl)-1,2,3,4-tetrahydro-isoquinolin-8-yl]-3-(2,2,2-trifluoro-ethoxy)-phenyl]-acetic acid | 8.1 |
| 288 | (±)-[4-[5-Fluoro-2-(3-pyridin-2-yl-butyryl)-1,2,3,4-tetrahydro-isoquinolin-8-yl]-3-(2,2,2-trifluoro-ethoxy)-phenyl]-acetic acid | 10.0 |
| 289 | [4-[5-Fluoro-2-((1R,2R)-2-phenyl-cyclopropanecarbonyl)-1,2,3,4-tetrahydro-isoquinolin-8-yl]-3-(2,2,2-trifluoro-ethoxy)-phenyl]-acetic acid | 1.4 |

| Example | Name | IC$_{50}$ [nM] |
|---|---|---|
| 290 | (±)-{3-[2-(2-Chroman-4-yl-acetyl)-5-fluoro-1,2,3,4-tetrahydro-isoquinolin-8-yl]-4-isopropoxy-phenyl}-acetic acid | 5.0 |
| 291 | {3-[5-Fluoro-2-(3-methyl-3-phenyl-butyryl)-1,2,3,4-tetrahydro-isoquinolin-8-yl]-4-isopropoxy-phenyl}-acetic acid | 5.9 |
| 292 | {3-[5-Fluoro-2-((R)-3-phenyl-butyryl)-1,2,3,4-tetrahydro-isoquinolin-8-yl]-4-isopropoxy-phenyl}-acetic acid | 2.5 |
| 293 | (±)-{3-[5-Fluoro-2-(3-pyridin-2-yl-butyryl)-1,2,3,4-tetrahydro-isoquinolin-8-yl]-4-isopropoxy-phenyl}-acetic acid | 1.6 |
| 294 | (±)-(3-{5-Fluoro-2-[3-(6-methyl-pyridin-2-yl)-butyryl]-1,2,3,4-tetrahydro-isoquinolin-8-yl}-4-isopropoxy-phenyl)-acetic acid | 3.2 |
| 295 | (3-{5-Fluoro-2-[3-(6-methyl-pyridin-2-yl)-propionyl]-1,2,3,4-tetrahydro-isoquinolin-8-yl}-4-isopropoxy-phenyl)-acetic acid | 1.7 |
| 296 | (±)-{3-[5-Fluoro-2-(2-isochroman-4-yl-acetyl)-1,2,3,4-tetrahydro-isoquinolin-8-yl]-4-isopropoxy-phenyl}-acetic acid | 0.8 |
| 297 | (±)-{3-[5-Fluoro-2-(2-isochroman-1-yl-acetyl)-1,2,3,4-tetrahydro-isoquinolin-8-yl]-4-isopropoxy-phenyl}-acetic acid | 1.9 |
| 298 | (±)-{3-[2-(2-2,3-Dihydro-benzofuran-3-yl-acetyl)-5-fluoro-1,2,3,4-tetrahydro-isoquinolin-8-yl]-4-isopropoxy-phenyl}-acetic acid | 1.2 |
| 299 | (±)-[3-[2-(2-Chroman-4-yl-acetyl)-5-fluoro-1,2,3,4-tetrahydro-isoquinolin-8-yl]-4-(2,2,2-trifluoro-ethoxy)-phenyl]-acetic acid | 14.8 |
| 300 | [3-[5-Fluoro-2-(3-methyl-3-phenyl-butyryl)-1,2,3,4-tetrahydro-isoquinolin-8-yl]-4-(2,2,2-trifluoro-ethoxy)-phenyl]-acetic acid | 14.8 |
| 301 | [3-[5-Fluoro-2-((R)-3-phenyl-butyryl)-1,2,3,4-tetrahydro-isoquinolin-8-yl]-4-(2,2,2-trifluoro-ethoxy)-phenyl]-acetic acid | 3.6 |
| 302 | (±)-[3-[5-Fluoro-2-(3-pyridin-2-yl-butyryl)-1,2,3,4-tetrahydro-isoquinolin-8-yl]-4-(2,2,2-trifluoro-ethoxy)-phenyl]-acetic acid | 8.1 |
| 303 | (±)-[3-{5-Fluoro-2-[3-(6-methyl-pyridin-2-yl)-butyryl]-1,2,3,4-tetrahydro-isoquinolin-8-yl}-4-(2,2,2-trifluoro-ethoxy)-phenyl]-acetic acid | 6.6 |
| 304 | [3-{5-Fluoro-2-[3-(6-methyl-pyridin-2-yl)-propionyl]-1,2,3,4-tetrahydro-isoquinolin-8-yl}-4-(2,2,2-trifluoro-ethoxy)-phenyl]-acetic acid | 12.6 |
| 305 | (±)-[3-[5-Fluoro-2-(2-isochroman-4-yl-acetyl)-1,2,3,4-tetrahydro-isoquinolin-8-yl]-4-(2,2,2-trifluoro-ethoxy)-phenyl]-acetic acid | 3.4 |
| 306 | (±)-[3-[5-Fluoro-2-(2-isochroman-1-yl-acetyl)-1,2,3,4-tetrahydro-isoquinolin-8-yl]-4-(2,2,2-trifluoro-ethoxy)-phenyl]-acetic acid | 7.4 |
| 307 | (±)-[3-[2-(2-2,3-Dihydro-benzofuran-3-yl-acetyl)-5-fluoro-1,2,3,4-tetrahydro-isoquinolin-8-yl]-4-(2,2,2-trifluoro-ethoxy)-phenyl]-acetic acid | 3.4 |
| 308 | (±)-{4-Ethoxy-3-[5-fluoro-2-(3-pyridin-2-yl-pentanoyl)-1,2,3,4-tetrahydro-isoquinolin-8-yl]-phenyl}-acetic acid | 13.1 |
| 309 | (4-Ethoxy-3-{5-fluoro-2-[3-(3-methoxy-pyridin-2-yl)-propionyl]-1,2,3,4-tetrahydro-isoquinolin-8-yl}-phenyl)-acetic acid | 32.3 |
| 310 | (4-Ethoxy-3-{5-fluoro-2-[3-(4-fluoro-phenyl)-propionyl]-1,2,3,4-tetrahydro-isoquinolin-8-yl}-phenyl)-acetic acid | 1.7 |
| 311 | (4-Ethoxy-3-{5-fluoro-2-[3-(3-fluoro-phenyl)-propionyl]-1,2,3,4-tetrahydro-isoquinolin-8-yl}-phenyl)-acetic acid | 3.9 |
| 312 | (4-Ethoxy-3-{5-fluoro-2-[3-(2-fluoro-phenyl)-propionyl]-1,2,3,4-tetrahydro-isoquinolin-8-yl}-phenyl)-acetic acid | 4.8 |
| 313 | (±)-{3-Ethoxy-4-[5-fluoro-2-(3-pyridin-2-yl-pentanoyl)-1,2,3,4-tetrahydro-isoquinolin-8-yl]-phenyl}-acetic acid | 7.8 |
| 314 | (3-Ethoxy-4-{5-fluoro-2-[3-(3-methoxy-pyridin-2-yl)-propionyl]-1,2,3,4-tetrahydro-isoquinolin-8-yl}-phenyl)-acetic acid | 46.1 |
| 315 | (3-Ethoxy-4-{5-fluoro-2-[3-(4-fluoro-phenyl)-propionyl]-1,2,3,4-tetrahydro-isoquinolin-8-yl}-phenyl)-acetic acid | 5.1 |
| 316 | (3-Ethoxy-4-{5-fluoro-2-[3-(3-fluoro-phenyl)-propionyl]-1,2,3,4-tetrahydro-isoquinolin-8-yl}-phenyl)-acetic acid | 2.1 |
| 317 | (3-Ethoxy-4-{5-fluoro-2-[3-(2-fluoro-phenyl)-propionyl]-1,2,3,4-tetrahydro-isoquinolin-8-yl}-phenyl)-acetic acid | 1.7 |
| 318 | (±)-{3-[2-(3-Cyclopropyl-pyridin-2-yl-propionyl)-5-fluoro-1,2,3,4-tetrahydro-isoquinolin-8-yl]-4-ethoxy-phenyl}-acetic acid | 114 |
| 319 | (±)-{4-[2-(3-Cyclopropyl-pyridin-2-yl-propionyl)-5-fluoro-1,2,3,4-tetrahydro-isoquinolin-8-yl]-3-ethoxy-phenyl}-acetic acid | 36.3 |
| 320 | (±)-(3-Ethoxy-4-{5-fluoro-2-[3-(6-methyl-pyridin-2-yl)-butyryl]-1,2,3,4-tetrahydro-isoquinolin-8-yl}-phenyl)-acetic acid | 11.7 |
| 321 | (3-Ethoxy-4-{5-fluoro-2-[3-(6-methyl-pyridin-2-yl)-propionyl]-1,2,3,4-tetrahydro-isoquinolin-8-yl}-phenyl)-acetic acid | 7.3 |
| 322 | (±)-{3-Ethoxy-4-[5-fluoro-2-(trans-2-pyridin-2-yl-cyclopropanecarbonyl)-1,2,3,4-tetrahydro-isoquinolin-8-yl]-phenyl}-acetic acid | 1.3 |
| 323 | (±)-(4-{2-[2-(2,2-Dimethyl-chroman-4-yl)-acetyl]-5-fluoro-1,2,3,4-tetrahydro-isoquinolin-8-yl}-3-ethoxy-phenyl)-acetic acid | 1.8 |
| 324 | (±)-{4-[2-(2-Chroman-3-yl-acetyl)-5-fluoro-1,2,3,4-tetrahydro-isoquinolin-8-yl]-3-ethoxy-phenyl}-acetic acid | 0.9 |

| Example | Name | IC$_{50}$ [nM] |
|---|---|---|
| 325 | (±)-{3-Ethoxy-4-[5-fluoro-2-(8-methoxy-1,2,3,4-tetrahydro-naphthalene-2-carbonyl)-1,2,3,4-tetrahydro-isoquinolin-8-yl]-phenyl}-acetic acid | 1.8 |
| 326 | (±)-(3-Ethoxy-4-{5-fluoro-2-[2-(1-methyl-1,2,3,4-tetrahydro-naphthalen-1-yl)-acetyl]-1,2,3,4-tetrahydro-isoquinolin-8-yl}-phenyl)-acetic acid | 2.0 |
| 327 | (±)-(3-Ethoxy-4-{5-fluoro-2-[2-(7-fluoro-chroman-4-yl)-acetyl]-1,2,3,4-tetrahydro-isoquinolin-8-yl}-phenyl)-acetic acid | 0.2 |
| 328 | (±)-(4-Ethoxy-3-{5-fluoro-2-[3-(6-methyl-pyridin-2-yl)-butyryl]-1,2,3,4-tetrahydro-isoquinolin-8-yl}-phenyl)-acetic acid | 1.8 |
| 329 | (4-Ethoxy-3-{5-fluoro-2-[3-(6-methyl-pyridin-2-yl)-propionyl]-1,2,3,4-tetrahydro-isoquinolin-8-yl}-phenyl)-acetic acid | 4.2 |
| 330 | (±)-{4-Ethoxy-3-[5-fluoro-2-(trans-2-pyridin-2-yl-cyclopropanecarbonyl)-1,2,3,4-tetrahydro-isoquinolin-8-yl]-phenyl}-acetic acid | 0.6 |
| 331 | (±)-(3-{2-[2-(2,2-Dimethyl-chroman-4-yl)-acetyl]-5-fluoro-1,2,3,4-tetrahydro-isoquinolin-8-yl}-4-ethoxy-phenyl)-acetic acid | 9.6 |
| 332 | (±)-{3-[2-(2-Chroman-3-yl-acetyl)-5-fluoro-1,2,3,4-tetrahydro-isoquinolin-8-yl]-4-ethoxy-phenyl}-acetic acid | 11.8 |
| 333 | (±)-{4-Ethoxy-3-[5-fluoro-2-(8-methoxy-1,2,3,4-tetrahydro-naphthalene-2-carbonyl)-1,2,3,4-tetrahydro-isoquinolin-8-yl]-phenyl}-acetic acid | 22.7 |
| 334 | (±)-(4-Ethoxy-3-{5-fluoro-2-[2-(1-methyl-1,2,3,4-tetrahydro-naphthalen-1-yl)-acetyl]-1,2,3,4-tetrahydro-isoquinolin-8-yl}-phenyl)-acetic acid | 10.2 |
| 335 | (±)-(4-Ethoxy-3-{5-fluoro-2-[2-(7-fluoro-chroman-4-yl)-acetyl]-1,2,3,4-tetrahydro-isoquinolin-8-yl}-phenyl)-acetic acid | 0.9 |
| 336 | {4-Ethoxy-3-[5-fluoro-2-((E)-3-pyridin-2-yl-acryloyl)-1,2,3,4-tetrahydro-isoquinolin-8-yl]-phenyl}-acetic acid | 3.8 |
| 337 | (4-Ethoxy-3-{5-fluoro-2-[(E)-3-(1-methyl-1H-pyrazol-3-yl)-acryloyl]-1,2,3,4-tetrahydro-isoquinolin-8-yl}-phenyl)-acetic acid | 30.4 |
| 338 | {3-Ethoxy-4-[5-fluoro-2-((E)-3-pyridin-2-yl-acryloyl)-1,2,3,4-tetrahydro-isoquinolin-8-yl]-phenyl}-acetic acid | 2.3 |
| 339 | (3-Ethoxy-4-{5-fluoro-2-[(E)-3-(1-methyl-1H-pyrazol-4-yl)-acryloyl]-1,2,3,4-tetrahydro-isoquinolin-8-yl}-phenyl)-acetic acid | 12.7 |
| 340 | {4-Ethoxy-3-[5-fluoro-2-(2-pyridin-2-yl-acetyl)-1,2,3,4-tetrahydro-isoquinolin-8-yl]-phenyl}-acetic acid | 897 |
| 341 | (4-Ethoxy-3-{5-fluoro-2-[(E)-3-(1-methyl-1H-pyrazol-4-yl)-acryloyl]-1,2,3,4-tetrahydro-isoquinolin-8-yl}-phenyl)-acetic acid | 5.8 |
| 342 | {3-Ethoxy-4-[5-fluoro-2-(2-pyridin-2-yl-acetyl)-1,2,3,4-tetrahydro-isoquinolin-8-yl]-phenyl}-acetic acid | 150 |
| 343 | (±)-{3-[5-Fluoro-2-(2-methyl-3-pyridin-3-yl-propionyl)-1,2,3,4-tetrahydro-isoquinolin-8-yl]-4-methoxy-phenyl}-acetic acid | 291 |
| 344 | (±)-{3-Ethoxy-4-[5-fluoro-2-(3-pyridin-2-yl-butyryl)-1,2,3,4-tetrahydro-isoquinolin-8-yl]-phenyl}-acetic acid | 0.9 |
| 345 | (±)-{4-Ethoxy-3-[5-fluoro-2-(3-pyridin-2-yl-butyryl)-1,2,3,4-tetrahydro-isoquinolin-8-yl]-phenyl}-acetic acid | 4.8 |
| 346 | (±)-{4-[5-Fluoro-2-(3-pyridin-2-yl-butyryl)-1,2,3,4-tetrahydro-isoquinolin-8-yl]-3-isopropoxy-phenyl}-acetic acid | 3.7 |
| 347 | [4-[5-Fluoro-2-((R)-3-phenyl-butyryl)-1,2,3,4-tetrahydro-isoquinolin-8-yl]-3-(2,2,2-trifluoro-ethoxy)-phenyl]-acetic acid | 1.5 |
| 348 | {4-Ethoxy-3-[5-fluoro-2-(3-pyridin-2-yl-propionyl)-1,2,3,4-tetrahydro-isoquinolin-8-yl]-phenyl}-acetic acid | 2.7 |
| 349 | {3-Ethoxy-4-[5-fluoro-2-(3-pyridin-2-yl-propionyl)-1,2,3,4-tetrahydro-isoquinolin-8-yl]-phenyl}-acetic acid | 0.5 |
| 350 | (±)-{4-Ethoxy-3-[5-fluoro-2-(2-5,6,7,8-tetrahydro-quinolin-8-yl-acetyl)-1,2,3,4-tetrahydro-isoquinolin-8-yl]-phenyl}-acetic acid | 8.2 |
| 351 | (±)-{4-Ethoxy-3-[5-fluoro-2-(2-methyl-3-pyridin-2-yl-propionyl)-1,2,3,4-tetrahydro-isoquinolin-8-yl]-phenyl}-acetic acid | 3.1 |
| 352 | (±)-{3-Ethoxy-4-[5-fluoro-2-(2-methyl-3-pyridin-2-yl-propionyl)-1,2,3,4-tetrahydro-isoquinolin-8-yl]-phenyl}-acetic acid | 8.1 |
| 353 | (±)-{4-[2-(2-Chroman-4-yl-acetyl)-5-fluoro-1,2,3,4-tetrahydro-isoquinolin-8-yl]-3-isopropoxy-phenyl}-acetic acid | 1.2 |
| 354 | {4-[5-Fluoro-2-(3-methyl-3-phenyl-butyryl)-1,2,3,4-tetrahydro-isoquinolin-8-yl]-3-isopropoxy-phenyl}-acetic acid | 4.2 |
| 355 | {4-[5-Fluoro-2-((S)-3-phenyl-butyryl)-1,2,3,4-tetrahydro-isoquinolin-8-yl]-3-isopropoxy-phenyl}-acetic acid | 10.3 |
| 356 | {4-[5-Fluoro-2-((R)-3-phenyl-butyryl)-1,2,3,4-tetrahydro-isoquinolin-8-yl]-3-isopropoxy-phenyl}-acetic acid | 2.1 |
| 357 | {4-[5-Fluoro-2-((1R,2R)-2-phenyl-cyclopropanecarbonyl)-1,2,3,4-tetrahydro-isoquinolin-8-yl]-3-isopropoxy-phenyl}-acetic acid | 1.6 |
| 358 | (4-{5-Fluoro-2-[3-(4-fluoro-phenyl)-3-methyl-butyryl]-1,2,3,4-tetrahydro-isoquinolin-8-yl}-3-methoxy-phenyl)-acetic acid | 1.1 |

-continued

| Example | Name | IC$_{50}$ [nM] |
|---|---|---|
| 359 | (±)-{4-[2-(2-Chroman-4-yl-acetyl)-5-fluoro-1,2,3,4-tetrahydro-isoquinolin-8-yl]-3-methoxy-phenyl}-acetic acid | 0.6 |
| 360 | (±)-{4-[5-Fluoro-2-(2-indan-1-yl-acetyl)-1,2,3,4-tetrahydro-isoquinolin-8-yl]-3-methoxy-phenyl}-acetic acid | 6.1 |
| 361 | (±)-{3-[5-Fluoro-2-(trans-2-pyridin-2-yl-cyclopropanecarbonyl)-1,2,3,4-tetrahydro-isoquinolin-8-yl]-4-methoxy-phenyl}-acetic acid | 2.2 |
| 362 | (±)-{3-[2-(2-1,3-Dihydro-isobenzofuran-1-yl-acetyl)-5-fluoro-1,2,3,4-tetrahydro-isoquinolin-8-yl]-4-methoxy-phenyl}-acetic acid | 22.9 |
| 363 | (3-{5-Fluoro-2-[3-(4-fluoro-phenyl)-3-methyl-butyryl]-1,2,3,4-tetrahydro-isoquinolin-8-yl}-4-methoxy-phenyl)-acetic acid | 2.4 |
| 364 | 8-(5-Carboxymethyl-2-ethoxy-phenyl)-5-fluoro-3,4-dihydro-1H-isoquinoline-2-carboxylic acid (R)-1-phenyl-ethyl ester | 6.0 |
| 365 | 8-(5-Carboxymethyl-2-ethoxy-phenyl)-5-fluoro-3,4-dihydro-1H-isoquinoline-2-carboxylic acid pyrazin-2-ylmethyl ester | 3.9 |
| 366 | 8-(5-Carboxymethyl-2-ethoxy-phenyl)-5-fluoro-3,4-dihydro-1H-isoquinoline-2-carboxylic acid 3-fluoro-5-methyl-pyridin-2-ylmethyl ester | 4.2 |
| 367 | 8-(5-Carboxymethyl-2-ethoxy-phenyl)-5-fluoro-3,4-dihydro-1H-isoquinoline-2-carboxylic acid 2-methyl-2H-pyrazol-3-ylmethyl ester | 8.8 |
| 368 | 8-(5-Carboxymethyl-2-ethoxy-phenyl)-5-fluoro-3,4-dihydro-1H-isoquinoline-2-carboxylic acid (S)-1-phenyl-ethyl ester | 5.5 |
| 369 | 8-(5-Carboxymethyl-2-ethoxy-phenyl)-5-fluoro-3,4-dihydro-1H-isoquinoline-2-carboxylic acid cyclopentylmethyl ester | 8.7 |
| 370 | 8-(5-Carboxymethyl-2-ethoxy-phenyl)-5-fluoro-3,4-dihydro-1H-isoquinoline-2-carboxylic acid 3-methyl-butyl ester | 7.0 |
| 371 | 8-(5-Carboxymethyl-2-ethoxy-phenyl)-5-fluoro-3,4-dihydro-1H-isoquinoline-2-carboxylic acid 6-methyl-pyridin-2-ylmethyl ester | 0.6 |
| 372 | 8-(5-Carboxymethyl-2-ethoxy-phenyl)-5-fluoro-3,4-dihydro-1H-isoquinoline-2-carboxylic acid cyclopropylmethyl ester | 5.5 |
| 373 | 8-(5-Carboxymethyl-2-ethoxy-phenyl)-5-fluoro-3,4-dihydro-1H-isoquinoline-2-carboxylic acid phenethyl ester | 1.7 |
| 374 | 8-(5-Carboxymethyl-2-ethoxy-phenyl)-5-fluoro-3,4-dihydro-1H-isoquinoline-2-carboxylic acid (R)-2-phenyl-propyl ester | 4.2 |
| 375 | 8-(5-Carboxymethyl-2-ethoxy-phenyl)-5-fluoro-3,4-dihydro-1H-isoquinoline-2-carboxylic acid 3-methyl-but-2-enyl ester | 8.7 |
| 376 | 8-(5-Carboxymethyl-2-ethoxy-phenyl)-5-fluoro-3,4-dihydro-1H-isoquinoline-2-carboxylic acid butyl ester | 6.3 |
| 377 | 8-(5-Carboxymethyl-2-ethoxy-phenyl)-5-fluoro-3,4-dihydro-1H-isoquinoline-2-carboxylic acid isobutyl ester | 3.4 |
| 378 | 8-(5-Carboxymethyl-2-ethoxy-phenyl)-5-fluoro-3,4-dihydro-1H-isoquinoline-2-carboxylic acid 2-methoxy-ethyl ester | 5.9 |
| 379 | 8-(5-Carboxymethyl-2-ethoxy-phenyl)-5-fluoro-3,4-dihydro-1H-isoquinoline-2-carboxylic acid 3-methyl-but-3-enyl ester | 2.5 |
| 380 | (±)-8-(5-Carboxymethyl-2-ethoxy-phenyl)-5-fluoro-3,4-dihydro-1H-isoquinoline-2-carboxylic acid 2-methyl-butyl ester | 4.2 |
| 381 | 8-(5-Carboxymethyl-2-ethoxy-phenyl)-5-fluoro-3,4-dihydro-1H-isoquinoline-2-carboxylic acid but-3-ynyl ester | 28.8 |
| 382 | 8-(5-Carboxymethyl-2-ethoxy-phenyl)-5-fluoro-3,4-dihydro-1H-isoquinoline-2-carboxylic acid 3-hydroxy-3-methyl-butyl ester | 14 |
| 383 | 8-(5-Carboxymethyl-2-ethoxy-phenyl)-5-fluoro-3,4-dihydro-1H-isoquinoline-2-carboxylic acid 3-methoxy-3-methyl-butyl ester | 19 |
| 384 | (±)-8-(5-Carboxymethyl-2-ethoxy-phenyl)-5-fluoro-3,4-dihydro-1H-isoquinoline-2-carboxylic acid tetrahydro-furan-2-ylmethyl ester | 14.8 |
| 385 | 8-(4-Carboxymethyl-2-ethoxy-phenyl)-5-fluoro-3,4-dihydro-1H-isoquinoline-2-carboxylic acid (R)-1-phenyl-ethyl ester | 35.8 |
| 386 | 8-(4-Carboxymethyl-2-ethoxy-phenyl)-5-fluoro-3,4-dihydro-1H-isoquinoline-2-carboxylic acid pyrazin-2-ylmethyl ester | 3.4 |
| 387 | 8-(4-Carboxymethyl-2-ethoxy-phenyl)-5-fluoro-3,4-dihydro-1H-isoquinoline-2-carboxylic acid 3-fluoro-5-methyl-pyridin-2-ylmethyl ester | 8.0 |
| 388 | 8-(4-Carboxymethyl-2-ethoxy-phenyl)-5-fluoro-3,4-dihydro-1H-isoquinoline-2-carboxylic acid 2-methyl-2H-pyrazol-3-ylmethyl ester | 3.8 |
| 389 | 8-(4-Carboxymethyl-2-ethoxy-phenyl)-5-fluoro-3,4-dihydro-1H-isoquinoline-2-carboxylic acid (S)-1-phenyl-ethyl ester | 16.7 |
| 390 | 8-(4-Carboxymethyl-2-ethoxy-phenyl)-5-fluoro-3,4-dihydro-1H-isoquinoline-2-carboxylic acid 6-methyl-pyridin-2-ylmethyl ester | 0.8 |
| 391 | 8-(4-Carboxymethyl-2-ethoxy-phenyl)-5-fluoro-3,4-dihydro-1H-isoquinoline-2-carboxylic acid cyclopropylmethyl ester | 1.6 |
| 392 | 8-(4-Carboxymethyl-2-ethoxy-phenyl)-5-fluoro-3,4-dihydro-1H-isoquinoline-2-carboxylic acid cyclopentylmethyl ester | 5.9 |

| Example | Name | IC$_{50}$ [nM] |
|---|---|---|
| 393 | 8-(4-Carboxymethyl-2-ethoxy-phenyl)-5-fluoro-3,4-dihydro-1H-isoquinoline-2-carboxylic acid 3-methyl-butyl ester | 49.4 |
| 394 | 8-(5-Carboxymethyl-2-ethoxy-phenyl)-5-fluoro-3,4-dihydro-1H-isoquinoline-2-carboxylic acid pyridin-2-ylmethyl ester | 1.2 |
| 395 | 8-(4-Carboxymethyl-2-ethoxy-phenyl)-5-fluoro-3,4-dihydro-1H-isoquinoline-2-carboxylic acid pyridin-2-ylmethyl ester | 3.7 |
| 396 | 8-(5-Carboxymethyl-2-ethoxy-phenyl)-5-fluoro-3,4-dihydro-1H-isoquinoline-2-carboxylic acid cyclohexylmethyl ester | 2.6 |
| 397 | 8-(4-Carboxymethyl-2-ethoxy-phenyl)-5-fluoro-3,4-dihydro-1H-isoquinoline-2-carboxylic acid cyclohexylmethyl ester | 6.8 |
| 398 | 8-(5-Carboxymethyl-2-ethoxy-phenyl)-5-fluoro-3,4-dihydro-1H-isoquinoline-2-carboxylic acid 4-fluoro-benzyl ester | 3.4 |
| 399 | 8-(5-Carboxymethyl-2-ethoxy-phenyl)-5-fluoro-3,4-dihydro-1H-isoquinoline-2-carboxylic acid 3-fluoro-benzyl ester | 4.7 |
| 400 | 8-(5-Carboxymethyl-2-ethoxy-phenyl)-5-fluoro-3,4-dihydro-1H-isoquinoline-2-carboxylic acid 2-fluoro-benzyl ester | 12.8 |
| 401 | 8-(5-Carboxymethyl-2-ethoxy-phenyl)-5-fluoro-3,4-dihydro-1H-isoquinoline-2-carboxylic acid 2,5-difluoro-benzyl ester | 4.5 |
| 402 | 8-(5-Carboxymethyl-2-ethoxy-phenyl)-5-fluoro-3,4-dihydro-1H-isoquinoline-2-carboxylic acid 5-chloro-2-fluoro-benzyl ester | 4.3 |
| 403 | 8-(5-Carboxymethyl-2-ethoxy-phenyl)-5-fluoro-3,4-dihydro-1H-isoquinoline-2-carboxylic acid 2,4-difluoro-benzyl ester | 1.7 |
| 404 | 8-(4-Carboxymethyl-2-ethoxy-phenyl)-5-fluoro-3,4-dihydro-1H-isoquinoline-2-carboxylic acid 4-fluoro-benzyl ester | 2.3 |
| 405 | 8-(4-Carboxymethyl-2-ethoxy-phenyl)-5-fluoro-3,4-dihydro-1H-isoquinoline-2-carboxylic acid 3-fluoro-benzyl ester | 2.7 |
| 406 | 8-(4-Carboxymethyl-2-ethoxy-phenyl)-5-fluoro-3,4-dihydro-1H-isoquinoline-2-carboxylic acid 2-fluoro-benzyl ester | 7.7 |
| 407 | 8-(4-Carboxymethyl-2-ethoxy-phenyl)-5-fluoro-3,4-dihydro-1H-isoquinoline-2-carboxylic acid 2,5-difluoro-benzyl ester | 2.1 |
| 408 | 8-(4-Carboxymethyl-2-ethoxy-phenyl)-5-fluoro-3,4-dihydro-1H-isoquinoline-2-carboxylic acid 5-chloro-2-fluoro-benzyl ester | 2.0 |
| 409 | 8-(4-Carboxymethyl-2-ethoxy-phenyl)-5-fluoro-3,4-dihydro-1H-isoquinoline-2-carboxylic acid 2,4-difluoro-benzyl ester | 3.9 |
| 410 | 8-(4-Carboxymethyl-2-ethoxy-phenyl)-5-fluoro-3,4-dihydro-1H-isoquinoline-2-carboxylic acid benzyl ester | 26.0 |
| 411 | 8-[4-Carboxymethyl-2-(2,2,2-trifluoro-ethoxy)-phenyl]-5-fluoro-3,4-dihydro-1H-isoquinoline-2-carboxylic acid benzyl ester | 1.0 |
| 412 | 8-(5-Carboxymethyl-2-difluoromethoxy-phenyl)-5-fluoro-3,4-dihydro-1H-isoquinoline-2-carboxylic acid benzyl ester | 1.8 |
| 413 | 8-[5-Carboxymethyl-2-(2,2-difluoro-ethoxy)-phenyl]-5-fluoro-3,4-dihydro-1H-isoquinoline-2-carboxylic acid benzyl ester | 0.8 |
| 414 | (±)-8-[5-(1-Carboxy-ethoxy)-2-methoxy-phenyl]-5-fluoro-3,4-dihydro-1H-isoquinoline-2-carboxylic acid benzyl ester | 430 |
| 415 | (±)-8-[5-(1-Carboxy-propoxy)-2-methoxy-phenyl]-5-fluoro-3,4-dihydro-1H-isoquinoline-2-carboxylic acid benzyl ester | 337 |
| 416 | 8-(2-Carboxymethyl-5-chloro-phenyl)-5-fluoro-3,4-dihydro-1H-isoquinoline-2-carboxylic acid benzyl ester | 575 |
| 417 | 8-(2-Carboxymethoxy-6-methoxy-phenyl)-5-fluoro-3,4-dihydro-1H-isoquinoline-2-carboxylic acid benzyl ester | 23.5 |
| 418 | 8-(2-Carboxymethyl-6-methoxy-phenyl)-5-fluoro-3,4-dihydro-1H-isoquinoline-2-carboxylic acid benzyl ester | 352 |
| 419 | 8-(2-tert-Butoxy-5-carboxymethyl-phenyl)-5-fluoro-3,4-dihydro-1H-isoquinoline-2-carboxylic acid benzyl ester | 2.8 |
| 420 | 8-(5-Carboxymethyl-2-dimethylamino-phenyl)-5-fluoro-3,4-dihydro-1H-isoquinoline-2-carboxylic acid benzyl ester | 2.4 |
| 421 | 8-[5-Carboxymethyl-2-(2,2,2-trifluoro-ethoxy)-phenyl]-5-fluoro-3,4-dihydro-1H-isoquinoline-2-carboxylic acid benzyl ester | 3.8 |
| 422 | 8-[5-Carboxymethyl-2-(2-fluoro-ethoxy)-phenyl]-5-fluoro-3,4-dihydro-1H-isoquinoline-2-carboxylic acid benzyl ester | 8.5 |
| 423 | 8-(3-Carboxymethyl-2-methoxy-phenyl)-5-fluoro-3,4-dihydro-1H-isoquinoline-2-carboxylic acid benzyl ester | 180 |
| 424 | 8-(4-Carboxymethoxy-2-methoxy-phenyl)-5-fluoro-3,4-dihydro-1H-isoquinoline-2-carboxylic acid benzyl ester | 444 |
| 425 | (±)-8-[4-(1-Carboxy-ethyl)-2-ethoxy-phenyl]-5-fluoro-3,4-dihydro-1H-isoquinoline-2-carboxylic acid benzyl ester | 11.3 |
| 426 | [3-[5-Fluoro-2-((1R,2R)-2-phenyl-cyclopropanecarbonyl)-1,2,3,4-tetrahydro-isoquinolin-8-yl]-4-(2,2,2-trifluoro-ethoxy)-phenyl]-acetic acid | 1.9 |
| 427 | {4-(2-Fluoro-ethoxy)-3-[5-fluoro-2-((1R,2R)-2-phenyl-cyclopropanecarbonyl)-1,2,3,4-tetrahydro-isoquinolin-8-yl]-phenyl}-acetic acid | 3.1 |
| 428 | {4-tert-Butoxy-3-[5-fluoro-2-((1R,2R)-2-phenyl-cyclopropanecarbonyl)-1,2,3,4-tetrahydro-isoquinolin-8-yl]-phenyl}-acetic acid | 3.7 |

| Example | Name | IC$_{50}$ [nM] |
|---|---|---|
| 429 | 1-{3-[5-Fluoro-2-((1R,2R)-2-phenyl-cyclopropanecarbonyl)-1,2,3,4-tetrahydro-isoquinolin-8-yl]-4-methoxy-phenyl}-cyclopropanecarboxylic acid | 50.7 |
| 430 | 8-(5-Carboxymethyl-2-cyclopropoxy-phenyl)-5-fluoro-3,4-dihydro-1H-isoquinoline-2-carboxylic acid benzyl ester | 14.9 |
| 431 | 8-(5-Carboxymethyl-2-isopropoxy-phenyl)-5-cyano-3,4-dihydro-1H-isoquinoline-2-carboxylic acid benzyl ester | 1.4 |
| 432 | {4-Ethoxy-3-[5-fluoro-2-(2-fluoro-benzylcarbamoyl)-1,2,3,4-tetrahydro-isoquinolin-8-yl]-phenyl}-acetic acid | 5.3 |
| 433 | {4-Ethoxy-3-[5-fluoro-2-(3-fluoro-benzylcarbamoyl)-1,2,3,4-tetrahydro-isoquinolin-8-yl]-phenyl}-acetic acid | 59.3 |
| 434 | {4-Ethoxy-3-[5-fluoro-2-(4-fluoro-benzylcarbamoyl)-1,2,3,4-tetrahydro-isoquinolin-8-yl]-phenyl}-acetic acid | 0.7 |
| 435 | [4-Ethoxy-3-(5-fluoro-2-phenethylcarbamoyl-1,2,3,4-tetrahydro-isoquinolin-8-yl)-phenyl]-acetic acid | 2.6 |
| 436 | {3-[2-(2-Chloro-benzylcarbamoyl)-5-fluoro-1,2,3,4-tetrahydro-isoquinolin-8-yl]-4-ethoxy-phenyl}-acetic acid | 5.4 |
| 437 | {4-Ethoxy-3-[5-fluoro-2-(2-methoxy-benzylcarbamoyl)-1,2,3,4-tetrahydro-isoquinolin-8-yl]-phenyl}-acetic acid | 10.9 |
| 438 | [3-(2-Benzylcarbamoyl-5-fluoro-1,2,3,4-tetrahydro-isoquinolin-8-yl)-4-ethoxy-phenyl]-acetic acid | 3.7 |
| 439 | [4-Ethoxy-3-(5-fluoro-2-propylcarbamoyl-1,2,3,4-tetrahydro-isoquinolin-8-yl)-phenyl]-acetic acid | 126 |
| 440 | {3-Ethoxy-4-[5-fluoro-2-(2-fluoro-benzylcarbamoyl)-1,2,3,4-tetrahydro-isoquinolin-8-yl]-phenyl}-acetic acid | 3.8 |
| 441 | {3-Ethoxy-4-[5-fluoro-2-(3-fluoro-benzylcarbamoyl)-1,2,3,4-tetrahydro-isoquinolin-8-yl]-phenyl}-acetic acid | 17.5 |
| 442 | {3-Ethoxy-4-[5-fluoro-2-(4-fluoro-benzylcarbamoyl)-1,2,3,4-tetrahydro-isoquinolin-8-yl]-phenyl}-acetic acid | 5.3 |
| 443 | [3-Ethoxy-4-(5-fluoro-2-phenethylcarbamoyl-1,2,3,4-tetrahydro-isoquinolin-8-yl)-phenyl]-acetic acid | 18.1 |
| 444 | {4-[2-(2-Chloro-benzylcarbamoyl)-5-fluoro-1,2,3,4-tetrahydro-isoquinolin-8-yl]-3-ethoxy-phenyl}-acetic acid | 2.0 |
| 445 | {3-Ethoxy-4-[5-fluoro-2-(2-methoxy-benzylcarbamoyl)-1,2,3,4-tetrahydro-isoquinolin-8-yl]-phenyl}-acetic acid | 2.5 |
| 446 | [4-(2-Benzylcarbamoyl-5-fluoro-1,2,3,4-tetrahydro-isoquinolin-8-yl)-3-ethoxy-phenyl]-acetic acid | 4.7 |
| 447 | [3-Ethoxy-4-(5-fluoro-2-propylcarbamoyl-1,2,3,4-tetrahydro-isoquinolin-8-yl)-phenyl]-acetic acid | 78.2 |
| 448 | (3-Ethoxy-4-{5-fluoro-2-[(pyridin-2-ylmethyl)-carbamoyl]-1,2,3,4-tetrahydro-isoquinolin-8-yl}-phenyl)-acetic acid | 9.2 |
| 449 | (4-Ethoxy-3-{5-fluoro-2-[(pyridin-2-ylmethyl)-carbamoyl]-1,2,3,4-tetrahydro-isoquinolin-8-yl}-phenyl)-acetic acid | 14.2 |

Eosinophil Shape Change Assay with Human Plasma

After obtaining informed consent, blood samples were drawn by venipuncture according to the protocol approved by the ethics committee of Basel, Switzerland. Polymorphonuclear leukocytes (containing eosinophils, basophils and neutrophils) were isolated using the Polymorphprep™ method (Axis-Shield). In brief, anticoagulated whole blood was layered onto a Polymorphprep gradient (density 1.113 g/ml) and centrifuged at 500 g for 30 min. The polymorphonuclear cell fraction was harvested and depleted for erythrocytes by hypotonic saline lysis.

The polymorphonuclear cells were resuspended in assay buffer (1×PBS with $Ca^{2+}/Mg^{2+}$ supplemented with 0.1% BSA, 10 mM HEPES, and 10 mM Glucose, pH 7.4) at $5 \times 10^6$ cells/ml and stained with anti-CD49d-APC ((APC=Allophycocyanin) for 1 hour at RT. Test compounds, at various concentrations, were preincubated 10 min in human plasma (anticoagulated with a thrombin inhibitor). Then, human plasma was added to the polymorphonuclear cells to 50% of final assay volume with polymorphonuclear cells at $4 \times 10^6$ cells/ml. After incubation for 10 minutes at 37° C., the polymorphonuclear cells were activated for 5 min at 37° C. by addition of $PGD_2$ at 100 nM final concentration. Activation was stopped by addition of 0.5 ml paraformaldehyde (1%).

Immediately after fixation with paraformaldehyde, the samples were analyzed by FACSCanto flow cytometer (BD Biosciences) and target cells were identified by their forward-scatter (FSC) and side-scatter (SSC) characteristics. Eosinophils were identified by the anti-CD49d-APC signal and their characteristic side-scatter (SSC) profile. Shape change responses, indicative of eosinophil activation, were quantified as the percent of cells with an increased forward-scatter. Antagonistic activities of selected compounds are displayed in the following Table:

| Example | Name | IC$_{50}$ [nM] |
|---|---|---|
| 1 | (±)-(3-{5-Fluoro-2-[trans-2-(4-fluoro-phenyl)-cyclopropanecarbonyl]-1,2,3,4-tetrahydro-isoquinolin-8-yl}-4-methoxy-phenyl)-acetic acid | 8 |

-continued

| Example | Name | IC$_{50}$ [nM] |
|---|---|---|
| 5 | (±)-(3-{5-Fluoro-2-[trans-2-(2-fluoro-phenyl)-cyclopropanecarbonyl]-1,2,3,4-tetrahydro-isoquinolin-8-yl}-4-methoxy-phenyl)-acetic acid | 12 |
| 21 | 8-(5-Carboxymethyl-2-trifluoromethoxy-phenyl)-5-fluoro-3,4-dihydro-1H-isoquinoline-2-carboxylic acid benzyl ester | 64 |
| 22 | 8-(5-Carboxymethyl-2-isopropoxy-phenyl)-5-fluoro-3,4-dihydro-1H-isoquinoline-2-carboxylic acid benzyl ester | 38 |
| 28 | {4-Chloro-3-[5-fluoro-2-((1R,2R)-2-phenyl-cyclopropanecarbonyl)-1,2,3,4-tetrahydro-isoquinolin-8-yl]-phenyl}-acetic acid | 42 |
| 29 | {3-[5-Fluoro-2-((1R,2R)-2-phenyl-cyclopropanecarbonyl)-1,2,3,4-tetrahydro-isoquinolin-8-yl]-4-methanesulfonyl-phenyl}-acetic acid | 20 |
| 31 | 8-(5-Carboxymethyl-2-methoxy-phenyl)-5,6-difluoro-3,4-dihydro-1H-isoquinoline-2-carboxylic acid benzyl ester | 436 |
| 32 | 8-(5-Carboxymethyl-2-methoxy-phenyl)-6-fluoro-3,4-dihydro-1H-isoquinoline-2-carboxylic acid benzyl ester | 356 |
| 34 | {3-[6-Fluoro-2-((1R,2R)-2-phenyl-cyclopropanecarbonyl)-1,2,3,4-tetrahydro-isoquinolin-8-yl]-4-methoxy-phenyl}-acetic acid | 25 |
| 36 | (±)-{3-[9-Fluoro-3-(trans-2-phenyl-cyclopropanecarbonyl)-2,3,4,5-tetrahydro-1H-benzo[d]azepin-6-yl]-4-methoxy-phenyl}-acetic acid | >1000 |
| 37 | (±)-{3-[7-Fluoro-2-(trans-2-phenyl-cyclopropanecarbonyl)-2,3-dihydro-1H-isoindol-4-yl]-4-methoxy-phenyl}-acetic acid | 289 |
| 39 | 8-(5-Carboxymethyl-2-methoxy-phenyl)-5,7-difluoro-3,4-dihydro-1H-isoquinoline-2-carboxylic acid benzyl ester | 404 |
| 42 | (3-{5-Fluoro-2-[3-(4-fluoro-phenoxy)-propionyl]-1,2,3,4-tetrahydro-isoquinolin-8-yl}-4-methoxy-phenyl)-acetic acid | 118 |
| 45 | (3-{5-Fluoro-2-[4-(2-fluoro-phenyl)-butyryl]-1,2,3,4-tetrahydro-isoquinolin-8-yl}-4-methoxy-phenyl)-acetic acid | 64 |
| 48 | (±)-(3-{5-Fluoro-2-[trans-2-(3-fluoro-phenyl)-cyclopropanecarbonyl]-1,2,3,4-tetrahydro-isoquinolin-8-yl}-4-methoxy-phenyl)-acetic acid | 42 |
| 54 | {3-[5-Fluoro-2-(3-phenyl-propionyl)-1,2,3,4-tetrahydro-isoquinolin-8-yl]-4-methoxy-phenyl}-acetic acid | 184 |
| 58 | (3-{2-[2-(2-Chloro-benzyloxy)-acetyl]-5-fluoro-1,2,3,4-tetrahydro-isoquinolin-8-yl}-4-methoxy-phenyl)-acetic acid | 122 |
| 59 | {3-[2-(3-2,3-Dihydro-indol-1-yl-propionyl)-5-fluoro-1,2,3,4-tetrahydro-isoquinolin-8-yl]-4-methoxy-phenyl}-acetic acid | 182 |
| 60 | (±)-{3-[5-Fluoro-2-(trans-2-phenyl-cyclopropanecarbonyl)-1,2,3,4-tetrahydro-isoquinolin-8-yl]-4-methoxy-phenyl}-acetic acid | 13 |
| 61 | (3-{5-Fluoro-2-[3-(2-methyl-1H-indol-3-yl)-propionyl]-1,2,3,4-tetrahydro-isoquinolin-8-yl}-4-methoxy-phenyl)-acetic acid | 52 |
| 62 | (3-{5-Fluoro-2-[3-(1-methyl-1H-indol-3-yl)-propionyl]-1,2,3,4-tetrahydro-isoquinolin-8-yl}-4-methoxy-phenyl)-acetic acid | 106 |
| 65 | (3-{5-Fluoro-2-[(1R,2R)-2-(3-fluoro-phenyl)-cyclopropanecarbonyl]-1,2,3,4-tetrahydro-isoquinolin-8-yl}-4-methoxy-phenyl)-acetic acid | 10 |
| 69 | (3-{5-Chloro-2-[(1R,2R)-2-(3-fluoro-phenyl)-cyclopropanecarbonyl]-1,2,3,4-tetrahydro-isoquinolin-8-yl}-4-methoxy-phenyl)-acetic acid | 78 |
| 71 | {3-[5-Chloro-2-((1R,2R)-2-phenyl-cyclopropanecarbonyl)-1,2,3,4-tetrahydro-isoquinolin-8-yl]-4-methoxy-phenyl}-acetic acid | 22 |
| 80 | {3-[5-Fluoro-2-((1R,2R)-2-phenyl-cyclopropanecarbonyl)-1,2,3,4-tetrahydro-isoquinolin-8-yl]-4-methoxy-phenyl}-acetic acid | 4.7 |
| 83 | (±)-{4-Methoxy-3-[2-(trans-2-phenyl-cyclopropanecarbonyl)-5-trifluoromethyl-1,2,3,4-tetrahydro-isoquinolin-8-yl]-phenyl}-acetic acid | >1000 |
| 84 | {3-[5,6-Difluoro-2-((1R,2R)-2-phenyl-cyclopropanecarbonyl)-1,2,3,4-tetrahydro-isoquinolin-8-yl]-4-methoxy-phenyl}-acetic acid | 5 |
| 106 | {3-[5-Fluoro-2-((R)-3-phenyl-butyryl)-1,2,3,4-tetrahydro-isoquinolin-8-yl]-4-methoxy-phenyl}-acetic acid | 37 |
| 108 | {3-[5-Fluoro-2-(3-methyl-3-phenyl-butyryl)-1,2,3,4-tetrahydro-isoquinolin-8-yl]-4-methoxy-phenyl}-acetic acid | 92 |
| 125 | (3-{5-Fluoro-2-[3-(3-methyl-indazol-1-yl)-propionyl]-1,2,3,4-tetrahydro-isoquinolin-8-yl}-4-methoxy-phenyl)-acetic acid | 113 |
| 132 | {3-[5-Fluoro-2-(4-fluoro-benzylcarbamoyl)-1,2,3,4-tetrahydro-isoquinolin-8-yl]-4-methoxy-phenyl}-acetic acid | >1000 |
| 138 | 8-(5-Carboxymethyl-2-methoxy-phenyl)-5-fluoro-3,4-dihydro-1H-isoquinoline-2-carboxylic acid 3-fluoro-benzyl ester | 908 |
| 139 | 8-(5-Carboxymethyl-2-methoxy-phenyl)-5-fluoro-3,4-dihydro-1H-isoquinoline-2-carboxylic acid 4-fluoro-benzyl ester | 97 |
| 146 | 8-(5-Carboxymethyl-2-methoxy-phenyl)-5-fluoro-3,4-dihydro-1H-isoquinoline-2-carboxylic acid 2-fluoro-benzyl ester | 266 |
| 147 | 8-(5-Carboxymethyl-2-methoxy-phenyl)-5-fluoro-3,4-dihydro-1H-isoquinoline-2-carboxylic acid 2,3-difluoro-benzyl ester | 622 |

-continued

| Example | Name | IC$_{50}$ [nM] |
|---|---|---|
| 154 | 8-(5-Carboxymethyl-2-methoxy-phenyl)-5-chloro-3,4-dihydro-1H-isoquinoline-2-carboxylic acid benzyl ester | 307 |
| 157 | 8-(5-Carboxymethyl-2-methoxy-phenyl)-5-fluoro-3,4-dihydro-1H-isoquinoline-2-carboxylic acid benzyl ester | 153 |
| 162 | 8-(5-Carboxymethoxy-2-trifluoromethoxy-phenyl)-5-fluoro-3,4-dihydro-1H-isoquinoline-2-carboxylic acid benzyl ester | 170 |
| 163 | 8-(5-Carboxymethoxy-2-isopropoxy-phenyl)-5-fluoro-3,4-dihydro-1H-isoquinoline-2-carboxylic acid benzyl ester | 141 |
| 166 | 8-(4-Carboxymethyl-2-methoxy-phenyl)-5-fluoro-3,4-dihydro-1H-isoquinoline-2-carboxylic acid benzyl ester | 117 |
| 168 | 8-(7-Carboxymethyl-2,3-dihydro-benzo[1,4]dioxin-5-yl)-5-fluoro-3,4-dihydro-1H-isoquinoline-2-carboxylic acid benzyl ester | 133 |
| 169 | 8-(5-Carboxymethyl-2-methoxy-phenyl)-5-cyano-3,4-dihydro-1H-isoquinoline-2-carboxylic acid benzyl ester | 146 |
| 177 | 8-(5-Carboxymethoxy-2-methoxy-phenyl)-5-fluoro-3,4-dihydro-1H-isoquinoline-2-carboxylic acid benzyl ester | 539 |
| 182 | {3-[5-Fluoro-2-((1R,2R)-2-phenyl-cyclopropanecarbonyl)-1,2,3,4-tetrahydro-isoquinolin-8-yl]-4-methoxy-phenoxy}-acetic acid | 34 |
| 183 | (4-{5-Fluoro-2-[3-(1-methyl-1H-indol-3-yl)-propionyl]-1,2,3,4-tetrahydro-isoquinolin-8-yl}-3-methoxy-phenyl)-acetic acid | 194 |
| 185 | (4-{5-Fluoro-2-[4-(2-fluoro-phenyl)-butyryl]-1,2,3,4-tetrahydro-isoquinolin-8-yl}-3-methoxy-phenyl)-acetic acid | 97 |
| 187 | {4-[5-Fluoro-2-(4-phenyl-butyryl)-1,2,3,4-tetrahydro-isoquinolin-8-yl]-3-methoxy-phenyl}-acetic acid | 91 |
| 188 | {4-[5-Fluoro-2-(3-methyl-3-phenyl-butyryl)-1,2,3,4-tetrahydro-isoquinolin-8-yl]-3-methoxy-phenyl}-acetic acid | 8 |
| 189 | {4-[5-Fluoro-2-((R)-3-phenyl-butyryl)-1,2,3,4-tetrahydro-isoquinolin-8-yl]-3-methoxy-phenyl}-acetic acid | 62 |
| 193 | (4-{2-[2-(2-Chloro-benzyloxy)-acetyl]-5-fluoro-1,2,3,4-tetrahydro-isoquinolin-8-yl}-3-methoxy-phenyl)-acetic acid | 94 |
| 194 | {4-[5-Fluoro-2-(3-o-tolyl-propionyl)-1,2,3,4-tetrahydro-isoquinolin-8-yl]-3-methoxy-phenyl}-acetic acid | 188 |
| 195 | 8-(5-Carboxymethyl-2-ethoxy-phenyl)-5-fluoro-3,4-dihydro-1H-isoquinoline-2-carboxylic acid benzyl ester | 21 |
| 196 | 8-(5-Carboxymethyl-2-cyclopropylmethoxy-phenyl)-5-fluoro-3,4-dihydro-1H-isoquinoline-2-carboxylic acid benzyl ester | 44 |
| 197 | 8-(5-Carboxymethyl-2-propoxy-phenyl)-5-fluoro-3,4-dihydro-1H-isoquinoline-2-carboxylic acid benzyl ester | 24 |
| 198 | 8-(5-Carboxymethyl-2-isobutoxy-phenyl)-5-fluoro-3,4-dihydro-1H-isoquinoline-2-carboxylic acid benzyl ester | 72 |
| 199 | 8-[5-Carboxymethyl-2-(2-methoxy-ethoxy)-phenyl]-5-fluoro-3,4-dihydro-1H-isoquinoline-2-carboxylic acid benzyl ester | 19 |
| 200 | {4-[2-(2-Chroman-4-yl-acetyl)-5-fluoro-1,2,3,4-tetrahydro-isoquinolin-8-yl]-3-methoxy-phenyl}-acetic acid (enantiomer 1) | 50 |
| 201 | {4-[2-(2-Chroman-4-yl-acetyl)-5-fluoro-1,2,3,4-tetrahydro-isoquinolin-8-yl]-3-methoxy-phenyl}-acetic acid (enantiomer 2) | 31 |
| 203 | {4-Ethoxy-3-[5-fluoro-2-(3-pyridin-2-yl-butyryl)-1,2,3,4-tetrahydro-isoquinolin-8-yl]-phenyl}-acetic acid (enantiomer 1) | 12 |
| 204 | {4-Ethoxy-3-[5-fluoro-2-(3-pyridin-2-yl-butyryl)-1,2,3,4-tetrahydro-isoquinolin-8-yl]-phenyl}-acetic acid (enantiomer 2) | 30 |
| 205 | {3-Ethoxy-4-[5-fluoro-2-(2-isochroman-1-yl-acetyl)-1,2,3,4-tetrahydro-isoquinolin-8-yl]-phenyl}-acetic acid (enantiomer 1) | 17 |
| 206 | {3-Ethoxy-4-[5-fluoro-2-(2-isochroman-1-yl-acetyl)-1,2,3,4-tetrahydro-isoquinolin-8-yl]-phenyl}-acetic acid (enantiomer 2) | 14 |
| 207 | {3-[2-(2-2,3-Dihydro-benzofuran-3-yl-acetyl)-5-fluoro-1,2,3,4-tetrahydro-isoquinolin-8-yl]-4-ethoxy-phenyl}-acetic acid (enantiomer 1) | 15 |
| 208 | {3-[2-(2-2,3-Dihydro-benzofuran-3-yl-acetyl)-5-fluoro-1,2,3,4-tetrahydro-isoquinolin-8-yl]-4-ethoxy-phenyl}-acetic acid (enantiomer 2) | 42 |
| 209 | {4-Ethoxy-3-[5-fluoro-2-(2-isochroman-4-yl-acetyl)-1,2,3,4-tetrahydro-isoquinolin-8-yl]-phenyl}-acetic acid (enantiomer 1) | 13 |
| 210 | {4-Ethoxy-3-[5-fluoro-2-(2-isochroman-4-yl-acetyl)-1,2,3,4-tetrahydro-isoquinolin-8-yl]-phenyl}-acetic acid (enantiomer 2) | 11 |
| 211 | (4-Ethoxy-3-{5-fluoro-2-[3-(4-fluoro-phenyl)-butyryl]-1,2,3,4-tetrahydro-isoquinolin-8-yl}-phenyl)-acetic acid (enantiomer 1) | 7 |
| 214 | {4-Ethoxy-3-[5-fluoro-2-(2-methyl-3-phenyl-propionyl)-1,2,3,4-tetrahydro-isoquinolin-8-yl]-phenyl}-acetic acid (enantiomer 2) | 11 |
| 217 | 8-(4-Carboxymethyl-2-isopropoxy-phenyl)-5-fluoro-3,4-dihydro-1H-isoquinoline-2-carboxylic acid benzyl ester | 46 |
| 221 | {4-Ethoxy-3-[5-fluoro-2-((R)-3-phenyl-butyryl)-1,2,3,4-tetrahydro-isoquinolin-8-yl]-phenyl}-acetic acid | 34 |
| 222 | (4-Ethoxy-3-{5-fluoro-2-[2-(1-phenyl-cyclopropyl)-acetyl]-1,2,3,4-tetrahydro-isoquinolin-8-yl}-phenyl)-acetic acid | 21 |
| 223 | (4-Ethoxy-3-{5-fluoro-2-[3-(4-fluoro-phenyl)-3-methyl-butyryl]-1,2,3,4-tetrahydro-isoquinolin-8-yl}-phenyl)-acetic acid | 19 |

-continued

| Example | Name | IC$_{50}$ [nM] |
|---|---|---|
| 224 | (±)-{4-Ethoxy-3-[5-fluoro-2-(2-isochroman-1-yl-acetyl)-1,2,3,4-tetrahydro-isoquinolin-8-yl]-phenyl}-acetic acid | 10 |
| 225 | {4-Ethoxy-3-[5-fluoro-2-(3-methyl-3-phenyl-butyryl)-1,2,3,4-tetrahydro-isoquinolin-8-yl]-phenyl}-acetic acid | 37 |
| 226 | (±)-{3-[2-(2-Chroman-4-yl-acetyl)-5-fluoro-1,2,3,4-tetrahydro-isoquinolin-8-yl]-4-ethoxy-phenyl}-acetic acid | 43 |
| 227 | (±)-{3-[2-(2-2,3-Dihydro-benzofuran-3-yl-acetyl)-5-fluoro-1,2,3,4-tetrahydro-isoquinolin-8-yl]-4-ethoxy-phenyl}-acetic acid | 38 |
| 228 | (±)-{4-Ethoxy-3-[5-fluoro-2-(2-isochroman-4-yl-acetyl)-1,2,3,4-tetrahydro-isoquinolin-8-yl]-phenyl}-acetic acid | 8 |
| 229 | (±)-{3-Ethoxy-4-[5-fluoro-2-(2-isochroman-1-yl-acetyl)-1,2,3,4-tetrahydro-isoquinolin-8-yl]-phenyl}-acetic acid | 15 |
| 230 | (3-Ethoxy-4-{5-fluoro-2-[2-(1-phenyl-cyclopropyl)-acetyl]-1,2,3,4-tetrahydro-isoquinolin-8-yl}-phenyl)-acetic acid | 19 |
| 234 | {3-Ethoxy-4-[5-fluoro-2-((R)-3-phenyl-butyryl)-1,2,3,4-tetrahydro-isoquinolin-8-yl]-phenyl}-acetic acid | 47 |
| 235 | (±)-{4-[2-(2-2,3-Dihydro-benzofuran-3-yl-acetyl)-5-fluoro-1,2,3,4-tetrahydro-isoquinolin-8-yl]-3-ethoxy-phenyl}-acetic acid | 20 |
| 236 | (±)-{4-[2-(2-Chroman-4-yl-acetyl)-5-fluoro-1,2,3,4-tetrahydro-isoquinolin-8-yl]-3-ethoxy-phenyl}-acetic acid | 12 |
| 237 | (3-Ethoxy-4-{5-fluoro-2-[3-(4-fluoro-phenyl)-3-methyl-butyryl]-1,2,3,4-tetrahydro-isoquinolin-8-yl}-phenyl)-acetic acid | 9 |
| 238 | {3-Ethoxy-4-[5-fluoro-2-(3-methyl-3-phenyl-butyryl)-1,2,3,4-tetrahydro-isoquinolin-8-yl]-phenyl}-acetic acid | 15 |
| 240 | (±)-(3-{2-[2-(2,2-Dimethyl-chroman-4-yl)-acetyl]-5-fluoro-1,2,3,4-tetrahydro-isoquinolin-8-yl}-4-methoxy-phenyl)-acetic acid | 31 |
| 243 | (±)-(3-{5-Fluoro-2-[2-(7-fluoro-chroman-4-yl)-acetyl]-1,2,3,4-tetrahydro-isoquinolin-8-yl}-4-methoxy-phenyl)-acetic acid | 92 |
| 252 | (3-{5-Fluoro-2-[3-(3-fluoro-phenyl)-3-methyl-butyryl]-1,2,3,4-tetrahydro-isoquinolin-8-yl}-4-methoxy-phenyl)-acetic acid | 258 |
| 253 | (±)-{3-[2-(2-{[(4-Chloro-phenyl)-phenyl-methyl]-methyl-amino}-acetyl)-5-fluoro-1,2,3,4-tetrahydro-isoquinolin-8-yl]-4-methoxy-phenyl}-acetic acid | 399 |
| 257 | (±)-{3-[5-Fluoro-2-(2-isochroman-1-yl-acetyl)-1,2,3,4-tetrahydro-isoquinolin-8-yl]-4-methoxy-phenyl}-acetic acid | 35 |
| 258 | (3-{5-Fluoro-2-[2-(1-phenyl-cyclopropyl)-acetyl]-1,2,3,4-tetrahydro-isoquinolin-8-yl}-4-methoxy-phenyl)-acetic acid | 101 |
| 260 | (±)-{3-[5-Fluoro-2-(2-1,2,3,4-tetrahydro-naphthalen-2-yl-acetyl)-1,2,3,4-tetrahydro-isoquinolin-8-yl]-4-methoxy-phenyl}-acetic acid | 56 |
| 261 | (±)-{3-[5-Fluoro-2-(2-indan-1-yl-acetyl)-1,2,3,4-tetrahydro-isoquinolin-8-yl]-4-methoxy-phenyl}-acetic acid | 86 |
| 262 | (±)-{3-[2-(2-Chroman-4-yl-acetyl)-5-fluoro-1,2,3,4-tetrahydro-isoquinolin-8-yl]-4-methoxy-phenyl}-acetic acid | 66 |
| 263 | (±)-{3-[5-Fluoro-2-(2-1,2,3,4-tetrahydro-naphthalen-1-yl-acetyl)-1,2,3,4-tetrahydro-isoquinolin-8-yl]-4-methoxy-phenyl}-acetic acid | 64 |
| 265 | (±)-{3-[5-Fluoro-2-(3-pyridin-2-yl-butyryl)-1,2,3,4-tetrahydro-isoquinolin-8-yl]-4-methoxy-phenyl}-acetic acid | 98 |
| 271 | (±)-{3-[5-Fluoro-2-(2-isochroman-4-yl-acetyl)-1,2,3,4-tetrahydro-isoquinolin-8-yl]-4-methoxy-phenyl}-acetic acid | 91 |
| 275 | [4-Ethoxy-3-(5-fluoro-2-{2-[1-(3-fluoro-phenyl)-cyclopropyl]-acetyl}-1,2,3,4-tetrahydro-isoquinolin-8-yl)-phenyl]-acetic acid | 76 |
| 277 | [4-Ethoxy-3-(5-fluoro-2-{2-[1-(4-fluoro-phenyl)-cyclopropyl]-acetyl}-1,2,3,4-tetrahydro-isoquinolin-8-yl)-phenyl]-acetic acid | 21 |
| 278 | (±)-(4-Ethoxy-3-{5-fluoro-2-[3-(4-fluoro-phenyl)-butyryl]-1,2,3,4-tetrahydro-isoquinolin-8-yl}-phenyl)-acetic acid | 19 |
| 279 | (±)-(4-Ethoxy-3-{5-fluoro-2-[3-(3-fluoro-phenyl)-butyryl]-1,2,3,4-tetrahydro-isoquinolin-8-yl}-phenyl)-acetic acid | 45 |
| 310 | (4-Ethoxy-3-{5-fluoro-2-[3-(4-fluoro-phenyl)-propionyl]-1,2,3,4-tetrahydro-isoquinolin-8-yl}-phenyl)-acetic acid | 7 |
| 321 | (3-Ethoxy-4-{5-fluoro-2-[3-(6-methyl-pyridin-2-yl)-propionyl]-1,2,3,4-tetrahydro-isoquinolin-8-yl}-phenyl)-acetic acid | 20 |
| 328 | (±)-(4-Ethoxy-3-{5-fluoro-2-[3-(6-methyl-pyridin-2-yl)-butyryl]-1,2,3,4-tetrahydro-isoquinolin-8-yl}-phenyl)-acetic acid | 15 |
| 329 | (4-Ethoxy-3-{5-fluoro-2-[3-(6-methyl-pyridin-2-yl)-propionyl]-1,2,3,4-tetrahydro-isoquinolin-8-yl}-phenyl)-acetic acid | 21 |
| 330 | (±)-{4-Ethoxy-3-[5-fluoro-2-(trans-2-pyridin-2-yl-cyclopropanecarbonyl)-1,2,3,4-tetrahydro-isoquinolin-8-yl]-phenyl}-acetic acid | 15 |
| 332 | (±)-{3-[2-(2-Chroman-3-yl-acetyl)-5-fluoro-1,2,3,4-tetrahydro-isoquinolin-8-yl]-4-ethoxy-phenyl}-acetic acid | 15 |
| 335 | (±)-(4-Ethoxy-3-{5-fluoro-2-[2-(7-fluoro-chroman-4-yl)-acetyl]-1,2,3,4-tetrahydro-isoquinolin-8-yl}-phenyl)-acetic acid | 26 |
| 344 | (±)-{3-Ethoxy-4-[5-fluoro-2-(3-pyridin-2-yl-butyryl)-1,2,3,4-tetrahydro-isoquinolin-8-yl]-phenyl}-acetic acid | 51 |
| 345 | (±)-{4-Ethoxy-3-[5-fluoro-2-(3-pyridin-2-yl-butyryl)-1,2,3,4-tetrahydro-isoquinolin-8-yl]-phenyl}-acetic acid | 31 |

-continued

| Example | Name | IC$_{50}$ [nM] |
|---|---|---|
| 348 | {4-Ethoxy-3-[5-fluoro-2-(3-pyridin-2-yl-propionyl)-1,2,3,4-tetrahydro-isoquinolin-8-yl]-phenyl}-acetic acid | 16 |
| 350 | (±)-{4-Ethoxy-3-[5-fluoro-2-(2-5,6,7,8-tetrahydro-quinolin-8-yl-acetyl)-1,2,3,4-tetrahydro-isoquinolin-8-yl]-phenyl}-acetic acid | 9 |
| 351 | (±)-{4-Ethoxy-3-[5-fluoro-2-(2-methyl-3-pyridin-2-yl-propionyl)-1,2,3,4-tetrahydro-isoquinolin-8-yl]-phenyl}-acetic acid | 26 |
| 352 | (±)-{3-Ethoxy-4-[5-fluoro-2-(2-methyl-3-pyridin-2-yl-propionyl)-1,2,3,4-tetrahydro-isoquinolin-8-yl]-phenyl}-acetic acid | 103 |
| 358 | (4-{5-Fluoro-2-[3-(4-fluoro-phenyl)-3-methyl-butyryl]-1,2,3,4-tetrahydro-isoquinolin-8-yl}-3-methoxy-phenyl)-acetic acid | 11 |
| 359 | (±)-{4-[2-(2-Chroman-4-yl-acetyl)-5-fluoro-1,2,3,4-tetrahydro-isoquinolin-8-yl]-3-methoxy-phenyl}-acetic acid | 28 |
| 360 | (±)-{4-[5-Fluoro-2-(2-indan-1-yl-acetyl)-1,2,3,4-tetrahydro-isoquinolin-8-yl]-3-methoxy-phenyl}-acetic acid | 30 |
| 363 | (3-{5-Fluoro-2-[3-(4-fluoro-phenyl)-3-methyl-butyryl]-1,2,3,4-tetrahydro-isoquinolin-8-yl}-4-methoxy-phenyl)-acetic acid | 20 |
| 365 | 8-(5-Carboxymethyl-2-ethoxy-phenyl)-5-fluoro-3,4-dihydro-1H-isoquinoline-2-carboxylic acid pyrazin-2-ylmethyl ester | 32 |
| 366 | 8-(5-Carboxymethyl-2-ethoxy-phenyl)-5-fluoro-3,4-dihydro-1H-isoquinoline-2-carboxylic acid 3-fluoro-5-methyl-pyridin-2-ylmethyl ester | 65 |
| 368 | 8-(5-Carboxymethyl-2-ethoxy-phenyl)-5-fluoro-3,4-dihydro-1H-isoquinoline-2-carboxylic acid (S)-1-phenyl-ethyl ester | 46 |
| 369 | 8-(5-Carboxymethyl-2-ethoxy-phenyl)-5-fluoro-3,4-dihydro-1H-isoquinoline-2-carboxylic acid cyclopentylmethyl ester | 266 |
| 370 | 8-(5-Carboxymethyl-2-ethoxy-phenyl)-5-fluoro-3,4-dihydro-1H-isoquinoline-2-carboxylic acid 3-methyl-butyl ester | 76 |
| 371 | 8-(5-Carboxymethyl-2-ethoxy-phenyl)-5-fluoro-3,4-dihydro-1H-isoquinoline-2-carboxylic acid 6-methyl-pyridin-2-ylmethyl ester | 23 |
| 372 | 8-(5-Carboxymethyl-2-ethoxy-phenyl)-5-fluoro-3,4-dihydro-1H-isoquinoline-2-carboxylic acid cyclopropylmethyl ester | 149 |
| 373 | 8-(5-Carboxymethyl-2-ethoxy-phenyl)-5-fluoro-3,4-dihydro-1H-isoquinoline-2-carboxylic acid phenethyl ester | 42 |
| 374 | 8-(5-Carboxymethyl-2-ethoxy-phenyl)-5-fluoro-3,4-dihydro-1H-isoquinoline-2-carboxylic acid (R)-2-phenyl-propyl ester | 28 |
| 376 | 8-(5-Carboxymethyl-2-ethoxy-phenyl)-5-fluoro-3,4-dihydro-1H-isoquinoline-2-carboxylic acid butyl ester | 59 |
| 377 | 8-(5-Carboxymethyl-2-ethoxy-phenyl)-5-fluoro-3,4-dihydro-1H-isoquinoline-2-carboxylic acid isobutyl ester | 123 |
| 389 | 8-(4-Carboxymethyl-2-ethoxy-phenyl)-5-fluoro-3,4-dihydro-1H-isoquinoline-2-carboxylic acid (S)-1-phenyl-ethyl ester | 122 |
| 394 | 8-(5-Carboxymethyl-2-ethoxy-phenyl)-5-fluoro-3,4-dihydro-1H-isoquinoline-2-carboxylic acid pyridin-2-ylmethyl ester | 12 |
| 396 | 8-(5-Carboxymethyl-2-ethoxy-phenyl)-5-fluoro-3,4-dihydro-1H-isoquinoline-2-carboxylic acid cyclohexylmethyl ester | 18 |
| 397 | 8-(4-Carboxymethyl-2-ethoxy-phenyl)-5-fluoro-3,4-dihydro-1H-isoquinoline-2-carboxylic acid cyclohexylmethyl ester | 15 |
| 398 | 8-(5-Carboxymethyl-2-ethoxy-phenyl)-5-fluoro-3,4-dihydro-1H-isoquinoline-2-carboxylic acid 4-fluoro-benzyl ester | 13 |
| 399 | 8-(5-Carboxymethyl-2-ethoxy-phenyl)-5-fluoro-3,4-dihydro-1H-isoquinoline-2-carboxylic acid 3-fluoro-benzyl ester | 29 |
| 400 | 8-(5-Carboxymethyl-2-ethoxy-phenyl)-5-fluoro-3,4-dihydro-1H-isoquinoline-2-carboxylic acid 2-fluoro-benzyl ester | 21 |
| 401 | 8-(5-Carboxymethyl-2-ethoxy-phenyl)-5-fluoro-3,4-dihydro-1H-isoquinoline-2-carboxylic acid 2,5-difluoro-benzyl ester | 26 |
| 402 | 8-(5-Carboxymethyl-2-ethoxy-phenyl)-5-fluoro-3,4-dihydro-1H-isoquinoline-2-carboxylic acid 5-chloro-2-fluoro-benzyl ester | 20 |
| 403 | 8-(5-Carboxymethyl-2-ethoxy-phenyl)-5-fluoro-3,4-dihydro-1H-isoquinoline-2-carboxylic acid 2,4-difluoro-benzyl ester | 15 |
| 404 | 8-(4-Carboxymethyl-2-ethoxy-phenyl)-5-fluoro-3,4-dihydro-1H-isoquinoline-2-carboxylic acid 4-fluoro-benzyl ester | 10 |
| 405 | 8-(4-Carboxymethyl-2-ethoxy-phenyl)-5-fluoro-3,4-dihydro-1H-isoquinoline-2-carboxylic acid 3-fluoro-benzyl ester | 20 |
| 406 | 8-(4-Carboxymethyl-2-ethoxy-phenyl)-5-fluoro-3,4-dihydro-1H-isoquinoline-2-carboxylic acid 2-fluoro-benzyl ester | 10 |
| 407 | 8-(4-Carboxymethyl-2-ethoxy-phenyl)-5-fluoro-3,4-dihydro-1H-isoquinoline-2-carboxylic acid 2,5-difluoro-benzyl ester | 9 |
| 408 | 8-(4-Carboxymethyl-2-ethoxy-phenyl)-5-fluoro-3,4-dihydro-1H-isoquinoline-2-carboxylic acid 5-chloro-2-fluoro-benzyl ester | 8 |
| 409 | 8-(4-Carboxymethyl-2-ethoxy-phenyl)-5-fluoro-3,4-dihydro-1H-isoquinoline-2-carboxylic acid 2,4-difluoro-benzyl ester | 5 |
| 410 | 8-(4-Carboxymethyl-2-ethoxy-phenyl)-5-fluoro-3,4-dihydro-1H-isoquinoline-2-carboxylic acid benzyl ester | 13 |

-continued

| Example | Name | IC$_{50}$ [nM] |
|---|---|---|
| 411 | 8-[4-Carboxymethyl-2-(2,2,2-trifluoro-ethoxy)-phenyl]-5-fluoro-3,4-dihydro-1H-isoquinoline-2-carboxylic acid benzyl ester | 13 |
| 412 | 8-(5-Carboxymethyl-2-difluoromethoxy-phenyl)-5-fluoro-3,4-dihydro-1H-isoquinoline-2-carboxylic acid benzyl ester | 47 |
| 413 | 8-[5-Carboxymethyl-2-(2,2-difluoro-ethoxy)-phenyl]-5-fluoro-3,4-dihydro-1H-isoquinoline-2-carboxylic acid benzyl ester | 44 |
| 419 | 8-(2-tert-Butoxy-5-carboxymethyl-phenyl)-5-fluoro-3,4-dihydro-1H-isoquinoline-2-carboxylic acid benzyl ester | 35 |
| 420 | 8-(5-Carboxymethyl-2-dimethylamino-phenyl)-5-fluoro-3,4-dihydro-1H-isoquinoline-2-carboxylic acid benzyl ester | 17 |
| 421 | 8-[5-Carboxymethyl-2-(2,2,2-trifluoro-ethoxy)-phenyl]-5-fluoro-3,4-dihydro-1H-isoquinoline-2-carboxylic acid benzyl ester | 16 |
| 422 | 8-[5-Carboxymethyl-2-(2-fluoro-ethoxy)-phenyl]-5-fluoro-3,4-dihydro-1H-isoquinoline-2-carboxylic acid benzyl ester | 8 |
| 431 | 8-(5-Carboxymethyl-2-isopropoxy-phenyl)-5-cyano-3,4-dihydro-1H-isoquinoline-2-carboxylic acid benzyl ester | 47 |
| 438 | [3-(2-Benzylcarbamoyl-5-fluoro-1,2,3,4-tetrahydro-isoquinolin-8-yl)-4-ethoxy-phenyl]-acetic acid | 14 |

Intracellular Calcium Mobilization Assay (FLIPR):

Cells (HEK-293), stably expressing the hCRTH2 receptor under the control of the cytomegalovirus promotor from a single insertion of the expression vector pcDNA5 (Invitrogen), are grown to confluency in DMEM (low glucose, Gibco) medium supplemented with 10% fetal calf serum (Bioconcept, Switzerland) under standard mammalian cell culture conditions (37° C. in a humidified atmosphere of 5% $CO_2$). Cells are detached from culture dishes using a dissociation buffer (0.02% EDTA in PBS, Gibco) for 1 min, and collected by centrifugation at 200 g at r.t. for 5 min in assay buffer (equal parts of Hank's BSS (HBSS, Bioconcept) and DMEM (low glucose, without phenol red, Gibco)). After incubation for 45 min (37° C. and 5% $CO_2$) in the presence of 1 μM Fluo-4 and 0.04% Pluronic F-127 (both Molecular Probes), and 20 mM HEPES (Gibco) in assay buffer, the cells are washed with and resuspended in assay buffer, then seeded onto 384-well FLIPR assay plates (Greiner) at 50,000 cells in 66 μl per well, and sedimented by centrifugation.

Stock solutions of test compounds are made up at a concentration of 10 mM in DMSO, and serially diluted in assay buffer to concentrations required for inhibition dose response curves. Prostaglandin $D_2$ (Biomol, Plymouth Meeting, Pa.) is used as an agonist.

A FLIPR Tetra instrument (Molecular Devices) is operated according to the manufacturer's standard instructions, adding 4 μl of test compound dissolved at 10 mM in DMSO and diluted prior to the experiment in assay buffer to obtain the desired final concentration. 10 μl of 80 nM prostaglandin $D_2$ (Biomol, Plymouth Meeting, Pa.) in assay buffer, supplemented with 0.8% bovine serum albumin (fatty acid content <0.02%, Sigma), is then added to obtain a final concentration of 10 nM and 0.1%, respectively. Changes in fluorescence are monitored before and after the addition of test compounds at $\lambda_{ex}$=488 nm and $\lambda_{em}$=540 nm. Emission peak values above base level after prostaglandin $D_2$ addition are exported after base line subtraction. Values are normalized to high-level control (no test compound added) after subtraction of base line value (no prostaglandin $D_2$ added). The program XLIfit 3.0 (IDBS) is used to fit the data to a single site dose response curve of the equation (A+((B−A)/(1+((C/x)^D)))) and to calculate the IC$_{50}$ values.

All compounds tested in the intracellular calcium mobilization assay have shown antagonistic activity.

The invention claimed is:
1. A compound of formula (I):

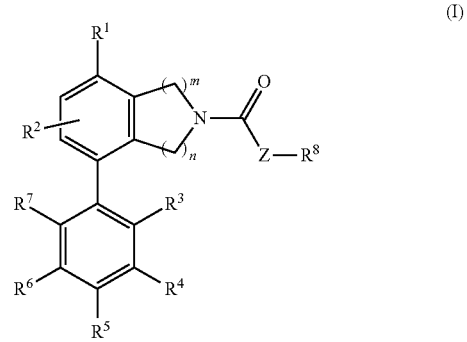

wherein
R$^1$ represents hydrogen, (C$_1$-C$_4$)alkyl, (C$_1$-C$_4$)alkoxy, (C$_1$-C$_4$)fluoroalkyl, (C$_1$-C$_4$)alkylsulfonyl, halogen or cyano;
R$^2$ represents hydrogen or halogen;
one of R$^3$, R$^4$ and R$^5$ represents carboxy-(C$_1$-C$_3$)alkyl, carboxy-cyclopropyl or carboxy-(C$_1$-C$_3$)alkoxy and the other two represent independently of each other hydrogen, (C$_1$-C$_4$)alkoxy or halogen;
R$^6$ represents hydrogen, (C$_1$-C$_4$)alkoxy or halogen;
R$^7$ represents hydrogen, (C$_1$-C$_4$)alkyl, (C$_1$-C$_4$)alkoxy, (C$_3$-C$_6$)cycloalkyl-methoxy, (C$_3$-C$_6$)cycloalkyloxy, methoxy-ethoxy, di-[(C$_1$-C$_2$)alkyl]-amino, (C$_1$-C$_4$)fluoroalkyl, (C$_1$-C$_4$)fluoroalkoxy, halogen or (C$_1$-C$_4$)alkylsulfonyl;
or R$^6$ and R$^7$ together represent methylendioxy or ethylendioxy;
R$^8$ represents
(C$_2$-C$_5$)alkyl;
(C$_1$-C$_5$)alkyl which is mono- or di-substituted wherein the substituents are independently selected from hydroxy, (C$_1$-C$_4$)alkoxy, oxo, —NR$^9$R$^{10}$, optionally substituted (C$_3$-C$_6$)cycloalkyl, optionally substituted aryl, optionally substituted heteroaryl, optionally substituted heterocyclyl, optionally substituted aryloxy, optionally substituted heteroaryloxy or optionally substituted aryl-(C$_1$-C$_2$)alkoxy;
(C$_3$-C$_5$)alkenyl;

($C_2$-$C_3$)alkenyl which is mono-substituted with optionally substituted aryl or optionally substituted heteroaryl;

($C_3$-$C_5$)alkynyl;

($C_3$-$C_6$)cycloalkyl which is unsubstituted, mono-, di-, tri- or tetra-substituted with methyl; mono-substituted with oxo; mono-substituted with optionally substituted aryl; or mono-substituted with optionally substituted heteroaryl; or heterocyclyl which is optionally mono-substituted with oxo;

$R^9$ represents ($C_1$-$C_4$)alkyl;

$R^{10}$ represents optionally substituted diphenylmethyl;

n represents 1 or 2;

m represents 1 or 2; and

Z represents —NH—, —O— or a bond;

or a salt thereof.

2. The compound according to claim 1, wherein $R^1$ represents hydrogen or halogen;

$R^2$ represents hydrogen or halogen;

one of $R^3$, $R^4$ and $R^5$ represents carboxy-($C_1$-$C_3$)alkyl or carboxy-($C_1$-$C_3$)alkoxy and the other two represent hydrogen;

$R^6$ represents hydrogen, methoxy or halogen;

$R^7$ represents hydrogen, ($C_1$-$C_4$)alkoxy, trifluoromethyl, trifluoromethoxy, halogen or methylsulfonyl;

$R^8$ represents ($C_1$-$C_4$)alkyl which is mono-substituted with optionally substituted aryl, optionally substituted heteroaryl or optionally substituted aryl-($C_1$-$C_2$)alkoxy; or cyclopropyl which is mono-substituted with optionally substituted aryl;

n represents 1 or 2;

m represents 1 or 2; and

Z represents —NH—, —O— or a bond;

or a salt thereof.

3. The compound according to claim 1, wherein $R^1$ represents fluoro;

$R^2$, $R^3$, $R^4$ and $R^6$ represent hydrogen;

$R^5$ represents carboxy-methyl or 1-carboxy-ethyl;

$R^7$ represents methoxy, ethoxy, isopropoxy or 2,2,2-trifluoroethoxy;

$R^8$ represents a methyl, ethyl or n-propyl group, which groups are independently mono-substituted with phenyl, wherein the phenyl is unsubstituted, mono-substituted with fluoro, chloro, methyl or methoxy, di-substituted with fluoro, or di-substituted with fluoro and chloro; or pyridin-2-yl, wherein the pyridin-2-yl is unsubstituted, mono-substituted with methyl, or di-substituted with methyl and fluoro;

n represents 1;

m represents 2; and

Z represents —O— or a bond;

or a salt thereof.

4. The compound according to claim 1, wherein $R^1$ represents fluoro, chloro or cyano;

$R^2$, $R^3$, $R^5$ and $R^6$ represent hydrogen;

$R^4$ represents carboxy-methyl or 1-carboxy-ethyl;

$R^7$ represents methoxy, ethoxy, n-propoxy, iso-propoxy, iso-butoxy, tert-butoxy, cyclopropyl-methoxy, methoxy-ethoxy, difluoromethoxy, trifluoromethoxy, 2-fluoroethoxy, 2,2-difluoroethoxy or 2,2,2-trifluoroethoxy;

$R^8$ represents a methyl, ethyl or n-propyl group, which groups are independently mono-substituted with phenyl, wherein the phenyl is unsubstituted, mono-substituted with fluoro, chloro or methoxy, di-substituted with fluoro, or di-substituted with fluoro and chloro; or pyridin-2-yl, wherein the pyridin-2-yl is unsubstituted, mono-substituted with methyl, or di-substituted with methyl and fluoro;

n represents 1;

m represents 2; and

Z represents —O— or a bond;

or a salt thereof.

5. The compound according to claim 1, wherein $R^1$ represents hydrogen, fluoro or chloro;

or a salt thereof.

6. The compound according to claim 1, wherein one of $R^3$, $R^4$ and $R^5$ represents carboxy-methyl, 1-carboxy-ethyl or carboxy-methoxy;

or a salt thereof.

7. The compound according to claim 1, wherein $R^7$ represents ($C_1$-$C_4$)alkoxy or trifluoromethoxy;

or a salt thereof.

8. The compound according to claim 1, wherein

Z represents —O— and $R^8$ represents ($C_1$-$C_4$)alkyl which is mono-substituted with optionally substituted aryl or optionally substituted heteroaryl; or Z represents a bond and $R^8$ represents ($C_1$-$C_4$)alkyl which is mono-substituted with optionally substituted aryl, optionally substituted heteroaryl, optionally substituted aryloxy or optionally substituted aryl-methoxy; or cyclopropyl which is mono-substituted with optionally substituted aryl;

or a salt thereof.

9. The compound according to claim 1, wherein

Z represents a bond;

or a salt thereof.

10. The compound according to claim 1, wherein the compound is:

(3-{5-Fluoro-2-[trans-2-(4-fluoro-phenyl)-cyclopropanecarbonyl]-1,2,3,4-tetrahydro-isoquinolin-8-yl}-4-methoxy-phenyl)-acetic acid;

(3-{2-[trans-2-(4-Chloro-phenyl)-cyclopropanecarbonyl]-5-fluoro-1,2,3,4-tetrahydro-isoquinolin-8-yl}-4-methoxy-phenyl)-acetic acid;

(3-{2-[trans-2-(2-Chloro-phenyl)-cyclopropanecarbonyl]-5-fluoro-1,2,3,4-tetrahydro-isoquinolin-8-yl}-4-methoxy-phenyl)-acetic acid;

(3-{2-[trans-2-(3-Chloro-phenyl)-cyclopropanecarbonyl]-5-fluoro-1,2,3,4-tetrahydro-isoquinolin-8-yl}-4-methoxy-phenyl)-acetic acid;

(3-{5-Fluoro-2-[trans-2-(2-fluoro-phenyl)-cyclopropanecarbonyl]-1,2,3,4-tetrahydro-isoquinolin-8-yl}-4-methoxy-phenyl)-acetic acid;

{3-[5-Fluoro-2-(trans-2-o-tolyl-cyclopropanecarbonyl)-1,2,3,4-tetrahydro-isoquinolin-8-yl]-4-methoxy-phenyl}-acetic acid;

8-(5-Carboxymethyl-2-methyl-phenyl)-5-fluoro-3,4-dihydro-1H-isoquinoline-2-carboxylic acid benzyl ester;

8-(5-Carboxymethyl-2-trifluoromethyl-phenyl)-5-fluoro-3,4-dihydro-1H-isoquinoline-2-carboxylic acid benzyl ester;

8-(5-Carboxymethyl-2-chloro-phenyl)-5-fluoro-3,4-dihydro-1H-isoquinoline-2-carboxylic acid benzyl ester;

8-(5-Carboxymethyl-2-fluoro-phenyl)-5-fluoro-3,4-dihydro-1H-isoquinoline-2-carboxylic acid benzyl ester;

8-(3-Carboxymethyl-4-chloro-phenyl)-5-fluoro-3,4-dihydro-1H-isoquinoline-2-carboxylic acid benzyl ester;

8-(3-Carboxymethyl-4-fluoro-phenyl)-5-fluoro-3,4-dihydro-1H-isoquinoline-2-carboxylic acid benzyl ester;

8-(3-Carboxymethyl-4-methoxy-phenyl)-5-fluoro-3,4-dihydro-1H-isoquinoline-2-carboxylic acid benzyl ester;

8-(3-Carboxymethyl-5-fluoro-phenyl)-5-fluoro-3,4-dihydro-1H-isoquinoline-2-carboxylic acid benzyl ester;

8-(3-Carboxymethyl-5-methoxy-phenyl)-5-fluoro-3,4-dihydro-1H-isoquinoline-2-carboxylic acid benzyl ester;

8-(3-Carboxymethyl-2-fluoro-phenyl)-5-fluoro-3,4-dihydro-1H-isoquinoline-2-carboxylic acid benzyl ester;

6-(5-Carboxymethyl-2-methoxy-phenyl)-9-fluoro-1,2,4,5-tetrahydro-benzo[d]azepine-3-carboxylic acid benzyl ester;

4-(5-Carboxymethyl-2-methoxy-phenyl)-7-fluoro-1,3-dihydro-isoindole-2-carboxylic acid benzyl ester;

8-(3-Carboxymethyl-5-chloro-phenyl)-5-fluoro-3,4-dihydro-1H-isoquinoline-2-carboxylic acid benzyl ester;

8-(5-Carboxymethyl-2-methanesulfonyl-phenyl)-5-fluoro-3,4-dihydro-1H-isoquinoline-2-carboxylic acid benzyl ester;

8-(5-Carboxymethyl-2-trifluoromethoxy-phenyl)-5-fluoro-3,4-dihydro-1H-isoquinoline-2-carboxylic acid benzyl ester;

8-(5-Carboxymethyl-2-isopropoxy-phenyl)-5-fluoro-3,4-dihydro-1H-isoquinoline-2-carboxylic acid benzyl ester;

8-(5-Carboxymethyl-2-fluoro-phenyl)-3,4-dihydro-1H-isoquinoline-2-carboxylic acid benzyl ester;

8-(3-Carboxymethyl-phenyl)-5-fluoro-3,4-dihydro-1H-isoquinoline-2-carboxylic acid benzyl ester;

8-(5-Carboxymethyl-2-methoxy-phenyl)-5-methanesulfonyl-3,4-dihydro-1H-isoquinoline-2-carboxylic acid benzyl ester;

{3-[5-Fluoro-2-((1R,2R)-2-phenyl-cyclopropanecarbonyl)-1,2,3,4-tetrahydro-isoquinolin-8-yl]-4-trifluoromethoxy-phenyl}-acetic acid;

{3-[5-Fluoro-2-((1R,2R)-2-phenyl-cyclopropanecarbonyl)-1,2,3,4-tetrahydro-isoquinolin-8-yl]-4-isopropoxy-phenyl}-acetic acid;

{4-Chloro-3-[5-fluoro-2-((1R,2R)-2-phenyl-cyclopropanecarbonyl)-1,2,3,4-tetrahydro-isoquinolin-8-yl]-phenyl}-acetic acid;

{3-[5-Fluoro-2-((1R,2R)-2-phenyl-cyclopropanecarbonyl)-1,2,3,4-tetrahydro-isoquinolin-8-yl]-4-methanesulfonyl-phenyl}-acetic acid;

8-(2-Carboxymethyl-phenyl)-5-fluoro-3,4-dihydro-1H-isoquinoline-2-carboxylic acid benzyl ester;

8-(5-Carboxymethyl-2-methoxy-phenyl)-5,6-difluoro-3,4-dihydro-1H-isoquinoline-2-carboxylic acid benzyl ester;

8-(5-Carboxymethyl-2-methoxy-phenyl)-6-fluoro-3,4-dihydro-1H-isoquinoline-2-carboxylic acid benzyl ester;

8-(5-Carboxymethyl-2-methoxy-phenyl)-7-fluoro-3,4-dihydro-1H-isoquinoline-2-carboxylic acid benzyl ester;

{3-[6-Fluoro-2-((1R,2R)-2-phenyl-cyclopropanecarbonyl)-1,2,3,4-tetrahydro-isoquinolin-8-yl]-4-methoxy-phenyl}-acetic acid;

{3-[7-Fluoro-2-((1R,2R)-2-phenyl-cyclopropanecarbonyl)-1,2,3,4-tetrahydro-isoquinolin-8-yl]-4-methoxy-phenyl}-acetic acid;

{3-[9-Fluoro-3-(trans-2-phenyl-cyclopropanecarbonyl)-2,3,4,5-tetrahydro-1H-benzo[d]azepin-6-yl]-4-methoxy-phenyl}-acetic acid;

{3-[7-Fluoro-2-(trans-2-phenyl-cyclopropanecarbonyl)-2,3-dihydro-1H-isoindol-4-yl]-4-methoxy-phenyl}-acetic acid;

{3-[5,7-Difluoro-2-((1R,2R)-2-phenyl-cyclopropanecarbonyl)-1,2,3,4-tetrahydro-isoquinolin-8-yl]-4-methoxy-phenyl}-acetic acid;

8-(5-Carboxymethyl-2-methoxy-phenyl)-5,7-difluoro-3,4-dihydro-1H-isoquinoline-2-carboxylic acid benzyl ester;

8-(4-Carboxymethyl-3-chloro-phenyl)-5-fluoro-3,4-dihydro-1H-isoquinoline-2-carboxylic acid benzyl ester;

8-(4-Carboxymethyl-phenyl)-5-fluoro-3,4-dihydro-1H-isoquinoline-2-carboxylic acid benzyl ester;

(3-{5-Fluoro-2-[3-(4-fluoro-phenoxy)-propionyl]-1,2,3,4-tetrahydro-isoquinolin-8-yl}-4-methoxy-phenyl)-acetic acid;

{3-[5-Fluoro-2-(2-phenoxy-acetyl)-1,2,3,4-tetrahydro-isoquinolin-8-yl]-4-methoxy-phenyl}-acetic acid;

(3-{5-Fluoro-2-[2-(4-fluoro-phenoxy)-acetyl]-1,2,3,4-tetrahydro-isoquinolin-8-yl}-4-methoxy-phenyl)-acetic acid;

(3-{5-Fluoro-2-[4-(2-fluoro-phenyl)-butyryl]-1,2,3,4-tetrahydro-isoquinolin-8-yl}-4-methoxy-phenyl)-acetic acid;

{3-[2-(2-Ethoxy-acetyl)-5-fluoro-1,2,3,4-tetrahydro-isoquinolin-8-yl]-4-methoxy-phenyl}-acetic acid;

{3-[2-(2-tert-Butoxy-acetyl)-5-fluoro-1,2,3,4-tetrahydro-isoquinolin-8-yl]-4-methoxy-phenyl}-acetic acid;

(3-{5-Fluoro-2-[trans-2-(3-fluoro-phenyl)-cyclopropanecarbonyl]-1,2,3,4-tetrahydro-isoquinolin-8-yl}-4-methoxy-phenyl)-acetic acid;

(3-{5-Fluoro-2-[2-(5-methoxy-benzo[d]isoxazol-3-yl)-acetyl]-1,2,3,4-tetrahydro-isoquinolin-8-yl}-4-methoxy-phenyl)-acetic acid;

{3-[5-Fluoro-2-(2,2,3,3-tetramethyl-cyclopropanecarbonyl)-1,2,3,4-tetrahydro-isoquinolin-8-yl]-4-methoxy-phenyl}-acetic acid;

{3-[5-Fluoro-2-(3-pyridin-3-yl-propionyl)-1,2,3,4-tetrahydro-isoquinolin-8-yl]-4-methoxy-phenyl}-acetic acid;

[3-(2-Cyclopropanecarbonyl-5-fluoro-1,2,3,4-tetrahydro-isoquinolin-8-yl)-4-methoxy-phenyl]-acetic acid;

{3-[2-(3-3,4-Dihydro-2H-quinolin-1-yl-propionyl)-5-fluoro-1,2,3,4-tetrahydro-isoquinolin-8-yl]-4-methoxy-phenyl}-acetic acid;

{3-[5-Fluoro-2-(3-phenyl-propionyl)-1,2,3,4-tetrahydro-isoquinolin-8-yl]-4-methoxy-phenyl}-acetic acid;

{3-[2-(2,2-Dimethyl-cyclopropanecarbonyl)-5-fluoro-1,2,3,4-tetrahydro-isoquinolin-8-yl]-4-methoxy-phenyl}-acetic acid;

{3-[5-Fluoro-2-(3-o-tolyl-propionyl)-1,2,3,4-tetrahydro-isoquinolin-8-yl]-4-methoxy-phenyl}-acetic acid;

(3-{5-Fluoro-2-[3-(3-methyl-indol-1-yl)-propionyl]-1,2,3,4-tetrahydro-isoquinolin-8-yl}-4-methoxy-phenyl)-acetic acid;

(3-{2-[2-(2-Chloro-benzyloxy)-acetyl]-5-fluoro-1,2,3,4-tetrahydro-isoquinolin-8-yl}-4-methoxy-phenyl)-acetic acid;

{3-[2-(3-2,3-Dihydro-indol-1-yl-propionyl)-5-fluoro-1,2,3,4-tetrahydro-isoquinolin-8-yl]-4-methoxy-phenyl}-acetic acid;

{3-[5-Fluoro-2-(trans-2-phenyl-cyclopropanecarbonyl)-1,2,3,4-tetrahydro-isoquinolin-8-yl]-4-methoxy-phenyl}-acetic acid;

(3-{5-Fluoro-2-[3-(2-methyl-1H-indol-3-yl)-propionyl]-1,2,3,4-tetrahydro-isoquinolin-8-yl}-4-methoxy-phenyl)-acetic acid;

(3-{5-Fluoro-2-[3-(1-methyl-1H-indol-3-yl)-propionyl]-1,2,3,4-tetrahydro-isoquinolin-8-yl}-4-methoxy-phenyl)-acetic acid;

(3-{5-Fluoro-2-[3-(5-methoxy-1H-indol-3-yl)-propionyl]-1,2,3,4-tetrahydro-isoquinolin-8-yl}-4-methoxyphenyl)-acetic acid;
(3-{2-[(1R,2R)-2-(4-Chloro-phenyl)-cyclopropanecarbonyl]-5-fluoro-1,2,3,4-tetrahydro-isoquinolin-8-yl}-4-methoxy-phenyl)-acetic acid;
(3-{5-Fluoro-2-[(1R,2R)-2-(3-fluoro-phenyl)-cyclopropanecarbonyl]-1,2,3,4-tetrahydro-isoquinolin-8-yl}-4-methoxy-phenyl)-acetic acid;
(3-{5-Fluoro-2-[(1R,2R)-2-(2-fluoro-phenyl)-cyclopropanecarbonyl]-1,2,3,4-tetrahydro-isoquinolin-8-yl}-4-methoxy-phenyl)-acetic acid;
{3-[5-Fluoro-2-(3-indazol-1-yl-propionyl)-1,2,3,4-tetrahydro-isoquinolin-8-yl]-4-methoxy-phenyl}-acetic acid;
(3-{5-Chloro-2-[(1R,2R)-2-(4-chloro-phenyl)-cyclopropanecarbonyl]-1,2,3,4-tetrahydro-isoquinolin-8-yl}-4-methoxy-phenyl)-acetic acid;
(3-{5-Chloro-2-[(1R,2R)-2-(3-fluoro-phenyl)-cyclopropanecarbonyl]-1,2,3,4-tetrahydro-isoquinolin-8-yl}-4-methoxy-phenyl)-acetic acid;
(3-{5-Chloro-2-[(1R,2R)-2-(2-fluoro-phenyl)-cyclopropanecarbonyl]-1,2,3,4-tetrahydro-isoquinolin-8-yl}-4-methoxy-phenyl)-acetic acid;
{3-[5-Chloro-2-((1R,2R)-2-phenyl-cyclopropanecarbonyl)-1,2,3,4-tetrahydro-isoquinolin-8-yl]-4-methoxyphenyl}-acetic acid;
{3-[5-Chloro-2-(3-indazol-1-yl-propionyl)-1,2,3,4-tetrahydro-isoquinolin-8-yl]-4-methoxy-phenyl}-acetic acid;
(3-{5-Chloro-2-[2-(2-chloro-benzyloxy)-acetyl]-1,2,3,4-tetrahydro-isoquinolin-8-yl}-4-methoxy-phenyl)-acetic acid;
(3-{5-Chloro-2-[4-(2-fluoro-phenyl)-butyryl]-1,2,3,4-tetrahydro-isoquinolin-8-yl}-4-methoxy-phenyl)-acetic acid;
(3-{5-Chloro-2-[3-(1-methyl-1H-indol-3-yl)-propionyl]-1,2,3,4-tetrahydro-isoquinolin-8-yl}-4-methoxy-phenyl)-acetic acid;
{3-[5-Chloro-2-(3-phenyl-propionyl)-1,2,3,4-tetrahydro-isoquinolin-8-yl]-4-methoxy-phenyl}-acetic acid;
{3-[5-Chloro-2-(3-3,4-dihydro-2H-quinolin-1-yl-propionyl)-1,2,3,4-tetrahydro-isoquinolin-8-yl]-4-methoxyphenyl}-acetic acid;
{3-[5-Chloro-2-(3-2,3-dihydro-indol-1-yl-propionyl)-1,2,3,4-tetrahydro-isoquinolin-8-yl]-4-methoxy-phenyl}-acetic acid;
(3-{5-Chloro-2-[3-(2-methyl-1H-indol-3-yl)-propionyl]-1,2,3,4-tetrahydro-isoquinolin-8-yl}-4-methoxy-phenyl)-acetic acid;
{3-[5-Fluoro-2-((1R,2R)-2-phenyl-cyclopropanecarbonyl)-1,2,3,4-tetrahydro-isoquinolin-8-yl]-4-methoxyphenyl}-acetic acid;
{3-[5-Fluoro-2-((1S,2S)-2-phenyl-cyclopropanecarbonyl)-1,2,3,4-tetrahydro-isoquinolin-8-yl]-4-methoxyphenyl}-acetic acid;
[3-(2-Cyclopropanecarbonyl-5-trifluoromethyl-1,2,3,4-tetrahydro-isoquinolin-8-yl)-4-methoxy-phenyl]-acetic acid;
{4-Methoxy-3-[2-(trans-2-phenyl-cyclopropanecarbonyl)-5-trifluoromethyl-1,2,3,4-tetrahydro-isoquinolin-8-yl]-phenyl}-acetic acid;
{3-[5,6-Difluoro-2-((1R,2R)-2-phenyl-cyclopropanecarbonyl)-1,2,3,4-tetrahydro-isoquinolin-8-yl]-4-methoxy-phenyl}-acetic acid;
(3-{5-Fluoro-2-[(E)-(3-phenyl-acryloyl)]-1,2,3,4-tetrahydro-isoquinolin-8-yl}-4-methoxy-phenyl)-acetic acid;
(3-{5-Fluoro-2-[(E)-3-(6-methoxy-pyridin-3-yl)-acryloyl]-1,2,3,4-tetrahydro-isoquinolin-8-yl}-4-methoxyphenyl)-acetic acid;
(3-{2-[(E)-3-(2,4-Dimethyl-thiazol-5-yl)-acryloyl]-5-fluoro-1,2,3,4-tetrahydro-isoquinolin-8-yl}-4-methoxy-phenyl)-acetic acid;
{3-[2-((E)-3-Benzothiazol-2-yl-acryloyl)-5-fluoro-1,2,3,4-tetrahydro-isoquinolin-8-yl]-4-methoxy-phenyl}-acetic acid;
{3-[5-Fluoro-2-((E)-3-pyridin-3-yl-acryloyl)-1,2,3,4-tetrahydro-isoquinolin-8-yl]-4-methoxy-phenyl}-acetic acid;
(3-{2-[(E)-3-(2,5-Dimethyl-2H-pyrazol-3-yl)-acryloyl]-5-fluoro-1,2,3,4-tetrahydro-isoquinolin-8-yl}-4-methoxy-phenyl)-acetic acid;
{3-[5-Fluoro-2-(3-pyridin-2-yl-propionyl)-1,2,3,4-tetrahydro-isoquinolin-8-yl]-4-methoxy-phenyl}-acetic acid;
(3-{5-Fluoro-2-[3-(6-methyl-pyridin-2-yl)-propionyl]-1,2,3,4-tetrahydro-isoquinolin-8-yl}-4-methoxy-phenyl)-acetic acid;
{3-[5-Fluoro-2-(3-pyrimidin-2-yl-propionyl)-1,2,3,4-tetrahydro-isoquinolin-8-yl]-4-methoxy-phenyl}-acetic acid;
(3-{5-Fluoro-2-[2-(pyridin-3-yloxy)-acetyl]-1,2,3,4-tetrahydro-isoquinolin-8-yl}-4-methoxy-phenyl)-acetic acid;
(3-{5-Fluoro-2-[trans-2-(2-trifluoromethyl-phenyl)-cyclopropanecarbonyl]-1,2,3,4-tetrahydro-isoquinolin-8-yl}-4-methoxy-phenyl)-acetic acid;
(3-{5-Fluoro-2-[trans-2-(4-methoxy-phenyl)-cyclopropanecarbonyl]-1,2,3,4-tetrahydro-isoquinolin-8-yl}-4-methoxy-phenyl)-acetic acid;
(3-{2-[3-(4-Chloro-phenyl)-3-phenyl-propionyl]-5-fluoro-1,2,3,4-tetrahydro-isoquinolin-8-yl}-4-methoxy-phenyl)-acetic acid;
(3-{2-[trans-2-(2,4-Dichloro-phenyl)-cyclopropanecarbonyl]-5-fluoro-1,2,3,4-tetrahydro-isoquinolin-8-yl}-4-methoxy-phenyl)-acetic acid;
{3-[8-Fluoro-2-((1R,2R)-2-phenyl-cyclopropanecarbonyl)-1,2,3,4-tetrahydro-isoquinolin-5-yl]-4-methoxyphenyl}-acetic acid;
{3-[8-Fluoro-2-(4-phenyl-butyryl)-1,2,3,4-tetrahydro-isoquinolin-5-yl]-4-methoxy-phenyl}-acetic acid;
{3-[8-Fluoro-2-(3-phenyl-propionyl)-1,2,3,4-tetrahydro-isoquinolin-5-yl]-4-methoxy-phenyl}-acetic acid;
{3-[8-Fluoro-2-(3-phenoxy-propionyl)-1,2,3,4-tetrahydro-isoquinolin-5-yl]-4-methoxy-phenyl}-acetic acid;
(3-{2-[2-(2-Chloro-benzyloxy)-acetyl]-8-fluoro-1,2,3,4-tetrahydro-isoquinolin-5-yl}-4-methoxy-phenyl)-acetic acid;
{3-[2-(3-3,4-Dihydro-2H-quinolin-1-yl-propionyl)-8-fluoro-1,2,3,4-tetrahydro-isoquinolin-5-yl]-4-methoxy-phenyl}-acetic acid;
(3-{8-Fluoro-2-[3-(1-methyl-1H-indol-3-yl)-propionyl]-1,2,3,4-tetrahydro-isoquinolin-5-yl}-4-methoxy-phenyl)-acetic acid;
{3-[5-Fluoro-2-((R)-3-phenyl-butyryl)-1,2,3,4-tetrahydro-isoquinolin-8-yl]-4-methoxy-phenyl}-acetic acid;
{3-[5-Fluoro-2-((S)-3-phenyl-butyryl)-1,2,3,4-tetrahydro-isoquinolin-8-yl]-4-methoxy-phenyl}-acetic acid;
{3-[5-Fluoro-2-(3-methyl-3-phenyl-butyryl)-1,2,3,4-tetrahydro-isoquinolin-8-yl]-4-methoxy-phenyl}-acetic acid;
{3-[5-Fluoro-2-(2-methyl-3-phenyl-propionyl)-1,2,3,4-tetrahydro-isoquinolin-8-yl]-4-methoxy-phenyl}-acetic acid;

{3-[5-Fluoro-2-(indane-2-carbonyl)-1,2,3,4-tetrahydro-isoquinolin-8-yl]-4-methoxy-phenyl}-acetic acid;

{3-[5-Fluoro-2-(2-indan-2-yl-acetyl)-1,2,3,4-tetrahydro-isoquinolin-8-yl]-4-methoxy-phenyl}-acetic acid;

{3-[5-Fluoro-2-(indane-1-carbonyl)-1,2,3,4-tetrahydro-isoquinolin-8-yl]-4-methoxy-phenyl}-acetic acid;

{3-[2-(Chroman-3-carbonyl)-5-fluoro-1,2,3,4-tetrahydro-isoquinolin-8-yl]-4-methoxy-phenyl}-acetic acid;

{3-[5-Fluoro-2-(4-oxo-1,2,3,4-tetrahydro-naphthalene-2-carbonyl)-1,2,3,4-tetrahydro-isoquinolin-8-yl]-4-methoxy-phenyl}-acetic acid;

{3-[2-(Chroman-2-carbonyl)-5-fluoro-1,2,3,4-tetrahydro-isoquinolin-8-yl]-4-methoxy-phenyl}-acetic acid;

{3-[2-(Bicyclo[4.2.0]octa-1(6),2,4-triene-7-carbonyl)-5-fluoro-1,2,3,4-tetrahydro-isoquinolin-8-yl]-4-methoxy-phenyl}-acetic acid;

{3-[5-Fluoro-2-(4-phenyl-butyryl)-1,2,3,4-tetrahydro-isoquinolin-8-yl]-4-methoxy-phenyl}-acetic acid;

{3-[5-Fluoro-2-(4-oxo-4-phenyl-butyryl)-1,2,3,4-tetrahydro-isoquinolin-8-yl]-4-methoxy-phenyl}-acetic acid;

(3-{5-Fluoro-2-[2-(1-methyl-1H-indol-3-yl)-acetyl]-1,2,3,4-tetrahydro-isoquinolin-8-yl}-4-methoxy-phenyl)-acetic acid;

2-{3-[5-Fluoro-2-((1R,2R)-2-phenyl-cyclopropanecarbonyl)-1,2,3,4-tetrahydro-isoquinolin-8-yl]-4-methoxy-phenyl}-propionic acid;

{3-[2-(2-Benzo[d]isoxazol-3-yl-acetyl)-5-fluoro-1,2,3,4-tetrahydro-isoquinolin-8-yl]-4-methoxy-phenyl}-acetic acid;

{3-[5-Fluoro-2-(3-oxo-indane-1-carbonyl)-1,2,3,4-tetrahydro-isoquinolin-8-yl]-4-methoxy-phenyl}-acetic acid;

{3-[5-Fluoro-2-(1,2,3,4-tetrahydro-naphthalene-2-carbonyl)-1,2,3,4-tetrahydro-isoquinolin-8-yl]-4-methoxy-phenyl}-acetic acid;

{3-[5-Fluoro-2-(2-1H-indazol-3-yl-acetyl)-1,2,3,4-tetrahydro-isoquinolin-8-yl]-4-methoxy-phenyl}-acetic acid;

(3-{5-Fluoro-2-[3-(3-methyl-indazol-1-yl)-propionyl]-1,2,3,4-tetrahydro-isoquinolin-8-yl}-4-methoxy-phenyl)-acetic acid;

(3-{5-Fluoro-2-[3-(5-fluoro-indazol-1-yl)-propionyl]-1,2,3,4-tetrahydro-isoquinolin-8-yl}-4-methoxy-phenyl)-acetic acid;

{3-[2-(2-Cyclohexyl-acetyl)-5-fluoro-1,2,3,4-tetrahydro-isoquinolin-8-yl]-4-methoxy-phenyl}-acetic acid;

(3-{5-Fluoro-2-[2-(1-hydroxy-cyclohexyl)-acetyl]-1,2,3,4-tetrahydro-isoquinolin-8-yl}-4-methoxy-phenyl)-acetic acid;

{3-[2-(3,3-Dimethyl-butyryl)-5-fluoro-1,2,3,4-tetrahydro-isoquinolin-8-yl]-4-methoxy-phenyl}-acetic acid;

{3-[5-Fluoro-2-(2-fluoro-benzylcarbamoyl)-1,2,3,4-tetrahydro-isoquinolin-8-yl]-4-methoxy-phenyl}-acetic acid;

{3-[5-Fluoro-2-(3-fluoro-benzylcarbamoyl)-1,2,3,4-tetrahydro-isoquinolin-8-yl]-4-methoxy-phenyl}-acetic acid;

{3-[5-Fluoro-2-(4-fluoro-benzylcarbamoyl)-1,2,3,4-tetrahydro-isoquinolin-8-yl]-4-methoxy-phenyl}-acetic acid;

[3-(5-Fluoro-2-phenethylcarbamoyl-1,2,3,4-tetrahydro-isoquinolin-8-yl)-4-methoxy-phenyl]-acetic acid;

{3-[2-(2-Chloro-benzylcarbamoyl)-5-fluoro-1,2,3,4-tetrahydro-isoquinolin-8-yl]-4-methoxy-phenyl}-acetic acid;

{3-[5-Fluoro-2-(2-methoxy-benzylcarbamoyl)-1,2,3,4-tetrahydro-isoquinolin-8-yl]-4-methoxy-phenyl}-acetic acid;

[3-(2-Benzylcarbamoyl-5-fluoro-1,2,3,4-tetrahydro-isoquinolin-8-yl)-4-methoxy-phenyl]-acetic acid;

[3-(5-Fluoro-2-propylcarbamoyl-1,2,3,4-tetrahydro-isoquinolin-8-yl)-4-methoxy-phenyl]-acetic acid;

8-(5-Carboxymethyl-2-methoxy-phenyl)-5-fluoro-3,4-dihydro-1H-isoquinoline-2-carboxylic acid 3-fluoro-benzyl ester;

8-(5-Carboxymethyl-2-methoxy-phenyl)-5-fluoro-3,4-dihydro-1H-isoquinoline-2-carboxylic acid 4-fluoro-benzyl ester;

8-[5-(1-Carboxy-ethyl)-2-methoxy-phenyl]-5-fluoro-3,4-dihydro-1H-isoquinoline-2-carboxylic acid 2-fluoro-benzyl ester;

8-(5-Carboxymethyl-2-methoxy-phenyl)-5-fluoro-3,4-dihydro-1H-isoquinoline-2-carboxylic acid ethyl ester;

8-(5-Carboxymethyl-2-methoxy-phenyl)-5-fluoro-3,4-dihydro-1H-isoquinoline-2-carboxylic acid isobutyl ester;

8-(5-Carboxymethyl-2-methoxy-phenyl)-5-fluoro-3,4-dihydro-1H-isoquinoline-2-carboxylic acid isopropyl ester;

8-(3-Carboxymethoxy-5-chloro-phenyl)-5-fluoro-3,4-dihydro-1H-isoquinoline-2-carboxylic acid benzyl ester;

8-(2-Carboxymethoxy-5-chloro-phenyl)-5-fluoro-3,4-dihydro-1H-isoquinoline-2-carboxylic acid benzyl ester;

8-(5-Carboxymethyl-2-methoxy-phenyl)-5-fluoro-3,4-dihydro-1H-isoquinoline-2-carboxylic acid 2-fluoro-benzyl ester;

8-(5-Carboxymethyl-2-methoxy-phenyl)-5-fluoro-3,4-dihydro-1H-isoquinoline-2-carboxylic acid 2,3-difluoro-benzyl ester;

8-(5-Carboxymethyl-2-methoxy-phenyl)-5-fluoro-3,4-dihydro-1H-isoquinoline-2-carboxylic acid 2-methyl-2H-pyrazol-3-ylmethyl ester;

8-(5-Carboxymethyl-2-methoxy-phenyl)-5-fluoro-3,4-dihydro-1H-isoquinoline-2-carboxylic acid 2,5-dimethyl-2H-pyrazol-3-ylmethyl ester;

8-(5-Carboxymethyl-2-methoxy-phenyl)-5-fluoro-3,4-dihydro-1H-isoquinoline-2-carboxylic acid 2-methyl-thiazol-4-ylmethyl ester;

8-(5-Carboxymethyl-2-methoxy-phenyl)-5-fluoro-3,4-dihydro-1H-isoquinoline-2-carboxylic acid 2-methyl-thiazol-5-ylmethyl ester;

8-(5-Carboxymethyl-2-methoxy-phenyl)-5-fluoro-3,4-dihydro-1H-isoquinoline-2-carboxylic acid pyrimidin-5-ylmethyl ester;

8-(5-Carboxymethyl-2-methoxy-phenyl)-5-fluoro-3,4-dihydro-1H-isoquinoline-2-carboxylic acid 2-(4-methyl-thiazol-5-yl)-ethyl ester;

8-(5-Carboxymethyl-2-methoxy-phenyl)-5-chloro-3,4-dihydro-1H-isoquinoline-2-carboxylic acid benzyl ester;

8-(5-Carboxymethyl-2-methoxy-phenyl)-5-methyl-3,4-dihydro-1H-isoquinoline-2-carboxylic acid benzyl ester;

8-(5-Carboxymethyl-2-methoxy-phenyl)-5-methoxy-3,4-dihydro-1H-isoquinoline-2-carboxylic acid benzyl ester;

8-(5-Carboxymethyl-2-methoxy-phenyl)-5-fluoro-3,4-dihydro-1H-isoquinoline-2-carboxylic acid benzyl ester;

8-(5-Carboxymethyl-2-methoxy-phenyl)-5-trifluoromethyl-3,4-dihydro-1H-isoquinoline-2-carboxylic acid benzyl ester;

5-(5-Carboxymethyl-2-methoxy-phenyl)-8-fluoro-3,4-dihydro-1H-isoquinoline-2-carboxylic acid benzyl ester;

{3-[5-Fluoro-2-((1R,2R)-2-phenyl-cyclopropanecarbonyl)-1,2,3,4-tetrahydro-isoquinolin-8-yl]-4-trifluoromethoxy-phenoxy}-acetic acid;
{3-[5-Fluoro-2-((1R,2R)-2-phenyl-cyclopropanecarbonyl)-1,2,3,4-tetrahydro-isoquinolin-8-yl]-4-isopropoxy-phenoxy}-acetic acid;
8-(5-Carboxymethoxy-2-trifluoromethoxy-phenyl)-5-fluoro-3,4-dihydro-1H-isoquinoline-2-carboxylic acid benzyl ester;
8-(5-Carboxymethoxy-2-isopropoxy-phenyl)-5-fluoro-3,4-dihydro-1H-isoquinoline-2-carboxylic acid benzyl ester;
8-(4-Carboxymethyl-2-fluoro-phenyl)-5-fluoro-3,4-dihydro-1H-isoquinoline-2-carboxylic acid benzyl ester;
8-(4-Carboxymethyl-2-chloro-phenyl)-5-fluoro-3,4-dihydro-1H-isoquinoline-2-carboxylic acid benzyl ester;
8-(4-Carboxymethyl-2-methoxy-phenyl)-5-fluoro-3,4-dihydro-1H-isoquinoline-2-carboxylic acid benzyl ester;
8-(6-Carboxymethyl-benzo[1,3]dioxol-4-yl)-5-fluoro-3,4-dihydro-1H-isoquinoline-2-carboxylic acid benzyl ester;
8-(7-Carboxymethyl-2,3-dihydro-benzo[1,4]dioxin-5-yl)-5-fluoro-3,4-dihydro-1H-isoquinoline-2-carboxylic acid benzyl ester;
8-(5-Carboxymethyl-2-methoxy-phenyl)-5-cyano-3,4-dihydro-1H-isoquinoline-2-carboxylic acid benzyl ester;
8-(5-Carboxymethyl-2-methoxy-phenyl)-3,4-dihydro-1H-isoquinoline-2-carboxylic acid benzyl ester;
8-[5-(1-Carboxy-ethyl)-2-methoxy-phenyl]-5-fluoro-3,4-dihydro-1H-isoquinoline-2-carboxylic acid benzyl ester;
8-(4-Carboxymethoxy-phenyl)-5-fluoro-3,4-dihydro-1H-isoquinoline-2-carboxylic acid benzyl ester;
8-(2-Carboxymethoxy-5-fluoro-phenyl)-3,4-dihydro-1H-isoquinoline-2-carboxylic acid benzyl ester;
8-[2-(3-Carboxy-propoxy)-5-fluoro-phenyl]-3,4-dihydro-1H-isoquinoline-2-carboxylic acid benzyl ester;
8-(3-Carboxymethoxy-phenyl)-5-fluoro-3,4-dihydro-1H-isoquinoline-2-carboxylic acid benzyl ester;
8-(5-Carboxymethoxy-2-chloro-phenyl)-5-fluoro-3,4-dihydro-1H-isoquinoline-2-carboxylic acid benzyl ester;
8-(5-Carboxymethoxy-2-methoxy-phenyl)-5-fluoro-3,4-dihydro-1H-isoquinoline-2-carboxylic acid benzyl ester;
8-(5-Carboxymethoxy-2-chloro-phenyl)-5-chloro-3,4-dihydro-1H-isoquinoline-2-carboxylic acid benzyl ester;
8-(5-Carboxymethoxy-2-chloro-phenyl)-5-methyl-3,4-dihydro-1H-isoquinoline-2-carboxylic acid benzyl ester;
8-(5-Carboxymethoxy-2-chloro-phenyl)-5-trifluoromethyl-3,4-dihydro-1H-isoquinoline-2-carboxylic acid benzyl ester;
8-(5-Carboxymethoxy-2-chloro-phenyl)-3,4-dihydro-1H-isoquinoline-2-carboxylic acid benzyl ester;
{3-[5-Fluoro-2-((1R,2R)-2-phenyl-cyclopropanecarbonyl)-1,2,3,4-tetrahydro-isoquinolin-8-yl]-4-methoxy-phenoxy}-acetic acid;
(4-{5-Fluoro-2-[3-(1-methyl-1H-indol-3-yl)-propionyl]-1,2,3,4-tetrahydro-isoquinolin-8-yl}-3-methoxy-phenyl)-acetic acid;
{4-[5-Fluoro-2-((1R,2R)-2-phenyl-cyclopropanecarbonyl)-1,2,3,4-tetrahydro-isoquinolin-8-yl]-3-methoxy-phenyl}-acetic acid;
(4-{5-Fluoro-2-[4-(2-fluoro-phenyl)-butyryl]-1,2,3,4-tetrahydro-isoquinolin-8-yl}-3-methoxy-phenyl)-acetic acid;
(4-{5-Fluoro-2-[3-(2-methyl-1H-indol-3-yl)-propionyl]-1,2,3,4-tetrahydro-isoquinolin-8-yl}-3-methoxy-phenyl)-acetic acid;
{4-[5-Fluoro-2-(4-phenyl-butyryl)-1,2,3,4-tetrahydro-isoquinolin-8-yl]-3-methoxy-phenyl}-acetic acid;
{4-[5-Fluoro-2-(3-methyl-3-phenyl-butyryl)-1,2,3,4-tetrahydro-isoquinolin-8-yl]-3-methoxy-phenyl}-acetic acid;
{4-[5-Fluoro-2-((R)-3-phenyl-butyryl)-1,2,3,4-tetrahydro-isoquinolin-8-yl]-3-methoxy-phenyl}-acetic acid;
(4-{5-Fluoro-2-[3-(5-fluoro-indazol-1-yl)-propionyl]-1,2,3,4-tetrahydro-isoquinolin-8-yl}-3-methoxy-phenyl)-acetic acid;
{4-[2-(3-2,3-Dihydro-indol-1-yl-propionyl)-5-fluoro-1,2,3,4-tetrahydro-isoquinolin-8-yl]-3-methoxy-phenyl}-acetic acid;
(4-{5-Fluoro-2-[3-(4-fluoro-phenoxy)-propionyl]-1,2,3,4-tetrahydro-isoquinolin-8-yl}-3-methoxy-phenyl)-acetic acid;
(4-{2-[2-(2-Chloro-benzyloxy)-acetyl]-5-fluoro-1,2,3,4-tetrahydro-isoquinolin-8-yl}-3-methoxy-phenyl)-acetic acid;
{4-[5-Fluoro-2-(3-o-tolyl-propionyl)-1,2,3,4-tetrahydro-isoquinolin-8-yl]-3-methoxy-phenyl}-acetic acid;
8-(5-Carboxymethyl-2-ethoxy-phenyl)-5-fluoro-3,4-dihydro-1H-isoquinoline-2-carboxylic acid benzyl ester;
8-(5-Carboxymethyl-2-cyclopropylmethoxy-phenyl)-5-fluoro-3,4-dihydro-1H-isoquinoline-2-carboxylic acid benzyl ester;
8-(5-Carboxymethyl-2-propoxy-phenyl)-5-fluoro-3,4-dihydro-1H-isoquinoline-2-carboxylic acid benzyl ester;
8-(5-Carboxymethyl-2-isobutoxy-phenyl)-5-fluoro-3,4-dihydro-1H-isoquinoline-2-carboxylic acid benzyl ester; or
8-[5-Carboxymethyl-2-(2-methoxy-ethoxy)-phenyl]-5-fluoro-3,4-dihydro-1H-isoquinoline-2-carboxylic acid benzyl ester;
or a salt thereof.

11. The compound according to claim 1, wherein the compound is:
{4-[2-((S)-2-Chroman-4-yl-acetyl)-5-fluoro-1,2,3,4-tetrahydro-isoquinolin-8-yl]-3-methoxy-phenyl}-acetic acid;
{4-[2-((R)-2-Chroman-4-yl-acetyl)-5-fluoro-1,2,3,4-tetrahydro-isoquinolin-8-yl]-3-methoxy-phenyl}-acetic acid;
8-[4-(1-Carboxy-ethoxy)-2-methoxy-phenyl]-5-fluoro-3,4-dihydro-1H-isoquinoline-2-carboxylic acid benzyl ester;
{4-Ethoxy-3-[5-fluoro-2-((S)-3-pyridin-2-yl-butyryl)-1,2,3,4-tetrahydro-isoquinolin-8-yl]-phenyl}-acetic acid;
{4-Ethoxy-3-[5-fluoro-2-((R)-3-pyridin-2-yl-butyryl)-1,2,3,4-tetrahydro-isoquinolin-8-yl]-phenyl}-acetic acid;
{3-Ethoxy-4-[5-fluoro-2-((S)-2-isochroman-1-yl-acetyl)-1,2,3,4-tetrahydro-isoquinolin-8-yl]-phenyl}-acetic acid;
{3-Ethoxy-4-[5-fluoro-2-((R)-2-isochroman-1-yl-acetyl)-1,2,3,4-tetrahydro-isoquinolin-8-yl]-phenyl}-acetic acid;
{3-[2-(2-[(S)-2,3-Dihydro-benzofuran-3-yl]-acetyl)-5-fluoro-1,2,3,4-tetrahydro-isoquinolin-8-yl]-4-ethoxy-phenyl}-acetic acid;
{3-[2-(2-[(R)-2,3-Dihydro-benzofuran-3-yl]-acetyl)-5-fluoro-1,2,3,4-tetrahydro-isoquinolin-8-yl]-4-ethoxy-phenyl}-acetic acid;

{4-Ethoxy-3-[5-fluoro-2-((S)-2-isochroman-4-yl-acetyl)-1,2,3,4-tetrahydro-isoquinolin-8-yl]-phenyl}-acetic acid;
{4-Ethoxy-3-[5-fluoro-2-((R)-2-isochroman-4-yl-acetyl)-1,2,3,4-tetrahydro-isoquinolin-8-yl]-phenyl}-acetic acid;
(4-Ethoxy-3-{5-fluoro-2-[(S)-3-(4-fluoro-phenyl)-butyryl]-1,2,3,4-tetrahydro-isoquinolin-8-yl}-phenyl)-acetic acid;
(4-Ethoxy-3-{5-fluoro-2-[(R)-3-(4-fluoro-phenyl)-butyryl]-1,2,3,4-tetrahydro-isoquinolin-8-yl}-phenyl)-acetic acid;
{4-Ethoxy-3-[5-fluoro-2-((S)-2-methyl-3-phenyl-propionyl)-1,2,3,4-tetrahydro-isoquinolin-8-yl]-phenyl}-acetic acid;
{4-Ethoxy-3-[5-fluoro-2-((R)-2-methyl-3-phenyl-propionyl)-1,2,3,4-tetrahydro-isoquinolin-8-yl]-phenyl}-acetic acid;
8-(5-Carboxymethyl-2-propyl-phenyl)-5-fluoro-3,4-dihydro-1H-isoquinoline-2-carboxylic acid benzyl ester;
8-(4-Carboxymethyl-2-isopropyl-phenyl)-5-fluoro-3,4-dihydro-1H-isoquinoline-2-carboxylic acid benzyl ester;
8-(4-Carboxymethyl-2-isopropoxy-phenyl)-5-fluoro-3,4-dihydro-1H-isoquinoline-2-carboxylic acid benzyl ester;
8-(4-Carboxymethyl-2,6-dimethoxy-phenyl)-5-fluoro-3,4-dihydro-1H-isoquinoline-2-carboxylic acid benzyl ester;
{4-Ethoxy-3-[5-fluoro-2-(2-indan-1-yl-acetyl)-1,2,3,4-tetrahydro-isoquinolin-8-yl]-phenyl}-acetic acid;
{4-Ethoxy-3-[5-fluoro-2-((1R,2R)-2-phenyl-cyclopropanecarbonyl)-1,2,3,4-tetrahydro-isoquinolin-8-yl]-phenyl}-acetic acid;
{4-Ethoxy-3-[5-fluoro-2-((R)-3-phenyl-butyryl)-1,2,3,4-tetrahydro-isoquinolin-8-yl]-phenyl}-acetic acid;
(4-Ethoxy-3-{5-fluoro-2-[2-(1-phenyl-cyclopropyl)-acetyl]-1,2,3,4-tetrahydro-isoquinolin-8-yl}-phenyl)-acetic acid;
(4-Ethoxy-3-{5-fluoro-2-[3-(4-fluoro-phenyl)-3-methyl-butyryl]-1,2,3,4-tetrahydro-isoquinolin-8-yl}-phenyl)-acetic acid;
{4-Ethoxy-3-[5-fluoro-2-(2-isochroman-1-yl-acetyl)-1,2,3,4-tetrahydro-isoquinolin-8-yl]-phenyl}-acetic acid;
{4-Ethoxy-3-[5-fluoro-2-(3-methyl-3-phenyl-butyryl)-1,2,3,4-tetrahydro-isoquinolin-8-yl]-phenyl}-acetic acid;
{3-[2-(2-Chroman-4-yl-acetyl)-5-fluoro-1,2,3,4-tetrahydro-isoquinolin-8-yl]-4-ethoxy-phenyl}-acetic acid;
{3-[2-(2-2,3-Dihydro-benzofuran-3-yl-acetyl)-5-fluoro-1,2,3,4-tetrahydro-isoquinolin-8-yl]-4-ethoxy-phenyl}-acetic acid;
{4-Ethoxy-3-[5-fluoro-2-(2-isochroman-4-yl-acetyl)-1,2,3,4-tetrahydro-isoquinolin-8-yl]-phenyl}-acetic acid;
{3-Ethoxy-4-[5-fluoro-2-(2-isochroman-1-yl-acetyl)-1,2,3,4-tetrahydro-isoquinolin-8-yl]-phenyl}-acetic acid;
(3-Ethoxy-4-{5-fluoro-2-[2-(1-phenyl-cyclopropyl)-acetyl]-1,2,3,4-tetrahydro-isoquinolin-8-yl}-phenyl)-acetic acid;
{3-Ethoxy-4-[5-fluoro-2-((1R,2R)-2-phenyl-cyclopropanecarbonyl)-1,2,3,4-tetrahydro-isoquinolin-8-yl]-phenyl}-acetic acid;
{3-Ethoxy-4-[5-fluoro-2-(2-isochroman-4-yl-acetyl)-1,2,3,4-tetrahydro-isoquinolin-8-yl]-phenyl}-acetic acid;
{3-Ethoxy-4-[5-fluoro-2-(2-indan-1-yl-acetyl)-1,2,3,4-tetrahydro-isoquinolin-8-yl]-phenyl}-acetic acid;
{3-Ethoxy-4-[5-fluoro-2-((R)-3-phenyl-butyryl)-1,2,3,4-tetrahydro-isoquinolin-8-yl]-phenyl}-acetic acid;
{4-[2-(2-2,3-Dihydro-benzofuran-3-yl-acetyl)-5-fluoro-1,2,3,4-tetrahydro-isoquinolin-8-yl]-3-ethoxy-phenyl}-acetic acid;
{4-[2-(2-Chroman-4-yl-acetyl)-5-fluoro-1,2,3,4-tetrahydro-isoquinolin-8-yl]-3-ethoxy-phenyl}-acetic acid;
(3-Ethoxy-4-{5-fluoro-2-[3-(4-fluoro-phenyl)-3-methyl-butyryl]-1,2,3,4-tetrahydro-isoquinolin-8-yl}-phenyl)-acetic acid;
{3-Ethoxy-4-[5-fluoro-2-(3-methyl-3-phenyl-butyryl)-1,2,3,4-tetrahydro-isoquinolin-8-yl]-phenyl}-acetic acid;
(3-{5-Fluoro-2-[2-(1-methyl-1,2,3,4-tetrahydro-naphthalen-1-yl)-acetyl]-1,2,3,4-tetrahydro-isoquinolin-8-yl}-4-methoxy-phenyl)-acetic acid;
(3-{2-[2-(2,2-Dimethyl-chroman-4-yl)-acetyl]-5-fluoro-1,2,3,4-tetrahydro-isoquinolin-8-yl}-4-methoxy-phenyl)-acetic acid;
{3-[5-Fluoro-2-(8-methoxy-1,2,3,4-tetrahydro-naphthalene-2-carbonyl)-1,2,3,4-tetrahydro-isoquinolin-8-yl]-4-methoxy-phenyl}-acetic acid;
{3-[2-(2-Chroman-3-yl-acetyl)-5-fluoro-1,2,3,4-tetrahydro-isoquinolin-8-yl]-4-methoxy-phenyl}-acetic acid;
(3-{5-Fluoro-2-[2-(7-fluoro-chroman-4-yl)-acetyl]-1,2,3,4-tetrahydro-isoquinolin-8-yl}-4-methoxy-phenyl)-acetic acid;
(3-{5-Fluoro-2-[2-(6-fluoro-chroman-4-yl)-acetyl]-1,2,3,4-tetrahydro-isoquinolin-8-yl}-4-methoxy-phenyl)-acetic acid;
{3-[2-(3-Cyclopropyl-butyryl)-5-fluoro-1,2,3,4-tetrahydro-isoquinolin-8-yl]-4-methoxy-phenyl}-acetic acid;
(3-{5-Fluoro-2-[2-(8-fluoro-chroman-4-yl)-acetyl]-1,2,3,4-tetrahydro-isoquinolin-8-yl}-4-methoxy-phenyl)-acetic acid;
{3-[5-Fluoro-2-(2-5,6,7,8-tetrahydro-isoquinolin-8-yl-acetyl)-1,2,3,4-tetrahydro-isoquinolin-8-yl]-4-methoxy-phenyl}-acetic acid;
(3-{5-Fluoro-2-[3-(6-methoxy-pyridin-2-yl)-butyryl]-1,2,3,4-tetrahydro-isoquinolin-8-yl}-4-methoxy-phenyl)-acetic acid;
(3-{5-Fluoro-2-[3-(6-methyl-pyridin-2-yl)-butyryl]-1,2,3,4-tetrahydro-isoquinolin-8-yl}-4-methoxy-phenyl)-acetic acid;
(3-{5-Fluoro-2-[2-(1-phenyl-cyclobutyl)-acetyl]-1,2,3,4-tetrahydro-isoquinolin-8-yl}-4-methoxy-phenyl)-acetic acid;
[3-(5-Fluoro-2-{2-[1-(4-fluoro-phenyl)-cyclobutyl]-acetyl}-1,2,3,4-tetrahydro-isoquinolin-8-yl)-4-methoxy-phenyl]-acetic acid;
(3-{5-Fluoro-2-[3-(3-fluoro-phenyl)-3-methyl-butyryl]-1,2,3,4-tetrahydro-isoquinolin-8-yl}-4-methoxy-phenyl)-acetic acid;
{3-[2-(2-{[(4-Chloro-phenyl)-phenyl-methyl]-methyl-amino}-acetyl)-5-fluoro-1,2,3,4-tetrahydro-isoquinolin-8-yl]-4-methoxy-phenyl}-acetic acid;
{3-[2-(2-Cyclopropyl-acetyl)-5-fluoro-1,2,3,4-tetrahydro-isoquinolin-8-yl]-4-methoxy-phenyl}-acetic acid;
{3-[5-Fluoro-2-((R)-2-phenyl-propionyl)-1,2,3,4-tetrahydro-isoquinolin-8-yl]-4-methoxy-phenyl}-acetic acid;
{3-[5-Fluoro-2-(3-hydroxy-3-phenyl-butyryl)-1,2,3,4-tetrahydro-isoquinolin-8-yl]-4-methoxy-phenyl}-acetic acid;
{3-[5-Fluoro-2-(2-isochroman-1-yl-acetyl)-1,2,3,4-tetrahydro-isoquinolin-8-yl]-4-methoxy-phenyl}-acetic acid;
(3-{5-Fluoro-2-[2-(1-phenyl-cyclopropyl)-acetyl]-1,2,3,4-tetrahydro-isoquinolin-8-yl}-4-methoxy-phenyl)-acetic acid;

(3-{5-Fluoro-2-[2-(2-methyl-1,2,3,4-tetrahydro-iso-quinolin-1-yl)-acetyl]-1,2,3,4-tetrahydro-isoquinolin-8-yl}-4-methoxy-phenyl)-acetic acid;
{3-[5-Fluoro-2-(2-1,2,3,4-tetrahydro-naphthalen-2-yl-acetyl)-1,2,3,4-tetrahydro-isoquinolin-8-yl]-4-methoxy-phenyl}-acetic acid;
{3-[5-Fluoro-2-(2-indan-1-yl-acetyl)-1,2,3,4-tetrahydro-isoquinolin-8-yl]-4-methoxy-phenyl}-acetic acid;
{3-[2-(2-Chroman-4-yl-acetyl)-5-fluoro-1,2,3,4-tetrahydro-isoquinolin-8-yl]-4-methoxy-phenyl}-acetic acid;
{3-[5-Fluoro-2-(2-1,2,3,4-tetrahydro-naphthalen-1-yl-acetyl)-1,2,3,4-tetrahydro-isoquinolin-8-yl]-4-methoxy-phenyl}-acetic acid;
{3-[5-Fluoro-2-(4-methyl-3-phenyl-pentanoyl)-1,2,3,4-tetrahydro-isoquinolin-8-yl]-4-methoxy-phenyl}-acetic acid;
{3-[5-Fluoro-2-(3-pyridin-2-yl-butyryl)-1,2,3,4-tetrahydro-isoquinolin-8-yl]-4-methoxy-phenyl}-acetic acid;
{3-[5-Fluoro-2-(3-pyridin-3-yl-butyryl)-1,2,3,4-tetrahydro-isoquinolin-8-yl]-4-methoxy-phenyl}-acetic acid;
{3-[5-Fluoro-2-(3-pyridin-4-yl-butyryl)-1,2,3,4-tetrahydro-isoquinolin-8-yl]-4-methoxy-phenyl}-acetic acid;
{3-[5-Fluoro-2-(3-phenyl-pentanoyl)-1,2,3,4-tetrahydro-isoquinolin-8-yl]-4-methoxy-phenyl}-acetic acid;
{3-[5-Fluoro-2-((R)-1,2,3,4-tetrahydro-naphthalene-1-carbonyl)-1,2,3,4-tetrahydro-isoquinolin-8-yl]-4-methoxy-phenyl}-acetic acid;
{3-[2-(2-2,3-Dihydro-benzofuran-3-yl-acetyl)-5-fluoro-1,2,3,4-tetrahydro-isoquinolin-8-yl]-4-methoxy-phenyl}-acetic acid;
{3-[5-Fluoro-2-(2-isochroman-4-yl-acetyl)-1,2,3,4-tetrahydro-isoquinolin-8-yl]-4-methoxy-phenyl}-acetic acid;
{3-[2-(Chroman-4-carbonyl)-5-fluoro-1,2,3,4-tetrahydro-isoquinolin-8-yl]-4-methoxy-phenyl}-acetic acid;
{3-[5-Fluoro-2-(isochroman-1-carbonyl)-1,2,3,4-tetrahydro-isoquinolin-8-yl]-4-methoxy-phenyl}-acetic acid;
{3-[5-Fluoro-2-(isochroman-3-carbonyl)-1,2,3,4-tetrahydro-isoquinolin-8-yl]-4-methoxy-phenyl}-acetic acid;
[4-Ethoxy-3-(5-fluoro-2-{2-[1-(3-fluoro-phenyl)-cyclopropyl]-acetyl}-1,2,3,4-tetrahydro-isoquinolin-8-yl)-phenyl]-acetic acid;
[4-Ethoxy-3-(5-fluoro-2-{2-[1-(2-fluoro-phenyl)-cyclopropyl]-acetyl}-1,2,3,4-tetrahydro-isoquinolin-8-yl)-phenyl]-acetic acid;
[4-Ethoxy-3-(5-fluoro-2-{2-[1-(4-fluoro-phenyl)-cyclopropyl]-acetyl}-1,2,3,4-tetrahydro-isoquinolin-8-yl)-phenyl]-acetic acid;
(4-Ethoxy-3-{5-fluoro-2-[3-(4-fluoro-phenyl)-butyryl]-1,2,3,4-tetrahydro-isoquinolin-8-yl}-phenyl)-acetic acid;
(4-Ethoxy-3-{5-fluoro-2-[3-(3-fluoro-phenyl)-butyryl]-1,2,3,4-tetrahydro-isoquinolin-8-yl}-phenyl)-acetic acid;
(4-Ethoxy-3-{5-fluoro-2-[3-(2-fluoro-phenyl)-butyryl]-1,2,3,4-tetrahydro-isoquinolin-8-yl}-phenyl)-acetic acid;
{4-Ethoxy-3-[5-fluoro-2-(3-pyrazin-2-yl-butyryl)-1,2,3,4-tetrahydro-isoquinolin-8-yl]-phenyl}-acetic acid;
(4-Ethoxy-3-{5-fluoro-2-[3-(2-methoxy-phenyl)-butyryl]-1,2,3,4-tetrahydro-isoquinolin-8-yl}-phenyl)-acetic acid;
{4-Ethoxy-3-[5-fluoro-2-(3-thiazol-2-yl-butyryl)-1,2,3,4-tetrahydro-isoquinolin-8-yl]-phenyl}-acetic acid;
(3-{2-[2-(2,2-Dimethyl-3,4-dihydro-2H-pyrano[2,3-b]pyridin-4-yl)-acetyl]-5-fluoro-1,2,3,4-tetrahydro-isoquinolin-8-yl}-4-ethoxy-phenyl)-acetic acid;
[4-[2-(2-Chroman-4-yl-acetyl)-5-fluoro-1,2,3,4-tetrahydro-isoquinolin-8-yl]-3-(2,2,2-trifluoro-ethoxy)-phenyl]-acetic acid;
[4-[5-Fluoro-2-(3-methyl-3-phenyl-butyryl)-1,2,3,4-tetrahydro-isoquinolin-8-yl]-3-(2,2,2-trifluoro-ethoxy)-phenyl]-acetic acid;
[4-[5-Fluoro-2-((S)-3-phenyl-butyryl)-1,2,3,4-tetrahydro-isoquinolin-8-yl]-3-(2,2,2-trifluoro-ethoxy)-phenyl]-acetic acid;
[4-[5-Fluoro-2-(3-pyridin-2-yl-butyryl)-1,2,3,4-tetrahydro-isoquinolin-8-yl]-3-(2,2,2-trifluoro-ethoxy)-phenyl]-acetic acid;
[4-[5-Fluoro-2-((1R,2R)-2-phenyl-cyclopropanecarbonyl)-1,2,3,4-tetrahydro-isoquinolin-8-yl]-3-(2,2,2-trifluoro-ethoxy)-phenyl]-acetic acid;
{3-[2-(2-Chroman-4-yl-acetyl)-5-fluoro-1,2,3,4-tetrahydro-isoquinolin-8-yl]-4-isopropoxy-phenyl}-acetic acid;
{3-[5-Fluoro-2-(3-methyl-3-phenyl-butyryl)-1,2,3,4-tetrahydro-isoquinolin-8-yl]-4-isopropoxy-phenyl}-acetic acid;
{3-[5-Fluoro-2-((R)-3-phenyl-butyryl)-1,2,3,4-tetrahydro-isoquinolin-8-yl]-4-isopropoxy-phenyl}-acetic acid;
{3-[5-Fluoro-2-(3-pyridin-2-yl-butyryl)-1,2,3,4-tetrahydro-isoquinolin-8-yl]-4-isopropoxy-phenyl}-acetic acid;
(3-{5-Fluoro-2-[3-(6-methyl-pyridin-2-yl)-butyryl]-1,2,3,4-tetrahydro-isoquinolin-8-yl}-4-isopropoxy-phenyl)-acetic acid;
(3-{5-Fluoro-2-[3-(6-methyl-pyridin-2-yl)-propionyl]-1,2,3,4-tetrahydro-isoquinolin-8-yl}-4-isopropoxy-phenyl)-acetic acid;
{3-[5-Fluoro-2-(2-isochroman-4-yl-acetyl)-1,2,3,4-tetrahydro-isoquinolin-8-yl]-4-isopropoxy-phenyl}-acetic acid;
{3-[5-Fluoro-2-(2-isochroman-1-yl-acetyl)-1,2,3,4-tetrahydro-isoquinolin-8-yl]-4-isopropoxy-phenyl}-acetic acid;
{3-[2-(2-2,3-Dihydro-benzofuran-3-yl-acetyl)-5-fluoro-1,2,3,4-tetrahydro-isoquinolin-8-yl]-4-isopropoxy-phenyl}-acetic acid;
[3-[2-(2-Chroman-4-yl-acetyl)-5-fluoro-1,2,3,4-tetrahydro-isoquinolin-8-yl]-4-(2,2,2-trifluoro-ethoxy)-phenyl]-acetic acid;
[3-[5-Fluoro-2-(3-methyl-3-phenyl-butyryl)-1,2,3,4-tetrahydro-isoquinolin-8-yl]-4-(2,2,2-trifluoro-ethoxy)-phenyl]-acetic acid;
[3-[5-Fluoro-2-((R)-3-phenyl-butyryl)-1,2,3,4-tetrahydro-isoquinolin-8-yl]-4-(2,2,2-trifluoro-ethoxy)-phenyl]-acetic acid;
[3-[5-Fluoro-2-(3-pyridin-2-yl-butyryl)-1,2,3,4-tetrahydro-isoquinolin-8-yl]-4-(2,2,2-trifluoro-ethoxy)-phenyl]-acetic acid;
[3-{5-Fluoro-2-[3-(6-methyl-pyridin-2-yl)-butyryl]-1,2,3,4-tetrahydro-isoquinolin-8-yl}-4-(2,2,2-trifluoro-ethoxy)-phenyl]-acetic acid;
[3-{5-Fluoro-2-[3-(6-methyl-pyridin-2-yl)-propionyl]-1,2,3,4-tetrahydro-isoquinolin-8-yl}-4-(2,2,2-trifluoro-ethoxy)-phenyl]-acetic acid;
[3-[5-Fluoro-2-(2-isochroman-4-yl-acetyl)-1,2,3,4-tetrahydro-isoquinolin-8-yl]-4-(2,2,2-trifluoro-ethoxy)-phenyl]-acetic acid;
[3-[5-Fluoro-2-(2-isochroman-1-yl-acetyl)-1,2,3,4-tetrahydro-isoquinolin-8-yl]-4-(2,2,2-trifluoro-ethoxy)-phenyl]-acetic acid;
[3-[2-(2-2,3-Dihydro-benzofuran-3-yl-acetyl)-5-fluoro-1,2,3,4-tetrahydro-isoquinolin-8-yl]-4-(2,2,2-trifluoro-ethoxy)-phenyl]-acetic acid;

{4-Ethoxy-3-[5-fluoro-2-(3-pyridin-2-yl-pentanoyl)-1,2,3,4-tetrahydro-isoquinolin-8-yl]-phenyl}-acetic acid;
(4-Ethoxy-3-{5-fluoro-2-[3-(3-methoxy-pyridin-2-yl)-propionyl]-1,2,3,4-tetrahydro-isoquinolin-8-yl}-phenyl)-acetic acid;
(4-Ethoxy-3-{5-fluoro-2-[3-(4-fluoro-phenyl)-propionyl]-1,2,3,4-tetrahydro-isoquinolin-8-yl}-phenyl)-acetic acid;
(4-Ethoxy-3-{5-fluoro-2-[3-(3-fluoro-phenyl)-propionyl]-1,2,3,4-tetrahydro-isoquinolin-8-yl}-phenyl)-acetic acid;
(4-Ethoxy-3-{5-fluoro-2-[3-(2-fluoro-phenyl)-propionyl]-1,2,3,4-tetrahydro-isoquinolin-8-yl}-phenyl)-acetic acid;
{3-Ethoxy-4-[5-fluoro-2-(3-pyridin-2-yl-pentanoyl)-1,2,3,4-tetrahydro-isoquinolin-8-yl]-phenyl}-acetic acid;
(3-Ethoxy-4-{5-fluoro-2-[3-(3-methoxy-pyridin-2-yl)-propionyl]-1,2,3,4-tetrahydro-isoquinolin-8-yl}-phenyl)-acetic acid;
(3-Ethoxy-4-{5-fluoro-2-[3-(4-fluoro-phenyl)-propionyl]-1,2,3,4-tetrahydro-isoquinolin-8-yl}-phenyl)-acetic acid;
(3-Ethoxy-4-{5-fluoro-2-[3-(3-fluoro-phenyl)-propionyl]-1,2,3,4-tetrahydro-isoquinolin-8-yl}-phenyl)-acetic acid;
(3-Ethoxy-4-{5-fluoro-2-[3-(2-fluoro-phenyl)-propionyl]-1,2,3,4-tetrahydro-isoquinolin-8-yl}-phenyl)-acetic acid;
{3-[2-(3-Cyclopropyl-3-pyridin-2-yl-propionyl)-5-fluoro-1,2,3,4-tetrahydro-isoquinolin-8-yl]-4-ethoxy-phenyl}-acetic acid;
{4-[2-(3-Cyclopropyl-3-pyridin-2-yl-propionyl)-5-fluoro-1,2,3,4-tetrahydro-isoquinolin-8-yl]-3-ethoxy-phenyl}-acetic acid;
(3-Ethoxy-4-{5-fluoro-2-[3-(6-methyl-pyridin-2-yl)-butyryl]-1,2,3,4-tetrahydro-isoquinolin-8-yl}-phenyl)-acetic acid;
(3-Ethoxy-4-{5-fluoro-2-[3-(6-methyl-pyridin-2-yl)-propionyl]-1,2,3,4-tetrahydro-isoquinolin-8-yl}-phenyl)-acetic acid;
{3-Ethoxy-4-[5-fluoro-2-(trans-2-pyridin-2-yl-cyclopropanecarbonyl)-1,2,3,4-tetrahydro-isoquinolin-8-yl]-phenyl}-acetic acid;
(4-{2-[2-(2,2-Dimethyl-chroman-4-yl)-acetyl]-5-fluoro-1,2,3,4-tetrahydro-isoquinolin-8-yl}-3-ethoxy-phenyl)-acetic acid;
{4-[2-(2-Chroman-3-yl-acetyl)-5-fluoro-1,2,3,4-tetrahydro-isoquinolin-8-yl]-3-ethoxy-phenyl}-acetic acid;
{3-Ethoxy-4-[5-fluoro-2-(8-methoxy-1,2,3,4-tetrahydro-naphthalene-2-carbonyl)-1,2,3,4-tetrahydro-isoquinolin-8-yl]-phenyl}-acetic acid;
(3-Ethoxy-4-{5-fluoro-2-[2-(1-methyl-1,2,3,4-tetrahydro-naphthalen-1-yl)-acetyl]-1,2,3,4-tetrahydro-isoquinolin-8-yl}-phenyl)-acetic acid;
(3-Ethoxy-4-{5-fluoro-2-[2-(7-fluoro-chroman-4-yl)-acetyl]-1,2,3,4-tetrahydro-isoquinolin-8-yl}-phenyl)-acetic acid;
(4-Ethoxy-3-{5-fluoro-2-[3-(6-methyl-pyridin-2-yl)-butyryl]-1,2,3,4-tetrahydro-isoquinolin-8-yl}-phenyl)-acetic acid;
(4-Ethoxy-3-{5-fluoro-2-[3-(6-methyl-pyridin-2-yl)-propionyl]-1,2,3,4-tetrahydro-isoquinolin-8-yl}-phenyl)-acetic acid;
{4-Ethoxy-3-[5-fluoro-2-(trans-2-pyridin-2-yl-cyclopropanecarbonyl)-1,2,3,4-tetrahydro-isoquinolin-8-yl]-phenyl}-acetic acid;
(3-{2-[2-(2,2-Dimethyl-chroman-4-yl)-acetyl]-5-fluoro-1,2,3,4-tetrahydro-isoquinolin-8-yl}-4-ethoxy-phenyl)-acetic acid;
{3-[2-(2-Chroman-3-yl-acetyl)-5-fluoro-1,2,3,4-tetrahydro-isoquinolin-8-yl]-4-ethoxy-phenyl}-acetic acid;
{4-Ethoxy-3-[5-fluoro-2-(8-methoxy-1,2,3,4-tetrahydro-naphthalene-2-carbonyl)-1,2,3,4-tetrahydro-isoquinolin-8-yl]-phenyl}-acetic acid;
(4-Ethoxy-3-{5-fluoro-2-[2-(1-methyl-1,2,3,4-tetrahydro-naphthalen-1-yl)-acetyl]-1,2,3,4-tetrahydro-isoquinolin-8-yl}-phenyl)-acetic acid;
(4-Ethoxy-3-{5-fluoro-2-[2-(7-fluoro-chroman-4-yl)-acetyl]-1,2,3,4-tetrahydro-isoquinolin-8-yl}-phenyl)-acetic acid;
{4-Ethoxy-3-[5-fluoro-2-((E)-3-pyridin-2-yl-acryloyl)-1,2,3,4-tetrahydro-isoquinolin-8-yl]-phenyl}-acetic acid;
(4-Ethoxy-3-{5-fluoro-2-[(E)-3-(1-methyl-1H-pyrazol-3-yl)-acryloyl]-1,2,3,4-tetrahydro-isoquinolin-8-yl}-phenyl)-acetic acid;
{3-Ethoxy-4-[5-fluoro-2-((E)-3-pyridin-2-yl-acryloyl)-1,2,3,4-tetrahydro-isoquinolin-8-yl]-phenyl}-acetic acid;
(3-Ethoxy-4-{5-fluoro-2-[(E)-3-(1-methyl-1H-pyrazol-4-yl)-acryloyl]-1,2,3,4-tetrahydro-isoquinolin-8-yl}-phenyl)-acetic acid;
{4-Ethoxy-3-[5-fluoro-2-(2-pyridin-2-yl-acetyl)-1,2,3,4-tetrahydro-isoquinolin-8-yl]-phenyl}-acetic acid;
(4-Ethoxy-3-{5-fluoro-2-[(E)-3-(1-methyl-1H-pyrazol-4-yl)-acryloyl]-1,2,3,4-tetrahydro-isoquinolin-8-yl}-phenyl)-acetic acid;
{3-Ethoxy-4-[5-fluoro-2-(2-pyridin-2-yl-acetyl)-1,2,3,4-tetrahydro-isoquinolin-8-yl]-phenyl}-acetic acid;
{3-[5-Fluoro-2-(2-methyl-3-pyridin-3-yl-propionyl)-1,2,3,4-tetrahydro-isoquinolin-8-yl]-4-methoxy-phenyl}-acetic acid;
{3-Ethoxy-4-[5-fluoro-2-(3-pyridin-2-yl-butyryl)-1,2,3,4-tetrahydro-isoquinolin-8-yl]-phenyl}-acetic acid;
{4-Ethoxy-3-[5-fluoro-2-(3-pyridin-2-yl-butyryl)-1,2,3,4-tetrahydro-isoquinolin-8-yl]-phenyl}-acetic acid;
{4-[5-Fluoro-2-(3-pyridin-2-yl-butyryl)-1,2,3,4-tetrahydro-isoquinolin-8-yl]-3-isopropoxy-phenyl}-acetic acid;
[4-[5-Fluoro-2-((R)-3-phenyl-butyryl)-1,2,3,4-tetrahydro-isoquinolin-8-yl]-3-(2,2,2-trifluoro-ethoxy)-phenyl]-acetic acid;
{4-Ethoxy-3-[5-fluoro-2-(3-pyridin-2-yl-propionyl)-1,2,3,4-tetrahydro-isoquinolin-8-yl]-phenyl}-acetic acid;
{3-Ethoxy-4-[5-fluoro-2-(3-pyridin-2-yl-propionyl)-1,2,3,4-tetrahydro-isoquinolin-8-yl]-phenyl}-acetic acid;
{4-Ethoxy-3-[5-fluoro-2-(2-5,6,7,8-tetrahydro-quinolin-8-yl-acetyl)-1,2,3,4-tetrahydro-isoquinolin-8-yl]-phenyl}-acetic acid;
{4-Ethoxy-3-[5-fluoro-2-(2-methyl-3-pyridin-2-yl-propionyl)-1,2,3,4-tetrahydro-isoquinolin-8-yl]-phenyl}-acetic acid;
{3-Ethoxy-4-[5-fluoro-2-(2-methyl-3-pyridin-2-yl-propionyl)-1,2,3,4-tetrahydro-isoquinolin-8-yl]-phenyl}-acetic acid;
{4-[2-(2-Chroman-4-yl-acetyl)-5-fluoro-1,2,3,4-tetrahydro-isoquinolin-8-yl]-3-isopropoxy-phenyl}-acetic acid;
{4-[5-Fluoro-2-(3-methyl-3-phenyl-butyryl)-1,2,3,4-tetrahydro-isoquinolin-8-yl]-3-isopropoxy-phenyl}-acetic acid;
{4-[5-Fluoro-2-((S)-3-phenyl-butyryl)-1,2,3,4-tetrahydro-isoquinolin-8-yl]-3-isopropoxy-phenyl}-acetic acid;

{4-[5-Fluoro-2-((R)-3-phenyl-butyryl)-1,2,3,4-tetrahydro-isoquinolin-8-yl]-3-isopropoxy-phenyl}-acetic acid;
{4-[5-Fluoro-2-((1R,2R)-2-phenyl-cyclopropanecarbonyl)-1,2,3,4-tetrahydro-isoquinolin-8-yl]-3-isopropoxy-phenyl}-acetic acid;
(4-{5-Fluoro-2-[3-(4-fluoro-phenyl)-3-methyl-butyryl]-1,2,3,4-tetrahydro-isoquinolin-8-yl}-3-methoxy-phenyl)-acetic acid;
{4-[2-(2-Chroman-4-yl-acetyl)-5-fluoro-1,2,3,4-tetrahydro-isoquinolin-8-yl]-3-methoxy-phenyl}-acetic acid;
{4-[5-Fluoro-2-(2-indan-1-yl-acetyl)-1,2,3,4-tetrahydro-isoquinolin-8-yl]-3-methoxy-phenyl}-acetic acid;
{3-[5-Fluoro-2-(trans-2-pyridin-2-yl-cyclopropanecarbonyl)-1,2,3,4-tetrahydro-isoquinolin-8-yl]-4-methoxy-phenyl}-acetic acid;
{3-[2-(2-1,3-Dihydro-isobenzofuran-1-yl-acetyl)-5-fluoro-1,2,3,4-tetrahydro-isoquinolin-8-yl]-4-methoxy-phenyl}-acetic acid;
(3-{5-Fluoro-2-[3-(4-fluoro-phenyl)-3-methyl-butyryl]-1,2,3,4-tetrahydro-isoquinolin-8-yl}-4-methoxy-phenyl)-acetic acid;
8-(5-Carboxymethyl-2-ethoxy-phenyl)-5-fluoro-3,4-dihydro-1H-isoquinoline-2-carboxylic acid (R)-1-phenyl-ethyl ester;
8-(5-Carboxymethyl-2-ethoxy-phenyl)-5-fluoro-3,4-dihydro-1H-isoquinoline-2-carboxylic acid pyrazin-2-ylmethyl ester;
8-(5-Carboxymethyl-2-ethoxy-phenyl)-5-fluoro-3,4-dihydro-1H-isoquinoline-2-carboxylic acid 3-fluoro-5-methyl-pyridin-2-ylmethyl ester;
8-(5-Carboxymethyl-2-ethoxy-phenyl)-5-fluoro-3,4-dihydro-1H-isoquinoline-2-carboxylic acid 2-methyl-2H-pyrazol-3-ylmethyl ester;
8-(5-Carboxymethyl-2-ethoxy-phenyl)-5-fluoro-3,4-dihydro-1H-isoquinoline-2-carboxylic acid (S)-1-phenyl-ethyl ester;
8-(5-Carboxymethyl-2-ethoxy-phenyl)-5-fluoro-3,4-dihydro-1H-isoquinoline-2-carboxylic acid cyclopentyl-methyl ester;
8-(5-Carboxymethyl-2-ethoxy-phenyl)-5-fluoro-3,4-dihydro-1H-isoquinoline-2-carboxylic acid 3-methyl-butyl ester;
8-(5-Carboxymethyl-2-ethoxy-phenyl)-5-fluoro-3,4-dihydro-1H-isoquinoline-2-carboxylic acid 6-methyl-pyridin-2-ylmethyl ester;
8-(5-Carboxymethyl-2-ethoxy-phenyl)-5-fluoro-3,4-dihydro-1H-isoquinoline-2-carboxylic acid cyclopropyl-methyl ester;
8-(5-Carboxymethyl-2-ethoxy-phenyl)-5-fluoro-3,4-dihydro-1H-isoquinoline-2-carboxylic acid phenethyl ester;
8-(5-Carboxymethyl-2-ethoxy-phenyl)-5-fluoro-3,4-dihydro-1H-isoquinoline-2-carboxylic acid (R)-2-phenyl-propyl ester;
8-(5-Carboxymethyl-2-ethoxy-phenyl)-5-fluoro-3,4-dihydro-1H-isoquinoline-2-carboxylic acid 3-methyl-but-2-enyl ester;
8-(5-Carboxymethyl-2-ethoxy-phenyl)-5-fluoro-3,4-dihydro-1H-isoquinoline-2-carboxylic acid butyl ester;
8-(5-Carboxymethyl-2-ethoxy-phenyl)-5-fluoro-3,4-dihydro-1H-isoquinoline-2-carboxylic acid isobutyl ester;
8-(5-Carboxymethyl-2-ethoxy-phenyl)-5-fluoro-3,4-dihydro-1H-isoquinoline-2-carboxylic acid 2-methoxy-ethyl ester;
8-(5-Carboxymethyl-2-ethoxy-phenyl)-5-fluoro-3,4-dihydro-1H-isoquinoline-2-carboxylic acid 3-methyl-but-3-enyl ester;
8-(5-Carboxymethyl-2-ethoxy-phenyl)-5-fluoro-3,4-dihydro-1H-isoquinoline-2-carboxylic acid 2-methyl-butyl ester;
8-(5-Carboxymethyl-2-ethoxy-phenyl)-5-fluoro-3,4-dihydro-1H-isoquinoline-2-carboxylic acid but-3-ynyl ester;
8-(5-Carboxymethyl-2-ethoxy-phenyl)-5-fluoro-3,4-dihydro-1H-isoquinoline-2-carboxylic acid 3-hydroxy-3-methyl-butyl ester;
8-(5-Carboxymethyl-2-ethoxy-phenyl)-5-fluoro-3,4-dihydro-1H-isoquinoline-2-carboxylic acid 3-methoxy-3-methyl-butyl ester;
8-(5-Carboxymethyl-2-ethoxy-phenyl)-5-fluoro-3,4-dihydro-1H-isoquinoline-2-carboxylic acid tetrahydrofuran-2-ylmethyl ester;
8-(4-Carboxymethyl-2-ethoxy-phenyl)-5-fluoro-3,4-dihydro-1H-isoquinoline-2-carboxylic acid (R)-1-phenyl-ethyl ester;
8-(4-Carboxymethyl-2-ethoxy-phenyl)-5-fluoro-3,4-dihydro-1H-isoquinoline-2-carboxylic acid pyrazin-2-ylmethyl ester;
8-(4-Carboxymethyl-2-ethoxy-phenyl)-5-fluoro-3,4-dihydro-1H-isoquinoline-2-carboxylic acid 3-fluoro-5-methyl-pyridin-2-ylmethyl ester;
8-(4-Carboxymethyl-2-ethoxy-phenyl)-5-fluoro-3,4-dihydro-1H-isoquinoline-2-carboxylic acid 2-methyl-2H-pyrazol-3-ylmethyl ester;
8-(4-Carboxymethyl-2-ethoxy-phenyl)-5-fluoro-3,4-dihydro-1H-isoquinoline-2-carboxylic acid (S)-1-phenyl-ethyl ester;
8-(4-Carboxymethyl-2-ethoxy-phenyl)-5-fluoro-3,4-dihydro-1H-isoquinoline-2-carboxylic acid 6-methyl-pyridin-2-ylmethyl ester;
8-(4-Carboxymethyl-2-ethoxy-phenyl)-5-fluoro-3,4-dihydro-1H-isoquinoline-2-carboxylic acid cyclopropyl-methyl ester;
8-(4-Carboxymethyl-2-ethoxy-phenyl)-5-fluoro-3,4-dihydro-1H-isoquinoline-2-carboxylic acid cyclopentyl-methyl ester;
8-(5-Carboxymethyl-2-ethoxy-phenyl)-5-fluoro-3,4-dihydro-1H-isoquinoline-2-carboxylic acid 3-methyl-butyl ester;
8-(5-Carboxymethyl-2-ethoxy-phenyl)-5-fluoro-3,4-dihydro-1H-isoquinoline-2-carboxylic acid pyridin-2-ylmethyl ester;
8-(4-Carboxymethyl-2-ethoxy-phenyl)-5-fluoro-3,4-dihydro-1H-isoquinoline-2-carboxylic acid pyridin-2-ylmethyl ester;
8-(5-Carboxymethyl-2-ethoxy-phenyl)-5-fluoro-3,4-dihydro-1H-isoquinoline-2-carboxylic acid cyclohexylmethyl ester;
8-(4-Carboxymethyl-2-ethoxy-phenyl)-5-fluoro-3,4-dihydro-1H-isoquinoline-2-carboxylic acid cyclohexylmethyl ester;
8-(5-Carboxymethyl-2-ethoxy-phenyl)-5-fluoro-3,4-dihydro-1H-isoquinoline-2-carboxylic acid 4-fluoro-benzyl ester;
8-(5-Carboxymethyl-2-ethoxy-phenyl)-5-fluoro-3,4-dihydro-1H-isoquinoline-2-carboxylic acid 3-fluoro-benzyl ester;
8-(5-Carboxymethyl-2-ethoxy-phenyl)-5-fluoro-3,4-dihydro-1H-isoquinoline-2-carboxylic acid 2-fluoro-benzyl ester;

8-(5-Carboxymethyl-2-ethoxy-phenyl)-5-fluoro-3,4-dihydro-1H-isoquinoline-2-carboxylic acid 2,5-difluorobenzyl ester;
8-(5-Carboxymethyl-2-ethoxy-phenyl)-5-fluoro-3,4-dihydro-1H-isoquinoline-2-carboxylic acid 5-chloro-2-fluoro-benzyl ester;
8-(5-Carboxymethyl-2-ethoxy-phenyl)-5-fluoro-3,4-dihydro-1H-isoquinoline-2-carboxylic acid 2,4-difluorobenzyl ester;
8-(4-Carboxymethyl-2-ethoxy-phenyl)-5-fluoro-3,4-dihydro-1H-isoquinoline-2-carboxylic acid 4-fluoro-benzyl ester;
8-(4-Carboxymethyl-2-ethoxy-phenyl)-5-fluoro-3,4-dihydro-1H-isoquinoline-2-carboxylic acid 3-fluoro-benzyl ester;
8-(4-Carboxymethyl-2-ethoxy-phenyl)-5-fluoro-3,4-dihydro-1H-isoquinoline-2-carboxylic acid 2-fluoro-benzyl ester;
8-(4-Carboxymethyl-2-ethoxy-phenyl)-5-fluoro-3,4-dihydro-1H-isoquinoline-2-carboxylic acid 2,5-difluorobenzyl ester;
8-(4-Carboxymethyl-2-ethoxy-phenyl)-5-fluoro-3,4-dihydro-1H-isoquinoline-2-carboxylic acid 5-chloro-2-fluoro-benzyl ester;
8-(4-Carboxymethyl-2-ethoxy-phenyl)-5-fluoro-3,4-dihydro-1H-isoquinoline-2-carboxylic acid 2,4-difluorobenzyl ester;
8-(4-Carboxymethyl-2-ethoxy-phenyl)-5-fluoro-3,4-dihydro-1H-isoquinoline-2-carboxylic acid benzyl ester;
8-[4-Carboxymethyl-2-(2,2,2-trifluoro-ethoxy)-phenyl]-5-fluoro-3,4-dihydro-1H-isoquinoline-2-carboxylic acid benzyl ester;
8-(5-Carboxymethyl-2-difluoromethoxy-phenyl)-5-fluoro-3,4-dihydro-1H-isoquinoline-2-carboxylic acid benzyl ester;
8-[5-Carboxymethyl-2-(2,2-difluoro-ethoxy)-phenyl]-5-fluoro-3,4-dihydro-1H-isoquinoline-2-carboxylic acid benzyl ester;
8-[5-(1-Carboxy-ethoxy)-2-methoxy-phenyl]-5-fluoro-3,4-dihydro-1H-isoquinoline-2-carboxylic acid benzyl ester;
8-[5-(1-Carboxy-propoxy)-2-methoxy-phenyl]-5-fluoro-3,4-dihydro-1H-isoquinoline-2-carboxylic acid benzyl ester;
8-(2-Carboxymethyl-5-chloro-phenyl)-5-fluoro-3,4-dihydro-1H-isoquinoline-2-carboxylic acid benzyl ester;
8-(2-Carboxymethoxy-6-methoxy-phenyl)-5-fluoro-3,4-dihydro-1H-isoquinoline-2-carboxylic acid benzyl ester;
8-(2-Carboxymethyl-6-methoxy-phenyl)-5-fluoro-3,4-dihydro-1H-isoquinoline-2-carboxylic acid benzyl ester;
8-(2-tert-Butoxy-5-carboxymethyl-phenyl)-5-fluoro-3,4-dihydro-1H-isoquinoline-2-carboxylic acid benzyl ester;
8-(5-Carboxymethyl-2-dimethylamino-phenyl)-5-fluoro-3,4-dihydro-1H-isoquinoline-2-carboxylic acid benzyl ester;
8-[5-Carboxymethyl-2-(2,2,2-trifluoro-ethoxy)-phenyl]-5-fluoro-3,4-dihydro-1H-isoquinoline-2-carboxylic acid benzyl ester;
8-[5-Carboxymethyl-2-(2-fluoro-ethoxy)-phenyl]-5-fluoro-3,4-dihydro-1H-isoquinoline-2-carboxylic acid benzyl ester;
8-(3-Carboxymethyl-2-methoxy-phenyl)-5-fluoro-3,4-dihydro-1H-isoquinoline-2-carboxylic acid benzyl ester;
8-(4-Carboxymethoxy-2-methoxy-phenyl)-5-fluoro-3,4-dihydro-1H-isoquinoline-2-carboxylic acid benzyl ester;
8-[4-(1-Carboxy-ethyl)-2-ethoxy-phenyl]-5-fluoro-3,4-dihydro-1H-isoquinoline-2-carboxylic acid benzyl ester;
[3-[5-Fluoro-2-((1R,2R)-2-phenyl-cyclopropanecarbonyl)-1,2,3,4-tetrahydro-isoquinolin-8-yl]-4-(2,2,2-trifluoro-ethoxy)-phenyl]-acetic acid;
{4-(2-Fluoro-ethoxy)-3-[5-fluoro-2-((1R,2R)-2-phenyl-cyclopropanecarbonyl)-1,2,3,4-tetrahydro-isoquinolin-8-yl]-phenyl}-acetic acid;
{4-tert-Butoxy-3-[5-fluoro-2-((1R,2R)-2-phenyl-cyclopropanecarbonyl)-1,2,3,4-tetrahydro-isoquinolin-8-yl]-phenyl}-acetic acid;
1-{3-[5-Fluoro-2-((1R,2R)-2-phenyl-cyclopropanecarbonyl)-1,2,3,4-tetrahydro-isoquinolin-8-yl]-4-methoxy-phenyl}-cyclopropanecarboxylic acid;
8-(5-Carboxymethyl-2-cyclopropoxy-phenyl)-5-fluoro-3,4-dihydro-1H-isoquinoline-2-carboxylic acid benzyl ester;
8-(5-Carboxymethyl-2-isopropoxy-phenyl)-5-cyano-3,4-dihydro-1H-isoquinoline-2-carboxylic acid benzyl ester;
{4-Ethoxy-3-[5-fluoro-2-(2-fluoro-benzylcarbamoyl)-1,2,3,4-tetrahydro-isoquinolin-8-yl]-phenyl}-acetic acid;
{4-Ethoxy-3-[5-fluoro-2-(3-fluoro-benzylcarbamoyl)-1,2,3,4-tetrahydro-isoquinolin-8-yl]-phenyl}-acetic acid;
{4-Ethoxy-3-[5-fluoro-2-(4-fluoro-benzylcarbamoyl)-1,2,3,4-tetrahydro-isoquinolin-8-yl]-phenyl}-acetic acid;
[4-Ethoxy-3-(5-fluoro-2-phenethylcarbamoyl-1,2,3,4-tetrahydro-isoquinolin-8-yl)-phenyl]-acetic acid;
{3-[2-(2-Chloro-benzylcarbamoyl)-5-fluoro-1,2,3,4-tetrahydro-isoquinolin-8-yl]-4-ethoxy-phenyl}-acetic acid;
{4-Ethoxy-3-[5-fluoro-2-(2-methoxy-benzylcarbamoyl)-1,2,3,4-tetrahydro-isoquinolin-8-yl]-phenyl}-acetic acid;
[3-(2-Benzylcarbamoyl-5-fluoro-1,2,3,4-tetrahydro-isoquinolin-8-yl)-4-ethoxy-phenyl]-acetic acid;
[4-Ethoxy-3-(5-fluoro-2-propylcarbamoyl-1,2,3,4-tetrahydro-isoquinolin-8-yl)-phenyl]-acetic acid;
{3-Ethoxy-4-[5-fluoro-2-(2-fluoro-benzylcarbamoyl)-1,2,3,4-tetrahydro-isoquinolin-8-yl]-phenyl}-acetic acid;
{3-Ethoxy-4-[5-fluoro-2-(3-fluoro-benzylcarbamoyl)-1,2,3,4-tetrahydro-isoquinolin-8-yl]-phenyl}-acetic acid;
{3-Ethoxy-4-[5-fluoro-2-(4-fluoro-benzylcarbamoyl)-1,2,3,4-tetrahydro-isoquinolin-8-yl]-phenyl}-acetic acid;
[3-Ethoxy-4-(5-fluoro-2-phenethylcarbamoyl-1,2,3,4-tetrahydro-isoquinolin-8-yl)-phenyl]-acetic acid;
{4-[2-(2-Chloro-benzylcarbamoyl)-5-fluoro-1,2,3,4-tetrahydro-isoquinolin-8-yl]-3-ethoxy-phenyl}-acetic acid;
{3-Ethoxy-4-[5-fluoro-2-(2-methoxy-benzylcarbamoyl)-1,2,3,4-tetrahydro-isoquinolin-8-yl]-phenyl}-acetic acid;
[4-(2-Benzylcarbamoyl-5-fluoro-1,2,3,4-tetrahydro-isoquinolin-8-yl)-3-ethoxy-phenyl]-acetic acid;
[3-Ethoxy-4-(5-fluoro-2-propylcarbamoyl-1,2,3,4-tetrahydro-isoquinolin-8-yl)-phenyl]-acetic acid;
(3-Ethoxy-4-{5-fluoro-2-[(pyridin-2-ylmethyl)-carbamoyl]-1,2,3,4-tetrahydro-isoquinolin-8-yl}-phenyl)-acetic acid; or
(4-Ethoxy-3-{5-fluoro-2-[(pyridin-2-ylmethyl)-carbamoyl]-1,2,3,4-tetrahydro-isoquinolin-8-yl}-phenyl)-acetic acid;
or a salt of such a compound.

12. A pharmaceutical composition comprising the compound according to claim 1, or a pharmaceutically acceptable salt thereof, and a pharmaceutically acceptable carrier.

13. A medicament comprising the compound according to claim 1, or a pharmaceutically acceptable salt thereof.

14. A method of treating a disease or disorder comprising administering an amount of the compound according to claim 1 to a subject in need thereof, wherein the disease is chronic and acute allergic/immune diseases; eosinophil-related diseases or basophil-related diseases.

15. A method of treating a disease or disorder comprising administering an amount of the compound according to claim 12 to a subject in need thereof, wherein the disease is chronic and acute allergic/immune diseases/disorders, eosinophil-related diseases; or basophil-related diseases.

16. The method according to claim 14, wherein the chronic and acute allergic/immune diseases/disorders are asthma, allergic asthma, eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, systemic mast cell disorders, anaphylactic shock, urticaria, eczema, ulcerative colitis, chronic obstructive pulmonary disease (COPD), inflammatory bowel disease or rheumatoid arthritis.

17. The method according to claim 14, wherein the eosinophil-related diseases are small vessel vasculitides, Wegener's granulomatosis, microscopic polyangiitis and organ-specific subsets, hypereosinophilic syndromes, eosinophilic esophagitis, reflux esophagitis, eosinophilic endocarditis (Loeffler's endocarditis), eosinophilia-myalgia syndrome, eosinophilic fasciitis, eosinophilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia or DRESS syndrome (Drug Rash with Eosinophilia and Systemic Symptoms).

18. The method according to claim 17, wherein the small vessel vasculitides is Churg-Strauss syndrome.

19. The method according to claim 17, wherein hypereosinophilic syndromes is eosinophilic pneumonia.

20. The method according to claim 14, wherein the basophil-related diseases are basophilic leukemia or basophilic leukocytosis.

* * * * *